US012460216B2

(12) United States Patent
Leveau et al.

(10) Patent No.: US 12,460,216 B2
(45) **Date of Patent: *Nov. 4, 2025**

(54) PHAGE-DERIVED PARTICLES FOR IN SITU DELIVERY OF DNA PAYLOAD INTO C. ACNES POPULATION

(71) Applicant: Eligo Bioscience, Paris (FR)

(72) Inventors: Aymeric Leveau, Paris (FR); Inès Canadas Blasco, Paris (FR); Aurélie Mathieu, Paris (FR); Antoine Decrulle, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/617,782

(22) Filed: Mar. 27, 2024

(65) Prior Publication Data

US 2024/0254496 A1 Aug. 1, 2024

Related U.S. Application Data

(63) Continuation of application No. 18/477,069, filed on Sep. 28, 2023, now Pat. No. 11,970,701, which is a continuation of application No. 17/518,936, filed on Nov. 4, 2021, now Pat. No. 11,820,989.

(60) Provisional application No. 63/145,969, filed on Feb. 4, 2021, provisional application No. 63/145,967, filed on Feb. 4, 2021, provisional application No. 63/109,832, filed on Nov. 4, 2020, provisional application No. 63/109,834, filed on Nov. 4, 2020.

(51) Int. Cl.

| | |
|---|---|
| ***C12N 7/00*** | (2006.01) |
| ***A61K 39/02*** | (2006.01) |
| ***A61K 39/05*** | (2006.01) |
| ***A61P 17/10*** | (2006.01) |
| ***C12N 9/22*** | (2006.01) |
| ***C12N 15/11*** | (2006.01) |
| ***C12N 15/76*** | (2006.01) |
| *A61K 39/00* | (2006.01) |
| *C12N 9/64* | (2006.01) |

(52) U.S. Cl.

CPC .............. *C12N 15/76* (2013.01); *A61K 39/02* (2013.01); *A61K 39/05* (2013.01); *A61P 17/10* (2018.01); *C12N 9/22* (2013.01); *C12N 15/11* (2013.01); *A61K 2039/53* (2013.01); *C12N 9/64* (2013.01); *C12N 2310/20* (2017.05); *C12N 2795/10343* (2013.01); *C12N 2800/101* (2013.01); *C12N 2800/80* (2013.01)

(58) Field of Classification Search

None

See application file for complete search history.

(56) References Cited

U.S. PATENT DOCUMENTS

| | | | |
|---|---|---|---|
| 2019/0030090 | A1 | 1/2019 | Li et al. |
| 2021/0252081 | A1 | 8/2021 | Feron et al. |

FOREIGN PATENT DOCUMENTS

| | | | |
|---|---|---|---|
| WO | 2007007055 | A1 | 1/2007 |
| WO | 2017185018 | A1 | 10/2017 |
| WO | 2019113066 | A1 | 6/2019 |
| WO | 2020181178 | A1 | 9/2020 |
| WO | 2020181180 | A1 | 9/2020 |
| WO | 2020181193 | A1 | 9/2020 |
| WO | 2020181195 | A1 | 9/2020 |
| WO | 2020181202 | A1 | 9/2020 |

OTHER PUBLICATIONS

Abudayyeh et al. RNA targeting with CRISPR-Cas13a. Nature. 2017, 550(7675), 280-284.

Adachi et al. Hair follicle-derived IL-7 and IL-15 mediate skin-resident memory T cell homeostasis and lymphoma. Nat Med. 2015, 21(11), 1272-1279.

Allhorn, M. et al. A novel enzyme with antioxidant capacity produced by the ubiquitous skin colonizer Propionibacterium acnes. Sci. Rep. 2016, 6, 36412, 1-12.

Anzalone, A. et al. Search-and-replace genome editing without double-strand breaks or donor DNA. Nature. 2019, 576(7785), 149-157.

Aoki et al., Transconjugation of erm(X) conferring high-level resistance of clindamycin for Cutibacterium acnes. Journal of Medical Microbiology, 2019, 68, 26-30.

Aoki et al., Transferable Multidrug-Resistance Plasmid Carrying a Novel Macrolide-Clindamycin Resistance Gene, erm(50), in Cutibacterium acnes. Antimicrob Agents Chemother. 2020, 64(3), e01810-19, 1-6.

Arazoe et al. Site-specific DNA double-strand break generated by I-SceI endonuclease enhances ectopic homologous recombination in Pyricularia oryzae. FEMS Microbiol Lett, 2014, 352, 221-229.

Armenteros, et al. SignalP 5.0 improves signal peptide predictions using deep neural networks. Nat Biotechnol, 2019, 37, 420-423.

(Continued)

*Primary Examiner* — Celine X Qian

(74) *Attorney, Agent, or Firm* — Arrigo, Lee, Guttman & Mouta-Bellum LLP

(57) ABSTRACT

The invention relates to *C. acnes* carrying DNA vectors with a *C. acnes* phage packaging signal and a gene of interest. The invention encompasses a *C. acnes* producer cell carrying DNA vectors, with a *C. acnes* phage packaging signal and a gene of interest, for the production of phage-derived particles that can robustly transduce *C. acnes* receiver cell allowing transgene expression. The invention encompasses *C. acnes* phage-derived particles carrying these vectors, *C. acnes* containing these vectors or modified by transduction of these phage-derived particles, and methods of using these phage-derived particles.

17 Claims, 12 Drawing Sheets

Specification includes a Sequence Listing.

(56) References Cited

OTHER PUBLICATIONS

Barnard E et al. Strains of the Propionibacterium acnes type III lineage are associated with the skin condition progressive macular hypomelanosis. Sci. Rep., 2016, 6, 31968, 1-9.
Barnard, E. et al. The balance of metagenomic elements shapes the skin microbiome in acne and health. Sci. Rep., 2016, 6, 39491, 1-12.
Bay L, et al. Universal dermal microbiome in human skin. mBio, 2020, 11, e02945-19, 1-13.
Brown et al. The Formulation of Bacteriophage in a Semi Solid Preparation for Control of Propionibacterium acnes Growth. PLoS ONE, 2016, 11(3), e0151184, 1-16.
Chen et al. Skin microbiota-host interactions. Nature. 2018, 553(7689), 427-436.
Chen et al. Decoding commensal-host communication through genetic engineering of *Staphylococcus* 5 epidermidis. bioRxiv, 2019, 664656, 1-40.
Chen et al. Precise and programmable C:G to G:C base editing in genomic DNA. bioRxiv, 2020, 213827, 1-19.
Davidsson, et al. Prevalence of Flp Pili-Encoding Plasmids in Cutibacterium acnes Isolates Obtained from Prostatic Tissue. Front. Microbiol., 2017, 8, 2241, 1-13.
Dreno, et al. Cutibacterium acnes (*Propionibacterium acnes*) and acne vulgaris: a brief look at the latest updates. J Eur Acad Dermatol Venereol, 2018, 32, 5-14.
Fitz-Gibbon et al. Propionibacterium acnes Strain Populations in the Human Skin Microbiome Associated with Acne. Journal of Investigative Dermatology, (2013, 133, 2152-2160.
Fonfara et al. Phylogeny of Cas9 determines functional exchangeability of dual-RNA and Cas9 among orthologous type II CRISPR-Cas systems .Nucleic Acids Research, 2014, 42, 4, 2577-2590.
Gaudelli et al. Programmable base editing of A•T to G•C in genomic DNA without DNA cleavage. Nature, 2017, 551 (7681), 464-471.
Di Girolamo, et al. Characterization of the housekeeping sortase from the human pathogen Propionibacterium acnes: first investigation of a class F sortase. Biochem J., 2019, 476 (4), 665-682.
Grunewald et al. A dual-deaminase CRISPR base editor enables concurrent adenine and cytosine editing. Nat Biotechnol. 2020, 38(7), 861-864.
Karberg, et al. Group II introns as controllable gene targeting vectors for genetic manipulation of bacteria. Nat Biotechnol, 2001, 19, 1162-1167.
Kasimatis et al. Analysis of Complete Genomes of Propionibacterium acnes Reveals a Novel Plasmid and Increased Pseudogenes in an Acne Associated Strain. Hindawi Publishing Corporation: BioMed Research International, 2013, 918320, 1-12.
Komor et al. Programmable editing of a target base in genomic DNA without double-stranded DNA cleavage. Nature, 2016, 533(7603), 420-424.
Koonin et al. Diversity, classification and evolution of CRISPR-Cas systems. Current Opinion in Microbiology. 2007, 37, 67-78.
Kurt et al. CRISPR C-to-G base editors for inducing targeted DNA transversions in human cells. Nat Biotechnol. 2021, 39(1), 41-46.
Li et al. Targeted, random mutagenesis of plant genes with dual cytosine and adenine base editors. Nature Biotechnology. 2020, 38, 875-882.
Liu et al. The diversity and host interactions of Propionibacterium acnes bacteriophages on human skin. The ISME Journal. 2015, 9, 2078-2093.
Lood et al. Characterization and genome sequencing of two Propionibacterium acnes phages displaying pseudolysogeny. BMC Genomics, 2011, 12, 198, 1-14.
McDowell, et al. Is Cutibacterium (previously Propionibacterium) acnes a potential pathogenic factor in the aetiology of the skin disease progressive macular hypomelanosis ?. J Eur Acad Dermatol Venereol, 2021, 35, 338-344.
McLaughlin et al. Propionibacterium acnes and Acne Vulgaris: New Insights from the Integration of Population Genetic, Multi-Omic, Biochemical and Host-Microbe Studies. Microorganisms, 2019, 7(5), 128, 1-29.
Nagao et al. Stress-induced production of chemokines by hair follicles regulates the trafficking of dendritic cells in skin. Nat Immunol., 2012, 13(8), 744-752.
Naik et al. Commensal-dendritic-cell interaction specifies a unique protective skin immune signature. Nature. 2015, 520(7545), 104-108.
Nakatsuji et al. The microbiome extends to subepidermal compartments of normal skin. Nat Commun. 2013, 4, 1431, 1-16.
Nazipi et al. The Skin Bacterium Propionibacterium acnes Employs Two Variants of Hyaluronate Lyase with Distinct Properties. Microorganisms, 2017, 5, 57, 1-16.
Oh et al. Biogeography and individuality shape function in the human skin metagenome. Nature. 2014, 514(7520), 59-64.
Pasparakis et al. Mechanisms regulating skin immunity and inflammation. Nature Reviews: Immunology. 2014, 14. 289-301.
Paus et al. The Hair Follicle and Immune Privilege. JID Symposium Proceedings. 2003, 1087-0024.
Petersen et al. Propionibacterium Acnes Phylogenetic Type III is Associated with Progressive Macular Hypomelanosis. Eur J Microbiol Immunol (Bp). 2017, 7(1), 37-45.
Rouet et al. Expression of a site-specific endonuclease stimulates homologous recombination in mammalian cells. Proc. Nati. Acad. Sci. USA, 1994, 91, 6064-6068.
Scharschmidt et al. A Wave of Regulatory T Cells into Neonatal Skin Mediates Tolerance to Commensal Microbes. Immunity, 2015, 43(5), 1011-1021.
Scholz et al. The natural history of cutaneous propionibacteria, and reclassification of selected species within the genus *Propionibacterium* to the proposed novel genera *Acidipropionibacterium* gen. nov., *Cutibacterium* gen. nov. and *Pseudopropionibacterium* gen. nov. International Journal of Systematic and Evolutionary Microbiology, 2016, 66, 4422-4432.
Sharon et al. Functional genetic variants revealed by massively parallel precise genome editing. Cell. 2018, 175(2), 544-557.e16.
Sievers et al. Fast, scalable generation of high-quality protein multiple sequence alignments using Clustal Omega. Molecular Systems Biology, 2011, 7(539), 1-6.
Sorenson et al. Mutagenesis of Propionibacterium acnes and analysis of two CAMP factor knock-out mutants. Journal of Microbiological Methods, 2010, 83, 211-216.
Wannier et al. Improved bacterial recombineering by parallelized protein discovery. PNAS, 2020, 117(24), 13689-13698.
Yu. Different Propionibacterium acnes Phylotypes Induce Distinct Immune Responses and Express Unique Surface and Secreted Proteomes. Society for Investigative Dermatology, 2016, 2221-2228.
Zhao et al. New base editors change C to A in bacteria and C to G in mammalian cells. Nature Biotechnology, 2020, 39, 35-40.
Simon et al. Survey and Summary. Retrons and their applications in genome engineering. Nucleic Acids Research, 2019, 47(21), 11007-11019.
Brede et al. Heterologous production of antimicrobial peptides in Propionibaterium freudenreichii. Applied and Environmental Microbiology, 2005, 71(12), 8077-8024.

| | | *C. acnes bacteriophage* | | | | | | | | | | | |
|---|---|---|---|---|---|---|---|---|---|---|---|---|---|
| | | 19 | 26 | 2 | 22 | 9 | 13 | 10 | 20 | 4 | 7 | ATCC29399 | 1 |
| C. acnes strains | Bacteriophage titer (PFU/μL) | ? | 4.00E+06 | 2.20E+07 | 2.00E+07 | 1.60E+07 | 4.00E+06 | 1.00E+07 | 4.00E+04 | 1.60E+07 | 4.00E+06 | 2.00E+06 | 8.00E+06 |
| | Ca0s2345-001 | 1 | 1 | 1 | 1 | 1 | 1 | 1 | 1 | 1 | 1 | 1 | 1 |
| | Ca0s2341-001 | 1 | 1 | 1 | 1 | 1 | 1 | 1 | 1 | 1 | 1 | 1 | 1 |
| | Ca0s2343-001 | 1 | 1 | 1 | 1 | 1 | 1 | 1 | 1 | 1 | 1 | 1 | 1 |
| | Ca0s2329-001 | 1 | 1 | 1 | 1 | 1 | 1 | 1 | 1 | 1 | 1 | 1 | 1 |
| | Ca0s2334-001 | 1 | 1 | 1 | 1 | 1 | 1 | 1 | 1 | 1 | 1 | 1 | 1 |
| | Ca0s2328-001 | 1 | 1 | 1 | 1 | 1 | 1 | 1 | 1 | 1 | 1 | 1 | 1 |
| | Ca0s2306-001 | 1 | 1 | 1 | 1 | 1 | 1 | 1 | 1 | 1 | 1 | 1 | 1 |
| | Ca0s2277-001 | 1 | 1 | 1 | 1 | 1 | 1 | 1 | 1 | 1 | 1 | 1 | 1 |
| | Ca0s2272-001 | 1 | 1 | 1 | 1 | 1 | 1 | 1 | 1 | 1 | 1 | 1 | 1 |
| | Ca0s2391-001 | 1 | 1 | 1 | 1 | 1 | 1 | 1 | 1 | 1 | 1 | 1 | 1 |
| | Ca0s2373-001 | 1 | 1 | 1 | 1 | 1 | 1 | 1 | 1 | 1 | 1 | 1 | 1 |
| | Ca0s2327-001 | 1 | 1 | 1 | 1 | 1 | 1 | 1 | 1 | 1 | 1 | 1 | 1 |
| | Ca0s2312-001 | 1 | 1 | 1 | 1 | 1 | 1 | 1 | 1 | 1 | 1 | 1 | 1 |
| | Ca0s2289-001 | 1 | 1 | 1 | 1 | 1 | 1 | 1 | 1 | 1 | 1 | 1 | 1 |
| | Ca0s2333-001 | 1 | 1 | 1 | 0.5 | 1 | 1 | 1 | 1 | 1 | 1 | 1 | 1 |
| | Ca0s2262-001 | 1 | 1 | 1 | 1 | 1 | 1 | 1 | 1 | 1 | 1 | 1 | 1 |
| | Ca0s2258-001 | 1 | 1 | 1 | 1 | 1 | 1 | 1 | 1 | 1 | 1 | 1 | 1 |
| | Ca0s2260-001 | 1 | 1 | 1 | 1 | 1 | 1 | 1 | 1 | 1 | 1 | 1 | 1 |
| | Ca0s2261-001 | 1 | 1 | 1 | 1 | 1 | 1 | 1 | 1 | 1 | 1 | 1 | 1 |
| | Ca0s2265-001 | 0.5 | 0.5 | 1 | 1 | 1 | 1 | 1 | 0.5 | 1 | 1 | 1 | 1 |
| | Ca0s2259-001 | 0.5 | 0.5 | 0.5 | 0.5 | 0.5 | 1 | 1 | 1 | 1 | 1 | 1 | 1 |
| | Ca0s2263-001 | 0.5 | 0.5 | 0.5 | 0.5 | 0.5 | 0.5 | 0.5 | 1 | 1 | 1 | 1 | 1 |
| | Ca0s2264-001 | 0.5 | 0.5 | 0.5 | 0.5 | 1 | 0.5 | 0.5 | 0.5 | 1 | 1 | 1 | 1 |
| | Ca0s2550-002 | 1 | 1 | 1 | 1 | 1 | 1 | 1 | 1 | 1 | 1 | 1 | 1 |
| | Ca0s2549-002 | 1 | 1 | 1 | 1 | 1 | 1 | 1 | 1 | 1 | 1 | 1 | 1 |
| | Ca0s2552-002 | 1 | 1 | 1 | 1 | 1 | 1 | 1 | 1 | 1 | 1 | 1 | 1 |
| | Ca0s2508-002 | 1 | 1 | 1 | 1 | 1 | 1 | 1 | 1 | 1 | 1 | 1 | 1 |
| | Ca0s2548-002 | 1 | 1 | 1 | 1 | 1 | 1 | 1 | 1 | 1 | 1 | 1 | 1 |
| | Ca0s2504-002 | 1 | 1 | 1 | 1 | 1 | 1 | 1 | 1 | 1 | 1 | 1 | 1 |
| | Ca0s2506-002 | 1 | 1 | 1 | 1 | 1 | 1 | 1 | 1 | 1 | 1 | 1 | 1 |
| | Ca0s2553-002 | 1 | 1 | 1 | 1 | 1 | 1 | 1 | 1 | 1 | 1 | 1 | 1 |
| | Ca0s2507-002 | 1 | 1 | 1 | 1 | 1 | 1 | 1 | 1 | 1 | 1 | 1 | 1 |
| | Ca0s2509-002 | 1 | 1 | 1 | 1 | 1 | 1 | 1 | 1 | 1 | 1 | 1 | 1 |

FIGURE 2A

| | | ***C. acnes bacteriophage*** | | | | | | | | | | | |
|---|---|---|---|---|---|---|---|---|---|---|---|---|---|
| | | 19 | 26 | 2 | 22 | 9 | 13 | 10 | 20 | 4 | 7 | ATCC29399 | 1 |
| C. acnes strains | Ca0s2247-002 | 1 | 1 | 1 | 1 | 1 | 1 | 1 | 1 | 1 | 1 | 1 | 1 |
| | Ca0s2243-002 | 1 | 1 | 1 | 1 | 1 | 1 | 1 | 1 | 1 | 1 | 1 | 1 |
| | Ca0s2228-002 | 1 | 1 | 1 | 1 | 1 | 1 | 1 | 1 | 1 | 1 | 1 | 1 |
| | Ca0s2225-002 | 1 | 1 | 1 | 1 | 1 | 1 | 1 | 1 | 1 | 1 | 1 | 1 |
| | Ca0s2220-002 | 1 | 1 | 1 | 1 | 1 | 1 | 1 | 1 | 1 | 1 | 1 | 1 |
| | Ca0s2218-002 | 1 | 1 | 1 | 1 | 1 | 1 | 1 | 1 | 1 | 1 | 1 | 1 |
| | Ca0s2255-002 | 1 | 1 | 1 | 1 | 1 | 1 | 1 | 1 | 1 | 1 | 1 | 1 |
| | Ca0s2227-002 | 1 | 1 | 1 | 1 | 1 | 1 | 1 | 1 | 1 | 1 | 1 | 1 |
| | Ca0s2211-002 | 1 | 1 | 1 | 1 | 1 | 1 | 1 | 1 | 1 | 1 | 1 | 1 |
| | Ca0s2219-002 | 1 | 1 | 1 | 1 | 1 | 1 | 1 | 1 | 1 | 1 | 1 | 1 |
| | Ca0s2209-002 | 1 | 1 | 1 | 1 | 1 | 1 | 1 | 1 | 1 | 1 | 1 | 1 |
| | Ca0s2208-002 | 1 | 1 | 1 | 1 | 1 | 1 | 1 | 1 | 1 | 1 | 1 | 1 |
| | Ca0s2233-002 | 1 | 1 | 1 | 1 | 1 | 1 | 1 | 1 | 1 | 1 | 1 | 1 |
| | Ca0s2232-002 | 1 | 1 | 1 | 1 | 1 | 1 | 1 | 1 | 1 | 1 | 1 | 1 |
| | Ca0s2239-002 | 1 | 1 | 1 | 1 | 1 | 1 | 1 | 1 | 1 | 1 | 1 | 1 |
| | Ca0s2235-002 | 1 | 1 | 1 | 1 | 1 | 1 | 1 | 1 | 1 | 1 | 1 | 1 |

FIGURE 2B

SEQUENCE LISTING

```
Sequence total quantity: 91
SEQ ID NO: 1            moltype = DNA  length = 38
FEATURE                 Location/Qualifiers
source                  1..38
                        mol_type = other DNA
                        note = oriT_pMRC01
                        organism = synthetic construct
SEQUENCE: 1
acaccaccca attttggagt ggtgtgtaag tgcgcatt                          38

SEQ ID NO: 2            moltype = DNA  length = 38
FEATURE                 Location/Qualifiers
source                  1..38
                        mol_type = other DNA
                        note = oriT_RSF1010
                        organism = synthetic construct
SEQUENCE: 2
ccagtttctc gaagagaaac cggtaagtgc gccctccc                          38

SEQ ID NO: 3            moltype = DNA  length = 40
FEATURE                 Location/Qualifiers
source                  1..40
                        mol_type = other DNA
```

```
                          note = oriT_pRS01
                          organism = synthetic construct
SEQUENCE: 3
tccgtaagat gctatcatct tactatgctt gcaaaaggtc                    40

SEQ ID NO: 4              moltype = DNA  length = 41
FEATURE                   Location/Qualifiers
source                    1..41
                          mol_type = other DNA
                          note = oriT_pMV158
                          organism = synthetic construct
SEQUENCE: 4
cactttatga atataaagta tagtgtgtta tactttacat g                  41

SEQ ID NO: 5              moltype = DNA  length = 42
FEATURE                   Location/Qualifiers
source                    1..42
                          mol_type = other DNA
                          note = oriT_pTF1
                          organism = synthetic construct
SEQUENCE: 5
gcacgggtaa tctcgaagag attactctaa gtgcgccctt gc                 42

SEQ ID NO: 6              moltype = DNA  length = 45
FEATURE                   Location/Qualifiers
source                    1..45
                          mol_type = other DNA
                          note = oriT_pSC101
                          organism = synthetic construct
SEQUENCE: 6
gggcgcacgt ttctgaacga agtgaagaaa gtctaagtgc gccct              45

SEQ ID NO: 7              moltype = DNA  length = 51
FEATURE                   Location/Qualifiers
source                    1..51
                          mol_type = other DNA
                          note = oriT_pBTK445
                          organism = synthetic construct
SEQUENCE: 7
agcctttaaa gcgaaaatag ggtactccat gctcgctata tcatcctgac a       51

SEQ ID NO: 8              moltype = DNA  length = 52
FEATURE                   Location/Qualifiers
source                    1..52
                          mol_type = other DNA
                          note = oriT_pBBR1
                          organism = synthetic construct
SEQUENCE: 8
ggtcacgact ttgcgaagca aagtctagtg agtatactca agcattgagt gg      52

SEQ ID NO: 9              moltype = DNA  length = 53
FEATURE                   Location/Qualifiers
source                    1..53
                          mol_type = other DNA
                          note = oriT_R721
                          organism = synthetic construct
SEQUENCE: 9
cacacgattg taacatgacc ggaacggtct tgtgtacaat cggtatcgtg cct     53

SEQ ID NO: 10             moltype = DNA  length = 59
FEATURE                   Location/Qualifiers
source                    1..59
                          mol_type = other DNA
                          note = oriT_pRmeGR4a
                          organism = synthetic construct
SEQUENCE: 10
gcaggaaaac ggcgtagcac atttttccgt atcctgcccc tccacattgt aaggggatt   59

SEQ ID NO: 11             moltype = DNA  length = 60
FEATURE                   Location/Qualifiers
source                    1..60
                          mol_type = other DNA
                          note = oriT_ColE1
                          organism = synthetic construct
SEQUENCE: 11
gggtgtcggg gcgcagccct gacccagtca cgtagcgata gcggagtgta tactggctta  60

SEQ ID NO: 12             moltype = DNA  length = 61
FEATURE                   Location/Qualifiers
```

```
source                  1..61
                        mol_type = other DNA
                        note = oriT_pTiC58
                        organism = synthetic construct
SEQUENCE: 12
ggatccaagg gcgcaattat acgtcgctga cgcgacgcct tgcgtagggg gccaaacagg  60
g                                                                  61

SEQ ID NO: 13           moltype = DNA  length = 64
FEATURE                 Location/Qualifiers
source                  1..64
                        mol_type = other DNA
                        note = oriT_pMdT1
                        organism = synthetic construct
SEQUENCE: 13
aggtttcggg gcgcagccct gaaccagtca cctagcgcta gcggagtgta tactggctta  60
gtat                                                               64

SEQ ID NO: 14           moltype = DNA  length = 71
FEATURE                 Location/Qualifiers
source                  1..71
                        mol_type = other DNA
                        note = oriT_R1
                        organism = synthetic construct
SEQUENCE: 14
agcaaatcag caaaaacttg tttttgcgtg gggtgtggtg cttttggtgg tgagaaccac  60
caacctgttg a                                                       71

SEQ ID NO: 15           moltype = DNA  length = 71
FEATURE                 Location/Qualifiers
source                  1..71
                        mol_type = other DNA
                        note = oriT_Tn5520
                        organism = synthetic construct
SEQUENCE: 15
cttattgggg aattttcagc gatacggagt attgcggctc ggaaaattcc ctaataagct  60
acggtatttt c                                                       71

SEQ ID NO: 16           moltype = DNA  length = 90
FEATURE                 Location/Qualifiers
source                  1..90
                        mol_type = other DNA
                        note = oriT_QKH54
                        organism = synthetic construct
SEQUENCE: 16
gtgaagatag ttaaccggct tgccggttag ctaacttcac ctatcttgcc cggctcttcg  60
agccgtttaa cgccaggtga gtatcgcata                                   90

SEQ ID NO: 17           moltype = DNA  length = 92
FEATURE                 Location/Qualifiers
source                  1..92
                        mol_type = other DNA
                        note = oriT_R64
                        organism = synthetic construct
SEQUENCE: 17
ggggtgtcgg ggcgaagccc tgaccagatg gcaattgtaa tagcgtcgcg tgtgacggta  60
ttacaattgc acatcctgtc ccgtttttcg gg                                92

SEQ ID NO: 18           moltype = DNA  length = 99
FEATURE                 Location/Qualifiers
source                  1..99
                        mol_type = other DNA
                        note = oriT_R751
                        organism = synthetic construct
SEQUENCE: 18
gaataaggga cagtgaagat agataaccgg ctcgccggtt agctaacttc acacatcctg  60
cccgccttac ggcgttaata acaccaagga aagtctaca                         99

SEQ ID NO: 19           moltype = DNA  length = 814
FEATURE                 Location/Qualifiers
source                  1..814
                        mol_type = other DNA
                        note = oriT_RP4
                        organism = synthetic construct
SEQUENCE: 19
cgacaggctc atgccggccg ccgccgcctt ttcctcaatc gctcttcgtt cgtctggaag  60
gcagtacacc ttgataggtg ggctgccctt cctggttggc ttggtttcat cagccatccg  120
cttgccctca tctgttacgc cggcggtagc cggccagcct cgcagagcag gattcccgtt  180
gagcaccgcc aggtgcgaat aagggacagt gaagaaggaa cacccgctcg cgggtgggcc  240
```

```
tacttcacct atcctgcccg gctgacgccg ttggatacac caaggaaagt ctacacgaac  300
cctttggcaa aatcctgtat atcgtgcgaa aaaggatgga tataccgaaa aaatcgctat  360
aatgaccccg aagcagggtt atgcagcgga aaagcgctgc ttccctgctg ttttgtggaa  420
tatctaccga ctggaaacag gcaaatgcag gaaattactg aactgagggg acaggcgaga  480
gacgatgcca aagagctaca ccgacgagct ggccgagtgg gttgaatccc gcgcggccaa  540
gaagcgccgg cgtgatgagg ctgcggttgc gttcctggcg gtgagggcgg atgtcgaggc  600
ggcgttagcg tccggctatg cgctcgtcac catttgggag cacatgcggg aaacggggaa  660
ggtcaagttc tcctacgaga cgttccgctc gcacgccagg cggcacatca aggccaagcc  720
cgccgatgtg cccgcaccgc aggccaaggc tgcggaaccc gcgccggcac ccaagacgcc  780
ggagccacgg cggccgaagc aggggggcaa ggct                               814

SEQ ID NO: 20          moltype = DNA  length = 100
FEATURE                Location/Qualifiers
source                 1..100
                       mol_type = other DNA
                       note = oriT_pKL1
                       organism = synthetic construct
SEQUENCE: 20
cggggtgtcg ggtgaagcc ctgaccaagt ggtaatcgta tcggcgtgca tgcgcggtta  60
tacgattaca catcctgtcc cgatttctga ggcgttttaa                        100

SEQ ID NO: 21          moltype = DNA  length = 112
FEATURE                Location/Qualifiers
source                 1..112
                       mol_type = other DNA
                       note = oriT_RK2
                       organism = synthetic construct
SEQUENCE: 21
ccggccagcc tcgcagagca ggattcccgt tgagcaccgc caggtgcgaa taagggacag  60
tgaagaagga acacccgctc gcgggtgggc ctacttcacc tatcctgccc gg          112

SEQ ID NO: 22          moltype = DNA  length = 160
FEATURE                Location/Qualifiers
source                 1..160
                       mol_type = other DNA
                       note = oriT_R1162
                       organism = synthetic construct
SEQUENCE: 22
ggccagtttc tcgaagagaa accggtaaat gcgccctccc ctacaaagta gggtcgggat  60
tgccgccgct gtgcctccat gatagcctac gagacagcac attaacaatg ggtgtcaag   120
atggttaagg ggagcaacaa ggcggcggat cggctggcca                        160

SEQ ID NO: 23          moltype = DNA  length = 174
FEATURE                Location/Qualifiers
source                 1..174
                       mol_type = other DNA
                       note = oriT_Tn4555
                       organism = synthetic construct
SEQUENCE: 23
ccctcgggag agcccacaac tacgtaagcg gagcgtgtag ttatagtggg ctatatcaat  60
ggcaagccat tgtctgcaaa ctccagccta cggcttccgc tctcctccgt cagggaggtt  120
tttcatcatc gttgccgatt ggagatgcac cgaccagcac aaggtctaaa tcgt        174

SEQ ID NO: 24          moltype = DNA  length = 192
FEATURE                Location/Qualifiers
source                 1..192
                       mol_type = other DNA
                       note = oriT_pHT
                       organism = synthetic construct
SEQUENCE: 24
ccaaagaatt aatgcaaaga gcataaggga aaactaatag caccttccta aaggaaggtg  60
gctaagttgg ctgtgccaac tggttttctt tcaaaatcac ttcatatttt ttgctatcac  120
aaaaaaatcc attttcgacc tattttcggt cataatatag tacctacttt tggtcatagt  180
ttcgtccgta gt                                                      192

SEQ ID NO: 25          moltype = DNA  length = 199
FEATURE                Location/Qualifiers
source                 1..199
                       mol_type = other DNA
                       note = oriT_Tn4399
                       organism = synthetic construct
SEQUENCE: 25
taaggtgatt atgttgtttt tcttcatctg ttctatctgt tttttagtga ataatccgat  60
tgatgtaatc tgaaaagtcc gtgaccatcg ggagccgttc ccctcatctt tttgaggggc  120
aagtggtcgg ggaatgtaat acgccgacat taacttgcta tcctaaaaaa gatgtgattt  180
acggcttaga tgccgaatc                                               199

SEQ ID NO: 26          moltype = DNA  length = 216
FEATURE                Location/Qualifiers
```

```
source                  1..216
                        mol_type = other DNA
                        note = oriT_Tn916
                        organism = synthetic construct
SEQUENCE: 26
aagcggaagt cgcaggtgtg gactgatctt gctggctggt gtggcaatag ccacgccagc  60
acttaacccc ccgtatctaa caggggggta caaatcgaca ggaaacagtc aaaaaaacat  120
tagaaaatcc tttggttaca agggatttac aaaatttcag cgtatgtcaa atgggcttta  180
aaagttgaca tacggccttt ttgattggag ggattt                            216

SEQ ID NO: 27           moltype = DNA  length = 242
FEATURE                 Location/Qualifiers
source                  1..242
                        mol_type = other DNA
                        note = oriT_pST12
                        organism = synthetic construct
SEQUENCE: 27
ttgtgtgatt atatcgcgta ccacttttcg actgttttac cgccggtatt ctgccgtctg  60
acgctttgac gggtatttct gcctgacaat actgtcactg ccaaaaaact gccgtgcctt  120
tgtcggtaat tcgagcttgc tgacaggaca ggatgtgcaa ttgttatacc gcgcatacat  180
gcacgctatt acaattaccc tggtcagggc ttcgccccga caccccatgt cagatacgga  240
gc                                                                 242

SEQ ID NO: 28           moltype = DNA  length = 268
FEATURE                 Location/Qualifiers
source                  1..268
                        mol_type = other DNA
                        note = oriT_pCU1
                        organism = synthetic construct
SEQUENCE: 28
gtattaccaa agtaataaag caaactcatt ataaaacaat gagttattag gtgtttttaa  60
tacctaatta ttaccgaata ttgacgctat ttattttttt atttttaaa tcagtgtgat   120
agcgtgattt atgccgctgc gttaggtgta tagcaggtta agggataaaa aatcatcttt  180
tttggtagga gcgatctacg taggttaagg actaactgac taaaaagcgt tcaatattcc  240
gtattcatgc ttgcatgaat accagtac                                     268

SEQ ID NO: 29           moltype = DNA  length = 279
FEATURE                 Location/Qualifiers
source                  1..279
                        mol_type = other DNA
                        note = oriT_pSU233
                        organism = synthetic construct
SEQUENCE: 29
cgctagcagc gcccctgacg gtatcctata aaaaaacaca ccgcgccgct agcagcaccc  60
ctaatataaa ataatgtttt ttataaaaat agtcagtacc acccctacaa agcggtgtcg  120
gcgcgttgct gtagctgcgt taacgacgct gctttaaata aatcagattt aaacaatata  180
aatccacaaa tacaactcna tgatattaaa gataaatcag caaaaacttg tttttgcgtg  240
gggtgtggtg cttttggtgg tgagaaccac caacctgtt                         279

SEQ ID NO: 30           moltype = DNA  length = 290
FEATURE                 Location/Qualifiers
source                  1..290
                        mol_type = other DNA
                        note = oriT_F
                        organism = synthetic construct
SEQUENCE: 30
cgcaccgcta gcagcgcccc tagcggtatc ctataaaaaa acacaccgcg ccgctagcag  60
cacccctaat ataaaataat gtttttttata aaaatagtca gtaccacccc tacaaaacgg  120
tgtcggcgcg ttgttgtagc cgcgccgaca ccgctttttt aaatatcata aagagagtaa  180
gagaaactaa tttttcataa cactctattt ataaagaaaa atcagcaaaa acttgttttt  240
gcgtggggtg tggtgctttt ggtggtgaga accaccaacc tgttgagcct             290

SEQ ID NO: 31           moltype = DNA  length = 304
FEATURE                 Location/Qualifiers
source                  1..304
                        mol_type = other DNA
                        note = oriT_pMAB01
                        organism = synthetic construct
SEQUENCE: 31
tgcctcgcag agcaggatga cccgttgagc gccccccggcg cgaataaggg acagtgaaga  60
tagataaccg gctcgccggt tagctaactt cacacatcct gcccgcctta cggcgttaat  120
aacaccaagg aaagtctaca ccagccatta cgatttatcc gcaactatcg cgctatcagg  180
ccgcaaaagc agcaacggat atagcgaaaa ccgccacaat ggcccataat gccgctatcg  240
aagcgtgcca atgcacgccg atagcggact ttttgcgttt ccgtagcgcc gcttagtagc  300
gtta                                                               304

SEQ ID NO: 32           moltype = DNA  length = 402
FEATURE                 Location/Qualifiers
source                  1..402
```

```
                       mol_type = other DNA
                       note = oriT_R388
                       organism = synthetic construct
SEQUENCE: 32
ccgcctcgtc ctccaaaagt gcctgctttt ccgggcttag ccgtacttgg atggggtcgc  60
ctagtgccat gtcctctccc gtagtgttac tgtagtggtt caatcctagc atttacaagg  120
ggttgcggca atattgtagt ggcataacac tacacaggtt ttcgtccttg gcgtggaagt  180
cattgtaaat caatgactta cgcgcaccga aaggtgcgta ttgtctatag cccagattta  240
aggataccaa cccggctttt aaggacggaa accatgcgat aacgccagcg tgaccctaaa  300
gagggtcaaa actgctccca atgcgctatg cgcattgggt tatcgtgcag caatgatgca  360
actataatgc tatgatggtg ctacaatgat gcagaaaatg ag                     402

SEQ ID NO: 33          moltype = DNA  length = 456
FEATURE                Location/Qualifiers
source                 1..456
                       mol_type = other DNA
                       note = oriT_pS7a
                       organism = synthetic construct
SEQUENCE: 33
ggatgatcaa acaaaatacg agagattttt tgttcgttca tccatggttt tagaaaaaag  60
agggacgatt tcggaagaag aaaatcgtct cttttttttc ttctttttgt atgacaaaaa  120
gaaagatctt ttgcccattt ttattttta taaaatgggc aggtggcgtt tgcgtaaagc  180
aaatcgacac aatccaaagg ggataaaagg ggaaagtgaa acttcccct tttcaagcca  240
cattgtaata caagaacgaa gtgctttgta ttacaatgtg atagcttgca gtatttatgg  300
ttttatatgg tctattttgt tgtgaggatt gtaaccgaat agggcgcaat acttattaca  360
aaatcaatga caaagggcga ttgagaaatg agcgctgggg cattttatct ttgaggaagt  420
tcttgatgga tcagaaaaat gtatcacaaa tttaaa                            456

SEQ ID NO: 34          moltype = DNA  length = 456
FEATURE                Location/Qualifiers
source                 1..456
                       mol_type = other DNA
                       note = oriT_pS7b
                       organism = synthetic construct
SEQUENCE: 34
tggatgatca aacaaaatac gagagatttt ttgttcgttc atccatggtt ttagaaaaaa  60
gagggacgat ttcggaagaa gaaaatcgtc tctttttttt cttctttttg tatgacaaaa  120
agaaagatct tttgcccatt tttattttt ataaaatggg caggtggcgt ttgcgtaaag  180
caaatcgaca caatccaaag gggataaaag gggaaagtga aacttccccc ttttcaagcc  240
acattgtaat acaagaacga agtgctttgt attacaatgt gatagcttgc agtatttatg  300
gttttatatt tcctattttg ttgtgaggat tgtaaccgaa tagggcgcaa tgcttattac  360
aaaatcaatg acaaagggcg agtgaggaat gagcgctgag gcattttatc tttgaggaag  420
ttcttgatgg atcagaaaaa tgtatcacaa atttaa                            456

SEQ ID NO: 35          moltype = DNA  length = 697
FEATURE                Location/Qualifiers
source                 1..697
                       mol_type = other DNA
                       note = oriT_R702
                       organism = synthetic construct
SEQUENCE: 35
ccctgcttcg gggtcattat agcgattttt tcggtatatc catccttttt cgcacgatat  60
acaggatttt gccaaagggt tcgtgtagac tttccttggt gtatccaacg gcgtcagccg  120
ggcaggatag gtgaagtagg cccacccgcg agcgggtgtt ccttcttcac tgtcccttat  180
tcgcacctgg cggtgctcaa cgggaatcct gctctgcgag gctggccggc taccgccggc  240
gtaacagatg agggcaagcg gatggctgat gaaaccaagc caaccaggaa gggcagccca  300
cctatcaagg tgtactgcct tccagacgaa cgacgagcga ttgaggaaaa ggcggcggcg  360
gccggcatga gcctgtcggc ctacctgctg gccgtcggcc agggctacaa aatcacgggc  420
gtcgtggact atgagcacgt ccgcgagctg gcccgcatca atggcgacct gggccgcctg  480
ggcggcctgc tgaaactctg gctcaccgac gacccgcgca cggcgcggtt cggtgatgcc  540
acgatcctcg ccctgctggc gaagatcgaa gagaagcagg acgagcttgg caaggtcatg  600
atgggcgtgg tccgcccgag ggcagagcca tgactttttt agccgctaaa acggccgggg  660
ggtgcgcgtg attgccaagc acgtccccat gcgctcc                           697

SEQ ID NO: 36          moltype = DNA  length = 475
FEATURE                Location/Qualifiers
source                 1..475
                       mol_type = other DNA
                       note = oriT_pMUR274
                       organism = synthetic construct
SEQUENCE: 36
actccgatac gttgccctcc gaacggtatt caaggtcgat tttttgcgct tcggtcactc  60
ttaaactgat agatggcata ggtttccttt gtgtaatacc gatgtaatac atacaaatct  120
agcatagatg cggcttaatt ccacatatgt aatacgttgt gtattacata ttaaaacaca  180
aattagaata atttgttttg ttttcaagca tttacgatga aaatcgtaat tgcgtatggt  240
gtatagccgt taagggatac cataccacgc cttttttaag ggagaaaccg gtgttacgtg  300
caagtgaatc gctcaaaaag cgttcacatt cacacctttc atgcttgcat gaaaggaaac  360
ggacgggaat tagacaaaaa taagacacga tgagtaagtt attgagacaa gaaaaggaca  420
caaataagac attttttaga aaaaaacatt gacttgagac tagaaatgga caata       475
```

```
SEQ ID NO: 37          moltype = DNA  length = 550
FEATURE                Location/Qualifiers
source                 1..550
                       mol_type = other DNA
                       note = oriT_R100
                       organism = synthetic construct
SEQUENCE: 37
ttactctggc cataagataa aacctttcat tattaagcaa cgaacttttc actataaata  60
tgcatatagt gtttacaagt aagaaagaca ctcctagcag cgcctctagg atcatcctat  120
aaaaaaatgc gatccggcgc taggggcgtc cctaatatat atcaatgttt ttcgtgaaaa  180
ttgtcagtac tgatcctaat aagagtcgct atagggtcgt aacaggatcg ccaacgactc  240
tctatttaat aattcagaat tattaaatat aaatagcgtt tgttaattac atgatttaaa  300
acgtaaatca gcaaaaactt gtttttgcgt agtgtgtggt gcttttggtg gtgagaacca  360
ccaacctgtt gagccttttt gtggagtggg ttaaattatt tacggataaa gtcaccagag  420
gtggaaaaat gaaaaaatgg atgttagcaa tctgcctgat gtttataaat gggatctgcg  480
aagccgccga ttgctttgat cttgcaggtc gggattacaa aatagacccg gatttactaa  540
gaatgatatc                                                         550

SEQ ID NO: 38          moltype = DNA  length = 551
FEATURE                Location/Qualifiers
source                 1..551
                       mol_type = other DNA
                       note = oriT_pVCR94deltaX
                       organism = synthetic construct
SEQUENCE: 38
gagcagagct atgtgtgaca agaagtatag agattacgag gtagccatca tggtcgatgt  60
gaaccctttc gacagggtta tgaatgaatt gaaaagtcgt ggccgcaaga acgctcacat  120
cctgagcatc ctccaattcg actggcctgc atcggaggcc atcatcgaga agctgagctg  180
ctacatcaca gacgggatta aggctaatca ggagcctgtg atttacccga tcattgaaga  240
agctctgcat cgctacagcc agctcgtgtt tcatgagcag agagagaaat atgaagaccc  300
ggccagaatt ggggcatttc tggaaaccct gatcaccgaa acctgccggg cgttggaagt  360
gcaaattgtc gatagtggcg gtgattcatg gtctgtcgat tcaggagagt cgttctcact  420
gtggctttct tcccatccag gagaactatc cattaacccg cagccccatg aggatgagac  480
ctctttgcgt ggcttgctgt atgagctcat cacctgtgag agcgtgaaaa ctgttttaag  540
gagaaccgac t                                                       551

SEQ ID NO: 39          moltype = DNA  length = 650
FEATURE                Location/Qualifiers
source                 1..650
                       mol_type = other DNA
                       note = oriT_R46
                       organism = synthetic construct
SEQUENCE: 39
agcgccgcag ataatctgac cgattacctc ctgaaaccag gtctatatag gccaaaaagt  60
tcatctgata cttttgcggt tattattggc attcagtcct cacattgtgc atttcttaaa  120
caaaagattg ggatctaaca agctgaaatc ttagtattac caaagtaata aagcaaactc  180
attataaaac aatgagttat taggtgtttt taatacctaa ttattaccga atattgacgc  240
tatttatttt tttatttttt aaatcagtgt gatagcgtga tttatgccgc tgcgttaggt  300
gtatagcagg ttaagggata aaaaatcatc ttttttggta ggagcgatct acgtaggtta  360
aggactaact gactaaaaag cgttcaatat tccgtattca tgcttgcatg aataccagta  420
caacactatt acaacaaaag tacatcaaaa ttacatcaaa agtacatcac ttgaaggttg  480
acagtacaac agaattacat cattatctgg tactgaggta gccagtacaa caaaagtaca  540
tcaaaaatac atcataaata catcagaaat acatcaaaat tacatcattc taaatgaggg  600
tactatgaag cccaaaagta tcagggcggc acttcagttg atgttgccgg             650

SEQ ID NO: 40          moltype = DNA  length = 36
FEATURE                Location/Qualifiers
source                 1..36
                       mol_type = other DNA
                       note = oriT_pGO1
                       organism = synthetic construct
SEQUENCE: 40
cacgcgaacg gaacgttcgc ataagtgcgc ccttac                           36

SEQ ID NO: 41          moltype = DNA  length = 38
FEATURE                Location/Qualifiers
source                 1..38
                       mol_type = other DNA
                       note = oriT_pIP501
                       organism = synthetic construct
SEQUENCE: 41
atacgaagta acgaagttac tgcgtataag tgcgccct                         38

SEQ ID NO: 42          moltype = DNA  length = 392
FEATURE                Location/Qualifiers
source                 1..392
                       mol_type = other DNA
                       note = R6K
```

```
                       organism = synthetic construct
SEQUENCE: 42
gatctgaaga tcagcagttc aacctgttga tagtacgtac taagctctca tgtttcacgt  60
actaagctct catgtttaac gtactaagct ctcatgttta acgaactaaa ccctcatggc  120
taacgtacta agctctcatg gctaacgtac taagctctca tgtttcacgt actaagctct  180
catgtttgaa caataaaatt aatataaatc agcaacttaa atagcctcta aggttttaag  240
ttttataaga aaaaaaagaa tatataaggc ttttaaagcc tttaaggttt aacggttgtg  300
gacaacaagc cagggatgta acgcactgag aagcccttag agcctctcaa agcaattttg  360
agtgacacag gaacacttaa cggctgacat gg                                392

SEQ ID NO: 43          moltype = DNA  length = 2222
FEATURE                Location/Qualifiers
source                 1..2222
                       mol_type = other DNA
                       note = RK2
                       organism = synthetic construct
SEQUENCE: 43
gcgatgcagg tggctgctga acccccagcc ggaactgacc ccacaaggcc ctagcgtttg  60
caatgcacca ggtcatcatt gacccaggcg tgttccacca ggccgctgcc tcgcaactct  120
tcgcaggctt cgccgacctg ctcgcgccac ttcttcacgc gggtggaatc cgatccgcac  180
atgaggcgga aggtttccag cttgagcggg tacggctccc ggtgcgagct gaaatagtcg  240
aacatccgtc gggccgtcgg cgacagcttg cggtacttct cccatatgaa tttcgtgtag  300
tggtcgccag caaacagcac gacgatttcc tcgtcgatca ggacctggca acgggacgtt  360
ttcttgccac ggtccaggac gcggaagcgg tgcagcagcg acaccgattc caggtgccca  420
acgcggtcgg acgtgaagcc catcgccgtc gcctgtaggc gcgacaggca ttcctcggcc  480
ttcgtgtaat accggccatt gatcgaccag cccaggtcct ggcaaagctc gtagaacgtg  540
aaggtgatcg gctcgccgat aggggtgcgc ttcgcgtact ccaacacctg ctgccacacc  600
agttcgtcat cgtcggcccg cagctcgacg ccggtgtagg tgatcttcac gtccttgttg  660
acgtggaaaa tgaccttgtt ttgcagcgcc tcgcgcggga ttttcttgtt gcgcgtggtg  720
aacagggcag agcgggccgt gtcgtttggc atcgctcgca tcgtgtccgg ccacggcgca  780
atatcgaaca aggaaagctg catttccttg atctgctgct tcgtgtgttt cagcaacgcg  840
gcctgcttgg cttcgctgac ctgttttgcc aggtcctcgc cggcggtttt tcgcttcttg  900
gtcgtcatag ttcctcgcgt gtcgatggtc atcgacttcg ccaaacctgc cgcctcctgt  960
tcgagacgac gcgaacgctc cacggcggcc gatggcgcgg gcagggcagg gggagccagt  1020
tgcacgctgt cgcgctcgat cttggccgta gcttgctgga ctatcgagcc gacggactgg  1080
aaggtttcgc ggggcgcacg catgacggtg cggcttgcga tggtttcggc atcctcggcg  1140
gaaaaccccg cgtcgatcag ttcttgcctg tatgccttcc ggtcaaacgt ccgattcatt  1200
caccctcctt gcgggattgc cccggaatta attccccgga tcgatccgtc gatcttgatc  1260
ccctgcgcca tcagatcctt ggcggcaaga aagccatcca gtttactttg cagggcttcc  1320
caaccttacc agagggcgcc ccagctggca attccggttc gcttgctgtc cataaaaccg  1380
cccagtctag ctatcgccat gtaagcccac tgcaagctac ctgctttctc tttgcgcttg  1440
cgttttccct tgtccagata gcccagtagc tgacattcat ccggggtcag caccgtttct  1500
gcggactggc tttctacgtg gctgccattt ttggggtgag gccgttcgcg gccgaggggc  1560
gcagcccctg gggggatggg aggcccgcgt tagcgggccg ggagggttcg agaagggggg  1620
gcaccccccct tcggcgtgcg cggtcacgcg cacagggcgc agccctggtt aaaaacaagg  1680
tttataaata ttggtttaaa agcaggttaa aagacaggtt agcggtggcc gaaaaacggg  1740
cggaaaccct tgcaaatgct ggattttctg cctgtggaca gcccctcaaa tgtcaatagg  1800
tgcgcccctc atctgtcagc actctgcccc tcaagtgtca aggatcgcgc ccctcatctg  1860
tcagtagtcg cgcccctcaa gtgtcaatac cgcagggcac ttatccccag gcttgtccac  1920
atcatctgtg ggaaactcgc gtaaaatcag gcgttttcgc cgatttgcga ggctggccag  1980
ctccacgtcg ccggccgaaa tcgagcctgc ccctcatctg tcaacgccgc gccgggtgag  2040
tcggcccctc aagtgtcaac gtccgcccct catctgtcag tgagggccaa gttttccgcg  2100
aggtatccac aacgccggcg gccctacatg gctctgctgt agtgagtggg ttgcgctccg  2160
gcagcggtcc tgatcccccg cagaaaaaaa ggatctcaag aagatccttt gatcttttct  2220
ac                                                                 2222

SEQ ID NO: 44          moltype = DNA  length = 1522
FEATURE                Location/Qualifiers
source                 1..1522
                       mol_type = other DNA
                       note = pBBR1
                       organism = synthetic construct
SEQUENCE: 44
ctaccggcgc ggcagcgtta cccgtgtcgg cggctccaac ggctcgccat cgtccagaaa  60
acacggctca tcgggcatcg gcaggcgctg ctgcccgcgc cgttcccatt cctccgtttc  120
ggtcaaggct ggcaggtctg gttccatgcc cggaatgccg ggctggctgg gcggctcctc  180
gccggggccg gtcggtagtt gctgctcgcc cggatacagg gtcgggatgc ggcgcaggtc  240
gccatgcccc aacagcgatt cgtcctggtc gtcgtgatca accaccacgg cggcactgaa  300
caccgacagg cgcaactggt cgcggggctg gccccacgcc acgcggtcat tgaccacgta  360
ggccgacacg gtgccggggc cgttgagctt cacgacggag atccagcgct cggccaccaa  420
gtccttgact gcgtattgga ccgtccgcaa agaacgtccg atgagcttgg aaagtgtctt  480
ctggctgacc accacggcgt tctggtggcc catctgcgcc acgaggtgat gcagcagcat  540
tgccgccgtg ggtttcctcg caataagccc ggcccacgcc tcatgcgctt tgcgttccgt  600
ttgcacccag tgaccgggct tgttcttggc ttgaatgccg atttctctgg actgcgtggc  660
catgcttatc tccatgcggt aggggtgccg cacggttgcg gcaccatgcg caatcagctg  720
caacttttcg gcagcgcgac aacaattatg cgttgcgtaa aagtggcagt caattacaga  780
ttttctttaa cctacgcaat gagctattgc ggggggtgcc gcaatgagct gttgcgtacc  840
cccctttttt aagttgttga tttttaagtc tttcgcattt cgccctatat ctagttcttt  900
ggtgcccaaa gaagggcacc cctgcggggt tcccccacgc cttcggcgcg gctccccctc  960
```

```
cggcaaaaag tggcccctcc ggggcttgtt gatcgactgc gcggccttcg gccttgccca  1020
aggtggcgct gccccccttgg aacccccgca ctcgccgccg tgaggctcgg ggggcaggcg  1080
ggcgggcttc gcccttcgac tgcccccact cgcataggct tgggtcgttc caggcgcgtc  1140
aaggccaagc cgctgcgcgg tcgctgcgcg agccttgacc cgccttccac ttggtgtcca  1200
accggcaagc gaagcgcgca ggccgcaggc cggaggcttt tccccagaga aaattaaaaa  1260
aattgatggg gcaaggccgc aggccgcgca gttggagccg gtgggtatgt ggtcgaaggc  1320
tgggtagccg gtgggcaatc cctgtggtca agctcgtggg caggcgcagc ctgtccatca  1380
gcttgtccag cagggttgtc cacgggccga gcgaagcgag ccagccggtg gccgctcgcg  1440
gccatcgtcc acatatccac gggctggcaa gggagcgcag cgaccgcgca gggcgaagcc  1500
cggagagcaa gcccgtaggg gg                                        1522

SEQ ID NO: 45          moltype = DNA  length = 1969
FEATURE                Location/Qualifiers
source                 1..1969
                       mol_type = other DNA
                       note = pRO1600
                       organism = synthetic construct
SEQUENCE: 45
gataatctca tgaccaaaat cccttaacgt gagttttcgt tccactgagc gtcagacccc  60
gtagaaaaga tcaaaggatc ttcttgagat cctttttttc tgcgcgtaat ctgctgcttg  120
caaacaaaaa aaccaccgct accagcggtg gtttgtttgc cggatcaaga gctaccaact  180
ctttttccga aggtaactgg cttcagcaga gcgcagatac caaatactgt tcttctagtg  240
tagccgtagt taggccacca cttcaagaac tctgtagcac cgcctacata cctcgctctg  300
ctaatcctgt taccagtggc tgctgccagt ggcgataagt cgtgtcttac cgggttggac  360
tcaagacgat agttaccgga taaggcgcag cggtcgggct gaacgggggg ttcgtgcaca  420
cagcccagct tggagcgaac gacctacacc gaactgagat acctacagcg tgagctatga  480
gaaagcgcca cgcttcccga agggagaaag gcggacaggc atccggtaag cggcagggtc  540
ggaacaggag agcgcacgag ggagcttcca gggggaaacg cctggtatct ttatagtcct  600
gtcgggtttc gccacctctg acttgagcgt cgatttttgt gatgctcgtc aggggggcgg  660
agcctatgga aaaacgccag caacgcggcc gtgaaaggca ggccggtccg tggtggccac  720
ggcctctagg ccagatccag cggcatctgg gttagtcgag cgcgggccgc ttcccatgtc  780
tcaccagggc gagcctgttt cgcgatctca gcatctgaaa tcttcccggc cttgcgcttc  840
gctggggcct tacccaccgc cttggcgggc ttcttcggtc caaaactgaa caacagatgt  900
gtgaccttgc gcccggtctt tcgctgcgcc cactccacct gtagcgggct gtgctcgttg  960
atctgcgtca cggctggatc aagcactcgc aacttgaagt ccttgatcga gggataccgg  1020
ccttccagtt gaaaccactt tcgcagctgg tcaatttcta tttcgcgctg gccgatgctg  1080
tcccattgca tgagcagctc gtaaagcctg atcgcgtggg tgctgtccat cttggccacg  1140
tcagccaagg cgtatttggt gaactgtttg gtgagttccg tcaggtacgg cagcatgtct  1200
ttggtgaacc tgagttctac acggccctca ccctcccggt agatgattgt ttgcacccag  1260
ccggtaatca tcacactcgg tcttttcccc ttgccattgg gctcttgggt taaccggact  1320
tcccgccgtt tcaggcgcag ggccgcttct ttgagctggt tgtaggaaga ttcgataggg  1380
acacccgcca tcgtcgctat gtcctccgcc gtcactgaat acatcacttc atcggtgaca  1440
ggctcgctcc tcttcacctg gctaatacag gccagaacga tccgctgttc ctgaacactg  1500
aggcgatacg cggcctcgac cagggcattg cttttgtaaa ccattggggg tgaggccacg  1560
ttcgacattc cttgtgtata aggggacact gtatctgcgt cccacaatac aacaaatccg  1620
tccctttaca acaacaaatc cgtcccttct taacaacaaa tccgtccctt aatggcaaca  1680
aatccgtccc tttttaaact ctacaggcca cggattacgt ggcctgtaga cgtcctaaaa  1740
ggtttaaaag ggaaaaggaa gaaaagggtg gaaacgcaaa aaacgcacca ctacgtggcc  1800
ccgttggggc cgcatttgtg cccctgaagg ggcgggggag gcgtctgggc aatccccgtt  1860
ttaccagtcc cctatcgccg cctgagaggg cgcaggaagc gagtaatcag ggtatcgagg  1920
cggattcacc cttggcgtcc aaccagcggc accagcggcg cctgagagg           1969

SEQ ID NO: 46          moltype = DNA  length = 3674
FEATURE                Location/Qualifiers
source                 1..3674
                       mol_type = other DNA
                       note = RSF1010
                       organism = synthetic construct
SEQUENCE: 46
tcagcctgcc gccttgggcc gggtgatgtc gtacttgccc gccgcgaact cggttaccgt  60
ccagcccagc gcgaccagct ccggcaacgc ctcgcgcacc cgctggcggc gcttgcgcat  120
ggtcgaacca ctggcctctg acggccagac atagccgcac aaggtatcta tggaagcctt  180
gccggttttg ccggggtcga tccagccaca cagccgctgg tgcagcaggc gggcggtttc  240
gctgtccagc gcccgcacct cgtccatgct gatgcgcaca tgctggccgc cacccatgac  300
ggcctgcgcg atcaaggggt tcagggccac gtacaggcgc ccgtccgcct cgtcgctggc  360
gtactccgac agcagccgaa acccctgccg cttgcggcca ttctgggcga tgatggatac  420
cttccaaagg cgctcgatgc agtcctgtat gtgcttgagc gccccaccac tatcgacctc  480
tgccccgatt tcctttgcca gcgcccgata gctacctttg accacatggc attcagcggt  540
gacggcctcc cacttgggtt ccaggaacag ccggagctgc cgtccgcctt cggtcttggg  600
ttccgggcca agcactaggc cattaggccc agccatggcc accagccctt gcaggatgcg  660
cagatcatca gcgcccagcg gctccgggcc gctgaactcg atccgcttgc cgtcgccgta  720
gtcatacgtc acgtccagct tgctgcgctt gcgctcgccc cgcttgaggg cacggaacag  780
gccgggggcc agacagtgcg ccgggtcgtg ccggacgtgg ctgaggctgt gcttgttctt  840
aggcttcacc acggggcacc cccttgctct tgcgctgcct ctccagcacg gcgggcttga  900
gcaccccgcc gtcatgccgc ctgaaccacc gatcagcgaa cggtgcgcca tagttggcct  960
tgctcacacc gaagcggacg aagaaccggc gctggtcgtc gtccacaccc cattcctcgg  1020
cctcggcgct ggtcatgctc gacaggtagg actgccagcg gatgttatcg accagtaccg  1080
agctgccccg gctggcctgc tgctggtcgc ctgcgcccat catggccgcg cccttgctgg  1140
catggtgcag gaacacgata gagcacccgg tatcggcggc gatggcctcc atgcgaccga  1200
```

```
tgacctgggc catggggccg ctggcgtttt cttcctcgat gtggaaccgg cgcagcgtgt  1260
ccagcaccat caggcggcgg ccctcggcgg cgcgcttgag gccgtcgaac cactccgggg  1320
ccatgatgtt gggcaggctg ccgatcagcg gctggatcag caggccgtca gccacggctt  1380
gccgttcctc ggcgctgagg tgcgccccaa gggcgtgcag gcggtgatga atggcggtgg  1440
gcgggtcttc ggcgggcagg tagatcaccg ggccggtggg cagttcgccc acctccagca  1500
gatccggccc gcctgcaatc tgtgcggcca gttgcagggc cagcatggat ttaccggcac  1560
caccgggcga caccagcgcc ccgaccgtac cggccaccat gttgggcaaa acgtagtcca  1620
gcggtggcgg cgctgctgcg aacgcctcca gaatattgat aggcttatgg gtagccattg  1680
attgcctcct ttgcaggcag ttggtggtta ggcgctggcg gggtcactac ccccgccctg  1740
cgccgctctg agttcttcca ggcactcgcg cagcgcctcg tattcgtcgt cggtcagcca  1800
gaacttgcgc tgacgcatcc ctttggcctt catgcgctcg gcatatcgcg cttggcgtac  1860
agcgtcaggg ctggccagca ggtcgccggt ctgcttgtcc ttttggtctt tcatatcagt  1920
caccgagaaa cttgccgggg ccgaaaggct tgtcttcgcg gaacaaggac aaggtgcagc  1980
cgtcaaggtt aaggctggcc atatcagcga ctgaaaagcg gccagcctcg gccttgtttg  2040
acgtataacc aaagccaccg ggcaaccaat agcccttgtc acttttgatc aggtagaccg  2100
accctgaagc gcttttttcg tattccataa aaccccccttc tgtgcgtgag tactcatagt  2160
ataacaggcg tgagtaccaa cgcaagcact acatgctgaa atctggcccg cccctgtcca  2220
tgcctcgctg gcggggtgcc ggtgcccgtg ccagctcggc ccgcgcaagc tggacgctgg  2280
gcagacccat gaccttgctg acggtgcgct cgatgtaatc cgcttcgtgg ccgggcttgc  2340
gctctgccag cgctgggctg gcctcggcca tggccttgcc gatttcctcg gcactgcggc  2400
cccggctggc cagcttctgc gcggcgataa agtcgcactt gctgaggtca tcaccgaagc  2460
gcttgaccag cccggccatc tcgctgcggt actcgtccag cgccgtgcgc cggtggcggc  2520
taagctgccg ctcgggcagt tcgaggctgg ccagcctgcg ggccttctcc tgctgccgct  2580
gggcctgctc gatctgctgg ccagcctgct gcaccagcgc cgggccagcg gtggcggtct  2640
tgcccttgga ttcacgcagc agcacccacg gctgataacc ggcgcgggtg gtgtgcttgt  2700
ccttgcggtt ggtgaagccc gccaagcggc catagtggcg gctgtcggcg ctggccgggt  2760
cggcgtcgta ctcgctggcc agcgtccggg caatctgccc ccgaagttca ccgcctgcgg  2820
cgtcggccac cttgacccat gcctgatagt tcttcgggct ggtttccact accagggcag  2880
gctcccggcc ctcggctttc atgtcatcca ggtcaaactc gctgaggtcg tccaccagca  2940
ccagaccatg ccgctcctgc tcggcgggcc tgatatacac gtcattgccc tgggcattca  3000
tccgcttgag ccatggcgtg ttctggagca cttcggcggc tgaccattcc cggttcatca  3060
tctggccggt ggtggcgtcc ctgacgccga tatcgaagcg ctcacagccc atggccttga  3120
gctgtcggcc tatggcctgc aaagtcctgt cgttcttcat cgggccacca agcgattccc  3180
acacattata cgagccggaa gcataaagtg taaagcctag atccgaagga tgagccgggc  3240
tgaatgatcg accgagacag gccctgcggg gctgcacacg cgccccccacc cttcgggtag  3300
ggggaaaggc cgctaaagcg gctaaaagcg ctccagcgta tttctgcggg gtttggtgtg  3360
gggtttagcg ggctttgccc gcctttcccc ctgccgcgca gcggtggggc ggtgtgtagc  3420
ctagcgcagc gaatagacca gctatccggc ctctggccgg gcatattggg caagggcagc  3480
agcgccccac aagggcgctg ataaccgcgc ctagtggatt attcttagat aatcatggat  3540
ggatttttcc aacaccccgc cagcccccgc ccctgctggg tttgcaggtt tgggggcgtg  3600
acagttattg caggggttcg tgacagttat tgcagggggg cgtgacagtt attgcagggg  3660
ttcgtgacag ttag                                                      3674
```

```
SEQ ID NO: 47           moltype = DNA  length = 2982
FEATURE                 Location/Qualifiers
source                  1..2982
                        mol_type = other DNA
                        note = pAMbeta1
                        organism = synthetic construct
SEQUENCE: 47
attctcccaa gaattagaaa tgagtagatc aaattattca cgaatagaat caggaaaatc  60
agatccaacc ataaaaacac tagaacaaat tgcaaagtta actaactcaa cgctagtagt  120
ggattttaat cccaaatgag ccaacagaac cagagccaga aacagaatca gaacaagtaa  180
cattggattt agaaatggaa gaagaaaaaa gcaatgactt cgtgtgaata atgcacgaaa  240
tcgttgctta tttttttttaa aagcggtata ctagatataa cgaaacaacg aactgaatag  300
aaacgaaaaa agagccatga cacatttata aaatgtttga cgacatttta taaatgcata  360
gcccgataag attgccaaac caacgcttat cagttagtca gatgaactct tccctcgtaa  420
gaagttattt aattaacttt gtttgaagac ggtatataac cgtactatca ttatataggg  480
aaatcagaga gttttcaagt atctaagcta ctgaatttaa gaattgttaa gcaatcaatc  540
ggaaatcgtt tgattgcttt ttttgtattc atttatagaa ggtggagttt gtatgaatca  600
tgatgaatgt aaaacttata taaaaaatag tttattggag ataagaaaat tagcaaatat  660
ctatacacta gaaacgttta agaaagagtt agaaaagaga aatatctact tagaaacaaa  720
atcagataag tatttttctt cggaggggga agattatata tataagttaa tagaaaataa  780
caaaataatt tattcgatta gtggaaaaaa attgacttat aaaggaaaaa aatctttttc  840
aaaacatgca atattgaaac agttgaatga aaaagcaaac caagttaatt aaacaaccta  900
ttttatagga tttataggaa aggagaacag ctgaatgaat atccctttttg ttgtagaaac  960
tgtgcttcat gacggcttgt taaagtacaa atttaaaaat agtaaaattc gctcaatcac  1020
taccaagcca ggtaaaagca aaggggctat ttttgcgtat cgctcaaaat caagcatgat  1080
tggcggtcgt ggtgttgttc tgacttccga ggaagcgatt caagaaaatc aagatacatt  1140
tacacattgg acacccaacg tttatcgtta tggaacgtat gcagacgaaa accgttcata  1200
cacgaaagga cattctgaaa acaatttaag acaaatcaat accttcttta ttgattttga  1260
tattcacacg gcaaaagaaa ctatttcagc aagcgatatt ttaacaaccg ctattgattt  1320
aggttttatg cctactatga ttatcaaatc tgataaaggt tatcaagcat attttgtttt  1380
agaaacgcca gtctatgtga cttcaaaatc agaatttaaa tctgtcaaag cagccaaaat  1440
aatttcgcaa aatatccgag aatattttgg aaagtctttg ccagttgatc taacgtgtaa  1500
tcattttggt attgctcgca taccaagaac ggacaatgta gaattttttg atcctaatta  1560
ccgttattct ttcaaagaat ggcaagattg gtctttcaaa caaacagata ataagggctt  1620
tactcgttca agtctaacgg ttttaagcgg tacagaaggc aaaaaacaag tagatgaacc  1680
ctggtttaat ctcttattgc acgaaacgaa attttcagga gaaaagggtt taatagggcg  1740
```

```
taataacgtc atgtttaccc tctctttagc ctactttagt tcaggctatt caatcgaaac  1800
gtgcgaatat aatatgtttg agtttaataa tcgattagat caacccttag aagaaaaaga  1860
agtaatcaaa attgttagaa gtgcctattc agaaaactat caaggggcta atagggaata  1920
cattaccatt ctttgcaaag cttgggtatc aagtgattta accagtaaag atttatttgt  1980
ccgtcaaggg tggtttaaat tcaagaaaaa aagaagcgaa cgtcaacgtg ttcatttgtc  2040
agaatggaaa gaagatttaa tggcttatat tagcgaaaaa agcgatgtat acaagcctta  2100
tttagtgacg accaaaaaag agattagaga agtgctaggc attcctgaac ggacattaga  2160
taaattgctg aaggtactga aggcgaatca ggaaattttc tttaagatta aaccaggaag  2220
aaatggtggc attcaacttg ctagtgttaa atcattgttg ctatcgatca ttaaagtaaa  2280
aaaagaagaa aaagaaagct atataaaggc gctgacaaat tcttttgact tagagcatac  2340
attcattcaa gagactttaa acaagctagc agaacgccct aaaacggaca cacaactcga  2400
tttgtttagc tatgatacag gctgaaaata aaacccgcac tatgccatta catttatatc  2460
tatgatacgt gtttgttttt tctttgctgt ttagcgaatg attagcagaa atatacagag  2520
taagatttta attaattatt aggggggagaa ggagagagta gcccgaaaac ttttagttgg  2580
cttggactga acgaagtgag ggaaaggcta ctaaaacgtc gaggggcagt gagagcgaag  2640
cgaacacttg atttttttaat tttctatctt ttataggtca ttagagtata cttatttgtc  2700
ctataaacta tttagcagca taatagattt attgaatagg tcatttaagt tgagcatatt  2760
agaggaggaa aatcttggag aaatatttga agaacccgat tacatggatt ggattagttc  2820
ttgtggttac gtggttttta actaaaagta gtgaattttt gatttttggt gtgtgtgtct  2880
tgttgttagt atttgctagt caaagtgatt aaatagaatt ctcatgtttg acagcttatc  2940
atcggagctc cgatgataag ctgtcaaaca tgagaattcc cg                    2982
```

```
SEQ ID NO: 48          moltype = DNA  length = 4154
FEATURE                Location/Qualifiers
source                 1..4154
                       mol_type = other DNA
                       note = pLME106
                       organism = synthetic construct
SEQUENCE: 48
gatccggcgg aacttcacgt cctggcggtg gagttggcgg gcgcgttcca gccgttcctc  60
cagcacggtg atccgggcct ccagacgctc acgctcaccc tgctccaggt gccgggtcac  120
cgtcaccgtc cgcaccggcc gggcctcggc ctgggcggcc cggcgttcct cactggcccg  180
cttccggcaa tcgtcggaac accacacccg gggccgaccc cgcccaccgt gggcctccac  240
cggcgccccg cagtggggac acgcccgcag cgccgacgca tcctcatcca aggccatcac  300
cgggtcggaa tccatacccg aaaccatatc gtccggacga tgaactgcgc cagacagcta  360
agaatgcacg aggtgtgtct ccgattctca ggaaacgctc agcattttcc gagacgttcg  420
gcgcacgcac acaccccccac aagaaccgac ccgcccagca tccgccgaca cgtcgatccg  480
cacccgcgat gggctggccg aggccgacta cgaccgctag tcagcacctg cgctgatcta  540
ccgtcgccct gaccgactct cccgtcggga ttgtcgccgg ccgctgccag catggacctg  600
cggccccgcc ccctcgccct gcaactcgag ggaggcgggg ccgtccaccc cccacaccac  660
cccgacaccg tgatgcgccc atgtcgccta acgggttgcc cgacctcccc gacatcaaga  720
aaacctgaca ccgtcgccgc aagcgctaca ctgactacta gtagtcagga ggtgcgtgat  780
gaccatcgcc acatcggtga aactctccga agagaccggc cgcaaactcg atgaactagc  840
ccgggccacc gggcgatcca agtcctacta cctgcgcgag gccatcgagg accacatcga  900
ccagatggtc cacgactacg ccatcgcccg actcgccgac gacgtgcgag ccggccgggc  960
cgccacctac agcgccgacg aagtggacca gatccttggc ctggacgatt gagtacaccg  1020
accccgccgt caaagcactg cgcaaactcg accgagccca ggcccgccgc atcaccgcct  1080
acatacgtga gctcaccggc ctggacgatc cccaccaacg cgggaaaggc ctcaccgggc  1140
ccctggccgg actctggcgc taccgcgtcg gggactaccg gatcatctgc gacctgaacg  1200
ccgaccgcct ggccatcatc gccctgacca tcgagcaccg atcccaggcc taccgctgac  1260
acgcaacccc gcaccctcgg ccaagacgtc acacaccacc cgccccaccg agcactgagg  1320
atgtcaactc gcccgagccg gcctgccggc cgtcttacgg gttgtcttgg cgggcggggt  1380
gtctttgccc tggcccagca gccccacgat ctcccgcagc gtgtcggcgg tggcggcgtc  1440
ccgggccgcc tgacgctccg cctccgccct ggcctgctcg gctgcctgcg cccgatcctc  1500
cgcggcggcg gcctgctccc tcgcctcggc cagctcgccg gtcagggcct cgacccgggc  1560
ctgcacctgc cccaggcgcg cctccgcctc ctgctgcacc tgctcggccc gggcctccgc  1620
ctggtcccgg gccgcctcgg cctcggcccg gtgctgatcc gccagggccg cctcggccac  1680
cgcttcggcc tgcccatcca ccgcctgctc ggcccgagcc ccgaactcct cgcgggccgc  1740
atcactcgcc tgacgccacg ccgccgccca caccagaccc aacggctccg acagatccgg  1800
cggggccggc gtctggaccg acgccgagac gtcgcgcagg aaccccgccg cagcgtcggt  1860
ggagcacccc gcctccgcct tcaacgaccg caccgtcacc cgccgacccg caccgctcaa  1920
ccgcgcatag gccgccgcca accttgaccc attcgactcc atgacccacc ctcccattct  1980
gtaccctgta cctgttccta ggtacgttcc taatgtacct caccggatgc agaacccgca  2040
acccccctca cactccccct gcacggggcc cgccccctgc acccccgctg ccgcgcccgc  2100
tcctgcgtcg cggccttgcc cctgcccaac gccgggccgg cgggcagccc accagaggct  2160
ctgtgagacg tcggcgcccc cgtccaccta ccctaaagac caaccggccg tggaaacgtc  2220
tgtgaggagc cttgtaggag ttcccaggac aagccagcaa ggccgggcct gacggcccgg  2280
aaaggaagtc gctgcgctcc tacgaagaag cccctctggg gacccccaga ccccggaact  2340
atctgatttg gtttagcggc gtacttccgt cataccggaa tttatggcat gctgtggtca  2400
tggcgacgac gacggtcgat gagcagtggg agcaggtgtg gctgccccgc tggcccctgg  2460
cctccgacga cctggcagcg ggcatctacc ggatggcccg cccctcggcg ctgggggtcc  2520
gatacatcga ggtcaacccc caagccatca gcaacctcct cgtggtcgac tgcgaccacc  2580
ccgacgctgc catgcgcgcc gtctgggacc gccacgactg gctgcccaac gccatcgtcg  2640
agaaccccga caacggccac gcccacgccg tgtgggccct ggaagcagcc atcccgcgca  2700
ccgagtacgc ccaccgcaag cccatcgcct acgccgccgc cgtcaccgag ggcctgcgcc  2760
gatccgtcga cggagacgcc tcctacgccg gcctgatcac caagaacccc gaacaccccg  2820
cctggaacac cacctggtgc accgaccacc tctaccggct ggccgagctc gacacccacc  2880
tggatgccgc cggcctcatg cccgcccccct cctggcgacg cacccgccgg cgcaaccccg  2940
tcggcctggg ccgcaactgc gccatcttcg agaccgcccg cacctgggcc taccgcgacg  3000
```

```
cccgccgcat ccgacaacgc cacgaatacc cgaccgccga ggactcggcc gacctgcacg  3060
ccgtcatcgc ctccaccgtc gaggcgctca acgccggcta cagcgaaccc ctgccggccc  3120
gcgaggccgc cggcatcgcc gccagcatcc accgatggat cacccaccgt ttctacggct  3180
ggatcgactc ccacaccgtc aacgaggcca ctttctccac catccagagc tacagaggac  3240
acaagggagc cggcaaggct cgtcctcgtg cccgccgtgc tgcttctatc accgattggg  3300
aggcatgatg gctgacgtcc agcaccgcgt gaagcgtcgg ggcacggccc gcgaggccgc  3360
agaacgtgta ggggcctcca tccgaaccgc ccagcggtgg acctccatcc cccgtgagga  3420
atggatcact cagaaggccg tcgagcgtga ggagatccgg gcctacaagt acgacgaggg  3480
gcacacgtgg ggcgagacct cgcgccactt cgggatcgcg aagaccaccg cccaggagcg  3540
ggcccggcgg gctcgaaggg agcgggcggc cgaagcggag aaggctgccg aggaggccga  3600
ggccgcgctg cgtccgacac tcttcgaggg ccaggagcaa ggttctgcat gagcaacccc  3660
gagtcctcgg gtagaccgtc tggcccgacg ttaagcatgg ctgaagcggc ccgtgcctgt  3720
ggggtttcag tgtccacggt gaggcgtcac cgtgatgccc tggtggccca cggtgctacc  3780
cgtcatgacg cgtcatgggt gataccccta tcagcgttga tttcatgcgg tttgatgccc  3840
cgggtgacac cccctgatgc cccgtcaccc aataacgtgg cgcctgccat gacgtcccac  3900
ggtgacgccc ccctgacggg ggaagtccaa gagctgcgcg agcgactggc caacgctgag  3960
catcgagccg agctagcagt agaggttggg gacgacgtct cggcgactcc ggagaacacc  4020
aagtcagggt ctcatgagtg tgcgatagct tgagctgtct accaatctgg atatagctat  4080
atcggtcgtt tgtgtctgat tcgccagtga gccaacggcg gggcgacac gcggtggcga  4140
aaccccctgg caga                                                   4154

SEQ ID NO: 49          moltype = DNA  length = 22046
FEATURE                Location/Qualifiers
source                 1..22046
                       mol_type = other DNA
                       note = pTZC1
                       organism = synthetic construct
SEQUENCE: 49
gcgagcacac ttccctcacg ctgactcgtc actccgacac gctcgctcgt gtccgtgaac  60
tggcgggcga cggcccgcca gtcacccgga tcgatgaccg ccgcattagt cgaaacccac  120
acgccatcct gggtcgcatc gggccgcgtg atgtacgcca gcgccttcgc cggcgtcgtc  180
ttgatctgcc ccatcttcac aacagccatc actccgcccc cgcttccgtt gcggcgtcga  240
tggcccgttg gacttgtccc agcagctccc gcgtggcacg catctgctca accgtcacca  300
catcatcagt gttcacctgc cgagcgatct ggttgatgtt gttcccgatc ctcgacaact  360
cggcgcgcag cggagccgga tcgaacgcca cgcgacgcac gacgatcttc ccctcagtga  420
gagcgcgccg cgcatagtcg gcgaacgtcc tcgcctccgc aagttccata cgccgttcca  480
cccgcttcca ttcagcatca ctgagccaca agcccttgaa gacccctcgc gaccgcttcg  540
cgccctgctc agccatgcat ccactcctac cgggtttggg cagagcccat agtgcccagg  600
gggccacgca actgtgtaac agttgctatg cttgctaccc cgtcagggtc agtctacaac  660
ctacggtcta catggcgcta gaatgagaaa cggatcgtcc ggctaaccgg acgatccgag  720
atcggaaggg ccgcccaggg gcggcccacg atgatccttg tacggggtgt cccgcgctgc  780
ccgcgcggga caccctaggg gtcgccgtcg gcggccccgc accaagatga aggagggcgt  840
atggccacca agtccgaccc cgatctaatc gacgacctgc tgcgccaaga cgaggcggag  900
ctgcgggcga agaagaagcg gctgcgcgcc tttcagacgg ctctggatga gcttcggcac  960
gccagcgagg cagtggccac ggccggtgcc gccctcatcg ctgccggcga tgtctcccgc  1020
gccgaggcga gcaaggtctt caagctctcc aagggagaac gcgccgccgc gttccctacc  1080
cggcctcgct cagagtcgag cgtcgcggat gcggtcgatg agccgccgaa ccccgtagac  1140
gatccatccg atgagtcgga tgaacagcac accgatctgg gtcagtagcc acaccgcgac  1200
gtggaagatc gcgctcagtc cgtacatcgc gatgatgagg atgagcgcga gcacggcgat  1260
cacgccggcg atcatcaacc acgcgagccc catcgctcat cctcccttca actctcggtg  1320
tctccatggt gccacttcgg gatgactctt gtcccgatgc catcaggatg gtgcgctcca  1380
ggtcgccgtc aagggcgctg cgcgtcgctg cgcgatgccg caagcggcac ccttgaccgc  1440
gaccctccac acaccgattg gcagttatcg gaacgaaggg gcgctctggg ctcggacgag  1500
ggctcggcgt accgacgacg tgctcacacc gagcacggtg gcgatatgcg cgttgctctg  1560
accctgcgcc ttcatgcgca aggcggcgtc ggtccgctcc ggacccatga cggtgggacg  1620
gccaccgact ctgccctggg cccgcgcgta ggccaggccc cgccgggtgt tctcccggat  1680
cgtgtccacg cgcagctggg cgaacacggc catgatcccc acaatggcct ggcccatcgg  1740
gctcgacgtg tcgatgctca acgccggctc cgtcaggctc ctgatactca ctccctgccc  1800
gatcaggtca tggacgatct cgatggccat gacctcgctt ccggccagcc ggtccagcgc  1860
ccggaacacc agcgtgtcgc ccggacgcag atagtcgcgg cacgccaacc actgcggccg  1920
gtcggccgca cggctggact cgccgtggtc cacgaacaca cgctcggccc cggccgcgcg  1980
cagctcggcc tcctgcgcgg ccgggttctg ctcgcgcgtg gacacgcgcg cgtacccgac  2040
gatggtcatc ttctccccg ccccacaggg ccgcctcggt gcggctcgtc gtcgccgcgc  2100
tccgctcgac gacgttccac ctcccgctcg atgcgctcgt gcaggccgct gcgggtactc  2160
tcccgccggg ctaggccgcg aatgctcgcc gcccacgcct tggtgcgcgt cttcacgtcg  2220
tcgagctgac tggccgtcag accgtagacg cgcacctctt cgggctggat gcgctccacg  2280
ttgtcgaggt tctgggcgaa ccgtcctagg tcgaagccgg catcagcgtt gcgggccaag  2340
ttcagcagtt ccttgtcgct gtacctgccg gaacgccgga tcgcgtccac atcgagatag  2400
tcgcgggtct cggcccgcga gaacagggca cccaccttgt tccctaccgc gtcctcgatg  2460
gcaagcacgg gcccgacctc cagccgcacg ggcgggtgag cccgccagtc cacgcccagg  2520
tccatgtcgg tactgcgccc ttgcgcactg acgatggtga gctgggcgaa cgtgtcctgg  2580
cggcggcggg tctccacggt gtagccggcc gcacgcagcg cggcgataat ccggtcgagc  2640
gacgtgccga atcgggcctg ggcctgctgg acggtgaaca ggtccacgtc ctctgtgggc  2700
cggtcgatca gcccatgctc acggatcgcg cccgagccgg ccagggcgaa gccggcatcg  2760
tcgccgacgg cctccagggc caggcgcgtg atgcgccgct gctcctcctg gtcaccgctc  2820
acacgggcac ccgaagccgg gggaaccgtc cctcccacaa gacgcggacg tgcgggtcca  2880
tgttcaggat cggccacgtc tcgatgagcc gatctcggtt catcaagcgg ccctgctcgt  2940
caaccgtccc ctcggcgagc agcgcctggt aggccatacg acgccaaccc aggttcgaca  3000
cgtccacacc gagccgatca gcctgccagc gcacagagtg aggcaggtcg atggcccgt   3060
```

```
catagggccc acgcagctcg tcgagcgaag cgggcgcgtc atagggcttg acatcgcgga  3120
accgcacacg agtcgctgcc acctcagcca tggcccgcct ccttccatct catcccagtt  3180
tacccggcca ggtcgaaaac ggtctatcac tggtttcggt ttcggtgggg gttttgaccg  3240
cccttccacc gccaacctac gcggattgtg aatgtgatcg ctatatgtcg tggattcttg  3300
atcactctat ggcgtgctgg tctggtggac cgggaagaca ttgctcttcg catggcaaac  3360
ggtgccgtct ttaggatttc tctgcgccag gatccggaag ggatggcact tcttctcctg  3420
ccgacatcgg tcggagcggc tgatggtatc gcgatcagct tgcctttagc accccacggc  3480
cgtaaacagt gtggcccact gccccgcgtc caactgtttc ggcagtgcgt gtgccggaac  3540
accggcctca cgcaagacct gggcacaccg tcgcgcacgc cgacgcccca caacccggga  3600
cacgatgtcg gcgacgccac ggcccttgcc ggtgaacacg tcatggacga aggacgcgta  3660
ccgcgcacgc tccgaccagt ccacgagagg ttcctcccgg cgacgtatca ccaggacacc  3720
ggcgtcgacg gtggggcggg gacggaaatg cgtggacggc acccgcccgt actgttcgaa  3780
gtcgacccac ggccaccact gggcagtcat catcgtggca ccaccgacac cggcgcggcg  3840
gcgcgcgacc tcccactgca ccaggagcac cgcgtgggtc caccccggtg agtgaaggac  3900
gtgccgcagg atcgcggtgg tcaggtggaa cggcaggttc cccaccagga cgtgcgggcc  3960
gtccggaagc acaaaatcaa ggacatcctg ctcgtacagg tggacctccg ggcgcagccg  4020
cttctccaac caccggacag aggccgggtc gatctcgacg gcggtcaacg atccaccggc  4080
agccaagaca cgatcctgaa ggggaaaggt cagcgccccg tgtcccgggc cgatctcgat  4140
gaccgggacg gaggcgttga cggggacgag gtcgacgatc cgtctgatcg tcgcctcatt  4200
gacgaggtag ttctggccgt tctcgtgacg gcccttgttc ggcctgtagg taggcatgga  4260
aagacactcc gcagcagata tcgtgctccg ggcatgccga aaaggccgcc cggctggaca  4320
agctgagcgg tgggtgtctc tacctccgtg gaacgtcccc cgttagcgca cacacccacc  4380
ggcggctccg gggttccgga gccgaccgaa ggtggtgaaa attgcattca ttgcacccat  4440
ggggtgaacc ataccacagc acgcggatgc ctgacctgcc ctgtcccggt catccaaaac  4500
tgtcatgtgg acctgacccg gtcggtctgc cgactggtgc tggatacgcc gccggggtca  4560
gattggtggg tgagtaccta cgcctccacg gaggtacggc agcaagcaac gtgcatgcgc  4620
tggcagaaac aattctgtct gatgttctcc ctcggctcgg gctaggtaat gagtagtagt  4680
acaaaactgt actgcccgtt ctctcttgta ttgaaatgct aaaggtttac aagacatcta  4740
cggcgaacgc actgaaacag ggcgctcctg cgagaatcga cccgaaaact gtctcgtata  4800
cctgtctcac cgtaatgtgt tccaccttct tccaatctgg ggtttggtga ggcatgatgg  4860
tggtcatgag actgttgggc tacacccggg tgtccaccgt cggtcaggat ccgactcttc  4920
aacacgacgc cttggtcacc gccggggttc aggaccgtga tgtcttcagc gatgtcacct  4980
ccggggcgaa aaacgccact gagcgtccgg ggatgaagaa gctcctcgcc tacgctcaac  5040
ccggtgacac ggtggtggtg tggcgcatcg accggctggg ccggtcccta ctcgatgtac  5100
tcaacacggt gaacctgtta cgcgaacgag acgtgaaaat caagtccgtc tccgacggca  5160
tcgacccgga gacctcctcg ggccggttga tgctcggcat gctgggcacc ctggctgagt  5220
acgaacgaga actgatcacc gaacgcgtca acgccggcat cgccgcagca aagtccaacg  5280
gcacccgctt cggccgacca cctgtggatc cagaggtggt cgaccgcaaa ctcgccatcg  5340
tcgccgagga acgagccaaa ggccgcagtg ccgaagacgc cgcgagcatg gtcggctggt  5400
cacgggcgac actgtaccgc catctgcagg gcgccaaacg acgacagtca gcactgcccg  5460
cctgacacgg acacaatgac cagcgcgtga ggtgacggtg atggacgaga tgcaacgctg  5520
ggagatcctc cggctccaca tcgaagacga catcaccctg accgacctgg cacaggccac  5580
cgacatcagc acccgaaccc tatcccggtg ggtagcccga taccgcgccg acggaatccg  5640
cgggctacgc aacaccacac gatccgacgc cggagcccat cgcatatccg cggaactcgt  5700
cgcctacatc gaacaccttg gtctcaccaa gccacgccca tcgatcgccg ccctgcatcg  5760
cctcgtgagc tgtcgagcac aacaactatc gctgaaacca cccagctacg ccaccgtgcg  5820
cagcatcatc caagcccttg acccggcgat ggtcaccctc gcattggagg gcccgacgtc  5880
ctaccgagat cgacacgaac tggtctaccg gcaccgggct gaacacccca acgccatctg  5940
gcaggccgat cacacccaac tcgacatcct catccagaac ccggacggca ccccgactcg  6000
cccctggctc accatcatca tcgacgacta ctcccgggca gtgtgcggct acatggtcac  6060
caccaccgca ccctcggcaa tgaacaccgc cctggcacta cgccaggcga tctggcgaaa  6120
aacagacccc acctgggcga tgtgcggtat tcccgacgtc ctctacgtcg atcacggctc  6180
cgacttcacc agtggccata tcacgtacac cacgacagca ctgaagatcc ggatcatcca  6240
ctcgaccatc gcccgtccgc agggccgcgg caagatcgag cggttcttca gcaccgtcaa  6300
caccgaactt ctcaccaccc tgcccggcca cctcgccccc ggcgtccgca acccacaccc  6360
cgtactagac ctgacgagcc tggataccgc cgtcggcgag ttcatcagca gctacaacca  6420
gcgcacgcat tcttcaatca acaccagccc gaaagccgcg tggatcgggc aggggtggat  6480
ccccagaatg ccggagaacc ttgaagaact cgacggactc ctgctgcggg tctccaccca  6540
ccgccgagtc cagcgagacg gcatccactt ccaaggccag cgctacatca gcccgaccct  6600
ggcacctttt gtcggccatg acgtcaccat ccgctacgac ccgcgggatc tctccgagat  6660
ccgggtctac gaccacgaca cgttgctgtg cgtcgctgtc gatgaagacc accccaacca  6720
gcgctacagc ctggccgata tccaggccgc tcgtcgacgc cgacggcgtc aactacgtgc  6780
cgggatcaac gagcgcatcc ccatccacga gccacgccca tcagaccttg cccctgtgaa  6840
ccccgatgtg agcgccgaag cgccacggcc gcgtggtcgt acgtctcgcc tgcggaccta  6900
tgaagaggac ctgtcaccat gaaccgcgac ttcatcgtca ccaaagagca ccgccgcttc  6960
gtcgagttcg ccaacgcgat ccgcaaagac gccaccatcg gcatctgcca cggtgatgca  7020
ggagtcggca aaacacagtc cgccagacgc tatgcccact gggatgctct gggctcgttc  7080
attgacgact ggggtccacg cagtgaatct gacctggcca tctacgcgac ggctcatcgg  7140
gcgcgcaccg tgttctacac ccctgaggtg caaccgaagt accggacgtt gatccgtgac  7200
atcgaatttt accggggcaa actcgacgtc tgcatcatgg agcatctgat ggccaccgga  7260
cagcgggaca ggctccacat gcgcagatcc agtggcgaga agctcaccca actgatcatt  7320
attgatgagg cagaacgtct gcctcccacc gccctggaga tgctgcgcga catccacgat  7380
cgtgacggtg tggcgatcat gttcatcggc atgcccggta ttgaccagcg cttccggcac  7440
taccctcagt tgttcagccg gctggggttc tcgcatcgct accgtgccct gggcaaagac  7500
gagctgctgt tcgtgctgaa ccggcactgg aggcgcctgg gtagagaatt gaacccggag  7560
gatttcacgg atgcgcaggc catcgccgcg atcgagcggc tgacccgcgg caatttccgt  7620
gtggtggagc gattgttccc acagatcaag cgagtgttga agatcaacga gttggagacc  7680
atcaccgacg atgtgattga agctgccgcc agcaccctgg tactcggcca ctgaccaggt  7740
cagtacgaca catagtgatc aaaaaagcag gccacatagc gatcacattc acagcggatc  7800
```

```
acacgacata ccgccaaccg gtgcaaaaac gatcgttttt gagacgcacc gcgagagcgg  7860
agccgttagc cgctcccgga gcgtccacaa cgcgtctcaa aaccggtcgt gtcgcaccct  7920
ggttttacgc ccgggcagtc tgcttatgtg tgataaagaa gcaatagaag tgcaaaaaat  7980
tttgccgttc ctatccgaca cttggccatt gtgtcggata ggtcgggcgg ttattcgggc  8040
aagtcaatct tgccgacaaa gctgtaataa atctcaatgt cctgcctgcg ggtgccgttc  8100
tcatcatagc tgcactcatg caccacaatt ttctcgatca tttcccgcaa gagagtgggg  8160
gtcagttctt caaaggcaag gtgcttgcgg acaatgccca taaatttctc ggcgttgacg  8220
gtagttgcct gtgacttgtc cagttcggct tgcagggcgg cggctctctt tttcagctcc  8280
gcttgctcgg cttcgtagtc agccgacagt tccatgaaac gctcatcgct gattttgccg  8340
tttacattgt cctcatacag ccgcttgata atgcggctga tttcagaaat gcgttcctgc  8400
gcctgttcaa gctgcttgat ggctgcggcg gtctttcgct tgccgccgat ctcgttctgc  8460
tggacaaaat gtaatccgca ggattaggag atagaagttc cgttactttg ggacgcacta  8520
cctctctgtg aaattcatta gattcgtcac ccattgcatt atcccaaaat tgtgcgttct  8580
cctcccagat ttttttactt tcctctgttc ccatgttctc tcccactccc caaatttgct  8640
tttttgcttc cattaaatct tccttactat attccattgt taccctccat aacttctgat  8700
tgttgccgtc ttgacgatta tgtatcttta cattaccttc tgaaacatat ggcgcacctt  8760
gtccaggcgg ctgtttggac ggcggggctg gatgaccggc tgaccgacag cggcctgata  8820
tcctttcagc tctgtaaggc atacgctccg cccgttggtg taaaaggcca gatcagtacg  8880
gtatgcctgt atacagcggg cgggaatctc gccagtaaag acaacttcat cctttttttac  8940
ctgggccgtt tcgatggtgg cacagtattt cggtgcatca tgataagccc tggaaaggta  9000
ttcctggggc gcatagagga tgaaggagag ataaggttcc agcagctgcg tccccgattc  9060
cttcaatgcc tgttccaata caatcggggc caatgagcgg aagtccgccg gcgtgctgac  9120
cggactgtaa taaagcccgt attcaaagca aatcttacag tccgttacgt tccagccgaa  9180
caagccctgc tccagcccgt aacggatacc atccctgaca gcgttttgaa aactctggtt  9240
caagtatccc agcgaaaccc ggctctcgta ttgtacaccg gagccaagcg agagtggtgt  9300
aacagacagt cctatggatg cccaaaacgg gttgggcggc acctcgatat ggatggtgtg  9360
gctggctgct ttgagcggcc gctccatata aatgacggag ggttccttta ccactgtttc  9420
aagcttgtat ttttccgaca gcaaagcgga aacaacctcc aactgcaccc ggcccaaaaa  9480
agaaagaatg atctcatggg tgatggaatc cacttcgcaa cgcaaaagcg ggtcagtatc  9540
cgcaagttgc gtaagagcgt ccagcagccg ttctctttgc gctgccgttt tcggcgcaat  9600
cgtcgtccgc agcatgggga gggggtcctc gcgccacctt ttacgaggga gccgggtttg  9660
gtcccctaat acatcgttta acctcacgct gtcgctggga aggataacaa tttcaccctg  9720
ataagcggtg tctgtccgaa caatttcccc tttggatgga atacgcatct ctgtgatttt  9780
cagcttttct ctcccggcca gggccaccgt atcccgcagg cgcagcgttc cgctgtataa  9840
ccgtagatag acacgccgct ggccgcaatc ggtgtactca accttgaaaa cgctgccgca  9900
tagggcggcg ccccccctgtt ccccaatcgg ttggaacagc cctgtcaccg catccatcaa  9960
cggttgaatg ccaaggccat ttttggcgct gccatgatag actgggaaca gggaggcgtc  10020
ttgaacccgc tgctgttcct cccgcgcaag tttttcccgg ctgattggtt ctcctgcgat  10080
atacttttcc aataattcat cgttattttc gatgaccgca tcccatgctt ctatgtcggt  10140
attttcctcc aggactattt ccggggacag cgacaccgtc tgcttgatga taatatcggc  10200
ggagagctta tcccgaacag actgaaccac gctctgcaaa tcaacgccag cctggtcgat  10260
cttgttgata aagataacgg tgggaatgtt cattttccgc agggcatgga acagaatacg  10320
ggtctgggcc tgcacgccat ctttagcgga gatcaccaag atggccccat ctaaaacagc  10380
caaagagcgg tacacctccg ccaaaaaatc catgtggccg ggcgtatcca caatgttaac  10440
tttacatctg tgccactgga aggaagtgac tgccgcttga atggtaatcc cacgctgccg  10500
ctccaaaaac atggtgtccg tcctcgttgt cccttttttcg acgctccccg gttctgaaat  10560
ggctccgctg gcatatagca ggctctccgt caaggtcgtc tttccagcgt ctacatgggc  10620
aagaattcca atattgatta ttttcatgtg attgtcctcc ctttacagcc ccaaagggca  10680
taaaaatccc cagcagtaaa atacttttac cactggggat tataagttgc ggacatacac  10740
atatacagca tacacctgtt tgtgattgct gtttttgggg atatgtcaaa attgataagg  10800
caaaagtatt cttaaattgg gtacaaaaaa ctaagcccct acaaaaggag ctatcataat  10860
cctttgttcc cactatttga ttatagtttt atttaagaat accttgccgc atatttttta  10920
ctccttttct ggattaaatc attgtatcac atcagtttta ggaaagcaag tacctaaaag  10980
aaatttttct tcccttata tgtaacaatc ataccggctt cctagcgttc agaatgtttt  11040
ctgctgtctg ctgtggtgtt tggttggaat tgtccaacca aaagccgatc cgtggtgttg  11100
tctgcatttt actaaataca aattcaatgt atacagaaag atataaggag tgggagggat  11160
tccgccgtag ttggcattgt aggaaaatcc aaaagtttag attttcccac aatgcttatc  11220
ttttggtctt tggttcggaa tagtgtagtg ctggcggtct atctcttgtt ttcggttgct  11280
tgcttcctta ccgtacatga gcattcggcc agtgcattcc cgaccacgtc cggcacggca  11340
cctcgaccgt ctgcgccgcg ctgaacattg cgacccgctt cgacaaactc gccatcacgt  11400
accgcgccgg cgtcaccctc tgcgccatcc tcacctgggt ccgactattg ggagacacga  11460
cctaggagaa gaccggctcc cacatccgct accgcttcgt gggaggccgt ggcccggctc  11520
ccgccgggca tgaagaaggg tccgctgaag gtttggttga cctcctacgg cagcagctca  11580
gccagttctc gcagctgctc aaggatccgc tcggcctggt cgggagcgac attcttgtcc  11640
agctgcttga gctgacgctg catcttctcg atgactgcgt cggaaccagc ggactcgctg  11700
tggagcttca ggaagtgtac ccaagcacgc gtctcgatac cgaggatggg cacacgcatc  11760
gtcgactcaa cgaacgaatc catgaggggg cgacaccgag gcagtcgtcc gaagttgcca  11820
ccgccatcgt tcaccggatg caccgtcacg cggtcagcct tcgacgggta cggcgtcgcg  11880
tcggccgggt actccagctc cgcactgcca tcggtctcct tgatgttggt ccaccagtag  11940
tcgcgccact cggcggcgta cttggcggac tcgacccacg gctcggccac caccggcacg  12000
ccgctgacgg cgctgtcgag gtgccacggc acgcagcaca ccaggtccca gtcggtgcag  12060
gcatcggggg agacctggta ccgcagcgaa gggaccttct ccttggccag catccaccag  12120
cccttgagct cgatgccgat cgcgatgggc tcaccctcgg ttccacgatt caccagacgc  12180
acgtcgggga aggcctgcgc cgaccgctcg aaccggtagg tcgaccactc ggagtccggg  12240
tcccagatct gccgaaggct gttcagcgtg cgcacgacct ccagctcgat gcccgagccc  12300
aagaagctgt tgaggctgaa caggtcggtg gcgttgaccc cgctgatctc gttcttcgac  12360
tcgaactcgc ccggaagggc ttggagggcc gcggagaccc ccttctggag cttggtatgc  12420
ggatcgttgg gatccagcac cgggcgggca ggacccgcac ccacctgggc gctcgtcgcc  12480
actgcatcaa ccgacattgc tctcctcctc ggggttggcg tcgaagaggg ccacgagctc  12540
```

```
gtcgttggtc tcggcctcct cggcggcgac gtcaagccgc tcgtgcgcaa gctccgcgaa  12600
gtaggggtca cgctcggcaa ggaaagcctg ccgacgcagg gccaccgcag ccacggagcc  12660
cgtgccaagc ccgccgaagg gctcccatac gacgtcgccc tccttcgtga cggcgtgcac  12720
caggcgctcc atgagctcca gtggcttctg gttcagatgg gtcgtgctgg ccttcgtggg  12780
cttgtacacg cgcggcgccg accgacgcat cgagcccttc atacgctcgc cgtcgtgcag  12840
cggggggcgg ctccacacgt tggtcaggcc atggacgtgg tgccactggt ggcgcatccg  12900
gtcccactgc ttcgcggtga ccgacgtcac accgtcgagc gagaagtacg ggcggccgct  12960
ctccaggccg tgctgattgc agtacgcggc catggcggcc acggcgactc ccggcggcca  13020
gtaccagagc cagtcgttcg tcaggtactt gcgcgtggcg gcgttcttca cgccgcaggc  13080
ctcattggcc aggtacatcg gcagaccaga gcggcgccac tcgtgccgca gccactgctg  13140
ggcatcgaga atgcccgcgt cggtcgccgc ctcgaagcgg cgctggtaga ggacgcagac  13200
ctccgtgacg acggggaagc ggcggatggt gttgccgttg acgttgcccg cgatgtggct  13260
cagacccttg tcccagacca cggtctggac gtagtcccag ccctgacgct tcaactcagg  13320
atgcaccgtg gcccagccca cctccgtacc ccagaaccac agcgccgtgc ccggggcggc  13380
agccttcgtc cactgctcga tgtgcggggc gtaccagtca acgagccctt cctcgtcggt  13440
ggtgtccccg taaaaaccgc ggacgccgta ggcgccgtcg ctgatgatgc acgtcggcga  13500
cggccaggac gcgtaggcgt ccgccacatc ccccacgtgc aggtcgtagg gcctcttctt  13560
ctcggccatg ctcccagcct ctcataatcg atggttactg gtcattcgcc cggtccaggt  13620
acgtcaggcc ggcgcggcgt agcgcgtcgg ccggcgtgcc gccgctccag tcgggggcgg  13680
tcccggtcat cggcaggggc gtggccgacc gggctgtgtt ctccagctcg tcggccagtt  13740
cgtcccactc gggcacgtcg aggacctggt tgaccgagac ctcgacgacg acgctcaccc  13800
cgcgctcggc cagcagccgg cccacggtct ccttgtacgc ctcggcgtag tcggcctggt  13860
cctgctccca ccgggcctct acagcgtcag cggcgcgccg cgcctcgatg agggtggccg  13920
ccagcggatg ggcactctcg gctgctcgct cctccacggc cttgatgatc tttccggcct  13980
cctcatacat cgcggtcacc cggtcggggt cactgtccca ctcgggtccc ccgagctggg  14040
gcatgtcggc ctggagcgcg gccagccggt cgcgctcctc ggccgtggcc acggcctccc  14100
agagtgcatc ggccgccgcg tcgacgcggc ggccgagttc ttcggccgcg tcctcgtaga  14160
gctggtagag cccgaagtcc tcgaagacgg cctccacgtc gagcgcgagg cgcaccggct  14220
cggtgcgcca ggccagcagg tcccgatcat cggtgccggc tgtcccctcg acgacctggc  14280
ggatgagggc ggcctcccac gatccgggcc ggccggccag cagctcgtcg acgctgccga  14340
tgttcgcggc cacggccgtg agcacgtggc acgcgatccc cgcgaagtcg tccggctccg  14400
tgtgctcgct tggggtgccc gctccgacga cgcgacgccg gcgcgccgcg tcggtcaggg  14460
ccgtgatcgc ctgggcgatc gggtccggga ctgtctcggt catgtctggc tccttcagtg  14520
ggtggtgatg ccgggcttgg ggcctggcgt cacggcgtcg aggtcgggga acgggcggcc  14580
gtcgttgtac tcggcttcca gccgggcgac tttctcgttg acggcttctt ggacgaactg  14640
ccagtagggg cggatgccga gcttcgcctg cgtgtagaac cacgctcccc tggcacgccg  14700
gccttcctcg atggtgtgct tgaagctggt gcgcgtccat ccttcgccgg tcccggtctt  14760
tttcgcggcc tcgtgccggg cctcgtcaac gttgggcggc tgcgccgcct cgacggcctg  14820
gggcacgagg gggttgctca ggttggtggt gcgccgctcg ggccgcttgc tcatttgatc  14880
gctcctttag tgatggtgtc gaggtgctgg cggtagaggt cggccagctc ggcggcgtcc  14940
ttgccgcccc actggtccag gccggtggca gcctccagcg cgtcggcgat gacggcgcgc  15000
ttcgggatgg gcggatcaag gatggtcagg ccctcgatct tctccaggtc ttccagagcg  15060
cttcgcgcgc cgatggtttg cgcctcgtac tggttgacga tcaccccggc cacggccaac  15120
tgcgggttgt agtacttgcg cacgatggcg atcgtctgaa gcagccgacc gagcccggcg  15180
atcgagtaga ccttggcctg ggtgacgatg gccacccgct cggcggccac taggccgttg  15240
agggtgaggt gatccagcga tggcgggcag tcgatgagca ccaggtcgta gcggtccgcg  15300
acgctggcca cggcctcgct cagccggtgc tcgacgccgg gggtctgcgt ggtcagcagt  15360
tcgttgcgaa cgctggtcag cgcctcgttg ggcggcgtcg gggccacgtc gaggccatcc  15420
cacacgccgg ggacgatgac gctctccagc gtctcggtac tgcgttcact cagcgcgtcg  15480
gccacgccga cgtcctcggg cgtgggcgtg tctttcgcgg ccgacatggt ggcgttaccc  15540
tgcgggtcga ggtcgatcag gagggtccgc cggccctcgg tgacggcggc gcgcgcgaag  15600
ttgacggcgg tggtcgtctt cccgacaccg cccttctggt tgctgattgc gagggtcatg  15660
ctcatgctgt tggttccgtt cgtgcgattg gtgcggttcg tggtgttagt gccattcgtt  15720
ctgttcgcac taactagtgt agtcgcttcc cgcctcgctg tcacggcgtc gaggacagtc  15780
gggagatcaa gtccggccgg aggccggcgc accgtggggg ctccggccgg acttgttctc  15840
actgttcatt ctattcgttc ctttcgttct aatggtgcga atcgcaccat tagaactagt  15900
cggtgatggc ttcgatgatc cggtgcgcgg cggccagcac acggctggcg ctcttgcgga  15960
tgaggtcggc gtctcccttg gaccatccgg cgacgtagcc gacgctgtag gcgctggtgt  16020
cgagtccaac gatgccggcg accacgtggg cgacgctttc ggcctcgacc tcgcattgtc  16080
cccggtgctc gtggtactcg gtgggggtga tgtcggcgtg catgagcgcg tgggcggcct  16140
cgtgaagggt cgtcttggcg gcttgggcgg gggagatatc ggccgcgatc acgattcgct  16200
tgtcgtcgtg gctggtgtag ccgttgagtc cggccccgag ctggtcgtgc tcgatggtcc  16260
agccctggcc ggtgagccag tcggtcacgg cctcggcgat gccggcgggg tcgtcgccgc  16320
tgagctggtg ggcgtcggcg gggttctcgg ggatcggctc ggctccctcg atggggtcgg  16380
tctgggcgag gtcgaagacg gacacgggga agaatcgcgt gcggcgtcgc tcggtctcct  16440
ctccggtggt ctcgtcctcg atcgtttcgg tgacctcgcg gccgccgaag attctgattc  16500
cgcgctcacc tttgcggacc tgccggccga gcttctgcca ggtgcggtac cccgcgacct  16560
gcgtcgcgtt ctcgcgctgg gcgaggatca ggagcaagtt gttcaggctg tagcggtgga  16620
acttcccggc gaaggcgagg aactgggccc atgcttccga ggtggccagg gcctcaacct  16680
gctgggcgat ggtctcgtgc agttcggccg cttcggtgcg gcgctgctcg gggtcttgt  16740
gggtcttgat cttccgggcc atgatgttgg ttcctttcgt gtgattggtg cggttcgtgc  16800
gaactgcctg tcttccctca cgttttttg ccattgaagg cactggaagt gccgccaggg  16860
agggagcccg gagtgcaagg gaccgtggaa taccggactg agcgcagcga gggaggatat  16920
gccgcgaaag cccttgcgcg tagggcggac gaccgtatgc tgccgaaggc ttcaatggca  16980
aaaacgtgcg ccgtaggcgc atgctgccgg ccgcgcagcg gccgtcctta tgatgacggt  17040
ccgccagggc cgcctgggga gggtcggcct gggggccggc tcgttgtggt cggctgtcca  17100
cctgtgggcg ggccagccgg tcgggagctg ggccgtccac aggtgcgtca ggcggtcccc  17160
tctacggagc ggccctgtgg ggcgttctgc gggccgtgac cccttccgc gtgtggttgc  17220
ctgggtgggg ttgagttcgg ccgtttcggg gcgttgtatg gcgtcgtttt tcgtggtcga  17280
```

```
tcatggctgc cgcctgtgga cggcccttcg gcccgcccac agttgccttc gaaaccgggt  17340
ggccgggttc cggcgtggtt gggacgaggg ttgcccccgg cggtcaggcg gcagtgacga  17400
ggctctgatg aaggtggtcg agtgctccgg cggcgatcgc ttcgcgggcc gctcgatggt  17460
cagcgcggcc gtctggtcgg cgcgggtagg gggggtagat gtcccagggt cggccgaacg  17520
tgagcgcaat ctgtcccgtg ggctggtggc gtcgtttgtg gcggcctggt gtggtcatcc  17580
attccagttc ggcctgccac cattcccaca gatcgcgctc ggccttgtag cggccttctc  17640
gtgcgtcgag acgcccctcg acgccgagcc gtcgggccgc gaggtcgcgc agctcgggcc  17700
gggttcgccg ccagccggtg ggcgtggcca cgatgagacc ggcgtaggcg agtcggtcga  17760
gtagggggggt gatctccgta gtggtgacct gggggtgatt gagcctggcg tagaggtttc  17820
ctgcggcgag gcccagggcg tgggggttgg tgaaggtgtc gtggcgggcg aggtctaggc  17880
ggtgggtgag ttcgtccagg aggaggtttc tccatcggct gcccgcccct gcggggcgtg  17940
cagccccttg tgaccgggca tggtctgcat ccatgtggat agcggtctgg ggctcgattg  18000
tccaggtggt ggcgtgcctg ccggtgcccg cctgggcctg gctgatccac ccgtcgccgg  18060
ccaggcgcag gagggcggtg cgggcggtct ctcggccgat gccggcgagc agggcgaggc  18120
ggcgcacgtc tgcttcgacg gctgcgctga cggcttggag ggcgagcagg cacagggcgt  18180
cgagcacgcg ccggtcggcc ggccctcctc cgcgtgtcca gcgccctggt gccgcatcgg  18240
cgcggcgctg cacctggtcg acggtggcgg cgatcgcttc ggctcggggg tcgaaggtgg  18300
gatcgtcgcc tgcctggcgc gcgtgggtgg ccacgaacct gacggcggcc tgccacactc  18360
ggccgagcgc ggcttcgctg ctttgggctc cgtgtgtggg gcgcgcctgg cgtgcacggc  18420
ctccgtggcg tgcgcgctgg gtgcgggcgt gctccatgcc gggtgccgtg gacacgaggg  18480
cggccgcgtc gcggtagtgc cagtgggcgg cggctgcacc gagcaggatc acgtagagga  18540
cgcgggaggc gtcctcactg gcggcggcgt cttcgtcgac ggcagcgcgg ctcttggcgg  18600
gcatggcacg gcggggtccg ggcagccacg gccgcccgtc ctcgtcgacg ggcacgcgca  18660
gctcggctgc gtgggggagc gaggtcaccg tggccacgtc gccgaactcc tcattgagtc  18720
gggtcgccag ggccacgagc tgggctggtg tggtggtcgg gtgtgtgagg gtggcgagat  18780
ttccggcgat cacgcgggat gctccaccgt ggcggtgggg cgtgccgggg gggcgcaagc  18840
atccggtggt cgggttgagc aggggagtgg ggtccaggct ggtggcgaga ccctggaggg  18900
agtgcgtcag gtggtgcacg agctgcgggt cggccgtctc ggccagggcg atccacacgt  18960
ggcggccgcc ggtggggccg gactcgcaga tgacgtgctc gatgccggcc tggtcgagca  19020
ccgtggcgat cgccgtggca tcccgctctg cttgggcggc tccgccctcg tgggcgtcga  19080
ggtcgaggcc gatgtagcgg tagcggcgct gcgcgtccgt caggtacatg gcccacgggc  19140
cggccggggc cggccccgcg acgggcacct gcgtcgggta ggcgttcacc tggtcgccgc  19200
tggcggcgcg cacctgcggg cgcgggctca acgtgcgtgt gagacgccac gccgcgccga  19260
tatgcgtagc gtcacggtta tcggcatctg ttgctatcat gtacgtgttc cttccgggga  19320
aagacgcaac gatccctcct tcggttggtg ggcccctgcc aagggcccta ggtgtttggg  19380
tgttgcatcg ggtgccgact gccaaaccgg cttccgtact tggttcgctt gatctggttg  19440
tgttggggaa ctcagcagat caggcgctta ctcttctgac ccccgccctg ccaagggcgg  19500
gggtctgttc atgtctatgc ggtgcccgta gggtcctcct cgatgctcag ttccggttgg  19560
gtgctatctg gggttggaag ctcccatccc tgtggccagc cgtccgggcc tgggacacca  19620
gagcggatcg cagcttcaag gactgcccac tggggggcac ccttggcgcg cgcgtaggcg  19680
tcgagcttgg ccttgacgtc cggcgcaacg aagatgtgaa gcgctacggt aggcgctcca  19740
cggtcgcgac ggaatcggct ggtcatgaca gtcatcatat aagggcggct gtacatgtac  19800
acgggccgac acgccggcgt gtcgcgactt cttttcagat atcagagtcc tcgggcgacg  19860
gcggcggctg cgcgcagcca tgcgcgttgt gtgctggggc gcaggctgtc ccattggagg  19920
atgccgtcca cgatggcggg gtcgtggggg atcgtgacga cttcgcgggc gaggtcctgg  19980
tagccggtga cgatgttggt gatgtcggtc ttgctggcgc gcgggtcggc ttgggtgacc  20040
acggcgacgg cgttgtccgc gagctggcgt gagtgttggt cgcggccgcg cagcgcgtcg  20100
aggaggagcg cgccggcttc ggcgtggtct gcgcgggtgg tggtgggcac gacgatctgg  20160
tcggcgtgtt cgatggcttc cagccacaca ggatcggatt cgtcgttgcc ggtgtcgatg  20220
aagatgaggc ggtagtactt gccgacgacg ttccagatga ggtcgacgtc gtgaggggtg  20280
acgcgctggt cggcggcgag ctggatgggc tggctgcgca gcacgtcgaa ccggtcggcg  20340
gtctggtggt gaacgtagtg cgccagatcg gccgactggg ctccggtgcc caacagtcgt  20400
tcggtttggg gaaggaggtc gaggacggtg gcctcgtggg gtccctgttc ggtccgccat  20460
cccagggtgc ccctggtttg gttggcgtcc caggcgacca cgcccgcgcc gccataacgc  20520
gcgaacacag cactgagtag caccgtggtg ggggttttgc ctgccccgcc cttccccgttg  20580
gccacgatga tcgtcctggg gccgggccag tgctgggaga cggcgtgcac gtcgtcccgt  20640
tccgcgcgct cctgctggct cgggttcatg cgcagcccga gccgggtggc aacgccgcgc  20700
cagccctgcg tggcgggctg ctcgatctcg gtggctttga ggaatgaatg gcggctctgg  20760
acctcgcgcc tgctgggcag gtgcgcgatg gggctgtcgg ccgagcgtgg gagagtgtgt  20820
gcctgggtgt gagggctgtc ctggcgtggg gttgggctgt catagaccgg ggccgccgtg  20880
gcggccgcgg cctcggcggg atcgtggagt tcgccgtcgg gggtgacgat gacggtccac  20940
acgccgtcgg ggtcggaggc ggtgagcgtg gcgctttcgc cggcggtggc tgcgcgctcc  21000
tgggcgatcg cgacgacctg ggcgcgggcg tcttcgaggc tggtggcggt gatcttctgc  21060
ggcgtgccgt cgatcgtgac gatggcgctg ccgtcgcggg ctgtggtggc ctctatgtcc  21120
atggggatgc tccttcgttc agctttgggt ggcctgggtc tgcatggctg tgatcgccca  21180
ctggccgttc tcttgggtcg cggtgaccca tgcgtcccag gccacgtcgt cgggggcgtc  21240
tgagccgtct cggggcgtgg tcttgacgag gtagtggacg atccggtgcg cgtcgccgtc  21300
ttggtcgggg tcgagtcctt cctcgacaat ctcgcggatg gtgacggtgg tgtaggagtc  21360
atgctgcgcg gcctgtgtga actgggcctg gcccttcgcg gtgtcggggt cgtagtcggc  21420
ggccgcttgg cgtagcgcgt cggttaggta gatcgccgcc cgttgggtgg cgtaggcgct  21480
ggtcttgtcg accgtggtgt cccaggtggc ggccgtggcc acgtaggcgc ggatgacggc  21540
ctcggggtcg gtgcggtcga cggtgctggg gttgggcagg tcggcgagcc aggtgggctt  21600
gcccccgggg atgggtgtgc cgtcgggtgc ctgcccgatt gtggggctgg tcgtggccgg  21660
cgtgctggtg gcgctcgtct gatccggtgc cggggtgtcg ttggctgtcg tgtgggcgca  21720
gccggtgatg gcggccagag tgatggtgcc gatgacgagg gcggcggcac gccggtgggt  21780
gcgcctcatt ggattctcct gtagttgctc ggtgagccgt agatgggctc gaagttgatg  21840
ccatcaatgt ggttgtcggc gctgaccatc cagccgttgc cggcgtagat ggcgacgtgg  21900
taggccggcg tgccgtagaa gatgaggtcg ccgaccttga gttcgccgcg ctcgatgccg  21960
gtgccgacct gctgctgctg ggcggctgtg cggggcaggc tgatgccgag gcggcggtag  22020
```

```
acggcgctgg tgagcccgga gcagtc                                   22046

SEQ ID NO: 50          moltype = DNA  length = 1615
FEATURE                Location/Qualifiers
source                 1..1615
                       mol_type = other DNA
                       note = pBC1
                       organism = synthetic construct
SEQUENCE: 50
ccccgatggt ttttcccccg acggctcgcc tttgggaagt ttgaagggcg caggttccac  60
acgaaaaacc acaaggcttt ttttgagtaa taaaaaagcg gacggcgagg gcgtgaaaaa  120
aacccgatga acccttgaaa ataaagggcg ggacgggttt tttcttatct tgataatata  180
tagaaacaat gagattttaa aaaaagccct caaacccttg ataatactgg gtttgtggcg  240
ttttttttggg gtggataaat aaaaaccctc tgtgttatgg ttatgttgac tagacaaaac  300
catacagagg gctttacgcc tttctgtatc cagaaaggag ttattaaatt ttatgcacgt  360
taatcatagc attaaaacgt caaatctatc aaatatcgaa tttttgcaag ataaaacgaa  420
aacaggaaaa gagagagatt ggaaaggcaa gaaacaacgg tctttgctga cagcggaaca  480
cttcgaggta gcagggctga ctagcaaagc ggaacagtgc gagagtgtgc tgacacgttg  540
gtgtttaagc gaactgccga aggttaaaa ctatatcaag catggttctg taaagtgagg  600
ttatgcccga tgtgcaattg gcgaagatcg ctgaaaatag cttaccagaa taaaagggtt  660
gtagaggcgg ttaatcaacg tgagaacgtt cagtggctat tcctaaccct taccgtccgc  720
aacacgagcc ctgagagcct tccagagacg atttcagcca tgtttgaggg gtttaatagg  780
ctgacgaagt acaaagcctt taaaacgtct gtaaagggct attttagggc tttagaggtc  840
acaaagaata gagaccctca tagtgaatgg tttggcacgt atcaccctca ttttcacgtt  900
ctgctgtgtg ttccatccag ctatttcaag aaaaaagaat tatacataac cgaacaagaa  960
tggactgacc tttggaaaaa ggctatgaag ttggattaca cgccgattgt ccacgtgcaa  1020
agggtaaaac ccaaagaaca gcttgaggac atggaaacct atgaagaaca gcttaaaaac  1080
gccattaggg aacaaaatgc gattttagaa gtctctaaat atccggtcaa agatacggac  1140
gtcattaaag ggaataaggt cacggccgaa aatgtggaaa ccgttttggc gttagacaac  1200
gccttggcaa ataagcggtt aatcgggtat ggcggtcttt tgaaacaggt tcacaaggaa  1260
ttaaaccttg gagatccgga agatggagat ttagttcatg tttcggaaga ggatgaaatc  1320
gctaatggtg catttgaggt catggcgaaa tggcatatcg gttttagaga ttattggatt  1380
caaaaatagc aggagagaaa actcctgctt ttttattttt tccgaagtta ttggcgaaag  1440
caaacttttt atcgagcgaa gcgaacccta ttgaatacct gcatggcaag gtatgtaaat  1500
gggcactctg tgatttttgg atacaaaata gactctagcg agccgatttt atgacgcagc  1560
aaaaaacgta gtctttttgc gttggagagc ccttcaagta aactgaccaa ggtgg       1615

SEQ ID NO: 51          moltype = DNA  length = 1854
FEATURE                Location/Qualifiers
source                 1..1854
                       mol_type = other DNA
                       note = pEP2
                       organism = synthetic construct
SEQUENCE: 51
atggtaaatc tgcgcagaca gccctgtgca gctgaaacgc ggttacgtat agcttgccat  60
atgtctagcc atacgtaacc gcaggtaaaa ggcatatttt tcgcgtgtca tggctagtaa  120
ataacaccgg tgtcatttag agtcagggaa agacaatgaa aaacgaagaa agccaccggg  180
cggcaacccg atgactttcg cttatcaccc agcacacacc tgggagaaat cacggtcatg  240
agtttacaga ctcatgcgca gaatgcgcac actaaaacac ctacccgcgt cgagcgcgac  300
cgtggtggac tggacaacac cccagcatct gccagtgacc gcgacctttt acgcgatcat  360
ctaggccgcg atgtactcca cggttcagtc acacgagact ttaaaaaggc ctatcgacgc  420
aacgctgacg gcacgaactc gccgcgtatg tatcgcttcg agactgatgc tttaggacgg  480
tgcgagtacg ccatgctcac caccaagcag tacgccgccg tcctggtcgt agacgttgac  540
caagtaggta ccgcaggcgg tgaccccgca gacttaaacc cgtacgtccg cgacgtggtg  600
cgctcactga ttactcatag cgtcgggcca gcctgggtgg gtattaaccc aactaacggc  660
aaagcccagt tcatatggct tattgaccct gtctacgctg accgtaacgg taaatctgcg  720
cagatgaagc ttcttgcagc aaccacgcgt gtgctgggtg agcttttaga ccatgacccg  780
cacttttccc accgctttag ccgcaacccg ttctacacag gcaaagcccc taccgcttat  840
cgttggtata ggcagcacaa ccgggtgatg cgccttggag acttgataaa gcaggtaagg  900
gatatggcag gacacgacca gttcaacccc accccacgcc agcaattcag ctctggccgc  960
gaacttatca acgcggtcaa gacccgccgt gaagaagccc aagcattcaa agcactcgcc  1020
caggacgtag acgcggaaat cgccggtggt ctcgaccagt atgacccgga acttatcgac  1080
ggtgtgcgtg tgctctggat tgtccaagga accgcagcac gcgacgaaac agcctttaga  1140
catgcgctta agactggcca ccgcttgcgc cagcaaggcc aacgcctgac agacgcagca  1200
atcatcgacg cctatgagca cgcctacaac gtcgcacaca cccacggcgg tgcaggccgc  1260
gacaacgaga tgccacccat gcgcgaccgc caaaccatgg caaggcgcgt gcgcgggtat  1320
gtcgcccaat ccaagagcga gacctacagc ggctctaacg caccaggtaa agccaccagc  1380
agcgagcgga aagccttggc cacgatggga cgcagaggcg gacaaaaagc cgcacaacgc  1440
tggaaaacag accccgaggg caaatatgcg caagcacaaa ggtcgaagct tgaaaagacg  1500
caccgtaaga aaaaggctca aggacgatct acgaagtccc gtattagcca aatggtgaac  1560
gatcagtatt tccagacagg gacagttccc acgtgggctg aaataggggc agaggtagga  1620
gtctctcgcg ccacggttgc taggcatgtc gcggagctaa agaagagcgg tgactatccg  1680
gacgtttaag ggtctcata ccgtaagcaa tatacggttc ccctgccgtt aggcagttag  1740
ataaaacctc acttgaagaa aaccttgagg ggcagggcag cttatatgct tcaaagcatg  1800
acttcctctg ttctcctaga cctcgcaacc ctccgccata acctcaccga attc        1854

SEQ ID NO: 52          moltype = DNA  length = 2178
FEATURE                Location/Qualifiers
source                 1..2178
```

```
                        mol_type = other DNA
                        note = pWV01
                        organism = synthetic construct
SEQUENCE: 52
cgatttttta ttaaaacgtc tcaaaatcgt ttctgagacg ttttagcgtt tatttcgttt  60
agttatcggc ataatcgtta aaacaggcgt tatcgtagcg taaaagccct tgagcgtagc  120
gtggctttgc agcgaagatg ttgtctgtta gattatgaaa gccgatgact gaatgaaata  180
ataagcgcag cgcccttcta tttcggttgg aggaggctca agggagtatg agggaatgaa  240
attccctcat gggtttgatt ttaaaaattg cttgcaattt tgccgagcgg tagcgctgga  300
aaatttttga aaaaaatttg gaatttggaa aaaaatgggg ggaaaggaag cgaattttgc  360
ttccgtacta cgacccccca ttaagtgccg agtgccaatt tttgtgccaa aaacgctcta  420
tcccaactgg ctcaagggtt taaggggttt ttcaatcgcc aacgaatcgc caacgttttc  480
gccaacgttt tttataaatc tatatttaag tagctttatt gttgttttta tgattacaaa  540
gtgatacact aactttataa aattatttga ttggagtttt ttaaatggtg atttcagaat  600
cgaaaaaaag agttatgatt tctctgacaa aagagcaaga taaaaaatta acagatatgg  660
cgaaacaaaa aggtttttca aaatctgcgg ttgcggcgtt agctatagaa gaatatgcaa  720
gaaaggaatc agaacaaaaa aaataagcga aagctcgcgt ttttagaagg atacgagttt  780
tcgctacttg tttttgataa ggtaattata tcatggctat taaaaatact aaagctagaa  840
attttggatt tttattatat cctgactcaa ttcctaatga ttggaaagaa aaattagaga  900
gtttgggcgt atctatggct gtcagtcctt tacacgatat ggacgaaaaa aaagataaag  960
atacatggaa tagtagtgat gttatacgaa atggaaagca ctataaaaaa ccacactatc  1020
acgttatata tattgcacga aatcctgtaa caatagaaag cgttaggaac aagattaagc  1080
gaaaattggg gaatagttca gttgctcatg ttgagatact tgattatatc aaaggttcat  1140
atgaatattt gactcatgaa tcaaaggacg ctattgctaa gaataaacat atatacgaca  1200
aaaaagatat tttgaacatt aatgattttg atattgaccg ctatataaca cttgatgaaa  1260
gccaaaaaag agaattgaag aatttacttt tagatatagt ggatgactat aatttggtaa  1320
atacaaaaga tttaatggct tttattcgcc ttaggggagc ggagtttgga attttaaata  1380
cgaatgatgt aaaagatatt gtttcaacaa actctagcgc ctttagatta tggtttgagg  1440
gcaattatca gtgtggatat agagcaagtt atgcaaaggt tcttgatgct gaaacggggg  1500
aaataaaatg acaaacaaag aaaaagagtt atttgctgaa aatgaggaat taaaaaaaga  1560
aattaaggac ttaaaagagc gtattgaaag atacagagaa atggaagttg aattaagtac  1620
aacaatagat ttattgagag gagggattat tgaataaata aaagccccct gacgaaagtc  1680
gaagggggtt tttatttttgg tttgatgttg cgattaatag caatacaatt gcaataaaca  1740
aaatgatcga tgctgtttgg caaaaaaaga aaaagtgatt aatttatatt ttatttatgg  1800
cgctaattta ttacggcttt ttttgttgtc ggctagccga ttctgataca tttttttaag  1860
cacaaaaacc acccaatttt ggagtggtgt gtaagtgcgc attgtcatga aaaaatggca  1920
cgcaatttca tcactttttta aagtgatgtg taagtgcgca ttgtcatgaa aaaatggcac  1980
gcaatttcat cactttttaa agtgatgtgt aagtgcgcat tgttcgaaaa atcgaactat  2040
gatttatttt tgctgttgta tttatttttc atcttttggg ttttggtttt gtttttttgtt  2100
gctatcgtag tttatttgct ttttaagggc tctatttttc gttctacggc atttttataa  2160
tttgccaata taatttat                                               2178

SEQ ID NO: 53           moltype = DNA  length = 2439
FEATURE                 Location/Qualifiers
source                  1..2439
                        mol_type = other DNA
                        note = pAP1
                        organism = synthetic construct
SEQUENCE: 53
aacaagggtt gttcgcgggg acaaaactag ccccaagctc gcgtttccgc gaacaatccg  60
cgttagtacc ttgacgcggc tttacccagc gcgcctacgc gccgagattt cgcagttcct  120
gcatacttta accagacagt tttaacacta cgagacaaga aagcgccccc ggcagtccgg  180
caagactccg agggcaactg gaagattggt ccttcctcta atgaatagat tatctgaaag  240
aacggcgtta agccttccgg ctcgccagat tcaaaaagtt atccccgccg caggcggaag  300
gtcgctgaag tccttcgaag ggatgacggc gacgtggtcg gcgcgaggag gagcctccag  360
cgacgaacgc agcagagaca agcgaagcca aatcccttcg aaccggaggg aaggacgctc  420
agcgacccat ccccttggca atacggtatt aacttttcca gtatcaaacg agagcaagaa  480
aacagctaaa tctcgccgtt ctgagagata cgaactcaga gacggattag ccgaaatctc  540
gaccattgag tccgtccgga agtgtggccg cgtgcccgtg gcacctctcg tctcgttgcg  600
agcaaaatct gacggtaaag gcgccggata tggtggtttg cacacttgtg gaagcgtctg  660
ggcgtgccca gtctgtagcg cgaaaatcgc cgctcgccga aaaaccgacc tccaacaggt  720
cgttgaccac gccgtaaaac acggaatgac cgtctcaatg cttacgctca cccagcgtca  780
ccacaaggga caagggctaa aacacctctg ggacgccttg tcgacggcat ggaatcgcgt  840
tacctctggt cgtcgttgga ttgagttcaa ggagcaattt ggtttagtcg gttatgttcg  900
agccaatgaa attactcatg gaaagcacgg ctggcatgtg cattcccatg ttctgattat  960
ttccgagaaa gacccgctga ccagcacgtt tgtctatcaa cgcaaacaag gacgccgccg  1020
ccttccctac cccccagaga tttatatgtc atccgatttc attgctgaac ggtgggaagc  1080
tggccttgcg aagcacggcg ttgattttct ccgcgattcc ggaggcttgg actggaccgt  1140
tgcgaaagac gcgcgagcca tcggcaacta tgtcagcaag atgcagacgt ccacagacgc  1200
gattagctcg gaagtcacgt tgggcggctt caaaaaagcc cgaaacggga acaggacgcc  1260
cttccagata ctcgcggata tcctttcgct cggcgatgtc gacgacctca agctctggaa  1320
agaatatgag aaagcttcgt tcggacgccg tgcacttaca tggtcgaaag ggctcagaga  1380
ttgggcaaat ctcggcgttg aacagtccga cgaagagatt gcctctgagg aaatcgggga  1440
cgaagcaata gcgctattta cgcatgacgc ttggcgtcag gtgcgacgtt ttggagccgc  1500
tgaactactc gatgtgaccg aatccggagg tcgtgcggcc gcttaccgct ggttggattt  1560
tagggaaatt gattggtcat tgcctccgaa aatcgagtga agtcgtcaaa ccatacttta  1620
agtagaggtc gagaagtccg tggaaaagtc gcggcgcctc tactgcgaaa gtaggtattt  1680
atcgatgttt ttcatcggaa aatatagaac taaattccag cccatcgcgc catgcaaacc  1740
ctccccgatt tttgacggca acggcaaacg cacaggtgaa ttttcttcgg agaagatgcg  1800
```

```
gactcaagca atcaccgaag acggccgcct cgtcgagctc acctcgattc ctccccagtt  1860
cgtccagttg attgatgacg ctgtgaagag tcgggaactt cttgaattcg agaaggtcaa  1920
tcttgccgta ttgccgcgca acggaggcgg aatttccacc tacctgacac taggggaagc  1980
cgtccacgtc cccgctccgg tcgtcgtgga ggtctcggaa tgatgagcga accctacgga  2040
atcagttcga acgctgaact gcaactcgtt tttagccgtc cagctaaacg agaagcccgt  2100
ctgtatatgt ctcggattct caagaaagaa ctggaatcag ggaagcactc gacgccgacg  2160
gaggccttgg aatcatgcga aaagctctac tggagcgttt ttgaaccgcg acttgttgat  2220
gttgttttgc acgaggtcgg agaatgccgg tgcgcgggta caaattccgc ggttgcccgc  2280
tcgctctcct ctcgcgcatt cattcctgca aggttcgttc aatctcttga aaatggggga  2340
cgcaacccag cccagctcct gacccaagac caagttgcag gtatgcggaa aactttagga  2400
acaaggtgac cacagcgtca cctgaccacc cttttcgtt                          2439
```

```
SEQ ID NO: 54          moltype = DNA  length = 2697
FEATURE                Location/Qualifiers
source                 1..2697
                       mol_type = other DNA
                       note = pWKS1
                       organism = synthetic construct
SEQUENCE: 54
gaattcatgg tgttccagga tgatgacgag ttgcgtttcg ggcgcaccat cggcggcagg  60
gtccagaccg ccccaggccg acgctttgca atcctgcgct gcgccaagat caagaccctc  120
ggcaacatgg gcgccagcct tcaacacacc ttccgggaac gcgaaacccc gaacgccgat  180
cctgcccgcc ggaccgacaa cacggttctg atcggcggaa cagacagcgc tgcggtcctc  240
gatgcatggc gcgcccgtgc gccggaaaaa atccgcgcca atgccgtgca tgggctggaa  300
tacttcgttg gcggatcacc cgaggccctg aaggccatga gccgggatca gcaggacgcc  360
tatttccgcg atgccctgaa ctggctcaag acccggcatg gagccgaaaa catcctctca  420
gccgtcatcc accgcgacga gaccaccccg cacatgacgg ttatgaccat cccgctggac  480
caacagggca agctcaatgc ccgcgctttg gtcggcagcc gtcagcagct ctcggctatg  540
cagaccgact tcgcaaaggt tgtgggacag gcgcatggcc ttcagcgcgg tctggaaggc  600
tccagagcca cccacgagcg ggtgaagcgg gtctatgccc atatcagcga cccggaagcc  660
tctgtgagcc tcccagagcg ccgcagaggc ggtttcatgg gtcggggtgg ggaaacggag  720
gcagaatggc gggaaagggc cacagaagcc gtcacagagg cgctggcggg ggtccagcac  780
gccttgcggc gggaacgccg cgacagggct gcagagaccg aggcactgcg tcagcgcctt  840
cagggcagtc cagatcagca gcaggtgaac cagagactgg aacggcaggt tgcccggctg  900
aaggccgaaa cggcccgcct gcacgacagg ctggccaagg tcaaagacga agccgatgca  960
tatcacctca atgcgctcaa gctggacgcg gcccgcgagg ttatcctgac ccatgcgatt  1020
gccttcgtcc gcgatcacgg cctagacgag gccgacatgc tggcgcggat ggaggccggt  1080
ctgaacgaag ctctggcgga gtttaagccg gtgcagcagg agcaggtcgg gacagaacac  1140
gatgccgtgc aaaaaacccg ccagcgcgat gaggggctgg atcacggaga ctaagccgat  1200
ccgccgccag ttcaggccgt ccggccccgg attctgacca taatttcatc gaaaaaaggg  1260
gcgcagccct tcttgttcta atagttctat aagttcaggc gaaaatcgtg cagcaattac  1320
aaaaggttgc gcgtctataa gtggggaatc cagccgcaaa agtggggaat ccagccgcaa  1380
aagtggggaa tccagccgaa atcgcggatt gacgagtggg atttcccgcc caataaatcc  1440
accatgggaa agacactcga cgttgcccgc gaccgggcct ttgaccagac cgcgaccgtg  1500
ctgcccgccg aaatggcgcg gggggtctat atgcgcaacg cccccagcct cgcggccctg  1560
aagctgatgc atctgatgat cgccacggcg ggcgggcgca tggccgatga cgtgcgccac  1620
gaaatgcggc tggccgacat ccgcaagatc gacggtatgg ataaccacac ccgggccagc  1680
ctgaccccgc tctttgcgga actggcggcg gcggtgctga cccacgacga cccggaaaag  1740
cgggtcgtga ccatcggtgg cctgctggac gaagcccgga tcgattaccg gcacgaggtc  1800
agcggcgatc ttctggtgtc gtggaccttc cgcagcatgt tccgccgcat ggcggcggaa  1860
tcgaaccatt gggcgattct cgaccggcag accgtgttcc acctcggcag caagtattcc  1920
gtgctgttgt tccagcacat cgccagcttc aaggaatacg accacattac cggcaagacc  1980
tttaccgtgc cggagttgcg ggctgtgttt ggtatccccg agggcaaaat caagcgtttc  2040
gcagacctca acagagacgt gctgacgccc gccattgccg aaatcaacca gctttcccgc  2100
ctgactctga ccgccacgcc gaacaagatc gggcgcaccg tggccagcgt gacgattgct  2160
tgggaagaaa agcccctcga aggcaagcgc tcgaccaagg ccgaactgga ccgcccgaag  2220
gtgggccgga aggcccggcg cgacggcacc gccgagacgg tggcacgggc cttcccggca  2280
tcgggcggga tcgagttcga ccagcattgg cgcgacctca agcgggcggc gggctgcaac  2340
atggacaaca ccatgatcgc cgacaaattc cgggcatggt gcgccgggaa gggcctcgct  2400
ctcgatgccc ggaacatcga acaggcgttc agcagcttct gcaccaaggt gggccgggtc  2460
tgagacccgc cgcgccggtc gctcgatacc tgtggtctcg ctccctctgc ggctaccgtc  2520
agcgcctcgc ctgcatcgcc gccctttccg atcctcatcc cgccccagcc ttatgggggg  2580
atgaggatcg ggccgggact gaaacccgaa gggtaatgaa tgtgtctttc cctgcttggc  2640
agggcgaacg acattcggca gaatgtctag tgagtacaca ttcattaccc ttcaggt     2697
```

```
SEQ ID NO: 55          moltype = DNA  length = 1952
FEATURE                Location/Qualifiers
source                 1..1952
                       mol_type = other DNA
                       note = pLME108
                       organism = synthetic construct
SEQUENCE: 55
gcagctcaag cgcctggtcg atccgttctc gcacaacgat gaagcgctcg aaaacatctt  60
cttcttcccc cggttctgac atcgctcccc cagtcatcgt gccgtgctag tgctaccggt  120
tcgggtgtgg cgggcgggct gcgccaccc aaggggtccc gcgcctcccc gtccgccgca  180
cccgaaccca tcagcccgag catcgccgca acgtccgcag gaagatcatc aggagtcggg  240
agaccgcaac agcacccacc cgacaaacag acctccacag ccacgagacg gcccccaggg  300
cggccagctg cccgacgatc agccctgttc atccgagacc ccctcagaag accgcagacg  360
cgccgcaacg tccgcacccc agacgtccac gtcctgcccg aacacccgcc gaaactcgtt  420
```

```
gacctggcgg tacatcgtgc tctcagccat gaccccggcc cccagcaggc cggagcgtcc  480
gccgtagatg tgccacatca gccagaaccc aagcagccgt tgcaccgtgc tccgagcaac  540
accgagggag agcgccgaca caccggggat catgccgctg atcagcgcca gcacgtccca  600
cggacccaca ttcttttccg acttcttctt cgccatttta gtccacctcc accaattcgt  660
gttcgattcc gtgctcttgc agccaccgcg ccaagccagc ttgaccgccc aattcgcaac  720
ttcgcagaca ctcgtagagc ttctgctgcc cgacgaggcg acgccatccg tcacccgtga  780
tcaaagcgac agtgtcagcg accgagccga cctcctcagc cgcgatcacg tcgtcagatt  840
cctcaaccat gaggccgagg cggtccctca ggcccgcaga ccagccaatc tgtctgcgtc  900
cccggctacc cttctcccac tcgaaccaca ggccaacctc tttcgccaag ccgttggccg  960
cgtcgcccag cacctcccaa gtcgatcgag tcgagagcgc agaacgcgcc gtcttgctct  1020
gggagttcgt caactcgtgg ccgatcttac cttgaaattg tgctttgctc aggtagcgcg  1080
cgaggtggtc gaggccagtt gctgcgctca tctgctgaac gtcttgcgcg cgagcaaggg  1140
gagtcccgag gcccgccgcg agcacgccgc gttcccaacg gccgaacatg gaccggtgca  1200
gcgccagagc gtcgccgaag tcgcccacga ggaacacgag cacatgcaga tgcacatgcc  1260
acccattgcg cccgtgcgta acctcgacca cacgcacgaa gccctcgacc ccgtgacgga  1320
gctggtccga ggtccagccc ttgcccgaag tgactcgccg ccaccccgaa gcgacaccat  1380
cccaaacagc cgtcaaggaa tccttacgag agtgccgaac cgtgaacgtc atgaacgcca  1440
cacgaccacc gtgcttagtc cacgtttcga ccgccgcgcc gagttcaagg ccacgccgag  1500
ccatgatctt cgcgttacac accgggcagg cccagaccga tccgcagctc tgcaacccag  1560
cgaaaccggc ccggccgtcg ctgcaccgca caccaaccga agcgaccgcc gaggcggcaa  1620
cacgaccgca gaacgcaacg cgcttgagcg acgtatgacg ccacaaccaa taacggaccg  1680
aaaaccggtg tttgcgcttg tcggcggcca cttcaccagc ggcgggcacg gccgaaggtg  1740
aaacattgtt cgcatgatta tctagggcgc cccctagcgg ggccaccgcc gggctgccgc  1800
ccccacaccc ccggacgcca cgacttcggg cgcgggcatc gaccaccatt ggtcgcgtac  1860
tctgggacaa ggaagacccc ctgctagttg atgctgattc gacaccagac acgctagcag  1920
gggttctctc agttttggga gttctcagtt ct                                1952

SEQ ID NO: 56          moltype = DNA  length = 4408
FEATURE                Location/Qualifiers
source                 1..4408
                       mol_type = other DNA
                       note = pLS1
                       organism = synthetic construct
SEQUENCE: 56
ctgcagaagt agtcgctgat tggctaattc agcgtatcaa agacaaaggc gaccaaaaat  60
agcttgagtt cttttagaac aaaaaagaaa gacagtagtt gcacctactg tctttctttt  120
gcgttgtgct tttagttcct cgaactttta gcgtcaagca tattatatca tggggcgaga  180
aattctgtca aaataatgct ataatgcttt tgaggcacct cagcgatacg gtcggtggtg  240
tgaatctcat ttacgtaggg cgactggaaa cggatagctc aaagggcgcg tttgagtgtc  300
gggtgtggga ctgccttcag cttcgggctg taaagacccc tgatactttt gaatgagatg  360
accctttggg gtctttttttg tttttttagg gagatgttgt gggggatttt ttctccgaaa  420
aaatctaaaa tatggggggg ctactacgac ccccccctata gtgccgagtg ccaaaatcaa  480
aaaaaaaacg cctttagcct tagagctgca agggtttgag gctcgtcaaa tctcggcgac  540
ttttcggcga cttttcggcg actttttaga gattttttgg gaaaaatacg aaaaagattg  600
cattgagtgc acggttatgc tactatagtt ttataaaatt ttgagaggtg acgcatgaaa  660
aaaagattga cgataacatt aagtgaatcg gtacttgaaa atcttgaaaa aatggcaaga  720
gagatggggt tatcaaaatc tgcaatgatt tctgttgcct tggaaaatta caagaaaggt  780
caagaaaaat aaaaaaagcc gtgctggcag gcactggcta aagtcaaaca tttcttgggt  840
atattatact ttatggctaa agaaaaagca agatacttca ctttttttact ttatcctgaa  900
tcaattccaa gcgactggga gctgaaactt gaaacgcttg gagtgccgat ggcaattagt  960
ccattgcatg ataaggataa gagtagtatc aaaggacaaa aatataagaa agctcattat  1020
catgtgcttt atatagctaa aaatccagtt actgcagata gtgtacgtaa aaagattaaa  1080
ttattgcttg gtgaaaaaag tcttgcaatg gtgcaggttg ttctcaatgt cgaaaatatg  1140
tatttgtatt taacgcacga gagcaaggac gctattgcta agaagaaaca tgtttatgat  1200
aaggctgata taaagctaat caataatttt gatattgacc gttatgtgac gttagatgtc  1260
gaggaaaaga ccgaactttt caatgtggtt gtatcgctta ttcgtgcgta cactctccaa  1320
aatattttttg atttgtatga tttcattgac gaaaatggag aaacttatgg gttgactata  1380
aatttggtta acgaagttat tgcagggaaa actggtttta tgaaattgtt gtttgacgga  1440
gcttatcaac gtagtaagcg tggaacaaag aacgaagaga gataaaaagt tgatctttgt  1500
gaaaactaca gaaagtaaag aatgaaaaga gtaatgctaa catagcatta cggattttat  1560
gaccgatgat gaagaaaaga atttgaaact tagtttatat gtggtaaaat gttttaatca  1620
agtttaggag gaattaatta tgaagtgtaa ttaatgtaac agggttcaat taaaagaggg  1680
aagcgtatca ttaaccctat aaactacgtc tgccctcatt attggagggt gaaatgtgaa  1740
tacatcctat tcacaatcga atttacgaca caaccaaatt ttaatttggc tttgcatttt  1800
atcttttttt agcgtattaa atgaaatggt tttgaacgtc tcattacctg atattgcaaa  1860
tgattttaat aaaccacctg cgagtacaaa ctgggtgaac acagccttta tgttaacctt  1920
ttccattgga acagctgtat atggaaagct atctgatcaa ttaggcatca aaaggttact  1980
cctatttgga attataataa attgtttcgg gtcggtaatt gggtttgttg gccattcttt  2040
cttttcctta cttattatgg ctcgttttat tcaaggggct ggtgcagctg catttccagc  2100
actcgtaatg gttgtagttg cgcgctatat tccaaaggaa aataggggta aagcatttgg  2160
tcttattgga tcgatagtag ccatgggaga aggagtcggt ccagcgattg gtggaatgat  2220
agcccattat attcattggt cctatcttct actcattcct atgataacaa ttatcactgt  2280
tccgtttctt atgaaattat taaagaaaga agtaaggata aaaggtcatt ttgatatcaa  2340
aggaattata ctaatgtctg taggcattgt attttttatg ttgtttacaa catcatatag  2400
catttctttt cttatcgtta gcgtgctgtc attcctgata tttgtaaaac atatcaggaa  2460
agtaacagat ccttttgttg atcccggatt agggaaaaat atacctttta tgattggagt  2520
tctttgtggg ggaattatat ttggaacagt agcagggttt gtctctatgg ttccttatat  2580
gatgaaagat gttcaccagc taagtactgc cgaaatcgga agtgtaatta ttttccctgg  2640
aacaatgagt gtcattattt tcggctacat tggtgggata cttgttgata gaagaggtcc  2700
```

```
tttatacgtg ttaaacatcg gagttacatt tctttctgtt agctttttaa ctgcttcctt  2760
tcttttagaa acaacatcat ggttcatgac aattataatc gtatttgttt taggtgggct  2820
ttcgttcacc aaaacagtta tatcaacaat tgtttcaagt agcttgaaac agcaggaagc  2880
tggtgctgga atgagtttgc ttaactttac cagcttttta tcagagggaa caggtattgc  2940
aattgtaggt ggtttattat ccataccctt acttgatcaa aggttgttac ctatggaagt  3000
tgatcagtca acttatctgt atagtaattt gttattactt ttttcaggaa tcattgtcat  3060
tagttggctg gttaccttga atgtatataa acattctcaa agggatttct aaatcgttaa  3120
gggatcaact ttgggagaga gttcaaaatt gatccttttt ttataacagg aattcaagag  3180
ggcaatggct gatatggaac tcaaagagga acttcttgaa aaatatcatg caccgctttt  3240
tgttgatgag agaacaggcg agttgaacaa tgacacggaa gctttttggc atgaaaaaga  3300
gtttgctgat atgtttgaag ttcaatctcc gatacgtgaa acaactaacc aagaaaaaat  3360
ggactggtta agaaaacagt accaagaaga gctgaaaaaa ctagaatcgt ctaaaaagcc  3420
cctagaagac gatttaagcc atttagaaga gttgcttgat aaaaagacca aggaatatat  3480
taaaatcgat tctgaggcct ctgagagggc ctcagagcta tctaaagccg agggatatat  3540
aaatacccta gaaaatcatt cgaagagctt agaagcgaaa atagagtgtt tagagagtga  3600
taatctacaa ttggaaaaac aaaaggcgac aaaactcgaa gcgaaagcgt tgaacgagag  3660
tgagttgcga gaactaaagc ctaagaagaa ttttctagga aaagagcatt atgagttaag  3720
tcctgaacaa tttgaagggt tgaaggcaga agtttatcgt agtagaactc tattgcacca  3780
caaagatatt gaactggagg aagcaaaacg tcaagtatct ctgagagcct ctaaaaacta  3840
ttttacagct agtttagagc gagctaagga aaaagctaaa ggtgagagta tagaccgtct  3900
taaaagcgaa ataaagcgac taaaaaacga aaattcaatt ttacgtcagc aaaatgacaa  3960
gatgctaggg aaattaagag agttaatgcc tgataaagcc tttaagaatt tgttatcaga  4020
acttaaggcg attaagccaa tcgtgaatat aattaaaaag gctattgaaa agagcttgtt  4080
ctgagcgatt tatgccgtga aagctatttg acaataagca gtgacagagt acgctaggac  4140
gtgccgagcc gaaaggcttt agcgtttcgg acggacacgg acaaaggacg gcagtcactg  4200
gttacttgtt gtcaaataga ccatggaata aaaagcgtca aaagtcttga gtggatgata  4260
ccctatggta ctctattcgc cttttgactt ttttgctata atttaagtgt cgccagttct  4320
tccgtcaggt aatgcgaact tagactggag gtgagcgttg tgaagacatt cctcgagctt  4380
gtctttgtcc cttttgtggt tggcgttg                                      4408

SEQ ID NO: 57           moltype = DNA  length = 5804
FEATURE                 Location/Qualifiers
source                  1..5804
                        mol_type = other DNA
                        note = pUB6060
                        organism = synthetic construct
SEQUENCE: 57
actgcgatgt acgatagatg ctgtattaag caagtacaca cagcgtcccc tctgcgaggt  60
gccgtctgtg actggttcag gggctcgcc gcccccgaa accccctagca tccactgcga  120
aaattcgcac gttgggtgcg aaactttctc agcggattct catggaaaag cgcaccaaag  180
agatcaaaat cagactcacc gaagcggagc atcagcggtt acttgaacgc tgtgaccgaa  240
cgcatttggc cgagtggtta cgtgccgttg gtttaggcga atcgcggaca gctcgtcgtc  300
gtccgctacc taccgtagac ccgatcttgt tacgtcaggt cagcgggatc ggtaataacc  360
tcaatcaaat agcccgttac ttgaatcagc atggcttacc gccgcaagaa cgggtgtcgt  420
tgttagatgt gctcaatagc attgaccaac atcttgccga actgctggag caacatcatg  480
atcgttaaga ttcatggtcg tggtgccggt ggcgggagtg gccctgtcga ttaccttctg  540
ggccctgatc gtcagcgtga acaagcgacg gtgttacggg gtaaccctga gcacgtcaaa  600
gagctgattg atggctgcga atttgcccga acctatacct ctggcgtgct ctcttttcag  660
gagagcgact tacccgcagg cgaaaaaaca gcgtttgatg gagaatggga gcagacattg  720
atgaccggtc tagataaaga ccagtatgcc tgcctctggg ttcaacatca ggacaaaggg  780
cgtcttgaat tgaattttgt tatcccgaac atcgaattgc agagcggaaa acggctgcaa  840
ccttactttg atcgggctga ccggcctcgc gttaacgcat ggcaaaccct caccaatgac  900
cggcttggat tacgcgaccc gaatgacccc gccaatcgcc gagcattaac cccctcgaat  960
gaccttcctc gcaacaaaca gcaggcagcg gaagccatta ccaaagggct aatcagcttg  1020
attgagcagg gagaaattac ggatcgtaaa ggggtgattt cccaccttac cgatgccgga  1080
ttgtcggtcg tacgggaaac caaatccagt atcagtattg ctgatccggc aggtggcccg  1140
aatattcgct taaaaggagt gctgtatgag cgagatttta aatttagcgc gggagttcga  1200
gagcaaatcg aagcagcaag ccaagactac cgcaacgagc gtcgcgagcg cattcgagaa  1260
gcacgagaaa cgtatcaccg aggccttgaa attaagctca gggaacatac agaccgctat  1320
ccaagaagag aacgacaacc agctaaaaca gatacaccgc ttagtcggaa tgacatggct  1380
gtacagcctg gcattaagcg cgatcctgtt tgcgacattg attggagtag cttggtatct  1440
cgggactatc gtggtcgaac gccagaacga aatcagcgag cagagccaga tcctgcagga  1500
cttaaagagc cagaccggag ccggcgtatc gataattcac gattccaaga acaagagcgt  1560
gtattacctg atccttccgc agggggcgaa gcagatcgac gagtacaaga acgctcaaca  1620
tcgtcaggtc atcaagtaca gcgccaaata acctcatcag acgccacaga atcgattctg  1680
ggcggtttta tctatcaggg tgaagagatt catgccgaaa tggcagcagc agcttctgag  1740
cgcattagag agcttacaga ggcactacga acaacagcag caagcgtggc aggacagcta  1800
cgccaactta cagcgcatgt tcgaggttac ctcgcaggag ttggcgaaaa acgacagggt  1860
ttgtcaggcc ttgagcatgc aagtcaccgg cttggcgcag caagtcgaga gcttaaacag  1920
aacagtgcgc cgcttgagca attagccaag cggcacgaac agcggcattc tcggcggtca  1980
cggcatgagt ttataagcgt ttatcggcag catcataagc ggcagaacgc tcgcgcttac  2040
cgaccgccac cacgaatacc gtaatggttt gatcgcgaac ctgatagacc aaacgataac  2100
cggatgctcg tagcttgatt ttgtagcaat ccggcagctc tcgcaggcga tttttatcga  2160
tccgcgggtg ctgtagaacc tgctcgagtt ttttcttgaa ctgcagacgg acatcatccc  2220
cgagcttgcg ccattccttc agggctcggg gatcaaactc aaggttatag ctcatccagt  2280
gacaccttta cgcccgcctg tgggttttcc agacgatccc gaacgatagc catcaaatcg  2340
gcatcatcct cggtcagcaa cacctgctgg aacggcaagc gtccgctttg ggccacatac  2400
tccagtgttt ggcgcagaac ctcggacggc gttacgccca gcttttccag tgcggcataa  2460
gagcggcttt tcagctcgtc atcgatccga atattaatcg tggccatcat ctcacctctt  2520
```

```
gatgtagtga caagtgtatc tacaagaagt agtatgagcg taaagccgtg cgagaacaag  2580
caggaataac ggattgtcgg ggatgacaaa aaccgttgtt gaggtgtaac ttagcggcag  2640
aaaaaacaaa gccccgaatt catgtgctca acttggcgga agactcatga aattcagggc  2700
taggtcgaaa cctagaaagg atattagcac atgcagcgtg caaaacaaca gccccgccat  2760
aaggctggga gccatggcta atcaggcttt aacgcttttt aacgaccggt taccccacaa  2820
gccgtacttc tccgatgatt tacagtttgg tgtccgcatt gccggtaaag agcgtgctct  2880
cctcgcaaaa tacatccagt ttaaccagcc ccacgccatg tactggcttt gctttgacgt  2940
ggacagggcc ggagccgcga ttgattgggc cgatctgggt gcacctgcgc cgacactcac  3000
catcaaaaac cccgataacg gacatgctca cctgttgtat gccttgaaca ttgcggtacg  3060
caccgcgccg gatggtcgag gccgcctcct caaatatgcc gccgccattg agaatgcgct  3120
gcgtaaaaaa ttgggcgccg atgcggggta ttcagggcta atttgcaaga atccgaacca  3180
cctgcactgg cagatcaccg tctggcagcc tgagctctac accctcgact ggctagccga  3240
ctatctcgac cttggcgctg ccaatgaccg agaaatcctg cccgactacg gtttaggccg  3300
taactgcacc ctattcgata aaacccgcaa gtgggcttac cgcgctatcc gccaaggctg  3360
gccggagtat agccaatggc tacaagcctg cattgaacgc gctaaagcct acaacctgca  3420
gttctccgca cctttagacg agaacgaagt catgggaatt gctaaaagca tttccaagtg  3480
gacaatggtc acttatcgca gtctggggtt tgatgagtat gtgaagttaa ctcattcacc  3540
cgaggtacaa gcatatcgcg gtcggcgaag taaaggcggt ggtagaccta gtattgggga  3600
accatggtta gctttaggta ttagtcgtcg aagttatttt agatggaaaa agctaggtaa  3660
attatgaaaa taattagttt tatcaatatg aaaggtggtg ttggtaagtc tacggttgct  3720
attaatgttg ctcattgctt agcggagcga aatcaaaaaa aggtattgat aattgatatt  3780
gatcctcagt ttaatgcaac tcagtgcgtt atgaaggcag aggattacat agagcatatg  3840
cgtacgggta aggatactat ttgttctttg tttaactctg accgagttgc agctaaaagc  3900
gttagtggac catcttttga aaaatgcaaa gatatcagta gcatatctcc tgttgaaatg  3960
tctgagtatt tgcatatttt acctggtgac cttggtttgc atcgaattga ggttacagct  4020
gggagcgggc aggagttcaa gttaaaacga tacttggatt ctatcagtga caagtatgat  4080
tatgtgattg tggatactcc gccaacacca tcaatatgga tgtctagcgc attgatagct  4140
tctgactatt atataatacc ggttaaacca gatccgttat caaggacggg gattgattgc  4200
ttgatagtat aatagcagat aaaaaaggaa actttgattt aaaaataaaa tgtgctggag  4260
tggtgtttaa tatggttgaa gaaaactgtg tttagagaga ctaagagttt ttttaataac  4320
agtgatactt ggcgcaatta catttttaga tctttcctgc ctaagaaagt tgcgatagct  4380
aaaaggcaga catcaggaga acatatatta aagacaaaag attcctcttt gcacatgaaa  4440
cttgtcagag tggtcgatga aatcgaagag agaatacagt aataggataa cgtatggata  4500
agttaacaac taaagaaata aagacgttat tgaatttcat tgaagagttc tcttggattt  4560
caaataaata taaaaatttg gataccaata agttatatga ggctcttaat aattgcgagt  4620
ctcgtcgtca aaatgaatat aatgattata tttcgtactc aaaaagtgta ggtaagaata  4680
atcatgtgtc atataggaat agccttaaag ataagacatt tctaattggt aagctcccat  4740
ctcttttgat ggataaagaa ttgttctcta aaaataagga gctatctgac tttgctcgac  4800
tacttggtgt tgaggtcaga ttccctgaga aacgttctag agatgagata atcggcacta  4860
ttatttgctc attacaagag gaaagtagtg ttaaaagaat tcatgagatt ggtgagttta  4920
tctatgcttt aactagcgat gaaaaactaa tgaataacat taaggttgag aagaaaatat  4980
ataatgatga gtatgattgg aataatgtaa ttagactttt atttatgggt aaatgatgtc  5040
tagattgata gggaaagact ttgatttatt tttaggcttc tttttaaatt acagccttaa  5100
agatttggca tctaatggtg attttaaaaa gaagctgcgt gaggcacaca aaaaatacta  5160
tccgttactc actcttagcg ctgagcttga tctcatgttt aggggggatg tgggagagga  5220
ttgtgctgat agggttaaag aaacttgctc tgatataggt tcgtctattt ttttattagc  5280
ccatggaatg tataagcaat ccaacatgtc attgcgtagt tctattgaga actttttaaa  5340
atcaataggt tgcaatcatt gccctgacat attaacagat aagagtgttt tttctgtttt  5400
tgaaaaggct gggcaattag agttattttt agatcctgtg ttcaaatgca agtttgatga  5460
gttgcaatct atttactcat cgttgtgctt atatactcat accgcaagtg ctgaacacat  5520
ggctaaaatt agtgctatgg gcagtattcc aaaacatgat aaagcgaaaa gcgctattct  5580
tgttaatgac ctcactaggc ttgttcgaat ttatcttttc atttacacga agttgtttag  5640
gtgtgaattc ttcaaattta accatgacaa ccgagatgtc attctcagcg cattaaccaa  5700
gtcgcaacga cgttcgttaa tggaaccatc ctgatgtggc actaaacaac ctatatcaga  5760
taacagccct gcttttgcgg ggcttttttgt ttgtgcgtga tgtg                   5804
```

```
SEQ ID NO: 58          moltype = DNA  length = 1711
FEATURE                Location/Qualifiers
source                 1..1711
                       mol_type = other DNA
                       note = p545
                       organism = synthetic construct
SEQUENCE: 58
ggtgccatga gggttctcac tgatacctga atgagtttga cggtggggcc gcatgcacga  60
ctgccatacc gtcaatccga gcgccgcaga ctgggcatgt ccccctgagt aacacttgcc  120
caccgggttc aacgtccgtt gctgatgccc cccattggct gtagccacaa tggccgcagg  180
ataagaacgt ggcgcgcact gtgcaaccgc acgcgaacgt agtgccaagc ggtgcacgat  240
caagaaaatg ctcatcgtgc ggcgttacgg tcatgcgtca gttcgattct tgttcagcgc  300
gtagtgcacg gtgcccacgg aaaccccgac ctcggcagca atcgcacgca tgctctgacc  360
ctccgagcgg agctcacgaa tccgcgcgtg gcgtgcggca acgcgggcca cgaactcctc  420
gcgtggctcg gaagtccacc gcttgacggt ggactcggag acaccgagct ttttcgcagc  480
agcggcgatg ctgtagccgt tgcgggggag acgttcacgt gtggtcatga gagaccctcc  540
aagaactgtt gacgggtatg ggcgcgccgt gatgcgccac tggcaatgcc gcctttgtgg  600
ccgccttctt tgccgccttt ggatgctcca cggaggctga tcgctttctg gcgtgcgcgg  660
aaggtttcgg gggtgaagtt gcgccagacc catcgggaaa tggatcgaga taagtgctta  720
agttcgttca agccgagggg gcctgtggcg aattcgtcgg cgatgatcgt ctcgttcagt  780
aggtggatgt gctcgaatac ggtgtgctcc cattcggcga ccgggccgcc ccaggagtgc  840
cggacggccc ggtatgccca catgcgggtg gtgtcgaaca gggtgacgtt gcggccgacc  900
gttgatcggg tgacgttgcg acgcgggttc cctgcctccg gcagtgcgtg gatctcgtcg  960
```

```
agggtgtgtg cgagggcgcg cagctcgtag agcgcgtctg cggggcccca gagggtcgca  1020
tgggcggtgc tgagcgggtt ctttgtgatc cggtgcccgt aggatgcatc gccgccgaga  1080
acgtcgcata ggccctgctc gacgcgggcg agcaggttga taggccgtcg ccgcgcggca  1140
tcggtcagac acacagggtt cttcaaggca tagacgatgt gtccggtggt cgtgacacgg  1200
ttcatggaca cgtaggacgg tgaaggcagc ccagcgaggt ctgcggccca gtcagcatcc  1260
gaagcatctc gatcggtgat gaccaaggac tgcatgacca acgggttcgc ttcgatgtaa  1320
ggcagctcca gcgccctctg ccgagtcacg tgccggtacg ccccagactt ctcggctgac  1380
gccagcggct tgcgtggcag ccagctctca gggaacaacg tctcgaacga atccatacat  1440
gcagtgaagc atgcgagtca cgttcagcgt ggtccattcc tcggcgtgtt caaagtgggc  1500
gacgaagacc ccatatcagt tagttacccg gttgagccat gtgagcaaag cgaactctct  1560
ttccacatcc cctgccaaac atcccccgac tcccctgacg ctgccacctg ctccaaggga  1620
tggctggggc gtgttcgggc attgcggcta gttcctcgcg cagctgtgcg atcttcgcct  1680
gaactgctcg ccggctgtca gggtcgacgg c                                 1711

SEQ ID NO: 59          moltype = DNA  length = 7426
FEATURE                Location/Qualifiers
source                 1..7426
                       mol_type = other DNA
                       note = pJD4
                       organism = synthetic construct
SEQUENCE: 59
ctgcagcaat ggcaacaacg ttgcgcaaac tattaactgg cgaactactt actctagctt  60
cccggcaaca attaatagac tggatggagg cggataaagt tgcaggacca cttctgcgct  120
cggcccttcc ggctggctgg tttattgctg ataaatctgg agccggtgag cgtgggtctc  180
gcggtatcat tgcagcactg gggccagatg gtaagccctc ccgtatcgta gttatctaca  240
cgacggggag tcaggcaact atggatgaac gaaatagaca gatcgctgag ataggtgcct  300
cactgattaa gcattggtaa ctgtcagacc aagtttactc atatatactt tagattgatt  360
taaaacttca tttttaattt aaaaggatct aggtgaagat cctttttgat aatctcatga  420
ccaaaatccc ttaacgtgag ttttcgttcc actgagcgtc agacccctat ctataaactc  480
ttggcttggt tctaatccct ctaaacgatt attatcaata gccgctctaa ccgctttttc  540
tcggcttaat ttttctgtct ctgttataaa attgctattc atcttgttct tcttcaaaaa  600
aaagttaagt aaaataccta cctaaatttt tactagttcg caatctacga gcttataacc  660
tcgtttttc aattcattta aaaaatcaga ttttgagcct aattttgatc tattgctatc  720
gttacccgct agaaataccc agtaattacg caaatcttca ttggtaactt tcgtaatatc  780
ggtgtaatga tcttcgagta tttttaagca atctctagcc cataaaccgt actcgtgatt  840
gctcatctta gggttttgct tatcgagttt gacgaacttc ccatacttgt ttttatgtgg  900
aaatactggc cgttttgcaa cttcttcaat tttttgagct gttcgttttt tactaccaat  960
cacaaaattt aaagagtgaa tagtacgccc acgcttgatt tgttcaacct caacgactaa  1020
atcagatttc tcgttaatct cagttattgc aggttccaaa acacgttgat ttaatgaatt  1080
aaatctaggg tatttatttt caacctgaag ccattctttt agtttttcta ctgtaatttc  1140
acgactacca acagagcgat attgtgtaat tagctcataa attcgaattg aatgtacact  1200
gttgaaataa gcgatatgtt tgagttgata ttgcgtgaat tgccctttaa gttgcgttag  1260
gtatggcata acttcatcag tcattgcaat tctaaaacgc ccctctttct tgaaatatgt  1320
tctagaggaa acccaacgaa attcagttac acggtcttta tcttcagttt taacacttcg  1380
gtcataaatc cgttttatag ccgcctgaat ttgcttatag gcgttatctt ggcttatttc  1440
tggaaactca cggacaaaat cagccaccgt aaaatcaaaa atcttttgat tagatttcgg  1500
atccatagtc ccaatagtta aagctaaaat tctgatttca tcaatactca atcggtaatt  1560
ggcttcaata aggctattag cctttacaac aactaaatca tttggcataa gacaacaaat  1620
ttcctgttta aaacaacaag caaaatatac ctgttgttta tatataaaac aacaagtatt  1680
ttcttaaaag ttgtctataa caggaaattt gttgtcttat aacaggaaat ttgttgtcgt  1740
ataacaggaa atttgttgtc gtataacagg aaatttgttg tcgtataagt ttgtaactta  1800
ttgattttac tggttttaaa aacgccgaaa acaagtaaaa aacaaaaata taaaaatata  1860
gggactttcg tccctttttt gggctttcag ccctaatttt ttcttttttc aggattaaaa  1920
attacaaaac ccttacagag caagtaaact tgtttgcttg ttctgcaagg gttcagcaac  1980
cgaagccgtt aggcgtaggc ggtagcctat aaaagccatt taattttatc tttaaatttc  2040
cgtttaaatg ctttgagtgg gtgtctttta tcgtactcat caatcctttt ttgcattctt  2100
tcgtttgctt tgtgatcggc aaattttgaa taagattttt ccatctcatc taacattcta  2160
tcaatccgtt ttttatgttg ccatttcagg taaacataaa cacttatagc aataaaagac  2220
aatatcaata cattgtaaaa aatgattgtt acaatttcgc tcacagttat tttttacctt  2280
tttcaatttc ttcattgata aatgcactca attcatcaaa tttcttgtca tcattgataa  2340
atttacgcaa cttagggaag tttctatcta catctaaaag agggttaaac gattattatc  2400
aatagccgct ctaaccgctt tttctcggct taatttttct gtctctgtta taaaattgct  2460
attcatcttg ttcttctctc acactttaac taattcacag ttcacaatct tataccctcg  2520
attttgcaac tcgtttaaaa aatctgaccg cttaccaagt tttgatctaa aactagcatt  2580
gctagtcaaa aaaacccaat aatgccgtaa atcttctgtt gtaacatcgg caagatcaga  2640
ataaaaatct tcaaggattt ttaggcaatc tctcgcatag tttccatatt cagcattact  2700
cattttggga ttttgagtat ccaatttcac aaacttcccg tacttgtttt tatgcggaaa  2760
tgcagggcgt ttctgttcga tttttaccgc actttctta ctcttgatcg tgaattttaa  2820
tgctacgatt gttcgcccac gcttgatagg ttcaacatca acaagcagat cggatttagc  2880
attaatttca tttatggatg gagttaatac tcgcttttta aaatccttaa acagtgggta  2940
cttatcagag atacttaacc aacttttaat atcttctacg cttgtttgtc gccaacctgt  3000
atcacgatat tgagaacaca attcataaag gcgaatagcg tgcgtactac ccaaagcccc  3060
aatattgatc aatttatatt ttgtgtagtt atcgtgtaat tcagaaatgt aaggaattag  3120
ctcatcgtgg aactcgatat aaaatcgccc ttcttttta aaataggaac gcttatgaat  3180
taaagctact tctgttaatt cgtgttcgtt atcaaccagt gtaacccaac gctttgagat  3240
ttttaaaacg gcatttctaa cttgtgtgta agctatatca ggatttacat cggggaagct  3300
tttacaaaaa tctgccaccg tgaaatcaaa tccacgctta gacggatttt taggattaaa  3360
aacccccaaa gttaaagcca gaatccgcat ttcatcaagt gtcattgaat agctggcttg  3420
tacaaaattg ttagctttat ggactgttaa atcatttgtc atatcatcaa ggtggacata  3480
```

```
aaataaagat tgtcccatta taaccataca gttaaatggt ggtcaataaa aaacaaagac  3540
cactataaca ataaatttgt ccacctataa caataaattt gtccacctat aacaataaat  3600
ttgtccacct ataaatctcg caagccttgt gtaacaaggg gagccagagc ctacaaacaa  3660
gaatacaaac aagaatacaa aaaaatagag cctaaaggct ctttttgggg ctttcagccc  3720
taattttttc tttttttcag gatttaaaat tacaaaaccc ttacagagca agtaaacttg  3780
tttgcttgtt ctgcaagggt tcagcaaccg tagccgtcag gcgtagggcg gtagcctata  3840
aaagccattt aattttatct ttaaacttcc ttttaaatgc tttgagtggg tgtcttttat  3900
cgtactcatc aatccttttt tgcattcttt cgtttgcttt gtgatcggca aattttgaat  3960
aagattttc catctcatct aacattctat caatccgttt tttatgttgc catttcaggt  4020
aaacataaac acttatagca attaaagaca atatcaatac attgtaaaaa atgattgtta  4080
caatttcgct cacagttatt ttttaccttt ttcaatttct tcattgataa atgcactcaa  4140
ttcatcaaat ttcttgtcat cattgataaa tttacgcaac ttagggaagt ttctatctac  4200
atctaaaaga gggttattta ttatttcatt tagccaaaaa gcccctaata aaaccttgta  4260
atgcgtagct ttcttacgct tttctgcttg ttcttttgac ttaatcgcac gaattttcgc  4320
tttgatttcg tcctgcttgc gttgtaaatc tgcttgttgc tgttccaatc ttgtaagttt  4380
ttcgcttgcc atactagccc ctttatatag ttagaaatta tcgttatttt attcagtagg  4440
tgctaggctt gcaagtgttc tgttcattac gttaaaataa cgtaatgccc acttatcagt  4500
ttctcttcga gaaactggtg ggcaagcgta ccgcttgacc gtttcgcaat actcaacact  4560
atggcaatct atcatttaaa cgttcgctat tgcagtaaaa gcaaagggca atcagctcaa  4620
gccaaaaacg actacatcaa ccgcaatgat aaatattcaa agcggttaga tgatttacag  4680
ttttcaggct atggtaatat gccaaaattt gccgaagata atccgcaaga attttggcga  4740
ttgtcagata tttacgagcg agctaatgcc cgagtttgta ctgaaattga atttgcttta  4800
cctagagaat taaccctaga acaacagcaa aaattagtaa gttcgtttat agaaaatacg  4860
gttgatagcg gtagcaataa actaccctac tctttcgcta tccataccga taaaaataat  4920
cataatcccc attgtcattt gatattttca gaacgccaac ttgacggcat agaccgtaca  4980
gccgagcagt tttttaaacg tgctaatact aaatccccag aaaagggcgg agcgatgaaa  5040
acggcagatt ttcgagatcg tgagtttatc caatctgtcc gaaaaacgtg gagagagcaa  5100
gctaatcaag ccttagagca atacggatat gccgcacgaa ttgacgaacg tagctacaag  5160
gaacaaggca tagagcaagc cccaagagca agaattgaca gggtaacgtg gcaagaattg  5220
aaccgattag agcaagaaga acgccaaatc gtgcaagagc ttgcacttaa aggacaagaa  5280
attaacaaag aaaaatccta cttgcagaaa atcgaagaaa aacaggctca aggaatgggc  5340
aaatatgaat ccaaattcgc agctgcgttt tctaaattat cggaaagtgc cctaaaacac  5400
gatttaagca acgaaaaaga aaaagacagt aaaatacaca ctcaagaaga aaaagtgcct  5460
caaaatcgca ttcaggggct ttctcaagca gattttgatc agtttttaat tgatgaatgg  5520
ctacctcaaa tagaaaaata cgttaaagcc caagaaaagc gggacggaat ggaagtagag  5580
atcacgcaat acgacaagga tttacagcgt attcagggag actataacaa gctcacagat  5640
aaaaatcagg gttttctcgg tttatgggaa actaaagagc aaaaagcaaa gaaaaaagag  5700
cttgaagatg aatacaaaca tacagcagag caacggaacg ctaaaagcca agaattagcc  5760
gagtatagcc aaaaaataaa agcatacgaa cagaaaacgc tagagccaat caacgagaag  5820
attgccaaat atcaagctga caaccctgaa ataaaaatgc ggagcttagg atttgtgaaa  5880
aaaattaagg ctcaaggggc atataaagcg gctcaagagc gaatggagcg agaaaaacag  5940
caccaacagg aaaaacaaca gagacattta gagcgagaga gtggtttgag cttgtagcta  6000
acgccctacg cctacggctt cggttgttca acccttaaag aactcgcaac aagttgcaaa  6060
ttctttaagg gttcgcaata aaaacaaccg ctaaacattt ctgcccagcg gttgaaaatt  6120
tacctattca ccattacaat gatcaagcag gaaatttttt tgattgccgt aaatgtccgt  6180
atatctagtt gaggcacaac ccgccaaagt cattgcccca accagaacgg cgataaaccg  6240
tatatttacc gataaggcat ccggcagttc aacagaccgg gaagggctgg atttgctgag  6300
gatgaaggtg gaggaaggtg atgtcattct ggttaagaag ctcgaccgtc ttggccgcga  6360
cactgccgat atgatccaac tgataaagga atttgacgct cagggcgtgg cagtccggtt  6420
cattgatgac gggatcagta ccgacggtga tatggggcaa atggtggtca ccatcctgtc  6480
ggctgtggca caggctgaac gccggaggat cctagaacgc acgaatgagg gccgacagga  6540
agcaaagctg aaaggaatca aatttggccg caggcgtacc gtggacagga acgtcgtgct  6600
gacgcttcat cagaagggca ctggtgcaac ggaaattgct catcagctca gtattgcccg  6660
ctccacggtt tataaaattc ttgaagacga aagggcctcg tgatacgctt atttttatag  6720
gttaatgtca tgataataat ggtttcttag acgtcaggtg gcacttttcg gggaaatgtg  6780
cgcggaaccc ctatttgttt atttttctaa atacattcaa atatgtatcc gctcatgaga  6840
caataaccct ggtaaatgct tcaataatat tgaaaaagga agagtatgag tattcaacat  6900
ttcgtgtcg cccttattcc cttttttgcg gcattttgcc ttcctgtttt tgctcaccca  6960
gaaacgctgg tgaaagtaaa agatgctgaa gatcagttgg gtgcacgagt gggttacatc  7020
gaactggatc tcaacagcgg taagatcctt gagagttttc gccccgaaga acgttttcca  7080
atgatgagca cttttaaagt tctgctatgt ggtgcggtat tatcccgtgt tgacgccggg  7140
caagagcaac tcggtcgccg catacactat tctcagaatg acttggttga gtactcacca  7200
gtcacagaaa agcatcttac ggatggcatg acagtaagag aattatgcag tgctgccata  7260
accatgagtg ataacactgc tgccaactta cttctgacaa cgatcggagg accgaaggag  7320
ctaaccgctt ttttgcacaa catgggggat catgtaactc gccttgatcg ttgggaaccg  7380
gagctgaatg aagccatacc aaacgacgag cgtgacacca cgatgc                7426
```

```
SEQ ID NO: 60          moltype = DNA  length = 8830
FEATURE                Location/Qualifiers
source                 1..8830
                       mol_type = other DNA
                       note = pIJ101
                       organism = synthetic construct
SEQUENCE: 60
ggatcctcgt tgccgtcctt gccttcggcg gcccgggtcg cctcgaggtc gagggcgcgg  60
cgggtgaccg cgtgccatcc gtcctcggtc acggcgaccc cggcccgcag ctccccgccg  120
tcggcgtcgg ccgccaggag cagatcgagg tcgtcggcct cggtgtcgcc gccgtcgagc  180
ccgagcatct gccgcaggta gcgggtccat tcgatggccc ggcgtccccg ggttgcccgc  240
tcgtactcgt gccagcgcga gaggttccac tccagcgagc cgaccccggc ggcgtcgtcc  300
```

-continued

```
tcggtcatgc cgccggtcag gtccccgatc cgtccgagga gttcgaacgg ggcgacgttc  360
ccgccggtcg ccgtcttgag gtcggcgcgg gcgagttcga gggcgggcgc cttcccgtcc  420
tgggtcttgg cgatgtactc ggcgaggtcg ttggcgtcgc gctcggtctc cagccgcttg  480
aagtcgacgc cgtgccggtc gtcgggcgtg aaggcggggt tgaccttgcg cagggcggcg  540
gtccacacgg accgccagtg cccctgccac tcgtcgagcg cggcgccggt cggctcgaag  600
gtggcgacga tctgcttcgc ggaccgctcc ccctcggtcc ggccgccgac caggacgatc  660
gcgtggatgt gcgggtgcca gccgttgatc tgccccacgg tgacttcggt cgcgcggatc  720
atgccgacgt acccgatccg gtctcggatg ccctcgcggt cggcggcccg gtgcccgtcc  780
ttggcccggc gtccggccca cgtgccgccc gtgatcagtc gctggtaggc gcccggccgc  840
cgggggctgt ccggcgtctt ccgggtgccc tggagggcgt ccatgaggtc cgcgagccgg  900
tccgtgtgcc catggcgggc cgtgaaggtg accaggtagg cggtccccc gcgcttgatc  960
cactcgacca cggcggcggt gatctcctcg gcccgcttgt gccggatcgt ggcggcgcag  1020
accgggcaga gccagatccg cccgcaccgc atcaggccca ggaccacgga cgttccggcc  1080
gccgtctggg cgacgatcac gccggaggca gggtccatca gggcgcggcc gcagcccttg  1140
cacgcggcgt ccccgctgat ccgccacagc gtccggcggc ggctgtaccg ggcggctttc  1200
cgcagtcggg cagcctcggt ccgcgacgtg cttcctactt cccagaggct gtcgcctctc  1260
gggctctccc catccacccc gtccggagaa accgcaggtc ggaggggtgc gggaaactct  1320
gttgtttctt tcccaaggtg ttcgcttttg cctcgggcgg catctcgcgt cacacgcgcg  1380
atcgcccgct tcgctgccat ccggcagcgg tctgagcagt agatacgcgg ccgtttgccc  1440
ggtgtgtggg caattgcggt cccgcagtgg cagcggggcc cggcgggccg atctggcaat  1500
gcctcggcat cgctccgtac tctgggcacg agcaacgttc ctgtctcgcc cggctaaggg  1560
gcgcgagtct gggagcggac gggtcggagg tgcgaagtcc ggcccgttgc tctttggtct  1620
ggtgggaatc ctggcaccaa tcgggccaga ggttccctcc gccactcccg acgccccttg  1680
gggctggtgt gacttggagg gccgaagaga gccccgccgg gtatccggcg gggctttgac  1740
gtgcggtcag tgcgtgtgtc ggcgagcgat ggccacgagg ccctggaagc cgagcggtcc  1800
ggcgaagtcg gcccagtcgc aaccgggctc agcgcagtgg gcggaccagc caccgccgtt  1860
ggggtcctgg accaggttca cggtcccctc ggtcaggcgt ccgtcgaagt cggtcatggt  1920
cggtctcctg gtgggtgggg gcggggcgcc agcacgaagt gccggcgccc cgcgggggtt  1980
ggtcgggtca ggcgccgaac cggcgggcgg cggcggcgac caggccgtcg gcggcggcca  2040
tggcgcggtc gcggtcggtg gtgagggcgg tgcggtcggc ggcggcccgc aggtcgtagg  2100
ccgcttgggc ggcggcggtc gctgcggggg cgagggcggg ggcgagcacc gacacggtgg  2160
tgaggggcgc ggtgatcgcg gagcgggtgg cgtgggactc ggtgcgggcc gcctcgtacg  2220
cctcggggga ggcgccggtc aggcgcaggt cctcgcgcac ccacatggcg cggcggtggt  2280
cggcgagggc ggcggcgagg gcggcgacgg cctggacggc cgcgtcgcgg cgggagtcgt  2340
cgcgggtggt gcgggcggtg cggtgctgga ggagtccggc gaggccggtc ccggcgagcg  2400
tgccgatcac ggcaatgagc gtggtcacca tgtgagcccc ctggcgtcgt gtccgtctgc  2460
ctacgtgtat cagtctgaca cgcacgtgtc aggttgcgca atgggtaggc cccgccggtt  2520
tccggcgggg ccatccgtca tgcggcggtg ctgagtcggg cggcgagctg gtgggtggcg  2580
gcgaggatga cgcggatctc cgcgccgccg tcgaccgccg cgagggcggg ggccggggcg  2640
ggtgccggcg gattggtcgg ggtcgggcgg cggcggaggg cgacggccag gaccatggcg  2700
gcgatcgcca cggtggcgag gtaggcgagg gcgatcacgc ggccacctcc ctcgtgacgc  2760
ggcgccagga cgcctgcagc cgtgcctccc cggcggagta gcccatgtcc cggaagcgtc  2820
cggcggcgac ccggtacgac ccggagtcga ccaggccgga catgatcccg tcgatctcct  2880
cgttgctgag cgggaccacg tcggccgacc cctcgatggc ggccgggacg ggctccgtgg  2940
gtccccagac gggcaggcgc caggagggcg gagacgtggg cgtgacacga gaggtgacgc  3000
aggtcagagc gcgtgccgtg ccctcgccct cgcgggcctc ctccagcgtc gaccaggccg  3060
acgccagctc cccggcggtc tcggcctgga cccgggcgac ccgggccccg gcgccggtca  3120
cggcctccag ccgggtgacc tccgtaccgg cctcggcccg gagctgagcg cgggccacgg  3180
ccgccctgtc gcgggcgtcc tgctggatgt cgcggatctg gtccagggcg gtcggggtga  3240
gcgcggtccg ctcccagagc ccgtgcacga gccagagcgc cttggcggcg agggggagcc  3300
aggcgaccgc gagccaggcc ccggccgact cctcacccag cgcgtgcgcg accaggacgc  3360
cggtcgccac ggcgccgaat ccccacccga cgccggtgat cgcgcggctg tggtcgcccc  3420
gcgcggcgag gcgccgctcg tacgcgaggg tggccagcca tccgccgtcg agcccgaggc  3480
cgacgaccaa ggcaacggcc cacggcatgg cctccccgag ccacatcacg atcacgacca  3540
cggtcaggac catggacacc gccgtcatgg cgacggccgg ggcggcggtc atcgaacgct  3600
tcttctccat gatcacttcc ccttccgggc cttgagcgag atggacaggc cgaccccggc  3660
gggggcggcg gcggcgagcg cggtcgccgt ggtggcggcg gtctggagca ggaggcagag  3720
cgtcatgacg acgccgaccg agccgccagc ggcgaccagc gccaggagga tcgggccggt  3780
ccagtcgcgg gcctcggcct ggtggtggac gacgacgacc gtgcgggggt cggtgccgtc  3840
cgggatcagg tgggccggaa tgtgaccggc cctcatctgc gcgtcggggg tgcgcatcag  3900
gccgacacct ccccgacctg cgtcacgacg gacagggagc cgtcctcgga ccgcaggacc  3960
tcgcccgcgt cgagcagctg cttgaccgcc ttcgacacgg agcccttgtt gatgccggtc  4020
acggtggcga cgtcggcgac ggtcgtagcg cccgtgccga tcgcggctgc gaccttctcc  4080
cggttggtcg gcgccttggt cggctgggcc gggacctcag ccgcgggggc ggtctccttc  4140
accagccgga gcggggccgg ggcggaggcg ccggcacttc gtgcaggcga ctcctggcga  4200
cgccagaccg gccggtcggg gagcgcgatc acgtcggccg gggagaacgc gcgggtgttg  4260
atcgggtgag gctgcacctt cgggccggac cggagcatcg caaccccggg catgggcagc  4320
tcgtgcgcgt gccagccctt ctccgtcgcg tcctcgccga acaccacgcg ggactccccg  4380
gaggtgctga gcgcgagggc ggcccggtag gtgatctgcg cgctgatctg cgggtcgatg  4440
ccgcccttgg cgtccatggt cggcttctgc gtggcccaga tcaggatgat ctcggccgcc  4500
cgtgccatcc gggccagcgt gctcaggttc tccatgatcc gggaccagtc cgggtcaccc  4560
ggctcttcct tcgacccctt cgcccgggtc ttcttggcca tggcgatgac ctcggcgccc  4620
tcgtcgatga acaccgtgat ccggggccgc tccgggctga tctggatcac gtcctggccg  4680
cgcgggatca gttcaagccg ctcgtgcatc tcctcgacca gctcgtcggt cacgtccagg  4740
acgtcttcga tcgagatggc cgtgcgagcc cggtgctgcc agttgatcgc ctcgacccgc  4800
ttggggtcga cgacgaccag gcggtgatcg gcgtactccg agccttccgc cagcagggcg  4860
cgggtggacc aggacttgcc cgagccggac gtaccggcga tcagcatccg gcgcccgagc  4920
ggcacctgca ccggctcgcc ggtcaccgtg tcgactcccc acggggcgcc gggcgtccag  4980
ccggtcaggt cgatcccgtc ggccgcgctg cgggtccgca gcgtgatcac ggcgcggtcg  5040
```

```
ccgtgcgatc cggccttgat ctccatgcgg aggtcggtcc gggctccgag cagggcgcgg  5100
atctcctcgt gcttggcctt gaaggcggac ggcttccacc ggccgtccag gcgcaccgtg  5160
gtgaccagcc cggccggggt gacctgaacc ggcgtcgtca ccgtgcctac gaggccgcgc  5220
tcgtcggcgt gctgagccca gtacgacggg tcgagccgct cgaccaggcg ccgctcctcc  5280
gctgacagtt cgtccgcgac cgcgaccgcg accttgcggc ggccgatcac cagcgcggcg  5340
acgttggccg cgatgagtgc gagcgagccc gcgaccggcc aggccccggc ctggtcccag  5400
ccgagagcgg agatgccggc gcccggcacc gcgtgcatgg cgtgcgcctg aacggctcgc  5460
gccccggaggg tcgccgggta gtccttgcgc gcggccttga gcttggtctt cgcctggtcg  5520
cggtgcgtgc gggccgcctt gtccgccgtg cgagccgccc gacgcacggt cgacagcggg  5580
ttcttggacg ccgcccgcgc ggccgtccgc tggctcttgg ccgtggccgc cgtcgaccgc  5640
gcggagttgt agcccttctg ggcgtccatc agcgccttca ggtgctccgg ggtccggagc  5700
gccatgcggc ggtcggcctc ggcgtcccag cgggccgcga acggcgcgag ggtcggggcc  5760
atggcgtcga gcgcgttcgt gatcgctccg gcggcgttct tggagccggt tgcgatcttc  5820
gtagagactg ccttcgggtc cacggtttgt cctttcgcga gggacgtgga tctagggccg  5880
gagaccgttc acgcggtctc cggtccgccc cgtttccggg gctgtgtgtg gcgtcgaaca  5940
aggtccatac tgtggtcgca cagttgctgt gtcaaggcat acactgtgct agacagctac  6000
acaccgcgca ccacactcga aggagtcgtc atgtccctgg agcgcacgcc cccgtacctc  6060
caagtcgtcg ccgcgctgaa ggcaaagatc gtcagcgggg agctgaagca cggggacacg  6120
ctgccgtccg tgcgggacct cgcggcgcag tacgagatct cgaccgccac ggcccagaag  6180
gtccaccgga cgctgaaggc ggaagggctg gcggaggcga agcagggcag cgcgaccacg  6240
gtcagcacgc gacggaccct gcaccggacc gcagccgacc ggctggagtc ggcgctcagc  6300
acgggccgga tctacgcgga cggggagtac gcggtcatca ccagcgccgc ccttgccgag  6360
ccgcccgagt gggtggccga tctcctcggc accgagagcg gccaggccgt gcgacgcgag  6420
cgcgtcaccc actcagccga cgaccagccg gtgagcgcca gcgtgagctg gttctccgca  6480
gacctcgcgg agaccgtgcc cgccctcctg gtccgcgacc ggatcatcgg cggcaccccg  6540
tccgcgatcg aggcagccac cggccgccgg gccgtcgcca ccgaggaagc caccacggcg  6600
gccgccgcga ccgaggacca ggccgcgctt ctgggcgtag ccgcaggcgc cccagtcctg  6660
ctctcacgca acgtctacgt ggacgctcag ggcgacacga tcgaggtcgg ggagtccgtc  6720
gctccggcgg gccgctggcg cgtccaccgg gactgatcac tcgcccattg agaagccccg  6780
tcaggcaccg cccgacgggg cttcttcacg tccagacgac gtggtttccg gggttgccc  6840
acccggttga gccgttgcac cccggttgac cccccgcaac cgggtctgac ctgcgaagtt  6900
gcaaggttgc gacggtttcc aggaggggc cctacgcgtg cgcgcgcgag gaagccattt  6960
ttgatctagc ttccggagcc cttctcggcc tccgccttgg cccacgcccg ggccgtgttc  7020
ggagcgaccg ccgtcacctc gttgatgcgg cggtagggga cctccatccg gaccgcctcc  7080
gcgatcagcg ggcgcagctc cttctcaatc tcgtccagct ccgcgaggag cttgatccgc  7140
tgctgcccca acggcttcag cgccgcctct gcctcggccc ggatctcgcc cggtgtcttt  7200
tgcgtcatga agtcatcctg accgactgtg tcagtctgcg caactagttc aggctgcgtt  7260
ttttgcggta caactttccc tacgtcatca aggcggcccg cgagcgggcc gcgcggcccg  7320
gcccacggcc cggccgacgc tcctgtcttc gccccgctcc ggcccggccg ccgaccggcc  7380
cgcgcacacg acgggggcgg catcggtggg cggtttacgt ggcgcctgct ccgccgactg  7440
cgggcatcgc cgttgtgctc gccgacaggg cagcggggag gggtgggggga ctcgcggccc  7500
tacgcggccg tctgagcgcc tgtcagcctc ccggagcgcc gtacccccgc cgtcgcggtg  7560
ctgagccgcg tgaggcgacc ctgagccccg tcgtgggttg ctggggagca cctgctgccg  7620
cgatgaggtg gcggccgtcg agctggtcag ccgtgcggct ccgtcgtggc cggtcatccg  7680
gctgcccgat cgtggtgggc aagatgccgg cggaaccggc ggacctcgac cgcgacggct  7740
atccggcggg ccgcgggcgg gcctccgtag agggcgaggg cgggcgccat gccgaccgcc  7800
acggcgggcc acaggcccag gagctcccgc acgatcagcg tcccgccgac caggagcagt  7860
gcggccagca ctgccgctaa cgcctggtcc tggtcccggt cctggtggtg catcagtcct  7920
ccccgtgatc acttcggcac ccaccgtagt gatcaccccc gacagcggat caaggggttt  7980
gcgggtcccg gtcggcgccg ggcgggggag gcaggagccg ccgacgctgc ctctgggacg  8040
ggccggacgg caggggggacc ggcggccggg cgagctgcag ccgggggtcc ggcagggccg  8100
gagcgggcgg aaccgtgctc tgacctgcgg cccgagtttc gtcacgtgac ggaatggaag  8160
gctgctgcat ttcgtcacgt gacgtatctc ggcgagcgac tgccgacgcc acggcggaca  8220
cgatcgcctc gcgctggcgc cgggcctcgt acgcccgctg gcggcaggag cggcggcagt  8280
agtcccggct ccggccgacg ccggattgct tgatctccga gccgcaccag gcgcagagct  8340
tcgcgccgtc ggcgtccctg ggggtggtgg tgctcatggc cgacgaccgt acgcggcacg  8400
tctcgtagcg aggcgagtcg ggcgcgaggt accgcctgca cgaagtgccg gcgggccga  8460
ccccgggcga gtaatcccag gattactccc gcggcttcga ccccggccgc cgtcgccgcg  8520
tacgtcaccg acccccgccg tacgtcaccg ggatgacgta cggcgggggg gagcgagtta  8580
gtgcgaagtg ggcccacttg cgagccgggc gatgtgccgg gcggcccgct cctggcggtc  8640
gtcggcgtcg tcgtcctggt cgtcgtcctg ctctcgccgt cggcgtgcag ttgcttcctc  8700
gcggcgctgg gcgagggcgg cgagcatgtc ggcgtacgcc tcggccacct cccccgccgt  8760
gagcaccacc actgtgtcgg ccgcgtcggc cagcgccagg acctcccgca cccgttcgcc  8820
cacggccgcc                                                          8830
```

```
SEQ ID NO: 61          moltype = DNA  length = 11046
FEATURE                Location/Qualifiers
source                 1..11046
                       mol_type = other DNA
                       note = pSN22
                       organism = synthetic construct
SEQUENCE: 61
ctgcaggccg gtgactccag agaagggttg aagcggagtt gcggggctag ccccccgagc  60
ctccatcgtt ccgaccgccc ggcctgtccg ggacgggagg acttttcgag cacctggagg  120
agcacgtgac caaccagcag caggaccagg agcagccgca gcgcccggcg gaccgtggcc  180
gccgcgagtt cgcgaagaag ggagccgtga ccgtgctcgc cgctctcgtc tccggagctg  240
ctcgggcggt ggtagcccac ctcctcacgg gaggtggcga gtgacgcggc tcggcagccg  300
ggccggccgc cggacggagg caggagcggc ccggccggaa gccgggccgc cgggcccgct  360
cgcgggccgc cttgatggag tagggaaagt tctaccgcgc ccactcgcca cgccacgaga  420
```

-continued

```
cgtgccgcgt acggtcgtcg gtcatgagca cagagacacc cacgaacggc gacggcgaga  480
cgctgtgcgc ctggtgcggc cgtggccccg tgccacccag ccggggaacc aagccgcggg  540
cctactgctc gcgcagctgc gtccagcgag cccacgagtc gcgaaagctc cgcaagaagc  600
tgctcggcgc gtacatgaag ggccgggccg aggaggctga gctgcgcgga ggaaagtcac  660
gtgacgatgc aggaaagtca cgtgactttc ccggtcggca ggccccagca aagtcacgtg  720
actttccaaa accccaggtc aaccctgggg ttccgcgtcc cgcggtcccg gtgacgtccg  780
cgcccccggtc gaaaggccgg cgcccgctgc tgccccccgc gccgggcgtg acgcgggaga  840
cgctcccgct gttcggcgac gacgacacgc agcccggccc cctcgatggc cgcgccgaca  900
cggagtgacc acgacggccg tcaccccatc gcggcagcag cccgctcccc atcgacccga  960
gacgggcggt gcggtcgcct cacgcagccc agccccgcga cggcggggggt acgggggggtc  1020
cggcgactcc tggcccgcca gacggccgca cagagccgcc gaccccccac ccctccccgc  1080
cagccgtcgg cgacgcgcac aacgacgatg cccggcggcc gggtgacggc ccgccatgta  1140
aaccgctcag ggatgccgct cgtgggcagc agaaagcccc cgccgggtct cggacggggg  1200
ctcaatgggg aggtagggcg ggggcctggg gtcactcgcc catgggcacc cgggcgccgg  1260
gggcgtagac gtcttcccag tagccgagcg cctgttcgtc gtcgtggaac gtgacggtgg  1320
tgaccatgac ggcgatggct gagtgggccg gggcgtcga tctcagagcg ttgagttcgt  1380
cctgggacgc ctgccgtgcg tgggcggccc gctgtccctt caccacttcg cgaccggtgc  1440
gctcgctgta gagcttgtcg aactgcttca ccatccgtac gtcctccccc agctcgggga  1500
cggcggccac cgtgtggggc gggtagacgg agacgccgac cgacgtcggc ttgtcgtcct  1560
ggcggaagac gcgaatgcgg atcacggctt cgtcgccggg ctccagggtg agagccgtgc  1620
agatctcggg atcgtggacc gaccgggtca tcacgcggtg gccggaggag gtctcgccgg  1680
gcgcgtagcg catcccgttc ttctccatgc gcttcaagcg gtccgcgcca gtgatgacga  1740
tggggttctt ctccacgacc gtacccagcg ccccgcgcga gctgaccagg ccctcgctct  1800
tcagcacggc caaggcccgg ctcacggtct tggccgccac gccgaactgg gcacggatgt  1860
cagcgacgga cggcagcgtg tcgcccggtg cgagttcccc gctcttgatc agcgtgcgga  1920
agtgggtggc cacgtcggca tagcccttcc cctccggtgc cttgtatggc atggcttctc  1980
cctgtttgtc ggagcgcggt acaccccccga aggtacatca atgacccccc caaggtacat  2040
ccttgcttcg aatcggtgct tgatgtacct tcgtggcgtc ggcaaggtac gttaagtacc  2100
tcccgctgac tgatgcgtac cttcggcaag agagggtctg tcgtggccac gaggaacgtt  2160
ccgccccccg gggcgaacaa cagcaggaac aacaagttcg ccgacatggg ggcggcggcc  2220
ggcggtttcg tcggtgcgat gggcggctcg ttcgtcccgc ccgtgaacgt cacggtcaac  2280
cgcacgacca acaagggcgg tggcggacag cagtccggcg gccgccagtc gcatttcatc  2340
ctcggggagc cggagttcaa ctcggctgag gacgtgcgca actactgcaa ccacgtccgc  2400
gccctgatgc tccaggccgc gatcgagctg gccatggccg ccaagatcct ggaggcccgc  2460
ctcgcccagg cgcagacgct gcccggtgac aatccgatcc agggccggat gcgggcgcgg  2520
aaggtcggcc ggagcctcaa gaaggccgcc gacggcgcca cgtccgccgc gaagggcgcg  2580
gtcaccacct acggcgcctt cacccgcgag tacgccgacc tgatgcgccc gcgcccccag  2640
cgtcaggcgc ccaccaaccc cttcaagttc tgagaggcgg taccgagatg ggcaaggacg  2700
ttcagcagca gcaggaagac cgcctcaact ccggcggcac gggaatgggt gcctggctgt  2760
ggcaccgggc caagccgtac accccgccgt ggatcgtcac gggcgcggtc ggcgcggcgg  2820
gcgccggcgc ccacgagctg tggggcaact cgccctgggc cggagtcggc ctcaccctcg  2880
cgggggtcgg cctgacggcc gcgacctggt gggcgggcaa gtccaccggg cagcagcgcc  2940
gcctccactc cgccatcacc gtggcggccg gggcgacctg gttcaccgcc tccgccctct  3000
ccggcccgct caccggcccg ctgcccgacc tgtacctgat gggcggcacg agcctcgccc  3060
tgacctggaa catccgccag gtcatgcgct cgtcgacgcc cgagggcgcc ggatccgact  3120
cggacaaggg actcctggag aaggtcgggc tcgcccggac caagctcaag gacgtcaagg  3180
tcgagcccaa ccgcgtcacg gtccccctacg agctgcctgc cggggagctg accaacgacg  3240
acatcaacaa ggccatcccg cgcatcgcgt cggctctcga cgtgccgacc acggccatcc  3300
gtgtccagca cgaccccgac tccgcgagga agggccagtt cgtgatcgtg cccgaggaca  3360
tgctgaagca gcccacgatc tggcccggcc cgttcgcgcc cggcgagtcc gtggccgtgc  3420
gctgcggatc gcgtctacga cgacgcagcg acctggttct cccgctcctc gacgcgatcc  3480
acctgctcgt catggggatg accggctcgg gcaagaccga gggcgccgtg gacctcctgc  3540
tggagatcct gacccgcaac gacgtgaccg tgtggctcgc cgacgcggcc aaggccgggc  3600
aggacttcca gcccctcgtg cccgccctcg actgggcagc cctggacacg gcgtcggccg  3660
gagcgatggt cgacgcggtc caggccgtca tccccgcccg caccgcctgg ctgcgggacc  3720
acagctaccg ggcctgggag cccgcggccg ccaagacgca gaccaacccc gcgcactcct  3780
gcgcgtcggc cggcgcctgc ggctgccccg ggatgccgta cctgctcacc tggttcgagg  3840
aggcggccaa gctcctgcgc gagctgggcg acgacgtgtt caccggcatc gcccaggagg  3900
cccggtcggc gggcgtctcc ctggtcgtct ccatgcagcg cgcctccggc taccagctct  3960
cgacggacac gagggcctcg ctcccggccg ccatgtgctt cggcgtccgg ggcgacgacg  4020
ccgggttcgc cctccccgag gaggtcctgg acgcaggtgc caacccggcc gcgtggggca  4080
acaagcgcaa gggctacgtg tacctggtgt ccgccggggt cgaggaggac ctgtacgcca  4140
accccgcccg gacgttctgg acgggccccc cggccgaggg cagctacgag cggatggccc  4200
gctacgtcgt cgagcacttc gcctcggttc gtgccgagct ggacccggtg accggcgccg  4260
ccgccgagca ggctgccgga ccgctgttca ccaaccgccg tgcccgcgcg ggcgccgcct  4320
ccgccccggc ccgcccggtc caggagcaga tgctcctcga cgacgacggc caggaggacg  4380
gcgacctcgt ggagatggag cacgacggca tcgacctgag cgccgacctc ccgcccgtgg  4440
agaacgacgc ggaactcccg ccggccaagc cgtcgaccga ggaggcccgc gagctcctcg  4500
acgaaatggt cgccacgctc gcctcggtcg gccccggcac ggtcgctgtc cgcgacctca  4560
agccgtacct ggagcagatc ggccgtgacc gctcctgggt ctcccgcgag atgaagcgga  4620
tggccgagga gggccgcctg gccgccacgg gcgaggaggg cgtctaccgc ctcatcccca  4680
cgctcgccgg ggtctgagac ggcccgcaca gccgcacagc cgcacagcgc gaatccccac  4740
gtcacacggc gtgtgaagag ggccgcacac cgcctcgcac accgtgcgca cagccggacc  4800
gcacaccccc cgcacaccga acgacgacgg accgccccgc agcaaccggg gcggcccgcc  4860
cgatgaccac ggaggtagag cccgtgacca ccgacccgaa gcatctcacc gactccgagg  4920
cttccgccga agctgcccgc ctgatccgcg aggcgtacca gccgaccccg gagccgcgcc  4980
ccatgacctt ccgcgacacc acccggtcac agcgttcggc ccgacccgcc cgtgccccag  5040
cccgagaccc ggatcgtccc cgagtgggcc gccggggtcg ccgtcgcctc catcggcatc  5100
ggcgccggcg tcaccggcct cggctgcgga gcctggctca tcttccaggg cctgtcctcc  5160
```

-continued

```
gtgaccctgc tcggagtcat cgctatcgcc gccccgttcg tcggcgtcgc cacggtggcc 5220
acggccatcg gcgccgccat ctccaaggcc aagcgctcgt cgaccacgaa cgtctaccag 5280
gggaccgtga tcaagcggac cgacatcacg tcgaccgccc gcggcatcgg cgcccgctcc 5340
cggatcgagg gctgagcgcc atgcagatga acactcagga gcaggtcgag caggcggaga 5400
aggtgctccg gctgagctgg atcatcgtct tcggcgtgat cctgttctcc gtcttcacgg 5460
tgacgcccct ggtagagcgg tccactccgg agggctggga gtggtcggcg ccgatcctgc 5520
cgctcgtggt cgacgtcgcc gtcgtcatct cgatccgggt cgacgcgatc gtgtcccggc 5580
tcggagggtc gaccaccggg tggccgctcg ccctgcgggt gctcaccggc ggcgcctccg 5640
tggcgctcaa cgtcgggcac tccgtactcc agggcgacct ggtgggcgcg ctcgtgcaca 5700
cggccgcccc ggcggtgctc atcgtcgtcg ccgaagcgtc gctcaagtgg cgcaaggaga 5760
tcgccgccgc cacggcccgg atcgaggctg agcaccgtga gcgcgaggac gcccgccgcc 5820
gtgagcagcg tgagcgcgag gagaaggcgc gggccgaccg cgagcgtgag caggaggccc 5880
ggcgcctgga gcgtgagcgg caggaggccg ccgaccgtga gcgccgccgc gaggaactcg 5940
ccgaccgtga gcgggagcgt gagcacgccg cccggctcgc ccaacaggag cgtgagacga 6000
ggcccggctg gaggccgagc gcgaggaccg ggccgacgcc cgccgccgcg aggagcagga 6060
ccgccaggag cgtgaacgcg agaaggagcg ggagcgcagg agcaggagcg ccgtgagcag 6120
gaggctgccc gcaaggccaa ggaggccgtg cagaaggccg aacgggaccg gaaggcagcc 6180
gaggcccgca agcccgccct cgcgcccgtg agcgctgctg tgagcacccc ccgcccggcc 6240
gtgagcgccg ccgtgagcac tcccgctcac gagactgctc acgacgccaa gcccgtccag 6300
aagatgagcg aggccgacgc ccgccaggcc gtcgccgacg cggtccgtga gggccgctca 6360
cagcgtcagg tggccacgct caccggctgg tcgaccggct gggtcgccgc ccgcttcaag 6420
gagcttgagg gggccgccgc atgagccgcg ccctgatgta cgcgctcatc ctgccgctgt 6480
tcgcggcgga gtgctgggcc cagttcgtgg tccatgacca gcgctggacg acgctcttcg 6540
ccctcctcgc cggggccgtg ctcgccgtcc gctacgccct cggtccgcgc acggacgacg 6600
aggaatgcct gcccgactgc ccgaagtgcc gcgaatccag gggggacctg tgagcaccac 6660
cgaccagcac ctgaccgcac agcacgccga agtgaaggcc gagatcaccc gcaccgacac 6720
gaagaccgcg ctcttgctcg ccttcgtcgg cgcggtcttg gccggcgcct ggtccctcgc 6780
ccgagacctc cacctcaacc ccgtcgcgta cctggtcggc gtcctcggac tcgccgccct 6840
cctcgccgcg gccggcctcc tgctccggtc ggtccgcccg aacctcaacg gcgggcacgg 6900
cttcccgctg tgggccaccc tcaccccgca gcagctcacc gccgccgccg agacccgcga 6960
cctggccgcc gacgtcgtcg cctgtcccgc ctcgccgttg ccaagttcac ctgcctgcgc 7020
ctggccgtcg acctgacctg cacagggacg gcgtcctcct cgtcctggcc gccgtgatcg 7080
ccctcggagg tgccgcatga cccgcaagcc cgccatccac gacgccgagg cccacgtcgt 7140
cacctcccac ggcagccgac ttcttcaggc gaggaccgcc acccgctcaa ccgggtcgcc 7200
tccctcgccg ggtacgccga gggctgcctg ccgtacgccg aacagccgcc cgctggtcct 7260
gctgctgacc aaccccggcg acggcgggac catgacgctg ctcaggccgg agagatggcc 7320
acgctcctgc ggaagctcgc ccgccaccgg ttcgtcaaga ccagcgccgc cgcccacgcc 7380
cgcgcactgg gcgacgccgc cgcccgcgcc gccgccgacg cgagccctgg gaatggcgga 7440
tcgaagccgc tgcctgaaca ccgaagcccc gccggccttt cggctggcgg ggcttccttc 7500
ggcccgtcaa atcacatctg ccccacgggc cgtgtcgcgt gccgggggga acctccggca 7560
caaaaagtgc caggatcacc cccagcaaag cgaaacggcc agggattagg gcccctgacc 7620
gcttctgacg tccgcccgga taccaaccaa gggactcgtc tgttgaacag ggtaagggac 7680
gctgaggcgt ccgcaagagc actcccggct cgcgccgtcc gtccgcgctg ccactgcggc 7740
actgcgatcg agcacacgcc cggcaaacgg ccgcgcgtgt actgctcgaa cgcctgcaag 7800
cagcgggcga agcgcgctct tgccaagatc gcccgggaag ccgccgacgc gcgtccgcga 7860
cccaaaacgt gtcgcgcctt gggaaagaaa caacagagtt tcccgcaccc ctccgacctg 7920
cggaaacgtc ggcgggggca aaaccggtcg cggacagccg ggacgacgcc gcccgcgccc 7980
ggaaggctcg ccggtacgcg aaccgccgga cgctgtggcg gatcaccggg gacgccgcgt 8040
gcaagggctg cggccgggcc ctgatggacc cgcgcctccgg cgtgatcgtc gcccagacgg 8100
cggccggaac gtccgtggtc cttgggctga tgcggtgcgg gcggatctgg ctctgcccgg 8160
tctgcgccgc cacgatccgg cacaagcggg ccgaggagat caccgccgcc gtggtcgagt 8220
ggatcaagcg cggggggacc gcctacctgg tcaccttcac cgcccggcac gggcacacgg 8280
accggctcgc ggacctcatg gacgccttgc agggcacgcg gaagacggcc gacgctcccc 8340
ggcggccggg tgcctaccaa cggctgatca cgggcggcac atgggcgcga cgccgggcca 8400
aggacgggca ccgggccgct gaccgcgaag gcatccgcga ccggatcggc tacgtcggca 8460
tgatccgcgc gaccgaagtc accgtgggcc agatcaacgg ctggcacccg cacatccacg 8520
cgatcgtcct ggtcggcggc cggaccgagg gcgagaggtc cgcgaagcag atcgtcggca 8580
ccttcgagcc gtccgaggcc gcgctcgacg agtggcaagg ccagtggcga gccgtgtgga 8640
ccgctgccct gcgcaaggtc aacccgcagt tcacgcccga cgaccggcac ggcgttgact 8700
tcaagcggct ggagaccgaa cgcgacgcca acgacctcgc cgagtacatc gccaagaccc 8760
aggacgggaa agcgccggca ctcgaactcg cccgcgccga cctcaagacg gcgaacggcg 8820
ggaacgtcgc cccgttcgaa ctcctcggac ggatcgggga cctgaccggc ggcatgaccg 8880
aggacgacgc cgccggggtc ggctcgctgg aatggaacct ggcccgctgg cacgagtacg 8940
agcgggcgac caaggggcgc cgggccatcg aatggacccg ctacctgcgg cagatgctcg 9000
ggctcgacgg cggcgacacc gaggccgacg acctcgacct gctcctggcg gccgacgccg 9060
acggcggcga actccgcgcc ggggtcgccg tgaccgagga cggatggcac gcggtcaccc 9120
gtcgcgccct cgaccttgcc gccacgcagg ccgccgaggg aaccgacggc aacaccgatc 9180
cggccgccat gggcgagagg gtgcgcgagg tcctggcgca cgccgacgcc gccgacgccg 9240
tggtggtgct cacctccggc gaggtcgccg aggcgtacgc cgacatgctc gccgccctcg 9300
ccctgcgccg cgaggaagca gctgcacgcc gccgccggga gcaggacgac gaccaggacg 9360
acgacgccga cgaccgccag gagcgggccg cccggcacat cgcccgactg cggaactgat 9420
atcgatccgc actaactcgc tgcccgcccc tactcccgcg ccgacctctc cgtgacccgc 9480
acggagaggt gtcggcggcg gtcggaggct tgcccacgag gcgcgacctg cgaggcagcc 9540
gcaggcttgc ccacggggcc tcccaccctc ggtcccaccc tcggtcccac cttcggtccc 9600
acggtggacg cgacggtggg agcaacggcc gagccccctg ctgaagcaac cccgcccggc 9660
gggcgtcact gatatcagtg acccacaact cgctctgcct gtggttactg cctccgaggc 9720
accgccatcg ggtccgccag cccaccgcca tacgcccgcc cacgaccgcc atccgaccgg 9780
aatgcatggc ggtcccatgg cggtcggatc ggaccccatg gcggaccctt ggcggtgcca 9840
tggcggaccc agcggagcga gcaagttatc gcgagagcaa tgctctcgcg ggcgctcgtt 9900
```

```
ggggcgagca agttatccgc ttggagactc cagcggtgcc ccgaccgagg gcggtcgggg  9960
ttccccgggg aggggaaccc cctttgtcct caccccggtt ttgatcacgt cggcctacgc  10020
cgacggaccc gcgcggcgcg agccgtgcgg aacggaaaac ccggctgccg atcccctcgc  10080
ccgccgcccg cgttcccgcc ccacctccct ctcctcctgg tgctcgtggc ggtcgtgggt  10140
ggcgtagagg ggatgtctgc ccaagcggaa gcccccgacc atgcgcggtg acgtgggacg  10200
ccgcgaagcc cggaaccgga tccccgcaac acccagcgca acccatggcg caacccatgg  10260
cgcaacaccc agcgcaaccc cgaccaagga cggccgggaa cccgctacga cacccccctcg  10320
acgggcagcg cgtcgactcc cggtccgagc gtccgccggc ctttccgggc ggccacgtcc  10380
tggtgctcga tgtcccccag gagtgcgtcc ggctccactc gctcgacggg cagcagccgc  10440
ggactcgcgt ccgccgtcgg cgtgctcctg gtggtgctcg ggccggtgcc gaggtgacgg  10500
cgcggggtgc tcatgacggg agtctcccgt gccgttcccg gagctcccgc agcggccctg  10560
atcgagccgt gcggcttgtg cgttcgtgaa tgcaagaggt gtgaccgttc ttcgcgtgca  10620
cgcgtgtgct cgtgcacctg tgcacgcggt acggcttcgc cgccgacttc gtcgtgaccg  10680
gagcggtcac acctcaggca ttacgaatga cctcggctgg tcgcgccctg cgttgtgccc  10740
tgggtcgcgt cctggattcc ggcctgagtc acgtcctggg tcgcaccgga cgggtccccg  10800
gccgcgcccg gttcggcgcc gtgacctggt ggacaagggg gcggtcggct gccgttccgc  10860
gcgccgactt cttgctggga gcggtgtcgg cgggcgcctt cggatcggaa tgcaagggtg  10920
tgcggcttgc tgctgccgta cgtcatctcg aagacgtacg cgggccgtcg gtgacgtact  10980
cgaggaacga ggccgggctc ggctcggctt ggtcgacccc aggggctttt tcgtctgcgg  11040
tcctgt                                                            11046
```

```
SEQ ID NO: 62          moltype = DNA  length = 3539
FEATURE                Location/Qualifiers
source                 1..3539
                       mol_type = other DNA
                       note = pGP01
                       organism = synthetic construct
SEQUENCE: 62
ccacggtgtt ggatgacagt cctttgttgc cactgtcgca gtttttcttt tcgcgaagtg  60
cttgagatcc ttgatgggtg gacagtacgg tatcctcaac cgtggattct acaacggaag  120
ccacaacgaa atcataggag gatatcccat gaacggacga gtgattgttt ggcctgatcc  180
tgcgctcttg tctgccatgc ctttaagttc cggattttcc ccggtcatgt cgtggaaccg  240
cgagctgaag tgtttcaccg atgtgcagac cacgactgac gacggactgc ctgtctgggg  300
ggcagatgcg tggttgagga tgggatggca accgcacgct gacacagtcc aactgcgcat  360
cgctgcacct cgaaagcctg cggtccagcc tgatcctgcg agaatcgctg attttttttgc  420
gcctcgacgt agtgaggctg agcactgatg gcaggcgaac gaacgactgt tctgaccggc  480
gtctactggt ggctccgtat cttgccggtc ttattactcg gcgttgcctt cgcgtgctgg  540
tgtttctcgg tgcatctggt ctacgtgatc ggcttcgctg ttgcggcctt ggcggtggag  600
gcttttccgc cgtctgtatg gcaggtgccc aagaacatgc aggtgccagc acgatacgtc  660
tatcgctggt ggtggtcctt ggcgaaagcg ttcaagccga ttgaatccta tggcggcgac  720
agaatttact atcgacccgg cttgcagtgg atccgctctg accgacatgt actgcatctg  780
gtgcttcgcg ttcctgcagg tcttgccgac tcggcggcat atctggagaa aggtgcagca  840
gagatccaac gacagctacg tggcaagaag tcttggagga cctgcatcgt caaacctgcc  900
gagcatggcc tggacatcat tcctcgcgac gcgacagctg gtgatgagtt acttcctgct  960
ccgtccacgt cgtcgtggaa cgtgccagtc ggggttaaac ctgacgggtc cgaggtcgtc  1020
ttggatctct cccatccatc ccacatcctc gtctccggaa agactcgttc cggcaagtca  1080
tcgttcgtct acggcctgct cgatcagatg cgtcatcttc ctgtcactgt ggctggtgtc  1140
gacccgaccg gaatcctctt taatgagctg ggcgacggct ggggcggtga tgctctgcgt  1200
tccaagcgca tcacgaatga cgctgatgct gcagcagttg tccaggtcct ctccatgatc  1260
accgatgaaa tggatcggcg tatctatctt cttaactgtg agcatcgcga caagtggagc  1320
cgcaacgatt tcgagtccga cccgggacgt cgactcatca tcgtcatcct cgaggaatat  1380
ccgggcttga ttgagcggct gcagaacttc gattccgccc gcggcgctcg ctccagtgat  1440
cgttttgcct cgaaggcagc tggcctcgtt ggccgcatcg cgtacgaagg cgccaaggtc  1500
ggggttgtcc tcctccttgt cacacagcga cctgacgcca aaattatcgg cggtccactg  1560
cgagcccagc tcactacgcg ggtgacgttc gcccaagact cagacggatt gcgtatgtcg  1620
catcctgagc tctcatctga gcaggtcaaa cagaattcat gggcctcagg tgtcgggttc  1680
atcgaagcag atggcgtgat tccgctcact cggttccggt cctatcgagc ggaactcacc  1740
gacctgcatc ggcccggggc gtcggtcggc cagatcgatc tgatccagtg aggagctgct  1800
gccgaccgat gccgcggaac tctgagatcg acacgaccac agatgccgta gtcacggaga  1860
cgctcgagga agagatagga ttcagtacca gataaaaaat gcctccccac agcgccaact  1920
gcggggaggc gagtaagacc tttttctccc gggtcatgac cgccaaggag gcgatcggtg  1980
ttaaacatag taacactatc caaggcgcag ccacatgatc ggttgtgctc tgagcatgag  2040
ccgtgtgcgg ctcgccgcag cgagcgtcag cgagcggcgg gcgaccgcct tggtaccacg  2100
cgagcaactt ttccggtatc agattccccc tgtagaaagc cgaatgaggg ccgtcgccat  2160
cgctatgaga tgagggatgg tctacgaaat ccgcaggtca tgccgctgga gcgcgttcgc  2220
aagtgcgggg cagtgccggt ttcgcaacgg atcgcgttga tggcgggtca tggtggtgcc  2280
ggttatgccg gtttggcgac gtgcggaagt gtgtgggctt gccctgtctg tgcggcaaag  2340
atttccgcgc accgtcgtga tgagctggcc cgtgttgtcc aggttgcggt tggactcggc  2400
ttcaaggtgt cgatgctgac gcttactcaa cgtcatcatg ctggtcagga tctcgccgag  2460
ctgtgggcgt cgctccagtc gggtttggaat gctgtcacga gtggtcgacg gtggcaggaa  2520
ttttgcgctc agctcggcgt ccagggatgg gtcaaggcag ttgaagtcac ccatgggtcg  2580
catgggtggc acgttcacgt gcacgtgctc gtcatctcta agcaggatcc gactagcgtt  2640
gacactaaga ttcggcatcg ccgcaaacaa ggtcggcgcc ggaccccgta tccagaagag  2700
gtacagaggc ccgaagactt catcgctgaa cggtggtcgc gaggtttgag gaagcgcggc  2760
gtcgacttca tcgccggtag tggtggcctc gattggcaga ctgctgattc tggagacgag  2820
gaagctctcg gtcggtacgt cgcgaagatg aactcgtccg tcgatggcct agcgaacgag  2880
gccacgttgg gcgggttcaa gaaggctcgt agaggtaatc ggacgccgtt ccagatcctc  2940
gaagatttcc tggatacggg ctcggagact gacctgagac tctggcgtac ctatgtttct  3000
gcaagtcatg gccgtaaggc attgacgtgg tccaagggtt tgcgtgactg ggctggcatg  3060
```

```
gaatctgaga tgagcgatga gcaggtcgcc gcccaagacc agtgcgggga agcggtcgcc  3120
ctttttgacc atgacgcgtg gcggcagatc cgcactgccg gtgccgcttt cctcctcgac  3180
gagctggagc tccacggatc cgagggcgtc tacgcctggc tgaagaagcg aagaatccat  3240
tatgagatac ctctagttcc ttggagtacg agtacctagg agccagtcgg ggtctgtcaa  3300
ttttttagct cctccatttc atcacactct ttctatgatg aagtcatcac aattcggtat  3360
tctttgactc ccctgagaag ccgataatca ggccagtaga gctatcttat gtgcctaggt  3420
ggatactatt tattcttcac ctatcaggga ctctggtcga tcacagcctc cgtcgacgat  3480
gacacatctg actaggtact atgatgactt catcatagac agaggtggag cacagacga   3539

SEQ ID NO: 63           moltype = DNA  length = 8136
FEATURE                 Location/Qualifiers
source                  1..8136
                        mol_type = other DNA
                        note = pIP501
                        organism = synthetic construct
SEQUENCE: 63
cctgctcggg acccccccta gaatttcgtt attcaccaaa aaaatacgca tggtataaag  60
caccaagcga ttataaaaaa cgtagtcgaa aaaattatga tatggacaca ataaggggaa  120
tgtatggaag ccaaaaaatt aaagaagaaa aagcagaaaa aaaatactta caagcccgat  180
agggtttgta agtttatcag aaaggaagtt ttaaagtgga tattaaaata aaaaaaataa  240
attttgaagg taatatttta aaagttataa aagcgacagt aacagaaatg agaggaataa  300
ataatcatca aaaatatgat tttgatttat atcaaataga agcacgttcg ccaatgtcaa  360
caagagaaat aactttaaca gttgacttta tagaaaaaaa gtatcaggtg atattatcgc  420
ttttggtgat tggtacgatt tggatataga atcagtaaat gaaatattaa agcaattaaa  480
aaaggaagaa caaacattaa gaacaatcaa ttttatttaa aaaagtatca aaaaaaggaa  540
aattattttt cctttttttg atacttttta ggtttatttg ctttaatata ttcagaaaaa  600
atttttaaaa attcttccgt ttcttctaca gttaaatagt caatttcaaa atacttttct  660
aacaaagcac ctttttcaat tagacgcttt gttcttcttt ttctgttaat attttgctcg  720
ctattcgctc gcaaaatatt tttttgaatt tttagttttt ctattctttt gttgatgtca  780
tttaaatcat tatttgccat aactatttaa gtaattcaga aaaattttga ctattcgcat  840
ttaataaagt ttctaattcg tcatagaata attctttgtt ttcttcaatt gattcaatag  900
aaatattatt ttttgaaagg gtagaaagaa caaagtcacc aatatctgct ttagacttta  960
gaattaattc ttcttttttc ttttgtaatt ctttaatttg aagttcaata tcagaaacag  1020
ttttcttctt tcttttttttt ggcttcgttt tagaattaaa attaccatta attgcattaa  1080
tattttgatc ttgattttcc atgaaatacg cctcctaata tattgtgtaa ctctatcata  1140
ttatattatt tttctaaaat caataaatat aaacggaaat gtcaggttaa acatatttac  1200
ttttataatg ataagtggta aaattaattt attaaggatt cccttagatt atttactaag  1260
ggcgcactta tacgcagtaa cttcgttact tcgtatttat gctataaaac ttaactgtta  1320
gttagtttta tcgtcaagcg tgtttgttaa aattcgctac gctcatgttt gaaaagaaag  1380
agaggtgata caattggcaa tcttccattt atcaatgaca atagcaaaaa gagaaaacgg  1440
aaaaagaagt ttaatcgcaa tggcttctta tcgaagtggt gaaaaattgt atagtgaact  1500
atatgaaaaa actaatctat acaaccatag aactgttaaa ccagaagctt ttattttaaa  1560
acctgattat gtacctaatg agtttttaga tagacagaca ttatggaata aaatggaatt  1620
agcagaaaaa agtccaaacg ctcaactttg tcgagaggta aatgtagcat tgccaattga  1680
attaaataat tcagaccaaa gaatgttgat tgaagatttt gttaaagata attttgtcaa  1740
tgaaggaatg attgcagacg tagccattca tagagatgat gaaaacaatc ctcatgctca  1800
cattatgcta acaatgagag aagtagatag tgaaggcaat atcttaaaca aaagtcatag  1860
aatacctaaa ctagatgaaa atggcaatca gatttttaat gaaaaggggc aaagagtaac  1920
cgtttcaatt aaaacaaatg attggggtag aaaatctctt gtttctgaaa ttcgtaaaga  1980
ttgggcagac aaagttaatc aatatttaaa agatagaaat atcgatcaac aaataacaga  2040
aaaatcgcat gcggaacttg gaaaaaaaga actaccaaca attcatgaag gtttttactc  2100
aaaaaaatta gaagacaaag gagttataag cgagttaaaa agaaaaaatt tagaaattca  2160
aagttacaat gatattctag ccgaacttga taaacttgaa aatcaagaaa aagtattaaa  2220
acaagaccaa aactttactt taaaatttga aaaaactttc tcacctttag aaaaaggaga  2280
actgaaaaat ctttcaaaag aattgaaatt atttattaat gatgaaaaca ttgataaacg  2340
attaggtgaa ttaaaacgat gggaaaattc acttatcttt aataataaaa tggaaattca  2400
aaaacaacgt ttgatgttaa gtaaaattag tagtgaacga gatatgctta caaaggcaaa  2460
tgaaatttta gacaaacaag cagaaagatt cttcaaaaaa tcttatccaa gtttgaatat  2520
tgacaaattt tcaaatcacg aagttagagc aatggttaat gaaaccatat ttagaaaaca  2580
gttattgaat aaagaccagt tagcagaggt catttacaat gaaagagtag tagaaaaaga  2640
agaaagtaaa aagattttta aagaaaaacc atttcaaact agccgttatc ttgattcaaa  2700
aattaaacaa attgaagata gtataacaaa agaaaataac cctgaaagaa aagaaatttt  2760
atcaattaaa aaagaaaaac taataggaat aaaacaagga ttgatagaat atgttcaatc  2820
agaagttgaa agaaaatttg ataaaaatgt ttcaatagat tcagtcatag aaggtgaaat  2880
gttacttgca aaagctgact attacaaaac aactgatttt tctaaagtcg aaggagttgc  2940
tagattcagc agtgaggaaa ttaattccat gttggaacaa tcaaaaggct tcttaactaa  3000
cattcagacg gtgaaaattc ctaatgattg tcaaggtgta ttttttgttc aagatagcat  3060
gaaacatatt gatgaactaa gcccattagc aaaacaaaat ctgaaaaagg ttgttaatcg  3120
caatgcttat ttacctgatt ctgataagat agaattaagt aaagaaattg aaaataccaa  3180
taaagatcaa tcccaagaat tggataaaga cgtaccagaa aaaaatgaag tgactgtaaa  3240
aatgttccaa tttgcgaagt caattaatcg tttgttgagt ggtaaccaac tacagaaaaa  3300
acgaaaccta gacaaattga ttaagcaaac aaaagcaaaa aaaaatcaat cattacaaag  3360
gaatattcct ttgcgataaa ataaaaacaa gaggtgtata aaatgaaaaa atttatcaaa  3420
gatacaaagt ttaagcttgg aagtgcggtt gttgcgttgg gtacattgtt tattactgat  3480
ccagtgtttg cagccactga tccacaagcg aaattagttc aagcgggtaa cactataaaa  3540
ggtgttttaa cagccttaat tgttgtagtt ggtgggattg cttgtgcgaa gattgttatt  3600
aaatacttgc cgtctattga tgacccacaa gaaaaaaata ccatgtataa agccttggga  3660
acagccttgc ttgttacggc attaggtggg gcgttggttt ggttagtacc ttgggcgtat  3720
ggcttacttg cttaatagag aagggagtta gttatgaata gcgatcaagt gaaacaagcc  3780
```

```
ctattagatt tgttaaatgc agacactgaa aaagggcgga cttggttttt tccgtctaat  3840
gtatctgatc ggtacacagt cattttaggg ctagatttaa aacaatcagc aaaagcgatc  3900
ggtacggcat taataagcgt gttattgaca attcttattt tccgtagcac agccgttttt  3960
cctttaatta tctatgtcat tgttggtttg gtgtcatttg gtggtgtatg ggcgttttat  4020
acgattaaac caattacaga ccgacctaac atttctatat ctgattttat gaagcaaaga  4080
aaagactttt ctaaaagacc aaaagtctat tacaaaaagc caaaagaacg agtgtaaaag  4140
agaggtgatt taattgtttg attttctaaa aaaaagttcc aaaagtaacg ataataaaaa  4200
aagcgatacg atgaaagaaa tgatttattg ggaagatagt tcccgatttc aaggcgtttt  4260
taaagacttt tttgtcgttt atcagccaga aaaaaagcaa ttcagccttg tgagtatgct  4320
aaaagttgac ggcttaaacg ttgatacctt gccagtatca gagcaagaag ggttaaacga  4380
agattttggt gtctttctat ctcaaaacgt tctatatgaa ccgcagatca cttctaagaa  4440
tgtaccagta gaaattgacg attttgtaga agcctggggg attacagtag aaaattatcg  4500
caaaatgcca gggcataacg aagctttatt acaattaaag gctagttact attatcatta  4560
tagaaattta gcaagtaaca tggaaacttc aaagaaacaa cattttgtaa ttaattctga  4620
accaatttca aaggaaacat atgatagttt agaattgtcc tatcaagtgt tacgtgataa  4680
gacaaggaca atcaggacgg ctttaattgc ttttttaagc aagtatgatt gccaagttga  4740
aatgtgtacg attggcgaga tgaaaaaggt tttgaatagt taggagcgtt aaaatggaga  4800
agataccaaa agagaaaatt gtcttgatac ccgaagttga tacggacgtt gtatctgatt  4860
tagcaccatt taactttaca gtagaacgtg acaaattatt gattgatgat tcatacgcag  4920
ttccctatgt cattacaaaa tacaacaata agccacgtgg gaattggttt aatcgtattc  4980
gtaaaatgag tggagatata accatatctc attactacac taaagcaaac ggtaactcat  5040
tgaatgatta ttacaacaga accattaaga acaagcaagc agagatcgat cgttcgcatg  5100
atccgttgac gattatccgt ttagaacgtg aaatgaaaat tgctcaaacg cagttagaac  5160
aagccgttga cgaaaacact tcttatcttt acttgtacac ctatgttttg attaaaagta  5220
agtcagaaga taaattaaaa aaattgtgtg aagattttga aacacgttgt atcgcaagtg  5280
gagtaaaagc gttaattcca tatactatga ttgataaggc gtattggagt tcattaccgt  5340
tacaatctaa tgaagtacct gaatacacct atacaatcgc taattcaatc agtgcaagca  5400
gtatttttcc ttttgatgat aatgaattaa gtgtatttac taaaaaatatg attattgagg  5460
gaattaataa agatactgaa aatatcgtta gtattgatta caccaacaga aaattagtag  5520
tcaatcgtaa taaattcgtt tttggtttat ctggtggggg aaagaccact tacttaacgt  5580
cagactattt aaaaaaatat gctttttctg ataactcaac agaattaagg cacagaattg  5640
ttttatttga tcccgaagat gaacaaacag agcgtgtacg ttctctaggg ggcgaaataa  5700
tcaatctatc gtctatgtca gatgttcgta tcaatccatt tcaaatttac tcacgcaata  5760
cgctagatgt tgatttaaaa gaatcattat ccgattttga agaggacgag cttgtagaaa  5820
atattgaaat aaagcataaa gattatgaaa tgactgacaa tgatattgat aaagaaatca  5880
gtaaacgaat gaatatttta acgccttatt tcctaatggt ggatcattct ttgactgata  5940
gtcaattatc cattattaaa atagaagcta aaaaatgcta taccacttta tacgagaaga  6000
aaaacttgtc aaaaatggaa aacaccgatt ttccaacatt ttcagactta gaaaatcgat  6060
tgaaagcctt agaagaaact gatccaaaaa gatacaaacg aattgaagat tttatttatt  6120
cattagaaga ttttacaatc ggaagtcgta ccatttttaa cggtcataca aatatagact  6180
taaacaatcc gttaatttgc ttttctttgc gagatttaca gaccgaagaa gggatcagag  6240
atttagcata cctcaacagc tttagttatc tatttgaaga aataaccaac aatccgcaaa  6300
ttgtaacgtc tgtttatgca gatgaatttc actttttatt gaagaataaa attagtgctg  6360
actttttctt ccaagcatat aaacgcttta gaaaatacaa tgctgattgt accgtatcaa  6420
cccaacagat tgatgatgta ttaaaagcac ctgataatat cggtaaagca attattggga  6480
atagctttac aaaagtattc ttcggacttg atgaaacgga agcacaaggt atttcaaatg  6540
agttgaaact taaactcaca aaaaaagaat tatcgttcat tacctcaaaa cgtcaagggg  6600
aagctttgct ttttcatggt acaaagcgag caaagataaa agtagattta acacaggaag  6660
aaatgcgttt gcttaaccca ggcgaatatg aagatattta cggcgttagt ccgaagaaag  6720
agatcaactg gttgttaaga tcgaaaattc aatagaaggg agaaaaaaat gaaatacaaa  6780
atcttgaaaa atttacaatt ctactatcaa gagaatgtca ttgtcgtcca aataaacgaa  6840
aaatatttga cgaatcgaga acatattttt gatgtagaag aaagtgaaca atattttgtt  6900
gatgtcgagg agattttgac caaagacgga aagctagaaa ttgtttataa ccgacctaat  6960
ggctatacac cactactaga tttaaaagaa tatgctgatt tttataaatt ggatatagtg  7020
aatcgattac ttgaaatgaa tgtactagaa aaaacaaaca cctatctagc aatgcaaaat  7080
atcctactca aagatacacg tgacttgctt tttatttata aagcagatca ctttgataat  7140
ttgccttact caactaaaga agaattagag cagtggaaaa attttatttg tagttttttt  7200
ggtaaattca cacttgagaa gtatgagaag aatcgtattg aggttctaac aaaagaaaaa  7260
aattcatttt taaatgatgt agaagcagtt gaaagcttgg aatcattaag agatttaata  7320
aaaaatcgac taaccgaaga acaaaagaat ttcttttctg ctgaattaca ggacaagaaa  7380
gcagacgtcc gaaaaattcg cagaaataaa agcttaaaaa ttgcgttagt tgtaggtgtt  7440
attgcgttat atggcggtac ggttttactt atgaaagtaa atgagaagaa acaagttacg  7500
gctacacagc aaagcgcaga aacagagatc actattttaa ataagattat tgataatgat  7560
agtgagaata tcgaagaaga tatgcaaaag ctcaattatc ctaagaaaaa acaagttgat  7620
atttacgtga aacttggtga ttataccaag gcttatgaac ttgataaaaa gtcagataaa  7680
aaaattattc aaagtctgta caaacaagga gaaaccgaaa aaatagaagc ccttgattta  7740
ccaggaagcg actatttagc agacttcaaa aagattttag cgtatgacaa ttcaacagat  7800
attgagtatc tggttcaaac tagtaccgat acaacaattg ttgaagcttt aatcgataaa  7860
tcagtaaaag aaaaagacat tccaacagtg aaaaatattc gtcaagtatc aattacacaa  7920
aagaaattag caatcgatcc taaacgtcaa atcagtatga ttgacttatt gattgaaaat  7980
aacagtgaag aattagaaaa tatgtataag gataattctt taaatgagga cttgaagaaa  8040
aaacaaacca atgacttgtt agaagaaaac aacacgttgc ttagtgaaaa gattgaatta  8100
acaaacgctg aaaaagatta ggaaggttgg tgattt                           8136
```

```
SEQ ID NO: 64          moltype = DNA  length = 2053
FEATURE                Location/Qualifiers
source                 1..2053
                       mol_type = other DNA
                       note = pCU1
```

```
                        organism = synthetic construct
SEQUENCE: 64
ctgtttccat tctgtttctg aaattctgtt tttctgagcc atctgtgggc ctccgtagtt  60
ttggttacag aaaggatata ctcagaataa ataggggtca atacaagtac gatttttata  120
aactttattt tatttgaggg tgaggcccgg tgcggcacga gcgcggcgtt gatggtgccg  180
cgaaaggtgc ctggcgccat gcttggatta aaacatgaac cgtgaagaac tgcgaaactt  240
gttttcgcgg ttctgagggg ttgaccgagc cgcgaagtgg taagcgatga tatgcacata  300
tccacaggca tatttttaaa aggtatttta tagatttttt atctttttaa agtcttttag  360
agctatataa ctcattgatt taaaatcata aataagtgtt atctctggga atccgcccac  420
cttgttatgg gaattggccc acctatctat gggaaacacc ccaccttact atgggaatta  480
gcccaccttg ttatgggaat tggcccacct tagacgaaac tgtaaaaaat gtatttactt  540
gtttgaactt tgtggtagtg tggagagtaa tttttaaccc acaaaggcaa ggctcatgga  600
taagttgctg aacaaaaaga taaaagttaa gcagtctaac gagcttaccg aagctgctta  660
ctacctctcg ctaaaagcaa agcgcgttct ctggttatgt cttatgcaga cgtatttcac  720
agcttcagta agcgaagatg atgatgagat ggctgtactc ggtgactcta ctttcaaagt  780
aaaggtggct gactatcagc aaatttttca ggtaagccgt aaccaggcta tcaaggatgt  840
taaagaaggc gtgtttgagt taagccgttc tgcggtaatc ttttacccga aagaagggag  900
ttttgactgc gtcgcgcgcc cctggctaac agaggctggc agccgatcag ctcgtggtat  960
ctgggaaatc gaatttaacc ataaactcct gcggtacatt tacggcctga cgaaccagtt  1020
caccacctac tcgctccgcg attgtggcag tcttcgaaat ccacggacga tccgccttta  1080
tgaaagtctt gctcaattca aatcttcagg cttatgggtt actactcatg cttggttaaa  1140
tgaccgtttc cttttgccgg aatcccaaca gaagaacttg gcagagttga aacgatcttt  1200
ccttgatcct gctctcaagc agataaatga gaaaacacct ttacttgcta agtatagtat  1260
tgatgattca ggaaaatttc tgttctcaat aattgataag caaaatcccg tctgacataa  1320
atcagcacac atgagcctgt catttgacaa atttttgtca tgaagatggg cgaatttcca  1380
cacagcaccg gcgcccggca aggtgggcgg attcccacac ggcaccgacg cccggcaagg  1440
tgggcggatt cccacacggc accggcgccc ggcaacggtg ggcggatttc cacacagcac  1500
cggcgcccgg caaggtgggc ggattcccac acggcaccgg cgcccggcaa ggtgggcgga  1560
ttcccacaca gcaccggcgc ccggcaaggt gggcggattt ccacacagca ccggcgcccg  1620
gcaaggtggg cggattccca cacggcaccg gcgcccggca aggtgggcgg attcccacac  1680
ggcaccggcg cccggcaagg tgggcggatt cccacacggc accggcgccc ggcaaggtgg  1740
gcggatttcc acacagcacc ggcgcccggc aaggtgggcg gatttccaca cagcaccggc  1800
gcccggcaag gtgggcggat ttccacacgg caccggcgcc cggcaaggtg ggcggatttc  1860
cataacttta attatacctt tgtgttattt gtggattgtg cagctcagtg ggcgctggc  1920
cgtgacggtg cggtgtcccc cgtaaccggc cgcgcggccg ctaactcgca gtacggcgcc  1980
gcgacccgca gcgggccgcc gtacccgcgc cgcacggcgc ccactgcgca cccccgtgga  2040
ggacgtgcgg cag                                                    2053

SEQ ID NO: 65           moltype = DNA  length = 1540
FEATURE                 Location/Qualifiers
source                  1..1540
                        mol_type = other DNA
                        note = pBAV1K-T5
                        organism = synthetic construct
SEQUENCE: 65
tccgccgccc tagacctagt gtcattttat ttcccccgtt tcagcatcaa gaacctttgc  60
ataacttgct ctatatccac actgataatt gccctcaaac cataatctaa aggcgctaga  120
gtttgttgaa acaatatctt ttacatcatt cgtatttaaa attccaaact ccgctcccct  180
aaggcgaata aaagccatta aatcttttgt atttaccaaa ttatagtcat ccactatatc  240
taagagtaaa ttcttcaatt ctcttttttg gctttcatca agtgttatat agcggtcaat  300
atcaaaatca ttaatgttca aaatatcttt tttgtcgtat atatgtttat tcttagcaat  360
agcgtccttt gattcatgag tcaaatattc atatgaacct ttgatataat caagtatctc  420
aacatgagca actgaactat tccccaattt tcgcttaatc ttgttcctaa cgctttctat  480
tgttacagga tttcgtgcaa tatatataac gtgatagtgt ggtttttat agtgctttcc  540
atttcgtata acatcactac tattccatgt atctttatct tttttttcgt ccatatcgtg  600
taaaggactg acagccatag atacgcccaa actctctaat tttccttcc aatcattagg  660
aattgagtca ggatataata aaaatccaaa atttctagct ttagtatttt taatagccat  720
gatataatta ccttatcaaa aacaagtagc gaaaactcgt atccttctaa aaacgcgagc  780
tttcgcttat tttttttgtt ctgattcctt tcttgcatat tcttctatag ctaacgccgc  840
aaccgcagat tttgaaaaac ctttttgttt cgccatatct gttaattttt tatcttgctc  900
ttttgtcaga gaaatcataa ctcttttttt cgattctgaa atcaccattt aaaaaactcc  960
aatcaaataa ttttataaag ttagtgtatc actttgtaat cataaaaaca acaataaagc  1020
tacttaaata tagatttata aaaaacgttg gcgaaaacgt tggcgattcg ttggcgattg  1080
aaaaacccct taaacccttg agccagttgg gatagagcgt ttttggcaca aaaattggca  1140
ctcggcactt aatggggggt cgtagtacgg aagcaaaatt cgcttccttt ccccccattt  1200
ttttccaaat tccaaatttt tttcaaaaat tttccagcgc taccgctcgg caaaattgca  1260
agcaattttt aaaatcaaac ccatgaggga atttcattcc ctcatactcc cttgagcctc  1320
ctccaaccga aatagaaggg cgctgcgctt attatttcat tcagtcatcg gctttcataa  1380
tctaacagac aacatcttcg ctgcaaagcc acgctacgct caagggcttt tacgctacga  1440
taacgcctgt tttaacgatt atgccgataa ctaaacgaaa taaacgctaa aacgtctcag  1500
aaacgatttt gagacgtttt aataaaaaat cgcctagtgc                       1540

SEQ ID NO: 66           moltype = DNA  length = 383
FEATURE                 Location/Qualifiers
source                  1..383
                        mol_type = other DNA
                        note = Cos PAC7 383
                        organism = synthetic construct
SEQUENCE: 66
```

```
gaccacatca cacccgtcag ccggggagga ctcaacaccc tcgacaacgg gcaaatcatc  60
tgcagaacat gcaacagaag caaaggcaac agaacacaac caaacatcaa attccaacaa  120
caaaccacaa aaacattgat tccatggtga aaaacccgcc aacccccacc gggcacaccc  180
cctgcacacc cgtgcaagac ctcgtacggc ttagtgaaat acctcccttt tgttgtttta  240
tcgttttgtc gactttttgt ttggtggtgt gtgtggtgca gcctgagctt cctgatagtc  300
gtgattggtg tggggagacg cgtcggtggt ggtgtgtgtg gggcgaggat ccgcgtgccg  360
ggtttgtgtc tgatgaggag tgg                                          383

SEQ ID NO: 67          moltype = DNA  length = 511
FEATURE                Location/Qualifiers
source                 1..511
                       mol_type = other DNA
                       note = phage PAC7 origin of replication
                       organism = synthetic construct
SEQUENCE: 67
cgacatcagt cttaaagtct taaacacttt aagtaacttt aaagcttcaa ggcttagccc  60
ttaaggatct aagttactat aaaagcttta aacacttaaa gtaactataa agctttaaga  120
gcttaacatt taaggatata aataaacatt aaagctttaa agtcttaaag taaatatata  180
accttaacac ttaagttaag tataaaacct taaaggctta gcacttaagg atataaactt  240
aacatcagtg tttaagactt aaagagttaa agtaactatt aagacttaaa ggcttataag  300
ctttaatact ttaagtagct ataagacttt aaaaacctga agtacttaaa gttaaccatc  360
agtcttaaac tttaatatta taagtattaa agcttataag ttataaaagt ttttagaaga  420
gttaaagggt taacttcttt acttctcttc tctctttggt tctttctctc ttctcttctt  480
ttcttcatca ggggagaaga ggaaccttta a                                 511

SEQ ID NO: 68          moltype = DNA  length = 29768
FEATURE                Location/Qualifiers
source                 1..29768
                       mol_type = other DNA
                       note = PAC7
                       organism = synthetic construct
SEQUENCE: 68
tgcaggtgct gacggtgtga acggcgttga cggcgctgat ggtcgggatg gttctgccgg  60
tgagcgcggc ccgcaaggcc cttcaggtcc tgccggcccg caaggtgcac agggtgaacg  120
gggtgagcgt ggtcccgccg gtgcgaatgg atcggatggc catgatggta aggatgggcg  180
ctcggtggtg tctgtgtact gttccggggg ccgcctggtt gtgaaatata gtgacggtgt  240
ggcttccacg atatcgggtt cggcggcctg ccagggtgtg aaaccgtcgc ctctagtgac  300
tatatcatcc cacaaataga aaggagtggc tgtgatggtg gtgtttggtg gtggtgtgtt  360
gtgagatata ttcctgcggc gcatcattct gccggctcga atagtccggt gaatagggtt  420
gtgattcatg cgacgtgccc ggatgtgggg tttccgtccg cctcgcgtaa aggacgggct  480
gtgtccacgg caaactattt cgcttcccca tcgtctggtg gttcggcgca ttatgtgtgt  540
gatattgggg agacggtgca atgcttgtcg gagtctacga ttgggtggca tgccccgccg  600
aatccgcata gtttgggtat agagatttgc gcggatgggg gttcgcacgc ctcgttccgg  660
gtgccggggc atgcttacac tcgtgagcag tggctggatc ctcgcgtgtg gcctgcggtt  720
gagcgtgccg ccatcctgtg tagacgtttg tgtgacaagc atggtgttcc gaaaaggaaa  780
ctgtctgtgg ccgatttgaa ggccggtaaa cggggtgttt gcgggcatgt ggatgttacg  840
gatgcgtggc atcagtcgga tcatgacgat ccggggccgt ggtttccgtg ggacaaattt  900
atggctgtgg ttaatggcca cggcggcggt tcaagtagtg aggagttgag tatggctgat  960
gtacaagcgt tacataatca gattaaacag ttgtcggcac aggtggccca gtcggtgaat  1020
aagctgcatc acgatgttgg tgtggttcag gttcagaatg gtgatttggg taaacgtgtt  1080
gatgccttgt cgtgggtgaa gaatcctgtg acggggaagc tgtggcgcac taaggatgct  1140
ttgtggagtg tctggtatta cgtgttggag tgtcgtagcc gtcttgacag gctcgagtct  1200
gctgtcaacg atttgaaaaa gtgatggtgg tttgttgtgg gtaaacagtt ttggttaggt  1260
ttgctggagc gtgccctgaa aacttttgtt caaacgtttg ttgccgtgtt gggggttact  1320
gcgggtgtca cctatactgc ggagtcgttt cgtggtttgc cgtgggaatc cgcgctgatc  1380
acggcaacgg ttgctgctgt cctgtcggtt gctacctcgt ttggtagccc gtcgtttgtg  1440
gccggcaagc ccggcaagca gccccaggtg gatgcgggtt tggttccacc ggatgatggg  1500
ggcttggttg agccgcatat ggtggatgtg tcggatcctg gcatgatcga gccgacggat  1560
gatgcggatc ttgccggcta tgagcctcgg cgtgcagccg agtcggaggt tggcacggta  1620
gagtctactg ttgcataatt gaatatagat gtgtgcccca gcggtgctgc cacgattgtg  1680
tggtggcggc tgctggggca ctatttttgt atatgcggtg tggctatgat tcgttgctgt  1740
cgatggtgtc ttcgagcatc tgatacaggt ggaggcaggt agagatagtt tcgctggcct  1800
gatcgagaac gttccggccg ataacgtttt tgtggttgtc gcggtggcgg atgatagccc  1860
acatgatctc gtcggctgcc gcctgtaata gtttggcctg gtatgcgatt ccggcgagcc  1920
agtctagtgc ttcctggctt gtataggggc tctggtcctc gctgttgccg cgggtgttgc  1980
tgttgtttgt ggggtgtcct gcactgtcgc atagccacag gatttcgctg cactcgtcta  2040
gcgtgtcttg gtcgatagcg agatcgtcga ggctgacatt gttgacggta aggttcacgt  2100
tgtcgaggga gatgggtaca ccgtactggt tttcgacact gtcaacaatg ttttccagct  2160
gttgcatgtt ggtgggctgt tgttggacga tacggtgtat cgctgtgttg agggtggtgt  2220
aggtgatgtt gtgtgtgttg tccatggttt ttatgccatt ccttcgttat cgtctggcat  2280
gtagtatgtg ctgtttgcgt actcggttaa cgtcatcagt gtttggtctg cccactgttt  2340
cacggtttgc cgggtgactc cgagtcgttg ggcggctgtg gcgtaggttt gatcataccc  2400
gtatacttcc cggaatgctg ccaacctagc taggtgtttc ctctgtttgg atggttcaca  2460
ggtgagggtg tagtcgtcga tggctagctg tagatcgatc atggagacga tgttgttgcc  2520
gtggtgttgt ggcgcggttg gtgggggtgg cattcctggc tccacggagg gtttccaggg  2580
gccgccgttc cagatccatt gggcagcttg gatgatgtcg gcggtggtgt aggttcggtt  2640
cactggtcac cccctgaaca ggtcgttggt gttgttggtg tcgaatcgtc cgacgcagtg  2700
gcagtagtcg tacatgagtt taataatgtg ttggtggtct cccaaatagg tgtttccgct  2760
gatgctgtat gtggctgtgc cgtctttcgc gatggtgtat ttggcggtga tggtttcggg  2820
```

-continued

```
gttttcggtg tcggtgatga ttgctgtggt ggtggcgcct actgtttgga gtatggtggt  2880
ttgggttccg tcgtcgatgg tggttttaac catggtgtgt gttttccctt ttgttagttg  2940
cttgtttggt tgtcggctag atgaataata tcgggtaaag gtttcggctg gtctaggtgt  3000
tgtatggttt tgttggctag ccgtttggct accctgtaac acattttggt gtagtgtttg  3060
ttgtctaggt tgtggtattg ttcccgcacc gcaatatata gcagggagtc ttggtacagg  3120
tcgtctgcac tgattgcggg gtagtgtgcg gctgttttgg tgcatgcccg gttgagtgtg  3180
cgaagatgat ggtctgtggc ccacacccac gatgcggtgg tggccaggtc ggcttttgtt  3240
ggtcgtctgc tcatggcact atttcatctc gctatctgat agttgtttgg tgttttgttg  3300
tggatagtgt agcacactag tcctgggtgg ccggtggtgc ctgtgcggtg acggaaccat  3360
gtggattcgc cttccatgga tgggcattgg atgaaggtgc gttgtccttg ctcggagatt  3420
tctaggtggt gccggtgccc ggccatgaga atattagata cggtgccgtt gtggaattct  3480
tggccgcgcc accaatcata gtgtttaccg gtgcgccatt ggtgcccgtg ggcgtgcagt  3540
atccgtgtgc ctgccacatc aacggtggtg gtcatttcgt ctcggctggg gaagtggaag  3600
tgtaggttgg ggtattggtt attgagctgg taggcttctg cgatggcccg gcagcagtcc  3660
acgtcgaatg agtcatcgta ggtggtgact cctttaccga agcgcacggc ttcaccatgg  3720
ttgccgggga tggatgtgat ggtcacattt ttgcagtggt cgaattggtg gatgagttgc  3780
atcatggcca tgcgggtgag cctgatttgt tcggtgaggg gtgtttgtgt tcgccaggcg  3840
ttgttgcctc cttgtgacac gtatccttcg atcatgtcgc cgaggaaggc gatgtggact  3900
cgttcgggtt tgcctgcttg ttgccagcag tgttttgcga ctatgaggga gtgtaggtag  3960
ttgtcggcga agtgtgctgt ttctccgccg gggatgcctt tgccgatttg gaagtctcct  4020
gccccgatga cgaaggctgc ggtgctgtag tcggtgtggg tgtcttgttc gggttttggg  4080
ggtgtccatt cggctagttt atcgacgagt tcgtctaccg ggtaggggtt tgttgcgggt  4140
tggtggtcga tgatttttg tatggatcgg cctgtttctc cgttggggag tgtccattcg  4200
gagatgcgtg tgcggcgcac ggtgccgttg gctagattgt cgtcgatggt gtcgatggcg  4260
ttgtcgtggt tggctagctg tgtgagtagc cggtcaatat tgtctatcac tgggtatcct  4320
cctcttgcgg ggtggtgctg gcttgtttgc ggcgatagtc tttaataacg gtggcggaga  4380
tggggtatcc tgcctgggtg agctgttttg ctagccatga ggcggggata gacctgtcgg  4440
cgagcacgtc ggcggctttg ttgccgtagc gttgaataag ggtttcagtt ttggttgcca  4500
tgatgtccta tcggttgtgt ggtgggctgc catcctgtgc ggcagtcgcc gtcgtgtcct  4560
ggtttgcgtg tgcaccacga tacggttccg tctgtgtggt tgagtgtttt accgcacatg  4620
acgtttcgga gatgctccgg cagctggtca tcctggttgc tggtttgtgt gtcgaagagt  4680
gttttctggt tggtgaaatg ttctgacacg gtgccgttat gcacgggtag tatccatgtt  4740
ttccattgtt gttgtagcct ggtgttccag tggaattgtt tggcggcgtt ttcggcctgt  4800
tttaaggttt tgtggtagcc gactagtatg cgttgatgct gctggtctgg agggtttggg  4860
cctcgccagt attgtgccgc cacggcgtag cggttgctgt ctgtgaaggc gtcccagcag  4920
tattcgataa tgtgttgcaa catactgtct ggcaggctgt cagggttgat gttgatgttt  4980
tgggtgataa tgtcacggat ggcttgccgg tttttggtgg tgggtttgaa cgagatgctc  5040
acgatagtac cggctggtcg tcttgcatga actggttgaa ggtgttgttc ccggcgtgtt  5100
gggcttgtgt tatttgttgg tcggtccagt ctgggtgttg ctgtttcaga tagtgccagt  5160
ggcacgcatt gtaggtttcg tcttgtagcc gtgtgagatg gtttcggtgg atgatttgtt  5220
tccacatggc ccatgacacg tcgagccggt cgaggatttc gagggctggg atgttgaatt  5280
ggttcaggaa gaggatttcg tgggtgtagt agtttttctc gtaggcgtcc catccgcttc  5340
ggtgcctgtt gggctggttt ttggggtagg cttcccggca tactttgtgt aaacgcttgg  5400
ccatgtcgtc gggtagttta atgtcggggt tggcgcggat catggatcgc atcccatcat  5460
aggtggtgcc ccaggtgtgc atgatgtagg tggggtcttc tccgtcggcc cattttctg  5520
cacagatggc gaggcggata cgcctcctgg cagcttggct ggtgttgcgc cggttgggga  5580
ttgggcacgt gtcgagggga tccatgatgt tttagtgtac ctttctggtt tcgtgttgtt  5640
gacaggtttt actgtagcac agtgtctagt gcgtgtgtca accctgtttt tccggcttga  5700
aggtaggtgt ctgtgacatc ccctagggtg aggggcacgt gcacagcttg ggggagtgcc  5760
gcctggaggg tttgggccat ctggtcgcct gcggggtctg ggtctgacca gatgtagatg  5820
tggtcgtagc cttcaaaaaa tttggtccaa aaaatttgcc acgaggttgc gccgggtagg  5880
gcgacggccg accatccgca ttgttcgagg atcatggagt cgaattcgcc ttcgcaaatg  5940
tgcatttcgg ctgccgggtt ggccatggcg gccatgttgt agatggagcc tgtgtctcct  6000
gccggggtta ggtatttggg gtggttgtgg gttttgcagt cgtgcgggag tgagcagcgg  6060
aaacgcattt ttcttatttc ggctgggccg ccccaaacgg ggtacatgta tgggatggtg  6120
atgcactggt tgtagttttc gtggcctggg atggggtcat tgtcgatgta tccaaggtgg  6180
tggtagcggg ctgtttcttc gctgatgcct cttgctgaga gcaggtcgag tatgttttcg  6240
aggtgggttt cgtagcgggc tgaggctttc tggattcggc ggcgttccgc aatgttgtat  6300
gggcgtatgc tgtcgtacat ttgggttttc ttcttctaat cgttgttgta gcttggcgag  6360
tccgcctccg acaccgcatg tgtggcagta ccagacgccc ttgtcgaggt tgatgctcat  6420
ggagggctgg tggtcgtcgt ggaacgggca gagtatgtgt tgctcgttcc tggacggatt  6480
gtaccgtatc tgataatggt cgaggaggcg gcaggtgtca gaggtgtggg aggagctcgt  6540
tgagggttga taccacatag gcttcactcc atggcttgtt gcgctgtttc atcactacga  6600
gtccgatggt ggaattgttt tgtttgtttc ggtgtgtttc gtagttgcgt gcctcccggc  6660
tggcttgttt cacgaattgg gctaggtgtg ttgcccggc tttcgcctcg ataatgtagg  6720
ttttatggcc ggttgtgagg atgaggtcgc cttcgtcttc gcggccgttg aggtggaggc  6780
gttcgatatt gtgtccggtg tcgcgtagct ggtggaggag tcttgtttcc cattcggctc  6840
cggcccgccg gttgcgtgcc tgctgtgtgg ccatagtttt ttagagtcct ttgtgtgttg  6900
tggtcatgtt ccagggctgt ttttcggcga gtggcccgaa gaatgtgtat tcggggtatg  6960
ctctgagtcg ttcgtatcgg gtgccgtcgg ggctggattt gcctgtgcgc tgtttgagta  7020
cggcgatgcg tgcctctgcc ggtatcgata gcccgttgcc gttatcctcg ccaccataca  7080
atgagactcc gaggatgagt tgtggttttt cggagaggcc gtttttgatt tctcgccgtg  7140
ctggcgggtg ttcgatgtcg gttccggttt tgtcggttgc gtggtgtgtg acaataatgg  7200
tggagccagt atccctgccc aatgctgtga tccattgcat ggcttcttgc tgtgcctggt  7260
agtcggattc gcagtcttga atgtccatca ggttgtcgat aacaatgagt ggtgggaagg  7320
tgttccacat ttccatgtag gcttgtaact ccatggtgat gtctgtccat gtgatgggtg  7380
actggaatga gaatgtgatg tgttggccgt ggtggatgct gtctcgatag tattctggcc  7440
cgtagtcgtc gatgttttgt tgtatttgtt gggtggtgtg ttgtgtgttg agggagatga  7500
ttcgtgtgga ggcctcccag ggtgtcatgt cccctgatat gtagagggcg ggctggttga  7560
```

```
gcatcgctgt gatgaacatg gctagccctg atttttggct gccggaccgc cccgcgatca  7620
tcaccaagtc gcccttatgg atgtgcaaat cttggttatc atatagtggt gcgagttgtg  7680
gtatgcgggg tagttcggct gcggtttggg aggctctctc gaaggatcgt tgtagagaga  7740
gcatcgggac cttaatctat ctgtctgttg gttgtgtggc tggtcagatg gagtcgatat  7800
cgatatcagc atcagcagag gctgaagtgt catctagctg accattatcg cgcttgtcta  7860
cgtattcggc aaccttatcg tagatggcgt cgtccaatgt tttgagcacg accgcgttga  7920
aaccgttttt ggtgcgcacg gtggctagtt tgaaggcctg ctcctcgcca aggtatgcct  7980
ctagttcgcg gatcatggag tgtgggcggt cgttattgcc gcgggctttc tcaataatag  8040
cgttggggat ggtttctggg gtgccgttgt tgagatcgtc tagggtgtgg aagatggtga  8100
catcagcgta gatgcggtct gcgacctgtc caccgtagcc ttcagtgttg tgctggacgt  8160
cgtgcacttt gaaggcgatg gccgtggcgt cctggtttcg ggaggggttg aagaaggtgc  8220
tgttgctgtt gttgcggtag tttgcgagtc ccataactat tgtttccttt tactgttgtg  8280
tctgtttttg ttggcttata ttggtttatc gggtgaggct gtttcgctta gtgcggaaag  8340
cgtcggaaac atcactgtta ctggtgatga tcttcttgta ctgttttaga aggtctgcta  8400
gctgtgcctt gcttgttgca ttgttgattt tgttgatgac gatggtgttt tctttggatg  8460
cgattttgtt gacgtagtct ttggctgcct ggttgtatcg gtcttggagg atgattgatg  8520
cgctcgctac gagtgttgct agatcccagt ctttggacac gtcatcgttt ttgagtccgc  8580
ctagcaggtc gatgatggcc tgttttgtct gctctgctgt gtctcctcgg atgaccgccc  8640
atggtgcagc atagtctcca ccatatttga gtgtgatcgt gagtcgatca ttgtcgatct  8700
tgtctttatc tgtcatttgg tgtccttttc tttattgtct gtttctggtg gctgtacggt  8760
ggattctacc gggtatctgt acgagttttt gccgttgacg gcccagcagg cgtctcgtac  8820
ggggcatcct ttacagagtg ttgtgacgtg ggggacgaag atgccttcgc tgattccttt  8880
cattgcttga ctgtacatgg atgatacatg ccggtaggtg ttgttgtcaa ggtcgtagag  8940
ttcggtggat gtgccttgtg tcggggactt gtcgtcgttg cggctggtgg ctggcgtcca  9000
aaacatgcct ttcgtgacat ggatgtcgtg ttggttgagc atgtaccggt atgtgtgcag  9060
ctgcatactg tcggcgggta ggcgtccggt tttgaggtcg aggatgaagg tttcgccggt  9120
gtcggtgtcg gtgaaaacac ggtcgatgta gccgactatt tttgtgtcat cgtcgaggat  9180
ggtttctacc gggtattcga tgcctggttt accgtccagg attgcggtga tgtattctgg  9240
gtggttgcgc ctccatgttt tccagcggtc cacaaaggtg gggccgtaaa ccatccacca  9300
gtcgtagtct ttcttgtgtg gtccgcctga ctcgcacatg tttttgcata ttctgccgga  9360
gggtttgatt tctgtgcctt cggattcggc gagggctacc tgggtgtcga aaatgttttt  9420
gaaggatgag agtttgtctg gcagtgcagg gtattcggcg ggattgtaca ggtgtaggtc  9480
gtattgttcg gtgatgtggt gtatggcgct tccggcgatg gtggcgtacc aggtgtggtg  9540
ttgggcgtga tagccgtggg ataggcgcca tttttctccg cattcggccc actgggtgag  9600
tgaactgtag gagatgtgtc ctgggtggct gatggttttc gggtattgtg ctagaggcat  9660
tacttgtcgc ttgtgttcca tgtgttgcgg gtgtcttggc cggcgtggtg ttgctggtag  9720
gcgaggagtg cgaggcagtg ccaggctgcg tgtgctagat ggggtagccc ggattcgtgg  9780
tcgaggttgt tgccttgctg ccatgatagt agatgcctgt agagggcgtc gacactgtgg  9840
ctccacgggt atcctccggt ccagttgttg tcgccatatt tggtggcacc gtatccggct  9900
acttcgccta gggcgtgaag ggatgctggg tcgatgaggg agagcctgca gagtttcaat  9960
tcttttcggg caccgctgtt ggggtcggtg tacatgcggg tgggctcatc catggggtgt  10020
gtgctcctta agggtgggtt actggttgtt gttgtgggct agggcggcgg cgagaataat  10080
gatggcgagg gtttcggcta tcagtatggg tgttgtgatc atttggtgtc tcggggattg  10140
ttggtgagtg ttgaggcacc caggagggtg gcgagggcgc atgcggcaat aatggcgagg  10200
gctgccttgt gtggggtgcc ggttgcgtac atccatgtga tgatggcacc ttggatccag  10260
gctaggctgg tgaagaaggt ttcgtagctg tgcagctcaa tgttgttgtt gggtgtgttc  10320
atgcttgctc ctgaagaatg gtgttgatgg ttttataaat gttgtacagg tcggtttcga  10380
tagataacag ttggttgatt tggtggtcga gatcaatgtc tgggttgagt gtgttgatgc  10440
gggaggcaat atcggtggct gtgcgtagtg tgccgccggt gtggtgaata atgtgtgccg  10500
tgtcggcgag tccggtggtg acggcgtagt gggataggag aggcatagcg gggatgctcc  10560
ttggcgggtt actgttgcgg gttgatgttg aggtcggtga cgtgcggtga gttttctgtt  10620
ccggtgacga ggcagtggac ggtgacgggt agtttggatg ctcccggctg gcggacggtg  10680
gcgccgtaga cgatgctgaa tgtgtcttta ccgatggttt tgtggagttg gaggtcgatg  10740
tcggggttgc cgttccagtt gacaccttgc gctgcggcct gttgttcggc tttgtggttg  10800
caggtgtgtg ctgccgtgat catggtgagt ccggtggcgg tttcttcacc ccttgcttgg  10860
gcttgcttgt gggctttggc ctgctcggct tgtagggatc gggtggcggc tgcctgccgt  10920
gccgctttct cggctttgcg ctgttgggta gtcttggggg tccatgtggt gttggctgtg  10980
gttgcctgtg gggctggctg tgaggtgagt ggcgggttgt cgtctggtgc tggcatgaat  11040
gaggcggcgg caatgatggc ggctgtgatg cctgcgatgg tgtagccgtt tttcttgttc  11100
atgttttgtg tccccttcc ggggtgttgt tcgttgctga catggttaat actttcagcg  11160
gctgggccca ctgtcaaggc tgcgctcagt ttgtgtgagc gtttggtgtg tggctagggg  11220
ttttgtcatg taagcgtgac atgtcactac cttgcgtcca gtatccatgg cggttgcgag  11280
ccatcccttt ggcgagcatc tcgtccacag tgaggcacct gcggcgattg gggccttcct  11340
tgaccccgtg atcgcctatg cggtgcatgt ccccggcata agtgccatta aatgtttcgt  11400
ggcagactgt gcagtgttct ggtcggtatc cgatgattgt gctatcgcac ttgtggcatg  11460
tccattgcat gattggtcct tctttcgtgt tttaagcttg tgctctgagg attagagcga  11520
ctttcagccc ttgggggtag gattatatag gtcaggtatt tctaggcgat tctaggctca  11580
ttgtgtgtgg ttggggtttt atcgggcgca tagggttagc aggtggccca cattggtgcg  11640
gctcacattc cagtagagtt gcgtggcttc cttactggtg agcggcttcc actcgtcatg  11700
gctgaacacg gtgccatcgg atgcgatgaa cgtgttgggg cgtagcttgt gaagctcggc  11760
ttccacatgc tgccggtagg cttcggcgag gctctcaaaa tccatgtggt cgcaggagag  11820
gttttcgagg cgtgtcaggt cgaaaggctc cgggcagtcg tagctggctg gagtgtagag  11880
ctgggtgaag tggtcggcga tcttctgcat ggcgggttcc tttctggtgt gtggatggtt  11940
tttatcgtgt ggatgcgaca aggatggcgt ctacgtcgat catgtcgatc atgtcgttga  12000
gttcctcggc ctcattctcg gagaggtggc gccagtcggg tggcccgtat acggcgccgt  12060
cgagggtgac agtccacagg ggccggatga gtcgtatggc ttcttcgact ttggcgtggt  12120
acatgcggcg caccatatcc agatcgatgt cgtctgaatg gtttccggtg aggctgtgga  12180
ggctgagcgg gtcgatttct gtctgcctgt agaggctggt gaatgatggt gtgatgagtg  12240
tgccatccat gagtgtgctc ctttctaggg gttgttgtgg tttctagagt gtgtgggctg  12300
```

```
tgaccccaca gtcaaggcta cgctcatttg gattgagcgt ttcatatggg tgtggcatgg  12360
aatctacacc ctcatactgt gtgagatgta tcacatcccc ctggcttggt gtgcacccct  12420
caagactact ctgccgacct ggcgtggagg gtgtagccca gaaatgccgt ttaaagcttc  12480
aggggtacgc ctaggagcgc cttacagggt gggggctagg tatttatacc cccagcatat  12540
tctgatcgat tctagacgac tcccagagcc cgatacacga tcaaccatct cgacatagac  12600
catcagcccc tatcctggtt agctaagcct caactatgtg gacagtgtgg gacactgtgg  12660
gggaagaagg acacggtaca agaaagaggg gggagcatca gccttaaagc cttaagatct  12720
tagcgcttag caccgatggt cttagcagtt agcaccgagc ccttgagggg gctcggcatc  12780
agcctcatcg ggctcagctc atcaggcaca gccctgaaaa gggtacacgc catcagggaa  12840
ggcttgagag tacgaggagc cctagcgacg agtactcgaa agcctgaggg aacaccctca  12900
gtactgatga gcctagcgta ttcggaaagg acgcaagagt aaagtgtgac agctatccgg  12960
gagtgaaacc cgttccgact aggggtttca gccttaacca ccctcaaagg ttacaagact  13020
ctaagaaaat ttaagaaact tcttaggaag aaagttgtgt tcatatcccc ctaaaaacac  13080
ccaaaatagt cctcaaaccc gcctatagag ccaaacagtc aagtttgact cgtctagacg  13140
gcgtatgata ggctggacag gtagccagct ggacgcaagg ccagaaagtg ctgacgcact  13200
tcccgacctc gcttaccatc agtctaccaa acactttaaa gcttcaaggc ttagcgctaa  13260
gcccttaaga tcttaacgct tagcaccgag ccccctcaa gggctcgaca tcagtcttaa  13320
agtcttaaac actttaagta actttaaagc ttcaaggctt agcccttaag gatctaagtt  13380
actataaaag ctttaaacac ttaaagtaac tataaagctt taagagctta acatttaagg  13440
atataaataa acattaaagc tttaaagtct taaagtaaat atataacctt aacacttaag  13500
ttaagtataa aaccttaaag gcttagcact taaggatata aacttaacat cagtgtttaa  13560
gacttaaaga gttaaagtaa ctattaagac ttaaaggctt ataagcttta atactttaag  13620
tagctataag actttaaaaa cctgaagtac ttaaagttaa ccatcagtct taaactttaa  13680
tattataagt attaaagctt ataagttata aaagttttta gaagagttaa agggttaact  13740
tctttacttc tcttctctct ttggttcttt ctctcttctc ttcttttctt catcagggga  13800
gaagaggaac ctttaaccgt caacgctgat ggacttttca ccgtgtgact cgtgtgcttc  13860
tggtcgcaag ctcccatcgc acactcccca cactctttca cccgtgcccc tttacggctt  13920
agcgtgttcg tcggaaggcg tacggcgtgt cacgcttaaa cccttaacac caggtaagac  13980
ttaaagtgca tattataagt agaagacttt aaaacctata aggtgttccc gcttagcccg  14040
tgttccttta acgctaggcg ctcagcgcta agatgtgaaa cgtgaacacc catccacccc  14100
catttttctt ccgtgtcctt ctccttttga caccgctggg gggcgatgtg atatttctca  14160
catgccaggg ggtagtggag aaaacaacca ccccggaacg tttaagacac cccctcaaac  14220
gaacaaaaca gggcctagaa tcgatcagca gggcaccggt agggtattcc tacccccaga  14280
cgattcaagg ccattacagg agcaatgaga ggctcacagg ggccatggga gattgggggg  14340
cgtgatggca cacaccaacc gcacagccag ccaagcccac cggcgctggc gggcaaggct  14400
catcacccaa gcccgacaac aaggccaaac cgaatgccca ctctgcggag tcaccatcac  14460
ctggaacacc cacgacctgc caaccagccc cgaagccgac cacatcacac ccgtcagccg  14520
gggaggactc aacaccctcg acaacgggca aatcatctgc agaacatgca acagaagcaa  14580
aggcaacaga acacaaccaa acatcaaatt ccaacaacaa accacaaaaa cattgattcc  14640
atggtgaaaa acccgccaac ccccaccggg cacacccccct gcacacccgt gcaagacctc  14700
gtacggctta gtgaaatacc tccctttttgt tgttttatcg ttttgtcgac tttttgtttg  14760
gtggtgtgtg tggtgcagcc tgagcttcct gatagtcgtg attggtgtgg ggagacgcgt  14820
cggtggtggt gtgtgtgggg cgaggatccg cgtgccgggt ttgtgtctga tgaggagtgg  14880
ttgtttctca tggatgctgc ggtgattcat gatgtggtgt ggcgtgaggg tcgcgcggat  14940
ttggtggctt cgttgcgtgc tcatgtgaag gcttttatgg gtatgttgga taggtattcg  15000
gttgatgtgg cgtctggtgg ccgtggtggg ggttctgcgg tagcgatgat tgaccggtat  15060
aggaagcgta ggggggcttg agtaggtgtc tggtgttgtt gggtctcagg ttcctcgtca  15120
ccgggtggct gtggcgtatt cggtgtctgc tggcggggat gctggggagc ttggtagggc  15180
ttatgggttg acgcctgatc cgtggcagca gcaggtgttg gatgattggc ttgctgtggg  15240
tggtaatggc aggcttgctt cgggtgtgtg tggggtgttt gttccgcggc agaatggcaa  15300
gaatgctatt ttggagattg tggagttgtt taaggcgact attcagggtc gccgtatttt  15360
gcatacggct cacgagttga agtcggctcg taaggcgttt atgcggttgc ggtcgttttt  15420
tgagaatgag cggcagtttc ctgacttgta tcgtatggtg aagtcgattc gtgcgacgaa  15480
tggccaggag gctattgtgt tgcatcatcc ggattgtgcc acgtttgaga agaagtgtgg  15540
ttgtccgggt tggggttcgg ttgagtttgt ggctcgtagc cggggttctg ctcgcgggtt  15600
tacggttgat gatttggtgt gtgatgaggc tcaggagttg tcggatgagc agttggaggc  15660
tttgcttcct accgtgagcg ctgccccgtc tggtgatcct cagcagattt ttttgggtac  15720
gccgccgggg ccgttggctg acgggtctgt ggtgttgcgt cttcgcgggc aggctttgtc  15780
gggtggtaaa cggtttgcgt ggacggagtt ttcgattcct gacgagtctg atccggatga  15840
tgtgtcgcgg cagtggcgga agttggcggg tgacactaat ccggcgttgg ggcgccgcct  15900
gaatttcggg acagtctcgg atgagcatga gtcgatgtct gctgccgggt ttgctcggga  15960
gcggcttggc tggtgggatc gtggccagtc tgcttcgtct gtgattccgg cggataagtg  16020
ggttcagtcg gctgtggttg aggcggctct ggttggcggg aaggtttttg gtgtctcgtt  16080
ttctcgctcg ggggatcgtg tcgcgttggc tggtgctggt aaaacggatt ctggtgtgca  16140
tgttgaggtt attgatggcc tgtctgggac gattgttgat ggtgtgggcc agctggctga  16200
ttggttggcg ttgcgttggg gtgacactga aaaggttatg gttgcagggt ctggtgcggt  16260
gttgttgcag aaggctttga cggatcgtgg tgttccgggt cgtggcgtga ttgtggctga  16320
tactggggtg tatgtggagg cgtgtcaagc cttcctggag ggtgtcaggt ctgggagcgt  16380
gtctcatcct cgtgccgatt cgaggcgtga catgttggat attgctgtga ggtcggctgt  16440
gcagaagaag aagggttctg cgtggggttg gggttcctcg tttaaggatg gttctgaggt  16500
tcctttggag gctgtgtctt tggcgtatct tggtgcgaag atggcgaaag cgaagcggcg  16560
tgaacggtct ggtaggaagc gggtgtctgt ggtatgaact cggatgagtt ggctctgatt  16620
gagggcatgt acgatcgtat tcaagggttg tcttcgtggc attgccgtat tgagggctac  16680
tatgagggct ctaatcgggt gcgtgatttg ggggttgcta ttccttcgga gttgcagcgg  16740
gtgcagacgg tggtgtcatg gcctgggatt gcggtggatg ctttggagga gcgtctggat  16800
tggcttggct ggactaatgg tgacggctac ggtttggatg gtgtgtatgc tgcgaatcgg  16860
cttgctacgg cgtcgtgtga tgttcacctt gatgcactga tttttgggtt gtcgtttgtg  16920
gcgatcattc cccaagagga tggtcggtg ttggttcgtc ctcagtcgcc gaagaattgt  16980
actggccggt tttctgccga tgggtcttgt ttggatgctg gccttgtggt gcagcagacg  17040
```

-continued

```
tgtgatcctg aggttgttga ggcggagttg ttgcttcctg atgtgattgt tcaggtggag  17100
cggcggggtt cgcgtgagtg ggttgagacg ggccgtatcg agaatgtgtt gggtgcggtt  17160
ccgttggtgc ctgttgtgaa tcgtcgccgt acttctagga ttgatggccg ttcggagatt  17220
acgaggtcta ttagggctta cacggatgag gctgttcgca cactgttggg gcagtctgtg  17280
aatcgtgatt tttatgcgta tcctcagcgt tgggtgactg gcgtgagcgc ggatgagttt  17340
tcgcagccgg gttgggttct gtcgatggct tctgtgtggg ctgtggataa ggatgatgat  17400
ggtgacactc cgaatgtggg gtcgtttcct gtgaattctc ctacaccgta ttctgatcag  17460
atgcgtttgt tggcgcagtt gactgcgggt gaggcggctg ttccggaacg ctatttcggg  17520
tttatcactt ctaacccgcc ttctggggag gctttggctg cggaggagtc tcggcttgtg  17580
aagcgtgctg aacgcaggca gacgtcgttt ggtcagggct ggctgtcggt tggtttcctg  17640
gctgcccggg cgttggattc gagtgttgat gaggccgcgt tttttggtga tgttggtttg  17700
cgttggcgtg atgcgtcgac gccgactcgg gcggctacgg ctgatgctgt gacgaagctt  17760
gtgggtgctg gtattttgcc tgctgattct cggacggtgt tggagatgtt gggtttggat  17820
gatgtgcagg ttgaggctgt gatgcgtcat cgtgccgagt cttcggatcc gttggcggca  17880
ctggctgggg ctatttcccg tcaaactaac gaggtttgat aggcgatggc ttcgggtgct  17940
gtgtcgaggc ttgctgcgac tgagtatcag cgtgaggctg tcaggtttgc tgggaagtat  18000
gcgggctatt atgccgagtt gggtcgtttg tggcgtgccg gcaggatgag tgacacgcag  18060
tatgtgcgtt tgtgtgtgga gttggagcgt gccggccatg acggttcagc agctatggcg  18120
ggcaaattcg tttcagattt tcgccggttg aatggtgtcg atcctggttt gatcgtgtat  18180
gacgagtttg atgctgcggc ggctttggct aggtcgtttt cgactatgaa gattatgaat  18240
agtgacccgg atagggcgaa tgatacgatt gatgcgatgg ctgcgggtgt taatcgggct  18300
gttatgaatg ctggtcgtga cacggttgag tggtcggcgg gtgcgcaggg taggtcgtgg  18360
cgtcgggtga ctgatggtga tccgtgtgct ttttgtgcca tgttggctac gaggtcggat  18420
tatacgacta aagagcgggc gcttactact ggtcatacgc ggcgtcataa gcgtgccggt  18480
aggcgtccgt ttggttcgaa gtatcatgat cattgtggtt gtacggtggt tgaggttgtt  18540
ggtccttggg aaccgaatag ggctgatgcc gagtatcaga ggacgtatga gaaggctcgt  18600
gagtgggttg atgatcatgg gttgcagcag tcgtctggca atattttgaa ggctatgcgt  18660
actgttggtg gcatgagata atttgatgtg gtttccggtt gtgtgccgcc ggttatcggt  18720
gcacagggtt gtctcccgca cgggggtcaa caatgttgtg ttgttttccg caaggagtgt  18780
agggttaggc tatggccgat cagagtattg aggaacagaa tgttgacaat gatgttgtgg  18840
agtccggaaa ggataacggc attgttgata cagtaaaaga cgatggcggg caggaggtag  18900
ccgacaatca gttgaagaat gaaggcgagg gtaaatcgcc ggggactgat tggaaggcgg  18960
aggcccgtaa gtgggagtct cgtgctaaaa gtaatttcgc cgagttggag aagcttcgta  19020
catcgagtga cgattctgga tctactattg atgagcttcg ccgcaagaat gaggaactcg  19080
aagaccggat taacgggttt gttcttgagg gtgtgaagcg cgaggtggct gccgagtgtg  19140
gcctgtcggg tgatgcgatc gcttttcttc acggtagcga taaggagtcg cttgccgagt  19200
ctgctaaggc tttgaagggt ttgatcgacc atagtagtgg tggtggcgcg ggtgtgcgcc  19260
gtcttgcggg gagtgccccc gttgatgatg ttaaacgacg tgagggtgtc gcgtttgtgg  19320
atgctcttgt caataattct aggagatgat ttatcatggc tgacgatttt ctttctgcag  19380
ggaagcttga gcttcctggt tctatgattg gtgcggttcg tgaccgtgct atcgattctg  19440
gtgttcttgc taaactgtca ccggagcagc cgactatttt cgggcctgtt aagggcgccg  19500
tttttagtgg tgttccgcgc gctaagattg ttggcgaggg cgatgttaag ccttccgcta  19560
gcgttgatgt ttctgcgttt actgcgcagc ctatcaaggt tgtgactcag cagcgtgtct  19620
cggacgagtt tatgtgggct gacgccgatt accgtctggg tgtgcttcag gatctgattt  19680
ccccggccct gggtgcttct attggtcgcg ccgttgatct tattgctttc catggtattg  19740
atcctgctac gggtaagcct gctgcggctg tcaaggtgtc gctggataag acgaataaga  19800
cggttgatgc caccgattcc gctacggctg atcttgttaa ggctgttggt ctgattgctg  19860
gtgctggttt gcaggttcct aacggtgttg ctttggatcc ggcgttctcg tttgctctgt  19920
caactgaggt gtatccgaag ggttcgccgc ttgccggtca gccaatgtat cctgccgccg  19980
ggttcgccgg cctggataat tggcgcggcc taaatgttgg ttcttcttcg actgtttctg  20040
gtgccccgga gatgtcgcct gcttctggtg ttaaggctat tgttggtgat ttctctcgtg  20100
tccattgggg gttccagcgt aacttcccga ttgagctgat cgagtatggt gacccggatc  20160
agacggggcg tgacttgaag ggccataatg aggttatggt tcgtgccgag gctgtgctgt  20220
atgttgcgat tgagtcgctt gattcgtttg ctgtcgtgaa ggagaaggct gccccgaagc  20280
ctaatccgcc ggccggtaac tgattcattt gttgcgataa tgtttatgct gtgtgcaggg  20340
ggtggtgttg atgggtatca ttttgaagcc tgaggatatt gagcctttcg ccgatattcc  20400
tagagagaag cttgaggcga tgattgccga tgtggaggct gtggctgtca gtgtcgcccc  20460
ctgtatcgct aaaccggatt tcaaatatag ggatgccgct aaggctattc tgcgtagggc  20520
tttgttgcgc tggaatgata ctggcgtgtc gggtcaggtg cagtatgagt ctgcgggccc  20580
gtttgctcag actacacggt cgaatactcc tacgaatttg ttgtggcctt ctgagattgc  20640
cgcgttgaag aagttgtgtg agggtgatag tggggctggt aaggcgttca ctattacacc  20700
gaccatgagg agtagtgtga atcattctga ggtgtgttcc acggtgtggg gtgagggttg  20760
ctcgtgcggg tcgaatatta acggctatgc tggcccgttg tgggagatat gatatgaccg  20820
gttttcctta cggtgaaacg gttgtgatgc ttcagccgac tgttcgtgtc gatgatcttg  20880
gtgacaaggt ggaggattgg tctaagcctg tcgagactgt gtaccataac gtggccatct  20940
atgcttccgt ttcgcaggag gatgaggccg cggggcgtga ctcggattat gagcattgga  21000
cactgctgtt caagcagcct gtcaaggctg ctggttatcg gtgtcgttgg cgtattcggg  21060
gtgttgtgtg ggaggctgac gggtctccta tggtgtggca tcatccgatg tctggctggg  21120
atgctggtac gcaggttaat gtgaagcgca agaagggctg atgggttgtg gcacgtgatg  21180
ttgatgtgaa gctgaacttg ccgggtattc gtgaggtgtt gaagtcttct ggggtgcagg  21240
gcatgttggc tgagcgtggt gagcgtgtca agcgtgcggc ctcggcgaat gtgggcggta  21300
acgcttacga tagggcccag tatcgtgccg ggttgtcgtc tgaggtgcag gttcaccgtg  21360
ttgaggctgt ggcgcgtatt ggcaccacct ataagggtgg taaaaggatt gaggctaagc  21420
atggcacgtt ggcgaggtcg attggggctg cgtcgtgatc gtttacggtg atcctcgaat  21480
atgggctaaa cgtgtgttgg cggatgatgg ttggctgtct gatgtaccgt gcacgggtac  21540
tgtgccggat acatttgagg gtgatctgat ttggttggcg ttggatggtg gcccggagtt  21600
gcatgttcgt gagcgtgttt ttttgcgtgt gaatgtgttt tcggatacgc cggatcgtgc  21660
tatgtctttg gctcgccggg ttgaggctgt gctggctgat ggtgtggatg gtgatccggt  21720
ggtgttttgc aggcgttcga ctgggcctga tttgctggtg gatggtgcac gttttgatgt  21780
```

```
gtattcgctt tttgagctga tatgtaggcc tgcggagtct gaataagctt attgtttttg  21840
ttttaatgta attgtttgat atttaatggg ggttgtgatg gctgctacac gtaaagcgtc  21900
taatgttcgt tcagcggtta ctggcgacgt ttatattggt gacgcgcacg cgggtgattc  21960
tattaagggt gtggaggcgg ttccttccgg gcttacagct ttggggtatc tgtctgatga  22020
cgggtttaag attaagcctg agcgtaaaac ggatgatttg aaggcttggc agaatgcgga  22080
tgttgttcgc actgtggcta cggagtcgtc tatcgagatt tctttccagc tgattgagtc  22140
gaagaaggag gttatcgaac tgttttggca gtcgaaggtt actgccggat ctgattcggg  22200
ttcgttcgat atttctcctg gtgccacaac aggtgttcac gccctgttga tggatattgt  22260
tgatggcgat caggttattc gctactattt ccctgaggtt gagctcattg atcgtgacga  22320
gattaagggc aagaatggcg aagtgtacgg gtatggtgtg acgttgaagg cgtatcctgc  22380
ccagattaat aagactggta atgcggtgtc gggtcggggg tggatgacgg ctttaaaagc  22440
tgatactcct ccgactcctc cgccggcccc ggttcctccg aagcctcagc cggatccgaa  22500
tccgccgtcc ggtaactgat acacgatttt aggggattgt taatagatga gtgacactgg  22560
tttcacgttg aagattggtg atcgtagctg ggtgttggcg gatgcggagg agacggctca  22620
ggctgttcct gcccgcgttt tccgtcgtgc cgccaggatt gcccagtcgg gggagtctgc  22680
ggatttcgcc caggttgagg tgatgttttc tatgttggag gctgccgccc cagctgacgc  22740
ggtggaggcc ctggaggggc ttcctatggt tcgtgtggcg gaggttttcc gtgagtggat  22800
ggaatacaag cctgacggta agggtgcctc gctgggggaa tagtttggct ccacggcctg  22860
attgatgatt atcgtggggc catcgaatac gatttccgca ccaagtttgg tgtttctgtt  22920
tatagtgttg gtggcccgca gatgtgttgg ggtgaggctg tccggctggc tggcgtgttg  22980
tgtaccgata cgtctagcca gttggcggcc caccttaatg gttggcagcg cccgtttgag  23040
tggtgcgagt gggctgtgtt ggacatgttg gatcattaca ggtctgctaa tagtgagggg  23100
cagccggagc ctgtggcgag gccgactgat gagcgtcggg caaggtttac gtctgggcag  23160
gtggacgata ttttggcgcg tgttcgtgcc ggtggcgggg tgtctcgcga gattgatatt  23220
atggggtgaa tagtgtatgt ctggtgagat tgcttccgca tatgtgtcgt tgtatacgaa  23280
gatgcctggc cttaaaagtg atgttggtaa acagttgtcg ggtgttatgc ctgctgaggg  23340
gcagcgttcg ggtagcctgt ttgctaaagg catgaagttg gcgcttggtg gtgcggcgat  23400
gatgggtgcc atcaatgttg ctaagaaggg cctcaagtct atctatgatg tgactattgg  23460
tggcggtatt gctcgcgcta tggctattga tgaggctcag gctaaactga ctggtttggg  23520
tcacacgtct tctgatacgt cttcgattat gaattcggct attgaggctg tgactggtac  23580
gtcgtatgcg ttgggggatg cggcgtctac ggcggcggcg ttgtctgctt cgggtgtgaa  23640
gtctggcggt cagatgacgg atgtgttgaa gactgtcgcg gatgtgtctt atatttcggg  23700
taagtcgttt caggatacgg gcgctatttt tacgtctgtg atggctcgcg gtaagttgca  23760
gggcgatgac atgttgcagc ttacgatggc tggtgttcct gtgctgtctt tgcttgccag  23820
gcagacgggt aaaacctcgg ctgaggtttc gcagatggtg tcgaaggggc agattgattt  23880
tgccacgttt gcggctgcga tgaagcttgg catgggtggt gctgcgcagg cgtctggtaa  23940
gacgtttgag ggcgctatga agaatgttaa gggcgctttg ggctatttgg gtgctacggc  24000
tatggcgccg tttcttaacg gcctgcggca gatttttgtt gcgttgaatc cggttattaa  24060
gtctatcacg gattctgtga agccgatgtt tgctgccgtc gatgctggta tccagcggat  24120
gatgccgtct attttggcgt ggattaaccg tatgccggct atgatcacga gaatgaatgc  24180
acagatgcgc gccaaggtgg agcagttgaa gggcattttt gcgagaatgc atttgcctgt  24240
tcctaaagtg aatttgggtg ccatgtttgc tggcggcacc gcagtgtttg gtattgttgc  24300
tgcgggtgtg gggaagcttg ttgcagggtt tgctccgttg gcggttgcgt tgaagaatct  24360
gttgccgtcg tttggtgctt tgagggggtgc cgccgggggg cttggtggcg tgtttcgcgc  24420
cctgggtggc cctgtcggga ttgtgatcgg cttgtttgcg gcaatgtttg ccacgaacgc  24480
ccagttccgt gccgctgtta tgcagctggt ggctgtggtt ggtcaggcgt tgggccagat  24540
tatggcagct gtgcagccgc tgtttggttt ggttgctggc gtggttgcca ggttggcgcc  24600
ggtgttcggc cagattatcg gtatggttgc tggtttggct gcccggctgg tgcctgttat  24660
tggtatgctt attgcccggc tggttcctgt tatcacccag attattggta tggtaaccca  24720
ggttgctgcc atgttgttgc ctatgctgat gccggttatt caggctgttg ttgctgtgat  24780
acggcaggtt attggtgtca ttatgcagtt gatacctgtt ttgatgccgg ttgtgcagca  24840
gattttgggt gctgtcatgt ctgttttgcc gccgattgtt ggtttgatac ggtcgctgat  24900
accggtgatc atgtcgatta tgcgtgtggt ggtgcaggtt gttggtgctg tgctacaggt  24960
ggtggcccgt attattccgg ttgttatgcc gatttatgtt tcggtgattg gattcattgc  25020
caagatttat gctgcggtta tcgtttttga ggctaaggtt attggcgcta ttcttcgtac  25080
tattacgtgg attgtgaatc attcagtgtc tggcgtgagg tctatgggca cggccatcca  25140
gaatggctgg aatcatatta aatcgtttac gtctgcgttt attaacggtt ttaagtcgat  25200
catttctggc ggcgtgaacg cggttgtggg gttttttacg cggcttggtt tgtcggttgc  25260
ttcccatgtg aggtccggtt ttaacgctgc gaggggtgct gtttcttccg ccatgaatgc  25320
tattcggagt gttgtgtctt cggtggcgtc tgctgttggc gggtttttca gttcgatggc  25380
gtctcgtgtt cggaatggtg ctgtgcgcgg gtttaatggt gcccggagtg cggcttcttc  25440
tgctatgcat gctatggggt ccgctgtgtc tagtggtgtg catggtgtgc tgggtttttt  25500
ccggaatttg cctgacaata ttcggcgtgc gcttggtaat atggggtccc tgttggtgtc  25560
ggctggccgt gatgtggtgt ccggtttagg taatggtatc aagaatgctt tgagtggcct  25620
gttggatacg gtgcgtaata tgggttctca ggttgctaat gcggcgaagt cggtgttggg  25680
tattcattcc ccgtctcggg tgtttcgtga cgaggttggc cggcaggttg ttgccggttt  25740
ggctgagggt attactggta atgctggttt ggcgttggat gcgatgtcgg gtgtggctgg  25800
gaggctgcct gatgcggttg atgcccggtt tggtgtgcga tcgtctgtgg gttcgtttac  25860
cccgtatggc aggtatcagc gcatgaatga taagagtgtt gtggtgaatg tgaatggcgc  25920
tacttatggg gatcctgccg agtttgcgaa gcggattgag cggcagcagc gtgacgcttt  25980
gaacgcgttg gcttacgtgt gattttgggg gtgtggtgca tgtttattcc tgacccgtct  26040
gatcgttctg gtttgactgt gacttggtct atgttgccgt tgattggtaa tgatccggag  26100
cgtgtgcttc atttgacgga ttatacgggg tcgtctccga taatgttgtt gaatgattcg  26160
ttgcgcggtt tgggtgttcc tgaggtggag catttttctc aaactcatgt tggggtgcat  26220
ggctcggagt ggcgcgggtt taatgtgaag cctcgcgagg tgacgctacc ggtgttggtg  26280
tcgggtgttg gcccggatcc ggtgggcggt tttcgtgacg gttttttgaa ggcgtatgac  26340
gagttgtggt ctgcttttcc tcctggcgag gtgggggagt tgtctgtgaa gactcctgcc  26400
ggtcgtgagc gtgtgttgaa gtgccggttt gattcggtgg atgacacgtt tacggtggat  26460
ccggtgaaca ggggttatgc gcgttatctg ttgcatttga cggcttatga cccgttttgg  26520
```

```
tatggggatg agcagaagtt tcgtttcagt aacgctaagt tgcaggattg gttgggtggc  26580
ggccctgtcg acggtaaggg taccgcgttt ccggtggtgt tgacgcctgg tgttggttcg  26640
ggttgggata atctgtctaa taagggtgat gtgcctgcgt ggcctgtgat tcgtgttgag  26700
gggccgttgt cgtcgtggtc tgtgcagatt gatggtttgc gtgtgtcctc ggattggccg  26760
gtggaggagt atgattggat cactattgat acggatcctc gtaagcagtc tgcgttgttg  26820
gacgggtttg aggatgtgat ggatcgtttg aaggagtggg agtttgcgcc tatcccgcct  26880
ggcggttctc ggagtgtgaa tattgagatg gttggtttgg gtgccattgt tgtgtcggtg  26940
cagtacaggt ttttgagggc ttggtgaata gttgatggct ggttttgttc cgcatgtaac  27000
attgtttaca ccggattatc gccgtgtggc gcctatcaat ttttttgagt cgttgaagtt  27060
gtcgttgaag tggaatggtt tgtccacttt ggagttggtg gtgtctggtg atcattctag  27120
gcttgacggg ttgactaggc cgggtgcgcg gcttgtggtt gattatggtg gtggccagat  27180
tttttctggg cctgtgcgtc gggtgcatgg tgtgggtccg tggcgttctt cgcgtgtgac  27240
tatcacgtgt gaggatgata ttcgtctgtt gtggcgtatg ttgatgtggc ctgtgaatta  27300
tcgtcctggt atggttggta tggagtggcg tgcggatcgg gattatgccc attattcggg  27360
tgcggcggag tcggtggcta agcgggtgtt gggggataat gcttggcgtt ttccgtctgg  27420
tttgtttatg aacgatgatg agagtcgtgg ccgctatatt aaggattttc aggtgcggtt  27480
tcacgtgttt gccgataagt tgttgccggt gttgtcgtgg gctcggatga ctgtcacggt  27540
gaaccagttt gagaatgcga agtttgatca gcgtggtttg gtgtttgatt gtgtgcctgc  27600
tgtgacccgg aaacatgtgt tgactgccga gtcgggttcg attgtgtcgt gggagtatgt  27660
gcgtgacgcc ccgaaggcga catctgtggt ggttggtggc cgtggcgagg gtaaggatcg  27720
gctgttttgt gaggatgttg attcggcggc cgaggatgat tggtttgatc gtgtcgaggt  27780
gtttaaggat gcccgtaaca cggattccga gaaggtgtct ctcttcgatg aggctgagcg  27840
ggtgttgtcc gagtcggggg ctacgtcggg gtttaagatt gagttggctg agtcggatgt  27900
gttgcggttt ggtcccggca atctgatgcc tggggatttg atctatgtgg atgtgggttc  27960
tgggcctatt gcggagattg tgcggcagat tgatgtggag tgtgtatcgc ctggtgatgg  28020
ttggacgaag gtgactccgg ttgcgggggga ttatgaggat aatccgtcgg ccctgttggc  28080
tcgccgtgtg gctggtttgg ctgcgggtgt gcgggatttg caaaagtttt agtaagtgat  28140
tggggtttgt tgtgggtatt gtgtgtaaag ggtttgatgg tgtgttgacc gagtatgatt  28200
gggctcaaat gtctggtctg atgggtaata tgccgtctgt gaaggggcct gacgattttc  28260
gtgtcggcac gacgattcag ggttctacgg tgttgtgtga gatcctgccg gggcaggctt  28320
gggctcacgg ggtgatgtgc acgtcgaata gtgttgagac ggtgacgggt cagcttccgg  28380
gcccgggtga gactcgatac gactatgtgg tgttgtctcg ggattggcag gagaatacgg  28440
ccaagttgga gattgttccc ggtgggcgtg cggagcgtgc caggatgtg ttgagggctg  28500
agcctggcgt gtttcatcag cagctactgg cgactttggt gttgtcgtct aacgggttgc  28560
agcagcagtt ggataggcgt gctgtggcgg ctagggttgc gtttggggag tctgctgcgt  28620
gtgatcctac ccctgtggag ggtgaccgtg tgatggttcc ttcgggggct gtgtgggcta  28680
accatgccgg cgagtggatg ttgttgtctc ccaggattga gacgggttcg aagtcgatca  28740
tgtttggtgg ttctgctgtg tatgcttaca cgatcccgtt tgagcgccag ttcagtagtc  28800
cgcctgttgt ggtggcgtct atggctacgg cggctggggg cacggcacag attgatgtga  28860
aagcctacaa tgtgactgcc caaaatttta gtttggcgtt tattacgaat gatggttcga  28920
agccgaatgg tgtgcctgcg gtggcgaatt ggattgctgt cggcgtgtga ctgcacgggt  28980
gttgtggcgg atggtgtgat gttggggggc tgtggtgtcg tggtttactc ctgcactggt  29040
ggcctctatt tgtaccgcgt tggccacggt tttgggttct gttcaggctg tcacatcccg  29100
gtctaggaag cgtttacgca ggctgtcggc tcaggtggat gcgatggaag agtatacgtg  29160
gggtgtgcgg cgcgaggtgc gaaggtttaa cgccgggctt cctgatgatg tggagccgat  29220
gcatcttcct gatttgcccg agtttttgaa agatactgtt gatggtggag gtgagtaggg  29280
ttgagggagt tggaggagga gaagcggcag cgccgcaatt ttgagaaggc ttcactggtg  29340
ttgttgtttt tgtcgcttgt gttgttggcg gtggttgctg cgggtgcttt gcgtttcggg  29400
gctgtatcct ctgagcggga ttcggagcag gcgagggccc agtcgaatgg tacggctgcc  29460
aggggtttgg ctgcccgtgt gaagcaggcg tgtgcttcgg gtggggtgga gtctgtgcgt  29520
cttcaccgtt ctggtttgtg tgtggatgct gtgcgtgttg agcagcgtgt tcagggtgtg  29580
ccgggtcctg ccggtgagcg cggcccgcaa ggcccttcag gtcctgccgg ccgggatggt  29640
gttaatggtt cggctgggct ggttggccct gttggtccgc aaggttctcc gggtttgaat  29700
ggtgtgaaag gtcctgacgg cttgcctggc gctaacggtt cggatggccg tgatggtgtt  29760
ccaggtcg                                                           29768
```

```
SEQ ID NO: 69          moltype = DNA  length = 29238
FEATURE                Location/Qualifiers
source                 1..29238
                       mol_type = other DNA
                       note = PAC1
                       organism = synthetic construct
SEQUENCE: 69
tagcgtacag ggtgtgccag gtcccgccgg tgagcgcggc ccgcaagggc cggctggtgc  60
tgatggtcgg gatggtgtta atggttcgac tgggctggtt ggccctgtgg gtccgcaggg  120
ttctcctggc ttgaatggtg tggctggccc ggacgggttg cctggtgcga acggatcgga  180
tggccatgat ggtgttccag gtcgtgcagg tgctgacggt gtgaacggcg ctgatggtcg  240
ggatggttcg gccggtgagc gcggtgatgt gggcccttca ggtcctgccg gcccgcaagg  300
tgcacagggt gaacggggtc ctattgggcc tcagggtccg cagggttctg ccggtgctga  360
cggcacgaat ggtaaagacg gtaaagatgg gcgctcggtt gtgtctgtgt actgttccga  420
gggccgcctg gttgtgaaat atagtgacgg tgtggcttct acaatatcga gctcggtggc  480
ctgccagggt gtgaaaccgt cgcctatagt gactatatca tcccacaagt aaaaaagaaa  540
agggaagggt gttactagtg ttgattgtgg tgttaggtgg tgtgtggtga gatacattcc  600
tgcggcgcat cattctgccg gctcgaatag tccggtgaat agggttgtga ttcatgcgac  660
gtgcccggat gtggggtttc cgtctgcctc gcgtaaaggg cgggcggtgt ctacagcaaa  720
ctatttcgcg tccccatcgt cgggtggttc ggcgcattat gtttgcgata ttagtgagac  780
ggtgcagtgc ttgtcggagt ctacgattgg gtggcatgcc ccgccgaatc cgcatagttt  840
gggtatcgag atttgcgcgg atgggggttc gcacgcctcg ttccgtgtgc cggggcatgc  900
ttacactcgg gagcagtggc ttgatcctag ggtgtggcct gcggtggaga aggctgccat  960
```

```
cctgtgtaga cgtttgtgtg acaaatataa tgttccgaag aggaagctta gtgcagccga  1020
tttgaaggct ggtaggcggg gcatctgcgg gcatactgat gtgacggatg cgtggcacca  1080
gtcggatcat gacgatcctg ggccgtggtt tccgtgggac aggtttatgg ccgtcgtcaa  1140
cggcaaagat gagagtgggg agttaacggt ggctgatgtg aaagccttgc atgatcagat  1200
taaacaattg tctgcccagc ttactggttc ggtgaataag ctgcaccatg atgttggtgt  1260
ggttcaggtt cagaatggtg atttgggtaa gcgtgttgac gccttgtcgt gggtgaagaa  1320
tccggtgacg gggaagctgt ggcgcacaaa ggatgctttg tggagtgtct ggtattacgt  1380
gctggagtgt cgcagccgca tcagtaggct ggagtctact gtcaacgatt taaagaagtg  1440
atctatggtg ggtaaacagt tttggttggg cttgtttgag cgtgccctga aaacttttat  1500
tcaaacgttt gttgctgtgt tgggtgtgac tgcgggtgtc acttatactg cggagtcgtt  1560
tcgcggtttg ccgtgggagt ctgctctgat tacggccggg gttgctgcaa tactgtcggt  1620
tgctacctcg tttggtagcc cgtcgtttgt ggctggcaaa cctaaaacta cggttgtgga  1680
tgcgggtttg gttccaccgg atgatggggg cttggttgag ccgcacatgg tggatgtgtc  1740
ggatcctggc atgatcgagc ctgcagatga tgcggatctt ggtgtaggct atgtgccgaa  1800
acacgctgcc gagtcggagg ttggcacggt agagtctact gttgcataat tgaatatgtg  1860
tgtgccccag cggtgctgcc acgatcgtgt ggtggttgcc gctggggcac tattttttgta  1920
tattgcggtg tggctatgat tcgttgctgt cgatggtgtc ttcgagcatc tgatacaggt  1980
ggaggcaggt agagatagtt tcgctggcct ggtctagaac gttccggccg ataacatttt  2040
tgtgattgtc gcggtggcgg atgatagccc acatgatctc gtcggctgcc gcttgcaata  2100
gttttgactg gtatgcgatt ccggcgagcc agtctatggc ttccgggctt gccggtgtgt  2160
cgtctggaat gccacaggtg ttgctgttgt ttgtggggta tcctgcactg tcgcaaaacc  2220
acaggatttc gctgcactcg tctagcgtgt cctggtcgat agcaagatcg tcgaggctga  2280
cttcgttgac ggtaaggttc acgttgtcga gggagatggg tacaccgtac tggttttcga  2340
cactgtcaac aatgtttttcc agctgttgca tgttggtggg ctgttgttgg acgatacggt  2400
gtatcgctgt gttgagggtg gtgtaggtga tattgtgtgt gttgttcatg gttttattcc  2460
atctctgtgc tgtcgtcttg gtcgtatcga ctgtttgcgt agcctgtgag ggtgatgagt  2520
gtttggtctg cccattgttt cactgtttgc cgggtgacac ccaatcgttg ggcggctgtg  2580
gcgtaggttt ggtcgtatcc gtatacttct cggaatgctg ccagccgtgc taaatgtttt  2640
cgctgtttgg atggctggca ggtgagggtg tagtcgtcga tggctagctg tagatcgatc  2700
atggcgacaa tgttgttgcc gtggtgttgt ggcgcggttg gtgggggtgg cattcccggc  2760
tccacggagg gtttccatgg gccgccgttc caaatccatt gggcggcctg aataatatct  2820
gcggtggtgt aggtcctgtt catgtgtcat cccctgaaca ggttgtcgaa gtcgtctgtg  2880
ttgctggtgt tggtggtatc gaatcgtccg acgcagtggc agtagtcgta catgagtttg  2940
ataatgtgtt ggtggtctcc caaataggtg ttgccgctga tgctgtaggt ggctgtgccg  3000
tctttgctga tggtgtattt ggcggtgatg gtttcggggt tttctgtgtt tgtgatgatg  3060
gctgtggtgg tggcgcctac ggtttgtagc ctggtggttt gggttccgtc gtcgagggtg  3120
gtagtaacca tagttggggt tctccttaaa tactggtttg gttgtcggct agatgaataa  3180
tatcggataa aggtttcggc tggtctaggt gttgtatggt tttgttggcg agccgtttgg  3240
ctaccctgta gcacattttg atgtagtgtt tgttgtctag gttgtggtat tgttcccgta  3300
ccgcaatata tagtagggag tcttggtaca ggtcgtctgc gttgattgcg gggtagtgtg  3360
tggctatttt tgtgcatgcc cggttgagtg tgcgtagatg atggtctgtg gcccatcccc  3420
acgatgctgt ggtggccagg tctgatttgg tgggtcgtct gctcatggcg ctatttcatc  3480
tcgctatctg atagttgttt ggtgttttgt tgttgatagt gtagcacact agtccgggat  3540
ggccggtggt gcctgtgcgg tgccggaacc atgtggattc tccttccatg gatgggcatt  3600
ggatgaaggt gcgttgtcct tgctcggaga tttctaggtg gtgccggtgc ccggccatga  3660
gaatattaga tgtggtgccg ttgtggaatt cttggccgcg ccaccattcg tattgtttgc  3720
cggttttcca ttggtgcccg tgtgcgtgca ggatttgtgt gccggctact tcgacggtgg  3780
tggtcatttc gtcccgtgcg gggaagtgga agtgaaggtt gggatattgg ttgtcgagct  3840
ggtaggcttc tgcgatggcg cggcagcagt ccacgtcgaa ggagtcatcg taggtggtga  3900
cgcctttacc gaaacgcacg gcttcaccgt ggttgccggg gatggatgtg atggtcacat  3960
ttttgcagtg gtcgaacatg tggacgagtt gcatcatggc catgcgagtc aaccggattt  4020
gttccgtcaa gggtgtttgt gtgcgccagg cgttgttgcc tccttgtgac acgtatcctt  4080
cgatcatgtc gccgaggaat gcgatgtgga ctcgttgcgg ctgtccggct tgctgccagt  4140
agtgttttgc gactatgagg gagtgcaaat agtcgtctgc gaagtgtgat gtttccccgc  4200
cggggatgcc tttgccgatt tgaaagtctc ccgcccctac cacgaacgca acattgctgt  4260
agtcggtgtg tgtgtcttgg ttgggtttgg ggggtgtcca ttcggctagt ttatcgacga  4320
gttcgtcgac cggatagggg tcggttgcgg gttggtggtc gatgattttt tgtatggatc  4380
ggccggtttc tccgttgggg agtgtccatt cggagatgcg tgtgcgccgt acggtgccgt  4440
ttgcgagatc atcgcggatg gtgtctgctt cgttgtcgtg gttggctagc tgtgtgagga  4500
gccggtctat attgtctatc atcgggtatc ctcctcttgt ggggtggtgt tggcttgttt  4560
gcggcgatag tcttttataa cggtggcgga gatggggtat cctgcctggg tgagctgttt  4620
tgctagccat gaggcgggga tagacctgtc ggcgaggacg tcggcggctt tagccccgta  4680
gcgttgaata agggtttcag ttttggttgc catgatgtcc taggggttgt gtggtgggct  4740
gccatcctgt gcggcagtcg ccgtcgtgtc ctggtttgcg ggtgcaccac gatacggttc  4800
cgtctgtgtg gttgagtgtt ttaccgcaca tgacgtcacg taggtgctcg ggaaactcat  4860
cgttgttgtt gtccccgtgc atgtcgatca agtgttgggt tttagtaacc atcatgcctc  4920
ctatgtgtga aagagtgtgc aaatactatg caggtgtcat ggatgtttat gcgggtatgg  4980
ttttcatcac cttgctgaac gttacttggt tactgtacat catctgagtg atttcctgat  5040
cagtcttatc ggggtgctgc tttcgcaggt tcgcccactg gcaggcgttg tcggtctcct  5100
gctgtaaacg tgtcaggtgc tgctcgttga tgatgtgttt ccacattgtc catgacacgt  5160
cgagcctgcg gagcatgttc atggctggca cgttgaagga gttgaggaag agtatttctt  5220
cggtgtagta ctgtttttcg tattggtccc atccgcttcg gtgcctgttg ggctggtttt  5280
tggggtaggc ttcccggcag attttgtgta accgtttggc catgtcgtcg ggtagtttaa  5340
tgtcggggtt ggcgcggatc atggatcgca tcccgtcata ggtggtgccc caggtgtgca  5400
tgatgtggag tgggtcttca ccatcggccc atttttcggc gatgatggcg aggcggatgc  5460
gcctcctggc ggctttactg gtgttgcgcc ggtgggggat ggggcatgtg tcgaggggat  5520
ccatgatatt ttagtgtacc tttccgtgtt gtggttgttt gtctggtttt attgtagcac  5580
tgtgttgagg gcttgtgtca accctgtttt gccggtttc aggtatgtgt ctgtgacatc  5640
ccccagggtg aggggcacgt gggtggcttg ggggagtgct gcctggaggg tttgggccat  5700
```

```
ctggtggcct gcctggtctg ggtcggacca gatgtagatg tggtcgtagc cttcgaagaa  5760
tttggtccag aaggtttgcc acgaggttgc gccgggtagg gcgacggctg gccatccgca  5820
ttgttcgagg atcatggagt cgaattcgcc ttcgcaaatg tgcatttcgg ctgccggggt  5880
ggccatggcg gccatgttgt agatggagcc tgtgtctcct gccggggtga ggtatttggg  5940
gtggttgtgg gttttgcagt cgtgtgggag tgagcagcgg aaacgcattt ttcgtatttc  6000
ggctggccgc ccccaaactg ggtacatgta tgggatggtg atgcactggt tgtagttttc  6060
gtggcctggt atggggtcat tgttgatgta tccaaggtgg tggtagcgag ctgtttcttc  6120
gctgatgcct cttgccgaga ggaggtcgag tatgttttcg aggtgggttt cgtagcgggc  6180
tgaggctttc tggattcggc ggcgttccgc aatgttgtat gggcgtatgc tgtcgtacat  6240
tcgggttttc tttctctaat tgttgttgta gtttggcgag tccgcctccg ataccgcatg  6300
tgtggcagta ccagacgccc ttgtcgaggt tgatgctcat ggagggctgg tggtcgtcgt  6360
ggaacgggca gaggatgtgt tgctcgtttt tggacgggtt gtaccgtatc tggtaggtgt  6420
cgaggaggcg gcaggtgtca gaggtgtggg aggagctcgt tgagggttga taccacatag  6480
gcttcgctcc atggcttgtt gcgctgtttc atcactacga gtccgatggt ggactgactt  6540
tcgcggtttc ggtgggtttc gtagttgcgt gcctcccggc tggcttgttt cacgaattcg  6600
gctaggtggg gctggccggc tttcgcctct atcacatagg ttttgtggcc ggttgtgagg  6660
ataaggtcgc cttcgtcttc acggccgttg aggtggaggc gttctatatc atggccggtg  6720
tcgcgtagtt ggtggaggag tcgtgtttcc cattctgcgc cggccctgcg gtttcttgat  6780
tgttgtgtcg acatgatagt cctttgtgtg ttgtggtcat attccagggc tgtttttcgg  6840
cgagggggccc gaagaaggtg tattcggggt aggctcgtag ccgctcgtat cgggtgccgt  6900
cggggctgga tttgcctgtg cgctgtttga ggacggcgat gcgtgcctct gccgggatcg  6960
atagcccgtt gccgttatcc tcgccaccat acaatgagac tccgaggatg agttgtggtt  7020
tttcggagag gccgtttttg atttctcgcc gggcgggcgg gtgttcgatg tcggagccgg  7080
ttttgtcggt tgcgtggtgt gtgacaataa tggtggagcc agtatcgcgg ccgagggctg  7140
tgatccattg catggcttct tgctgggcct gatagtcact ctcgcagtct tggatgtcca  7200
tcaggttgtc gataacgatg atgagtggga aggtgttcca catttccatg taggcttgca  7260
gttccatggt gatatcggtc caggtgatgg gtgactggaa tgagaatgtg atgtgttggc  7320
cgtggtggat gctgtctcga tagtattctg gcccgtaatc gtcgatgttt tgttgtatct  7380
gggcggtggt gtgttgggtg ttgagtgaga tgattcgtgt ggaggcctcc cagggtgtca  7440
tgtcccctga tatgtagagg gctggctggt tgagcatcgc tgtgatgaac atggctagcc  7500
ctgatttttg gctgccggac cgcccccgcga tcatgacgag atccccttg tggatgtgca  7560
tatcctggtt gcggtagagg ggttctagtt gtggtatgcg gggcagctcg gctgcggttt  7620
gggaggccct ctcgaaggat cgttggagag agagcatcgg gaccttatct atctatcggt  7680
tacgatttgt atgaatattg gcggttagat ggagtcgatg tctacatcat cactaccagt  7740
ggtgttgggc tgactgtctc gctggtcaac gtaggctgct acaaggtcgt agatggcgtc  7800
gtccaatggt ttgagcacga ccgcgttgaa gccgtttttg gtgcgcacgg tggcgagttt  7860
gaaggcttgc tcttcgccaa ggtaggtttc gaggtcgcgg atcatggagt gtgggcggtc  7920
gttgctgccg cgtacttttt cgatgatggc gttggggatg gtttctgggg tgctgttgtt  7980
gaggtcgtct agggtgtgga agatggtgac atcagcgtag atgcgatcgg cggtctgtcc  8040
accgtagcct tcagtgttgt gctcgacgtc gtggactttg aaggcgatgg cggtggcgtc  8100
ctggtttcgg gaggggttga agaaggtgct gttgctgttg tttcggtagt ttgcgagtcc  8160
cattgttgtt tcctttacta tttttgttgg tttgtgtcgg tttttatcgg gtgaggctgt  8220
ttcgtttgct gcggaacgcc tcggatacgt cagtgttgct ggtgatgatc ttcttgtact  8280
gtttcagaag gtcggctagc tgtgctttgc ttgttgcatt gttgattttg tcaatgatgg  8340
tgttgtttcc ttcactggca atgttgtcta cgtagtcttt ggcggcctgg ttgtatcggt  8400
cttggaggat gatggatgcg gaggcgatca gtgttgccag gtcccagttc cttgccgccg  8460
aactgttttt gagtccgcct agcaagtcga tgatagtctt ctttacttcg tcggcggtgt  8520
ctccacggat gactgtccat ggggcggcgt agtctccgcc gtatttgagt gtgatggtga  8580
tgcgatcatc agtgctgttg gtgttatcgt tcactggtgc tccttgcttt cttctgttgg  8640
ggctgtgatg gtggtttctg tagggtacct gtaggcgtct ttcccgttga cggcccagca  8700
ggcgtccttg acggggcatc ctttgcagag tgctgtgacg tggggtacga agatgccttg  8760
actgattcct ttcattgctt gactgtacat ggatgataca tgccggtagg tgttgttgtc  8820
aaggtcgtac agttcggtgg atgtgccttg tgtcggggac ttgtcgtcgt tgcggctggt  8880
ggcgggtgtc caaaacatgc ctttcgtcac atgaatgtcg tgttgggcga gcatgtaccg  8940
gtatgtgtgc agctgcatac tgtcggcggg taggcggccg gttttgaggt cgaggatgaa  9000
ggtttcgccg gtgtcggtat ctgtgaaaac acggtcgatg tagccgacaa tctgggtgcc  9060
gtcggggagg gtggtttcta ccgggtattc gatgcctggc tggccgtcaa taacagcggt  9120
gatgtattct gggtggttgc gcctccatgt tttccagcgg tctacaaagg tggggccgta  9180
aaccatccac cagtcgtagt cttttttgtg tggtccgccc gactcgcaca tgtttttgca  9240
tattctgccg gagggtttga tttctgtgcc ttcggattcg gcgagggcta cttgggtgtc  9300
gaaaatgttt ttgaaggatg cgagtttgtc tggcagtgca gggtattcgg cgggattgta  9360
caggtgtagg tcgtattgtt cggtgatgtg atgtatggcg cttccggcga tggtggcgta  9420
ccaggtgtgg tgttgggcgt ggtagccgtg ggataggcgc catttttctc cgcattcggc  9480
ccactgggtg agtgaactgt aggagatgtg gcctggatgg ttgatggttt tcggatattg  9540
tgctaggggc attactggtc gcctttgtgt gtgttccatg ggttgcgggt gtcttggccg  9600
gcgtggtgtt gctggtaggc gaggagtgcg aggcagtgcc aggcagcatg ggctagatgg  9660
ggtagcccgg attcataatc gaggttgttg ccttgctgcc atgatagtag gtgcctgtag  9720
agggcgtcga cgctgtggct ccacgggtag ccgccggtcc agttgttgtc gccgtatttg  9780
gtggcaccgt agcctgccac ggagccgagg gcgtgcaagg ctgtagggtc gatgagggat  9840
agcctgcaaa gtttcaattc ttttttggca ccgctgttgg ggtcggtgta catgcgggtt  9900
ggcttatcca tgggggtgtg ctccttaggg gtgggttact ggttggggtt gtgggcgagt  9960
gctacggcga gaataatgat ggcgagggtt tcagcaataa gtatgggtgt tgtgatcatt  10020
tgctgtctcg gggattgttg gtgagtgtgg aggcgcctag gagggtggcg agggcgcatg  10080
cggcaataat ggcgagggct gccttgtgtg gggtgccggt tgcgtacatc catgtgatga  10140
tggcgccttg gatccaggcg aggctggtga agaacgtttc gtagctgtgt agctcaatgt  10200
tgttgggtgt gttcatgctt gctcctgaag aatggtgttg atggttttat aaatgttgta  10260
caggtcggtt tcgatagata acagttggtg gatttcgtgg tcgagatcaa tgtctgggtt  10320
gagggtgttg atgcgggagg caatatcggt ggctgtgcgt agtgtgccgc cggtgtggtg  10380
aataatgtgt gccgtgtcgg cgagtccggt ggtgacagcg tagtgggaga ggagaggcat  10440
```

```
agctgggggt gctccttggc gggttactgt tgcgggttga tgttgaggtc ggtgacgtgc  10500
ggtgagcttt ctgttccggt gacgaggcag tggacggtga cgggtagttt ggatgctccc  10560
ggctggcgta cggtggcgcc gtaggcgatg gagaaggtgt ctttgccaat aattttgtgg  10620
agttggaggt cgatgtcggg gttgccgttc catttgacac cgtgtgcggc ggcctgttgt  10680
tcggctttgc ggttgcaggt gtgtgctgcc gtgatcatgg tgagtccggt ggcggtttct  10740
tccccccttg cttgggcttg ccggtggttt ttggcctgct cggctcgcag tgactgttct  10800
gcggctgcct ggcgggcttt cttttcggct ttgcgctgtt ggacggtttt gggggtccac  10860
gcggtgttgg ctgtggtggc ctgtggggct ggctgtgagg caagtggcgg attgtcgtct  10920
ggggctggca tgaatgaggc ggcggcaatg atggcgactg tggcgccggc gatggtgtag  10980
cctttttttct tgttcatgac tgttgtcccc tttccggggt gttgttcgtt gctgacatga  11040
tcaatacttc cagcgaatga acctcgtgtc aaggctgcgc tcaacgattg tgagcgattc  11100
gtgtgtggct agggtgttta tcggctgtac agggtgagga ggtggcctac gttgatgcgg  11160
gtcacattcc agtagagttg cgtggcttca cccccggtga gtggcttcca ctcgttgtgg  11220
ctgaacacgg tgccgtcggt ggcgatgaat gtgttggggc gtagcttgtg gagttcggct  11280
tccacgctct gccggtaggc ttcggcgagg ccctcaaaat ccatgtggtc gcaggagagg  11340
ttttcgaggc gtgtcaggtc gaagggtgtg ggacagtcgt agctggcggg gctgtagagc  11400
tgggtgaagt ggttggcgat cttctgcatc atgattcctt ttctggtgat ggtgtgttga  11460
tggttttatc gtgtggcttc ggcgatgatg gcgtccacat cgattgtgtc gatcatgtcg  11520
tggagttcct cagcctcatc cgcggtgagt ggctgccagt cctggggtcc gtatatggca  11580
ccgtcgaggg tgacagtcca caggggccgg atgagtcgta cggcttcttc gactttggca  11640
cggtgcaggc ggcagatgat agacgtgtgg gtgttgccta tgtcacatcc tgccaggtgt  11700
gtggggtgga gtgggttgat ttctgtctgc ccgtagaggt tggtgaagga tggtgtgatg  11760
agtgtgccat ccatgagggt gtgctccttt cggtggtgta tgggttgttg tggtttctag  11820
agtgtgtagg ttgcgatccc atagtcaagg ctgcactcat tcggattgag cgtttcatgg  11880
gatgtggcag gggatgtggc gtatctcact taagccttta tggcctctct cagtgcctca  11940
aatcctctga gggtaggatt atgcagggtt gaccctgctg atcgattcta ggggccttct  12000
agggcgtctc aggggtatgt ctgggttatg gcgggtgtgg cagatgatct agcgagtcaa  12060
ggtgccgagc tgagacataa gatctatcat ctaggtgtgt gagatgcatc acatcctcct  12120
ggcgtggtgt acacccttaa ggctactcgg tcgatctggc gtggagggtg tagtaaagaa  12180
atgccgttta aagccttcgc acggcgccta ggagcgcctt acggggtggg ggctaggtat  12240
ttataccccc agcacattct gatcgattct agacgcctcc aggatcctga tacacgatca  12300
gctatccaga cgcagatcac cagtccctat cctggttagc taagcctcaa ctatgtggac  12360
agtgtgggat actgtggggg aagaaggaca cggtaaaaag aagagggggg agcatcagcc  12420
ttcacacctt caagccttaa ggttttagcg cttagcaccg atggtcttag cagttagcac  12480
cgagccccct cacgggctcg gcatcagccc gaacaggcac agccctgaaa ggagtacacg  12540
ccatcaggga aggcttgaga gtacgaggag ccctagcgac gagtactcga aagcctgagg  12600
gaacaccctc agcactgatg ggcctagcgt gttcggaaag gacacaagag tgaagtgtga  12660
cagctatccg ggagtgaaac ccgttctgac taggggtttc agccttaacc acctgtaaag  12720
gttacaagac tctaagaaaa tttaaggaaa agtttaggtt taatttttgg acctttacta  12780
ccaaaaacac ccgtttacac ccctcaaacc cgcctataga gccaaatcca ccagtttgac  12840
tcatcccagg tggggtatga taggctggac aggtagccag ctggacgcaa ggccgaaatc  12900
cgctgacgcg gctttcaccc ttacatccat cagtctacca aagacttaaa gacctaaggg  12960
cttagcgcta aggtgctgat agcttagcac cgagcccctc aagggctcgg catcagtctt  13020
aaagctttaa acactttaag taaacttaag agcttagcac ttaaagttaa ttaataacct  13080
taaaggctta cacacttagc actgagccct ttaaggctca gcatcagtat aaagatctta  13140
acacctaagt taagtataaa accttaaagg cttagcactt aaggatataa acttaacatc  13200
agtgtttaag actttaaaac ttaaaataac tattaagact taaagactta taagctttaa  13260
acacttaaag taactataag actttaaaga ccttaagtat ttaaagttaa ccatcagtct  13320
taaactttaa tattataacc tataagtctt aaagcttata ggtataataa tataatataa  13380
gttataaaag ttttagaaga gctaaggggt taacttcttt acttctctac tctctttggt  13440
actttctctc ttctcttctt ttcttcatca ggggagaaga ggaaccttta accgtcaacg  13500
ctgatggact tttcaccgtg tgactcgtgt gcttctggtc gcacgctccc atcgcacact  13560
ccccacactc tgacacccgt gccccctttca ggcttgacgt gttcggctga aggcgtacgg  13620
cgtgtcacgc ttaaaccctt aacaccaggt aagacttaaa gtgtatatta taagtagaag  13680
actttaaaac cttaaggtgt tcccgcttag cctgtgtcct ttagcgctag gcgccaagcg  13740
ctaagctgtg aaacgcgaac acccatccac ccccattttt cttccgtgtc cttcttcttt  13800
tgacaccgct ggggggcgat gtgatatttc tcacatgcca gggggtagtg gagaaaacaa  13860
acaccccggc acaaacagaa caccccctca aacgaacaaa acaccccccca gaatcgatca  13920
gcagggcaag ggcaaggtat tcataccccc aacaccttc aggccgttac aggagcaatg  13980
agaggctcac aggggcaagg ggagatcagg ggacgcgatg gcacacacca accgcaccgc  14040
atcatcagcc caccggcgtt ggcggcaacg actcatcacc caagcccaac aacaaggcca  14100
aaccgaatgc ccactctgcg gagcccagat agcctgggac acccatgacc taccaaccag  14160
ccccgaagcc gaccacatca cacccgtcag cagaggagga ctcaacaccc tcgacaacgg  14220
gcaaatcatc tgcagaacat gcaacagaag caaaggcaat cgcagcgaac caaacatcaa  14280
attccaacaa caaaccacaa aaacattgat tccatggtga aaaacctgtc aacccccacc  14340
ggggacaccc cctgcacagg cgtgcaagac ctcgtacggc ttagtgaaat acctcccttt  14400
tgtggatttg tctgtttgtc gactttttgt gttggtggtg agtgttgtgc agcctgagct  14460
tcctgatggt cgtgattggt gtggggagac gcgtcgttgg tggcgtgtgt ggggtgagga  14520
ttcgcgtgcc gggttggtgt ctgatgagga gtggctgttt ctcatggatg ctgcggtgat  14580
tcatgatgtg gtgtggcgtg agggtcgcgc ggatttggtg gcttcgcttc gtgctcatgt  14640
gaaggcgttt atgggcatgc tggaggctca ttctggggat gctggcacta ctgtgggtgg  14700
tgggggttct gcggtggcga tgattgaccg gtataggaag cgcaaggggg cctgattagg  14760
tgtctggtgt tgtgggttct caggttcctc gtcaccgtgt ggctgcggcg tatcaggtga  14820
ctgccggcaa tgatgctggt gctcttgggg ctgcgtatgg gttgactccg gatccgtggc  14880
agcagcaggt gttggatgat tggctggctg tcggtggtaa tggcaggctt gctgcgggtg  14940
tgtgtggggt gtttgtgcct cgccagaacg gcaaaaacgc gatccttgag gttgttgagc  15000
tttttaagat ggtggttcag ggtcggcgta ttttgcatac ggctcacgag ttgaagtcgg  15060
ctcgtaaggc gtttatgcgg ttgagatcgt tttttgagaa tgagcgccgc tatccggatt  15120
tggctcgtat ggtgaaggcg attcgggcga cgaatggtca ggagtcgatc attttgcatc  15180
```

```
atcctgattg cagtgtgggt ggtaagaagt gtggctgccc tggttggggt tcggttgagt  15240
ttgtggctcg tagccggggt tcggctcgcg ggtttacggt tgatgatttg gtgtgtgatg  15300
aggctcagga gttgtcggat gagcagttgg aggctttgct tcctacggtg tctgcggctc  15360
cttcgggtga tccgcagcag attttccttg gtaccccgcc ggggcctttg gctgatggtt  15420
ctgtggtgtt gcgtttgcgt gggcaggctt tgtcgggtgg taaaaggttt gcgtggacgg  15480
agttttcgat tcctgacgag tctgatccgg atgatgtgtc gcggcagtgg cggaagttgg  15540
cgggtgacac taatccagcc ttgggtaggc gtctgaattt tgggactgtg tcggatgagc  15600
atgaatcgat gtctgctgcc gggtttgctc gggagcggct tggctggtgg gatcgtggcc  15660
agtctgctac gtctgttgtt ccggcggata agtgggctca gtctgctgtg gatgaggcgg  15720
ctctggttgg cggcaaggtg tttggtgtct cgttttctcg ttctggggat cgggttgctt  15780
tggcgggtgc cggccggact gatgctgggg ttcatgttga ggttattgat gggctgtcgg  15840
ggacgattgt tgatggtgtg ggccggttgg ctgactggtt ggcggttcgt tggggtgata  15900
ctgaccggat catggttgcc gggtctggtg cggtgttgtt gcagaaggcg ttgacggatc  15960
gtggtgttcc gggccgtggc gtggtggttg ctgatactgg cacctatgtg gaggcgtgtc  16020
aggcgttttt ggagggtgtg aggtctggga atgtttctca tcctcgtgct gattctcgcc  16080
gtgacatgtt ggatattgct gtgaggtcgg cggttcagaa gaagaagggt tctgcgtggg  16140
gttggggttc ctcgtttaag gatggttctg aggttccttt ggaggctgtg tctttggcgt  16200
atcttggtgt gaagatggcg aaggctaggc ggcgtgagag gtctggtagg aagcgggtgt  16260
ctgtggtatg aactcggatg agttggcttt gattgagggc atgtacgatc gtatccaaag  16320
gttgtcttcg tggcattgtc gtattgaggg ctactatgag ggttctagcc gggtgcgtga  16380
tttgggggtg gctattcctc cggagttgca gcgtgtgcag acggtggtgt cgtggcctgg  16440
tatagctgtg gatgctttgg aggagcgtct ggattggctt ggctggacta atggtgacgg  16500
ctacggcctg gatggtgtgt atgctgcgaa tcggcttgct acggcgtcgt gtgatgtgca  16560
tttggatgcg ctgatttttg gtttgtcgtt tgtggctgtt atccctcagg gggatgggtc  16620
ggtgttggtt cgtccgcagt caccaaagaa ttgtactggc cggttttcgg ctgacgggtc  16680
tcgtttggat gctggccttg tggtgcagca gacgtgtgat cctgaggttg ttgaggcgga  16740
gttgttgctg cctgatgtga ttgttcaggt ggagcggcgt gggtctcgtg agtgggttga  16800
gacgggccgt atcgtgaata gtcttggtgc ggttccgttg gtgccgattg tgaatcgtcg  16860
ccgtacgtct aggattgatg gccgttcgga gatcactcgg tcgattaggg cttacacgga  16920
tgaggctgtg cgcacactgt tggggcagtc tgtgaatcgt gacttctatg cctaccctca  16980
gcgttgggtg actggcgtgt cggctgacga gttttcgcag cctggctggg tcctgtcgat  17040
ggcttctgtg tgggctgttg ataaggatga tgacggtgac accccgaatg tggggtcgtt  17100
tcctgtgaat tcgcctacac cgtattcaga tcagatgcgg ctgttggcgc agttgactgc  17160
gggtgaggct gcggttcctg aacgctattt cgggtttatc acgtctaacc cacctagtgg  17220
ggaggctttg gctgcggagg agtctcggct tgtgaagcgt gctgaacgca ggcagacgtc  17280
gtttggtcag ggctggttgt cggttggttt cctggctgcc agggcgcttg attcgagtgt  17340
tgatgaggcc gcgtttttcg gtgatgtggg tttgaggtgg cgtgatgctt cgacgccgac  17400
tcgggcggct acggcggatg ctgtgacgaa gcttgttggt gccggtattt tgcccgcgga  17460
ttctcggacg gtgttggaga tgttggggct tgatgatgtg caggttgagg ctgtgatgcg  17520
gcatcgtgcc gagtcgtcgg atccgttggc tgcgcttgct ggggctatat cgcgtcaaac  17580
taacgaggtt tgataggcga tggcttcggg ggttgcgtcg aggttggctg ctgccgggta  17640
tcagcggcag gcgattcgtt ttgccgggaa gtatgcgggc tattatgccg agttggggcg  17700
tttgtggcat tccgggaaga tgacagatgc gcagtatgtg cgtttgtgtg tggagttgga  17760
gcgtgccggc catgacggtt ccgcggcgct ggcgggcaag ttcgtgtcgg attttcggaa  17820
gcttaacggt gtggatcctg gtttgatcgt gtatgacgag tttgatgctg ccgccgcgtt  17880
ggctaggtcg ttttcgacta tgaagattat gaatagtgac ccggataggg cgaatgatac  17940
gattgatgct atggcggcgg gtgttaatcg ggctgtcatg aatgctggcc gtgacacggt  18000
tgagtggtct gctggcgcgc agggtaggtc gtggcgcagg gtgactgatg gtgatccgtg  18060
cgcgttttgt gccatgttgg ctacgaggtc ggattatacg accaaagagc gggcgcttac  18120
tactggtcat acgcggcgtc ataagcgtgc cggtaggcgt ccgtttggtt cgaagtatca  18180
tgatcattgt gggtgtacgg tggttgaggt tgttgggcgt tgggagccaa atagggctga  18240
tgccgagtat cagaggacgt atgagaaggc ccgtgagtgg gttgatgatc atggtttgca  18300
gcagtcgcct ggcaatattt tgaaggctat gcgtactgtt ggcggcatga gataatttga  18360
tgtggtttcc ggttgtgcgc cgccggttat cggtgcacag ggttgtctcc cgcacggggg  18420
tcaacaatgt tgtgttgttt tccgcaagga gtgtaaggtt aggctatggc cgatcagagt  18480
gttgaggaac agaatgtcga caatgatgct gttgagcccg gaaagggtgg agacattgtt  18540
gatgttgtga aggatgggcg ggctgccggc gatgatcatg ccggtgatgt ttccgtgaag  18600
ggtgaggctt ctgggtcttc gggcacggat tggaaggctg aggctcgtaa gtgggagtct  18660
cgtgctaaaa gtaatttcgc cgagttggag aagcttcgta catcgagtga cgattctgga  18720
tctactattg atgagcttcg ccgcaagaat gaggaactcg aagacaggat caacgggttt  18780
gttcttgagg gtgtgaagcg tgaggtggct gccgagtgtg gcctgtcggg tgatgcggtc  18840
gctttcttgc acggtagcga tcgtgaagca ctggtggagt ctgctaaggc tttgaagggt  18900
ttgattgacc atagtagtgg tggcgcgggt gtgcgccgtc ttgcggggag tgccccccgtt  18960
gatgatgtta aacgacgtga gggtgtcgcg tttgtggatg ctcttgtcaa taattctagg  19020
agatgatttg tgatggctga cgatttttctt tctgcaggga agcttgagct tcctggttct  19080
atgattggtg cggttcgtga ccgtgctatc gattctggtg ttttggcgaa gctttcgccg  19140
gagcagccga ctatttttgg ccctgttaag ggtgccgtgt ttagtggtgt tcctcgcgcc  19200
aagattgttg gtgagggtga ggttaagcct tctgcgtctg ttgatgtttc ggcgtttact  19260
gcgcagccta tcaaggttgt gactcagcag cgtgtctcgg acgagtttat gtgggctgat  19320
gctgattacc gtctgggtgt tttgcaggat ctgatttcgc ctgctcttgg cgcttcgatt  19380
ggtcgcgctg ttgatctgat tgctttccac ggtattgatc cggctacggg taagcctgct  19440
gcggctgtca agtcttcgct ggataagacg aagaatattg ttgatgcaac cgatagtgct  19500
acggctgatc tgattaaggc ggttgggctg attgctggtg ccggtttgca ggttcctaac  19560
ggggttgctt tggatccggc gttctcgttt gccctgtcta ctgaggtgta tccgaagggg  19620
tctccgcttg ccggccagcc tatgtatcct gccgccgggt tcgccggttt ggataattgg  19680
cgtggcttga atgttggtgc ttcttcgact gtttctggcg ccccggagat gtcgcctgcc  19740
tctggtgtta aggctattgt tggtgatttc tctcgtgttc attggggttt ccagcgtaac  19800
ttcccgatcg agcttatcga gtatggtgac ccggatcaga ctgggcgtga cctgaagggc  19860
cataatgagg ttatggttcg cgccgaggcg gtgctgtatg tggctatcga gtcgcttgat  19920
```

-continued

```
tcgtttgctg ttgtgaagga gaaggctgcc ccgaagccta atcctccggc cgagaactga  19980
tttattgttg cggtgatgtg tcaatgtgca gggggtggtg ttgatgggta tcattttgaa  20040
gcctgaggat attgagcctt tcgccgatat tcctagagag aagcttgagg cgatgattgc  20100
cgatgtggag gctgtggctg tcagtgtcgc cccctgtatc gctaaaccgg atttcaaata  20160
caaggatgcc gctaaggcta ttctgcgcag ggctttgttg cgctggaatg ataccggggt  20220
ttctggtcag gtgcagtatg agtctgcggg tcctttcgct cagactacac ggtctaatac  20280
tcccacgaat ttgttgtggc cttctgagat tgccgcgttg aagaagctgt gtgagggtga  20340
tggtggggct ggtaaagcgt tcactatcac tccaactatt aattgtcgat atgcacattc  20400
tgaggtgtgt tccacggtgt ggggtgaggg ttgctcgtgc gggtcgaata ttaacggcta  20460
cgctggccct ttgtgggaga tatgatatga ccagttttcc ttatggtgaa acgattgtga  20520
tgcttcagcc gactgttcgt gtcgatgatc ttggtgacaa ggtggaagac tggtctaagc  20580
ctgtcgagac tgtgttccat aacgtggcca tctatgcttc gttgtcgcag gaggatgagg  20640
ccgcggggcg tgactcggat tatgagcatt ggtcgatgct tttcaagcag cctattgtgg  20700
gtgctgatta tcgttgcagg tggcgtatcc ggggtgttgt gtgggaggct gacgggtctc  20760
ctatcgtgtg gcatcatccg atgtctggct gggatgcggg cacgcaggtt aatgtgaagc  20820
gcaagaaggg ctgataggtt gtggctcagg atgtgaatgt gaagctgaac ttgccgggta  20880
ttcgtgaggt gttgaagtct tctggggtgc agtctatgtt ggctgagcgt ggcgaaaggg  20940
ttaggcgtgc ggcctcggcg aatgttggcg gtaacgcttt cgatagggcc caatacagta  21000
atggtttgtc gtcggaggtg caggttcacc gggttgaggc tgtggcgagg attggtacca  21060
cctataaggg tggtaaaagg attgaggcga agcatggcac gttggcgagg tcgattgggg  21120
ctgcgtcgtg atcgtttacg gtgatccgcg cgtgtgggct aaacgcgtac tcaaggatga  21180
tggctggctg tctgatatac catgtaccgg gacagtgccg gatagctttg agggtgacct  21240
tatttggttg gctcttgatg gtggcccaca gttgcatgtg cgtgagcagg tttttttgcg  21300
cgtgaatgtg ttttcggata cgccggatcg tgctatgtcg ttggcgcgtc gtgttgaggc  21360
tgtgctggct gatggtgtgg acggtgaccc tgtggtgtac tgtaaacggt ctactggccc  21420
tgatttgctg gttgacggtg cacgttttga tgtgtattcg ctttttgagc tgatatgtag  21480
gcctgcggag tctgaataag cttattgttt ttgttttaat gtaattgttt gatatttaat  21540
gggggttgtg atggctgcaa cacgtaaagc gtctaatgtt cgctctgctg ttacgggtga  21600
cgtttatatt ggtgccgctc atgctggtga cgctattgat ggtgtgaaga cggttcctga  21660
cggtcttacc gctttagggt acctgtctga tgacgggttt aagattaagc ctgagcgtaa  21720
aacggatgat ttgaaggctt ggcagaatgc ggatgttgtt cgcacggttg ctactgagtc  21780
gtctatcgag atttcttttc agctgatcga gtctaagaag gaggttatcg aactgttttg  21840
gcagtcgaag gttactgccg gatccgattc gggttcgttt gatatttctc cgggtgccac  21900
gacgggtgtt cacgccctgt tgatggatat tgtggatggc gatcaggtta tccgttacta  21960
tttccctgag gttgagcttg tcgatcgtga cgagattaag ggtaagaatg gcgaggtgta  22020
cgggtatggt gtgacgttga aggcgtatcc tgcccagatt aataagaagg gtgatgcggt  22080
gtctggtcgg gggtggatga cggctttaaa agctgatact cctccggttc cgccttctcc  22140
gaagcctcag ccggatccga atccgccgtc cgataattga tacacgagtt tgagggattg  22200
ttgatagatg agtgacacag gttacacgtt gaagatcggt gaccgtagtt gggtgttggc  22260
ggatgcggag gagacggctc aggctgttcc tgcccgcgtg tttcgtcgtg cagctaagat  22320
tgcccagtcg ggggagtctg cggatttcgc ccaggttgag gtgatgtttt ctatgttgga  22380
ggctgccgcc ccggctgacg cggtggaggc tctggagggg cttcctatgg ttcgtgttgc  22440
cgagattttc cgccagtgga tggagtggaa gcctgaaggt aagggtgcct ctttggggga  22500
atagtttggc tccacggcct gattgatgag tatcgtgggg ccatcgaata tgattggcgc  22560
acaaggtttg gtgtgtgcat atacgatata ggtggtcctg caatggggtg gggtgaggct  22620
gtccggctgg ctggcgtgtt gtgtaccgat acgtctagcc agttggcggc ccacctgaat  22680
ggttggcagc gcccgtttga gtggtgcgag tgggctgtgt tggacatgct ggatcattac  22740
aggtctgcta atagtgaggg gcagccggag cctgtggcga ggcctacgga tgagcgtagg  22800
gcccggttta cgtctgggca ggtggacgat attttggcgc gtgttcgtgc cggtggcggg  22860
gtgtctcgcg agattaatat tttggggtga atagtgtatg tctggtgaga ttgcttccgc  22920
atatgtgtcg ttgtatacga agatgccggg tttgaaatca gatgttggta aacagctttc  22980
tggggtgatg ccggctgagg gtcagcgttc gggtagcttg tttgctaaag gcatgaagct  23040
ggctttgggt ggcgccgcaa tggtgggcgc cattaatgtt gctaagaagg gcctcaagtc  23100
gatttatgat gtgactattg gtggcggtat tgctcgcgct atggctattg atgaggctca  23160
ggctaagttg actggtttgg gtcatacgtc ttctgatacg tcttcgatta tgaattcggc  23220
tattgaggct gtgactggta cgtcgtatgc gttgggggat gcggcttcta ctgcggcggc  23280
gttgtctgct tcgggtgtga agtctggcgg gcagatgacg gatgtgttga agactgtcgc  23340
cgatgtgtct tatatttcgg gtaagtcgtt tcaggatacg ggcgctattt ttacgtctgt  23400
gatggctcgc ggtaagttgc agggcgatga catgttgcag cttactatgg cgggtgttcc  23460
tgtcctgtct ttgcttgcca ggcagacggg taaaacgtct gctgaggtgt cgcagatggt  23520
gtcgaagggg cagattgatt ttgccacgtt tgcggctgcg atgaagcttg gcatgggtgg  23580
tgctgcgcag gcgtctggta agacgtttga gggcgctatg aagaatgtta agggtgccct  23640
gggctatctt ggtgctacgg ctatggcgcc gtttcttaac gggttgcggc agatttttgt  23700
tgcgttgaat ccggttatca agtcggtgac ggattctgtg aagccgatgt ttgctgccgt  23760
cgatgctggt attcagcgta tgatgccgtc tattttggcg tggattaacc gtatgccggg  23820
catgatcact cgaatgaatg cacagatgcg cgccaaggtg gagcagttga agagtatttt  23880
tgcaaggttg catttgcctg ttcctaaagt gaatttgggt gccatgtttg cgggtggcac  23940
agccgtgttc ggtattgtgg ctgccggtgt ggggaagctt gttgcagggt ttgccccgtt  24000
ggcggtgtcg ttgaagaatc tgttgccgtc gtttggtgct ttgaagggtg ccgctggtgg  24060
gcttggcggc gtgtttcgcg ccctgggtgg ccctgttggt attgtgatcg gcttgtttgc  24120
ggccatgttt gctacgaacg cccagttccg tgccgctgtt atgcagcttg tggctgtggt  24180
tggccaggcg ttgggccaga ttatggccgc tgtgcagccg ctgttgggtt tggttgctgg  24240
gctggtggca cggttggctc ccgtttttgg ccagattgtt ggtttggtgg ctggtttggc  24300
tgcgcagctt gttcctttga ttagtatgct ggttgcccgg ctagttcctg tgatcaccca  24360
gattattggt gcagtgacgc aggtggcggc catgttgttg ccggcgttga tgccggtgct  24420
tcaggcgatt gttgctgtga tacggcaggt tgttggtgtt gtgatgcaac tggtgcctgt  24480
tttgatgcct gtgattcagc agattttggg tgctgtcatg tctgtgctgc cgcctatcat  24540
cggcctgatc cggtcgttga taccagtcat catgtcggtt atgcgtgtgg tggttcaggt  24600
tgttgcggtt gtgatacagg tggtggcccg tattcttgct gttgtggctc cgatggtggc  24660
```

```
tgctgtggtg ggttttgttg cccgtattgt tggtgctgtc gtgtcggctg tggcccgtgt  24720
gattgcggct gtggcccgtg tgatcggatg ggttgtggcc cattttgtgt ctggtttggc  24780
acgcatgggt tcggttattc aggctggctg gaatcatatt agagcgttta cgtcggcgtt  24840
tatgagcggt ttcaagtcga tcatttctgg cggcgtgaac gctgttgtgg ggtttttttac  24900
gcggcttggt tcttcggttg cttcccatgt gaggtctggt tttaacgcgg ctcgtggcgc  24960
tgtttcttct gcgatgaatg ctatccggag tgttgtgtct tcggtggcgt ctgctgttgg  25020
cgggtttttc agttcgatgg cgtctagggt tcgtagtggt gctgtgcgcg ggtttaatgg  25080
tgcccggagt gcggcttctt ctgctatgca tgctatgggg tccgctgtat ctagcggggt  25140
gcatggtgtg ctgggttttt tccggaattt gcctggtaat attcggcgtg cgcttggtaa  25200
tatggggtcc ttgttggtgt ctgcgggccg tgatgtggtg tctggtttgg gtaatggtat  25260
ccggaatgct atgagtggct tgttggatac ggtgcgtaat atgggttctc aggttgcgaa  25320
tgcggcgaag tcggtgttgg gtattcattc accgtctagg gtgtttcgtg accaggttgg  25380
ccggcaggtt gttgccggtt tggctgaggg gatcacaggg aatgctggtt tggcgttgga  25440
tgcgatgtcg ggtgtggctg gaaggctgcc ggatgctgtt gatgcccggt ttggtgtgcg  25500
atcgtctgtg ggctcgttta ccccgtacga ccggtatcgg cgtgcgagcg agaagagtgt  25560
tgtggtgaat gtgaatgggc ctacttatgg ggatccgaac gagtttgcga agcggattga  25620
gcggcagcag cgtgacgctt tgaacgcgtt ggcttacatg tgatcgaggg ggtgttgtgc  25680
atgtttattc ctgacccgtc tgatcgttct ggtttgactg ttacctggtc tatgttgccg  25740
ttgattggta atgatccgga gcgtgtgctt catttgacgg attatacggg tgcgtcgcct  25800
gtcatgttgt tgaatgattc gttgcgcggt ttgggtgttc ctgaggttga gcattttttct  25860
caaactcatg ttggggtgca cggctcggag tggcgcgggt ttaatgtgaa gcctcgcgag  25920
gtgacattac ctgtcctggt gtcgggtgtg gatccggatc cggtgggcgg gtttcgtgac  25980
ggtttcatga aagcctatga cgagttgtgg tcggcgtttc cccgggcggg ggtgggggag  26040
ttgtctgtga agactcctgc tggtcgtgag cgtgtgttga agtgccggtt tgattcggtg  26100
gatgatacgt ttacggttga tccggtgaat cgtggctatg ctcgctatct gttgcatttg  26160
acagcttatg acccgtttg gtatggggat gagcagaggt ttcgttttag taacgcgaag  26220
ttgcaggatt ggttgggtgg cggccctgtc ggtaaggatg gcacggcgtt tcctgtggtg  26280
ttgacgcctg gtgttggttc gggttgggat aatctgtcga ataagggtga tgtgcctgcg  26340
tggcctgtga ttcgtgttga ggggcctttg gagtcgtggt ctgtgcagat tgatggtttg  26400
cgtgtgtctt cggattatcc tgttgaggag tatgattgga tcactattga tacggatcct  26460
cgtaagcagt ctgcgttgtt ggatgggttt gaggatgtga tggatcgttt gacagagtgg  26520
gagtttgcgc ctatcccgcc tggcggttct cggagtgtga atattgagat ggttggtttg  26580
ggtgccattg ttgtgtcggt gcagtacagg tttttgaggg cttggtgaat agttgatggc  26640
tggtcttgtc ccgcatgtaa cgttgtttac gccggattat cgtcgtgtgg cgcctatcaa  26700
ttttttgag tcgttgaagt tgtcgttgaa gtggaatggt ttgtctacgc tggagttggt  26760
ggtgtctggg gatcattcta ggcttgacgg gttgactagg ccgggtgcgc ggctggttgt  26820
tgattatggt ggtggccaga ttttttctgg gcctgtgcgt aaggttcatg gtgtgggtcc  26880
gtggcgttct tcgcgggtga ctatcacgtg tgaggatgat atccgcctgt tgtggcgtat  26940
gctaatgtgg cctgtgaatt atcgtcccgg catggttggt tcggagtggc gtgccgacag  27000
ggattatgct cactattcgg gtgcggcgga gtcggtggct aagcaggtgt tgggggataa  27060
tgcttggcgt tttccgcctg gtttgtttat gaacgatgat gagagtcgtg gccgctatat  27120
taaggatttt caggcccggt tccatgtgtt tgccgataag ttgttgccgg tgttgtcgtg  27180
ggctcggatg actgtttcgg tgaaccagtt tgagaatgcg cagtttgatc agcggggttt  27240
gctgtttgat tgtgtgcctg ctgtgacccg gaagcatgtg ttgactgccg agtctggttc  27300
gattgtgtcg tgggagtatg tgcgtgacgc cccgaaggct acgtctgtgg tggttggtgg  27360
ccgcggcgag ggcaaagatc ggctgttttg tgaggatgtt gattcgatgg ccgaggggga  27420
ttggtttgat cgtgtcgagg tgtttaagga tgcccgtaac acggattctg aacatgtgca  27480
tctcatcgat gaggctgagc aggtgctgtc cgagttaggg gccacgtcgg ggtttaagat  27540
cgagttggct gagtcggatg tgttgcggtt tgggccaggc aatctgatgc cgggtgatct  27600
tatctatgtg gatgtgggtt ctggccctat tgcggagatt gtgcggcaga ttgatgtgga  27660
gtgtgattcg cctggtgatg gttggacgaa ggtgactcct gttgcggggg attatgagga  27720
taatccgtcg gcgttgttgg ctcgccgtgt ggctggtttg gctgcgggtg tgcgggattt  27780
gcaaaagttt tagtaagtga ttggggtttg ttgtgggtat tgtgtgtaaa gggtttgatg  27840
gtgtgttgac cgagtatgat tgggctcaaa tgtctggtct gatgggtaat atgccgtctg  27900
tgaagggccc ggatgatttt cgtgtcggta cgacggttca gggtgccaca gtgttgtgta  27960
gtgttttgcc ggggcaggcg tggctcacg gggtgatgtg cacgtcgaat agtgttgaga  28020
cggtgacggg gcagcttccg ggccctggcg agactagata cgactatgtt gtcctgtctc  28080
gggattggga gcagaacacg gccaagttgg agattgttcc tggggggcgt gcggagcgtg  28140
ccagggatgt gttgcgcgcc gagcctggcg tgtttcatca gcaactgttg gcgactttgg  28200
tggtgtcgtc taacgggttg cagcagcagt tggataggcg tgctatagcg gctagggtgg  28260
cgtttggcga gtctgctgcg tgtgatccta cccctgtgga gggtgaccgg gtgatggttc  28320
cttcgggggc tgtgtgggct aatcatgcta acgagtggat gctactgtct ccgaggattg  28380
agacgggttc taagtcgatc atgtttggcg ggtctgctgt gtatgcttac acgatcccgt  28440
ttgcccgccc gtttagtagt ccgcctgttg tggtggcgtc tatggctacg gcggctgggg  28500
gcacgcagca gattgatgtg aaagcctaca atgtgactgc caaggatttt ggtttagcgt  28560
ttattacgaa tgacgggtct aagccttctg gtgtgcctgc ggtagctaac tggattgctg  28620
tcggcgtgta atgcgctgct tgtgtgtgcg ggatatgttg tggtggttgt agtggtaggg  28680
ggctgtagtg tcatggttta cacccacact tgtagcctct atttgtaccg ctatcgctac  28740
tgtccttggt tcgattcagg cggttactta caggtcgaag aagaggctta ggcagttgtc  28800
tgcacaggtt gatgcgatgg aagaatacac atggaatatt cgccatattg ttcatcgcta  28860
taacgcgaat ttgcctgaga atgttgagcc tgtaaaaatg cctgatttgc ccgagttttt  28920
gaaggatact gttgatagtg gtgggggtg aattgtgagg gagttggagg aagagaaacg  28980
gcagcgccgc aattttgaga aggcttcact ggtgttgttg tttttgtcgc ttgtgttgtt  29040
ggctgtggtt gctgtgggtg ctttgcgttt cggggctgta tcctctgagc gggattcgga  29100
gcaggctagg gcccagtcga atggtacggc cgctaagggg ttggctgcga gtgtaaggcg  29160
ggcgtgcgtc tctggtgggc aggagtcggt gcgtcttcac cagtctggct tgtgtgtgga  29220
tgctcagcgt gttgagcg                                                29238
```

SEQ ID NO: 70 moltype = DNA length = 29699

```
FEATURE                Location/Qualifiers
source                 1..29699
                       mol_type = other DNA
                       note = PAC9
                       organism = synthetic construct
SEQUENCE: 70
tgatggtcgg gatggttcgg ccggtgagcg cggtgatgtg ggcccttcag gtcctgccgg  60
cccgcaaggt gcacagggtg aacggggtga gcgcggcccc gccggtgcga acggatccga  120
tggtaaagac ggtaaggatg gtgctgatgg ccgtgatggg cgttcggtga tatcggtgta  180
ctgttccggg ggccgcctgg ttgtgaaata tagtgacggt acggcctcta ccgtgtcggg  240
ttctgcggcc tgcgagagtg tgaaaccatc acctgtggtt actgtatcat cccataggtg  300
aacaagaaga gggaagggtg ttactagtgt tgattgtggt gtttgggggt ggtgtgtggt  360
gagatacatt ccagcggcgc atcactctgc cggttcgaat agtccggtga acagggttgt  420
gattcatgca acatgcccgg atgtggggtt tccgtccgct tcgcgtaagg gtcgggctgt  480
gtctacagcg aactatttcg cttccccatc atcggggggt tcggcgcatt atgtttgtga  540
tattggggag acggtgcagt gcctgtcaga ggggactata gggtggcatg ccccgccgaa  600
tccgcattct ttgggtatag agatttgcgc ggatgggggt tcgcatgcct cgttccgtgt  660
accggggcat gcttacacga gggagcagtg gcttgatccg caggtgtggc ccgcagtgga  720
gagggccgct atcctgtgtc ggcagttgtg tgacaagcat ggtgttccga aaaggaaact  780
gtctgtggcc gatttgaagg ccggtaaacg gggtgtgtgc gggcatgtgg atgttacgga  840
tgcgtggcat cagtcggatc atgacgatcc ggggccgtgg tttccgtggg acaaatttat  900
ggctgtggtg aatggccacg gcggcggttc aagtagtgag gagttgagta tggctgatgt  960
acaagcgtta cataatcaga ttaaacagtt gtcggcacag gtggcccagt cggtgaataa  1020
gctgcatcac gatgttggtg tggttcaggt tcagaatggt gatttgggta aacgtgttga  1080
tgccctgtcg tgggtgaaga atccggtgac cgggaagctg tggcgcacca aagacgccct  1140
gtggagcatc tggtattacg tgttggagtg tcgcagccgc atagacaggc ttgagtctgc  1200
tgttaatggt ttgaaaaagt gatggtggtt tgttgtgggt aaacagtttt ggttgggctt  1260
gtttgagcgt gccctgaaaa cttttattca aacgtttgtt gctgtgcttg ggtgacggc  1320
gggtgttact tatactgcgg agtcgtttcg cggtttgccg tgggagtctg ccctgataac  1380
agcaacggtt gctgcggtgc tgtctgttgc tacatcgttt ggtagcccgt catttgtggc  1440
cggcaaacct aaaaccacgg ttgtggatgc tgggcttgtt ccacccgacg atgggggcat  1500
ggttgagccg cactcggtgg atgtgtcgga tcctggcatg atcgagccga cagatgatgt  1560
ggatggtttt gctggctatg tgccgaagcg tgcagccgag tcggaggtta gcacggtgga  1620
gtctactgtt gcataattga acatagatgt gtgccccagc ggtgctgcca cgatcgtgtg  1680
gtggttgccg ctggggcact ctttttgtgt ctataggagt tttacaggtt gtcgtctagt  1740
gtgtcttcga gcatctggtc caggtagagg caggcggaga tagtatcgtt ggcctggtct  1800
agaacgttct ggccgataac atttttatga ttgtcgcggt ggctgatgat agaccgcatg  1860
atatcgtcgg ccgccgcctg caatagtttg gcctggtatg cgattcctgc gagccagtct  1920
agtgcttcct ggcttgccag tgtgtcgtct ggaatgccac gggtgttgct gttgtttgtg  1980
gggtgtcctg cactgtcgca gcaccacaag atttcgctgc actcgtctag cgtgtcctgg  2040
tcgatagcaa gatcgtcgag gctgacttct ttgacggtaa ggttcacatt gtcgagggag  2100
atgggtacac cgtattggtt ttcgacactg tcaacaatgt tttccaactg ttgcatgttg  2160
gtgggctgtt gttggatgat acggtgtact actgttttga tggcggtgta ggggatattg  2220
tgtgtgttgt tcatggtttt tatcccaccc ctgtgttgtc gtcgttattg tctggatagt  2280
atctactgtt tgcgtagcct gtgagggtga tgagtgtttg gtctgcccac tgtttcactg  2340
tctgccgggt gacacccaat cgttgggcgg ctgtggcgta ggtttgatca tacccgtata  2400
cttcacggaa tgcggctagc ctggctaggt gttttcgctg tttggagggt tcacatgata  2460
gggtgtagtc gtcgatggcg agctgtagat cgatcatggt ggcaatgttg ttgccgtgat  2520
gctgggggc ggttggtggg ggtggcattc ctggctccac actgggtttc catgggccgc  2580
cgttccagat ccattgggcg gcttggatga tgtcggcggt ggtgtaggtt cggttcatgt  2640
gtcacccct gaacaggtcg ttgctggtgc tggtgttggt ggtgtcgaat cgtccgacgc  2700
agtggcagta gtcgtacatg agtttgataa tgtgttggtg gtctcccaaa taggtgtttc  2760
cgctgatact gtaggtggct gtgccgtctt tactgatggt gtatttggcg gtgatggttt  2820
cggggtttc ggtgtcggtg atgattgctg tggtggtggt gcctactgtt tgtagcacgg  2880
tggtttgggt tccgtcgtcg atagtggttt taaccatggt gtgtgttctc ccttttaga  2940
tgctggtttg gttgtcggct agatgaatga tgtcgggtaa gggtttcggc tggtctaggt  3000
gttgtatggt tttgttggct agccgtttgg ctaccctgta acacattttg gtgtagtgtt  3060
tgttgtctag gttgtggtat tgttcccgca ccgcaatata tagtagagag tcttggtaca  3120
ggtcgtctgc actgattgcg gggtagtgtg cggctgtttt ggtgcatgcc cggttgagtg  3180
tgcgtagatg atggtctgtg gcccacaccc acgatgcggt ggtggctagg tcggcttttg  3240
ttggtcgtct gctcatggca tttctttcat cgggctatct ggtagttgtt tggtgttttg  3300
ttgttgatag tgtagcacac gagtccgggg tttccggtgg tgccagtctt gtgccggtac  3360
catgtggatt cgccttccat ggatgggcat tggatgaagg tgcgttgtcc ttgttcggag  3420
atttctaggt ggtgccggtg cccggccatg aggatgtggg atgtggtgcc gttgtggaat  3480
tcttggccgc gccaccaatc atagtgtttg ccggtgcgcc attggtgtcc gtgggcgtgc  3540
aggatttgtg tgccggccac gtcgacggtg gtggtcattt cgtcccgttg gggaagtgg  3600
aagtgaaggt tggggtattg gttgttgagc tggtaagctt ctgcgatggc gcggcagcag  3660
tccacgtcaa aggagtcgtc gtaggtggtg actcctttgc cgaagcgcac ggcttcgccg  3720
tggttgccgg ggatggatgt gatggtcaca tttttgcagt ggtcgaacat gtggacgagt  3780
tgcatcatgg ccatgcgggt gagcctgatt tgttcggtga ggggtgtttg tgtgcgccag  3840
gcgttgttgc ctccttgtga cacgtatcct tcgatcatgt cgccgaggaa tgcgatgtgg  3900
actcgttcgg gtttgcctgc ctgttgccag tagtgttttg cgactatgag ggagtgcaaa  3960
tagtcgtctg cgaatcggct ggtttctccg ccggggatgc ctttgccgat ttggaagtcg  4020
cctgccccga taacgaaggc tgtctcgtca ctgctttggg tgtcttgttc gggtttgggt  4080
ggctgccatt cggctagttt gttgacgagt tcgtcgacgg ggtaggggtc ggttgcgggt  4140
tggtggtcga tgatttttg tatggatcgg cctgtttctc cgttggggag tgtccattcg  4200
gagatgcgtg tgcggcgtac agtaccgttg gctagattgt cgtcgatggt gtcgatggcg  4260
ttgtcgtggt tggctagctg tgtgagtagc cggtctatat tgtctatcac tggttttcct  4320
cctctggcgg ggtggtgttg gcttgtttgc ggcggtagtc ttttataacg gtggcggaga  4380
```

```
tggggtatcc tgcctgggtg agctgttttg ctagccacga ggcgggtata gacctgtcgg  4440
cgaggacgtc tgcagccttg ttgccgtagc gttgaataag ggtttcagtt ttggttgcca  4500
tgatgtccta tcggttgtgt ggcgggctgc catcctgtgc ggcagtcgcc gtcgtggcct  4560
ggtttgcgtg tgcaccacga tacggttccg tctgtgtggt tgagtgtttt gccgcacatg  4620
acgttttgta gatgctcggg cagggcgccg tcaccctggt tgctggtttg tgtgtcgaag  4680
agtgttttct ggttggtgaa atgctctgac acggtgccgt tgtgtacggg tagtatccat  4740
gttttccatt gttgttgtag ccgggtgttc cagtggaatt gtttggccgc gttcgtggct  4800
tgtttgatgg ttttgtagta gccgacgagg atgcgctggt gttcactgtc gggtgggttt  4860
tggcctcgcc agtattgtgc cgcgacggca tacctgttgt tgtctgtgaa ggcgtcccag  4920
cagtattcga taatgtgttg tagtacacta tcgggaatgt ctcgtacttg gttttcgtcg  4980
agccacgcgt cgacaatgat gttgcgtatg gcgtgtttgt ctttggtggt gggtttgaac  5040
gagatactca ccatgctggc ctgtcgtctt gcatgaaatc gttaaaggat gattcgcttg  5100
tgcggcgtgc ctgggtgatt tgctggtcag tccagtcggg gtgttgctgt ttcagatagt  5160
accagcggca ggcatcatat gtttcgttct gcaagcgggt gagatggttt tcggtgatga  5220
tttgtttcca cattgtccac gaaacgtcga gcctgcggag catgtccatg gccggcacat  5280
taaacgagtc aaggaagagt atttcgtggg tgtagtagtt tttctcgtag gcgtaccatc  5340
cgcttcggtg cctgtggggc tggtttttgg ggtaggcttc ccggcatact ttgtgtaaac  5400
gtttggccat gtcgtcgggt agttcaatgt cggggttggc gcggatcatg gatcgcatcc  5460
cgtcgtaggt ggtgccccag gtgtgcatga tgtgtagtgg gttgtctcca tcggcccatt  5520
tttctgcaca gatggcgagg cggatgcgcc tcctggctgt ttggctggtg ttgcgccggt  5580
tggggattgg gcacgtgtcg aggggatcca ttatgtttta gtgtaccttt ctggtttcgt  5640
gttgttgacg tgttttactg tagcacagtg tctagtgctt gtgtcaaccc tgtttttccg  5700
gcctgcaggt aggtgtctgt gacatctccg accgtgaggg gcacatgggt ggcttggggg  5760
agtgctgcct ggatggtttg tgccatctgg tcgcctgcgg ggtctgggtc tgaccagatg  5820
tagatgtggt cgtagccttc gaagaatttg gtccagaagt tttgccacga ggttgcgccg  5880
ggtagggcta cggccggcca tccgcattgt tcgaggatca tggagtcgaa ttcgccttcg  5940
caaatgtgca tttcggctgc cgggttggcc atggcggcca tgttgtagat ggagcctgtg  6000
tccccggctg gggtcaagta tttggggtgg ttgtgggttt tgcagtcgtg tgggagtgag  6060
cagcggaaac gcatttttcg tatttcggct ggccgctccc aaacggggta catgtatggg  6120
atggtgatgc actggttgta gttttcgtgg cctggtatgg ggtcattgtc gatgtatcca  6180
aggtggtggt agcgggctgt ttcttcgctg atgcctcttg ctgagagcag gtcgagtatg  6240
ttttcgaggt gggtttcgta gcgggctgag gctttctgga ttcggcggcg ttccgcaatg  6300
ttgtagggtt gtatgctgtc gtacattcgg gttttcttct tctagtcgtt gttgtagttt  6360
gtggagtcct cctccgacac cgcatgtgtg gcagtaccag acgcccttgt cgaggttgat  6420
gctcatggag ggctggtggt cgtcgtggag cgggcagagt atgtgttgct cgtttttgga  6480
cgggttgtag cgtatctggt agatgtcgag gatgcggcgg gtgtcagagg tgtgggagga  6540
gctcgttgag ggttgatacc acataggctt cgctccaggg tttgttgcgt tgtttcatca  6600
ctacgagtcc gatggtggaa ttgttttcgc ggtttcggtg tgtttcgtag ttgcgtgcct  6660
cccggctggc ttgtttcacg aattcggcta ggtggggctg gccggctttc gcctcgataa  6720
tgtaggtttt gttgctggtt gtgaggatga ggtcgccttc gtcttcgcgg ccgttgaggt  6780
ggaggcgttc gatatcgtgt ccggtgtcgc gtagctggtg caataatcgt gtttcccatt  6840
cggctccggc ccgccggttg cgtgcctgct gtgtggccat agtttttaga gtcctttgtg  6900
tgttgtggtc atgttccagg gctgtttttc ggcgaggggc ccgaagaatg tgtattcggg  6960
gtaggctcgt agtcgttcat atcgggtgcc gtcggggctg gatttgccgg tgcgctgttt  7020
caatactgcg atgcgtgcct cggccggtat cgtgagaccg ttgccgttat cctcgccacc  7080
atacaatgag actcccaata tgagttgtgg tttttcggag aggccgtttt tgatttctcg  7140
ccgtgccggg gggtgttcga tgtcggttcc ggttttgtcg gtggcgtggt gtgtgacaat  7200
aatggtggat ccggtgtcgc ggcctaatgc tgtgatccat tgcatggctt cttgctgtgc  7260
ctgatagtca ctctcgcagt cttggatgtc catcaggttg tcgataacaa tgagtggcgg  7320
gaaggtgttc cacatttcca tgtaggcttg cagctccatg gtgatgtctg tccatgtgat  7380
gggtgactgg aatgagaatg tgatgtgttg gccgtggtgg atgctgtctc gatagtattc  7440
tggtccgtag tcgtcgatgt tttgttgtat ctgtgtggtg gtgtgttggg tgttgagtga  7500
gatgattcgt gtggaggcct cccagggtgt catgtcccct gatatgtaga gggcgggctg  7560
gttgagcatg gcggtgatga acatggctag cccggatttt tggctgcctg agcgccccgc  7620
aatcatgacg agatcccctt tgtggatgtg catgtcctgg ttgcggtaga ggggttctag  7680
ttgtggtatg cggggcagct cggctgcggt ttgggaggct ctctcgaagg atcgttggag  7740
agagagcatc gggaccttat ctatctatcg gttgggtgtg ttttggtggt cagatggagt  7800
cgatgtcgat gtcagcatcg gcgggggctg tggtgtcgtc tagctggccg ttatcgcgct  7860
tgtctacgta ttcggcaacc ttatcgtaga tggcgtcatc gagggggtgg tgtcgtctag  7920
ctggccgtta tcgcgcttgt ctacgtattc ggcaacctta tcgtagatgg cgtcatcgag  7980
gggtttgagc acgaccgcat tgaacccgtt tttggtgcgc acggtggcga gtttgaaggc  8040
ctgctcctcg ccaaggtagg cttcgaggtc gcggatcatg gaatgtgggc ggtcgttgtt  8100
gccgcgcgct ttctcaataa tagcgttggg aatgatttct ggggtgccgt tgttgagatc  8160
gtctagggtg tggaagattg tgacatcagc gtagatgcga tcggctgtct gtccaccgta  8220
gccttcggtg ttgtgttcta cgtcgcggat tttgaaggcg atggcggtgg cgtcctggtt  8280
tcgggagggg ttgaagaagg tgctgttgct gttgttgcgg tagttggcga gtcccatggt  8340
tgtttccttt actgtttgtg ttggtttgtg tcggttttat cgggtgaggc tgtttcgttt  8400
gctgcggaaa gcctcggaca cgtcactgtt actggtgatg attttcttgt actgtttcag  8460
aaggtcggct agctgtgcct tgcttgttgc attgttgatt ttgtcgatga taatctcgtt  8520
ttcgtttgat gcgatgttgt ctacgtagtc tttggctgcc tggttgtagc ggtcttggag  8580
gatgatggat gcgcttgcta cgagtgttgc tagatcccag tctttggaca cgtcaccgtt  8640
tttgaggccg cctagcagat caataatgga ttgtttgatg tcttctgcgg tgtctccgcg  8700
gatgactgtc catggggctg cgtagtctcc accgtatttg agtgtgatag ttagctttcc  8760
gctgtctgtg gtgtgctcgt cggtcacgtg ttttcctttt cgttgttttc ggcttctggt  8820
ggctgtacgg tggtttctac cgggtatctg tacgagtttt tcccgttgac ggcccagcag  8880
gcgtccttga cggggcatcc tttgcagagt gctgtgacgt ggggtacgaa gatgccttgg  8940
ctgattcctt tcattgcttg actgtacatg gatgatacat gccggtaggt gttgttgtca  9000
agatcaatga gttcggtgga tgtgccctgc tcaaccgatt gctcgtctcc cttggtggta  9060
gcgggtgtcc aaaacattcc tttcgtcaca tggatgccgt gttggttgag catgtaacgg  9120
```

```
taggtgtgca gctgcatact gtcggcgggt aggcgtccgg ttttgaggtc caaaatgaag  9180
gtttcacccg tattcgtatc tgtgaatacc cggtcgatgt agccaacgat ctgggtgccg  9240
tcggggaggg tggtttctac cgggtattcg atgcccggct cgccgtcaat aacagcggta  9300
gcatattctg ggtggttgcg cctccatgtt ttccaccggt ccacaaaggt ggggccgtaa  9360
atcatccacc aattgtagtc tttcttgtgt gtcccgcccg actcgcacat gtttttgcat  9420
attctgccgg agggtttgat ttctgtgcct tcggattcgg cgagggcgac ttgggtgtcg  9480
aaaatgtttt tgaaggatga gagtttgtct ggcagtgcag ggtattcggc gggattgtac  9540
aggtgtaggt cgtattgttc ggtgatgtgg tgtatggcgc ttccggcgat ggtggcatac  9600
caggtgtggt gttgggcgtg gtagccgtgg gataggcgcc atttttcacc gcattcggcc  9660
cactgtgaca gtgatgagta ggagatgtgg cctggatggt caatggtgga cggtttttgt  9720
gctaggggca ttacttgtcg cttttgtggg tgttccatgg gtttcgggtg tcttggccgg  9780
cattgtgttg ctggtatgcg aggagtgcga ggcagtgcca ggcagcatgg gccagatggg  9840
gtagcccgga ttcatcatcg aggttgttgc cttgctgcca tgataacagg tgccggtaga  9900
gggcgtcaac actgtggctc cacggatagc cgccggtcca gttgttgtcg ccgtatttgg  9960
tggcgccgta tccggccaca gagccgaggg cgtgtaaggc tgtagggtcg atgagggata  10020
gcctgcaaag tttcaattct ttcttggcgc cagtatcagg gtcggtgtac atgctggtgg  10080
gctcatccat ggtgtgtgtg ctccttaagt atggggttac tggttggggt tgtgggcgag  10140
tgctacggcg agaataatga tggcgagggt ttcagcgatc agtatgggtg ttgtgatcat  10200
ttgtggtcgc ggggattgtt ggtgagggtt gaggcgccca ggaggatagt gagggcgcat  10260
gcggcgatga tggcgagggc tgccttgtgt ggggtgccgg tggcgtacat ccatgtgatg  10320
atgccgcctt ggatccaggc gaggctggtg aagaacgttt cgtagctgtg tagctcaatg  10380
ttgttgttgg gtgtgttcat gcttgctcct gaagaatggt gttgatggtt gtgtaaatgt  10440
tgtacaggtc ggtttcgata gataacagtt ggtggatttg gtggtcgaga tcaatgtcgg  10500
ggttgagggt gttgatgcgg gaggcgatgt cggtggctgt gcgtagtgtg ccgccggtgt  10560
ggtgaatgat gtgtgccgtg tcggcgagtc cggtggtgac agtgtagtgg gagaggagag  10620
gcatagctgg gggtgctcct tgacggggtt actgttgcgg gttgatgttg aggtcggtga  10680
cgttggggtg gtcttctgtt ccggtgacga ggcagtggac ggtgactggg agtttggatg  10740
cgccgggctg tttcgcggtt gcgccgtaga cgatggagaa ggtgtctttg ccaataattt  10800
tgtggagttg gaggtcgatg tcggggttgc cgttccattt gacgccttgt gtggcggcct  10860
gttgttcggc tttgcggttg caggtgtgtg ctgcggtgat catggtgagt ccggtggcgg  10920
tttcttcacc ccttgcttgg gcttgcttgt gggttttctg ctgttcggct cgcagtgact  10980
gttctgctgc tgcctgccgt gctttctttt cggctttgcg ctgttgggta gtcttggggg  11040
tccattcggt gttggctgtg gtggcttgcg gtgcgggttg tgatgcgagt ggcggattgt  11100
cgtctggggc tggcatgaag gatgctgcgg cgatgatggc ggctgtgatt ccggcgatgg  11160
tgtagccgtt tttcttgttc atgattttgt gttcccottt ccggggtgtt gttcgttgct  11220
gacatgatta atactttcag cggctgggcc cactgtcaag gctgcgctca acgattgtga  11280
gcgatacttg tgtggctagg ggttttgtcc ttgaggtggg agatgtcttt cccttgcgtc  11340
cagtatccat ggcggttgcg agtcatccct ttggcgagca tctcgtccac ggtgagacac  11400
ctgcgacgat ctggaccctc cttgactccc tgatcgcctg tgcggtgcat gtcaccggca  11460
caagtaccat taaatgtctc gtggcagatt gtgcaatgct ctggtcggta tccgatgatt  11520
gtgctatcgc acttgtggca tgtccattgc atgattggtc cttctttcgt gttttaagct  11580
tgtactctga ggattagagc gactttcagc ccttgggggg tatgattata taggtcaggt  11640
atttctaggc gattctaggc tcattgtgtg tggctggggg ttatcgggca cacagggtga  11700
ggagttggcc aacattgatg cgggtcacat tccagtagag ttgcgtggct tccccaccgg  11760
tgagtggctt ccactcgtca tggctgaaca cggtgccgtc ggttgcgatg aatgtgttgg  11820
ggcgtagctt gtgaagctca gtctctacac gctgccggta ggcttcggcg aggccctcga  11880
aatccatgtg gtcgcagggg aggttttcga ggcgtgtcag gtcgaagggt gtggggcagt  11940
cgtagctggc ggggctgtag agctgggtga aatggttggc gatcttctgc atgacgggtt  12000
ccttttctcg tatggtgagt tgatagtttt atcgggtgga tgcgacaagg atggcgtcta  12060
catcgatcat gtcgatgaga tcgtggagtt cctcggcctc attctcggag aggtggcgcc  12120
agccatagtc gccgtatacg gcgccgtcga gggtgacagt ccacaggggc cggatgagtc  12180
gtatggcttc ttgtacttta gcgtggtaca tgcggcgcac catatccaga tcgatgtcgt  12240
ctgaatggtt tccagtgagg ctgtagaggc tgagcgggtc gatttctgtc tgcctgtaga  12300
gggatgtgaa tgatggtgtg atgagtgtgc catccatgag agtgtgctcc tttcggtggt  12360
ggaggggttg ttgtggtttc tagagtgtgt aggctgcgac ccatagtcaa ggctgcgctc  12420
attcggattg agcgtttcat atgggtgtgg catggaatct acacccccat actgtgtgag  12480
ataggccaca tcctcctggc ttggtgtgaa ccctcgagac tactctgcct atctggcgtg  12540
gagggtgtag cccagaaata ccgtttaaag ccttcatacg gcgcctagga gcgccttaca  12600
gggtgggggc taggtattta tacccccaag caattctgat cgattctaga cgcctcccag  12660
gagcccgata cacgatccgc tatccagaca cagatcatca gcccctatcc tggttagcta  12720
agcctcaact atgtggacag tgttgattac tgtggggtaa gaaggacacg gtaaaagaaa  12780
gaggggggag catcggcttt caagccttaa ggtcttagca gttagcaccg agcccctcaa  12840
gggctcgtcg tcagcccatc aggcacggcc ctgaacgggg tacacgccat cagggaaggc  12900
ttgagagtac gaggagcctt agcgacgagt actcgaaagc ctgagggaac accctcagca  12960
ctgatgggtc tagcgtgttc ggaaaggaca caggagtaaa gcgtgacagc tgtccgggag  13020
tgaaacccgt tctgactagg ggtttcagcc ttaaccaccc tcaaaggtta caagactcta  13080
agaaaattta aggaaaagtt taggtttaat ttttggacct ttactaccaa aaacacccgt  13140
ttacacccct caaacccgcc tatagagcca aatccaccag tttgactcat cccaggtggc  13200
atatgatagg ctggacaggt agccagctgg acgcaaggcc gaaatccgct gacgcggctt  13260
tcacccttac atccatcagt ctaccaaaga cttaaagacc taagggctta gcgctaaggt  13320
gctgatagct tagcaccgag cccttgaggg gctcggcatc agccctaaag ccttaaacac  13380
ttaaagtaca tataaaactt taaaagctta acacttaagg ttataaataa acattaaagc  13440
tttaaagtct taaagtacat atataacctt aacacctaag ttaagtataa aaccttaaag  13500
gcttagcact gaaggatata aacttcacat cagtttttaa gactttaaaa cttaaaataa  13560
ctattaagac ttaaagactt ataagtttta aacacttaaa gtaactataa gactttaaag  13620
accttaagta cttaaagtta accatcagtc ttaaacttta atattataac ctataagtct  13680
taaagcttat aagttataaa agttttagaa gagctaagag gttaacttct ttacttctct  13740
tctctctttg gttctttctc tcttctcttc ttttcttcat caggggagaa gaggaacctt  13800
ttaccatcag cgccgatgga ctgtcaccgt gtgactcgtg taccaccggt cgcacgctcc  13860
```

-continued

```
cggtttcaca ctccccacac tctgacaccc gtgtcccttt caggcttagc gtgttcggct  13920
gaaggcgtac ggcgtgtcgc gccaacaccc ttaacaccag gtaagactta aagtgtatat  13980
tatatgtaga agactttaaa acctataagg tgttcccgct tagcctgtgt cctacaccgc  14040
taggcgccaa gcgttaagtc ttgaaacgcg aacacacacc cacccccatt tttctttcgt  14100
gtccttctct tttgacaccg ctggggggcg atgtgatctt tctcactacc catgggggta  14160
gtggagaaca cacccacccc accatcaaca gaacaccccc tcaaacgaac aaaacagggc  14220
ctagaatcga tcggcagggc aagggcaagg tattcatacc cccaacacat tccaggccgt  14280
cagagaggca aataagaccc gtacagggct agtcgaggat cggagacgtg atggcacaca  14340
ccaatcgcac cgcatccgcc gcacaccgac actggcggca acgactcatc acccaagccc  14400
gacagcaagg ccaaaccgaa tgcccactct gcggagcaac catcacctgg gacacctacc  14460
agctgccaac tagccccgaa gccgaccaca tcacacccgt cagcagggga ggactcaaca  14520
ccctcgacaa cgggcaaatc atctgcagaa catgcaacag aagcaaaggc aacagaacac  14580
aaccaaacat caaattccaa caacaaacca caaaaaacct tgttccatgg tgacaaaacc  14640
cgccaacccc caccggggac accccctgca cacccgtgca agacctcgta cggcttagtg  14700
aaatacctcc cttttgtgga tttgtctgtt tgtcgacttt ttgtgttggt ggtgagtgtt  14760
gtgcagcctg agcttcctga gggacacgag tggtgtgggg agacgcgtcg ttggtggcgt  14820
gtgtggggtg aggatagccg cgcgcagtac gtgtctgatg aggagtggct gtttcttatg  14880
gatgctgcgg tgattcatga ttgtgtgtgg cgtgagggtc gcgcggattt ggtggcttcg  14940
cttcgtgctc atgtgaaggc ttttatgggt atgttggatc gttattcggt tgatgtggcg  15000
tctggtggcc gtggtggggg ttctgcggtg gcgatgattg accggtatag gaagcgtagg  15060
ggggcctgat taggtgtctg gtgttgttgg gtctcaggtt cctcgtcatc gtgtggctgc  15120
ggcgtattcg gtgtctgctg gcggtgatgc tggggagttg ggtcgtgcgt atgggttgac  15180
gcctgatccg tggcagcagc aggtgttgga tgattggcta gctgtgggtg gtaatggcag  15240
gcttgcttcg ggtgtgtgtg gggtgtttgt gcctcgccag aatggcaaga atgctatttt  15300
ggaggttgtg gagttgttta aggcgactat tcagggtcgc cgtattttgc atacggctca  15360
cgagttgaag tcggctcgta aggcgtttat gcggttgagg tcgtttttttg agaatgagcg  15420
gcagtttcct gacttgtatc gtatggtgaa gtcgattcgt gcgacgaatg gccaggaggc  15480
tattgtgttg catcatccgg attgtgccac gtttgagcgt aagtgtggtt gtccgggttg  15540
gggttcggtt gagtttgtgg cccgttctcg tggttctgct cgcgggttta cggttgatga  15600
tttggtgtgt gatgaggctc aggagttgtc ggatgagcag ttggaggcgt tgcttcctac  15660
ggtgtctgcg gctccttcgg gtgatcctca gcagattttc ttgggtacgc cgcctgggcc  15720
gttggctgac gggtctgtgg tgttgcgttt gcgcgggcag gctttgtcgg gtggtaaaag  15780
gtttgcgtgg acggagtttt ctatcccgga tgagtctgat ccggatgatg tgtcgcggca  15840
gtggcggaag cttgctggtg agacgaatcc tgcgctgggt aggcgtctga atttcgggac  15900
ggtgagcgat gagcatgagt cgatgtctgc tgccgggttt gctcgggagc ggcttggctg  15960
gtgggatcgt ggccagtctg cttcttcggt gattccggcg gataagtggg ttcagtcggc  16020
tgtggatgag gcggctctgg ttggcgggaa agtgtttggt gtctcgtttt ctcgttcggg  16080
ggatcgtgtc gctttggctg gtgctggccg gactgatgct ggtgttcatg ttgaggtgat  16140
tgatgggctg tcggggacga ttgttgatgg tgtgggccgg ttggctgact ggttggcggt  16200
tcgttggggt gatactgacc ggatcatggt tgccgggtct ggtgcggtgt tgttgcagaa  16260
ggcgttgacg gatcgtggtg ttccgggccg tggcgtgatt gtggctgata ctggggtgta  16320
tgtggaggcg tgtcaggcgt ttttggaggg tgtcaggtcg ggtgtggttt ctcatcctcg  16380
tgccgattcg aggcgtgaca tgttggatat tgctgtgagg tcggctgtgc agaagaagaa  16440
gggttctgcg tggggttggg gttcctcgtt taaggatggt tctgaggttc ctttggaggc  16500
tgtgtctttg gcgtatcttg gtgcgaagat ggcgaaggct aggcggcgtg aacggtctgg  16560
taggaagcgg gtgtctgtgg tatgaattcg gatgagttgg ctctgattga gggcatgtac  16620
gatcgtatcc gaaggttgtc ttcgtggcat tgccgtattg agggctacta tgagggctct  16680
agccgggtgc gtgatttggg ggttgctatt cctccggagt tgcagcgtgt gcagacggtg  16740
gtgtcgtggc ctggtattgc ggtggatgct ttggaggagc gtctggattg gcttggctgg  16800
actaatggtg acggctacgg tctggatggt gtgtatgctg cgaatcggct tgctacggcg  16860
tcgtgtgatg tgcatttgga tgcgctgatt tttgggttgt cgtttgtggc tgttattccc  16920
cagggtgatg ggtcggtgtt ggttcgtccg cagtcgccga agaattgcac gggccggttt  16980
tcggctgacg ggtctcgtct ggatgctggc cttgtggtgc agcagacgtg tgatcctgag  17040
gttgttgagg ctgagctttt gttgcctgat gtgattgttc aggtggagcg gcgaggtagc  17100
cgtgagtggg ttgagacggg ccgtataccg aatgtgcttg gggctgttcc gttggtgcct  17160
gttgtgaatc gtcgccgtac gtctaggatt gatgggcgtt cggagatcac tcggtcgatt  17220
agggcttaca cggatgaggc tgttcgcaca ctgttggggc agtctgtgaa tcgtgacttt  17280
tatgcctatc ctcagcgttg ggtgacgggt gtgtcggctg acgagttttc gcagcctggc  17340
tgggtcctgt cgatggcttc tgtgtgggct gtggataagg atgacgacgg tgacactccg  17400
aatgtggggt cgtttcctgt gaattctcct acaccgtatt cggatcagat gcgtttgttg  17460
gctcagctga cggcgggtga ggctgcggtt ccggagcgct atttcgggtt tatcacgtct  17520
aacccgcctt ctggggaggc tttggctgcg gaggagtcga ggcttgtgaa gcgtgccgag  17580
cggcgtcaga cgtcgtttgg tcagggctgg ctgtcggttg gtttcctggc tgccagggcg  17640
cttgattcga gtgttgatga ggccgcgttt ttcggcgatg tgggtttgcg ttggcgtgac  17700
gcttcaaccc cgactcgggc ggctacggct gatgctgtga cgaagcttgt gggtgccggt  17760
attcttccgg cggattctcg tacggtgttg gagatgctgg ggcttgatga tgtgcaggtt  17820
gaggctgtga tgcgtcatcg tgccgagtct tcggatccgt tggcggcact ggctggggct  17880
atatcgcgtc aaactagcga ggtttgatag gcgatggctt cgggtgttgc gtcaaggttg  17940
gctgctgccg ggtatcagcg tgaggcggtc aggtttgccg ggaagtatgc gggctattat  18000
gccgagcttg gtcgtttgtg gcattccggg aagatgacag atgcgcagta tgtgcgtttg  18060
tgtgtggagt tggagcgtgc cggccatgac ggttcagcgg cgttggcggg taagttcgtg  18120
tcggattttc ggaagcttaa cggtgtggat cctggtttga tcgtgtatga cgagtttgat  18180
gctgccgccg cgttggctag gtcgttttcg actattaaga tgatgaatag tgacccggat  18240
agggctaagg atacggttga tgcgatggcg gcgggtgtta atcgggctgt catgaatgct  18300
ggccgtgaca cggttgagtg gtctgcgggt gcgcagggta ggtcgtggcg ccgggtgacg  18360
gatggtgatc cgtgcgcgtt ttgtgccatg ttggctacga ggtcggatta tacgaccaaa  18420
gagcgggcgc ttactactgg tcatactcgg cgtcataagc gtggcggtag gcgtccgttt  18480
ggttcgaagt atcatgatca ttgtggttgt acggtggttg aggttgttgg cccttgggag  18540
ccaaataggg ctgatgccgc atatcagagg acgtatgaga aggctcgtga gtgggttgat  18600
```

-continued

```
gatcatgggt tgcagcagtc gcctggcaat attttgaagg ctatgcgtac tgttggtggc  18660
atgagataat ttgatgtggt ttccggttgt gtgccgccgg ttatcggtgc acagggttgt  18720
ctcccgcacg ggggtcaaca atgttgtgtt gttttccgca aggagtatag ggttaggcta  18780
tggccgatca aaaagttgaa gaacagaatg ttgacaatga tgctgttgag cccggaaagg  18840
gtggagacgt tgttgatgtt gtgaaggatg ggcaggctgc cggcgatgat catgccggtg  18900
atgtttccgt gaaggaggag tcttcttctg gcacggattg gaaggctgag gctcgtaagt  18960
gggagtctcg tgctaaaagt aatttcgccg agttggagaa gcttcgcgcc tcggatggtg  19020
atgcggggtc tgtgattgat gagcttcgcc gcaagaatga ggaactcgaa gaccggatta  19080
atgggtttgt tcttgagggt gtgaagcgcg aggtggctgc cgagtgtggc ctgtcgggtg  19140
atgctgtcgc ttttttgcac ggtggcgatc gtgaagcact ggtggagtct gctaaggctt  19200
tgaagggttt gatcgaccat agtagtggtg gcgcgggtgt gcgccgtctt gcggggagtg  19260
cccccgttga tgatgttaaa cgacgtgagg gtgtcgcgtt tgtggatgct cttgtcaata  19320
attctaggag atgatttgtg atggctgacg attttctttc tgcagggaag cttgagcttc  19380
ctggttctat gattggtgcg gttcgtgacc gtgctatcga ttctggtgtt ttggcgaagc  19440
tttcgccgga gcagccgact atttttggcc ctgttaaggg tgccgtgttt agtggtgttc  19500
ctcgcgctaa gattgttggt gagggcgagg ttaagccttc cgcgtctgtt gatgtttcgg  19560
cgtttactgc gcagcctatc aaggttgtga ctcagcagcg tgtctcggac gagtttatgt  19620
gggctgatgc tgattaccgt ctgggtgttt tgcaggatct gatttccccg gctcttggtg  19680
cttcgattgg tcgcgccgtg gatctgattg ctttccatgg tattgatcct gccactggta  19740
aagcggctgc cgctgtgcat acttcgctgg ataagacgac gcatattgtt gatgccacgg  19800
attctgctac ggctgatctt gttaaggctg tcggcctgat tgctggtgct ggtttgcagg  19860
ttcctaacgg ggttgctttg gatcccgcgt tctcgtttgc cctgtctact gaggtgtatc  19920
cgaaggggtc tccgcttgcc ggccagccta tgtatcctgc cgccgggttt gccggtttgg  19980
ataattggcg cggcctgaat gttggtgctt cttcgactgt ttctggcgcc ccggagatgt  20040
cgcctgactc gggtgttaag gctattgtgg gtgatttctc tcgtgttcat tggggtttcc  20100
agcgtaactt cccgatcgag cttatcgagt atggcgatcc ggatcagact ggccgcgatt  20160
tgaagggcca taatgaggtt atggttcgtg ccgaggctgt gctgtatgtg gctatcgagt  20220
cgcttgattc gtttgctgtt gtgaaggaga aggctgcccc gaagcctaat ccgccggccg  20280
agaactgatt tattgttgcg gtgatgtgtc aatgtgcagg gggtggtgtt gatgggtatc  20340
attttgaagc ctgaggatat tgagcctttc gccgatattc ctagagagaa gcttgaggcg  20400
atgattgccg atgtggaggc tgtggctgtc agtgtcgccc cctgtatcgc taaaccggat  20460
ttcaaataca aggatgccgc taaggctatt ctgcgcaggg ctttgttgcg ctggaatgat  20520
actggcgtgt cgggtcaggt gcagtacgag tctgcgggtc ctttcgctca gactacacgg  20580
tctagtactc ccacgaattt gttgtggcct tctgagattg tcgcgttgaa gaagctgtgt  20640
gagggtgatg gtggggctgg taaagcgttc actattacac cgaccatgag gagtagtgtg  20700
aatcattctg aggtgtgttc cacggtgtgg ggtgagggtt gctcgtgcgg gtcgaatatt  20760
aacggctacg ctggcccctt gtgggagata tgatatgacc agttttcctt atggtgaaac  20820
ggttgtgatg cttcaaccga ctgttcgtgt cgatgatctt ggcgacaagg tggaagactg  20880
gtctaagcct gtcgagactg tgtaccataa cgtggccata tatgcttccg tttcgcagga  20940
ggatgaggct gcggggcgtg actcggatta tgagcattgg tcgatgctgt tcaagcagcc  21000
tgttgtgggc gctgattatc gttgtaggtg gcgtattcgg ggtgttgtgt gggaggctga  21060
cgggtctcct atggtgtggc atcaccccat gtccggttgg gatgctggta cgcaggttaa  21120
tgtgaagcgt aagaagggct gatgggtagt ggctcaggat gtgaatgtga agctgaactt  21180
gccgggtatt cgtgaggtgt tgaagtcttc tggagtgcat ggcatgttgg ctgagcgtgg  21240
cgagcgtgtc aagcgtgccg cagcggcgaa tgtgggtggt aacgcgtttg atagggccca  21300
ataccgtaat ggtttgtcgt cggaggtgca ggttcaccgt gttgaggctg tggcgaggat  21360
tggcaccacc tataagggtg ggaagcgtat tgaggcgaag catggcacgt tggcgaggtc  21420
gattggggct gcgtcgtgat cgtttacggt gatccgcgtg tgtgggctaa acgcgtgctc  21480
aaggatgatg gctggctgtc tgggataccg tgtacgggga cggtgcctga ggatttcagc  21540
ggtgacctga tctggttggc gttggatggt ggcccacagt tgcatgttcg tgagcgtgtt  21600
tttttgcgcg tgaacgtgtt ttcggatacg ccggatcgtg ctatgtcgtt ggcgcgtcgt  21660
gtcgaggctg tgctggctga tagtgtggac ggtgaccctg tggtgtactg taaacggtct  21720
actggccctg atttgctggt tgatggtgca cgttttgatg tgtattcgct ttttgagctg  21780
atatgtaggc ctgcggagtc tgaataagct tattgttttt gttttaatgt aattgtttga  21840
tatttaatgg ggttatgat ggctgcaaca cgtaaagcgt ctaatgttcg ctcagcggtt  21900
actggcgacg tttatattgg tgacgcgcac gcgggtgata ctattaaggg tgtggaggcg  21960
gttccttccg ggcttaccgc tttagggtat ctgtctgatg acgggtttaa gattaagcct  22020
gagcgtaaaa cggatgattt gaaggcttgg cagaatgcgg atgttgttcg cactgtggct  22080
acggagtctt ctatcgagat ttcttttcag ctgatcgaat ccaaaaaaga ggttatcgaa  22140
ctgttttggc agtcgaaggt tactgccgga tccgattcgg gttcttttga tatttctcct  22200
ggtgccacga cgggtgttca cgctctgttg atggatattg ttgatggtga tcaggttatt  22260
cgctactatt tccctgaggt tgagctcatt gatcgtgacg agatcaaggg taagaatggt  22320
gaagtgtacg ggtatggtgt gacgttgaag gcgtatcctg cccagattgg taagactggt  22380
aatgcggtgt ctggtcgggg gtggatgacg gctttaaaag ctgatactcc tccttctccg  22440
aagcctcagc cggatccgaa tccgccggcc gagaactgat acacgatttt aggggattgt  22500
tgatagatga gtgacactgg tttcacgttg aagattggtg atcgtagctg ggtgttggcg  22560
gatgctgagg agacggcgca ggctgttcct gcccgcgttt tccgtcgtgc cgccaggatt  22620
gcccagtcgg gggagtctgc ggatttcgcc caggttgagg tgatgttttc tatgttggag  22680
gctgccgccc cggctgacgc tgtggaggcc ctggaggggc ttcctatggt tcgtgtggcg  22740
gaggttttcc gtgagtggat ggaatataag cctgacggta agggtgcctc gctgggggaa  22800
tagtttggct ccacggcctg attgatgatt atcgtggggc catcgaatac gatttccgca  22860
ctaaatttgg tgtttctgtt tatagtgttg gtggcccgca gatgtgttgg ggtgaggctg  22920
tccggctggc tggcgtgttg tgtactgata cgtctagcca gttggcggcc cacctgaatg  22980
gttggcagcg cccgtttgag tggtgtgagt gggctgtgtt ggacatgttg gatcattaca  23040
ggtctgctaa tagtgagggg cagccggagc ctgtggcgag gccgacggat gagcgtaggg  23100
cccggtttac gtctgggcag gtggacgata ttttggcgcg tgttcgtgcc ggtggcgggg  23160
tgtctcgcga gattaatatt atggggtgaa tagtgtatgt ctggtgagat tgcttccgcg  23220
tatgtgtcgt tgtatacgaa gatgcctggc cttaaaagtg atgttggtaa acagctttct  23280
ggggtgatgc ctgcggaggg tcagcgttcg ggtagcttgt ttgctagcgg gatgaagttg  23340
```

```
gcgcttggtg gtgcggcgat gatgggtgcc atcaatgttg ctaagaaggg cctcaagtct  23400
atctatgatg tgactattgg tggcggtatt gctagggcga tggctattga tgaggctcag  23460
gctaaactga ctggtttggg tcatacgtcg tctgacacgt cttcgattat gaattcggct  23520
attgaggctg ttactggtac gtcgtacgcg ttgggggatg cggcgtctac ggctgcggcg  23580
ttgtctgctt cgggtgtgaa gtctggcggg cagatgacgg atgtgttgaa gactgtcgcc  23640
gatgtgtctt atatttcggg taagtcgttt caggatacgg gcgctatttt tacgtccgtg  23700
atggctcgcg gtaagttgca gggcgatgac atgttgcagc ttactatggc gggtgttcct  23760
gtgctgtctt tgcttgccag gcagacgggt aaaacgtctg ctgaggtgtc gcagatggtg  23820
tcgaaggggc agattgattt tgccacgttt gcggctgcga tgaagcttgg catgggtggt  23880
gctgcgcagg cgtctggtaa gacgtttgag ggcgctatga agaatgttaa gggtgccctg  23940
ggttatttgg gtgctacggc tatggcgccg tttcttaacg ggttgcggca gatttttgtt  24000
gcgttgaatc cggttattaa gtctatcacg gattctgtga agcctatgtt tgcgtcggtg  24060
gatcagggga ttcagcgggt gatgccgtct attttggcgt ggattaaccg tatgccgggc  24120
atgattacga gaatgaatgc acagatgcgc gccaaggttg agcagttgaa gggcgttttt  24180
gcgaggctgc atttgcctgt tcctaaggtg aattttggtg ccatgtttgc tggcggcacc  24240
gcagtgttcg gtattgttgc tgcgggtgtt gggaagcttg ttgcggggtt tgccccgttg  24300
gcggtgtctt tgaagaatct gttgccgtcg tttggtgctt tgaggggtgc cgctggggg  24360
cttggtggcg tgtttcgcgc cctgggtggc cctgttggta ttgtgatcgg gctgtttgct  24420
gccatgtttg ctacgaacgc ccagttccgt gccgctgtta tgcagcttgt gggggttgtt  24480
ggccgggctt tggggcagat tatggtcgct gtgcagccac tgttcgggat tgttgctggc  24540
gtggttgcca ggttggcgcc agtgttcggc cagattatcg gtatggttgc tggtttggct  24600
gcccggctgg tgcctgttat tggtatgctt attgcccggc tggttcctgt tatcacccag  24660
attattggta tggtaaccca ggttgctgcc atgttgttgc ctatgctgat gccggttatt  24720
caggctgttg ttgctgtgat acggcaggtt attggtgtga tcatgcagtt gatacctgtt  24780
ttgatgccgg ttgtgcagca gattttgggt gctgtcatgt ctgttttgcc gccgattgtt  24840
ggtttgatac ggtcgctgat accggtgatc atgtcgatta tgcgtgtggt ggtgcaggtt  24900
gttggtgccg tgttgcaggt ggtggcccgt attattccgg ttgttatgcc gatttatgtt  24960
tcggtgattg gattcattgc caagatttat gctgcggtta tcgtttttga ggctaaggtt  25020
attggcgcta ttcttcgtac tattacgtgg attgtgaatc attcagtgtc tggcgtgagg  25080
tctatgggca cggccatcca gaatggctgg aatcatatca aatcgtttac gtcggcgttt  25140
attaacggtt tcaagtcgat catttctgcc ggtgttgccg cggttgtggg gtttttttacg  25200
cggcttggtt tgtcggttgc ttctcatgtt cggtctgggt ttaacgcggc ccgtggcgct  25260
gtttcggctg cgatgaatgc tattcggagt gttgtgtctt cggtggcgtc tgctgttggc  25320
gggtttttcg ggtcgatggc gtctagggtt cgtagtggtg ctgtgcgcgg gtttaatggt  25380
gcccggagtg cggcttcttc tgctatgcat gctatgggct cggctgtgtc tagtggtgtg  25440
catggtgtgc taggattttt ccggaatttg cctggcaata ttcggcatgc tctcggcaat  25500
atggggttct tgttggtgtc ggctggccgt gatgtggtgt ctggtttggg taacggtatt  25560
aagaatgcta tgagtggcct gttggatacg gtgcgtaaca tgggttctca ggttgctaat  25620
gcggctaagt ctgtgttggg tattcattcc ccgtctcgag tgtttcgtga ccaggttggc  25680
cggcaggttg ttgccggttt ggccgagggg atcaccggga atgcgggttt ggcgttggat  25740
gcgatgtcgg gtgtggctgg acggctgcct gatgcggttg atgcccggtt tggtgtgcga  25800
tcatcggtgg gctcgtttac cccgtatgac aggtatcggc ggatgggcga gaagagtgtt  25860
gtggtgaatg tgaatgggcc tacttatggt gatcctaacg agtttgcgaa gcggattgag  25920
cggcagcagc gtgacgcttt gaacgcgttg gcttacgtgt gattgggggt gttgtgcatg  25980
tttattcctg acccgtctga tcgtgccggt ttgactgtta cctggtctat gttgccgttg  26040
attggtaatg atccggagcg tgtgcttcat ttgacggatt atacgggtgc gtctcctgtc  26100
atgttgttga atgattcgtt gcgcggtttg ggtgttcctg aggtggagca tttttctcaa  26160
actcatgttg gggtgcacgg ctcggagtgg cgcgggttta atgtgaagcc tcgcgaggtg  26220
acattacctg tcctggtgtc gggtgttggt gtggatccgg ttggcgggtt tcgtgacggt  26280
tttttgaagg cgtatgacga gttgtggtct gcttttcctc cgggcgagga gggggagttg  26340
tctgtgaaga ccccgtctgg ccgtgagcgt gtgctaaaat gccggtttga ttcggtggat  26400
gacacgttta ctgtggatcc ggtgaacagg ggttatgcgc gctatctgtt gcatttgaca  26460
gcttatgacc cgttttggta tggggatgag cagaagtttc gttttagtaa tgcgaagttg  26520
caggattggt taggtggcgg ccctgtcggc aagaagggta ccgcttttcc ggtggtgttg  26580
acgcctggtg ttggttcggg ttgggataat ctgtctaata ggggtgatgt gcctgcgtgg  26640
cctgtgattc gtgtggaggg cccgttggag tcgtggtctg tgcagattga tggtttgcgt  26700
gtgtcttcgg attacccggt ggaggagttt gattggatca ctattgatac ggatcctcgc  26760
aaacagtctg cattgttgaa cggtttgag gatgtgatgg atcgtttgac agagtgggag  26820
tttgccccta tcccgcctgg cggttctaag agtgtgaata ttgagatggt tggtttgggt  26880
gccattgttg tgtcggtgca gtacaggttt ttgagggctt ggtgaatagt tgatggctgg  26940
tcttgttccg catgtaacat tgtttacacc tgattatcgc cgtgtggcgc ctatcaattt  27000
ttttgagtcg ttgaagttgt cgttaaagtg gaatggtttg tccactttgg agttggtggt  27060
gtctggtgat cattctaggc ttgacgggtt gactaggccg ggtgcacggc tggttgttga  27120
ttatggtggt ggccagattt tttctgggcc tgtgcgtcgg gttcatggtg tgggtccgtg  27180
gcgttcttcc catgtgacta tcacgtgtga ggatgatatt cgtctgttgt ggcgtatgtt  27240
gatgtggcct gtggattatc gtcctggttt ggttggtatg gagtggcgtg ctgaccggga  27300
ttatgcccac tattcgggtg cggctgagtc ggtggctaag caggtgttgg gggataatgc  27360
ttggcgtttt ccgcctggtt tgtttatgaa cgatgatgag agtcgtggac ggttcattaa  27420
ggattttcag gtgcggtttc acgtgtttgc cgataagttg ttgccggtgt tgtcgtgggc  27480
tcggatgact gtcacggtga accagtttga gaatgcgaag tttgatcagc gtggtttggt  27540
gtttgattgt gtgcctgctg tgacgcgtaa gcatgtgttg actgccgagt ctggttcgat  27600
tgtgtcgtgg gagtatgtgc gtgacgcccc gaaggcgaca tcggtggtgg ttggtggccg  27660
cggcgagggc aaagatcggc tgttttgtga ggatgttgat tcgatggccg aggatgactg  27720
gtttgatcgt gtcgaggtgt ttaaggatgc ccgtaacacg gattctgagc atgtgcatct  27780
cattgatgag gctgagcagg tgttgtccga gttgggggcc acgtcggggt ttaagatcga  27840
gttggctgag tcggatgtgt tgcggtttgg gcccggcaat ctgatgcccg gggatttgat  27900
ctatgtggat gtgggttctg gccctatcgc agagattgtg cggcagattg atgtggagtg  27960
tgagtcgccg ggtgacgggt ggacgaaggt gactcctgtt gcaggggatt atgagaataa  28020
tccgtcggcc ctgttggcgc ggcgtgttgc tggtttggct gcgggtgtgc gggatttgca  28080
```

```
aaaattctag aaaagattag gggtttgttg tgggtattgt gtgtaaaggg tttgatggtg  28140
tgttgaccga gtatgattgg gctcaaatgt ctggtctgat gggtaatatg ccgtccgtga  28200
aagggccgga cgattttcgt gtcggcacta ctgttcaggg tgccacagtg ttgtgtgagg  28260
tcctgccggg gcaggcttgg gcccacgggg tgatgtgcac gtcgaatagt gttgagacgg  28320
tgaccggcca gcttccgggc ccgggtgaga cccgatacga ctatgtggtg ttgtctcggg  28380
attgggaggc gaatacggcc aagttggaga ttgttcctgg ggggcgtgcg gagcgtgccc  28440
gtgacgtgtt gagggccgag cctggcgtgt accatcagca gttgttggct actttggtgg  28500
tgtcgtctaa cgggttgcag cagcagctgg ataggcgtgc tatagcggct agggtggcgt  28560
ttggcgagtc tgctgcgtgt gatcctaccc cagtggaggg tgaccgtgtg atggttccct  28620
ctggggctgt gtgggctaat catgccggcg agtggatgct gttgtccccc aggattgaga  28680
cgggttctaa gtcgatcatg tttggcgggt ctgctgtgta tgcttacacg attccgtttg  28740
agcggccgtt tagtagtgcg cctgttgtgg tggcgtctat ggctacggcg gctgggggca  28800
cgcagcagat caatgtgaaa gcctacaatg tgactgtcca aaattttagt ttggcgttta  28860
ttacgaatga tggttcgaag ccgaatggtg tgcctgcggc ggctaattgg attgctgtcg  28920
gcgtgtgact gtacaggtgt tgtggcggat ggtgtgatgt tggggggctg tggtgtcgtg  28980
gtttactcct gcactggtgg cctctatttg taccgcgttg gccacggttt tgggttctgt  29040
tcaggctgtc acatcccggt ctaggcggcg tttacgcagg ctgtctgcgc aggtggatgc  29100
gatggaagag tatacgtggg gtgtgcggcg cgaggtgcga aggtttaacg ccgggcttcc  29160
tgatgatgtg gagccgatgc atcttcctga tgtgcccgag tttttgaagg atactgttga  29220
tggtggaggt gagtagggtt gagggagttg gaggaggaga agcggcagcg ccgcaatttt  29280
gagaaggctt ccctgatact gttatttttg tcgcttgtgt tgttggcggt ggttgccggg  29340
ggtgctttgc ggtacgggtc tgtggcttct caaagggatt cggagcaggc gagggcccag  29400
tcgaatggta cagccgctaa agggttggct gcccgtgtga agcaggcgtg tacccaggt  29460
ggcgtggagt ctgtgaagct gcacaggtct ggtttgtgtg tggatgctgt gcgtgttgag  29520
cagcgtgttc agggtgtgca gggtcctgcc ggtgagcgtg gcccgcaagg gcccgctggt  29580
gttgatggcc gggatggtag caatggttct gctgggctgg ttggccctgt tgggccgcag  29640
ggttcccctg gtttgaatgg tgttccaggt cgtgcaggtg tcgatggtgt gaacggcgc   29699
```

```
SEQ ID NO: 71          moltype = DNA  length = 29596
FEATURE                Location/Qualifiers
source                 1..29596
                       mol_type = other DNA
                       note = PAC2
                       organism = synthetic construct
SEQUENCE: 71
ctggtttgaa tggtgtgaaa ggtcctgacg ggttgcctgg cgctaacggt tcggatggcc  60
gtgatggtgt tccaggtcgt gcaggtgtcg atggtgtgaa cggcgctgat ggtcgggatg  120
gttcggccgg tgagcgcggt gatgtgggcc cttcaggtcc tgccggcccg caaggtgcac  180
agggtgaacg gggtgagcgc ggccccgccg gtgcgaacgg atccgatggt aaagacggta  240
aggatggtgc tgatggccgt gatgggcgtt cggtgatatc ggtgtactgt tccgggggcc  300
gcctggttgt gaaatatagt gacggtacgg cctctaccgt gtcgggttct gcggcctgcg  360
agagtgtgaa accatcacct gtggttactg tatcatccca taggtgaaca agaagaggga  420
agggtgttac tagtgttgat tgtggtgttt gggggtggtg tgtggtgaga tacattccag  480
cggcgcatca ctctgccggt tcgaatagtc cggtgaacag ggttgtgatt catgcaacat  540
gcccggatgt ggggtttccg tccgcttcgc gtaagggtcg ggctgtgtct acagcgaact  600
atttcgcttc cccatcatcg gggggttcgg cgcattatgt ttgtgatatt ggggagacgg  660
tgcagtgcct gtcagagggg actatagggt ggcatgcccc gccgaatccg cattctttgg  720
gtatagagat ttgcgcggat gggggttcgc atgcctcgtt ccgtgtaccg gggcatgctt  780
acacgaggga gcagtggctt gatccgcagg tgtggcccgc agtggagagg gccgctatcc  840
tgtgtcggca gttgtgtgac aagcatggtg ttccgaaaag gaaactgtct gtggccgatt  900
tgaaggccgg taaacggggt gtgtgcgggc atgtggatgt tacggatgcg tggcatcagt  960
cggatcatga cgatccgggg ccgtggtttc cgtgggacaa atttatggct gtggtgaatg  1020
gccacggcgg cggttcaagt agtgaggagt tgagtatggc tgatgtacaa gcgttacata  1080
atcagattaa acagttgtcg gcacaggtgg cccagtcggt gaataagctg catcacgatg  1140
ttggtgtggt tcaggttcag aatggtgatt tgggtaaacg tgttgatgcc ctgtcgtggg  1200
tgaagaatcc ggtgaccggg aagctgtggc gcaccaaaga cgccctgtgg agcatctggt  1260
attacgtgtt ggagtgtcgc agccgcatag acaggcttga gtctgctgtt aatggtttga  1320
aaaagtgatg gtggtttgtt gtgggtaaac agttttggtt gggcttgttt gagcgtgccc  1380
tgaaaacttt tattcaaacg tttgttgctg tgcttggggt gacggcgggt gttacttata  1440
ctgcggagtc gtttcgcggt ttgccgtggg agtctgccct gataacagca acggttgctg  1500
cggtgctgtc tgttgctaca tcgtttggta gcccgtcatt tgtggccggc aaacctaaaa  1560
ccacggttgt ggatgctggg cttgttccac ccgacgatgg gggcatggtt gagccgcact  1620
cggtggatgt gtcggatcct ggcatgatcg agccgacaga tgatgtggat ggttttgctg  1680
gctatgtgcc gaagcgtgca gccgagtcgg aggttagcac ggtggagtct actgttgcat  1740
aattgaacat agatgtgtgc cccagcggtg ctgccacgat cgtgtggtgg ttgccgctgg  1800
ggcacacttt ttgtgtctat aggagtttta caggttgtcg tctagtgtgt cttcgagcat  1860
ctggtccagg tagaggcagg cggagatagt atcgttggcc tggtctagaa cgttctggcc  1920
gataacattt ttatgattgt cgcggtggct gatgatagac cgcatgatat cgtcggccgc  1980
cgcctgcaat agtttggcct ggtatgcgat tcctgcgagc cagtctagtg cttcctggct  2040
tgccagtgtg tcgtctggaa tgccacgggt gttgctgttg tttgtggggt gtcctgcact  2100
gtcgcagcac cacaagattt cgctgcactc gtctagcgtg tcctggtcga tagcaagatc  2160
gtcgaggctg acttctttga cggtaaggtt cacattgtcg agggagatgg gtacaccgta  2220
ttggttttcg acactgtcaa caatgttttc caactgttgc atgttggtgg gctgttgttg  2280
gatgatacgg tgtactactg ttttgatggc ggtgtagggg atattgtgtg tgttgttcat  2340
ggtttttatc ccacccctgt gttgtcgtcg ttattgtctg gatagtatct actgtttgcg  2400
tagcctgtga gggtgatgag tgtttggtct gcccactgtt tcactgtctg ccgggtgaca  2460
cccaatcgtt gggcggctgt ggcgtaggtt tgatcatacc cgtatacttc acggaatgcg  2520
gctagcctgg ctaggtgttt tcgctgtttg gagggttcac atgatagggt gtagtcgtcg  2580
atggcgagct gtagatcgat catggtggca atgttgttgc cgtgatgctg gggggcggtt  2640
```

```
ggtgggggtg gcattcctgg ctccacactg ggtttccatg ggccgccgtt ccagatccat  2700
tgggcggctt ggatgatgtc ggcggtggtg taggttcggt tcatgtgtca ccccctgaac  2760
aggtcgttgc tggtgctggt gttggtggtg tcgaatcgtc cgacgcagtg gcagtagtcg  2820
tacatgagtt tgataatgtg ttggtggtct cccaaatagg tgtttccgct gatactgtag  2880
gtggctgtgc cgtctttact gatggtgtat ttggcggtga tggtttcggg gttttcggtg  2940
tcggtgatga ttgctgtggt ggtggtgcct actgtttgta gcacggtggt ttgggttccg  3000
tcgtcgatag tggttttaac catggtgtgt gttctccctt tttagatgct ggtttggttg  3060
tcggctagat gaatgatgtc gggtaagggt ttcggctggt ctaggtgttg tatggttttg  3120
ttggctagcc gtttggctac cctgtaacac attttggtgt agtgtttgtt gtctaggttg  3180
tggtattgtt cccgcaccgc aatatatagt agagagtctt ggtacaggtc gtctgcactg  3240
attgcggggt agtgtgcggc tgttttggtg catgcccggt tgagtgtgcg tagatgatgg  3300
tctgtggccc acacccacga tgcggtggtg gctaggtcgg cttttgttgg tcgtctgctc  3360
atggcatttc tttcatcggg ctatctggta gttgtttggt gttttgttgt tgatagtgta  3420
gcacacgagt ccggggtttc cggtggtgcc agtcttgtgc cggtaccatg tggattcgcc  3480
ttccatggat gggcattgga tgaaggtgcg ttgtccttgt tcggagattt ctaggtggtg  3540
ccggtgcccg gccatgagga tgtgggatgt ggtgccgttg tggaattctt ggccgcgcca  3600
ccaatcatag tgtttgccgg tgcgccattg gtgtccgtgg gcgtgcagga tttgtgtgcc  3660
ggccacgtcg acggtggtgg tcatttcgtc ccgttggggg aagtggaagt gaaggttggg  3720
gtattggttg ttgagctggt aagcttctgc gatggcgcgg cagcagtcca cgtcgaagga  3780
gtcgtcgtag gtggtgactc ctttgccgaa gcgcacggct tcgccgtggt tgccggggat  3840
ggatgtgatg gtcacatttt tgcagtggtc gaacatgtgg acgagttgca tcatggccat  3900
gcgggtgagc ctgatttgtt cggtgagggg tgtttgtgtg cgccaggcgt tgttgcctcc  3960
ttgtgacacg tatccttcga tcatgtcgcc gaggaatgcg atgtggactc gttcgggttt  4020
gcctgcctgt tgccagtagt gttttgcgac tatgagggag tgcaaatagt cgtctgcgaa  4080
tcggctggtt tctccgccgg ggatgccttt gccgatttgg aagtcgcctg ccccgataac  4140
gaaggctgtc tcgtcactgc tttgggtgtc ttgttcgggt ttgggtggct gccattcggc  4200
tagtttgttg acgagttcgt cgacggggta ggggtcggtt gcgggttggt ggtcgatgat  4260
tttttgtatg gatcggcctg tttctccgtt ggggagtgtc cattcggaga tgcgtgtgcg  4320
gcgtacagta ccgttggcta gattgtcgtc gatggtgtcg atggcgttgt cgtggttggc  4380
tagctgtgtg agtagccggt ctatattgtc tatcactggt tttcctcctc tggcggggtg  4440
gtgttggctt gtttgcggcg gtagtctttt ataacggtgg cggagatggg gtatcctgcc  4500
tgggtgagct gttttgctag ccacgaggcg ggtatagacc tgtcggcgag gacgtctgca  4560
gccttgttgc cgtagcgttg aataagggtt tcagttttgg ttgccatgat gtcctatcgg  4620
ttgtgtggcg ggctgccatc ctgtgcggca gtcgccgtcg tggcctggtt tgcgtgtgca  4680
ccacgatacg gttccgtctg tgtggttgag tgttttgccg cacatgacgt tttgtagatg  4740
ctcgggcagg gcgccgtcac cctggttgct ggtttgtgtg tcgaagagtg ttttctggtt  4800
ggtgaaatgc tctgacacgg tgccgttgtg tacgggtagt atccatgttt tccattgttg  4860
ttgtagccgg gtgttccagt ggaattgttt ggccgcgttc gtggcttgtt tgatggtttt  4920
gtagtagccg acgaggatgc gctggtgttc actgtcgggt gggttttggc ctcgccagta  4980
ttgtgccgcg acggcatacc tgttgttgtc tgtgaaggcg tcccagcagt attcgataat  5040
gtgttgtagt acactatcgg gaatgtctcg tacttggttt tcgtcgagcc acgcgtcgac  5100
aatgatgttg cgtatggcgt gtttgtcttt ggtggtgggt ttgaacgaga tactcaccat  5160
gctggcctgt cgtcttgcat gaaatcgtta aaggatgatt cgcttgtgcg gcgtgcctgg  5220
gtgatttgct ggtcagtcca gtcggggtgt tgctgtttca gatagtacca gcggcaggca  5280
tcatatgttt cgttctgcaa gcgggtgaga tggttttcgg tgatgatttg tttccacatt  5340
gtccacgaga cgtcgagcct gcggagcatg tccatggccg gcacattaaa cgagtcaagg  5400
aagagtattt cgtgggtgta gtagtttttc tcgtaggcgt accatccgct tcggtgcctg  5460
tggggctggt ttttggggta ggcttcccgg catactttgt gtaaacgttt ggccatgtcg  5520
tcgggtagtt caatgtcggg gttggcgcgg atcatggatc gcatcccgtc gtaggtggtg  5580
ccccaggtgt gcatgatgtg tagtgggttg tctccatcgg cccatttttc tgcacagatg  5640
gcgaggcgga tgcgcctcct ggctgtttgg ctggtgttgc gccggttggg gattgggcac  5700
gtgtcgaggg gatccattat gttttagtgt acctttctgg tttcgtgttg ttgacgtgtt  5760
ttactgtagc acagtgtcta gtgcttgtgt caaccctgtt tttccggcct gcaggtaggt  5820
gtctgtgaca tctccgaccg tgaggggcac atgggtggct tgggggagtg ctgcctggat  5880
ggtttgtgcc atctggtcgc ctgcggggtc tgggtctgac cagatgtaga tgtggtcgta  5940
gccttcgaag aatttggtcc agaagttttg ccacgaggtt gcgccgggta gggctacggc  6000
cggccatccg cattgttcga ggatcatgga gtcgaattcg ccttcgcaaa tgtgcatttc  6060
ggctgccggg ttggccatgg cggccatgtt gtagatggag cctgtgtccc cggctggggt  6120
caagtatttg gggtggttgt gggttttgca gtcgtgtggg agtgagcagc ggaaacgcat  6180
ttttcgtatt tcggctggcc gctcccaaac ggggtacatg tatgggatgg tgatgcactg  6240
gttgtagttt tcgtggcctg gtatggggtc attgtcgatg tatccaaggt ggtggtagcg  6300
ggctgtttct tcgctgatgc ctcttgctga gagcaggtcg agtatgtttt cgaggtgggt  6360
ttcgtagcgg gctgaggctt tctggattcg gcggcgttcc gcaatgttgt agggttgtat  6420
gctgtcgtac attcgggttt tcttcttcta gtcgttgttg tagtttgtgg agtcctcctc  6480
cgacaccgca tgtgtggcag taccagacgc ccttgtcgag gttgatgctc atggagggct  6540
ggtggtcgtc gtggagcggg cagagtatgt gttgctcgtt tttggacggg ttgtagcgta  6600
tctggtagat gtcgaggatg cggcgggtgt cagaggtgtg ggaggagctc gttgagggtt  6660
gataccacat aggcttcgct ccagggtttg ttgcgttgtt tcatcactac gagtccgatg  6720
gtggaattgt tttcgcggtt tcggtgtgtt tcgtagttgc gtgcctcccg gctggcttgt  6780
ttcacgaatt cggctaggtg gggctggccg gctttcgcct cgataatgta ggttttgttg  6840
ctggttgtga ggatgaggtc gccttcgtct tcgcggccgt tgaggtggag gcgttcgata  6900
tcgtgtccgg tgtcgcgtag ctggtgcaat aatcgtgttt cccattcggc tccggcccgc  6960
cggttgcgtg cctgctgtgt ggccatagtt tttagagtcc tttgtgtgtt gtggtcatgt  7020
tccagggctg tttttcggcg aggggcccga agaatgtgta ttcggggtag gctcgtagtc  7080
gttcatatcg ggtgccgtcg gggctggatt tgccggtgcg ctgtttcaat actgcgatgc  7140
gtgcctcggc cggtatcgtg agaccgttgc cgttatcctc gccaccatac aatgagactc  7200
ccaatatgag ttgtggtttt tcggagaggc cgtttttgat ttctcgccgt gccgggggt   7260
gttcgatgtc ggttccggtt ttgtcggtgg cgtggtgtgt gacaataatg gtggatccgg  7320
tgtcgcggcc taatgctgtg atccattgca tggcttcttg ctgtgcctga tagtcactct  7380
```

-continued

```
cgcagtcttg gatgtccatc aggttgtcga taacaatgag tggcgggaag gtgttccaca  7440
tttccatgta ggcttgcagc tccatggtga tgtctgtcca tgtgatgggt gactggaatg  7500
agaatgtgat gtgttggccg tggtggatgc tgtctcgata gtattctggt ccgtagtcgt  7560
cgatgttttg ttgtatctgt gtggtggtgt gttgggtgtt gagtgagatg attcgtgtgg  7620
aggcctccca gggtgtcatg tcccctgata tgtagagggc gggctggttg agcatggcgg  7680
tgatgaacat ggctagcccg gatttttggc tgcctgagcg ccccgcaatc atgacgagat  7740
cccctttgtg gatgtgcatg tcctggttgc ggtagagggg ttctagttgt ggtatgcggg  7800
gcagctcggc tgcggtttgg gaggctctct cgaaggatcg ttggagagag agcatcggga  7860
ccttatctat ctatcggttg ggtgtgtttt ggtggtcaga tggagtcgat gtcgatgtca  7920
gcatcggcgg gggttgagca cgaccgcatt gaacccgttt ttggtgcgca cggtggcgag  7980
tttgaaggcc tgctcctcgc caaggtaggc ttcgaggtcg cggatcatgg aatgtgggcg  8040
gtcgttgttg ccgcgcgctt tctcaataat agcgttggga atgatttctg gggtgccgtt  8100
gttgagatcg tctagggtgt ggaagattgt gacatcagcg tagatgcgat cggctgtctg  8160
tccaccgtag ccttcggtgt tgtgttctac gtcgcggatt ttgaaggcga tggcggtggc  8220
gtcctggttt cgggaggggt tgaagaaggt gctgttgctg ttgttgcggt agttggcgag  8280
tcccatggtt gtttccttta ctgtttgtgt tggtttgtgt cggttttatc gggtgaggct  8340
gtttcgtttg ctgcggaaag cctcggacac gtcactgtta ctggtgatga ttttcttgta  8400
ctgtttcaga aggtcggcta gctgtgcctt gcttgttgca ttgttgattt tgtcgatgat  8460
aatctcgttt tcgtttgatg cgatgttgtc tacgtagtct ttggctgcct ggttgtagcg  8520
gtcttggagg atgatggatg cgcttgctac gagtgttgct agatcccagt ctttggacac  8580
gtcaccgttt ttgaggccgc ctagcagatc aataatggat tgtttgatgt cttctcgcggt  8640
gtctccgcgg atgactgtcc atggggctgc gtagtctcca ccgtatttga gtgtgatagt  8700
tagctttccg ctgtctgtgg tgtgctcgtc ggtcacgtgt tttccttttc gttgttttcg  8760
gcttctggtg gctgtacggt ggtttctacc gggtatctgt acgagttttt cccgttgacg  8820
gcccagcagg cgtccttgac ggggcatcct ttgcagagtg ctgtgacgtg gggtacgaag  8880
atgccttggc tgattccttt cattgcttga ctgtacatgg atgatacatg ccggtaggtg  8940
ttgttgtcaa gatcaatgag ttcggtggat gtgccctgct caaccgattg ctcgtctccc  9000
ttggtggtag cgggtgtcca aaacattcct ttcgtcacat ggatgccgtg ttggttgagc  9060
atgtaacggt aggtgtgcag ctgcatactg tcggcgggta ggcgtccggt tttgaggtcc  9120
aaaatgaagg tttcacccgt attcgtatct gtgaataccc ggtcgatgta gccaacgatc  9180
tgggtgccgt cggggagggt ggtttctacc gggtattcga tgcccggctc gccgtcaata  9240
acagcggtag catattctgg gtggttgcgc ctccatgttt tccaccggtc cacaaaggtg  9300
gggccgtaaa tcatccacca attgtagtct ttcttgtgtg tcccgcccga ctcgcacatg  9360
tttttgcata ttctgccgga gggtttgatt tctgtgcctt cggattcggc gagggcgact  9420
tgggtgtcga aaatgttttt gaaggatgag agtttgtctg gcagtgcagg gtattcggcg  9480
ggattgtaca ggtgtaggtc gtattgttcg gtgatgtggt gtatggcgct tccggcgatg  9540
gtggcatacc aggtgtggtg ttgggcgtgg tagccgtggg ataggcgcca tttttcaccg  9600
cattcggccc actgtgacag tgatgagtag gagatgtggc ctggatggtc aatggtggac  9660
ggtttttgtg ctaggggcat tacttgtcgc ttttgtgggt gttccatggg tttcgggtgt  9720
cttggccggc attgtgttgc tggtatgcga ggagtgcgag gcagtgccag gcagcatggg  9780
ccagatgggg tagcccggat tcatcatcga ggttgttgcc ttgctgccat gataacaggt  9840
gccggtagag ggcgtcaaca ctgtggctcc acggatagcc gccggtccag ttgttgtcgc  9900
cgtatttggt ggcgccgtat ccggccacag agccgagggc gtgtaaggct gtagggtcga  9960
tgagggatag cctgcaaagt ttcaattctt tcttggcgcc agtatcaggg tcggtgtaca  10020
tgctggtggg ctcatccatg gtgtgtgtgc tccttaagta tggggttact ggttggggtt  10080
gtgggcgagt gctacggcaa gaataatgat ggcgagggtt tcagcgatca gtatgggtgt  10140
tgtgatcatt tgtggtcgcg gggattgttg gtgagggttg aggcgcccag gaggatagtg  10200
agggcgcatg cggcgatgat ggcgagggct gccttgtgtg gggtgccggt ggcgtacatc  10260
catgtgatga tgccgccttg gatccaggcg aggctggtga agaacgtttc gtagctgtgt  10320
agctcaatgt tgttgttggg tgtgttcatg cttgctcctg aagaatggtg ttgatggttg  10380
tgtaaatgtt gtacaggtcg gtttcgatag ataacagttg gtggatttgg tggtcgagat  10440
caatgtcggg gttgagggtg ttgatgcggg aggcgatgtc ggtggctgtg cgtagtgtgc  10500
cgccggtgtg gtgaatgatg tgtgccgtgt cggcgagtcc ggtggtgaca gtgtagtggg  10560
agaggagagg catagctggg ggtgctcctt gacggggtta ctgttgcggg ttgatgttga  10620
ggtcggtgac gttggggtgg tcttctgttc cggtgacaag gcagtggacg gtgactggga  10680
gtttggatgc gccgggctgt ttcgcggttg cgccgtagac gatggagaag gtgtctttgc  10740
caataatttt gtggagttgg aggtcgatgt cggggttgcc gttccatttg acgccttgtg  10800
tggcggcctg ttgttcggct ttgcggttgc aggtgtgtgc tgcggtgatc atggtgagtc  10860
cggtggcggt ttcttcaccc cttgcttggg cttgcttgtg ggttttctgc tgttcggctc  10920
gcagtgactg ttctgctgct gcctgccgtg ctttcttttc ggctttgcgc tgttgggtag  10980
tcttggggt ccattcggtg ttggctgtgg tggcttgcgg tgcgggttgt gatgcgagtg  11040
gcggattgtc gtctggggct ggcatgaagg atgctgcggc gatgatggcg gctgtgattc  11100
cggcgatggt gtagccgttt ttcttgttca tgattttgtg ttccccttc cggggtgttg  11160
ttcgttgctg acatgattaa tactttcagc ggctgggccc actgtcaagg ctgcgctcaa  11220
cgattgtgag cgatacttgt gtggctaggg gttttgtcct tgaggtggga gatgtctttc  11280
ccttgcgtcc agtatccatg gcggttgcga gtcatccctt tggcgagcat ctcgtccacg  11340
gtgagacacc tgcgacgatc tggaccctcc ttgactccct gatcgcctgt gcggtgcatg  11400
tcaccggcac aagtaccatt aaatgtctcg tggcggatgg tgtgatgctc tggtcggtat  11460
ccgatgattg tgctatcgca cttgtggcat gtccattgca tgattggtcc ttctttcgtg  11520
ttttaagctt gtactctgag gattagagcg actttcagcc cttgggggt atgattatat  11580
aggtcaggta tttctaggcg attctaggct cattgtgtgt ggctgggggt tatcgggcac  11640
acagggtgag gagttggcca acattgatgc gggtcacatt ccagtagagt tgcgtggctt  11700
ccccaccggt gagtggcttc cactcgtcat ggctgaacac ggtgccgtcg gttgcgatga  11760
atgtgttggg gcgtagcttg tgaagctcag tctctacacg ctgccggtag gcttcggcga  11820
ggccctcgaa atccatgtgg tcgcagggga ggttttcgag gcgtgtcagg tcgaagggtg  11880
tggggcagtc gtagctggcg gggctgtaga gctgggtgaa atggttggcg atcttctgca  11940
tgacgggttc cttttctcgt atggtgagtt gatagtttta tcgggtggat gcgacaagga  12000
tggcgtctac atcgatcatg tcgatgagat cgtggagttc ctcggcctca ttctcggaga  12060
ggtggcgcca gccatagtcg ccgtatacgg cgccgtcgag ggtgacagtc cacaggggcc  12120
```

```
ggatgagtcg tatggcttct tgtactttag cgtggtacat gcggcgcacc atatccagat  12180
cgatgtcgtc tgaatggttt ccggtgaggc tgtagaggct gagcgggtcg atttctgtct  12240
gcctgtagag ggatgtgaat gatggtgtga tgagtgtgcc atccatgaga gtgtgctcct  12300
ttcggtggtg gaggggttgt tgtggtttct agagtgtgta ggctgcgacc catagtcaag  12360
gctgcgctca ttcggattga gcgtttcata tgggtgtggc atggaatcta cacccccata  12420
ctgtgtgaga taggccacat cctcctggct tggtgtgaac cctcgagact actctgccta  12480
tctggcgtgg agggtgtagc ccagaaatac cgtttaaagc cttcatacgg cgcctaggag  12540
cgccttacag ggtgggggct aggtatttat acccccaagc aattctgatc gattctagac  12600
gcctcccagg agcccgatac acgatccgct atccagacac agatcatcag cccctatcct  12660
ggttagctaa gcctcaacta tgtggacagt gttgattact gtggggtaag aaggacacgg  12720
taaaagaaag aggggggagc atcggccttc aagccttaag gtcttagcag ttagcaccga  12780
gcccctcaag ggctcgtcgt cagcccatca ggcacggccc tgaacggggt acacgccatc  12840
agggaaggct tgagagtacg aggagcctta gcgacgagta ctcgaaagcc tgagggaaca  12900
ccctcagcac tgatgggtct agcgtgttcg gaaaggacac aggagtaaag cgtgacagct  12960
gtccgggagt gaaacccgtt ctgactaggg gtttcagcct taaccaccct caaaggttac  13020
aagactctaa gaaaatttaa ggaaaagttt aggtttaatt tttggacctt tactaccaaa  13080
aacacccgtt tacacccctc aaacccgcct atagagccaa atccaccagt ttgactcatc  13140
ccaggtggca tatgataggc tggacaggta gccagctgga cgcaaggccg aaatccgctg  13200
acgcggcttt caccccttaca tccatcagtc taccaaagac ttaaagacct aagggcttag  13260
cgctaaggtg ctgatagctt agcaccgagc ccttgagggg ctcggcatca gccctaaagc  13320
cttaaacact taaagtacat ataaaacttt aaaagcttaa cacttaaggt tataaataaa  13380
cattaaagct ttaaagtctt aaagtacata tataacctta acacctaagt taagtataaa  13440
accttaaagg cttagcactg aaggatataa acttcacatc agtttttaag actttaaaac  13500
ttaaaataac tattaagact taaagactta taagttttaa acacttaaag taactataag  13560
actttaaaga ccttaagtac ttaaagttaa ccatcagtct taaactttaa tattataacc  13620
tataagtctt aaagcttata agttataaaa gttttagaag agctaagagg ttaacttctt  13680
tacttctctt ctctctttgg ttctttctct cttctcttct tttcttcatc aggggagaag  13740
aggaaccttt taccatcagc gccgatggac tgtcaccgtg tgactcgtgt accaccggtc  13800
gcacgctccc ggtttcacac tccccacact ctgacacccg tgtccctttc aggcttagcg  13860
tgttcggctg aaggcgtacg gcgtgtcgcg ccaacaccct taacaccagg taagacttaa  13920
agtgtatatt atatgtagaa gactttaaaa cctataaggt gttcccgctt agcctgtgtc  13980
ctacaccgct aggcgccaag cgttaagtct tgaaacgcga acacacaccc acccccattt  14040
ttctttcgtg tccttctctt ttgacaccgc tggggggcga tgtgatcttt ctcactaccc  14100
ccatgggtag tggagaacac acccacccca ccatcaacag aacacccccct caaacgaaca  14160
aaacagggcc tagaatcgat cggcagggca agggcaaggt attcataccc ccaacacatt  14220
ccaggccgtc agagaggcaa ataagacccg tacagggcta gtcgaggatc ggagacgtga  14280
tggcacacac caatcgcacc gcatccgccg cacaccgaca ctggcggcaa cgactcatca  14340
cccaagcccg acagcaaggc caaaccgaat gcccactctg cggagcaacc atcacctggg  14400
acacctacca gctgccaact agccccgaag ccgaccacat cacacccgtc agcaggggag  14460
gactcaacac cctcgacaac gggcaaatca tctgcagaac atgcaacaga agcaaaggca  14520
acagaacaca accaaacatc aaattccaac aacaaaccac aaaaaaacctt gttccatggt  14580
gacaaaaccc gccaaccccc accggggaca ccccctgcac acccgtgcaa gacctcgtac  14640
ggcttagtga aatacctccc ttttgtggat ttgtctgttt gtcgactttt tgtgttggtg  14700
gtgagtgttg tgcagcctga gcttcctgag ggacacgagt ggtgtgggga gacgcgtcgt  14760
tggtggcgtg tgtggggtga ggatagccgc gcgcagtacg tgtctgatga ggagtggctg  14820
tttcttatgg atgctgcggt gattcatgat tgtgtgtggc gtgagggtcg cgcggatttg  14880
gtggcttcgc ttcgtgctca tgtgaaggct tttatgggta tgttggatcg ttattcggtt  14940
gatgtggcgt ctggtggccg tggtgggggt tctgcggtgg cgatgattga ccggtatagg  15000
aagcgtaggg gggcctgatt aggtgtctgg tgttgttggg tctcaggttc ctcgtcatcg  15060
tgtggctgcg gcgtattcgg tgtctgctgg cggtgatgct ggggagttgg gtcgtgcgta  15120
tgggttgacg cctgatccgt ggcagcagca ggtgttggat gattggctag ctgtgggtgg  15180
taatggcagg cttgcttcgg gtgtgtgtgg ggtgtttgtg cctcgccaga atggcaagaa  15240
tgctattttg gaggttgtgg agttgtttaa ggcgactatt cagggtcgcc gtattttgca  15300
tacggctcac gagttgaagt cggctcgtaa ggcgtttatg cggttgaggt cgttttttga  15360
gaatgagcgg cagtttcctg acttgtatcg tatggtgaag tcgattcgtg cgacgaatgg  15420
ccaggaggct attgtgttgc atcatccgga ttgtgccacg tttgagcgta agtgtggttg  15480
tccgggttgg ggttcggttg agtttgtggc ccgttctcgt ggttctgctc gcgggtttac  15540
ggttgatgat ttggtgtgtg atgaggctca ggagttgtcg gatgagcagt tggaggcgtt  15600
gcttcctacg gtgtctgcgg ctccttcggg tgatcctcag cagatttctt tgggtacgcc  15660
gcctgggccg ttggctgacg ggtctgtggt gttgcgtttg cgcgggcagg ctttgtcggg  15720
tggtaaaagg tttgcgtgga cggagttttc tatcccggat gagtctgatc cggatgatgt  15780
gtcgcggcag tggcggaagc ttgctggtga gacgaatcct gcgctgggta ggcgtctgaa  15840
tttcgggacg gtgagcgatg agcatgagtc gatgtctgct gccgggtttg ctcgggagcg  15900
gcttggctgg tgggatcgtg gccagtctgc ttcttcggtg attccggcgg ataagtgggt  15960
tcagtcggct gtggatgagg cggctctggt tggcgggaaa gtgtttggtg tctcgttttc  16020
tcgttcgggg gatcgtgtcg ctttggctgg tgctggccgg actgatgctg gtgttcatgt  16080
tgaggtgatt gatgggctgt cggggacgat tgttgatggt gtgggccggt tggctgactg  16140
gttggcggtt cgttggggtg atactgaccg gatcatggtt gccgggtctg gtgcggtgtt  16200
gttgcagaag gcgttgacgg atcgtggtgt tccgggccgt ggcgtgattg tggctgatac  16260
tggggtgtat gtggaggcgt gtcaggcgtt tttggagggt gtcaggtcgg gtgtggtttc  16320
tcatcctcgt gccgattcga ggcgtgacat gttggatatt gctgtgaggt cggctgtgca  16380
gaagaagaag ggttctgcgt ggggttgggg ttcctcgttt aaggatggtt ctgaggttcc  16440
tttggaggct gtgtctttgg cgtatcttgg tgcgaagatg gcgaaggcta ggcggcgtga  16500
acggtctggt aggaagcggg tgtctgtggt atgaattcgg atgagttggc tctgattgag  16560
ggcatgtacg atcgtatccg aaggttgtct tcgtggcatt gccgtattga gggctactat  16620
gagggctcta gccgggtgcg tgatttgggg gttgctattc ctccggagtt gcagcgtgtg  16680
cagacggtgg tgtcgtggcc tggtattgcg gtggatgctt tggaggagcg tctggattgg  16740
cttggctgga ctaatggtga cggctacggt ctggatggtg tgtatgctgc gaatcggctt  16800
gctacggcgt cgtgtgatgt gcatttggat gcgctgattt ttgggttgtc gtttgtggct  16860
```

gttattcccc agggtgatgg gtcggtgttg gttcgtccgc agtcgccgaa gaattgcacg 16920
ggccggtttt cggctgacgg gtctcgtctg gatgctggcc ttgtggtgca gcagacgtgt 16980
gatcctgagg ttgttgaggc tgagcttttg ttgcctgatg tgattgttca ggtggagcgg 17040
cgaggtagcc gtgagtgggt tgagacgggc cgtataccga atgtgcttgg ggctgttccg 17100
ttggtgcctg ttgtgaatcg tcgccgtacg tctaggattg atgggcgttc ggagatcact 17160
cggtcgatta gggcttacac ggatgaggct gttcgcacac tgttggggca gtctgtgaat 17220
cgtgactttt atgcctatcc tcagcgttgg gtgacgggtg tgtcggctga cgagttttcg 17280
cagcctggct gggtcctgtc gatggcttct gtgtgggctg tggataagga tgacgacggt 17340
gacactccga atgtggggtc gtttcctgtg aattctccta caccgtattc ggatcagatg 17400
cgtttgttgg ctcagctgac ggcgggtgag gctgcggttc cggagcgcta tttcgggttt 17460
atcacgtcta acccgccttc tggggaggct ttggctgcgg aggagtcgag gcttgtgaag 17520
cgtgccgagc ggcgtcagac gtcgtttggt cagggctggc tgtcggttgg tttcctggct 17580
gccagggcgc ttgattcgag tgttgatgag gccgcgtttt tcggcgatgt gggtttgcgt 17640
tggcgtgacg cttcaacccc gactcgggcg gctacggctg atgctgtgac gaagcttgtg 17700
ggtgccggta ttcttccggc ggattctcgt acggtgttgg agatgctggg gcttgatgat 17760
gtgcaggttg aggctgtgat gcgtcatcgt gccgagtctt cggatccgtt ggcggcactg 17820
gctggggcta tatcgcgtca aactagcgag gtttgatagg cgatggcttc gggtgttgcg 17880
tcaaggttgg ctgctgccgg gtatcagcgt gaggcggtca ggtttgccgg gaagtatgcg 17940
ggctattatg ccgagcttgg tcgtttgtgg cattccggga agatgacaga tgcgcagtat 18000
gtgcgtttgt gtgtggagtt ggagcgtgcc ggccatgacg gttcagcggc gttggcgggt 18060
aagttcgtgt cggattttcg gaagcttaac ggtgtggatc ctggtttgat cgtgtatgac 18120
gagtttgatg ctgccgccgc gttggctagg tcgttttcga ctattaagat gatgaatagt 18180
gacccggata gggctaagga tacggttgat gcgatggcgg cgggtgttaa tcgggctgtc 18240
atgaatgctg gccgtgacac ggttgagtgg tctgcgggtg cgcagggtag gtcgtggcgc 18300
cgggtgacgg atggtgatcc gtgcgcgttt tgtgccatgt tggctacgag gtcggattat 18360
acgaccaaag agcgggcgct tactactggt catactcggc gtcataagcg tggcggtagg 18420
cgtccgtttg gttcgaagta tcatgatcat tgtggttgta cggtggttga ggttgttggc 18480
ccttgggagc caaatagggc tgatgccgca tatcagagga cgtatgagaa ggctcgtgag 18540
tgggttgatg atcatgggtt gcagcagtcg cctggcaata ttttgaaggc tatgcgtact 18600
gttggtggca tgagataatt tgatgtggtt tccggttgtg tgccgccggt tatcggtgca 18660
cagggttgtc tcccgcacgg gggtcaacaa tgttgtgttg ttttccgcaa ggagtatagg 18720
gttaggctat ggccgatcaa aaagttgaag aacagaatgt tgacaatgat gctgttgagc 18780
ccggaaaggg tggagacgtt gttgatgttg tgaaggatgg gcaggctgcc ggcgatgatc 18840
atgccggtga tgtttccgtg aaggaggagt cttcttctgg cacggattgg aaggctgagg 18900
ctcgtaagtg ggagtctcgt gctaaaagta atttcgccga gttggagaag cttcgcgcct 18960
cggatggtga tgcggggtct gtgattgatg agcttcgccg caagaatgag gaactcgaag 19020
accggattaa tgggtttgtt cttgagggtg tgaagcgcga ggtggctgcc gagtgtggcc 19080
tgtcgggtga tgctgtcgct tttttgcacg gtggcgatcg tgaagcactg gtggagtctg 19140
ctaaggcttt gaagggtttg atcgaccata gtagtggtgg cgcgggtgtg cgccgtcttg 19200
cggggagtgc ccccgttgat gatgttaaac gacgtgaggg tgtcgcgttt gtggatgctc 19260
ttgtcaataa ttctaggaga tgatttgtga tggctgacga ttttctttct gcagggaagc 19320
ttgagcttcc tggttctatg attggtgcgg ttcgtgaccg tgctatcgat tctggtgttt 19380
tggcgaagct ttcgccggag cagccgacta tttttggccc tgttaagggt gccgtgttta 19440
gtggtgttcc tcgcgctaag attgttggtg agggcgaggt taagccttcc gcgtctgttg 19500
atgtttcggc gtttactgcg cagcctatca aggttgtgac tcagcagcgt gtctcggacg 19560
agtttatgtg ggctgatgct gattaccgtc tgggtgtttt gcaggatctg atttccccgg 19620
ctcttggtgc ttcgattggt cgcgccgtgg atctgattgc tttccatggt attgatcctg 19680
ccactggtaa agcggctgcc gctgtgcata cttcgctgga taagacgacg catattgttg 19740
atgccacgga ttctgctacg gctgatcttg ttaaggctgt cggcctgatt gctggtgctg 19800
gtttgcaggt tcctaacggg gttgctttgg atcccgcgtt ctcgtttgcc ctgtctactg 19860
aggtgtatcc gaaggggtct ccgcttgccg gccagcctat gtatcctgcc gccgggtttg 19920
ccggtttgga taattggcgc ggcctgaatg ttggtgcttc ttcgactgtt tctggcgccc 19980
cggagatgtc gcctgactcg ggtgttaagg ctattgtggg tgatttctct cgtgttcatt 20040
ggggtttcca gcgtaacttc ccgatcgagc ttatcgagta tggcgatccg gatcagactg 20100
gccgcgattt gaagggccat aatgaggtta tggttcgtgc cgaggctgtg ctgtatgtgg 20160
ctatcgagtc gcttgattcg tttgctgttg tgaaggagaa ggctgccccg aagcctaatc 20220
cgccggccga gaactgattt attgttgcgg tgatgtgtca atgtgcaggg ggtggtgttg 20280
atgggtatca ttttgaagcc tgaggatatt gagcctttcg ccgatattcc tagagagaag 20340
cttgaggcga tgattgccga tgtggaggct gtggctgtca gtgtcgcccc ctgtatcgct 20400
aaaccggatt tcaaatacaa ggatgccgct aaggctattc tgcgcagggc tttgttgcgc 20460
tggaatgata ctggcgtgtc gggtcaggtg cagtacgagt ctgcgggtcc tttcgctcag 20520
actacacggt ctagtactcc cacgaatttg ttgtggcctt ctgagattgt cgcgttgaag 20580
aagctgtgtg agggtgatgg tggggctggt aaagcgttca ctattacacc gaccatgagg 20640
agtagtgtga atcattctga ggtgtgttcc acggtgtggg gtgagggttg ctcgtgcggg 20700
tcgaatatta acggctacgc tggccccttg tgggagatat gatatgacca gttttcctta 20760
tggtgaaacg gttgtgatgc ttcaaccgac tgttcgtgtc gatgatcttg gcgacaaggt 20820
ggaagactgg tctaagcctg tcgagactgt gtaccataac gtggccatat atgcttccgt 20880
ttcgcaggag gatgaggctg cggggcgtga ctcggattat gagcattggt cgatgctgtt 20940
caagcagcct gttgtgggcg ctgattatcg ttgtaggtgg cgtattcggg gtgttgtgtg 21000
ggaggctgac gggtctccta tggtgtggca tcaccccatg tccggttggg atgctggtac 21060
gcaggttaat gtgaagcgta agaagggctg atgggtagtg gctcaggatg tgaatgtgaa 21120
gctgaacttg ccgggtattc gtgaggtgtt gaagtcttct ggagtgcatg gcatgttggc 21180
tgagcgtggc gagcgtgtca agcgtgccgc agcggcgaat gtgggtggta acgcgtttga 21240
tagggcccaa taccgtaatg gtttgtcgtc ggaggtgcag gttcaccgtg ttgaggctgt 21300
ggcgaggatt ggcaccacct ataagggtgg gaagcgtatt gaggcgaagc atggcacgtt 21360
ggcgaggtcg attggggctg cgtcgtgatc gtttacggtg atccgcgtgt gtgggctaaa 21420
cgcgtgctca aggatgatgg ctggctgtct gggataccgt gtacggggac ggtgcctgag 21480
gatttcagcg gtgacctgat ctggttggcg ttggatggtg gcccacagtt gcatgttcgt 21540
gagcgtgttt ttttgcgcgt gaacgtgttt tcggatacgc cggatcgtgc tatgtcgttg 21600

```
gcgcgtcgtg tcgaggctgt gctggctgat agtgtggacg gtgaccctgt ggtgtactgt  21660
aaacggtcta ctggccctga tttgctggtt gatggtgcac gttttgatgt gtattcgctt  21720
tttgagctga tatgtaggcc tgcggagtct gaataagctt attgtttttg ttttaatgta  21780
attgtttgat atttaatggg ggttatgatg gctgcaacac gtaaagcgtc taatgttcgc  21840
tcagcggtta ctggcgacgt ttatattggt gacgcgcacg cgggtgatac tattaagggt  21900
gtggaggcgg ttccttccgg gcttaccgct ttagggtatc tgtctgatga cgggtttaag  21960
attaagcctg agcgtaaaac ggatgatttg aaggcttggc agaatgcgga tgttgttcgc  22020
actgtggcta cggagtcttc tatcgagatt tctttccagc tgatcgaatc caaaaaagag  22080
gttatcgaac tgttttggca gtcgaaggtt actgccggat ccgattcggg ttcttttgat  22140
atttctcctg gtgccacgac gggtgttcac gctctgttga tggatattgt tgatggtgat  22200
caggttattc gctactattt ccctgaggtt gagctcattg atcgtgacga gatcaagggt  22260
aagaatggtg aagtgtacgg gtatggtgtg acgttgaagg cgtatcctgc ccagattggt  22320
aagactggta atgcggtgtc tggtcggggg tggatgacgg ctttaaaagc tgatactcct  22380
ccttctccga agcctcagcc ggatccgaat ccgccggccg agaactgata cacgatttta  22440
ggggattgtt gatagatgag tgacactggt ttcacgttga agattggtga tcgtagctgg  22500
gtgttggcgg atgctgagga gacggcgcag gctgttcctg cccgcgtttt ccgtcgtgcc  22560
gccaggattg cccagtcggg ggagtctgcg gatttcgccc aggttgaggt gatgttttct  22620
atgttggagg ctgccgcccc ggctgacgct gtggaggccc tggaggggct tcctatggtt  22680
cgtgtggcgg aggttttccg tgagtggatg gaatataagc ctgacggtaa gggtgcctcg  22740
ctgggggaat agtttggctc cacggcctga ttgatgatta tcgtggggcc atcgaatacg  22800
atttccgcac taaatttggt gtttctgttt atagtgttgg tggcccgcag atgtgttggg  22860
gtgaggctgt ccggctggct ggcgtgttgt gtactgatac gtctagccag ttggcggccc  22920
acctgaatgg ttggcagcgc ccgtttgagt ggtgtgagtg ggctgtgttg gacatgttgg  22980
atcattacag gtctgctaat agtgaggggc agccggagcc tgtggcgagg ccgacggatg  23040
agcgtagggc ccggtttacg tctgggcagg tggacgatat tttggcgcgt gttcgtgccg  23100
gtggcggggt gtctcgcgag attaatatta tggggtgaat agtgtatgtc tggtgagatt  23160
gcttccgcgt atgtgtcgtt gtatacgaag atgcctggcc ttaaaagtga tgttggtaaa  23220
cagctttctg ggtgatgcc tgcggagggt cagcgttcgg gtagcttgtt tgctagcggg  23280
atgaagttgg cgcttggtgg tgcggcgatg atgggtgcca tcaatgttgc taagaagggc  23340
ctcaagtcta tctatgatgt gactattggt ggcggtattg ctagggcgat ggctattgat  23400
gaggctcagg ctaaactgac tggtttgggt catacgtcgt ctgacacgtc ttcgattatg  23460
aattcggcta ttgaggctgt tactggtacg tcgtacgcgt tgggggatgc ggcgtctacg  23520
gctgcggcgt tgtctgcttc gggtgtgaag tctggcgggc agatgacgga tgtgttgaag  23580
actgtcgccg atgtgtctta tatttcgggt aagtcgtttc aggatacggg cgctattttt  23640
acgtccgtga tggctcgcgg taagttgcag ggcgatgaca tgttgcagct tactatggcg  23700
ggtgttcctg tgctgtcttt gcttgccagg cagacgggta aaacgtctgc tgaggtgtcg  23760
cagatggtgt cgaaggggca gattgatttt gccacgtttg cggctgcgat gaagcttggc  23820
atgggtggtg ctgcgcaggc gtctggtaag acgtttgagg gcgctatgaa gaatgttaag  23880
ggtgccctgg gttatttggg tgctacggct atggcgccgt ttcttaacgg gttgcggcag  23940
atttttgttg cgttgaatcc ggttattaag tctatcacgg attctgtgaa gcctatgttt  24000
gcgtcggtgg atcaggggat tcagcgggtg atgccgtcta ttttggcgtg gattaaccgt  24060
atgccgggca tgattacgag aatgaatgca cagatgcgcg ccaaggttga gcagttgaag  24120
ggcgtttttg cgaggctgca tttgcctgtt cctaaggtga attttggtgc catgtttgct  24180
ggcggcaccg cagtgttcgg tattgttgct gcgggtgttg ggaagcttgt tgcggggttt  24240
gccccgttgg cggtgtcttt gaagaatctg ttgccgtcgt ttggtgcttt gaggggtgcc  24300
gctgggggc ttggtggcgt gtttcgcgcc ctgggtggcc ctgttggtat tgtgatcggg  24360
ctgtttgctg ccatgtttgc tacgaacgcc cagttccgtg ccgctgttat gcagcttgtg  24420
ggggttgttg gccgggcttt ggggcagatt atggtcgctg tgcagccact gttcgggatt  24480
gttgctggcg tggttgccag gttggcgcca gtgttcggcc agattatcgg tatggttgct  24540
ggtttggctg cccggctggt gcctgttatt ggtatgctta ttgcccggct ggttcctgtt  24600
atcacccaga ttattggtat ggtaacccag gttgctgcca tgttgttgcc tatgctgatg  24660
ccggttattc aggctgttgt tgctgtgata cggcaggtta ttggtgtgat catgcagttg  24720
atacctgttt tgatgccggt tgtgcagcag attttgggtg ctgtcatgtc tgttttgccg  24780
ccgattgttg gtttgatacg gtcgctgata ccggtgatca tgtcgattat gcgtgtggtg  24840
gtgcaggttg ttggtgccgt gttgcaggtg gtggcccgta ttattccggt tgttatgccg  24900
atttatgttt cggtgattgg attcattgcc aagatttatg ctgcggttat cgtttttgag  24960
gctaaggtta ttggcgctat tcttcgtact attacgtgga ttgtgaatca ttcagtgtct  25020
ggcgtgaggt ctatgggcac ggccatccag aatggctgga atcatatcaa atcgtttacg  25080
tcggcgttta ttaacggttt caagtcgatc atttctgccg gtgttgccgc ggttgtgggg  25140
ttttttacgc ggcttggttt gtcggttgct tctcatgttc ggtctgggtt taacgcggcc  25200
cgtggcgctg tttcggctgc gatgaatgct attcggagtg ttgtgtcttc ggtggcgtct  25260
gctgttggcg ggtttttcgg gtcgatggcg tctagggttc gtagtggtgc tgtgcgcggg  25320
tttaatggtg cccggagtgc ggcttcttct gctatgcatg ctatgggctc ggctgtgtct  25380
agtggtgtgc atggtgtgct agggtttttc cggaatttgc ctggcaatat tcggcatgct  25440
ctcggcaata tggggttctt gttggtgtcg gctggccgtg atgtggtgtc tggtttgggt  25500
aacggtatta agaatgctat gagtggcctg ttggatacgg tgcgtaacat gggttctcag  25560
gttgctaatg cggctaagtc tgtgttgggt attcattccc cgtctcgagt gtttcgtgac  25620
caggttggcc ggcaggttgt tgccggtttg gccgaggga tcaccgggaa tgcgggtttg  25680
gcgttggatg cgatgtcggg tgtggctgga cggctgcctg atgcggttga tgcccggttt  25740
ggtgtgcgat catcggtggg ctcgtttacc ccgtatgaca ggtatcggcg gatgggcgag  25800
aagagtgttg tggtgaatgt gaatgggcct acttatggtg atcctaacga gtttgcgaag  25860
cggattgagc ggcagcagcg tgacgctttg aacgcgttgg cttacgtgtg attgggggtg  25920
ttgtgcatgt ttattcctga cccgtctgat cgtgccggtt tgactgttac ctggtctatg  25980
ttgccgttga ttggtaatga tccggagcgt gtgcttcatt tgacggatta tacgggtgcg  26040
tctcctgtca tgttgttgaa tgattcgttg cgcggtttgg gtgttcctga ggtggagcat  26100
ttttctcaaa ctcatgttgg ggtgcacggc tcggagtggc gcgggtttaa tgtgaagcct  26160
cgcgaggtga cattacctgt cctggtgtcg ggtgttggtg tggatccggt tggcgggttt  26220
cgtgacggtt ttttgaaggc gtatgacgag ttgtggtctg cttttcctcc gggcgaggag  26280
ggggagttgt ctgtgaagac cccgtctggc cgtgagcgtg tgctaaaatg ccggtttgat  26340
```

```
tcggtggatg acacgtttac tgtggatccg gtgaacaggg gttatgcgcg ctatctgttg  26400
catttgacag cttatgaccc gttttggtat ggggatgagc agaagtttcg ttttagtaat  26460
gcgaagttgc aggattggtt aggtggcggc cctgtcggca agaagggtac cgcttttccg  26520
gtggtgttga cgcctggtgt tggttcgggt tgggataatc tgtctaatag gggtgatgtg  26580
cctgcgtggc ctgtgattcg tgtggagggc ccgttggagt cgtggtctgt gcagattgat  26640
ggtttgcgtg tgtcttcgga ttacccggtg gaggagtttg attggatcac tattgatacg  26700
gatcctcgca aacagtctgc attgttgaac gggtttgagg atgtgatgga tcgtttgaca  26760
gagtgggagt ttgcccctat cccgcctggc ggttctaaga gtgtgaatat tgagatggtt  26820
ggtttgggtg ccattgttgt gtcggtgcag tacaggtttt tgagggcttg gtgaatagtt  26880
gatggctggt cttgttccgc atgtaacatt gtttacacct gattatcgcc gtgtggcgcc  26940
tatcaatttt tttgagtcgt tgaagttgtc gttaaagtgg aatggtttgt ccactttgga  27000
gttggtggtg tctggtgatc attctaggct tgacgggttg actaggccgg gtgcacggct  27060
ggttgttgat tatggtggtg gccagatttt ttctgggcct gtgcgtcggg ttcatggtgt  27120
gggtccgtgg cgttcttccc atgtgactat cacgtgtgag gatgatattc gtctgttgtg  27180
gcgtatgttg atgtggcctg tggattatcg tcctggtttg gttggtatgg agtggcgtgc  27240
tgaccgggat tatgcccact attcgggtgc ggctgagtcg gtggctaagc aggtgttggg  27300
ggataatgct tggcgtttc cgcctggttt gtttatgaac gatgatgaga gtcgtggacg  27360
gttcattaag gattttcagg tgcggtttca cgtgtttgcc gataagttgt tgccggtgtt  27420
gtcgtgggct cggatgactg tcacggtgaa ccagtttgag aatgcgaagt ttgatcagcg  27480
tggtttggtg tttgattgtg tgcctgctgt gacgcgtaag catgtgttga ctgccgagtc  27540
tggttcgatt gtgtcgtggg agtatgtgcg tgacgccccg aaggcgacat cggtggtggt  27600
tggtggccgc ggcgagggca aagatcggct gttttgtgag gatgttgatt cgatggccga  27660
ggatgactgg tttgatcgtg tcgaggtgtt taaggatgcc cgtaacacgg attctgagca  27720
tgtgcatctc attgatgagg ctgagcaggt gttgtccgag ttgggggcca cgtcggggtt  27780
taagatcgag ttggctgagt cggatgtgtt gcggtttggg cccggcaatc tgatgcccgg  27840
ggatttgatc tatgtggatg tgggttctgg ccctatcgca gagattgtgc ggcagattga  27900
tgtggagtgt gagtcgccgg gtgacgggtg gacgaaggtg actcctgttg caggggatta  27960
tgagaataat ccgtcggccc tgttggcgcg gcgtgttgct ggtttggctg cgggtgtgcg  28020
ggatttgcaa aaattctaga aaagattagg ggtttgttgt gggtattgtg tgtaaagggt  28080
ttgatggtgt gttgaccgag tatgattggg ctcaaatgtc tggtctgatg ggtaatatgc  28140
cgtccgtgaa agggccggac gattttcgtg tcggcactac tgttcagggt gccacagtgt  28200
tgtgtgaggt cctgccgggg caggcttggg cccacggggt gatgtgcacg tcgaatagtg  28260
ttgagacggt gaccggccag cttccgggcc cgggtgagac ccgatacgac tatgtggtgt  28320
tgtctcggga ttgggaggcg aatacggcca agttggagat tgttcctggg gggcgtgcgg  28380
agcgtgcccg tgacgtgttg agggccgagc ctggcgtgta ccatcagcag ttgttggcta  28440
ctttggtggt gtcgtctaac gggttgcagc agcagctgga taggcgtgct atagcggcta  28500
gggtggcgtt tggcgagtct gctgcgtgtg atcctacccc agtggagggt gaccgtgtga  28560
tggttccctc tggggctgtg tgggctaatc atgccggcga gtggatgctg ttgtccccca  28620
ggattgagac gggttctaag tcgatcatgt ttggcgggtc tgctgtgtat gcttacacga  28680
ttccgtttga gcggccgttt agtagtgcgc ctgttgtggt ggcgtctatg gctacggcgg  28740
ctgggggcac gcagcagatc aatgtgaaag cctacaatgt gactgtccaa aattttagtt  28800
tggcgtttat tacgaatgat ggttcgaagc cgaatggtgt gcctgcggcg gctaattgga  28860
ttgctgtcgg cgtgtgactg tacaggtgtt gtggcggatg gtgtgatgtt ggggggctgt  28920
ggtgtcgtgg tttactcctg cactggtggc ctctatttgt accgcgttgg ccacggtttt  28980
gggttctgtt caggctgtca catcccggtc taggcggcgt ttacgcaggc tgtctgcgca  29040
ggtggatgcg atggaagagt atacgtgggg tgtgcggcgc gaggtgcgaa ggtttaacgc  29100
cgggcttcct gatgatgtgg agccgatgca tcttcctgat gtgcccgagt ttttgaagga  29160
tactgttgat ggtggaggtg agtagggttg agggagttgg aggaggagaa gcggcagcgc  29220
cgcaattttg agaaggcttc cctgatactg ttgtttttgt cgcttgtgtt gttggcggtg  29280
gttgccgggg gtgctttgcg gtacgggtct gtggcttctc aaagggattc ggagcaggcg  29340
agggcccagt cgaatggtac agccgctaaa gggttggctg cccgtgtgaa gcaggcgtgt  29400
acccagggtg gcgtggagtc tgtgaagctg cacaggtctg gtttgtgtgt ggatgctgtg  29460
cgtgttgagc agcgtgttca gggtgtgcag ggtcctgccg gtgagcgtgg cccgcaaggg  29520
cccgctggtg ttgatggccg ggatggtagc aatggttctg ctgggctggt tggccctgtt  29580
gggccgcagg gttccc                                                  29596
```

```
SEQ ID NO: 72          moltype = DNA  length = 29124
FEATURE                Location/Qualifiers
source                 1..29124
                       mol_type = other DNA
                       note = PAC10
                       organism = synthetic construct
SEQUENCE: 72
gggtttagcc agccgtgtgc ggcaggcgtg tgcttcgggt ggggtggagt ctgcgcggct  60
tcaccggtct ggtttgtgtg tggatgctgt gcgtgttgag cgtagcgtgc agggtgtgcc  120
gggtcctgcc ggtgtacggg gcccgcaagg ccctgcaggt gctgacggca gggatggtgt  180
taatggttcg gctgggctgg ttggccctgt tggtccgcaa ggttcccctg gcttgaatgg  240
tgtgaaaggt cctgacgggt tgcctggtgc gaatggatcg gatggccatg atggtgttcc  300
aggtcgtgca ggtgctgacg gtatgaacgg cgttgacggc agggatggtg ttaatggttc  360
ggctggtgag cgcggtgatg tgggcccttc aggtcctgcc ggcccgcaag gtgcacaggg  420
tgaacggggt gagcgcggcc ccgccggtac gaacggatac gatggtaagg atggtaagga  480
tggccgttct gttgtgtccg tgtactgttc cgggggcagc ctggttgtga aatatagtga  540
cggtgtggtt tctaccgtat cggactcggc ggcctgccag ggtgtgaaac cgtcgcctat  600
agtgactata tcatcccaca aatagaaagg agtggctgtg atggtagtgt ttggtggtgt  660
gtggtgaggt ttattcctgc ggcgcatcac tcaagcggtt cgaatagtcc ggtgaatagg  720
gttgtgattc atgcgacatg cccggatgtg gggtttccgt ctgcctcgcg taaggggcgg  780
gcggtgtcta cagcaaacta ttttgcttcc ccgtcttcgg gtggttcggc gcattatgtg  840
tgtgatattg gggagacggt gcagtgcttg tctgagtcta cgattgggtg gcatgccccg  900
ccgaatccgc atagtttggg tatagagatt tgcgcggatg gggttcgca cgcctcattc  960
```

-continued

```
cgggtgccgg ggcatgctta cactcgtgag cagtggctgg atcctagggt gtggcctgcg  1020
gtggagaagg ctgccatcct gtgtagacgt ttgtgtgaca aatataatgt tccgaaaagg  1080
aagcttagtg cagccgattt gaaggctggt aaacgtggtg tttgcgggca tgtggatgtt  1140
acggatgcgt ggcatcagtc ggatcatgat gatcctgggc cgtggtttcc gtgggacagg  1200
tttatggccg tcgtcaacgg cggcagtgga gatagtgggg agttaactgt ggctgatgtg  1260
aaagccttgc atgatcagat taaacaattg tctgctcagc ttactggttc ggtgaataag  1320
ctgcaccacg atgtgggtgt ggttcaggtt cagaatggtg atttgggtaa acgtgttgat  1380
gccctgtcgt gggtgaagaa tccggtgacg gggaagctgt ggcgcgccaa ggatgctttg  1440
tggagtgtct ggtattacgt gctggagtgt cgtagccgta ttgacaggct tgagtcgact  1500
gttaatggtt tgaaaaagtg atggtggtgt gttgtgggta aacagttttg gttgggcctg  1560
ttggagcgtg ccctgaaaac ttttattcaa acgtttgttg ctgtgcttgg ggtgacggcg  1620
ggtgtcacgt atactgcgga gtcgtttcgc ggtttgccgt gggagtctgc actgattacg  1680
gctacggttg ctgctgtgtt gtcggtggct acttcgtttg gtagcccgtc gtttgtggcc  1740
ggcaagccta aaaccacggt tgtggatgcg ggtttggttc caccggatga tgggggcttg  1800
gttgagccgc atatggttga tgtgtcggat cctggcatga tcgagcctgc agatgatgcg  1860
gatcttggtg taggctatgt gccgaaacac gctgccgagt cggaggttgg gacggtagag  1920
tctactgttg cataattgaa catagatgcg tgccccagcg gtgctgccac gatcgtgtgg  1980
tggttgccgc tggggcacta tttctgttta tgcggtgtgg ctatgattcg ttgcggtcga  2040
tggtgtcttc gagcatctga tacaggtgga ggcaggtaga gatcgtatcg ctggcctggt  2100
ctagaacgtt ccggccgata acgtttttgt ggttgtcgcg gtggcggatg atagcccaca  2160
tgatctcgtc ggcctccgct tgtaatagtt ttgcctggta tgcgattccg gcgagccagt  2220
ctagtgcttc ctggcttgca taggggctct ggtcctcgct gttgtcacgg gtgttgctgt  2280
tgtttgtggg gtgtcctgca ctgtcgcata accacaggat ttcgctgcac tcgtctagcg  2340
tgtcctggtc gatagcgaga tcgtcgaggc tgacttcgtt gacggtaagg ttcacgttgt  2400
cgagtgagat gggtacaccg tactggtttt cgacactgtc aacaatgttt tccagctgtt  2460
gcatgttggt gggctgttgt tggacgatac ggtgtatcgc tgtgttgagg gtggtgtagg  2520
tgatattgtg tgtgttgttc atggttttat cccatccctg tgctgtcgtc gttttcgtct  2580
ggatagtatc tactgtttgc gtagcctgtt agggtgatga gtgtttggtc tgcccactgt  2640
ttcacggttt gtcttgtcac cccgagtcgt tgggctgcca ccgaataggt ttgatcatac  2700
ccgtatactt ctctgaatgc tgccagccgt gccaaatgtt ttcgctgttt ggatggctgg  2760
caggtgaggg tgtagtcgtc gatggctagc tgcaaatcga tcatggtgac aatgttgttg  2820
ccgtggtgtt gtggcgcggt tggtggtggt ggcattcctg gttcgacact cggtttccat  2880
gggcctccgt tccagatcca ttgggcggct tggatgatgt cggcggtggt gtaggttcgg  2940
ttcactggta atccttaaac aagtcgttca tgttgctggt gttgctggtg ttgctggtgt  3000
cgaatcgtcc cacacagtgg cagtagtcgt acatgagttt aataatgtgt tggtggtctc  3060
ccaaataggt gttgccgctg atgctgtagg tggctgtgcc gtctttactg atggtgtatt  3120
tggcggtgat ggtttcgggg ttttcggtgt cggtgatgat ggctgtggtg gtggtgccta  3180
cggtttgtag cacggtggtt tgggttccgt cgtcgatggt ggttttaacc atgaggggtt  3240
ctccttttaa atgcttgttt ggttgtcggc tagatgaata atatcggata aaggtttcgg  3300
ctggtctagg tgttgtatgg ttttgttggc tagccgtttg gctaccctgt agcacatttt  3360
ggtatagtgt ttgttgtcta ggttgtggta ttgttcccgc accgcaatat atagtaggga  3420
gtcttgatag aggtcgtctg cactgattgc ggggtagtgt gtggctgttt tggtgcatgc  3480
ccggttgagt gtgcgtagat gatggtttgt ggcccatccc cacgatgcgg tggtggctat  3540
gtctgctttt gttggtcgtc tgctcatggc atctctttca tctggctatc tggtagttgt  3600
ttggtgtttt gttgttgata gtgtagcaca cgagtccggg gtttccggtg gcgcctgtgc  3660
ggtgccggaa ccatgtggat tcgccttcca tggatgggca ttggatgaag gtgcgttggc  3720
cttgctcgga gatttctagg tggtgccggt gcccggccat gaggatgtgg gatgtggtgc  3780
cgttgtggaa ttcttggccg cgccaccatt cgtagtgttg gttgttgcgc cattggtggc  3840
cgtgggcgtg caggatttgt gtgccggcca ccccaacggt ggtggtcatt tcgtcccggc  3900
tggggaagtg gaagtgaaga ttggggtagt tgttgttgag ctggtaggct tctgcgatgg  3960
cccggcagca gtccacgtcg aaggagtcgt cgtaggtggt gactcctttg ccgaagcgta  4020
cggcttctcc gtggttgccg gggattgagg tgatggtgac gttttggcag tggtcgaaca  4080
tgtggatgag ttgcatcatg gccatgcggg tgagcctgat ttgttccgtc aagggtgttt  4140
gggtgcgcca ggcgttgttg cctccttgtg acacgtatcc ttcgatcatg tcgccgagga  4200
aggcgatgtg gactcgttgc ggctgtcctg cctgttgcca gtagtgtttt gctgctgtga  4260
gggagtgcaa atagtcgtcg gcgaagtgtg ctgtttctcc gttggggatg cctttgccga  4320
tttggaagtc tcccgcccct accacgaacg caaccttgtt gttgctgcgg gtgtgggtgt  4380
ctggttttgg gggtgtccat tcggctagtt tatcaacgag ttcgtccacg gggtaggggt  4440
ctgttgcggg ttggtggtcg atgatttttt gtatggatcg gcctgtttct ccgttgggga  4500
gtgtccattc ggagatgcgt gtgcggcgta cggtgccgtt ggctagattg tcgcagatgg  4560
tgtctgcttc gctatcgtgg ttggctagct gtgtgaggag ccggtctata ttgtctatca  4620
ctggttttcc tcctcttgcg gggtggtgtt ggcttgtttg cggcgatagt ctttaataac  4680
ggtggcggag atggggtatc ctgcctgggt gagctgtttt gctagccatg aggcggggat  4740
ggttttgtcg gcgagcacgt ctgcagcttt gttgccgtag cgttgaataa gggtttcagt  4800
tttggttgcc atgatgtggt tttgtcggcg agcacgtctg cagctttgtt gccgtagcgt  4860
tgaataaggg tttcagtttt ggttgccatg atgtcctagg ggttgtgtgg tgggctgcca  4920
tcctgtgcgg cagtcgccgt cgtgtcctgg tttgcgtgtg caccacgata cgttgccggc  4980
attgtggatg atggcacggc cgcatatgac gtcacgtaga tgctcgggaa acttgtcgtt  5040
gttgtttccg ttcgtgtcga tcaagtgttg ggttttagta accatcatgt ctcctatgtg  5100
tgaaagagtg tgcaaatact atgcaggtgt catggatgtt tatgcgggta tggttttcat  5160
caccttgctg aatgtgactt ggttactgta catcatctgg gtgatttcct gatcggtctt  5220
gtcggggtgc tgctttcgca ggttcgccca ttggcaggcg ttgtcggtct cttgctggag  5280
ccgggtcagg tgctgctcgt tgatgatgtg tttccacatt gtccacgaca cgtcgagcct  5340
gcggagcatg ttcatggctg gcacgttaaa cgagtcgagg aagagtattt cttcggtgta  5400
gtactgtttt tcgtattggt cccatccgct tcggtgcctg ttgggctggt ttttggggta  5460
ggcttcccgg catactttgt gtaaccgttt ggccatgtcg tcgggtagtt taatgtcggg  5520
gttggcgcgg atcatggatc gcatcccatc gtaggtggtg ccccagcggt gcatgatgct  5580
gagtgggtct tcaccatcgg cccatttttc tgcacagatg gcgaggcgta tgcgcctcct  5640
ggcggctttg ctggtgtcgc ggcggccggg gatggggcac gtgtcgagag gatccatgat  5700
```

```
gttttatatg cctttctttg tttggtttgc ttgtgtggtt ttattgtagc actgtgtcta  5760
gtgcttgtgt caaccctgtt tttccggcct gcaggtaggt gtctgtgaca tcgcccaggg  5820
tgaggggcac gtgtatggct tgggggagtg ctgcctggag ggtttgtgcc atctggtggc  5880
ctgccttgtc tgggtcggac cagatgtaga tgtggtcgta gccttcgaag aatttggtcc  5940
aaaagttttg ccacgaggtt gcgccgggta gggcgacggc cgaccatccg cattgttcga  6000
ggatcatgga gtcgaattca ccttcgcaaa tgtgcatttc tgctgccggg ttggccatgg  6060
cggccatgtt gtagatggag cctgtgtcac cggccggggt taggtatttg gggtggttgt  6120
gggttttgca gtcgtgcggg agtgagcagc ggaaacgcat ttttcttatt tcggctggcc  6180
gcccccaaac ggggtacatg tatgggatgg tgatgcactg gttgtagttt tcgtggccgg  6240
gtatggggtc attgtcgatg tatccaaggt ggtggttgcg ggctgtttct tcgctgatgc  6300
ctcttgctga gagcaggtcg agtatgtttt cgaggtgggt ttcgtagagg gccgaggctt  6360
tctggattcg gcggcgttcc gcaatgttgt atgggcgtat gctgtcgtac attcgggttt  6420
tctttctcta gttgttgttt cagttgggcg agtccgcctc cgataccgca tgtgtggcag  6480
taccagacgc ccttgtcgag gttgatgctc atggagggct ggtggtcgtc gtggaatggg  6540
cagaggatgt gttgctcgtt cctggatggg ttgtaacgga tgcggtaggt gtcgaggagg  6600
cggcaggtgt cagaggtgtg ggaggagctc gttgagggtt gataccacat aggcttcgct  6660
ccagggtttg ttgcgctgtt tcatcactac gagtccgatg gtggactggc tttctcggtt  6720
tcggtgggtt tcgtagttgc gtgcctccag gctggcttgt ttcacgaatt cggctaggtg  6780
gggctgcccg gctttcgcct cgataatgta ggttttatgg ccggttgtga ggatgaggtc  6840
gccttcatcc tctttaccgt tgaggtggag gcgttctata tcatagccgg tgtcgcgtag  6900
ctggtggagg agtcttgttt cccattcggc cccggcccgc cggttgcgtg cctgctgtgt  6960
aaccatcata gtcctttgtg tgttgtggtc atgttccagg gatgttttc ggcgagtggc  7020
ccgaagaatg tgtattcggg gtaggctcgt agccgctcat atttgttcc gtctgggctg  7080
gatttgccgg tgcgctgttt caacactgcg atgcgcgcct cggctggtat cgtgagcccg  7140
ttgccgttat cctcgccacc ataaagtgag actcccaata tgagttgtgg tttttcggag  7200
aggccgtttt taatttcccg tctagctggc gggtgttcga tgtcggagcc ggttttgtcg  7260
gttgcgtggt gtgtgacaat aatggtggag ccagtatccc tgcccaatgc tgtgatccat  7320
tgcatggctt cttgctgtgc ctggtagtcg gattcgcagt cttgaatgtc catcaggttg  7380
tcgataacaa tgagtggtgg gaaagtgttc cacatttcca tgtaggcttg tagctccatg  7440
gtgatgtcgg tccaggtgat gggtgactgg aatgagaagg tgatgtgttg gccgtggtgg  7500
atgctgtctc gatagtattc tggcccgtag tcgtcgatgt tgtgttgtat ctgtgtggtg  7560
gtgtgttggg tgttgagtga gatgattcgt gtggaggcct cccagggtgt catgtcccct  7620
gatatgtaga gggcgggctg gttgagcatg gcggtgatga acatggctag cccggatttt  7680
tggctgccgg agcgccccgc gatcatgacc aaatcccctt tgtggatgtg catgtcctgg  7740
ttgcggtaga ggggttctag ttggggtatg cggggcagct cggctgcggt ttgggaggct  7800
ctcgcaaagg atctttggag agagagcatc ggagccttta tctatcgatc ggttggatgt  7860
gttgtggtgg tcagatggag tcgatgtcta catcatcact atcagtggtg ttgggctggc  7920
tgtctcgccg atcaacgtag gctgctacaa ggtcgtagat ggcgtcgtcc aatggtttga  7980
gcacgaccgc gttgaacccg tttttagtgc gcacctgatc gagtttgaag gcctgctcct  8040
cgccaagata tgcctctaaa tcgcggatca tggagtgtgg gcggtcgttg ttgcctcgca  8100
ctttttcgat aatggcgttg gggatggttt ctggggtgcc gttgttgagg tcgtctaggg  8160
tgtggaagat ggtgacatca gcgtagatac gatcggcgac ctgtccaccg tagccttcag  8220
tgttgtgctg aacgtcgtgg actttgaagg cgatggcggt ggcgtcctgg tttcgggagg  8280
ggttgaagaa ggtgctgttg ctgttgttgc ggtagtttgc gagtcccatt attgtttcct  8340
ttactgtttt gttggtttgt gtcggttttt atcgggtgag gctgtttcgt ttgctgcgga  8400
aagcctcgga aacgtcactg ttactagtga tgatcttttt gtactgtttc agtagatcgg  8460
ctagctgtgc tttgcttgtt gcattgttga ttttgtcgat gatggtgttg tttccttctg  8520
aggcgatgtt gtctacgtag tctttggcgg cctggttgta tcggtcttgg aggatgatgg  8580
atgctgtggc gatcagtgtt gccaggtccc agttccttgc cgcggagctg tttttgagtc  8640
cgcctaacag gtcgatgatg gctttcttta cctggtcggc ggtgtctcct cggatgacgg  8700
tccatggggc ggcgtagtct ccgccgtatt tgagggtgac ggtgaatcgg tcgtcgtctg  8760
tgttgtcggt cactggtgct ccttgtcttc ttgtgttggg gctgtgatgg tggtttctat  8820
agggtacctg taggcgtctt tcccgttgac ggcccagcag gcgtctctga cggggcatcc  8880
tttacagagt gctgtgacgt gtgggacgaa gatgccttgg ctgattcctt tcattgcttg  8940
actgtacatg gatgatacat gccggtaggt gttgttgtca aggtcgtaca gttcggtggc  9000
cgttccctgc ttggcggact gtttgtctgt tttggttgat gcgggtgtcc aaaacatgcc  9060
ttttgtcaca tcgttgccgt gttgggcgag catgtaccgg taggtgtgca gctgcatgct  9120
gtctgctggt aggcggccgg ttttgaggtc gaggatgaag gtttcgccgg tgtcggtgtc  9180
ggtgaagata cggtcgatgt agccaacgat ctgggtgccg tcctggaggg tggtttctac  9240
cgggtattcg atgcctggct ggccgtctag gactgctgtg tggtattgcg gattgtttgt  9300
gcgccagtgt ttccaccggt cgacgaaggt ttgcccgtaa accatccacc agtcgtagtc  9360
tttttgtgt ggcccgcccg actcgcacat gtttttgcac accctgccgg agggtttaat  9420
ctccataccc tctgatcggg tgagggcgac ttgggtgtcg aaaatgtttt tgaaggatga  9480
gagtttgtct ggcagtgcag ggtattcggc ggggttgtac aggtgtaggt cgtattgttc  9540
ggtgatgtgg tgtatggcgc ttccggcgat ggtggcgtac caggtgtggt gttgggcgtg  9600
gtagccgtgg gataggcgcc atttttctcc gcattcggcc cactgtgaca gtgatgagta  9660
ggagatgtgg cctggatggt ggatggtttt cggatattgt gctagaggca ttacttgtcg  9720
cttttgttcc atgggttgcg ggtgtctacc ccggcattgt gttgctggta tgcgaggagt  9780
gctaggcagt gccaggcagc atgtgccagg tggggtagcc cggattcata atcgaggttg  9840
tttccttgct gccaggatag cacatggcgg tagagggcgt caacgctgtg gctccacgga  9900
tagccgccgg tccagttgtt gtcgccgtat ttggtggcac cgtagcctgc aacctcgccg  9960
agggcgtgta aggctgcggg gtcgatgagg gagagcctgc aaagtttgag ttctttcttg  10020
gcgccagtat cagggtcggt gtacatgcgg gtgggctcat ccatggggtg tgtgctcctt  10080
aagggtgggt tactggttgg ggttgtgggc gagtgctact gcgagaataa tgatggcgag  10140
ggtttctgcg atgaggatgg gtgttgtgat catttgttgt ctcggggatt gctggtgagt  10200
gtggaggcgc ctaggagggt ggtgagggcg catgcggcga tgatggcgag ggctgccttg  10260
tgtggggtgc cggtggcgta catccatgtg atgatggcgc cttggatcca ggcgaggctg  10320
gtgaagaacg tttcgtagct gtgtagctcg ctgttgttgc tggtgatgtc attcatggta  10380
gttttctgct ttgtgtgcga tggttgtgta catgtcgttg agtgtggttt cgatggtgat  10440
```

gagagtgttg atttcttggt tgaggtcgat gttgtctttg agggtgtcga tgcgggcggc 10500
gatgtcggtg gcggtgcgta ggcttactgc tgcaccgtgg atgatgtggc acatgtcggt 10560
gaggccgacc ttggcgatat agtgtgacat gagaggcatg atgggtgtgt cgtctttctg 10620
gtcagcgtga cgggttgatg gacatgtctt ctacctgtgg cttgtcttcg gtgcctgata 10680
cttggcaaaa gactttcacg tgcgccttgg atgctccggg ttgcttggcg gtggcaccgt 10740
aggcgatagt aaaggcgtct ttgtgggcgc cgatgacttt gtgtaggaag aggtcgatgt 10800
cggggtttcc gttccatttg acaccgtttt ctgcggctgc ctgggtggct ttctggttgc 10860
aggcgtgtgc tgccgtaatc atggtgagtc cggtggcggt ttcttcaccc cttgcttggg 10920
cttgcttgtg ggtttttgct tgttcggctt gtagggagcg gactgcggct gcctgccgtg 10980
ctttctttc ggctttgcgc tgctgggtag tcttgggggt ccattcggtg ttggctgtgg 11040
tggcctgtgg ggctggctgt gaggcgagtg gcggattgtc gtctggggct ggcatgaatg 11100
aggcggcggc aatgatggcg gctgtgattc cggcgatggt gtagccgttt ttcttgttca 11160
tgactgttgt cccctttccg gggtgttgtt cgttgctgac atgattaatc atggtgtgga 11220
cggttcccca tgtcaaggct gcgctcaacg attgtgagcg tttggtgtgt ggctaggggt 11280
tttatcgggc acacagggtg agtagatggc caacattgat gcggctcaca ttccagtaga 11340
gttgtgtggc ttcaccgccg gtgagcggct tccactcgtt gtggctgaac acggtgccat 11400
cggatgcgat gaatgtgtcg gggcgtagct tgtgaagctc ggcttccacg ctctgccggt 11460
aggtttcggc gaggccctca aaatccatgt ggtcgcagga gaggttttcg aggcgtgtca 11520
ggtcgaaggg tgtggggcag tcgtagctgg cgggggtgta gagctgggtg aagtggttgg 11580
cgatcttctg catgatgatg tccttttggt tgctgataac cttgttgagg gtttatcggg 11640
tggatgtgat aaggatggcg tccacgtcga tcatgtcgat gagatcgtgg agttcctcgg 11700
cctcgttttc ggtgagtggc tgccagttgt tgtcgccgta cacggcgccg tcgagggtga 11760
cagtccacag tggccggatg aggcgtacgg cttcttgtac tttagcgtgg tacatgcggc 11820
gcaccatatc cagatccatg tcgtctgaat ggtttccgat gaggttgtgg aggctgagcg 11880
ggtcgatttc tgtctgcctg tagagggatg tgaaggatgg ggtgatgagt gtgccatcca 11940
tgggtgatgt tcctttctgg attgtcttgg ttggttgttg tggtttctag agtgtgcggg 12000
ttgcaaccgg gagtcaaggc tgcgctcatt cggattgagt gtttcatgct ggagtgtcgg 12060
gtgtgacaga tgtcacttaa gcctttattg cctctctcgg cgtctcacat catctggggg 12120
taagattatg cagggttgac cctgctgatc gattctaggg cccttctagg gcgtctcagg 12180
ggtacgtctg ggtgatagcg ggtgtggcag atgatctagc gagtcaaggt accgagctta 12240
gacgtaagat ctatcatcta ggcgtgtgag atgtatcaca tcctcctggc tgggtgtgca 12300
ccctcaaggc tactctgccg atctggcgtg gagggtgtag cccagaaatg ccgtttaaag 12360
ccttcacatg gcgcctagaa gcgccttgca gggtgggggc taggtattta tacccccaac 12420
acattctgat cgattctaga cgcctatagg agcctgatac acgatcaacc atctcggcat 12480
agatcatcag cccctatcct agttagctaa gcctgaacta tgtggacagt gtaggatgct 12540
aagagggaag aaggacacgg taaaagaaag aggggggggc atcaaccttc acgcccgagg 12600
tacttaagtt aaccttaggg tcttagcacc gagcccctca agggctcggc atcagcatca 12660
tcgggatcag ccgatccggc acagccttag caagtacaca ccatcaggga aggcttgaga 12720
gtacgaggag ccctagcgac gagtactcga aagcctgagg gaacaccctc agcactgatg 12780
ggcctagcgt gttcggaaag tacacagggg tacagtgtga gagctgttcg ggagctaaac 12840
cccttccggc tagggcaaac accagtccta gactatccca caccctcatc tgttaacctt 12900
ccgttcatta aacgttaagg aaacttttag gtttgatttt tggaccttaa ccaccaaaaa 12960
cacccattta cacccctcaa acccgccaat agagccaaac gccggtgttg agggtatctc 13020
tacctagtgt gataggctgg acaggtagcc agctggacgc aaggccagaa agtgctgacg 13080
cacttcccga cctcgcttac catcagtcta ccaaacactt aaaagcttaa cagctaagcg 13140
ctaagccctt aagacctcaa cgcttagcac cgagcccttg aggggctcgg catcagtctt 13200
aggtacttaa agtaacttta aaccttaaag gcttagcact taaggatata aacttaacat 13260
cagtgtttaa gactttaata ctttaagtaa ctataagacc ttaaagcttt aaacacttaa 13320
agttaaccat cagtcttaaa ctttaatatt ataacttata agctttaata cttatattat 13380
attataacct ataagtctta aagcttatag gttataaaag ttttagaaga gctaagaggt 13440
taacttcttt acttctctac tctctttggt tctttctctc ttctcttctt ttcttcatca 13500
ggggagaaga ggaatcttta ccatcagcgc cgatgacctt tcaccgtgtg gatcgtgtgc 13560
ttctggtcgc aagctcccat cgcacactcc ccacactctt acacccgtgt ccctttcggg 13620
cttggcgtgt tcggctaaag gcgtacggcg tgtcacgcta acacccttaa caccgggtaa 13680
gacttaaagt gtatattata tgtagaagac tttaaaacct ataaggtgtt cccgcttagc 13740
ccgtgtccta caccgctagg cgccaagcgc taagccttga aacgcgaaca cacacccacc 13800
cccttttttc ttccgtgtcc ttctcttttg acaccgctgg ggggcgatgt gatctttctc 13860
acacccatgg gggtagtgga gaaaacaaac accccggcac aaacagaaca ccccctcaaa 13920
cgaacaaaac agccccccag aatcgaccag cagggcaagg gtagagtatc cataccccca 13980
acggtttcca ggccgttaca gaggcaaata agacccgtac agggctaggc gaggaacaga 14040
cacatcatgg cacgcaccaa ccgcacagcc gccacggcac accgacgctg gcggcaacga 14100
ctcatcaccc aagcccaaca gcaaggccaa accacctgcc cactctgcgg agtcaccatc 14160
acctgggaca cccaccagct accaaccagc cccgaagccg accacatcac acccgtcagc 14220
cggggaggac tcaacaccct agacaacggg caaatcatct gcagaacatg caacagaagc 14280
aaaggcaatc gcagcgaacc aaacatcaaa ttccaacaac aaaccacaaa aaaccttgtt 14340
tcatggtaga aaacctgcca gcccccaccg gggacacccc ctgcacaggc gtgcaagacc 14400
tcgtacggct tagtgaaata cctccctttt gtggatttgt ctgtttgtcg actttttgtg 14460
ttggtggtga gtgttgtgca gcctgagctt cctgatagtc gtgattggtg tggggagacg 14520
cgtcgttggt ggcgtgtgtg gggtgaggat agccgtgcat cgtacgtgtc tgatgaggag 14580
tggttgtttc tccttgatgc ggctgtgatt catgatgtgg tgtggcgtga gggtcgcgcg 14640
gatttggtgg cttcgcttcg tgctcatgtg aaggctttta tgggtatgtt ggatcggtat 14700
tcggttgatg tggtgtctgg tggccgtgcc ggtggttctg cggtggcgat gattgatcgg 14760
tataggaagc gtaaaggggc ctaatgtcga gtgttgttgg ttctcaggtt cctcgtcatc 14820
gtgtggctgc ggcgtattcg gtgtctgctg gtggtgatgc tggggagttg ggtcgtgcgt 14880
atgggttgac gcctgatccg tggcagcagc aggtgttgga tgattggctg gctgtcggta 14940
gcaatggcag gcttgcttcg ggtgtgtgtg gggtgtttgt gcctcgccag aatggcaaga 15000
atgctatttt ggaggttgtg gagttgttta aggcgactat tcagggtcgc cgtattttgc 15060
atacggctca cgagttgaag tcggctcgta aggcgtttat gcggttgagg tcgttttttg 15120
agaatgagcg gcagtttcct gacttgtatc gtatggtgaa gtcgattcgg gcgacgaatg 15180

```
gtcaggaggc tattgtgttg catcacccgg attgtccgac ttttgagaag aagtgtggct  15240
gcagcggttg gggttcggtt gagtttgtgg cccgttctcg gggttctgct cgcgggttta  15300
cggttgatga tttggtgtgt gatgaggctc aggagttgtc ggatgagcag ttggaggcgt  15360
tgcttcctac ggtaagtgct gccccgtctg gtgatccgca gcagattttc cttggtacgc  15420
cgcctgggcc gttggctgat ggttctgtgg tgttgcgttt gcgtgggcag gcgcttggtg  15480
gcggtaaaag gtttgcgtgg acggagtttt cgattcctga cgagtctgat ccggatgatg  15540
tgtcgcggca gtggcggaag ttggcggggg atacgaatcc ggcgttgggg cgtcgcctga  15600
attttgggac cgtaagcgat gagcatgagt cgatgtctgc tgccggtttt gctcgggagc  15660
ggcttggctg gtgggatcgt ggccagtctg ctgtgtctgt ggttcctgct gataagtggg  15720
ctcagtctgc ggtggatgag gcgagtctgg ttggcgggaa agtgtttggt gtctcgtttt  15780
ctcgttctgg ggatcgggtt gctttggcgg gtgccggcaa gactgatgct ggggttcatg  15840
ttgaggttat tgatgggctg tcgggaacga ttgttgatgg tgtgggccgg ttggcggact  15900
ggttggcggt tcgttggggt gatactgacc ggatcatggt tgccgggtct ggtgcggtgt  15960
tgttgcagaa ggcgttgacg gatcgtggta ttccgggccg tggcgtggtg gttgctgata  16020
ctggcgttta tgtggaggct tgtcaggcgt ttcttgaggg tgtcaggtcg ggtgtgatca  16080
gtcatcctcg tgctgattct cgccgtgaca tgttggatat tgctgtgagg tcggctgtgc  16140
agaagcgtaa ggggtctgcg tggggttggg gttcctcgtt taaggatggt tctgaggttc  16200
ctttggaggc tgtgtctttg gcgtttttgg gggctaaacg tgttcgtcgt ggccgtcggg  16260
agcgtagtgg taggaagcgg gtgtctgtgg tatgaactcg gatgagttgg ctctgattga  16320
gggcatgtac gatcgtatcc aaaggttgtc ttcgtggcat tgtcgtattg agggctacta  16380
tgagggctct aatcgggtgc gtgatttggg ggtggctatt cctccggagt tgcagcgtgt  16440
gcagacggtg gtgtcgtggc ctggtatagc tgtggatgct ttggaggagc gtctggattg  16500
gcttggctgg atgaatggtg acggctacgg cctggatggt gtgtatgctg cgaatcggct  16560
tgctacggcg tcgtgtgatg tgcatttgga tgcgctgatt tttgggttgt cgtttgttgc  16620
gataattcct catggtgatg gtacggtgtc ggttcgtccg cagtcaccaa agaattgtac  16680
gggcaagttt tcggctgacg ggtctcgttt ggatgctggt ttggtggtgc agcagacgtg  16740
tgatcctgag gttgttgagg ctgagctttt gcttcctgat gtgattgttc aggtggagcg  16800
gcgtggttcg cgtgaatggg ttgaggtgga tcgtataccg aatgtgttgg gtgcggttcc  16860
gttggtgcct attgtgaatc gtcgccgtac ttctaggatt gatggccgtt cggagattac  16920
gaggtctatt agggcttaca cggatgaggc tgtgcgcaca ctgttggggc agtctgtgaa  16980
tcgtgatttt tatgcgtatc ctcagcgttg ggtgactggc gtgagcgcgg atgagttttc  17040
gcagcctggc tgggtcctgt cgatggcttc tgtgtgggct gtggataagg atgatgacgg  17100
tgacactccg aatgtggggt cgtttcctgt caatagtcct acaccgtatt cggatcagat  17160
gagactgttg gcgcagttga ctgcgggtga ggcggctgtt ccggaacgct atttcgggtt  17220
tatcacgtct aacccaccta gtggggaggc tttggctgcc gaggaatctc ggcttgtgaa  17280
gcgtgctgag cggcgtcaaa cgtcgtttgg tcagggttgg ctgtcggttg gtttttggc  17340
tgccaaggcg ttggattctc gtgttgatga ggccgatttt tttggtgatg ttggtttgcg  17400
ttggcgtgat gcttcgacgc ctacccgggc ggctacagct gatgctgtga cgaagcttgt  17460
tggtgccggt attttgcctg ctgattctcg tacggtgttg gagatgttgg ggcttgatga  17520
tgtgcaggtt gaggctgtga tgcgtcatcg tgctgagtcg tctgacccgt tggcggtgct  17580
tgctggggct atatcgcgtc aaactaacga ggtatgatag gcgatggctt cgggggttga  17640
ggcgaggctt gcggcgactg agtatcagcg tgaggcggtc aggtttgctg ggaagtatgc  17700
gggctattat tctgagcttg gtcgtttgtg gcgtgccggc aggatgagtg acacgcagta  17760
tgtgcgtttg tgtgtggagt tggagcgtgc cggccatgat ggttcggcat cgttggctgc  17820
caggtttgtg tcggattttc gccggttgaa tggtgtggat ccgggtttga ttgtgtatga  17880
cgagtttgat gctgcggcgg ctttggctag gtctatttcg accacgaaga ttcttgagag  17940
tgacccggat agggcgaatg acacgattga tgcgatggcg gcgggttttg atcgggctgt  18000
tatgaatgct ggtcgtgaca cggttgagtg gtctgcgggt gcgcagggta ggtcgtggcg  18060
tcgtgtgacg gatggtgatc cgtgtgcttt ttgtgccatg ttggctacga ggtcggatta  18120
tacgacaaaa gagagggcac ttactactgg acatactcgg cgtcataagc gtggtggtaa  18180
gcgtccgttt ggttcgaagt atcatgatca ttgtggttgt acggtggttg aggttgttgg  18240
cccttgggaa ccaaataggg ctgatgccga gtatcagagg acgtatgaga aggcccgtga  18300
gtgggttgat gatcatgggt tgcagcagtc gcctggcaat attttgaagg ctatgcgtac  18360
tgttggcggc atgagataat ttgatgtggt ttccggttgt gcgccgccgg ttattggtgc  18420
acagggttgt ctcccgcacg gggtcaaca atgttgtgtt gttttccgca aggagtgtag  18480
ggttaggcta tggccgatca gagtgttgag gaacagaatg ttgacaatga tgttgtggag  18540
tccggaaagg ataacggcat tgttgataca gtaaaagacg atggcggaca ggaggtggcc  18600
gacaatcagt tgaagaatga aggcgagggt aaatcgccgg ggactgattg gaaggcggag  18660
gcccgtaagt gggagtctcg tgctaaaagt aatttcgctg agttggagaa gcttcgcgcc  18720
tcggatggtg atgcggggtc tgtgattgat gatcttcgcc gcaagaatga ggaactcgaa  18780
gaccggatta acgggtttgt tcttgagggt gtgaagcgcg aggtggcttc agagtgtggc  18840
ctgtcgggtg atgctgtcgc tttcttgcac ggtagcgatc gtgaagcgct ggtggagtct  18900
gcgaaagctt tgaagggttt gatcgaccat agtagtggtg gcgcgggtgt gcgccgtctt  18960
gcggggagtg cccccgttga tgatgttaaa cgacgtgagg gtgtcgcgtt tgtggatgct  19020
cttgtcaata attctaggag atgatttgtg atggctgacg attttctttc tgcagggaag  19080
cttgagcttc ctggttctat gattggtgcg gttcgtgacc gtgctatcga ttctggtgtt  19140
ttggcgaagc tttcgccgga gcagccgact atttttggcc ctgttaaggg tgccgtgttt  19200
agtggtgttc ctcgcgctaa gattgttggt gagggcgagg ttaagccttc cgcgtctgtt  19260
gatgtttcgg cgtttactgc gcagcctatc aaggttgtga ctcagcagcg tgtctcggac  19320
gagtttatgt gggctgatgc tgattaccgt ctgggtgttt tgcaggatct gatttccccg  19380
gctcttggtg cttcgattgg tcgcgccgtg gatctgattg ctttccatgg tattgatcct  19440
gccactggta aagcggctgc cgctgtgcat acttcgctgg ataagacgaa gcatattgtt  19500
gatgccacgg attctgctac gaccgatctg gtcaaggctg tcggtcttat cgctggtgct  19560
ggtttgcagg ttcctaacgg ggttgctttg gatccggcgt tctcgtttgc tttgtctact  19620
gaggtgtatc ctaagggttc gcctcttgct ggccagccga tgtatcctgc cgccgggttt  19680
gccggtttgg ataattggcg tggcttgaat gttggttctt cttcgactgt ttctggcgcc  19740
ccggagatgt cgcctgcctc tggtgttaag gctattgtgg gtgatttctc tcgtgttcat  19800
tggggtttcc agcgtaactt cccgatcgag cttatcgagt atggtgaccc ggatcagact  19860
gggcgtgacc tgaagggcca taatgaggtt atggttcgtg ctgaggctgt gctgtatgtg  19920
```

-continued

```
gctatcgagt cgcttgattc gtttgctgtt gtgaaggaga aggctgcccc gaagcctaat  19980
ccgccggccg agaactgatt tattgttgcg gtgatgtgtc aatgtgcagg gggtggtgtt  20040
gatgggtatc attttgaagc ctgaggatat tgagcctttc gccgatattc ctagagagaa  20100
gcttgaggcg atgattgccg atgtggaggc tgtggctgtc agtgtcgccc cctgtatcgc  20160
taaaccggat ttcaaataca aggatgctgc taaggctatt ctgcgtaggg ctttgttgcg  20220
ctggaatgat actggcgtgt cgggtcaggt gcagtatgag tctgcgggtc ctttcgctca  20280
gactacacgg tctagtactc ccacgaattt gttgtggcct tctgagattg ccgcgttgaa  20340
gaagctgtgt gagggtgatg gtggggctgg taaagcgttc actattacac cgaccatgag  20400
gagtagggtg aatcattctg aggtgtgttc cacggtgtgg ggtgagggtt gctcgtgtgg  20460
gtcgaatatt aacggctacg ctggcccttt gtgggagata tgatatgacc agttttcctt  20520
atggtgaaac ggttgtgatg cttcaaccga ctgttcgtgt cgatgatctt ggtgacaagg  20580
ttgaggattg ggggcatctt gtagaaacag tgtaccataa cgtggccatc tatgcttccg  20640
tttcgcagga ggatgaggcc gcggggcgtg actctgacta tgagcattgg tcgatgcttt  20700
tcaagcagtc tgttgttggt gctgattatc gttgcaggtg gcgtatccgg ggtgttgtgt  20760
gggaggctga cgggtctcct atggtgtggc atcatccgat gtctggctgg gatgcgggca  20820
cgcagatcaa tgtgaagcgt aagaagggct gatgggtagt ggctcaggat gtgaatgtga  20880
agctgaactt gccgggtatt cgtgaggtgt tgaagtcttc tggggtgcag gctatgttgg  20940
ctgagcgtgg cgagcgtgtc aagcgtgcgg cctcggcgaa tgtgggcggg aacgctttcg  21000
ataaggccca ataccgtaat ggtttgtcgt cggaggtgca ggttcaccgt gttgaggctg  21060
tcgctcgtat aggcaccaca tataagggtg ggaagcgtat tgaggcgaag catggcacgc  21120
tggctcgttc gattggggct gcgtcgtgat cgtctacgat gaccccagga agtgggctaa  21180
acgcgtgctc aaggatgatg gctggctgtc tgatataccc tgtgtgggga cggtgcccga  21240
tgattttatg ggtgacctgg tttggttggc gttggatggt ggcccgcagt tgcatgttcg  21300
tgagcgtgtt tttttgcgcg tgaatgtgtt ttctgatacg cctgatcggg ctatgtcttt  21360
ggcgcgtcgt gttgaggctg tgctggctga cggggttgat ggtgatccgg tggtgtactg  21420
taaacggtct actggtcctg atttgctggt tgatggtgca cgttttgatg tgtattcgct  21480
gttcgagctg atatgtaggc ctgtcgaatc cgagtaaacg tatttgtttt tgttttaatg  21540
taattgtttg atatttaatg ggggttgtga tggctgcaac acgtaaagcg tctaatgttc  21600
gttcagcggt tactggcgac gtttatattg gtgacgcgca cgcgggtgat actattaagg  21660
gtgtggaggc ggttccttcc gggcttacag ctttagggta tctgtcggat gacgggttta  21720
agattaagcc tgagcgtaaa acggatgatt tgaaggcttg gcagaatgcg gatgttgttc  21780
gcacggttgc taccgagtct tctatcgaga tttcttttca gctgatcgag tctaagaagg  21840
aggttatcga actgttttgg cagtcgaagg ttactgccgg agccgattcg ggttcgttcg  21900
atatttctcc tggtgccacc actggcgtgc acgctttact gatggatatt gttgatgggg  21960
atcaggttat tcgctactat ttccctgagg ttgagctatt cgatcgtgac gagattaagg  22020
gtaagaatgg cgaagtgtac gggtatggtg tgacgttgaa ggcttaccct gctcagatta  22080
ataagactgg taatgcggtg tcgggtcgag ggtggatgac ggctttaaaa gctgatactc  22140
cccttctcc gaagcctcag ccggatccga atccgccgtc tgagaactga tacacgattt  22200
tagggattgt tgatagatga gtgacacagg ttacacgttg aagattggtg accgtagctg  22260
ggtgttggcg gatgcggagg agacggctca ggctgttcct gctcgcgttt ttcgtcgtgc  22320
agctaagatt gcccagtctg gggagtctgc ggatttcgct caggttgagg tgatgttttc  22380
tatgttggag gctgcagccc cggctgacgc ggtggaggcc ctggaggggc ttcctatggt  22440
tcgtgttgcc gagattttcc gccagtggat ggagtggaag cctgaaggta agggtgcctc  22500
tttgggggaa tagtttggct ccacggcctg attgatgagt atcgtggggc catcgaatat  22560
gattggcgca caaggtttgg tgtgtgcata tacgatatag gtggtcctgc gatggggtgg  22620
ggtgaggctg tccggctggc tggcgtgttg tgtggtgata cgtcgagcca gttggcggcc  22680
cacctgaatg gttggcagcg cccgtttgag tggtgcgagt gggctgtgtt ggacatgctg  22740
gatcattaca ggtctgctaa tagtgagggg cagccggagc ctgtggcgag gcctacggat  22800
gagcgtaggg gccggtttac gtctgggcag gtggatgata ttttggcgcg tgttcgtgct  22860
ggtggcgggg tgtctcgcga gattaatatt atggggtgaa tagtgtatgt ctggtgagat  22920
tgcttccgca tatgtgtctt tgtatacgaa gatgcctggt ttgaaggcgg atgttggtaa  22980
acagctttct ggtgtgatgc ctgctgaggg tcagcgttcg ggtagtcttt ttgctaaggg  23040
catgaagttg gcgcttggtg gtgccgcaat ggtgggtgcc atcaatgttg ctaagaaggg  23100
cctcaagtcg atttatgatg tgactattgg tggtggtatt gctagggcga tggctattga  23160
tgaggctcag gctaaactga ctggtttggg tcatacgtct tctgacacgt cttcgattat  23220
gaattcggct attgaggctg tgactggtac gtcgtatgcg ttgggtgatg cggcttctac  23280
tgcggcggcg ttgtctgctt cgggtgtgaa gtctggcggg cagatgacgg atgtgttgaa  23340
gactgtcgcc gatgtgtctt atatttcggg taagtcgttt caggatacgg gcgctatttt  23400
tacgtctgtg atggcccgcg gtaagttgca gggcgatgac atgttgcagc ttacgatggc  23460
gggtgttcct gtgttgtctt tgcttgccag gcagacgggt aaaacgtcgg ctgaggtgtc  23520
gcagatggtg tcgaaggggc agattgattt tgccacgttt gcggctgcga tgaagcttgg  23580
catgggtggt gctgcgcagg cgtctggtaa gacgtttgag ggcgctatga agaatgtgaa  23640
gggcgccctg ggttatttgg gtgctacggc tatggccccg tttcttaatg ggttgcggca  23700
gatttttgtt gcgttgaatc cggttatcaa gtcggtgacg gattctgtga agccgatgtt  23760
tgctgccgtc gatgctggta ttcagcgtat gatgccgtct attttggcgt ggattaatcg  23820
tatgccgggc atgatcactc gaatgaatgc acagatgcgc gccaaggttg agcagttgaa  23880
gggcattttt gcgagaatgc atttgcctgt tcctaaagtg aatttgggtg ccatgtttgc  23940
tggcggcacc gcagtgtttg gtgttgttgc tgccggtgta gggaagcttg ttgcagggtt  24000
tgccccgttg gcggtgtcgt tgaagaatct gttgccgtcg tttggtgctt tgaagggtgt  24060
cgctggcggg cttggtggcg tgtttcgcgc cctgggtggc cctgttggta ttgtgatcgg  24120
cttgtttgct gccatgtttg ctacgaacgc ccagttccgt ggcgcggtga tgcagcttgt  24180
gggggttgtt ggccaggctt tggggcagat tatggccgct gtgcagcctg tgtttggttt  24240
ggttgccggt ttggtggccc ggttggcgcc agtgtttgcc cagattatcg gtttggttgc  24300
aggtttggct gcccagctta tgccggtgat tagtatgctt gttgcccggc tggttcctgt  24360
gatcacccag attattggtg cggtgacaca ggttgctgca atgttgttgc ctgcgttgat  24420
gccggtgttg caggctgttg tggctgtgat tcggcaggtt gttggcgtga tcatgcagtt  24480
ggtgcctgtt ttgatgcctg tgattcaaca gattttgggt gctgtcatgt ctgtgctgcc  24540
acccattatt ggtcttatcc ggtcgttgat gcctgtgatt gcggcggtta tgcgtgtggt  24600
ggtgcaggtt gttgcggttg tgatacaggt ggtggcccgt attcttgcgg ttgtggctcc  24660
```

```
gatggtggcg gctgtggtag ggtttgtggc ccgtattgtt ggtgctgtcg tgtcggctgt  24720
tgcccgtgtt attgctgctg ttgcccgtgt catcgggtgg attgtggccc attttgtgtc  24780
tggtttggca cgtatgggtt cggtggttca ggctggctgg aatcggatta gggcgtttac  24840
gtcagcgttt attaacggtt tcaagtcggt gatttctggc ggcgtgaacg cggttgtggg  24900
gtttttgcc cggctgggtt cttctgttgc ttctcatgtg aggtctggtt ttaacgcggc  24960
ccgtggcgct gtttcttctg cgatgaatgc tatccggagt gtggtgtctt cggtggcgtc  25020
tgctgttggc gggtttttca gttcgatggc gtctagggtt cgtagtggtg ctgtgcgcgg  25080
gtttaatggt gcccggagtg cggcatcttc tgctatgcat gctatggggt ccgctgtgtc  25140
taacggtgtg catggtgtgc tgggtttttt ccggaatttg cctggcaata ttcggcgtgc  25200
gcttggtaat atggggtccc tgttggtgtc ggctggccgt gatgtggtgt ctggtttggg  25260
taatggtatc cggaatgcta tgagtggcct gttggatacg gtgcgtaata tgggttctca  25320
ggttgctaat gcggcgaagt cggtgttggg tattcattcc ccgtctcggg tgtttcgtga  25380
ccaggttggc cgtcaggttg ttgctggttt ggctgagggt attactggta atgctggttt  25440
ggcgttggat gcgatgtcgg gtgtggcggg acggctgcct gatgcggttg atgcccggtt  25500
tggtgtgcga tcgtctgtgg gctcgtttac cccgtatggc aggtatcagc gtatgaatga  25560
taagagtgtt gtggtgaatg tgaatgggcc tacttatggt gatcctaacg agtttgcgaa  25620
gcggattgag cggcagcagc gtgacgcgtt gaatgcgttg gcttacgtgt gattggggt  25680
gttgtgcatg tttattcctg acccgtctga tcgttcgggt ttgactgtga catggtcgat  25740
ggatccgctg tttggtgggg ggcgtgtgct tcatttgacg gattatacgg gtgcgtctcc  25800
tgctatgttg ttgaatgatt cgttgcgcgg tttgggtgtt cccgaggttg agcatttttc  25860
tcaaacacat gttggggtgc acggctcgga gtggcgcggg tttaatgtga agcctcgcga  25920
ggtgacgcta ccggtgttgg tgtcgggtgt tgactcggat ccggatggcg ggtttcgtga  25980
cggtttttttg aaagcctatg gcgagttgtg gtctgctttt cctcctggcg aggaggggga  26040
gttgtcggtg aagactcctg caggtcgtga gcgtgtgttg aagtgtcggt ttgattcggt  26100
ggatgacacg tttacggttg atcctgtgaa tcgtggctat gcgcgttatg tgattcattt  26160
gacagcttat gacccgtttt ggtatgggga ggagcagaag tttcgtttta gtaacgcgaa  26220
gttgcaggat tggttgggtg gcggccctgt cggcaaggat ggcacggcgt ttcctgtggt  26280
gttgacgcct ggtgttggtt ctggttggga taatctgtct aataagggtg atgtgcctgt  26340
gtggcctgtg attcgtgttg aggggccttt ggagtcgtgg tctgtgcaga ttgatggttt  26400
gcgtgtgtct tcggattatc ctgtcgagga gtttgattgg atcactattg atacggatcc  26460
tcgtaaacag tctgcgttgt tgaatgggtt tgaggatgtg atggatcgtt tgacagagtg  26520
ggagtttgcc ccgattccgc ctggcggttc gaagagtgtg aatattgaga tggttggttt  26580
gggtgccatt gttgtgtcgg tgcagtacag gtttttgagg gcttggtgaa tagttgatgg  26640
ctggtctggt tccgcagata acattgttta cgccggatta tcgccgggtt gcgcctatca  26700
atttttttga gtcgttgaag ttgtcgttga agtggaatgg tttgtcgacg ctggagttgg  26760
tggtgtcggg ggatcattct aggcttgacg ggttgactag gccgggtgca cggctggtgg  26820
ttgattatgg tggtggccag atttttttctg ggcctgtgcg tcgggtgcat ggtgtgggtc  26880
cgtggcgttc ttcgcgggtg actatcacgt gtgaggatga tattcgcctg ttgtggcgta  26940
tgttgatgtg gcctgtgaat tatcgtcctg gtttggttgg tatggagtgg cgtgccgaca  27000
gggattatgc tcactattct ggtgcggcgg agtcggttgc taagcaggtg ttgggggata  27060
atgcttggcg ttttccgcct ggtttgttta tgaacgatga tgagagtcgt ggccgctata  27120
ttaaggattt tcaggtgcgg tttcacgtgt ttgccgataa gttgttgccg gtgttgtcgt  27180
gggctcggat gactgtttcg gtgaaccagt ttgagaatgc gaagtttgat cagcggggtt  27240
tgctgtttga ttgtgtgcct gctgtgacgc gtagtcatgt gttgactgcc gagtctgggt  27300
ctattgtgtc gtgggagtat gtgcgtgacg ccccgaaggc tacttcggtg gtggttggtg  27360
gccgtggcga gggtaaggat cggctgtttt gtgaggatgt tgattcgatg gccgaggggg  27420
attggtttga tcgtgtagag gtgtttaagg atgcccgtaa cacggattct gaacatgtgc  27480
atctcatcga tgaggctgag caggtgctgt ccgagttagg ggccacgtcg gggtttaaga  27540
tcgagttggc tgagtcggat gtgttgcggt ttgggccagg ccgcctgatg cccggggatt  27600
tgatctatgt ggatgtgggc tcggggccta ttgcggagat tgttcggcag attgatgtgg  27660
agtgtgattc gcctggtgat ggttggacga aggtgacacc ggttgcgggg gattatgagg  27720
ataatccgtc ggcactgttg gctcgccgtg tggctggttt ggctgccggt gtgcgggatt  27780
tgcaaaaatt ttagtaagtg attggggttt gttgtgggta ttgtgtgtaa agggtttgat  27840
ggtgtgttga ccgagtatga ttgggctcaa atgtctggtc tgatgggtaa tatgccgtct  27900
gtgaaagggc cggacgattt tcgtgtcggc acgacgattc agggtgccac agtgttgtgt  27960
gaggtcctgc cggggcaggc ttgggctcac ggggtgatgt gcacgtcgaa tagtgttgag  28020
acggtgacgg ggcagctgcc tggtcctggt gagacccgct acgactatgt ggtgttgtcg  28080
cgggattggg agcagaacac agccaagttg gagattgttc agggtggccg tgcggagcgt  28140
gcccgggatg tgttgcgtgc cgagcctgc gtgtttcatc agcagctact ggcgactttg  28200
gtgttgtcgt ctaacgggtt gcagcagcag ctggataggc gtgctgttgc ggctagggtt  28260
gcgtttggcg agtctgcggc ttgcgatccc acccctgtgg agggtgaccg tataatggtg  28320
ccttcggggg ctgtgtgggc taaccatgcc ggcgagtgga tgctgttgtc acccagaatt  28380
gagacgggtt cgaagtcgat catgtttggt ggttctgctg tgtatgctta cacgatcccg  28440
tttgagcgcc agttcagtag tccgcctatt gtggtggcgt ctatggctac ggcggctggg  28500
ggcacgcagc agatcgatgt gaaagcctac aatgtgactg cccaaaattt tagtttggcg  28560
tttattacga atgatggttc gaagccgaat ggtgtgcctg cggttgcgaa ttggattgct  28620
gtcggagtgt gactgcacgg gtgttgtggc ggatggtgtg atgttggggg gctgtagtgt  28680
cgtggtttac tcctgcactg gtggcctcta tctgtaccgc gttggccacg gttttgggtt  28740
ctgttcaggc tgtcacatcc cggtctagga agcgtttacg caggctgtcg gctcaggtgg  28800
atgcgatgga agagtatacg tggggtgtgc ggcgcgaggt gcgaaggttt aacgccgggc  28860
ttcctgacga tgtggagccg atgcatcttc ctgatttgcc cgagtttttg aaagatactg  28920
ttgatggtgg aggtgagtag ggttgaggga gttggaggaa gagaaacggc agcgccgcaa  28980
ttttgagaaa gcttcactgt tgctgttgtt tttgtcgctt gtactgttgg cggtggttgc  29040
tgcgggtgct ttgcgtttcg gggctgtatc ctctgagcgg gattcggagc aggcgagggc  29100
ccagtcgaat ggtacggctg ccag                                          29124

SEQ ID NO: 73          moltype = DNA  length = 30016
FEATURE                Location/Qualifiers
source                 1..30016
```

```
                        mol_type = other DNA
                        note = PAC22
                        organism = synthetic construct
SEQUENCE: 73
gcgcagggtg agcgtggccc cgccggtgtg aacggatccg atggtaaaga cggtaaagat  60
ggtaaggatg gcgctgatgg gcgttcggtg atatcggtgt actgttccgg gggccgcctg  120
gttgtgaaat atagtgacgg tacagcctcc accgtgtcgg gttctgcggc ctgtgagagt  180
gtgaaaccgt cacctgtggt taccgtatca tcccacaaat agaatatgaa gagggaaggg  240
tgttactagt gttgattgtg gtgtttggtg gtggtgtgtt gtgagataca ttccagcggc  300
gcatcactcg gccggttcga atagtccggt gaacagggtt gtgattcatg cgacatgccc  360
ggatgtgggg tttccgtctg cttcgcgtaa ggggcgggcg gtgtctacgg cgaactattt  420
tgcttcccca tcgtctggtg gttcggcgca ttatgtgtgt gatgttgggg agactgtgca  480
gtgcctgtcg gagtctacga ttggttggca tgccccgccg aatccgcatt ctttgggtat  540
agagatttgc gcggatggcg gttcgcacgc ctcgtttcgt gtgccagggc atgcttacac  600
tcgtgagcag tggcttgatc cgcaggtgtg gcccgcggtg gagagggcgg ctgtcctgtg  660
tcggcagttg tgtgacaagc atggtgttcc gaaaagaaaa ctgtctgtgg ccgatttgaa  720
ggccggtaaa cggggcatct gcgggcacac tgatgtgacg gatgcgtggc atcagtcgga  780
tcatgacgat ccggggccgt ggtttccgtg ggacaaattt atggctgtgg tgaatggcca  840
cggctgcggt tcaagtagtg aggagttaac ggtggctgat gtgaaagcgt tacatgatca  900
gattaaacaa ttgtctgccc agcttactgg ttcggtgaat aagctgcatc acgatgttgg  960
tgtggttcag gttcagaatg gtgacctggc gcgccgcgtg gaggctttgt cgtgggtgaa  1020
gaatccggtg acggggaagc tgtggcgcag caaggatgcc ctgtggagtg tctggtatta  1080
cgtgttggag tgtcgtagcc gtattgacag gcttgagtct gctgtcaacg atttgaaaaa  1140
gtgatggtgg tttgttgtgg gtaaacagtt ttggttgggc ctgctggagc gggcgttgaa  1200
gacttttgtg caaacgtttg ttgctgtgtt gggggtgacg gcgggtgtca cgtatactgc  1260
ggagtcgttt cgtggtttgc cgtgggagtc ggcgctgatt acggctacgg ttgctgcggt  1320
tttgtcggtt gctacctcgt ttggtagccc gtcgtttgtg gctggtaagc caagcaagcc  1380
tcaggtggat gcgggtttgg ttgagcctca catggtggat gtgtcggatc ctggcatgat  1440
cgagccgacg gatgatgctg atcttggtgt gggctatgtg ccgaaacacg ctgccgagtc  1500
ggaggttggc acggtagagt cgactgttgc ataagtgaat atagatgtgt gccccagcgg  1560
tgctgccacg gttgtgtggt ggttgccgct ggggcactat ttttgtgtct atagtatttt  1620
atgattcgtt gctgtcgatg gtgtcttcga gcatctggta caggtggagg caggtgcaga  1680
tggtttcgct ggcctggtct agaacggttc ggccgataac gtttttgtgg ttgtcgcggt  1740
ggcggatgat agcccacatg atctcgtcgg ctgccgcctg taatagtttt gcctggtatg  1800
cgattccggc gagccagtct agtgcttcct ggcttgcgta ggggctctgg tcctcgctgt  1860
tgccgcgggt gttgctgttg tttgtggggt gtccttcact gtcgcatagc cataggattt  1920
cgctgcactc gtctagcgtg tcttggtcga tagcgagatc gtcgaggctg acattgttga  1980
cggtaaggtt cacgttgtcg atggagatgg gtacaccgta ctggttttca acactgtcaa  2040
caatgttttg tagttgttgc atgttggtgg gctgttgttg gacgatgcgg tgtatcgctg  2100
tgttgagggt ggtgtaagtg atgttgtgtg tgttgttcat ggtttttatg ccattccttc  2160
gttatcgtct ggcatgtagt atgtgctgtt tgcgtactcg gtgagggtga tgagtgtttg  2220
gtctgcccac tgtttcacgg tttgccgggt gactccgagt agttgggcgg ctgtggcgta  2280
ggtttggtcg tatccgtata cttcccggaa tgctgccaac ctagctaaat gttttcgctg  2340
tttggagggt tcacaggcga gggtgtagtc gtcgatggcg agttgtagat cgatcatggt  2400
aacaaggttg ttgccgtgat gctggggggc ggttggtggg ggtggcatgc ccggctccac  2460
actgggtttc catggtccgc cgttccagat ccattgtgcg gcttggatga tgtcggcggt  2520
agtgtaggtt cggttcatgt gtcacccccct gaacaggtcg ttggtgttgc tggtgcgggt  2580
ggtgtcgaat cgtccgacgc agtggcagta gtcgtacatg agtttgataa tgtgttggtg  2640
gtctcccaaa taggtgttgc cgctgatgct gtaggtggct gtgccgtctt tgctgatggt  2700
gtatttggcg gtgatggttt cggggttttc ggtgtcggtg atgattgctg tggtggtggt  2760
gcctactgtt tggagcacgg tggtttgggt tccgtcgtcg atggtggttt taaccatggt  2820
gtgtgttctc ccctttgtgt tagttgctgg tttggttgtc ggctagatga atgatgtcgg  2880
gtaagggttt cggctggtct aggtgttgtg tggttttgtt ggctaaacgt ttggctaccc  2940
tgtagcacat tttggtgtag tgtttgttgt cgaggttgtg gtattgttcc cgcaccgcaa  3000
tatatagcag ggagtcttgg tataggtcgt ctgcactgat tgcggggtag tgtgcggctg  3060
ttttggtgca tgcccggttg agtgtgcgta gatgatggtt tgtggcccac acccacgatg  3120
cggtggtggc taggtcggct tttgttggtc gtcggctcat ggcatctctt tcatctggct  3180
atctggtagt tgtttggtgt tttgttgttg atagtgtagc acacgagtcc ggggttgccg  3240
gtggtgcctg ttttgtgccg gaaccatgtg gattctcctt ccatggaggg gcattggatg  3300
aaggtgcgtt gtccttgctc ggagatttct aggtggtgcc ggtgcccggc catgagaatg  3360
tgggatgtgg tgccgttgtg gaattcttgt ccgcgccacc attcgtagtg tttgccggtg  3420
cgccattggt ggccgtgggc gtgcagtatc cgtgtgcctg ccacatcaac ggtggtggtc  3480
atttcgtcgc gttgggggaa gtggaagtgt aggttggggt attggttgtt gagctggtag  3540
gcttctgcga tggcgcggca gcagtccagc tcgaaggagt cgtcgtaggt ggtgactcct  3600
ttgccgaagc gtacggcttc tccgtggttg ccggggatgg atgtgatggt gacgtttttg  3660
cagtggtcga attggtggat gagttgcatc atggccatgc gtgtcaaccg gatttgttcc  3720
gtcaaggggg tttgtgtgcg ccaggcgttg ttgccgcctt gtgacacgta tccttcgatc  3780
atgtcgccga ggaatgcgat gtggactcgt tgcggttttc cggcttgttg ccagtagtgt  3840
ttagctgatg tgagggtgtg taggtagtcg tcggcgaagt gtgatgtttc tcctccgggg  3900
atgcctttgc cgatttggaa gtctcctgcc ccgatgacga aggccgcggt gctgtagtcg  3960
gtgcgggtgt cttgttcggg ttttgggggt gtccattcgg ctagcttgtc gacgagttcg  4020
tctaccgggt aggggttggt tgcgggttgg tggtcaataa tttttgtat ggatcggcct  4080
gtttctccgt tcggtaaggt ccattcggag atgcgtgtgc ggcgcacggt gccgttggct  4140
agattgtcgt cgatggtgtc gatggcgttg tcgtggttgg cgagctgtgt gaggagccgg  4200
tctatgttgt ctatcatcgg gtatcctcct cttctgtttg tggtgtggtg gcttgtttgc  4260
ggcggtagtc tttgatgacg gtggcggaga tggggggggta tcctcctctt ctgtttgtgg  4320
tgtggtggct tgtttgcggc ggtagtcttt gatgacggtg gcggagatgg ggtatccggc  4380
ttcagtgagc attcgggcta gctgtgtggc ggggatcgtc ttgtcggcga ggacgtctgc  4440
agccttatca ccgtagcgtt ggatgagggt ttcagttttg gttgccatgg tgtcctatcg  4500
```

```
gttgtgtggt gggctgccat cctgtgcggc agtcgccgtc gtgtcctggt ttgcgtgtgc  4560
accacgatac ggttccgtct gtgtggttga gtgttttgcc gcacatgacg ttttgtagat  4620
gctcgggcag tgcgccgtta ctctggttgc tggtttgtgt gtcgaagagt gttttctggt  4680
tggtgaaatg ctcggatacg gtgccgttgt ggactgggag tatccatgtt ttccattgtt  4740
gttgcatccg ggtgttccag tggaattgtt tagccgcgtt ttctgcctgt ttggcggttt  4800
tgtagtagcc tacaatgatt cgctggtggt tgttgtctgg ctggtgtggc cctttccagt  4860
attgtgccgc cacggcgtag cggttgctgg ctgtgaagcg ctcccagcag tattcaataa  4920
tgtgttgcag tacactatcg ggaatgtctt gtgcttggtt ttcgttaagc cattcttcaa  4980
caatgatgtc gcgtatggcg cgtttgtctt tagtggtggg tttgaacgag atgctcacga  5040
tagcaccggc tggtcgtctt gcatgaactg gttgaaggtg ttgttcccgg cgtgttgggc  5100
ttgtgtgatt tgctggtcgg tccagtctgg gtgttgctgt ttcagatagt gccagtggca  5160
cgcattgtag gtttcgtctt gtagccgtgt gagatggttt tcggtgatga tttgtttcca  5220
catagtccac gagacgtcga gcctgttgag gatttcgagg gctgggatgt tgaattggtt  5280
gaggaacagg atttcgtggg tgtagtattc cttctcgtag gcgtcccatc cgcttcggtg  5340
cctgttgggc tggtttttgg ggtaggcttc ccggcagatt ttgtgcaaat gtttggccat  5400
gtcgtcgggt agtttaatgt cagggttggc gcggatcatg gatcgcatcc catcataggt  5460
ggtgccccag gtgtgcatga tgtaggtggg gtcttcacca tcagtccatt tttctgcaca  5520
gatggcgagg cggatacgcc tcctggcggc ttggctggtg ttgcgccggt tggggattgg  5580
gcacgtgtcg aggggatcca tgatgctttt tatgcctttc tttgtttggg ttgtttgtct  5640
agttttactg tagcacagtg tctagtgctt gtgtcaaccc tgtttttccg gcctgcaggt  5700
aggtgtctgt gacgtcgccg agggtgaggg gcacatgggt ggcttggggg agtgctgcct  5760
ggagggtgtg ggccatctgg tcgcctgctt tgtctgggtc tgaccatatg tagatgtggt  5820
cgtagccttc aaaaaatttg gtccaaaagt tttgccacga ggtggcgccg ggtagggcga  5880
cggccgacca tccgcattgt tcgaggatca tggagtcgaa ttcgccttcg caaatgtgca  5940
tttcggctgc ctggttggcc atggcggcca tgttgtagat ggagcctgtg tcccctgccg  6000
gtgtcaagta tttggggtgg ttgtgggttt tgcaatcatg gggagtgagg cagcggaaac  6060
gcatttttcg tatttcggct ggcccttccc agacggggta catgtagggg atggtgatgc  6120
actggttgta gttttcgtgg cctgggatgg ggtcattgtc gatgtatcca aggtggtggt  6180
agcgggctgt ttcttcgctg attcctcttg ccgagagcag gtcgagtatg ttttcgaggt  6240
gggtttcgta tagggccgag gctttctgga ttcggcggcg ttccgcaatg ttgtaggggc  6300
gtatgctgtc gtacattcgg gttttcttcc tctaatcgtt gtttcagttt gtggagtcca  6360
cctccgatac cgcatgtgtg gcagtaccag acgcccttgt cgaggttgat gctcatggag  6420
ggctggtggt cgtcgtggaa cgggcagagg atgtgttgct cgttcctgga cgggttgtag  6480
cgtatctggt gggcgtcgag gaggcggcag gtgtcagagg tgtgggagga gctcgttgag  6540
ggttgatacc acataggctt cgctccaggg tttgttgcgc tgtttcatga tgacgagtcc  6600
gatggtggac tggttttctc ggtttcggtg ggtttcatag ttgcgtgcct cccggctggc  6660
ttgtttcacg aattcggcga gatgtggttg cccggctttc gcctcgataa tgtaggtttt  6720
gtggccggtt gtgaggatga ggtcgccttc gtcttcgcgg ccgttgaggt ggaggcgttc  6780
gatatcatgt ccgatgtcgc gtagctggtg gaggagtctt gtttcccatt cggccccagc  6840
tcgcctattc ctggattgct gtgtagccat catagtcctt tgtgtgttgg ggtcatgttc  6900
cagggctgtt tttctactag gggtccgaag aatgtgtatt cggggtaggc tcgtagtcgt  6960
tcgtatcggg tgccgtctgg gctggatttg ccggttctct gtttgagtac ggcgatgcgc  7020
gcctcggcgg ggatggtgag cccgttgccg ttgtcttcgc caccgtagag tgagactccc  7080
aggattagtt gtggtttttc ggagaggccg tttttgattt cccgcctagc tggggggtgt  7140
tcgatgtcgg tgccggtttt gtcggttgcg tggtgggtga caataatggt ggagccagtg  7200
tcgcggccta gtgctgtgat ccattgcatg gcttcttgct gtgcctgata gtcactttcg  7260
cagtcttgga tgtccatcag gttgtcgatg acgatgatgg gtgggaaggt gttccacatt  7320
tccatgtagg cttggagttc catggtgatg tctgtccatg tgatgggtga ctggaatgag  7380
aatgtgatgt gtccgccgtg gtggatgctg tctcgatagt attctggccc gtagttgtcg  7440
atgttgtgtt gtatctgttg ggtggtgtgt tgggtgttga gtgagatgat tcgtgtggag  7500
gcctcccagg gtgtcatgtc ccctgatatg tagagggctg gctggttgag catcgcggtg  7560
atgaacattg ctagccctga tttttggctg ccggaccgcc ccgcgatcat gactaggtcc  7620
cctttgtgga tgtgcatgtc ctggttgtca tacaagggtg ctagttgggg tatgcggggc  7680
agttcggcgg cggtttggga ggccctctcg aaggatcttt ggagagagag catcggagcc  7740
ttaatctatc tgtctgttgg ttgggtgttg gtggtcagat ggagtcgatg tcgatgtcag  7800
catcggcggg ggctgtggtg tcgtctagct ggccggtgtc gcgcttgtct acgtattcgg  7860
caaccttatc gtagatggcg tcgtccaatg gtttgaggac gaccgcgttg aacccgtttt  7920
tggtgcgaac ggtggcgagt ttgaaggcct gctcttcgcc gagataggct tctaggtcgc  7980
ggatcatgga gtgtgggcgg tcgttgttgc ctcgcgcttt ctcgatgata gcgttgggga  8040
tagtttctgg ggtgccattg ttgagatcct ggagtgtgtg gaagatggtg acatcggcgt  8100
aaatacggtc ggcgacctgt ccgccgtagc cttcggtgtt gtgctggacg tcgcggattt  8160
tgaaggcgat ggcggtggcg tcctggtttc gggaggggtt gaagaaggtg ctgttgctgt  8220
tgttgcggta gttggcgagt cccattgttg tttcctttac tatttgtgtt ggtttttgtt  8280
gtcttatatt ggtttatcgg gtgaggctgt ttcgtttact gcggaacgcc tcagacacgt  8340
cactgttact ggtgatgatc ttcttgtact gtttgaggag gtctgctagt tgtgtcttgc  8400
tggtggcttt gttgatccgg tcgatgatga tgtcgttttc ctggttggcg attttgttga  8460
cgtagtcttt ggcggcttta tcgtatcgat cttgaagcag gattgctgcg ctagcgatca  8520
aggtggctaa atcccagtct ttggatacgg tttcgtcttt caatcctcct agcaggtcaa  8580
tgatggattg tttgatgtct tctgcggtgt ctccgcggat gactgtccat ggggcggcat  8640
agtctccacc gtatttgagt gtgatagtta gttttccgtt gtctgtggtg tgctcgtcgg  8700
tcacgtgttt tccttttcgt tactgtcggt ttggggtggc tgtacggtgg tttctatcgg  8760
gtatctgtac gagtttttgc cgttgacggc ccagcaggcg tccttgacgg ggcatccttt  8820
gcagagtgct gtgacgtggg gtacgaagat gccttggctg attcctttca ttgcttgact  8880
gtacatggat gatacatgcc ggtaggtgtt gttgtcaagg tcgtagagtt cggttgctgt  8940
gccctgctcg actgattgct cgtctccctt ggtggtggcg ggtgtccaaa acatgccttt  9000
cgtcacatgg atgccgtgtt ggttgagcat gtaccggtat gtgtgcagct gcatactgtc  9060
ggcgggtagg cggccggttt tgaggtcgag gatgaaggtt tcgccggtgt tggtgtcggt  9120
gaatacccgg tcaatatatc cgacaatctg ggtgccgtct tggagggtgg tttctaccgg  9180
gtattcgatg cctggctggc cgtcaataac agcggtagcg tattctgggt ggttgcgcct  9240
```

```
ccatgttttc caccggtcca caaaggtggg gccgtatatc atccaccaat tgtagtcttt  9300
cttgttgggg cccccgcttt cgcacatgtt tttgcacact cggccggagg gtttgatgtt  9360
tgtgccttcg gattcggcga gggcgatttg ggtgtcgaaa atgtttgtga aggatgcgag  9420
tttgtctggt agtgcagggt attcggcggg attgtacagg tgtaagtcgt attgttcggt  9480
gatgtggtgt atggcgcttc cggcgatggt ggcgtaccag gtgtggtgtt gggtgtggta  9540
gccgtgggat aggcgccatt tttctccgca ttcggcccac tgtgacagtg aactgtagga  9600
gatgtggcct ggatggtgga tggttttcgg gtattgtgct aggggcatta cttgtcgcct  9660
ttgtgggtgt tccatgggtt gcgggtgtct accccggcat cgtgttgctg gtaggcgagg  9720
agtgccaagc agtgccaggc agcatgtgcc agatgcggca aatgtgattc gtggtcgagg  9780
ttgtttcctt gctgccatga tagcaggtgc ctgtagaggg cgtcgacact gtggctccac  9840
gggtagccgc cggtccagtt gttgtcgccg tatttggtgg caccgtagcc tgccacttcg  9900
ccgagggcgt gcaaggcggt agggtcgatg agggatagcc tgcaaagttt caattctttc  9960
ttggcacccg tatcagggtc ggtgtacatg ctggttggct catccatggt gtgtgtgctc  10020
cttacgtgtg gggttactgg ttggggttgt gggcgagtgc tacggcgaga ataatgatgg  10080
cgagggtttc tgcgatcagt attggtgttg tgatcatttg ctgtcgcggg gattgttggt  10140
gagggtggat gcgcctagca gggtggtgag ggcgcatgcg gcgatgatgg cgagggcggc  10200
tttgtggctg gtgccggtgg cgtacatcca tgtgatgatg gcgccctgta tccatgccag  10260
tgtggtgaag aacgtttcgt agctgtgcag ctcgatactg ttgggtgtgt tcatgcttgc  10320
tcctgaagaa tggtgttgat ggttgtgtaa atgttgtaca ggtcggcttc gatggtttgt  10380
agctgtttga tttggtggtc gaggtcaatg tttgggttga gggtgttgat gcgggatgcg  10440
atgtcggtgg ctgtgcgtag tgtgccgccg gtgtggtgaa tgatgtgtgc cgtgtcggcg  10500
agtccggtgg tgacagcgta gcgggagagg agaggcatga ctggggggtg ctccttgacg  10560
gggttactgt tgcgggttga tgttgaggtc ggtgacgtgc ggtgagcttt ctgttcctgt  10620
gacgaggcag tggacggtga cggggagttt ggatgctccc ggctggcgga cggtggcgcc  10680
gtagacgatg ctgaacgtgt ctttgccaat aattttgtgg agttggaggt cgatgtcggg  10740
gttgccgttc catttgacac cctgtgctgc agctgcctgt tcagccttgt cattgcaggc  10800
gtgtgccgcg gtgatcatgg tgagacctgt ggaggtttct tcaccccgtg tttgggcttg  10860
ccggtgggcg cgctgctgtt cggcttggag ggagcggact gctgcagcct gcttggcggc  10920
tttctcggct ttgcgctgtt ggacggtttc aggtgtccat tcggtgttgg ctgtggtggc  10980
ttgtggggct ggctgtgagg cgagtggcgg attatcatcg ggtgccggga ggaaggatgc  11040
tgcggcgatg atggcgatgg tggcgccggc gatggtgtag cctgttttct tgttcatgat  11100
tttgtgttcc cctttccggg gtgttgttcg ttgctgacat gatcaatact ttcagcggct  11160
ggaccctgtg tcaaggtgtc gctcagtatt cttgagcgaa tgtggtttga ctggggggtga  11220
tggcttcttt cgcccaatag gatgtgccac cgctggtcca gtatccgagt ttgttgcgct  11280
gcatgccctt ggcttccatc tcatccacgg tgaggcacct gcggcgattg gggccttcct  11340
tgaccccgtg gtcgcctacc cggtgcatgt cgcctgaggt ggtactcgtg aatgtttcgt  11400
ggcagattgt gcagtgctct ggtcggtatc cgatgattgt gctatcgcac ttgtggcatg  11460
tccattgcat gattgctcct attttccatt ataagacttc ctgtagtgcc attttagcgc  11520
cttgcgggtc ttgggggtac aactatatag gtcaggtatt tctaggcgat tctaggctca  11580
ttgtgtgcga ctggtggtta tcgggcgcac agagtgagca ggtggccaac attgatgcgg  11640
gtcacattcc agtagagttg cgtggcttcc tcactggtga gcggcttcca ctcgttgtgg  11700
ctgaacacgg tgccatcgga tgctatgaac gtgttggggc gtagcttgtg gagttcagtc  11760
tctacatgcc gacggtaggt ttcggcgagg ccctcgaaat cgaggtggtc gcaggagagg  11820
ttttcgaggc gtgtcaggtc gaaaggctca gggcagtcgt agctggcggg gctgtagagc  11880
tgggtgaagt ggttggcaat cttctgcatc atgattcctt ttctggtgat ggtgtgttga  11940
tggttttatc gggtggatgc tttgaggatg gcgtctacat cgatcatgtc gatcatgtcg  12000
ttgagttcct cggcctcatt ctcggagagg tggcgccagc cgggtggccc gtatagggcg  12060
ccgtcgaggg tgacagtcca caggggccgg atgagtcgta tggcttcttc gactttggcg  12120
tggtacatgc ggcgcaccat atccagatcg atgtcgtctg aatggtttcc ggtgaggctg  12180
tggaggctga gtgggtcgat ttctgtctgc ccgtagaggc tggtgaatga tggtgtgatg  12240
agtgtgccat ccatgagggt gctcccttct gaactgtttg ggttggttgt tgtggtttct  12300
agagtgtgta ggttgcaacc ccatagtcaa ggctacgctc attcggattg agcgtttcat  12360
gctggagtgt gtcgggtgtg acagatgtca ctgaatcctt gatggcctct ctcagcgcct  12420
gaaatatgtc cggggtggga ttatgcaggg ttgaccctgc tgatcgattc taggcccct  12480
acagggcgtc tcaggggtat gtctgggtga tagcaggttc ggtagatgat ctagcgagtc  12540
aaggtgccaa gctgagacag aagatctacc atctaggtgt gtgagatgta tcacactcgc  12600
ctggcttagt gtgcaccctc aagaccacct agtcgatctg gcgtggaggg tgcagcccag  12660
aaataccgtt taaagccttc gcgcggagcc taggagcgcc ttacagggtg ggggctaggt  12720
attcataccc ccaagcaatt ctgatcgatt ctagacgcct ccaggggccc gatacacgat  12780
cagtagtcca gacacagatc atcaacccct atcctggtta gctaagcctc aactatgtgg  12840
acagtgtggg atgctaagag ggaagaagga cacggtaaaa gaaagagggg ggagcatcag  12900
ccttcaagcc tgaaggtctt agcgcttagc accgagcccc ctcaagggct cggcatcagc  12960
ccgaacaggc tcagctcatc aggcacagcc ctgaaaaggg tacacgccat cagggaaggc  13020
ttgagagtac gaggagccct agcgacgagt actcgaaagc ctgaggaaac accctcagca  13080
ctgatgggcc tagcgtgttc ggaaaggaca caagagtaaa gtgtgacagc tgtccgggag  13140
tgaaacccgt tccggctagg ggtttcagcc ttaaccaccc tcaaaggtta caagactcta  13200
agaaaattta agaaaactct taggaagaaa gttgtgttca tatcccccta aaaacaccca  13260
aaatagccct caaacccgcc tatagagcca aaaccaccag tttgactcat cccaggtggg  13320
gtatgatagg ctggacaggt agccagctgg acgcgaggcc agaaagtgct gacgcacttc  13380
ccgacctcgc ttaccatcag tctaccaaac actttaaagc ttcaaggctt agcgctaagc  13440
ccttaagacc ttaacactga acaccgagcc ccctcaaggg ctcggcatca gccttaaagc  13500
cttaaacact ttaagtaact ttaaaacctt aacagcttaa cacttaaggt tataaataaa  13560
cattaaagct ttaaagtctt aaagtaaata tataacctta acacttaagt taagtataaa  13620
accttaaaag ctaagcactt aaagatataa acttaacatc agtgtttaag acttaaagag  13680
ttaaagtaac tattaagact taaaggctta taagctttaa acacttaaag taactataag  13740
actttaaaaa ccttaagtac ttaaagttaa ccatcagtct taaactttaa tactataacc  13800
tataagtctt aaagcttata ggtataataa tataatataa gtattaaagc ttataagtta  13860
taaaagtttt agaagagtta aagggttaac ttctttactt ctcttctctc tttggttctt  13920
tctctcttct cttcttttct tcatcagggg agaagaggaa cctttaaccg tcaacgctga  13980
```

```
tggactttca accgtgtgac tcgtgtacca ccggtcgcac gctcccgatg gcacactccc  14040
cacatgctac ctgtgtccct ttcaggctta gcgtgttcgg ctgaaggcgt acggcgtgtc  14100
acgcttaaac ccttaacacc aggtaagact taaagtgtat attataagta gaagacttta  14160
aaacctttaa ggtgttcccg ctgagcctgt gttcttcacc gctaggcgct aagcgctaag  14220
ccttgaaacg cgaacaccca tccacccttt tcttttaccg tgtccttctt cttttgacac  14280
cgctgggggg cgatgtgatc tttttcacat gccagggggt aggagaagaa aacaaccacc  14340
ccggcacaaa cagaacaccc ccctaaacga acaaaacagg gcccaggatc gaacagcagg  14400
gcaccggtag agtattccta cccccagaca attccaggcc gttacaggag caatgagagg  14460
ctcacagggg ccataggaga tcaggggacg tgatggcaca caccaaccgc acagccagcc  14520
aagcccaccg gcgctggcgg caacgactca tcacccaagc caaacagcaa ggccaaaccg  14580
aatgcccact ctgcggagcc accatcacct ggggcacaca tgacctgcca accagccccg  14640
aagccgacca catcacaccc gtcagcaggg gaggactcaa caccctcgac aacgggcaaa  14700
tcatctgcag aacatgcaac agaagcaaag gcaatcgcag cgaaccaaac attcaattcc  14760
aacaacaaac cacaaaaacg ttgatcccat ggtgaaaaaa cagccaaccc ccacgggaac  14820
cacccccctgc acacccgtgc aagacctcgt acggcttagt gaaatacctc cctttttgtgg  14880
ttttgtctgt ctgtcgactt tttgtgttgg tggtgagtgt tgtgcagcct gagcttcctg  14940
atagtcgtgg atggtgtggg gagacgcgtc gttggtggcg tgtgtggggt gaggatagtc  15000
gcgcgcagta cgtgtctgat gaggagtggc tgtttctcat ggatgctgcg gtgattcatg  15060
attgtgtgtg gcgtgagggt cgcgcggatt tggtggcttc gcttcgtgct catgtgaagg  15120
cttttatggg catgttggat cggtattcgg ttgatgtggt gtctggtggc cgtggtgggg  15180
gttctgctgt ggcgatgatt gaccggtatc ggaagcgtaa aggggcctaa tgtcgagcgt  15240
tgttggttct caggttcctc gtcaccgggt ggctgcggct tattcggtgt ctgctggcgg  15300
tgatgcgggt gagcttggta gggcttacgg gttgacgcct gatccgtggc agcagcaggt  15360
gttggatgat tggctggctg tgggtggtaa tggcaggctt gcttcgggtg tgtgtggggt  15420
gtttgtgcct cgccagaatg gcaagaatgc tattttggag attgtggagt tgtttaaggc  15480
gactattcag ggtcgccgta ttttgcatac ggctcacgag ttgaagtcgg ctcgtaaggc  15540
gtttatgcgg ttgaggtcgt tttttgagaa tgagcggcag tttcctgact tgtatcgtat  15600
ggtgaagtcg attcgggcga cgaatggcca ggaggctatt gtgttgcatc atccggattg  15660
tgccacgttt gagaagaagt gtggctgtcc gggttggggt tcggttgagt ttgtggcccg  15720
tagccggggt tcggctcgcg ggtttactgt tgatgatttg gtgtgtgatg aggctcagga  15780
gttgtcggat gagcagttgg aggctttgct tcctacagtg agcgctgccc cgtctggtga  15840
tccgcagcag attttccttg gcacgccgcc tgggccgttg gctgacgggt ctgtggtgtt  15900
gcgtcttcgc gggcaggcgc ttggtggcgg taagcggatt gcgtggacgg agttttcgat  15960
tcctgacgag tctgatccgg atgatgtgtc gcggcagtgg cggaagcttg ctggtgacac  16020
taatccggcg ttgggtcgtc gtctgaattt tgggactgtg tcggatgagc atgagtcgat  16080
gtctgctgcc ggttttgctc gggagcggct tggctggtgg gatcgtggcc agtctgcttc  16140
gtcggtgatt ccggcggata agtgggttca gtctgctgtg ggtgaggcga gtcttgttgg  16200
cggtaaagtg tttggtgtct cgttttctcg ctcgggggat cgtgtcgcgt tggcgggtgc  16260
tggccggact gatgctgggg ttcatgttga ggttattgat ggcctgtctg gcacgattgt  16320
tgatggtgtg ggccagctgg ctgactggtt ggcgttgcgt tggggtgaca ctgaaaagat  16380
tatggttgcc gggtcgggtg cggtgttgtt gcagaaggcg ttgacggatc gtggtgttcc  16440
gggccgtggc gtgattgtgg ccgatactgg ggtgtatgtg gaggcgtgtc aagccttcct  16500
ggagggtgtc aggtcgggtg tgatcagtca ccctagggct gattcgaggc gtgacatgtt  16560
ggatattgct gtgaggtcgg ctgtgcagaa gaagaagggt tctgcgtggg gttggggttc  16620
ctcgtttaag gatggttctg aggttccttt ggaggctgtg tctttggcgt atcttggtgc  16680
gaagatggcg aaagcgaagc ggcgtgaacg gtctggtagg aagcgggtgt ctgtggtatg  16740
aactcggatg agttggctct gattgagggc atgtttgatc gtatccgaag gttgtcttcg  16800
tggcattgtc gtattgaggg ctactatgag ggttctgccc gggtgcgtga tttgggggtg  16860
gctattcctc cggagttgca gcgtgtgcag acggtggtgt cgtggcctgg gattgcggtg  16920
gatgctttgg aggagcgtct ggattggctt ggctggacga atggtgacgg ctacggcctg  16980
gatggtgtgt atgctgcgaa tcggcttgct acggcgtcgt gtgatgtcca ccttgatgcg  17040
ctgatttttg ggttgtcgtt tgttgcgatc attccccaag aggatgggtc ggtgttggtt  17100
cgtccgcagt cgccgaagaa ttgtacgggc cggttttctg ccgatgggtc tcgtttggat  17160
gctggccttg tggtgcagca gacgtgtgat cctgaggttg ttgaggcgga gttgttgctt  17220
cctgatgtga ttgttcaggt ggagcggcga ggtagccgtg agtgggttga gacgggccgt  17280
atcgagaatg tgttgggtgc ggttccgttg gtgcctgttg tgaatcgtcg ccgtacttcg  17340
aggattgatg gccgttcgga gatcactcgg tcgattcgtg cttacacgga tgaggctgtt  17400
cgcacactgt tggggcagtc tgtgaatcgt gatttttatg cctatccgca aaggtgggtt  17460
acgggtgtgt cggctgacga gttttcgcag cctggctggg ttctgtcgat ggcttctgtg  17520
tgggctgttg ataaggatga tgacggcgat accccgaatg tggggtcgtt tcctgtgaat  17580
tctcctacac cgtattcgga tcagatgcgt ttgttggcgc agttgactgc gggtgaggcg  17640
gctgttccgg aacgctattt cggtttatc acgtctaacc cgccttcggg tgaggctttg  17700
gctgcggagg agtctcggct tgtgaagcgt gctgagcgga ggcagacgtc gtttggtcag  17760
ggctggttgt cggttggttt cttggctgcc agggcgttgg attcgagtgt tgatgaggcc  17820
gcgttttttg gtgatgtggg tttgcgttgg cgtgatgctt cgacgccgac tcgggcggct  17880
acggcggatg ctgtgacgaa gcttgtgggt gtcggtattt tgccggcgga ttctcggacg  17940
gtgttggaga tgttggggct tgatgatgtg caggttgagg ctgtgatgcg gcatcgtgcc  18000
gagtcgtcgg atccgttggc ggcgctggct ggggctattt ctcgtcaaac taacgaggtt  18060
tgataggcga tggcttcggg ggttgtgtcg aggcttgctg cgactgagta tcagcgtgag  18120
gcggtcaggt ttgccgggaa gtatgcgggc tattatgccg agctgggtcg tttgtggcat  18180
tccgggaaga tgacagatgc gcagtatgtg cgtttgtgtg tggagttgga gcgtgccggc  18240
catgacggtt ccgcggcgtt ggcgggcaaa ttcgtgtccg attttcgccg gttgaatggt  18300
gtggatccgg gtttgatcgt gtatgacgag tttgatgctg cggcggcgtt ggctaggtcg  18360
ttttcgacta tgaagattct taagagtgac ccggataggg cgaatgatac gattggtgcg  18420
atggctgcgg gttttgatcg ggctgtgatg aatgctggcc gtgacacggt tgagtggtct  18480
gcgggtgtgc agggtaggtc gtggcgcagg gtgactgatg gtgatccgtg tgctttttgt  18540
gccatgttgg ctacgaggtc ggattatacg actaaagagc gggcgcttac tacgggtcat  18600
actcggcgtc ataagcgtgc cggtaggcgt ccgtttggtt cgaagtatca tgatcattgt  18660
ggttgtacgg tggttgaggt tgttggccct tgggagccga atagggctga tgccgcatat  18720
```

```
cagaggacgt atgagaaggc tcgtgagtgg gttgatgatc atgggttgca gcagtcgcct  18780
ggcaatattt tgaaggctat gcgtactgtt ggcgatatga gatgatggtt tccggttgtg  18840
tgccgccggt tattggtgca cagggttgtc tcccgcacgg gggtcaacaa tgttgtgttg  18900
ttttccgcaa ggagtgtagg ttaggctatg gccgatcaga gtgttgaaga acagaatgtt  18960
gacaatgatg ctgttgagcc cggaaagggt ggagacgttg ttgatgttgt gaaggatggg  19020
caggctgccg gcgatgatca tgccggtgat gtttccgtga aggaggagtc ttcttctggc  19080
acggattgga aggctgaggc ccgtaagtgg gagtctcgtg ctaaaagtaa ttttgccgag  19140
ttggagaagc ttcgcgcctc ggatggtgat gcggggtctg tgattgatga gcttcgccgc  19200
aagaatgagg aactcgaaga ccggattaat gggtttgttc ttgagggtgt gaagcgtgag  19260
gtggctgccg agtgtggcct gtcgggtgat gcggtcgctt tcttgcacgg tggcgatcgt  19320
gaagcactgg tggagtctgc taaggctttg aagggtttga tcgaccagag tggtggtggc  19380
gcgggtgtgc gccgtcttgc ggggagtgcc cccgttgatg atgttaaacg acgtgagggt  19440
gtcgcgtttg tggatgctct tgtcaataat tctaggagat gatttataat ggctgacgat  19500
tttctttctg cagggaagct tgagcttcct ggttctatga ttggtgcggt tcgtgaccgt  19560
gctatcgatt ctggtgtttt ggcgaagctt tcgccggagc agccgactat tttcggcccg  19620
gtgaagggtg ccgtgtttag tggtgttcct cgcgcgaaga ttgttggtga gggcgaggtt  19680
aagccttccg cgtctgttga tgtttcggcg tttactgcgc agcctatcaa ggttgtgact  19740
cagcagcgtg tgagcgacga gtttatgtgg gctgacgcgg attaccgtct gggtgttttg  19800
caggatctga tttcgcctgc tctgggtgcc tcgattggtc gcgccgtgga tttgattgct  19860
ttccacggta ttgatcctgc cactggtaag cctgccgcgg ctgtcaaggt gtcgctggat  19920
aagacgaagc atattgttga tgccacggat tccgctacga ctgatcttgt gaaggctgtc  19980
ggcctgatcg ctggtgctgg tttgcaggtt cctagcgggg ttgctttgga tccggcgttc  20040
tcgtttgctc tgtctactga ggtgtatccg aaggggtctc cgcttgccgg tcagccgatg  20100
tatcctgccg ccgggtttgc cggtttggat aattggcgtg ggctgaatgt tggtgcttct  20160
tcgactgttt cgggtgcccc ggagatgtcg cctgcctctg gtgttaaggc tattgttggt  20220
gatttctctc gtgttcattg gggttccag cgtaacttcc cgatcgagct gatcgagtat  20280
ggtgacccgg atcagactgg gcgtgatctg aagggccata atgaggttat ggttcgtgcc  20340
gaggctgtgc tgtatgtggc tatcgagtcg cttgattcgt ttgctgttgt gaaggagaag  20400
gctgcaccga ctcctcctcc ggctggtaac tgatacaaga taagcgaatg tgtactatgt  20460
gcagggggtg gtgttgatgg gtatcatttt gaagcctgag gatattgagc ctttcgctga  20520
tattcctaga gagaagcttg aggcgatgat cgctgatgtg gaggctgtgg ctgtcagtgt  20580
cgccccctgt atcgctaaac cggatttcaa atacaaggat gccgctaagg ctattctgcg  20640
cagggctttg ttgcgctgga atgataccgg ggtttcgggt caggtgcagt atgagtctgc  20700
gggcccgttt gctcagacta cacggtctaa tactcccacg aatttgttgt ggccttccga  20760
gattgctgcg ttgaagaagt tgtgtgaggg tgatggtggg gctggtaaag cgttcactat  20820
cacacccact attaatagta gatatgcaca ttctgaggtg tgttccacgg tgtggggtga  20880
gggttgctcg tgcgggtcga atattaacgg ctacgctggc cctttgtggg agatatgata  20940
tgaccagttt tccttatggt gaaacggttg tgatgcttca gccgactgtt cgtgtcgatg  21000
atcttggcga caaggtggaa gactggtcta agcctgtcga gactgtgtac cataacgtgg  21060
ccatttatgt ctctgtttcg caggaggatg aggctgccgg ccgtgactct gattatgagc  21120
attggtcgat gcttttcaag cagcctgttg tgggtgccgg ttatcgttgc cggtggcgta  21180
ttcggggtgt tgtgtgggag gctgacgggt ctcctatcgt gtggcatcac cccatgtccg  21240
gttgggatgc tggtacgcag gttaatgtga agcgtaagaa gggctgatgg gttgtggctc  21300
aggatgtgaa tgtgaagctg aacttgccgg gtattcgtga ggtgttgaag tcttctgggg  21360
tgcagtcgat gttggctgag cgtggcgagc gtgtcaagcg tgcggcctcg gcgaatgtgg  21420
gcggtaatgc ttttgataag gcccaatacc gtagcggttt gtcgtcggag gtgcaggttc  21480
accgtgttga ggctgtggcc cgtattggca ccacctataa gggtgggaag cgtattgagg  21540
cgaagcatgg cacgctggcc cggtcgattg gggctgcgtc gtgatcgttt atggtgatcc  21600
gcgtgtgtgg gctaaacgtg tgctcaagga tgatggctgg ctgtccgata taccttgtgt  21660
ggggacggtg cctgaggatt ttagcggtga cttgatttgg ttggctcttg atggtggccc  21720
gcagttgcat gttcgtgagc gtgttttttt gcgtgtgaat gtgttttctg atatgccgga  21780
tcgtgctatg tcgttagcta ggcgtgttga ggctgtgctg gctgatggtg tggacggtga  21840
cccggtggtg ttttgtcggc gttctactgg ccctgatttg ctggttgatg gtgcacgttt  21900
tgatgtgtat tcgctttttg agctggtgtg tcggcctgtc gaatccgagt aagcgtatcg  21960
ttgtttttta gtttgattgt tttgtagttt gattgttttt tgggggttat gatggctgaa  22020
acacgtaaag cgtctaatgt tcgctctgct gttactggcg acgtttatat tggtaaagcg  22080
cacgcgggtg attctattaa gggtgtggag gcggttcctt ccgggcttac agctttaggg  22140
tatctgtctg atgacgggtt taagattaag cctgagcgta aaacggatga tttgaaggct  22200
tggcagaatg cggatgttgt tcgcactgta gctacggagt cgtctatcga gatttctttc  22260
cagctgatcg agtctaagaa agaggttatc gaactgtttt ggcagtcgaa ggttactgcc  22320
ggatccgatt cgggttcgtt cgatatttca ccaggcgcca ccactggcgt gcatgcttta  22380
ctgatggata ttgttgatgg tgatcaggtt attcgctact atttccctga ggtcgagttg  22440
atcgatcgtg acgagattaa gggcaagaat ggcgaggtgt atgggtatgg tgtgacgttg  22500
aaggcgtatc ctgcccagat taataagact ggtgatgcgg tgtctggtcg ggggtggatg  22560
acggctttaa aagctgatac tcctccgact cctcctccag ccccggttcc tccgaagcct  22620
cagccggatc cgaatccgcc gtccgataac tgatacacga ttttagggga ttgttgatag  22680
atgagtgaca ctggttacac gttgaagatt ggtgaccgta gctgggtgtt ggcggatgcg  22740
gaggagacgg ctcaggctgt tcctgcccgc gtgtttcgcc gtgccgccag gattgcccag  22800
tcgggtgagt ctgcggattt cgcccaggtt gaggtgatgt tttcgatgtt ggaggctgcc  22860
gcaccggctg acgcggtgga tgctttggag gggcttccta tggttcgtgt tgccgagatt  22920
ttccgcgagt ggatggaata taagcctgac ggtaagggtg cctcgctggg ggaatagttt  22980
ggctccacgg cctgattgat gattatcgtg gggccatcga atacgatttc cgcaccaagt  23040
ttggtgtttc tgtttatagt gttggtggcc cgcagatgtg ttggggtgag gctgtccggc  23100
tggctggcgt gttgtgtacc gatacgtcta gccagttggc ggcccatctg aatggttggc  23160
agcgcccgtt tgagtggtgt gagtgggctg tgttggacat gttggatcat tacaggtctg  23220
ctaatagtga ggggcagccg gagcctgtgg tgaggccgac ggatgagcgt agggcccggt  23280
ttacgtctgg gcaggtggac gatattttgg cgcgtgttcg tgctggtggc ggggtgtctc  23340
gcgagattaa tattatgggg tgaatagtgt atgtctggtg agattgcttc cgcgtatgtg  23400
tcgttgtata cgaagatgcc tggccttaaa agtgatgttg gtaaacagct ttctggggtg  23460
```

```
atgcctgcgg agggtcagcg ttcgggtagc ttgtttgctg gcgggatgaa gttggcgctt  23520
ggtggtgcgg cgatgatggg tgccatcaat gttgctaaga agggcctcaa gtcgatttat  23580
gatgtgacta ttggtggcgg tatagctagg gctatggcta ttgatgaggc tcaggctaaa  23640
ctgactggtt tgggtcatac gtcgtctgac acgtcttcga ttatgaattc ggctattgag  23700
gctgtgactg gtacgtcgta tgcgttgggt gatgcggcgt ctacggcggc ggcgttgtct  23760
gcttcgggtg tgaagtctgg cgggcagatg acggatgtgt tgaagactgt cgccgatgtg  23820
tcttatattt cgggtaagtc gtttcaggat acgggtgcta tttttacgtc tgtgatggct  23880
cgcggtaagt tgcagggcga tgacatgttg cagcttacga tggcgggtgt tcctgtgctg  23940
tctttgcttg ccaggcagac tggtaaaacg tctgctgagg tgtcgcagat ggtgtcgaag  24000
gggcagattg attttaacac gtttgcggct gcgatgaagc ttggcatggg tggtgctgcg  24060
caggcgtctg gtaagacgtt tgagggcgct atgaagaatg ttaagggtgc cctgggttat  24120
cttggtgcta cggctatggc gccgtttctt aacgggttgc ggcagatttt tgttgcgttg  24180
aatccggtta tcaagtcggt gacggattct gtgaagcccc tgtttgcatc ggtggatcag  24240
gggattcagc ggatgatgcc gtctattttg gcgtggatta accggatgcc gggcatgatc  24300
actcgaatga atgcacagat gcgcgccaag gtggagcagt tgaagggcgt ttttgcgagg  24360
ctgcatttgc ctgtccctaa agtgaatttg ggtgccatgt ttgctggcgg caccgcagtg  24420
tttggtattg ttgccgccgg tgtggggaag cttgttgcag ggtttgcccc gttggcggtg  24480
tcgttgaaga atttgttgcc gtcttttggt gctttgaggg gtgccgctgg ggggcttggt  24540
ggcgtgtttc gcgccttggg tggccctgtt ggtattgtga tcggcttgtt tgctgccatg  24600
tttgctacga atgcccagtt ccgtgccgct gttatgcagc ttgtgggggt tgttggccgg  24660
gctttggggc agattatggt cgccttgcag ccactgttcg ggattgttgc tggcgtggtt  24720
gccaggttgg ctcccgtttt tggccagatt attggtatgg ttgctggttt ggcggcccgg  24780
ctggtgcctg ttattggtat gcttattgcc aggctggttc ctgttatcac ccagattatt  24840
ggtatggtaa cccaggttgc tgccatgttg ttgcctatgc tgatgccggt tattcaggct  24900
gttgttgctg tgatacggca ggttattggt gtggtcatgc agttgatacc tgttttgatg  24960
ccggttgtgc agcagatttt gggtgctgtc atgtctgttt tgccgccgat tgttggtttg  25020
atacggtcgc tgataccggt gatcatgtcg attatgcgtg tggtggtgca ggttgttggt  25080
gccgtgctac aggtggtggc ccgtattatt ccggttatta tgccgattta tgtttcggtg  25140
attggattca ttgccaagat ttatgctgcg gttatcgttt ttgaggctaa ggttattggc  25200
gctattcttc gtactattac gtggattgtg aatcattcag tgtctggcgt gaggtctatg  25260
ggcacggcca tccagaatgg ctggaatcat atcaaatcgt ttacgtctgc gtttattaac  25320
ggtttcaagt cgatcatttc tgccggtgtt gccgcggttg tggggttttt tacgcggctt  25380
ggtttgtcgg ttgcctccca tgtgaggtct ggttttaatg cggcccgtgg agctgtttct  25440
tccgctatgg gtgcgattcg gagtgttgtg tcttcggtgg cgtctgctgt tggcgggttt  25500
ttcgggtcga tggcttctcg ggtccggaat ggtgctgtgc gcgggtttaa cggggccagg  25560
agtgcggctt cttctgctat gcatgctatg gggtccgcgg tgtctaacgg tgtgcatagt  25620
gtgctggggt ttttccggaa tctgcccagc aatattaggg gcgccttggg tagtatgggg  25680
tctttgttgg tgtctgctgg ccgtgatgtg gtggccggtt tgggtaacgg tattaagaat  25740
gctttgagtg gcctgttgga tacggtgcgt aatatgggtt ctcaggttgc gaacgcggcg  25800
aagtctgtgt tgggtattca ttctccgtct cgggtgtttc gtgacgaggt tggccgtcag  25860
gttgttgccg gtttggctga gggtattact gggaatgctg gtttggcgtt ggatgctatg  25920
tcgggtgtgg ctggtcggct gccggatgtt gtggatgccc ggtttggtgt gcgatcgtct  25980
gtgggctcgt ttaccccgta tgaccggtat cggagtgcga gcgagaagag tgttgtggtg  26040
aatgtgaatg ggcctactta tggtgatcct aatgagtttg cgaagcggat tgagcggcag  26100
cagcgtgacg ctttgaacgc gttggcttac gtgtgattgg gggtgttgtg catgtttatt  26160
cctgaccctt ctgatcgtgc cggtttgact gttacttggt ctatgttgcc gttgattggt  26220
aatgatcctg agcgtgtgct tcatttgacg gattatacgg gtgcgtctcc tgtcatgttg  26280
ttgaatgatt cgttgcgtgg ccttggtgtt cctgaggttg agcatttttc tcaaactcat  26340
gttggggtgc atggctcgga gtggcgcggg tttaatgtga agcctcgcga ggtgacgttg  26400
ccggtgttgg tgtcgggtgt cgacgaggat ccggtgggcg ggtttcgtga cggtttttttg  26460
aaagcctatg atgcgttgtg gtctgctttt cctcccggcg aggaggggga actgtcggtg  26520
aagactcctg ccggcaaaga gcgtgtgttg aagtgccggt ttgattcggc tgatgacacg  26580
tttacggtgg atccggtgaa caggggttat gcccgctatc tgttgcattt gacagcttat  26640
gacccgtttt ggtatgggga tgagcaaaag tttcgtttca gtaacgcgaa gttgcaggat  26700
tggttgggtg gcggccctgt cggcaagaag ggtaccgcgt ttcctgtggt gttaacaccg  26760
ggtgtgggct ctggctggga taacctgtct aacaggggtg atgtgccggc gtggcctgtg  26820
attcgtgttg agggccccct ggagtcgtgg tctgtgcaga ttgatggttt gcgtgtgtct  26880
tcggactatc cggtggagga gtatgattgg attactattg atacggatcc tcgtaagcag  26940
tctgcgttgt tggacgggtt tgaggatgtg atggatcgtt tgacggagtg ggagtttgct  27000
cctattcctc cgggtggttc gaagagtgtg aatattgaga tggttggttt gggtgccatt  27060
gttgtgtcgg tgcagtacag gtttttgagg gcttggtgaa tggttgatgg ctggtcttgt  27120
tccgcatgtc acattgttta cacctgatta tcgccgggta gcccctatca atttttttga  27180
gtcgctaaaa ctgtcgttga agtggaatgg tttgtccact ttggagttgg tggtgtcggg  27240
ggatcattcc aggcttgacg ggttgacgaa gcctggggct cggctggttg ttgattatgg  27300
tggtggccag atttttctg ggcctgtgcg taaagtgcat ggtgtgggtc cttggcgttc  27360
ttcccgtgtg actatcacgt gtgaggatga tatccgcctg ttgtggcgta tgctgatgtg  27420
gcctgtgaat tatcgtcctg gtttggtggg ttcggagtgg cgtgcggacc gggattatgc  27480
ccactattcg ggtgcggctg agtcggttgc taagcaggtg ttgggggata atgcttggcg  27540
ttttccgcct ggtttgttta tgaacgatga tgagagtcgt ggccgctata ttaaggattt  27600
tcaggcccgg tttcacttgt ttgccgataa actgttgccg gtgttgtcgt gggctcggat  27660
gactgtcacg gtgaaccagt ttgaggatgc gaagtttgat cagcgtggtt tgctgtttga  27720
ttgtgttccg gctgtgactc gtgagcatgt gttgactgcc gagtcgggtt cgattgtgtc  27780
gtgggagtat gtgcgtgacg caccgaaggc tacgtcggtg gttgtgggtg gccgcggcga  27840
gggccgggac aggctgtttt gtgaggatgt tgattcggcg gccgaggagg actggtttga  27900
tcgtgtagag gtgtttaagg atgcccgtaa cacggattct gagaaggtgt ctctcttcga  27960
tgaggctgag caggtgctgc aagagtcggg ggccacgtcg gggtttaaga tcgagttggc  28020
cgagtcggat gtgttacggt ttgggcccgg caatctgatg cccggtgatc ttatctatgt  28080
ggatgtgggc tcggggccta ttgcggagat tgttcggcag attgatgtgg agtgcgattc  28140
gccgggtgac gggtggacga aggtgactcc tgttgctggg gattatgagg ataatccgtc  28200
```

```
ggcgctgttg gctcgccgtg tggctggttt ggctgcgggt gtgcgggatt tacaaaaatt  28260
ctaattgttg ggggtttgtt gtgggtattg tgtgtaaagg gtttgatggt gtgttgaccg  28320
agtatgattg ggctcaaatg tctggtctga tgggtaatat gccgtccgtt catggcccgg  28380
atgattttcg tgtcggcacg acgattcagg gttccacggt gttgtgtgag gtcctgccgg  28440
ggcaggcttg ggctcacggg gtgatgtgca cgtcgaatgc tgttgagacg gtgacaggtc  28500
agcttccggg cccgggtgag acccgctatg actatgtggt gttgtcgcgg gattgggagc  28560
agaatacggc gaagttggag attgttcctg gtgggcgtgc tgagcgtgct agggatgtgt  28620
tgcgtgcgga gcctggcgtg ttccatcagc agttgttggc tactttggtg gtgtcgtcta  28680
acgggttgca gcagcagctt gacaggcgtg ctatagctgc ccgtgtggcg tttggggagt  28740
ctgctgcgtg tgaccctacc cctgtggagg gtgaccgtgt gatggttcct tcgggggctg  28800
tgtgggctaa ccatgctaac gagtggatgc tcctgtctcc tcgggttgag acgggttcta  28860
agcagatcca gtttggcggg tctgctgtgt atgcttacac gatcccgttt gcccggccgt  28920
ttagtagccc gcctatcgtg gtggcgtcta tggctacggc ggctgggggc acgacacaga  28980
ttgatgtgaa agcctacaat attactagca aggattttag tttggcgttt attacgaatg  29040
atggttcgaa gccgaatggt gtgcctgcgg cggctaattg gattgctgtc ggcgtgtaat  29100
gtacggcttg cgtgtgcggg acgtgttgtg gtggttgtag tggtaggggg ctgtagtgtc  29160
atggtttaca cctacgcttg tggcctctct ttgtaccgct atcgctactg ttcttggttc  29220
gattcaggcg gctatgtaca ggtcgaagaa gaggcttagg cagttgtctg cgcaggttga  29280
tgcgatggaa gagtacacgt ggaatattcg ccatattgtt caccgctata acgcgaattt  29340
gccggatgat gttgagccgg tgaagatgcc tgatttgccc gagtttttga aggatactgt  29400
tgatggtggt ggggggtgaa ttgtgaggga gttagaggag gagaagcggc agcgccgctc  29460
gtttgagaag gcttccctga tattgttgtt cttgtcgctt gtcctgttgg cggtggttgc  29520
cgggggtgct ttacgtttcg gggctgtatc ctctgagcgg gattcggagc aggctaaagc  29580
ccagtctaat ggtacagccg ccaggggttt ggctgcccgt gtgtggcagg tgtgtgcttc  29640
tggtggatgg gagtctgtgc ggcttcacca gtctggtttg tgtgtggatg ctgtgcgtgt  29700
tgagcggagt gtgcagggtg ttccgggtcc ggctggtgtg cgtggcccgc aggggccggc  29760
tggtgttgat ggccgggatg gtagcaatgg ttctgctggg ctggttgggc ctgttggtcc  29820
gcagggttcc cctggcttga atggcgtgaa gggtcctgac gggctgcccg gcagtgacgg  29880
ccaggatggc cgtgatggtg ttccgggccg tgcaggagtg gacggtgtga acggatccga  29940
tggcaaggat ggtcgtgatg gttcggctgg tgagcgcggc gatgtggggc cttcgggtcc  30000
tgccggaccc cctggc                                                  30016

SEQ ID NO: 74          moltype = DNA  length = 29913
FEATURE                Location/Qualifiers
source                 1..29913
                       mol_type = other DNA
                       note = PAC13
                       organism = synthetic construct
SEQUENCE: 74
tgagcgtggc cccgccggtg tgaatggatc cgatggtaaa gatggtaagg atggccgctc  60
ggtggtgtct gtgtactgtt ctgatggtcg cctggttgtg aaatatagtg acggtgtggc  120
ttctaccata tcgggttcgg tggcctgcca gggtgtgaaa ccgtcgccta tagtgactat  180
atcatcccaa aaatagaaag gagtggctgt gatggtagtg tttggtggtg gtgtgtggtg  240
agatacattc ctgcagcgca tcactcggcc ggttcgaata gtccggtgaa cagggttgtg  300
attcatgcga catgcccgga tgtggggttt ccgtccgcct cgcgtaaggg tcgggcggtg  360
tctacagcaa actattttgc ttccccatcg tcgggtggtt ctgctcatta tgtttgcgat  420
attagtgaga cagtgcaatg tttgagtgag tctacgattg gttggcatgc cccgccgaat  480
ccgcattctt tgggtataga gatttgcggc gatgggggtt cgcacgcctc gttccgtgtg  540
ccggggcatg cttacacgag ggagcagtgg ctggatccta gggtgtggcc tgcggtggag  600
aaggctgcca tcctgtgtag acgtttgtgt gacaaatata atgttccgaa aaggaaactg  660
tcggctgccg atttgaaggc cggtaaacgt ggtgtttgcg ggcatgtgga tgttacggat  720
gcgtggcatc agtcggatca tgacgatccg gggccgtggt ttccgtggga caaatttatg  780
gctgtggtga atggccacgg cggcggttca agtagtgagg agttgagtat ggctgatgta  840
caagcgttac atgatcagat taaacagttg tcggcacagg tggcccagtc ggtgaataag  900
ctgcatcacg atgttggtgt ggttcaggtt cagaatggtg atttgggtaa gcgtgttgat  960
gccttgtcgt gggtgaagaa tcctgtgacg gggaagctgt ggcgcactaa ggatgctttg  1020
tggagtgtct ggtattacgt gttggagtgt cgtagccgta ttgacaggct cgagtctgct  1080
gtcaacgatg tgaaaaagtg atggtggttt gtggtgggta aacagttttg gttgggcctg  1140
ctggagcggg cgttaaagac ttttgtgcaa acgtttgtgg ctgtgttggg ggtgacggcg  1200
ggtgtcacgt atacggcgga gtcgtttcgt ggtttgccgt gggaatcggc cctgatcaca  1260
gccggggttg ctgcggtttt gtcggttgct acctcgtttg gtagcccgtc gtttgtggcc  1320
ggcaaacctg gcaagcagcc cctggtggat gagggtttgg ttccaccgga tgatcctgga  1380
atagtggagt ctcactcggt ggatgtgtcg gatcctggca tgatcgagcc gacggatgat  1440
gcggatcttg gtgtaggcta tgtgccgaaa catgctgccg agtcggaggt tggcatgata  1500
gagtctactg ttgcataagt gaatatagat gtgtgcccca gcggtgctgc cacggttgtg  1560
tggtggttgc cgctggggca ctctttttat gttctatagt attctatgat tcgttgctgt  1620
cgatggtgtc ttcgagcatc tggtacaggt ggaggcaggt agagatagtt tcgctggcct  1680
ggtcgagaac ggttcggccg ataacgtttt tgtgattgtc gcggtggcgg atgatagccc  1740
acatgatctc gtcggccgcc gcctgcaata gtttggcctg gtatgcgatc ccggcgagcc  1800
agtctagtgc ttccgggctt gcatgggggc tctggtcctc gctgttgccg cgggtgttgc  1860
tgttgtttgt ggggtgtcct gcactgtcgc ataaccacag gatttcgctg cactcgtcta  1920
gcgtgtcctg gtcgatagcg agatcgtcga ggctgacatt gttgacggta aggttcacgt  1980
tgtcgaggga gatgggtaca ccgtactggt tttcgacact gtcaacaatg ttttgtagtt  2040
gttgcatgtt ggtgggctgt tgttggacga tgcggtgtat cgctgtgttg agggtggtgt  2100
aggtgatgtt gtgtgtgttg tccatggttt ttatgccatt ccttcgttat cgtctggcat  2160
gtagtatgtg ctgtttgcgt actcggttaa cgtcatcagt gtttggtctg cccactgttt  2220
cacagtctgc cttgtcactc cgagtcgttg ggcggcagac gcatatgttt ggtcataccc  2280
gtatacttcc ctgaatgctg ccaaccgtgc caaatgtttt cgctgtttgg atggctggca  2340
ggtgagggtg tagtcgtcga tggctagctg tagatcgatc atggtaacga tgttgttgcc  2400
```

```
gtggtgttgt ggcgcggttg gtgggggtgg catgcctggc tccacactgg gtttccatgg  2460
tccgccgttc cagatccatt gggcggcttg aataatgtcg gcggtagtat aggttcggct  2520
cacttggtca cccccctgaac aggtcgttgc tggtggtggt gtcgaatcgt ccgacgcagt  2580
ggcagtagtc gtacatgagt ttaataatgt gttggtggtc tcccaaatag gtgtttccgc  2640
tgatactgta ggtggctgtg ccgtctttac tgatggtgta tttggcggtg atggtttcgg  2700
ggttttcggt gtcggtgatg atggctgtgg tggtggcacc tactgtttgg agcacggtgg  2760
tttgggttcc gtcgtcgatg gtggttttaa ccatgaggtg ttctcccttt gtgttagttg  2820
ctggtttggt tgtcggctag atgaatgatg tcgggtaagg gtttcggctg gtcgaggtgt  2880
tgtatggttt tgttggctag ccgtttggct accctgtaac acattttggt gtagtgtttg  2940
ttgtctaggt tgtggtattg ttcccgcacc gcaatatata gcagggagtc ttggtatagg  3000
tcgtctgcac tgattgcggg gtagtgtgcg gctactttgg tacatgcccg gttgagtgtg  3060
cgtagatgat ggtctgtggc ccacacccac gatgcggtgg tggctaggtc ggcttttgtt  3120
ggtcgtctac tcatggcatc tctttcatct ggctatctgg tagttgtttg gtgttttgtt  3180
gttgatagtg tagcacacga gcccggggtt tccggtggtg cccgtcttgt gccggtacca  3240
tgtggattcg ccttccatgg atgggcattg gatgaaggtg cgttgtcctt gctcggagat  3300
ttctaggtgg tgccggtgcc ctgccatgag aatatgggat gtggtgccgt tgtggaattc  3360
ttggccgcgc caccaatcat agtgtttgcc ggtgcgccat tggtggccgt gggcgtgcag  3420
tatccgtgtg cctgccacat caacggtggt ggtcatttcg tctcggctgg ggaaatggaa  3480
gtgtaggttg gggtattggt tgttgagctg gtaggcttct gcgatggcgc ggcagcagtc  3540
tacgtcgaag gagtcgtcgt aggtggtgac gcctttgccg aagcgtacgg cttctccgtg  3600
gttgccgggg atggatgtga tggtgacgtt tttgcagtgg tcgaattggt ggatgagttg  3660
catcatggcc atgcgggtga gcctgatttg ttctgtcagg ggtgtttggg tgcgccaggc  3720
gttgttgcct ccttgtgaca cgtatccttc gatcatgtcg ccgaggaagg cgatgtggac  3780
tcgttgcggt ttgcctgcct gttgccagta gtgttttgcg actatgaggg agcgtaggta  3840
gttgtcggcg aagtgtgctg tttctcctcc ggggatgcct ttgccgattt ggaagtctcc  3900
cgcccccgatg acgaaggccg cggtgctgta gtcggtgtgg gtgtcttgtt cgggttttgg  3960
gggtgtccat tcggctagtt tatcaacgag ttcgtctacc gggtaggggt tggttgctgg  4020
ttggtggtca ataatttttt gtatggatcg gccggtttct ccgttcggta aggtccattc  4080
ggagatgcgt gtgcggcgca cggtgccgtt ggctagattg tcgtcgatgg tgtcgatggc  4140
gttgtcgtgg ttggctagct gtgtgagtag ccggtctatg ttgtctatca ctgggtatcc  4200
tcctcgtgtg tggtggtggc ttgtttgcgg cggtagtctt tgataacggt ggcggagatg  4260
gggtatccgg cttgggtgag ttgttttgct agccacgagg cggggatggt tttgtcggcg  4320
agcacgtctg cagccttatc accgtagcgt tggatcaatg tttcagtttt ggttgccatg  4380
atgtcctatc ggctgtgtgg cgggctgcca tcctgtgcgg cagtcgccgt cgtgtcctgg  4440
tttgcgggtg caccacgata cggttccgtc tgtgtggtgg agtgttttgc cgcacaggac  4500
gttttggaga tgctccggca gctggtcatt ctggttgctg gtttgtgtgt cgaagagtgt  4560
tttctggttg gtgaaatgct cggacacggt gccattatgc acgggtagta tccatgtttt  4620
ccattgttgt tgcatccggg tgttccagtg gaattgtttg gcagctgtct cggcttgttt  4680
ggcggttttg tagtagccga ctagtatgcg ctggtgttca ctgtcgggcg ggttttggcc  4740
tcgccagtat tgtgccgcaa ccgcgtacct gttgttgtcg gtgaagcgct gccagcagta  4800
ttcgatgatg tgttgcagta cactatcggg aattttttgt gtttggtttt cgttgagcca  4860
ttcggcttcg atgatgccgt gtatggcgcg tttgtctttg gtggtgggtt tgaacgagat  4920
gctcacgata gtaccggctg atcgtcttgc atgaactggt tgaaggtgtt gttcccggcg  4980
tgttgggctt gtgtgatttg ctggtcggtc cagtctgggt gttgctgttt cagatagtgc  5040
cagtggcacg cattgtaggt ttcgtcttgt agccgtgtga gatggttttc ggtgatgatt  5100
tgtttccaca tagtccatga cacgtcgagc ctgttgagga tttctatggc tgggatgttg  5160
aattggtcga ggaagaggat ttcgtgggtg tagtagtttt tctcgtaggc gtcccatccg  5220
cttcggtgcc tgttgggctg gtttttgggg taggcttccc ggcatacttt gtgtaaccgt  5280
ttggccatgt cgtcgggtag tttaatgtcg gggttggcgc ggatcatgga tcgcatccca  5340
tcataggtgg tgccccaggt gtgcatgatg taggtggggt cttcaccatc ggcccatttt  5400
tctgcacaga tggcgaggcg gatgcgcctc ctggctgttt ggctgatgtt gcgccggttg  5460
gggatggggc acgtgtcgag gggatccatg atgtttttta tgcctttctt ggtttcgtgt  5520
tgttgacggg ttttactgta gcacagtgtc tagtgcttgt gtcaaccctg tttttccggc  5580
ctgcaggtag gtgtctgtga catcccccag ggtgaggggc acgtgggtgg cttgggggag  5640
tgctgcctgg agggtttgtg ccatctggtc gcctgctttg tctgggtcgg accagatgta  5700
gatgtggtcg tagccttcga agaatttggt ccaaaagttt tgccacgagg tggcgccggg  5760
tagtgctacg gccgaccatc cgcattgttc gaggatcatg gagtcgaatt cgccttcgca  5820
aatgtgcatt tcggctgccg ggttggccat ggcggccatg ttgtagatgg agcctgtgtc  5880
ccctgccggg gtcaaatatt tggggtggtt gtgggttttg cagtcgtgcg ggagtgagca  5940
gcggaaacgc atttttcgta tttcggctgg ctgtccccaa acggggtaca tgtatgggat  6000
ggtgatgcac tggttgtagt tttcgtggcc tgggatgggg tcattgtcga tgtatccaag  6060
gtggtggtag cgggctgttt cttcgctgat gcctcttgcc gagagcaggt cgagtatgtt  6120
ttcgaggtgg gtttcgtagc gggctgaggc tttctggatt cggcggcgtt ccgcaatgtt  6180
gtaggggcgt atgctgtcgt acattcgggt tttttttctc tagtcgttgt tgtagtttgg  6240
cgagtcctcc tccgataccg catgtgtggc agtaccagac gcccttgtcg aggttgatgc  6300
tcatggaggg ctggtggtcg tcgtggaacg ggcagaggat gtgttgctca ttcctagacg  6360
gattgtaccg tatctggtag gtgtcgagga ggcggcaggt gtcagaggtg tgggaggagc  6420
tcgttgaggg ttgataccac ataggcttcg ctccatggct tgttgcgttg tttcatgacg  6480
acgagtccga tggtggactg gttttcgcgg tttcggtgtg tttcgtagtt gcgtgcctcc  6540
cggctggctt gtttcacgaa ttgggctagg tggggttgtc ctgctttcgc ctcgataatg  6600
taggttttat ggccggttgt gaggatgagg tcgccttcgt cctctttacc gttgaggtgg  6660
aggcgttcta tatcatggcc ggtgtcgcgt agctggtgca ataatcgtgt ttcccattct  6720
gcgcctgccc tgcggttgcg tgactgttgt gtcgacatga tagtcctttg tgtgttgtgg  6780
tcatgttcca tggctgtttt tcggcgagtg gcccgaagaa tgtgtattcc gggtatgccc  6840
tgagccgctc atattttgtt ccgtctgggc tggatttgcc tgtgcgctgt ttcaacactg  6900
agatgcgtgc ctcggcgggg atcgtgagcc cgttgccgtt atcctcgcca ccataaagtg  6960
agactcccaa tatgagttgt ggtttttcgg agaggccgtt tttgatttcc cgcctagccg  7020
gggggtgttc gatgtcggtg ccggttttgt cggtggcgtg gtgggtgaca atgatggtgg  7080
agccagtatc tctacctaat gctgtgatcc attgcatggc ttcctgctgg gcctggtagt  7140
```

```
cgctctcgca gtcttggatg tccatcaggt tgtcgataac gatgatgggt gggaaggtgt  7200
tccacatttc catgtaggct tgcagttcca tggtgatgtc tgtccatgtg atgggtgact  7260
ggaatgagaa tgtgatgtgt tggccgtggt ggatgctgtc tcgatagtat tctggcccgt  7320
agtcgtcgat gttttgttgt atctgtgtgg tggtgtgttg ggtgttgagt gagatgattc  7380
gcgtggaggc ctcccagggt gtcatgtccc ctgatatgta gagggcgggc tggttgagca  7440
tggcggtgat gaacattgct agcccggatt tttggctgcc ggaccgcccc gcgatcatga  7500
ctaggtcccc tttgtggatg tgcatgtcca ggttgtcata caagggtgct agttgtggta  7560
tgcggggcag ttcggcggct gtttgggagg ctctctcgaa ggatcgttgg agagagagca  7620
tcggagcctt aatctatctg tctatcggtt ggatgatgtt ttggtggtca gatggagtcg  7680
atgtcgatgt cagcatcagc aggggctgtg gtgtcgtcta gctgaccgtt atcgcgtttg  7740
tctacgtatt cggcaacctt atcgtagatg gcgtcatcga ggggtttgag cacgaccgcg  7800
ttgaagccgt ttttggtgcg cacggtggcg agtttgaagg cctgctcctc gccaaggtag  7860
gcttcgaggt cgcggatcat ggagtgtggg cggtcgttgt tgccgcgggc tttctcaatg  7920
atagcgttgg ggatggtttc tggggtgccg ttgttgagat cctcgagggt gtggaagata  7980
gtcacatcag cgtaaatacg atcggcggtc tgtccaccgt agccttcggt gttgtgttcc  8040
acgtcgcgga ttttgaaggc gatggcggtg gcgtcctggt ttcgggaggg gttgaagaag  8100
gtgctgttgc tgttgttgcg gtagtttgcg agtcccattg ttgtttcctt tactgtttgt  8160
gttgttttgt ttgttggttt gtgtcggttt ttatcgggtg aggctgtttc gtttgctgcg  8220
gaaagcctca gacacgtcac tgttactagt gatggtcttc ttgtactgtt tgaggaggtc  8280
ggctagctgt gccttgcttg ttgcattgtt gattttgtcg atgacgatgc tgtttttcttt  8340
ggatgcgatg ttgtccacgt agtctttggc ggcctggttg tatcggtctt ggaggatgat  8400
ggatgctgtg gcgatcaggg ttgccaggtc ccagttcctt gccgcggagc tgtttttgag  8460
tccgcctagc aggtcgatga tagtcttctt tacctggtcg gcggtgtctc cgcggatgac  8520
ggtccatggg gcggcgtagt cgcctccgta tttgagtgtg acggtgaatc ggtcgtcgtc  8580
tgtgttgtcg gtcactggtg ctccttgcct tcttttgttg gggctgtgat ggtggtttct  8640
atagggtacc tgtaggcgtc tttcccgtta acagcccagc aggcgtcctt gacggggcat  8700
cctttacaga gtgctgtgac gtggggtacg aagatgcctt gactgattcc tttcattgct  8760
tgactgtaca tggatgatac atgccggtag gtgttgttgt caagatcgta cagttcggtg  8820
gatgtgccct gttcgaccga ttgctcgtcc cccttggtgg tggcgggtgt ccaaaacatg  8880
cctttcgtca catcgttgcc gtgttgggcg agcatgtacc ggtaggtgtg cagctgcata  8940
ctgtcggcgg gtaggcgtcc tgttttgagg tcgagaatga aggtttcgcc agtgtcggtg  9000
tcggtgaaaa cgcggtcgat gtagccaacg atctgggtgc cgtcctggag ggtggtttct  9060
accgggtatt cgatgcctgg ctggccgtct aggattgcgg tgatgtattc tgggtggttg  9120
cgcctccatg ttttccagcg gtccacaaag gtggggccgt acatcatcca ccagtcgtag  9180
tctttcttgt gtggcccgcc cgactcgcac atgtttttgc atattctgcc ggagggtttg  9240
atttctgtgc cttcggattc ggcgagggcg acttgggtgt cgaaaatgtt tttgaaggat  9300
gagagtttgt ttggtagtgc agggtattcg gtggggttgt acaggtgtag gtcgtattgt  9360
tcggtgatgt ggtgtatggc gcttccggcg atggtggcat accaggtgtg gtgttgggca  9420
tggtagccgt gggataggcg ccatttttca ccacattcgg cccactgtga cagtgatgag  9480
taggagatgt ggcctggatg gtggatggtt ttcgggtatt gtgctagggg cattactggt  9540
cgcctttgtg ggtgttccat gggtttcggg tgtcttggcc ggcattgtgt tgctggtagg  9600
cgaggagtgc gaggcagtgc caggcagcat gggctagatg gggtagcccg gattcgtggt  9660
cgaggttgtt gccttgctgc catgatagta ggtgcctgta gagggcgtcg acgctgtggc  9720
tccacgggta tccgccggtc cagttgttgt cgccgtattt ggtggcaccg tagcctgcga  9780
cttcgccgag ggcgtgtaag gctgcggggt cgatgaggga gagtcggcat agtttgagtt  9840
ctttttggc gcctgtgtct gggttggtgt acatgcgggt gggcttatcc atggggtgtg  9900
tgctccttag gggtgggtta ctggttgggg ttgtgggcga gtgctacggc gaggatgatg  9960
atggcgaggg tttctgcgat gatgatgggt gttgtgatca tttggtgtct cggggattgt  10020
tggtgagggt tgaggcgcct aggagggtgg tgagggcgca tgcggcgatg atggcgaggg  10080
ctgccttgtg tggggtgccg gttgcgtaca tccatgtgat gatggcgcct tggatccatg  10140
ccagtgtggt gaagaatgtt tcgtagctgt gtagctcgct tttgttgctg gtgatgtcat  10200
tcatggtagt tttctgcttt gtgtgcgatg gttgtgtaca tgtcgttgag tgtggtttcg  10260
atggtgatga gagtgttgat ttcttggttg aggtcgatgt tgtctttgag ggtgtcgatg  10320
cgggcggcga tgtcggtggc ggtgcgtagg cttactgctg caccgtggat gatgtggcat  10380
atgtcggtga ggccgacttt ggcgatgtag tgtgacatga gaggcatagc ggggatgctc  10440
cttggcgggt tactgttgcg ggttgatgtt gaggtcggtg acgttggggt ggtcttctgt  10500
tccggtgacg aggcagtgga cggtgactgg gagtttggat gcgccgggct gtttcgcggt  10560
tgcgccgtag acgatggaga aggtgtcttt accaataatt ttgtggagtt ggaggtcgat  10620
gtcggggttg ccgttccagt tgacaccgtg tgctgcggcc tgctgttcgg ctttgcggtt  10680
gcaggtgtgt gctgcggtga tcatggtgag accctgtgag gtttcttcac cccttgcttg  10740
ggcttgccgg tgggttttct gctgttcggc tcgcagtgac tgttctgcgg cggcctggcg  10800
tgctttcttt tcggctttgc gctgttggat agtcttgggt gtccattcgg tgttggctgt  10860
ggtggcttgc ggtgcgggct gtgatgcgag tggcggattg tcgtcgggtg ctggcaggaa  10920
ggatgctgcg gcgatgatgg cggctgtgat tccggcgatg gtgtagcctg ttttcttgtt  10980
catggctttg tgttcccctt tccggggtgt tgttcgttgc tgacatgatt aatactttca  11040
gcggctgggc ccactgtcaa ggctgcgctc agtttgcgtg agcgatactt gtgtggctag  11100
gggtgatggc ttctttcgcc caataggatg tgccaccgct ggtccagtat ccgagtttgt  11160
tgcgctgcat gcccttggcg tccatctcgt cgatcgtgag gcacctgcga cgactggggc  11220
ctgtcttgac tccatggtcg cctacccggt gcatgtcgcc tgaggtggta ctcgtgaatg  11280
tttcgtggca gattgtgcag tgctctggct tgtatccgat gatggtgcta tcgcacttgt  11340
ggcatgtcca ttgcatgatt gctcctattt tccattataa gacttcctgt agtgccattt  11400
tagcgccttg cgagtcttgg gggtacaact atataggtcg ggtatttcta ggcgattcta  11460
ggctcgttgt gtgtggttgg gggtttatcg ggcgcacagg gtgagcaggc ttccgatgtt  11520
gatgcgtatc acattccagt agagttgtgt ggcttcaccg tcggtgagtg gcttccactc  11580
gtcatggctg aacacggtgc catcggatgc gatgaacgtg ttggggcgta gcttgtggag  11640
ttcagtctct acacgctgcc ggtaggcttc ggcgaggccc tcaaaatcca tgtggtcgca  11700
ggagaggttt tcgaagcgtg tcaagtcgat gggtgtgggg cagtcgtcgt tggtgggggt  11760
gtagagctgg gtgaagtggt tggcgatctt ctgcatgacg ggttcctttt ctcgtgtgat  11820
gggttgatag ttttatcggg ttgcggcggc aataatggca tccacgtcga tcatgtcgat  11880
```

```
catgtcgttg agttcctcgg cctcattctc ggagaggtgg cgccagccat agtcgccgta  11940
tacggcgccg tcgagggtga cagtccacag gggccggatg agtcgtacgg cttcttcgac  12000
tttggcgtgg tacatgcggc gcaccatatc cagatcgatg tcgtctgaat ggtttccggt  12060
gaggctgtgg aagctgagcg ggtcgatttc tgtctgcctg tcgaggctgg tgaatgatgg  12120
tgtgatgagt gtgccatcca tagggtgtgt gctcctttcg gtggtggagg ggttgttgtg  12180
gtttctagag tgtgtaggtt gcgaccccac agtcaaggtg gcgctcattc ggattgagcg  12240
tttcatggaa ggtgacggat gtcactgaag ccttgatggc ctctctcatc gcctgaaatc  12300
ttctagaggt aggattatgc agggtttacc ctgctgatcg attctagggg ccttctaggg  12360
cgtctcaggg gtgtatctgg gtgatagcag gtccggtaga tctatcttgg ctttcatgac  12420
gggggtcgag gtgccagatc tggtcatgga atccacaccc tcatactgtg tgagatgtat  12480
cacatcctcc tggcttggtg tgccctctcg aggctactct gccgatctgg cgtgaagggt  12540
gtagcccaga aatgccgttt aaagcctccc tatggcgcct aggagcgcct tacagagtgg  12600
gggctaggta ttcatacccc caagcaattc tgatcgattc tagacgcctc ccagagcctg  12660
atacacgatc aaccatctcg gcatagacca gcagccccta tcctggttag ctaagcctca  12720
actatgtgga cagtgtggga tactaagggg gaagaaggac acggtaaaag aaagaggggg  12780
agcatcagcc ttagggtctt agcacttagc gcttagcacc gagcccctca agggctcggc  12840
atcagcccga cagcccgagc aggctcagcc gatcaggcac agccctgaaa ggggtacacg  12900
ccatcaggga aggcttgaga gtacgaggag ccctagcgac gagtactcga aagcctgagg  12960
gaacacccat cagcactgat gggcctagcg tgttcggaaa ggacacaaga gtacagtgtg  13020
acagctgttc gggagtgaaa cctgttctga ctaggggttt cagccttaac caccctcaaa  13080
ggttacaaga ctctaagaaa atttaaggaa aagtttaggt ttaatttttg gacctttact  13140
accaaaaaca cccgtttaca cccctcaaac ccgcctatag agccaaaacc accagtttga  13200
ctcatcccag gtggggtatg ataggctgga caggtagcca gctggacgca aggccgaaat  13260
ccgctgacgc ggctttcacc cttacatcca tcagtctacc aaagacttaa aagcttaaca  13320
gctaagcgct aagcccttaa gaccttaaca cttagcaccg agcccctcaa gggctcggca  13380
tcagtcttaa agccttaaac acttaaagtt ataaataaac attaaagctt taaagtctta  13440
aagtaaatat ataaccttaa cagttaaacg tttaaagctt taaaccttaa cacctaagtt  13500
aagtataaaa ccttaaaggc ttagcactta aggatataaa cttaacatca gtgtttaaga  13560
ctttaagact ttaaaactta aaataactat taatacttaa aagcttataa gtattaaaca  13620
cttaaagtaa ctataagact ttaaaaacct taagtactta aagttaacca tcagtcttaa  13680
actttaatat tataacctat aagtcttaaa gcttataggt gtaataatat aatataagta  13740
ttaaagctta taagttataa aagttttaga agagttaaag ggttaacttc tttacttctc  13800
tactctcttt ggtactttct ctcttctctt cttttcttca tcaggggaga agaggaacct  13860
ttaccatcag cgccgatgga cttttcgccg tgtgtctcgt gtaccaccgg tcgcacgctc  13920
ccggtttgta cactccccac actctgacac ctgtgtccct ttacggcttg gcgtgttcgg  13980
ctgaaggcgt acggcgtgtc acgctcacac ccttaacacc aggtaagact taaagtgtat  14040
attataagta gaagacttta aaacctgtaa ggtgttcccg cttagcccgt gtccttccac  14100
gctaggcgcc aagcgctaag ctgtgaaacg cgaacacaca cccacccct tttttcttc  14160
gtgtccttct ctttttgaca cagctggggg gcgatgtgat ctttttcaca tgccaggggg  14220
tagtggagaa aacaagcacc ccggaatgtt caagacaccc cctcaaacga acaaaacgcc  14280
ccccataatc gatgagcagg gcaagggcaa ggtattcata cccccaacgg ttcccaggct  14340
gttagagagg caaataagac ccctgcaagg gtaggcgagg aacagacaca tcatggcacg  14400
caccaaccgc accgcatcat cagcccaccg ccgctggcgg gcaagactca tcacccaagc  14460
acgcaagcaa ggccaaaccg aatgcccact ctgcggagcc accatcacct ggaacacaca  14520
tgacctgcca accagccccg aagccgacca catcacaccc gtcagcaggg gaggactcaa  14580
caccctcgac aacgggcaaa tcatctgcag aacatgcaac agaagcaaag gcaatcgcag  14640
cgaaccaaac atccaattcc aacaacaaac cacaaaaacg ctgatcccat ggtgaaaaaa  14700
ctgtcaaccc ccaccgggac ccccccctgca cacccgtgca agacctcgta cggcttagtg  14760
aaatacctcc cttttgtggt tttgtctgtt tgtcgacttt ttgtgttggt ggtgagtgtt  14820
gtgcagcctg agcttcctgg tggtcgtgag tggtgtgggg agacgcgtcg ttggtggcgt  14880
gtgtggggtg aggatagccg cgcatcgtat gtgtctgatg aggagtggtt gtttcttatg  14940
gatgctgcgg tgattcatga ttgtgtgtgg cgtgagggca gggcggattt ggtggcttcg  15000
cttcgtgctc atgtgaaggc gtttatgggc atgttggatc gttattcggt tgatgtggtg  15060
tctggtggcc gtggtggggg ttctgcggtg gcgatgattg accggtatag gaagcgcagg  15120
ggggcttgag taggtgtctg gtgttgtggg ttctcaggtt cctcgtcatc gtgtggctgc  15180
ggcgtattcg gtgtctgctg ggggtgatgc tggggagttg ggtcgtgcgt atgggttgac  15240
gcctgatccg tggcagcagc aggtgttgga tgattggctt gctgtgggtg gtaatggtag  15300
gcttgcttcg ggtgtgtgtg gggtgtttgt tccgcggcag aatggcaaga atgctatttt  15360
ggagattgtg gagttgttta aggcgactat tcagggtcgt cgtattttgc atacggctca  15420
cgagttgaag tcggctcgta aggcgtttat gcggttgagg tcgttttttg agaatgagcg  15480
gcagtttcct gatttgtatc gtatggtgaa gtcgattcgt gcgacgaatg gccaggaggc  15540
tattgtgttg catcatccgg attgtgccac gtttgagcgt aagtgtggtt gtccgggttg  15600
gggttcggtt gagtttgtgg ctcgtagccg gggttctgct cgcgggttta cggttgatga  15660
tttggtgtgt gatgaggctc aggagttgtc ggatgagcag ttggaggctt tgcttcctac  15720
ggtgagcgct gccccgtctg gtgatccgca gcagattttt ttgggtacgc cgcctggccc  15780
gttggctgac gggtctgtgg tgttgcgttt gcgcgggcaa gccctcggtg gggggaaacg  15840
tatcgcgtgg actgagtttt cgattcctga cgagtctgat ccggatgatg tgtcgcggca  15900
gtggcggaag cttgctggtg atactaatcc ggcgttgggg cgtcgtctga attttgggac  15960
cgtaagcgat gagcatgagt cgatgtctgc tgccggtttt gctcgggagc ggcttggctg  16020
gtgggatcgt ggccagtctg ctgcgtctgt gataccggct gataagtggg ctcattctgc  16080
ggtggatgag gcggctctgg ttggcgggaa ggtttttggt gtctcgtttt ctcgttcggg  16140
ggatcgtgtc gcgttggcgg gtgctggccg gactgatgct ggtgtgcatg ttgaggtgat  16200
tgatggcctg tcggggacga ttgttgatgg tgtgggccag ttggctgatt ggttggcgtt  16260
gcgttggggt gacactgaaa agatcatggt tgccgggtct ggtgcggtgt tgttgcagaa  16320
ggcgttgacg gatcgtggtg ttccgggtcg tggcgtgatt gtggctgata ctggggtgta  16380
tgtggaggcg tgtcaggctt ttctggaggg tgttcgttcg ggtgtgatca gtcatccgcg  16440
tgccgattcg aggcgtgaca tgttggatat tgctgtgagg tcggctgtgc agaagaagaa  16500
gggttctgcg tggggttggg gttcctcgtt taaggatggt tctgaggttc ctttggaggc  16560
tgtgtctttg gcgtatcttg gtgcgaagat ggcgaaggct aggcggcgtg aacggtctgg  16620
```

```
taggaagcgg gtgtctgtgg tatgaactcg gatgagttgg ctctgattga gggcatgtac  16680
gatcgtattc aaaggttgtc ttcgtggcat tgtcgcattg agggctacta tgagggttct  16740
gcccgggtgc gtgatttggg ggttgctatt cctccggagt tgcagcgtgt gcagacggtg  16800
gtgtcgtggc ctggtattgc tgtggatgct ttggaggagc gtctggattg gcttggctgg  16860
actaatggtg acggctacgg cctggatggt gtgtatgctg cgaatcgtct atcaaccgcg  16920
tcatgcgacg tccaccttga tgcactgatt tttgggttgt cgtttgttgc gatcattccc  16980
cagggggatg gttcggtgtc tgttcgtccg cagtcgccca agaattgtac tggccggttt  17040
tcggctgacg ggtctcgttt ggatgcgggt ttggtggttc agcagacgtg tgatcctgag  17100
gtggttgagg ctgagttgtt gcttcctgat gtgattgttc aggtggagcg gcgtgggtct  17160
cgtgagtggg ttgagacggg ccgtatcgag aatagtcttg gtgcggttcc gttggtgcct  17220
attgtgaatc gtcgccgtac ttctaggatt gatggccgtt cggagattac gaggtctatt  17280
agggcttaca cggatgaggc tgtgcgcaca ttgttgggcc agtctgtgaa tcgtgacttc  17340
tacgcctacc cgcaaaggtg ggttacgggt gtgtcggctg acgagttttc gcagcctggc  17400
tgggtcctgt cgatggcttc tgtgtgggct gtggataagg atgatgacgg cgacacaccg  17460
aatgtgggat cgtttcctgt gaattctcct acaccgtatt cggatcagat gcgtttgttg  17520
gcgcagttga ctgcgggtga ggcggctgtt ccggaacgct atttcgggtt tatcacgtct  17580
aacccgcctt ctggggaggc tttggctgcg gaggagtctc ggcttgtgaa gcgtgctgaa  17640
cgccggcaga cgtcgtttgg tcagggctgg ttgtcggttg gtttttggc tgcccgggcg  17700
ttggattcga gtgttgatga ggctgcgttt tttggtgatg tgggtttgcg ttggcgtgat  17760
gcttcgacgc cgactcgggc ggctacggcg gatgctgtga cgaagcttgt tggtgccggt  17820
attttgcccg cggattctcg gacggtgttg gagatgttgg gtttggatga tgtgcaggtt  17880
gaggctgtga tgcgtcatcg tgctgagtct tcggatccgt tggcggcgct ggctggggct  17940
atatcgcgtc aaactaacga ggtttgatag gcgatggctt cgggtgctat gtcgaggctt  18000
gctgcgactg agtatcagcg tgaggcggtc aggtttgctg ggaagtatgc gggctattat  18060
gccgagcttg gtcgtttgtg gcattccggg aagatgacag atgcgcagta tgtgcgtttg  18120
tgtgtggagt tggagcgtgc cggccatgat ggttcggcat cgttggcggg caggtttgtg  18180
tcggattttc gccggttgaa tggtgtggat cctggtttga ttgtgtatga cgagtttgat  18240
gctgccgccg cgttggctag gtcgttttcg actattaaga ttcttaagag tgatccggat  18300
agggtgaatg acacgattga tgcgatggct gcgggtgtta atcgggctgt catgaatgct  18360
ggccgtgaca cggttgagtg gtctgcgggt gcgcagggta ggtcgtggcg cagggtgacg  18420
gatggtgatc cgtgcgcgtt ttgtgccatg ttggctacga ggtcggatta tacgaccaaa  18480
gaaagggcac tcactactgg tcatacgcgg cgtcataagc gtggtggtaa gcgtccgttt  18540
ggttcgaagt atcatgatca ttgtgggtgt acggtggttg aggttgttgg cccttgggaa  18600
ccaaataggg ctgatgccgc atatcagagg acgtacgaga aggcccgtga gtgggttgat  18660
gatcatgggt tgcagcagtc gcctggcaat attttgaagg ctatgcgtac tgttggcgac  18720
atgagatgat ggtttccggt tgtgtgccgc cggttatcgg tgcacagggt tgtctcccgc  18780
acgggggtca acaatgttgt gttgttttcc gcaaggagta taggttaggc tatggccgat  18840
cagagtgttg aagaacagaa tgtcgacaat gatgctgttg agcccggaaa gggcgaggac  18900
attgttgctg ttgtgaagga tgggcaggct gccggcgatg atcatgccgg tgatgtttcc  18960
gtgaaggagg agtcttcttc tggcacggat tggaaggctg aggcccgtaa gtgggagtct  19020
cgtgctaaaa gtaatttcgc cgagttggag aagcttcgcg cctcggatgg tgatgcggga  19080
tctactattg atgagcttcg ccgcaagaat gaggaactcg aagacaggat caacggettt  19140
gttcttgagg gtgtgaagcg cgaggtggct gccgagtgtg gcctgtcggg tgatgcggtc  19200
gctttcttgc acggcgacga tcgtgaagca ctggtggagt ctgctaaggc tttgaagggt  19260
ttgatcgacc atagcagtgg tggcgcgggt gtgcgccgtc ttgcggggag tgccccegtt  19320
gatgatgtta aacgacgtga gggtgtcgcg tttgtggatg ctcttgtcaa taattctagg  19380
agatgatttg tgatggctga cgattttctt tctgcaggga agcttgagct tcctggttct  19440
atgattggtg cggttcgtga ccgtgctatc gattctggtg ttttggcgaa gctgtcgccg  19500
gagcagccga ctattttcgg cccggtgaag ggtgccgtgt ttagtggtgt tcctcgcgct  19560
aagattgttg gtgagggtga ggttaagcct tccgcgtctg ttgatgtttc ggcgtttact  19620
gcgcagccta tcaaggttgt gactcagcag cgtgtctcgg acgagtttat gtgggctgac  19680
gctgattacc gtttgggtgt tttgcaggat ctgatttccc ctgctcttgg tgcttcgatt  19740
ggtcgcgctg tggatctgat tgctttccat ggtattgatc ctgctacggg taagcctgct  19800
gcggctgtca aggtgtcgct ggataagact tcgaagacgg ttgatgcaac cgattccgct  19860
acggctgatc ttgttaaggc tgtcggcctg attgctgggg ctggtttgca ggttcctaat  19920
ggtgttgctt tggatccggc gttctcgttt gctctgtcga ctgaggtgta tccgaagggg  19980
tctccgcttg ccggtcagcc gatgtatcct gcggccgggt ttgccggttt ggataattgg  20040
cgtgggctga atgttggtgc ttcttcgact gtttctggtg ccccggagat gtcgcctgcc  20100
tctggtgtta aggctattgt tggtgatttc tctcgtgttc attggggttt ccagcgtaac  20160
ttcccgatcg agcttatcga gtatggtgac ccggatcaga ctgggcgtga cctgaagggc  20220
cataacgagg ttatggttcg tgccgaggct gtgctgtatg tggctatcga gtcgcttgat  20280
tcgtttgctg ttgtgaagga gaaggctgcc ccgaagccta atccgccggc cgagaactga  20340
tttattgttg cggtgatgtg tcaatgtgca gggggtggtg ttgatgggta tcattttgaa  20400
gcctgaggat attgagcctt tcgccgatat ccctgagggg aagcttgagg cgatgattgc  20460
tgatgtggag gctgtggctg tcagtgtcgc cccctgtatc gctaaaccgg atttcaaata  20520
caaggatgcc gctaaggcta ttctgcgtag ggctttgttg cgctggaatg ataccggggt  20580
ttcgggtcag gtgcagtatg agtctgcggg cccgtttgct cagactacac ggtcgaatac  20640
tcctacgaat ttgttgtggc cttctgagat tgctgcgttg aagaagttgt gtgaggggga  20700
tggtggggct ggtaaagcgt tcactatcac cccaacgatt aatggtcgat atgcacattc  20760
tgaggtgtgt tccacggtgt ggggtgaggg ttgctcgtgc ggatctgata ttaacggcta  20820
cgctggccct ttgtgggaga tatgatatga ccggttttcc ttacggtgaa acggttgtga  20880
tgcttcagcc gactgttcgt gtcgatgatc ttggtgacaa ggtggaagac tggtctaagc  20940
ctgtcgagac tgtgtactat aacgtggcca tctatgcttc cgtttcgcag gaggatgagg  21000
ccgcgggccg tgactctgac tatgagcatt ggtcgatgct tttcaagcag cctgttgtgg  21060
gtgccggtta tcgttgccgg tggcgtattc gtggtgttgt gtgggaggct gacgggtctc  21120
ctatcgtgtg gcatcacccc atgtccggtt gggatgctgg cacgcaggtt aatgtgaagc  21180
gtaagaaggg ctgataggtt gtggctcagg atgtgaatgt gaagctgaac ttgtctggta  21240
ttcgtgaggt gttgaagtct tctggggtgc agggcatgtt ggctgagcgt ggcgagaggg  21300
tgaggcgtgc ggcctcggcg aatgtgggcg gtaatgcttt cgatagggcc cagtatcgtg  21360
```

```
ccgggttgtc gtcggaggtg caggttcacc gtgttgaggc tgtggcccgt attggcacca  21420
cctataaggg tgggaagcgt attgaggcga agcatggcac gctggcccgg tcgattgggg  21480
cggcgtcgtg atcgtctacg gtgaccccag gaaatgggct aaacgcgtgc tcaaggatga  21540
tggctggctg tctgatatac cctgtgtggg gacggtgcct gatgatttca gcggtgatct  21600
gatttggttg gctcttgatg gtggcccgca gttgcatgtt cgtgagcgtg tttttttgcg  21660
ggtgaatgtg ttttctgata tgccggatcg tgctatgtcg ttggcgcgtc gtgttgaggc  21720
tgtgctggct gatggtgtgg acggtgaccc tgtggtgtac tgtaggcgtt ctactggccc  21780
tgatttgctg gttgatggtg cacgttttga tgtgtattcg ctttttgagc ttatatgtag  21840
gcctgcggag tctgaataag cttattgttt ttgttttaat gtaattgttt gatatttaat  21900
gggggttatg atggctgcaa cacgtaaagc gtctaatgtt cgctctgctg ttactggcga  21960
cgtttatatt ggtgacgcgc acgcgggtga tactattaag ggtgtggagg cggttccttc  22020
cgggcttaca gctttagggt atctgtcgga tgacgggttt aagattaagc ctgagcgtaa  22080
aacggatgat ttgaaggctt ggcagaatgc ggatgttgtt cgcacggttg ctaccgagtc  22140
gtctatcgag atttcttttc agctgatcga gtctaagaag gaggttatcg agctgttttg  22200
gcagtcgaag gttactgctg gcgccgattc gggttcgttt gatatttctc caggcgccac  22260
cactggcgtg cacgctttac tgatggatat tgttgatggg gatcaggtta ttcgctacta  22320
tttccctgag gttgagttga tcgatcgtga cgagattaag ggtaagaatg gcgaggtgta  22380
tgggtatggt gtgacgttga aggcgtatcc tgcccagatt aataagaagg gtgatgcggt  22440
gtctggtcgg gggtggatga cggctttaaa agctgatact cctccgacgc ctcctccggc  22500
cccggttcct ccgaagcctc agccggatcc gaatcctccg gctggtaact gatacacgat  22560
tttagggatt gttgatagat gagtgacacg ggtttcacgt tgaagattgg tgaccgtagc  22620
tgggtgttgg cggatgcgga ggagacggcg caggctgttc ctgcccgtgt ttttcgccgt  22680
gccgccagga ttgcccagtc gggggagtct gcggatttcg cccaggttga ggtgatgttt  22740
tctatgttgg aggctgccgc cccggctgat gctgtggagg ccttggaggg gcttcctatg  22800
gttcgtgtgg cggaggtttt ccgtcagtgg atggaataca agcctgacgg taagggtgcc  22860
tcgctggggg aatagtttgg ctccacggcc tgattgatga ttatcgtggg gccatcgaat  22920
atgattggag gacccggttc ggttgctcgg tttatgatgt tggtggcccg gtgatgtgtt  22980
ggggtgaggc tgtccggctg gctggcgtgt tgtgtaccga tacgtctagc cagttggcgg  23040
cccacctgaa tggttggcag cgcccgtttg agtggtgtga gtgggcggtg ttggacatgt  23100
tggatcatta caggtctgct aatagtgagg ggcagccgga gcctgtggcg aggcctacgg  23160
atgagcgtag ggcccggttt acgtctgggc aggtggacga tattttggcg cgtgttcgtg  23220
ccggtggcgg ggtgtctcgc gagattaata ttatggggtg aatagtgtat gtctggtgag  23280
attgcttccg catatgtgtc gttgtatacg aagatgcctg gtttgaaggc tgatgttggt  23340
aaacatttgt cgggtgtgat gcctgctgag ggtcagcgtt ctggtagcct gtttgctaag  23400
ggcatgaagt tggctcttgg tggtgcggcg atgatgggcg ctatcaatgt tgctaagaag  23460
ggcctcaagt ctatctatga tgtgactatt ggtggcggta ttgctagggc gatggctatt  23520
gatgaggctc aggctaagtt gactggtttg ggtcatacgt cttctgatac gtcttcgatt  23580
atgaattcgg ctattgaggc tgtgactggt acgtcgtatg cgttgggtga tgcggcgtct  23640
acggctgcgg cgttgtctgc ttcgggtgtg aagtctggcg ggcagatgac ggatgtgttg  23700
aagactgtcg ccgatgtgtc ttatatttcg ggtaagtcgt ttcaggatac gggtgctatt  23760
tttacgtcgg ttatggcgcg cggtaagttg cagggcgatg acatgttgca gcttacgatg  23820
gcgggtgttc ctgtgctgtc tttgcttgcc aggcagactg gtaaaacgtc tgctgaggtg  23880
tcgcagatgg tgtcgaaggg gcagattgat tttaacacgt ttgcggctgc gatgaagctt  23940
ggcatgggtg gtgctgcgca ggcgtctggt aagacgtttg agggcgctat gaagaatgtt  24000
aagggcgccc tgggttattt gggtgctacg gctatggccc cgtttttgaa cggtctgcgg  24060
cagattttg  ttgcgttgaa tccggttatc aagtctatca cggattctgt gaagcccctg  24120
tttgcgtcgg tggatcaggg gattcagcgg gtgatgccgt ctattttggc gtggattaat  24180
cgtatgccgg ctatgatcac gagaatgaat gcacagatgc gcgccaaggt ggagcagttg  24240
aagggcgttt ttgcgaggct gcatttgcct gttcctaagg tgaatttggg tgccatgttt  24300
gctggcggca ccgcggtgtt tggtattgtt gctgcgggtg ttgggaagct tgttgcgggg  24360
tttgccccgt tggcggtgtc gttgaagaat ctgttgccgt cgtttggtgc tttgaggggt  24420
gccgccgggg ggcttggtgg cgtgtttcgc gccctgggtg gccctgttgg tattgtgatc  24480
ggcttgtttg ctgccatgtt tgctacgaat gcccagttcc gtgccgctgt tatgcagctt  24540
gtgggggttg ttggccgggc tttggggcag atcatggtcg ctattcagcc actgttcggg  24600
attgttgctg gcgtggttgc caggttggcg ccagtgttcg gccagattat cggtatggtt  24660
gctggtttgg ctgcccaatt ggtgcctgtt attggtatgc ttattgcccg gctggttcct  24720
gttatcaccc agattattgg tatggtaacc caggttgctg cgatgatttt gcctatgctg  24780
atgccggtta ttcaggctgt tgttgctgtg atacggcagg ttattggtgt gatcatgcag  24840
ttggtgcctg ttttgatgcc ggttgtgcag cagattttgg gtgctgtcat gtctgttttg  24900
ccgccgattg ttggtttgat acggtcgctg ataccggtga tcatgtcgat tatgcgtgtg  24960
gtggtgcagg ttgttggtgc cgtgctacag gtggtggccc gtattattcc ggttgttatg  25020
ccgatttatg tttcggtgat tggattcatt gccaagattt atgctgcggt tatcgttttt  25080
gaggctaagg ttattggcgc tattcttcgt actattacgt ggattgtgaa tcattcggtg  25140
tctggcgtga ggtctatggg cacagccatc cagaatggct ggaatcatat caaatcgttt  25200
acgtctgcgt ttattaacgg tttcaagtcg atcatttctg gcggcgttgc cgcggttgtg  25260
gggtttttta cgcggcttgg tttgtcggtt gcctcccatg tgaggtccgg ttttaacgcg  25320
gctcgtggcg ctgtttcttc tgcgatgggt gctatccgga gtgttgtgtc ttcggtggcg  25380
tctgctgttg gcgggttttt cgggtcgatg gcttctcggg ttcgtagtgg tgctgtgcgc  25440
gggtttaatg gcgcccggag tgcggcttct tctgctatgc atgctatggg gtccgcggtg  25500
tctaacggcg tgcatggtgt gctagggttt ttccggaatc tgccgggcaa tattcggcgt  25560
gctctcggta atatggggtc cttgttggtg tctgctggcc gtgatgtggt gtctggtttg  25620
ggtaatggta tccggaatgc tatgagtggc ctgttggata cggtgcgtaa tatgggttct  25680
caggttgcta atgcggcgaa gtcggtgttg ggtattcatt cgccgtcgag ggtgtttcgt  25740
gacgaggttg gccgtcaggt tgttgctggt ttggctgagg gtattactgg taatgctggt  25800
ttggcgttgg atgcgatgtc gggtgttgct tcgcagcttc cggatgctgt tgatgcccgg  25860
tttggtgtgc gatcgtctgt gggctcgttt accccgtacg accggtatcg gcgtgcgagc  25920
gagaagagtg ttgtggtgaa tgttaacggg ccgacgtatg gggatccgaa cgagtttgcg  25980
aagcggattg agcggcagca gcgtgacgct ttgaacgcgt tggcttacgt gtgatagggg  26040
ggtgtggttc atgtttattc ctgacccgtc tgatcgtgcc ggtttgactg tgacctggtc  26100
```

```
tatgttgccg ttgattggtg atgctccgga gcgtgtgctt catttgacgg attatacggg  26160
gtcgtctccg gtgatgttgt tgaatgattc gttgcgcggt ttgggtgttc ctgaggttga  26220
gcatttttct cagactcatg ttggggtgca cggctcggag tggcgcgggt ttaatgtgaa  26280
gcctcgcgag gtgactttgc cggtgttggt gtcgggtgtt gaccctgatc cggtgggcgg  26340
gtttcgtgac ggtttttga aagcctatga cgagttgtgg tctgcgtttc ctcctggcga  26400
ggtgggggag ttgtcggtga agaccccgtc tggtcgtgag cgtgtgctgc ggtgccggtt  26460
tgattcggtg gatgacactt ttacggtgga tccggtgaac aggggttatg cgcgttatct  26520
gttgcatttg acggcttatg acccgttttg gtatggggat gagcaaaagt ttcgttttag  26580
taacgcgaag ttgcaggatt ggttgggtgg cggccctgtt aataagaagg gtaccgcgtt  26640
tcctgtggtg ttaacaccgg gtgtgggctc gggctgggat aacctgtcta ataagggtga  26700
tgtgcctgcg tggcctgtga ttcgtgttga gggtcctttg gagtcgtggt ctgtgcagat  26760
tgatggtttg cgtgtgtctt cggattggcc tgtcgaggag tatgattgga tcactattga  26820
tacggatcct cgtaagcagt ctgcgttgtt ggacgggttt gaggatgtga tggatcgttt  26880
gacggagtgg gagtttgcgc ctattcctcc tggcggttct cggagtgtga atattgagat  26940
ggttggtttg ggtgccattg ttgtgtcggt gcagtacagg tttttgaggg cttggtgaat  27000
agttgatggc tggtcttgtt ccgcatgtaa cattgtttac gccggattat cgccgtgtgg  27060
cgcctatcaa tttttttgag tcgttgaaac tgtcgttgaa gtggaatggt ttgtccactt  27120
tggagttggt ggtgtcgggg gatcattcta ggcttgacgg gttgacgagg ccgggtgcgc  27180
ggctggttgt tgattatggt ggtggccaga ttttttctgg gcctgtgcgt agggtgcatg  27240
gtgtgggtcc gtggcggtct tcccgtgtga ctatcacgtg tgaggatgat attcgtctgt  27300
tgtggcgtat gttgatgtgg cctgtgaatt atcgtcctgg tttggtgggt atggagtggc  27360
gtgcggatag ggattatgct cactattcgg gtgcggcgga gtcggtggct aagcaggtgt  27420
tgggggataa tgcttggcgt tttcctcctg gtttgtttat gaacgatgat gagagtcgtg  27480
gccgctatat taaggatttt caggtgcggt ttcacgtgtt tgccgataaa ttgttgccgg  27540
tgttgtcgtg ggctcggatg actgtcacgg tgaaccagtt tgagaatgcg aagtttgatc  27600
agcgtggttt ggtgtttgat tgtgtgccgg ctgtgacccg gaagcatgtg ttgactgccg  27660
agtcgggttc gattgtgtcg tgggagtatg tgcgtgacgc cccgaaggct acttcggtgg  27720
tggttggtgg ccgcggcgag ggcaaggatc ggctgttttg cgaggatgtt gattcgatgg  27780
ccgaggatga gtggtttgat cgtgtcgagg tgtttaagga tgcccgtaac acggattcag  27840
agcatgtgca tcttattgat gaggctgagc aggtgttgtc cgagttaggg gctacgtcgg  27900
ggtttaagat cgagttggct gagtcggatg tgttgcgttt tgggccaggc aatctgatgc  27960
cgggtgattt gatctatgtg gatgtgggct cggggcctat tgcggagatt gtgcggcaga  28020
ttgatgtgga gtgtgattcg cctggtgatg ggtggacgaa ggtgacacct gttgcggggg  28080
attatgagga taatccgtcg gccctgttgg cgcggcgtgt tgccggtttg gctgcgggtg  28140
tgcgggattt gcaaaaattc tagaaaagat gaggggtttg ttgtgggtat tgtgtgtaaa  28200
gggtttgatg gtgtgttgac cgagtatgat tgggctcaaa tgtctggtct gatgggtaat  28260
atgccgtctg tgaagggccc ggatgatttt cgtgtgggca cgactgttca gggtgccaca  28320
gtgttgtgtg aggttttgcc ggggcaggct tgggctcacg gggtgatgtg cacgttgaat  28380
agtgttgaga cggtgacagg gcagctgccg ggccctgggg gggcccgcta cgactatgtg  28440
gtcctgtctc gggattggca ggagaatacg gccaagttgg agattgttcc tggggggcgt  28500
gcggagcgtg cccgtgacgt gttgagggct gagcctggcg tgtttcatca gcagttgttg  28560
gcgactttgg tgttgtcgtc tgacgggttg cagcagcagc tggataggag ggctatagcg  28620
gctagggttg cgtttggcga gtctgctgcg tgtgacccga ccccggtgga gggtgaccgt  28680
gtgatggttc cttcgggggc tgtgtgggct aatcatgcta acgagtggat gttgttgtct  28740
ccgaggattg agacgggttc gaagtcgatc atgtttggcg gttctgctgt gtatgcttac  28800
acgatcccgt ttgatcgcca gtttgctagt ccgccggttg tggtggcgtc tatggctacg  28860
gcggctgggg gcacggcaca gattgatgtg aaagcctaca atattactgc caaagatttt  28920
agtttggcgt ttattacgaa tgatggttcg aagccgaatg gtgtgcctgc ggttgcgaat  28980
tggattgctg tcggcgtgtg accgggttgt tgttgtggcg gatggtgtga tgttgggggg  29040
ctgtggtgtc gtggtttact cctgcactgg tggcctctat ttgtaccgcg ttggccacgg  29100
ttttgggttc tgttcaggcg gtcacgtcta aatctcggag gcgtttgcgg cggctgtcgg  29160
cgcaggtgga tgcgatggaa gagtatacgt ggggtgtgcg gcgtgaggtt cgcccggttta  29220
acgctgggct tccggatggg gtggagccga tgcatcttcc tgatgtgcct gagtttttga  29280
aggatactgt tgatggtgga ggtgagtagg gttgagggag ttggaggagg agaagcggca  29340
gcgccgcaat tttgagaagg cttcactggt gttgttgttt ttgtcgcttg tgttgttggc  29400
ggtggttgct gtgggtgctt tgcgtttcgg ggcggtatcc tctgagcggg attcggagca  29460
ggcgagggcc cagtcgaatg gtacagcggc tcggggttta gccagcagtg tgaagcaggc  29520
gtgtgcttcg agtggggtgg agtcggtgcg gcttcaccgg tctggtttgt gtgtggatgc  29580
tgtgcgtgtt gagcggagtg tgcagggtgt gccgggtcct gccggtgagc gcggcccgca  29640
aggccctgca ggggttgacg gccgggatgg tgttaatggt tcggctgggc tggttggccc  29700
tgttggtccg cagggttctc ctggtttgaa tggtgtgaag ggtcctgacg ggttgcctgg  29760
tgtgaatgga tcggatggcc atgatggtgt tccaggtcgt gcaggtgctg acggtgtgaa  29820
cggcgctgat ggtcgggatg gttcgggcgg tgagcgcggc gatgtgggcc cttcaggtcc  29880
tgtcggaccc cctggtgcgc agggtgaacg ggg                              29913
```

```
SEQ ID NO: 75          moltype = DNA  length = 29562
FEATURE                Location/Qualifiers
source                 1..29562
                       mol_type = other DNA
                       note = PAC263
                       organism = synthetic construct
SEQUENCE: 75
aatggtgtga agggtcctga cgggttgcct ggcgttaacg gttcggatgg ccgtgatggt  60
gttccgggtc gtgcaggtgc tgacggtgtg aacggcgttg acggccggga tggtgttaat  120
ggttcggctg gtgagcgcgg cgaacagggc ccttcaggtc ctgccggccc ccaaggcgaa  180
cggggtgagc gcggccccgc cggtgctaac ggatccgatg gtaaagatgg taaagatggt  240
aaagatggcc gttctgtggt gtctgtgtac tgttctgatg gtcgcctggt tgtgaaatat  300
agtgacggtg tggcttccac gatatcggc tcggtagcct gccagggtgt gaaaccgtcg  360
cctatagtga ctatatcatc ccacaaataa aagaggaagg gtgttactgt gattgtcatg  420
```

-continued

```
ttttggggtg gtgtgtggtg aggtttattc ctgcggcgca tcattcttcc ggttcgaata  480
gtccggtgaa tagggttgtg attcacgcga catgcccgga tgtggggttt ccgtccgcgt  540
cccgtaaagg gcgggcggtg tccacggcaa actatttcgc gtccccatcg gcgggtgggt  600
ggggtttccg tccgcgtccc gtaaagggcg ggcggtgtcc acggcaaact atttcgcgtc  660
cccatcggcg ggtggttcgg cgcattatgt gtgtgatatt tcggagactg tgcagtgctt  720
gtcggagtct acgattgggt ggcatgcccc gccgaatccg catagtttgg gtatagagat  780
ttgcgcggat gggggttcgc atgcctcgtt ccgggtgcca ggccatgctt acacgaggga  840
gcagtggctt gatccgcggg tgtggcccgc ggttgagaag gcggctgtcc tgtgccggcg  900
tttgtgtgac aaatataatg ttccgaagag gaaactgtct gtggccgatt tgaaggccgg  960
taaacggggt gtgtgtggcc atgtggatgt gacggatgcg tggcatcagt cggatcatga  1020
cgatccgggg ccgtggtttc cgtgggacaa gtttatggcc gtagtcaacg gcaaagatga  1080
gagtggggag ttaactgtgg ctgatgtgaa agccttgcat gatcagatta aacaattgtc  1140
tgctcagctt agtggttcgg tgaataagct gcatcacgat gttggtgtgg ttcaggttca  1200
gaatggtgat ttgggtaaac gtgttgatgc cttgtcgtgg gtgaagaatc ctgtgacggg  1260
gaagctgtgg cgcagcaagg atgctttgtg gagtgtctgg tattacgtgt tggagtgtcg  1320
tagccgtctt gacaggctcg agtctgctgt caacgatttg aaaaagtgat ggtggtttgt  1380
tgtgggtaaa cagttttggt taggtgtgct ggagcgggcg gctaagactt ttgtgcaaac  1440
gtttgttgcg gtgttggggg tgacggcggg tgtcacctat acggcggagt cgtttcgcgg  1500
tttgccgtgg gagtctgccc tgatcacggc tacggtggct gcggtgctgt cggttgctac  1560
atcgtttggt agcccagcgt ttgtggccgg taaacctaaa accacgcctg tggatgcggg  1620
tttggttcca ccggatgatg gggcttggt tgagccgcac tcggtggatg tgtcggatcc  1680
tggcatgatt gagcctgcag atgatgtgga tcttggtgta ggctatgagc ctcggcgtgc  1740
tgccgagtcg gaggttggca cggtagagtc tactgttgca taagtgaata tatgtgtgtg  1800
ccccagcggt gctgccacga tcgtgtggtg gttgccgctg gggcactatt tttgtatatt  1860
gcggtgtggc tatgattcgt tgctgtcgat ggtgtcttcg agcatctgat acaggtggag  1920
gcaggtagag atcgtttcgc tggcctggtc gagaacgttc cggccgataa cgtttttgtg  1980
gttgtcgcgg tggcggatga tagaccacat gatctcgtcg gctgccgcct gcaatagttt  2040
tgcctgatat gcgatcccgg cgagccagtc tagtgcttcc tggcttgcat aggggctctg  2100
gtcctcgctg ttgccgcggg tgttgctgtt gtttgtgggg tgtcctgcac tgtcgcagaa  2160
ccataggatt tcgctgcact cgtctagcgt gtcttggtcg atagcgagat cgtcgaggct  2220
gacattgttg acggtaaggt tcacgttgtc gagggagatg ggtacaccgt actggttttc  2280
gacactgtca acaatgtttt gcagctggtt catgttggtg ggctgttgtt ggatgattcg  2340
gtgtaccgct gttttgaggg cggtgtaggg gatattggtt atgttgttca tggttttatc  2400
ccatccctgc gctgtcgtct tggtagtatc gactgtttgc gtaacctgtg agggtgatga  2460
gtgtttggtc tgcccactgt ttcacggttt gccgggtgac tccgagtcgt tgggctgcca  2520
ccgaataggt ttggtcatac ccgtatactt ccctgaaggc tgccaggcgt gctagccgtt  2580
tccgctgttt ggatggctgg caggtgaggg tgtagtcgtc tatcgctaat tgtaggtcga  2640
tcatggtgac gatgttgttg ccgtggtgtt ggggggcggt tggtggggt ggcatgcctg  2700
gctccacact gggtttccat gggcctccgt tccagatcca ttgggcggct tggatgatgt  2760
cggcggtggt gtaggttcgg ttcactggtc atcccctgaa taggttgtcg aggttgtctg  2820
ggttgctggt gttggtggtg tcgaatcgtc ccacacagtg gcagtagtcg tacatgagtt  2880
taataatgtg ttggtggtct cccaaatagg tgtttccgct gatactgtag gtggctgtgc  2940
cgtctttact aatagtgtat ttggcggtga tggtttcggg tgtttctgtg ttggtgatga  3000
ttgctgtggt ggtggcgcct acggtttgta gcctggtggt ttgggttccg tcgtcgagga  3060
tggtagtaac catgagggtt gtcctttagt tgctggtttg gttgtcggct agatgaatga  3120
tatcgggtaa aggtttcggc tggtcgaggt gttgtatggt tttgttggct agccgtttgg  3180
ctaccctgta gcacattttg gtgtagtgtt tgttgtctag gttgtggtat tgttcccgca  3240
ccgcaatata tagtagggag tcttggtata ggtcgtctgc actgattgcg gggtagtgtg  3300
tggctgtttt ggtgcatgcc cggttgagtg tgcgtagatg atggtctgtg gcccacaccc  3360
acgatgcggt ggtggctagg tcggcttttg ttggtcgtct gctcatggca ctattacctg  3420
gctatctggt agttgtttgg tgttttgttg ttgatagtgt agcacacgag tccggggttg  3480
ccggtggtgc ctgtgcggtg cctataccag acggattctc cttccatgga tgggcattgg  3540
atgaaggtgc gttgtccttg ctcggagatt tcgaggtggt gccggtgtcc ggccatgagg  3600
atgtgggatg tggtgccgtt gtggaattct tggccgcgcc accattcgta gtgttggttg  3660
ttgcgccatt ggtgtccgtg ggcgtgcagt atttgtgtgc cggccacatc aacggtggtg  3720
gtcatttcgt ctcgtctggg gaagtggaag tgaaggttgg ggtagttgtt ggtgagttgg  3780
taggcttcgg cgatggcgcg gcagcagtct acatcgaagg agtcgtcgta ggtggtgact  3840
cctttgccga atcgtacggc ttcaccgtgg ttgccgggga tggaggtgat ggtgacgttg  3900
gcgcagtggt cgaacatgtg gacgagttgc atcatggcca tgcgggtgag cctgatttgt  3960
tccgtcaagg gtgtttgtgt gcgccacgcg ttagagccgc cttgtgacac gtatccttcg  4020
atcatgtcgc cgaggaatgc gatgtggacc cgttgcggct ggcctgcctg ttgccagtag  4080
tgttttgcga ctatgaggga gtgcaaatag tcgtcggcga agtgtgctgt ttctccgccg  4140
gggatgcctt tgccgatttg gaagtcgcct gccccgatga cgaaggccgc agtgctgtag  4200
tcggtgtggg tgtcttgttc gggtttgggt ggctgccatt cggctagctt gtcgacgagt  4260
tcgtctatag ggtaggggtt tgttgcgggt tggtggtcga tgattttttg tatggatcgg  4320
cctgtttctc cgttggggag tgtccattcg gagatgcgtg tgcggcgtac ggtgccgttg  4380
gctaggttgt cgtcgatggt gtcgatggcg ttgtcgtggt tggctagttg tgtgagtagc  4440
cggtctatat tgtctatcac tgggtatcct cctcttcctc gtgtgtggtg gtggcttgtt  4500
tgcggcggta gtctttaatg acggtggcgg agatggggta tcctgcctgg gtgagcattt  4560
gggctagctg tgtggcgggg atagacctgt cggcgagcac gtctgcagcc ttgcggccgt  4620
agcgttggat gagggtttca gttttggttg ccatgatgtc ccatcggttg tgtggtgggc  4680
tgccatcctg tgcggcagtc gccgtcgtgt cctggtttgc gtgtgcacca cgatacggtt  4740
ccgtctgtgt ggttgagtgt tttaccgcac atgacgtttt gtagatgctc cggcagctcg  4800
ctattgctat cgtcttgctc gtctagcaaa gttttttgtt gggtgaaaaa ctcggacacg  4860
gtgccgttgt ggactgggag tatccatgtt ttccattgtt gttgtagccg ggtgttccag  4920
tggaattgtt ttgctgcgtt cgtggcttgt ttgatggttt tgaagtagcc tacaatgatc  4980
cgttgatggt cactatcggg cttgtgtggc cctttccaat attgggcagc tacagcgtac  5040
ctgttgttgt ctgtgaagcg cccccagcag tattccacca tgtgtgatag taccttgtcg  5100
ggcatgtctc gtacttggtt ttcgtcgagc catgcgtcga caataatgtt gcgtatggct  5160
```

```
cgcttgtctt tggtggtggg tttgaatgcg atgctcacaa tgcgggcctg tcgtcttgca  5220
tgaactggtt gaaggtgttg ttcccggcgt gttgggcttg tgtgatttgc tggtcggtcc  5280
agtcggggtg ttgctgtttc agatagtgcc agtggcacgc attgtaggtt tcgtcttgga  5340
gccgtgtgag atggttttcg gtgatgattt gtttccacat ggcccatgac acgtcgagcc  5400
ggttgaggat ttcgagggct gggatgttga attggttcag gaagaggatt tcatgggtgt  5460
agtagttttt ctcgtaggcg tcccatccgc ttcggtgcct gttgggctgg tttttggggt  5520
aggcttcccg gcagattttg tgtaaccgtt tggccatgtc tttgggtagt ttaatgtcgg  5580
ggttggcgcg gatcatggat cgcatcccat cataggtggt gccccaggtg tgcatgatgc  5640
ggagtgggtc ttcaccatcg gcccattttt ctgcacagat ggcgaggcgt atgcgtctcc  5700
tggcggcttt actggtgtcg cggcggccgg ggatggggca ggtgtcgagg ggatccatga  5760
tgttttagtg tacctttccg tgttgtggtt gtttgtctgg ttttattgta gcactgtgtt  5820
gagggcttgt gtcaaccctg tttttccgac ctgaaggtag gtgtctgtga catcccccag  5880
ggtgaggggc acatgggtgg cttgggggag tgccgtctgg aaggtttggg ccatctggtc  5940
tcctgctttg tctgggtcgg accagatgta gatgtggtcg tagccttcga agaatttggt  6000
ccaaaagttt tgccacgagg ttgcgccggg tagggcgacg gccgaccatc cgcattgttc  6060
gaggatcatg gagtcgaatt cgccttcgca aatgtgtatt tcggctgccg ggttggccat  6120
ggcggccatg ttgtagatgg agcctgtgtc tcctgccggg gttaggtatt tggggtggtt  6180
gtgggttttg cagtcgtgct ggagtgagca gcggaaacgc atttttctta tttcggctgg  6240
cccttcccaa acggggtaca tgtatgggat ggtgatgcac tggttgtagt tttcgtggcc  6300
tgggatgggg tcattgtcga tgtatccaag gtggtggtag cgggctgttt cttcgctgat  6360
gcctcttgct gagaggaggt cgagtatgtt ttcgaggtgg gtttcgtaga gggccgaggc  6420
tttctggatt cggcggcgtt ccgcaatgtt gtatgggcgt atgctgtcgt acattcgggt  6480
tttcttcttc taattgttgt tgtagtttgg cgaggcctcc tccgataccg catgtgtggc  6540
agtaccagac gcccttgtcg aggttgatgc tcatggaggg ctggtggtcg tcgtggaacg  6600
ggcagaggat gtgttgctcg ttcttggacg ggttgtaccg tatgtggtag gtgtcgagga  6660
ggcggcgggt gtcagaggtg tgggaggagc tcgttgaggg ttgataccac ataggcttcg  6720
ctccagggtt tgttgcgctg tttcatcact acgagtccga tagtggactg gttttcgcgg  6780
tttcggtggg tttcgtagtt gcgtgcctcc cggctggctt gtttcacgaa ttcggcgagg  6840
tggggctgcc cggctttggc ttcgataatg taggttttgt tgccggtggt gaggatgagg  6900
tcgccttcat cctctttacc gttgaggtgg aggcgttcta tatcatggcc ggtgtcgcgt  6960
agctggtgga ggagtcgtgt ttcccattcg gctccggctc ggcggtttct tgattgttgt  7020
gtcgacatga tagtcctttg tggtgttcgg tcatgttcca tggctgtttt tcggcgagtg  7080
gcccgaagaa tgtgtattcg gggtaggctc tgagtctttc gtatcgggtt ccgtctgggc  7140
tggatttgcc tgtgcgctgt ttgagtacag cgatgcgtgc ctctgccggt atcgataggc  7200
cgttgccgtt gtcttcgcca ccatacaggg agactcccaa tatgagttgt ggtttttcgg  7260
agaggccgtt tttgatttcc cgcctagccg gggggtgttc gatgtcggag ccggttttgt  7320
cggttgcgtg gtgtgtgaca ataatggtgg agcccgtgtc cctacctaat gctgtgatcc  7380
attgcatggc ttcttgctgg gcctgatagt cactctcgca gtcttgtatg tccatcaggt  7440
tgtcgataac gatgatgggt gggaaggtgt tccacatttc catgtaggct tgcagttcca  7500
tggtgatgtc tgtccatgtg atgggtgact ggaatgagaa tgtgatgtgt ccgccgtggt  7560
ggatgctgtc tcgatagtat tctggcccgt agtcgtcgat gttgtgttgt atctgggcgg  7620
tggtgtgttg ggtgttgagt gagatgattc gtgtggaggc ctcccagggg gtcatgtccc  7680
ctgatatgta gagggctggc tggttgagca ttgctgtgat gaacatggct agcccggatt  7740
tttggctgcc ggagcgcccc gcgatcatga cgagatcccc tttgtggatg tgcatgtcca  7800
ggttgcggta gaggggttct agctggggga tgcggggcag ctcggctgcg gtttgggagg  7860
ctctctcgaa ggatcgttgg agagagagca tcgggacctt atctatctgt ctatcggttg  7920
gatgatgttt tggtggtcag atggagtcga tgtcgatgtc agcatcagca ggggctgtgg  7980
tgtcgtctag ctggccgtta tcgcgtttgt ctacgtattc ggcaacctta tcgtagatgg  8040
cgtcgtcgag gggtttgagc acgaccgcgt tgaagccgtt tttggtgcgt acggtggcga  8100
gtttgaaggc ttgttcttcg ccaaggtagg cttcgaggtc gcggatcatg gagtgtgggc  8160
ggtcgttgct gccgcgtact ttttcgatga tggcgttggg gatggtttct ggggtgccgt  8220
tgttgaggtc gtctagggtg tggaagatgg tgacatcagc gtagatgcga tcggcggtct  8280
gtccaccgta gccttcggtg ttgtgttcta cgtcgtggat tttgaaggcg atggcggtgg  8340
cgtcctggtt tcgggagggg ttgaagaagg tgctgttgct gttgtttcgg tagtttgcga  8400
gtcccattgt tgtatccttt actgttttgt tggtttgtgt aggttttatc gggtgaggct  8460
gtttcgtttg ctgcggaaag cctcggaaac gtcactgtta ctggtgatga tctttttgta  8520
ctgtttgaga aggtcggcta gctgtgcttt gctggttgca ttgttgattt tgtcgatgat  8580
ggtgttgttt ccttctgagg cgatgttgtc tacgtagtct ttggcggcct ggttgtagcg  8640
atcttggagg atgatggatg ctgtggcgat cagtgttgcc aggtcccagt tccgtgccgc  8700
cgaactgttt ttgagtccgc ctaacaggtc gatgatggcc tgttttgtct gctctgctgt  8760
gtctcctcgg atgaccgccc atggtgcagc atagtctcca ccgtatttga gtgtgatcgt  8820
gagtcgatca ttgtcgatct tgtctttatc ggtcatttgg tgtccttttc tttattgtct  8880
gtttctggtg gctgtacggt agattctacc gggtacctgt aggcgtcttt cccgttgacg  8940
gcccagcagg cgtcttgtac ggggcagcct ttacagagtg ttgtgacgtg tgggacgaag  9000
atgcctgcgc tgattccttt cattgcttga ctgtacatgg atgatacatg ccggtaggtg  9060
ttgttgtcaa ggtcgtacag ttcggtggat gtgccttgtg tcggggactt gtcgtcgttg  9120
cggctggtgg ccggcgtcca aaacatgcct tttgttacat cgttgccgtg ttggttgagc  9180
atgtaccggt aggtgtgcag ctgcatactg tcggcgggta ggcgtccggt tttgagatcg  9240
aggatgaagg tttcgccggt gtcggtgtcg gtgaagatac ggtcgatgta gccaacgatc  9300
tgggtgccgt cggggagggt ggtttctacc gggtattcga tgcctggttt accgtccagg  9360
attgcggtga tgtattctgg gtggttgcgt ctccatgttt tccagcggtc cacaaaggtg  9420
gggccgtaca tcatccacca attgtagtct tttttgtgtg gcccgcccga ttcgcacatg  9480
tttttgcata ttctgccgga gggtttgatt tctgtgcctt cggattcggc gagggctact  9540
tgtgtggcga aaatgttttt gaaggatgcg agtttgtctg gtagcgcagg gtattcggcg  9600
gggttgtata ggtgtaggtc gtattgttcg gtgatgtggt gtatggcgct tccggcgatg  9660
gtggcgtacc aggtgtggtg ttgggtgtgg tatccgtgtt ggagacgcca tttttcgccg  9720
cattcggccc attgtgacag tgatgagtag gagatgtggc ctggatggtt gatggttttc  9780
gggtattgtg ctagaggcat tacttgtcgc ttttgttcca tgggtttcgg gtgtcttggc  9840
cggcatcgtg ttgctggtat gcgaggagtg cgaggcagtg ccaggcagca tgggctagat  9900
```

```
gcggtagccc ggattcataa tcgaggttgt tgccttgctg ccatgataac aggtgccggt  9960
agagggcatc aacgctgtgg ctccacgggt atcctccggt ccagttgttg tcgccgtatt  10020
tggtggcacc gtagcctgct acgtcgccga gagcgtgaag ggatgctggg tcgatgaggg  10080
agagcctgca aagtttgagt tcttttcggg caccgctgtt ggggtcggtg tacatgcggg  10140
ttggctcatc catgagatat gtgctcctta agcgtgggtt actggttagg gttgtgggcg  10200
agtgctacgg cgagaataat gatggcgagg gtttcagcga tgatgatggg tgttgtgatc  10260
atttgctgtc tcggggattg ttggtgagtg ttgatgcgcc taggagggtg gtgagggcgc  10320
atgcggcaat gatggcgagg gctgccttgt gtggggtgcc ggttgcgtac atccatgtga  10380
tgatgccgcc ttggatccag gctaggctgg tgaagaacgt ttcgtagctg tgtagctcaa  10440
tgttgttgtt gggtgtgttc atgcttgctc ctgaagaatg gtgttgatgg ttttataaat  10500
gttgtacagg tcggcttcga tggtttgtag ctgtttgatt tggtggtcga gattaatgtc  10560
tgggttgagg gtgttgatgc gggaggcaat atctgtggct gtgcgtagtg ttccgccggt  10620
gtggtgaata atgtgtgccg tgtcggcgag tccggtgatg acagcgtagt gggataggag  10680
aggcatagct ggggggtgct ccttggcggg ttactgttgc gggttgatgt tgaggtcggt  10740
gacgtgcggg tggtcttctg ttccggtgac gaggcagtgg acggtgacgg gtagtttgga  10800
tgcgccggga tgtttcgcgg ttgcgccgta gacgatggag aaggtgtctt taccaataat  10860
tttgtggagt tggaggtcga tgtcggggtt gccgttccag ttgaggccgt gtgcggcggc  10920
ctgttgttcg gctttgcggt tgcaggtgtg tgctgccgtg atcatggtga gtccggtggc  10980
ggtttcttca ccccgtgttt gggcttgctt gtgggctttc tgctgttctg cttgtaggga  11040
gcggactgcg gctgcctgct tggctgtttt ctcggctttg cgctgttgga cggttttggg  11100
ggtccattcg gtgttggctg tggtggcttg tggggctggt tgtgaggcga gtggcggatt  11160
gtcgtcgggt gctgggagga aagagcatgc ggcgatgatg gcggctgtga ttccggcgat  11220
ggtgtagccg tttttcttgt tcatggctgt tgtccccttt ccggggtgtt gttcgttgct  11280
gacatgatca atacttccag cgaatggacc tcgtgtcaag actgcgctca aatgttctga  11340
gcgatccttg tgtggctagg ggttttatcg ggcgcatagg gtgagtaggt ggcctacgtt  11400
gatgcggctc acattccagt agagttgtgt ggcttcaccg ccggtgagcg gcttccactc  11460
gtcgtggctg aacacggtgc catcggatgc gatgaacgtg tcggggcgta gcttgtgaag  11520
ttcggcttcc acgctctgcc ggtaggtttc ggcgaggccc tcaaaatcca tgtggtcgca  11580
ggagaggttt tcgaggcgtg tcaggtcgaa gggtgtgggg cagtcgtagc tggcgggggt  11640
gtagagctgg gtgaagtggt cggcgatctt ctgcatgacg ggttcctttt ctcgtgtggt  11700
gggttgatgg tttttatcgt gtggcttcgg cgatgatggc gtctacatag atcatgtcga  11760
tgagatcgtg gagttcctcg gcctcattct cggagaggtg gcgccagtcg ggtggcccat  11820
atactgcgcc gtcgagggtg acagtccaca gtggccggat gagtcgtatg gcttcttgta  11880
ctttagcgtg gtacatgcgg cgcaccatat cgagatcgat gtcgtctgaa tggtttccgg  11940
tgaggctgtg gaggctaagc gggtcgattt ctgtctgcct gtagagggat gtgaaggatg  12000
gtgtgatgag tgtgccatcc atgatgggtg tgctcctttc ggtggtgtag gggttgttgt  12060
ggtttttatg gtgtgagggt tgtgatccat agtcaaggct gcgctcaatc ggattgagcg  12120
tttcatggag tgtgtcgggt gtgacagatg tcactgaagc ctttattgcc tctctcagcg  12180
tctcaaatct tctaggggta gaaatatact agggcagccc tataaatcga ttctaggccc  12240
ctttctgtga ctctgagggg catatgtgag tggagggtgg tatgacaggt ggcatggact  12300
tggaggaagg tgtccagtcg ggagcgctcg atgatccggc tgcacgggtg tctggaaggc  12360
ttatggtctg cgtgagatat gtcacatcac ctagactcta ggaacactac ccacacctgt  12420
agagtctatt ctgcagatgg caccagagcc aagaatgcct ctctaaggca cgtaaaggcc  12480
cctctgaggc tcttacaccc tcaactctag gtatttgtac cccagcata ttctgatcga  12540
ttctagggcc ctttttgagg cttacgcgag aacagcaccc aaagactagc ccatcaaccc  12600
ttactctggt tagctaagcc tgcactatgt ggacagtgtg ggatgctaag agggaagaag  12660
gacacggtaa aagaaaaaag ggggagtacc agccttcacg ccttcaagcc ttaaggtctt  12720
agcactaagc acttagcacc gagccccctc aagggctcgg catcagcccg agcaggctca  12780
gccctgaaag gggtacacgc catcagggaa ggcttgagag tacgaggagc cttagcgacg  12840
agtactcgaa agcctgagga aacaccatca gcactgatgg gcctagcgcg ttcggaaagg  12900
acacaagagt aaagtgtgac agctatccgg gagtgaaacc cgttctggct aggggtttca  12960
gccttaacca cctgtaaagg ttacaagact ctaagaaaat ttaagaaact tcttaggaag  13020
aaagttgtgt tgatgtcacc ccaaaaacac ctaaaatagc cctcaaaccc gcctatagag  13080
ccaaacagtc aagtttgact cgtcttgacg gcgtatgcta ggctggacag gtagccagct  13140
ggacgcaagg ccagaaagtg ctgacgcact tcccgacctt gcttaccatc agtctaccaa  13200
agacttaaaa gtttaacagc taagcgctaa gcccttaaga cctaaacgct tagcaccgag  13260
ccccctcaag ggctcggcat cagtcctaag agcttagccc ttaaggatct aaggttacta  13320
taaagcttta aacactttaa gtaaacttaa gagcttagca cttaaagtta attaataacc  13380
ttaaaggctt acacacttag cactgagccc ttcaaggctc agcatcagta taaagacctt  13440
aacacctaag ttaagtataa aactttaaag gcttagcgct taaggatata aacttaacat  13500
cagtgtttaa gacttaaaga gttaaacact taaagtaact ataatacttt aaaaatctta  13560
agtacttaaa gttaaccatc agtcttaaac tttaatatta taacctataa gtattaaagc  13620
ttataagtta taaaagtttt agaagagcta aggggttaac ttctttactt ctcttctctc  13680
tttggttctt tctctcttct ctccttttct tcatcagggg agaagaggaa cctttaccat  13740
cagcgccgat gggcttttca tcgtgtgact cgtgtgcttc tggtcgcaag ctcccatcgc  13800
acactcccca cactcttaca cccgtgcccc tttcaggctt agcgtgttcg gctgaaggcg  13860
tacggcgtgt cacgctcaca cccttaacac cgggtgagac ttaaagtgta tattatatgt  13920
agaagacttt aaaacctata gagtgtttct gctgagcctg tgtcctacac cgctaggcgc  13980
caagcgctaa gccttgaaac gcgaacacac acccaccccc ttttctcttt cgtgtccttc  14040
tcttttgaca ccgctggggg gcgatgtgat ctttctcaca tgccaggggg tagtggagaa  14100
aacaaacacc ccggcacaaa cagaacaccc cctcaaacga acaaaacagc ccccaggatc  14160
gactagcagg gcaagggtag agtattcata cccccagacg attccaggcc gttagagagg  14220
caatgagagg ctcacagggg tcatgggaga tcggggaacg cgatggcaca caccaaccgc  14280
acagccagcc aagcccaccg acgctggcgg caacgactca tcacccaagc ccgacaacaa  14340
ggccaaaccg aatgcccact ctgcggagca accatcacct gggacacaca ccagctgcca  14400
accagccccg aagccgacca catcacaccc gtcagcaggg gaggactcaa caccctcgac  14460
aacgggcaaa tcatctgcag aacatgcaac agaagcaaag gcaatcgcag cgaaccaaac  14520
atcaaattcc aacaacaaac cacaaaaaca cttgtttcat ggtgacaaac ccgccaaccc  14580
ccaccgggca caccccctgc acacccgtgc aagacctcgt acggcttagt gaaatacctc  14640
```

cctttgtgg atttgtctgt ttgtcgactt tttgtgttgg tggtgagtgt ggtgcagcct 14700
gagcttcctg atggtcgtga gtggtgtggg gagacgcgtc gttggtggcg tgtgtggggt 14760
gaggatagtc gcgcgcagta cgtgtctgat gaggagtggc tgtttctcat ggatgctgcg 14820
gtgattcatg attgtgtgtg gcgtgagggt cgcgcggatt tggtggcttc gcttcgtgct 14880
catgtgaagg cttttatggg tatgttggat cggtattcgg ttgatgtggc gtctggtggc 14940
cgtggtgggg gttctgcggt ggcgatgatt gaccggtata ggaagcgcaa gggggcctga 15000
ttaggtgtct ggtgttgttg ggtctcaggt tcctcgtcat cgtgtggctg cggcgtattc 15060
ggtgtctgct ggcggtgatg cgggtgagct tggtagggcg tatgggttga cgcctgatcc 15120
gtggcagcag caggtgttgg atgattggct ggctgtcggt ggtaatggca ggcttgcttc 15180
gggtgtgtgt ggtgtgtttg tgcctcgcca gaatggcaag aatgcgatcc ttgaggttgt 15240
ggagttgttt aaggcgacta ttcagggtcg ccgtattttg catacggctc acgagttgaa 15300
gtcggctcgt aaggcgttta tgcggttgag gtcgtttttt gagaatgagc ggcagtttcc 15360
tgacttgtat cgtatggtga agtcgattcg tgcgacgaat ggtcaggagg ctattgtgtt 15420
gcatcatccg gattgtgcca cttttgagaa gaagtgtggc tgtccgggtt ggggttcggt 15480
tgagtttgtg gcccgttctc gtggttctgc tcgcgggttt acggttgatg atttggtgtg 15540
tgatgaggct caggagttgt cggatgagca gttggaggct ttgcttccta cggtgagcgc 15600
tgcccccgtct ggtgatccgc agcagatttt cctgggtacg ccgcctgggc cgttggcgga 15660
cgggtctgtg gtgttgcgtt tgcgtggtca ggctttgtcg ggtggtaaaa ggtttgcgtg 15720
gacggagttt tcgattcctg acgagtctga tccggatgat gtgtcgcggc agtggcggaa 15780
gttggcgggg gatacgaatc ctgcgttggg tcgtcgcctg aatttcggga ccgtaagcga 15840
tgagcatgag tcgatgtctg ctgccggttt tgctcgggag cggcttggct ggtgggatcg 15900
tggccagtct gctacgtcgg tgattccggc tgataagtgg gctcagtcgg ctgtggatga 15960
ggcgagtctg gttggcggga aagtgtttgg tgtctcgttt tctcgttctg gggatcgggt 16020
tgctttggct ggtgccggcc ggactgatgc tggggttcat gttgaggtta ttgatgggct 16080
gtctggcacg attgttgatg gtgtgggccg gttggctgac tggttggcgg ttcgttgggg 16140
tgatactgac cggatcatgg ttgccgggtc tggtgcggtg ttgttgcaga aggcgttgac 16200
ggatcgtggt attccgggcc gtggcgtggt ggttgccgat actggcgtgt atgtggaggc 16260
gtgtcaagcc ttcctggaag gtgtaaggtc tgggaatgtt tctcatcctc gtgctgattc 16320
tcgccgtgac atgttggata ttgctgtgag gtcggctgtg cagaagcgta aggggtctgc 16380
gtggggttgg ggttcctcgt ttaaggatgg cagtgaggtg cctttggagg ctgtgtcttt 16440
ggcgtatctt ggtgcgaaga tggcgaaagc gaagcggcgt gaacggtctg gtaggaagcg 16500
ggtgtctgtg gtatgaactc ggatgagttg gctctaattg agggcatgta cgatcgtatc 16560
caaaggttgt cttcgtggca ttgtcgcatt gagggctact atgagggctc gaatcgggtg 16620
cgtgaccttg gtgtggctat tccgccggag ttgcagcgtg tgcagactgt ggtgtcgtgg 16680
cctggtatag ccgtggatgc tttggaggag cgtctggatt ggcttggctg gactaatggt 16740
gacggctacg gcctggatgg tgtgtatgct gcgaatcggc ttgctacggc gtcgtgtgat 16800
gtgcatttgg atgcactaat ttttgggttg tcgtttgttg cgattattcc tcatggtgat 16860
gggtcggttt tggttcgtcc gcagtcacca aagaattgca caggtaagtt ttcggctgac 16920
ggttctcgtc tggaggctgg ccttgtggtg cagcagacgt gtgatcctga ggtggttgag 16980
gctgagcttt tgttgcctga tgtgattgtt caggtggagc ggcggggttc gcgtgaatgg 17040
gtcgagacgg gccgtattga gaatgtgttg ggtgcggttc cgttggtgcc tattgtgaat 17100
cgtcgtcgta cttctaggat tgatggccgt tctgagatta cgaggtctat tagggcttac 17160
acggatgagg ctgttcgcac actgttgggg cagtctgtga atcgtgattt ttatgcgtat 17220
cctcaacgtt gggtgactgg cgtgtcggct gacgagtttt cgcagccggg ttgggtcctg 17280
tcgatggctt ctgtgtgggc tgtggataag gatgatgacg gtgacactcc gaatgtgggg 17340
tcgtttcctg tcaattcgcc tacaccgtat tcggatcaga tgagactgtt ggcgcagttg 17400
actgcgggtg aggcggctgt tccggaacgc tatttcgggt ttatcacgtc taacccacct 17460
agtggggagg ctttggctgc cgaggaatct cggcttgtga agcgtgctga acgcaggcag 17520
acgtcgtttg gtcagggctg gttgtcggtt ggtttttggg ctgccaaggc gttggattct 17580
cgtgttgatg aggccgattt ttttggtgat gttggtttgc gttggcgtga tgcttcaacc 17640
ccgactcggg cggctacggc tgatgctgtg acgaagcttg ttggtgccgg tattttgcct 17700
gctgattctc gtacggtgtt ggagatgctg gggcttgatg atgtgcaggt tgaggctgtg 17760
atgcgtcatc gtgccgaatc tgcggatccg ttggcggcac tggctggggc tatatcgcgt 17820
caaactaacg aggcatgata ggcgatggct tcgggtgcta tgtcgaggct tgctgcgact 17880
gagtatcagc gtgaggcggt caggtttgct gggaagtatg cgggctatta tgccgagctg 17940
ggtcgtttgt ggcgtgccgg gaagatgaca gacgcgcagt atgtgcgttt gtgtgtggag 18000
ttggagcgtg ccggccatga tggttcggca tcgttggctg ccaggtttgt gtcggatttt 18060
cgccggttga atggtgtgga tccgggtttg attgtgtatg acgagtttga tgctgccgcc 18120
gcgttggcta ggtcgtttc gactatgaag attcttgaga gtgacccgga tagggcgaat 18180
gacacgattg atgcgatggc tgcgggtgtt aatcgggctg tcatgaatgc tggccgtgac 18240
acggttgagt ggtctgcggg tgcgcagggt aggtcgtggc gtagggttac tgatggtgat 18300
ccgtgtgctt tttgtgccat gttggctacg aggtcggatt atacgacaaa agaaagggca 18360
ctcactaccg gtcatacgcg gcgtcataag cgtggtggta agcgtccgtt tggttcgaag 18420
tatcatgatc attgtggttg tacggtggtt gaggttgttg gcccttggga gccaaatagg 18480
gctgatgtcg agtatcagag gacgtatgag aaggcccgtg agtgggttga tgatcatggg 18540
ttgcagcagt cgcctggcaa tattttgaag gctatgcgta ctgttggcga tatgagataa 18600
tttgatgtgg tttccggttg tgcgccgccg gttattggtg cacagggttg tctcccgcac 18660
gggggtcaac aatgttgtgt tgttttccgc aaggagtgta gggttaggct atggccgatc 18720
agagtgttga ggaacagaat gttgacaatg atgttgtgga gtccggaaag gataacggca 18780
ttgttgatac agtaaaagac gatggcgggc aggaggtagc cgacaatcag ttgaagaatg 18840
aaggcgaggg taaatcgccg gggactgatt ggaaggcgga ggcccgtaag tgggagtctc 18900
gtgctaaaag taatttcgcc gagttggaga agcttcgcgc ctcggatggt gattctggat 18960
ctactattgc tgagcttcgc cgcaagaatg aggaactcga agacaggatc aacgggtttg 19020
ttcttgaggg tgtgaagcgc gagatggctt cagagtatgg tttgtccagt gatgcgatcg 19080
ttttcttgtc gggtggcgat aaggagtcgc ttgccgagtc tgcgaaagct ttgaagggtt 19140
tgatcgacca tagtagtggt ggcgcgggtg tgcgccgtct tgcggggagt gcccccgttg 19200
atgatgttaa acgacgtgag ggtgtcgcgt ttgtggatgc tcttgtcaat aattctagga 19260
gatgatttgt gatggttgac gattttcttt ctgcagggaa gctggagctt cctggttcta 19320
tgattggtgc ggttcgtgac cgtgctatcg attctggtgt tttggcgaag ctttcgccgg 19380
agcagccgac tatttttggc cctgttaagg gtgccgtgtt tagtggtgtt cctcgtgcta 19440
agattgttgg tgagggcgag gttaagcctt ccgctagcgt tgatgtttcg gcgtttactg 19500
cgcagcctat caaggttgtg actcagcagc gtgtctcgga cgagtttatg tgggctgatg 19560
ctgattaccg tctgggtgtt ttgcaggatc tgatttcccc ggctcttggt gcttcgattg 19620
gtcgcgccgt ggatctgatt gctttccatg gtattgatcc tgccactggt aaagcggctg 19680
ccgctgtgca tacttcgctg gataagacga agcatattgt tgatgccacg gattctgcta 19740
cgaccgatct ggtcaaggct gtcggtctta tcgctggtgc tggtttgcag gttcctaacg 19800
gggttgcttt ggatccggcg ttctcgtttg ccctgtctac tgaggtgtat ccgaaggggt 19860
ctccgcttgc cggccagcct atgtatcctg ccgccgggtt tgctggtttg gataattggc 19920
gtggcttgaa tgttggttct tcttcgactg tttctggcgc cccggagatg tcgcctgcct 19980
ctggtgttaa ggctattgtt ggtgatttct cgcgtgttca ttggggtttc cagcgtaact 20040
tcccgatcga gcttatcgag tatggtgacc cggatcagac tgggcgtgac ctgaagggcc 20100
ataatgaggt tatggttcgt gccgaggctg tgctgtatgt ggctatcgag tcgcttgatt 20160
cgtttgctgt tgtgaaggag aaggctgccc cgaagcctaa tccgccggcc gagaactgat 20220
ttattgttgc ggtgatgtgt caatgtgcag gggtggtgt tgatgggtat catttgaag 20280
cctgaggata ttgagccttt tgccgatatt cctagagaga agcttgaggc gatgattgcc 20340
gatgtggagg ctgtggctgt cagtgtcgcc ccctgtatcg ctaaaccgga tttcaaatac 20400
aaggatgccg ctaaggctat tctgcgcagg gctttgttgc gctggaatga tactggcgtg 20460
tcgggtcagg tgcagtatga gtctgcgggt cctttcgctc agactacacg gtctagtact 20520
cccacgaatt tgttgtggcc ttctgagatt gccgcgttga agaagctgtg tgagggtgat 20580
ggtggggctg gtaaagcgtt cactattaca ccgaccatga ggagtagtgt gaatcattct 20640
gaggtgtgtt ccacggtgtg gggtgagggt tgctcatgcg ggtcgaatat taacggctac 20700
gctggccctt tgtgggagat atgatatgac cagttttcct tatggtgaaa cggttgtgat 20760
gcttcaaccg actgttcgtg tcgatgatct tggtgacaag gttgaggatt gggggcatcc 20820
tgtagaaacc gtgtaccata acgtggccat ctatgcttcc gtttcgcagg aggatgaggc 20880
cgcggggcgt gactctgact atgagcattg gtcgatgctt ttcaagcagt ctgttgttgg 20940
tgctgattat cgttgccggt ggcgtattcg gggtgttgtg tggggggctg acgggtctcc 21000
tatggtgtgg catcacccca tgtccggttg ggatgcgggc acgcagatca atgtgaagcg 21060
caagaagggc tgatagattg tggctcagga tgtgaatgtg aagctgaact tgccgggtat 21120
tcgtgaggtg ttgaagtctt ctggggtgca ggctatgttg gctgagcgtg gcgagcgtgt 21180
caagcgtgcg gcctcggcga atgtgggcgg taacgctttc gataaggccc aataccgtaa 21240
tggtttgtcg tcggaggtgc aggttcaccg tgttgaggct gtcgctcgta taggtaccac 21300
atataagggt gggaagcgta ttgaggcgaa gcatggcacg ctggctaggt cgattggggc 21360
ggcgtcgtga tcatctacga tgaccccagg aagtgggcta aacgcgtgct caaggatgat 21420
ggctggctgt ctgggatacc atgcaccggg acagtgcccg atgattttac gggtgacctg 21480
atttggttgg cgttggatgg tggcccacag ttgcatgttc gcgagcaagt ttttttgcgc 21540
gtgaatgtgt tttctgatac gccggatcgt gctatgtcgc tagccaggcg ggtggaggct 21600
gtccttgcgg atggggttga tggcaaccct gtggtgtact gtaaacggtc tactggtcct 21660
gatttgctgg ttgatggtgc acgttttgat gtgtattcgc tgttcgagct gatatgtagg 21720
cctgtcgagt ctgagtaaac gtatttgttt ttgttttaat gtaattgttt gatatttaat 21780
gggggttgtg atggctgcaa cacgtaaagc gtctaatgtt cgttcagcgg ttactggcga 21840
cgtttatatt ggtgacgcgc acgcgggtga tactattaag ggtgtggagg cggttcctga 21900
cggtcttacc gctttagggt atctgtcgga tgacgggttt aagattaagc ctgagcgtaa 21960
aacggatgat ttgaaggctt ggcagaatgc ggatgttgtt cgcacggttg ctaccgagtc 22020
ttctatcgag atttctttcc agctgatcga gtctaagaag gaggttatcg agctgttttg 22080
gcagtcgaag gttactgccg gatccgattc aggttcgttc gatatttctc cgggtgccac 22140
gacgggtgtt cacgccctgt tgatggatat tgtggatggt gatcaggtta ttcgctacta 22200
tttccctgag gttgagttga tcgatcgtga cgagatcaag ggcaagaatg gcgaggtgta 22260
cgggtatggt gtgacgttga aggcgtatcc tgcccagatt aataagaagg gtgatgcggt 22320
gtcgggtcgg gggtggatga cggctttaaa agctgatact cctccggttc cgccttctcc 22380
gaagccgaag ccggatccta atccgccgtc tgagaactga tacacgattt taggggattg 22440
ttgatagatg agtgacacgg gttacacgtt gaagattggt gaccgtagct gggtgttggc 22500
ggatgcggag gagacggctc aagctgtgcc tgcccgcgtg tttcgccgtg cagctaagat 22560
tgcccagtcg gggagtctg cggatttcgc ccaggttgag gtgatgtttt ctatgttgga 22620
ggctgccgcc ccagtggatg ctgtggaggc cctggagggg cttcctatgg ttcgtgtggc 22680
cgagattttc cgtgagtgga tggaatataa gcctgacggt aagggtgcct cgctgggga 22740
atagtttggc tccacggcct gattgatgat tatcgtgggg ccatcgaata tgattggagg 22800
acccggttcg gttgctcggt ttatgatgtt ggtggcccga taatgtgttg gggtgaggct 22860
gttcggctgg ctggcgtgtt gtgtaccgat acgtctagcc agttggcggc ccacctgaat 22920
ggttggcagc gcccgtttga gtggtctgag tgggcggtgt tggacatgtt ggatcattac 22980
aggtctgcta atagtgaggg gcagccggag cctgtggcga ggcctacgga tgagcgtagg 23040
gcccggttta cgtttgggca ggtggacgat attttggcgc gtgttcgtgc cggtggcggg 23100
gtgtctcgcg agattaatat tatggggtga atagtgtatg tctggtgaga ttgcttccgc 23160
atatgtgtcg ttgtatacga agatgcctgg tttgaaggct gatgttggta aacagttgtc 23220
gggtgttatg cctgctgagg gtcagcgttc gggtagtctt tttgctaagg gtatgaagtt 23280
ggcgcttggt ggtgccgcaa tggtgggtgc catcaatgtt gctaagaagg gcctcaagtc 23340
gatttatgat gtgactattg gtggcggtat tgctcgcgct atggctattg atgaggctca 23400
ggctaagttg actggtttgg gtcatacgtc gtctgacacg tcttcgatta tgaattcggc 23460
tattgaggct gtgactggta cgtcgtatgc gttgggggat gcggcttcta ctgcggcggc 23520
gttgtctgct tcgggtgtga agtctggcgg gcagatgacg gatgtgttga agactgtcgc 23580
cgatgtgtct tatatttcgg gtaagtcgtt tcaggatacg ggcgctattt ttacgtctgt 23640
gatggcccgc ggtaagttgc agggtgatga catgttgcag cttacgatgg cgggtgttcc 23700
tgtactgtct ttgcttgcca ggcagacggg taaaacgtcg gctgaggtgt cgcagatggt 23760
gtcgaagggg cagattgatt ttgccacgtt tgcggctgcg atgaagcttg gcatgggtgg 23820
tgctgcgcag gcgtctggta agacgtttga gggcgctatg aagaatgtta agggcgcttt 23880
gggctatctt ggtgctacgg ctatggcgcc gtttcttaac gggttgcggc agatttttgt 23940
tgcgttgaat ccggttatca agtctatcac ggattctgtg aagccgatgt ttgctgccgt 24000
cgatgctggt attcagcgta tgatgccgtc tattttggcg tggattaacc gtatgccggg 24060
catgatcact cgaatgaatg cacagatgcg cgccaaggtg gagcagttga agggcatttt 24120

```
tgcaaggttg catttgcctg tccctaaagt gaatttgggt gccatgtttg ctggcggcac  24180
cgcagtgttt ggtattgttg ctgccggtgt ggggaagctt gtcgcggggt ttgccccgtt  24240
ggcggtgtcg gtgaagaatc tactgccgtc gtttggtgct ttgaagggtg ccgccggcgg  24300
gcttggcggc gtgtttcgcg ccctgggtgg ccctgtcggg attgtgatcg gcttgtttgc  24360
tgccatgttt gctacgaacg cccagttccg tgccgctgtt atgcagcttg tggctgtggt  24420
tggtcaagcc ctggggcaga ttatggccgc tgtgcagcct gtgtttggtt tggttgcggg  24480
tctggtggcc cggttggcgc cagtgtttgc ccagattatt ggtttggttg ccgggctggc  24540
tgcccagttg atgcctgtga ttggtatgct tgttgcccgg ctggttcctg tgatcaccca  24600
gattattggt gcggtgacgc aggtggcggc catgttgctg ccggcgttga tgccggtgtt  24660
gcaggctgtt gttgctgtga tacggcaggt tgttggcgtg atcatgcagt tggtgccggt  24720
gttgatgccg gtgattcagc agattttggg tgcggtcatg tctgtgctgc cgccgattat  24780
tggtttgatc cggtcgttga tgcctgtgat tgcggcggtt atgcgtgtgg tggtgcaggt  24840
tgtttcggtt gtgatacagg tggtggcccg tattcttgct gttgtggctc cgatggtggc  24900
tgccgtggta gggtttgttg cccgtattgt tggtgctgtc gtgtcggctg ttgcccgtgt  24960
tattgctgct gttgcccgtg ttatcgggtg gattgttgct cattttgtgt cgggtttggc  25020
gcgtatgggt tcggttattc aggctggctg gaatcatatt agggcgttta cgtctgcgtt  25080
tattaacggt tttaagtcgg tgatttctgg cggcgtgaac gctgttgtgg ggttttttac  25140
gcggcttggt ttgtcggttg cttctcatgt tcggtctggt tttaacgcgg ctcgtggtgc  25200
tgtttcttct gcgatgaatg ctattcggag tgttgtgtct tcggtggcgt ctgctgttgg  25260
cgggtttttc agttcgatgg cgtctagggt tcgtagtggt gttgtgcgcg ggtttaatgg  25320
ggccaggaat gcggcatctt ccgctatgca tgctatgggg tccgctgtgt ctagcggcgt  25380
gcatagtgtg ctagggtttt tccggaatct gcctggcaat attcggcatg ctctcggtaa  25440
tatggggtct ttgttggtgt ctgctggccg tgatgtggtg gccggtttgg gtaacggtat  25500
taagaatgct ttgagtggcc tgttggatac ggtgcgtaat atgggttctc aggttgctaa  25560
tgctgcgaag tcggtgttgg gtattcattc cccgtcgagg gtgtttcgtg acgaggttgg  25620
ccgtcaggtt gttgccggtt tggctgaggg tattactggt aatgcgggtt tggcgttgga  25680
tgcgatgtct ggtgtggctg gtcggctgcc tgatgtggtg gatgcccggt ttggtgtgcg  25740
atcgtctgtg ggctcgttta ccccgtacga ccggtatcgg cgtgcgagtg agaagagtgt  25800
tgtggtgaat gttaacgggc ccacgtatgg tgatcctaac gagtttgcga agcggattga  25860
gcgtcagcag cgtgacgctt tgaacgcttt ggcttacgtg tgatagggggg tgtggttcat  25920
gtttcttcct gacccgtctg atcgttctgg tttgactgtt acctggtcta tggatccgct  25980
gtttggcgat gagcgtgtgc ttcatttgac ggattatacg gggtcgtctc cggtgatgtt  26040
gttgaatgat tcgttgcgcg gtttgggtgt tcctgaggtg gagcattttt ctcaaactca  26100
tgttggggtg catggctcgg agtggcgcgg gtttaatgtg aagcctcgcg aggtgacgct  26160
gcctgtcctg gtgtcgggtg ttggtgtgga tcctgtgggc gggtttcgtg acggtttttt  26220
gaaagcctat gacgcgttgt ggtctgcttt tcctcccggg gaggagggtg aactgtcggt  26280
gaagactcct gccggcaaag agcgtgtgct gaagtgccgg tttgattcgg ctgatgacac  26340
gtttacggtg gatccggtga acaggggtta tgcgcgttat ctgttgcatt tgacggctta  26400
tgacccgttt tggtatgggg atgagcagaa gtttcgtttc agtaacgcga agttgcagga  26460
ttggttgggt ggcggccctg tcggcaagaa gggtacagcg tttcctgtgg tgttgacgcc  26520
tggtgttggt tcgggttggg ataacttgtc taatagggggt gatgtgccgg cgtggcctgt  26580
gattcgtgtg gagggccccc tggagtcgtg gtctgtgcag attgatggtt tgcgtgtgtc  26640
ttcggattgg cctgtcgagg agtatgattg gatcactatt gatacggatc ctcgtaaaca  26700
gtctgcgttg ttgaacgggt ttgaggatgt gatggatcgt ttgaaggagt gggagtttgc  26760
gcctatcccg cctggcggtt ctaagagtgt gaatattgag atggttggtt tgggtgccat  26820
tgttgtgtcg gtgcagtaca ggtttttgag ggcttggtga atagttgatg gctggtcttg  26880
ttccgcggat aacattgttt acaccggatt atcaccgtgt ggcgcctatc aattttttttg  26940
aatcgttgaa actgtcgttg aagtggaatg gtttgtccac tttggagttg gtggtgtctg  27000
gtgatcattc taggcttgac gggttgacta agccgggtgc acggctggtt gttgattatg  27060
gtggtggcca gattttttct gggcctgtgc gtaaggttca tggtgtgggt ccgtggcgtt  27120
cttcgcgggt gactatcacg tgtgaagatg atattcgtct gttgtggcgt atgttgatgt  27180
ggcctgtgaa ttatcgtcct ggtatggttg gtatggagtg gcgtgccgac agggattatg  27240
cccactattc gggtgcggct gagtcggtgg ctaagcaggt gttgggggat aatgcttggc  27300
gttttccgcc tgatatattt atggtggatg ataagagtcg tggccgctat attaaggatt  27360
ttcaggcgcg gtttcacgtg tttgccgata agttgttgcc ggtgttgtcg tgggctcgga  27420
tgactgtcac ggtgaaccag tttgagaatg cgaagcagga tcagcggggt ttgctgtttg  27480
attgtgtgcc tgccgtgacc cgtaagcatg tgttgactgc cgagtctggg tctattgtgt  27540
cgtgggagta tgtgagggat gccccgaagg cgacatctgt ggtggttggt ggccgcggcg  27600
agggtaagga tcggctgttt tgtgaggatg ttgattcggc ggccgaggat gactggtttg  27660
atcgtgtcga ggtgtttaag gatgcccgta acacggattc tgaacatgtg catcttattg  27720
atgaggcgga gcaggtgctg caggagtctg gggccacgtc ggggtttaag atcgagttgg  27780
ccgagtcgga tgtgttgcgg tttgggccag gcaatctgat gccgggtgat ttgatctatg  27840
tggatgtggg ctcgggctct atcgcggaga ttgttcggca gattgatgtg gagtgtgatt  27900
cgccgggtga tggttggacg aaagtgactc ctgttgcggg ggattatgag gataatccgt  27960
cagcattgtt ggctcgccgt gttgccggtt tggctgcggg tgtgcgggat ttgcaaaagt  28020
tttagaagga ttggggtttg ttgtgggtat tgtgtgtaaa gggtttgatg gtgtgttgac  28080
cgagtatgat tgggctcaaa tgtctggtct gatgggtaat atgccgtcgg tgaaagggcc  28140
ggatgatttt cgtgtcggta cgactattca gggtgccaca gtgttgtgtg aggtcctgcc  28200
ggggcaggct tgggctcacg gggtgatgtg cacgtcgaat agtgttgaga cggtgacggg  28260
gccgcttccg ggccctggcg agacccgata cgactatgtg gtgttgtctc gggattggga  28320
gcagaatacg gccaagttgg agattgtttc tggggggcgt gcggagcgtg ccagggatgt  28380
gttgcgtgcc gagcctggcg tgtttcatca gcagttgttg gcgactttgg tgttgtcgtc  28440
taacgggttg cagcagcagt tggataggcg tgctatagcg gctagggttg cgtttggcga  28500
gtctgctgcg tgtgatccta ccccggtgga gggtgaccgg gtgatggttc cttcgggggc  28560
tgtgtgggct aatcatgcta acgagtggat gctactgtct ccgaggattg agacgggttc  28620
taagcagatc cagtttggcg ggtctgccgt gtatgcttac acgatcccgt ttgatcgcca  28680
gttcactagt gcgcctgtcg tggtggcgtc tatggctacg gcggctgggg gcacggcaca  28740
gatcgatgtg aaagcctaca atgttactgc caaggatttt cggttggcgt ttatcacgaa  28800
tgacgggtct aagccgaatg gtgtgcctgc ggtggctaac tggattgctg tcggcgtgtg  28860
```

```
actgtacagg tgttgtggcg gatggtgtga tgttgggggg ctgtggtgtc gtggtttact  28920
cctgcactgg tggcctctat ctgtacggcg ttggccacgg ttttgggttc tgttcaggct  28980
gtcacatccc ggtctaggaa gcgtttacgc aggctgtctg cgcaggtgga tgcgatggaa  29040
gagtatacgt ggggtgtgcg gcgcgaggtt cgaaggttta acgccgggct tcctgacgag  29100
gtggagccta tgcatcttcc tgatttgccc gagtttttga aagatactgt tgatggtggt  29160
ggggggtgaa ttgtgaggga gttggaggaa gaaaaaaggc agcgccgctc gtttgagaag  29220
gcttccctga tactgttgtt cctgtcgctt gtgctgttgg cggtggttgc tgcgggtgct  29280
ttacggtacg ggtctgtggc ttcccagcgg gattcggagc aggcgagggc ccagtctaat  29340
ggtacagccg ctaaagggtt ggccagccgt gtgaagcggg tgtgtgcttc gggtgggcag  29400
gagtcggtgc ggcttcacca gtctggcttg tgtgtggatg ctcggcgtgt tgagcggagt  29460
gtgcagggtg tgccgggtcc tgcaggtgct gatggccggg atggtgttaa tggttcggct  29520
gggctggttg gccctgttgg tccgcagggt tctcctggtt tg                    29562

SEQ ID NO: 76          moltype = DNA  length = 83
FEATURE                Location/Qualifiers
source                 1..83
                       mol_type = other DNA
                       note = Cos PAC7 pIC405
                       organism = synthetic construct
SEQUENCE: 76
aaaacccgcc aacccccacc gggcacaccc cctgcacacc cgtgcaagac ctcgtacggc  60
ttagtgaaat acctcccttt tgt                                          83

SEQ ID NO: 77          moltype = DNA  length = 300
FEATURE                Location/Qualifiers
source                 1..300
                       mol_type = other DNA
                       note = Cos PAC7 pIC400
                       organism = synthetic construct
SEQUENCE: 77
aggcaacaga acacaaccaa acatcaaatt ccaacaacaa accacaaaaa cattgattcc  60
atggtgaaaa acccgccaac cccccaccggg cacacccct gcacacccgt gcaagacctc  120
gtacggctta gtgaaatacc tcccttttgt tgttttatcg ttttgtcgac tttttgtttg  180
gtggtgtgtg tggtgcagcc tgagcttcct gatagtcgtg attggtgtgg ggagacgcgt  240
cggtggtggt gtgtgtgggg cgaggatccg cgtgccgggt ttgtgtctga tgaggagtgg  300

SEQ ID NO: 78          moltype = DNA  length = 300
FEATURE                Location/Qualifiers
source                 1..300
                       mol_type = other DNA
                       note = Cos PAC7 pIC401
                       organism = synthetic construct
SEQUENCE: 78
gaccacatca cacccgtcag ccggggagga ctcaacaccc tcgacaacgg gcaaatcatc  60
tgcagaacat gcaacagaag caaaggcaac agaacacaac caaacatcaa attccaacaa  120
caaaccacaa aaacattgat tccatggtga aaaacccgcc aacccccacc gggcacaccc  180
cctgcacacc cgtgcaagac ctcgtacggc ttagtgaaat acctcccttt tgttgtttta  240
tcgttttgtc gactttttgt ttggtggtgt gtgtggtgca gcctgagctt cctgatagtc  300

SEQ ID NO: 79          moltype = DNA  length = 217
FEATURE                Location/Qualifiers
source                 1..217
                       mol_type = other DNA
                       note = Cos PAC7 pIC402
                       organism = synthetic construct
SEQUENCE: 79
aggcaacaga acacaaccaa acatcaaatt ccaacaacaa accacaaaaa cattgattcc  60
atggtgaaaa acccgccaac cccccaccggg cacacccct gcacacccgt gcaagacctc  120
gtacggctta gtgaaatacc tcccttttgt tgttttatcg ttttgtcgac tttttgtttg  180
gtggtgtgtg tggtgcagcc tgagcttcct gatagtc                           217

SEQ ID NO: 80          moltype = DNA  length = 150
FEATURE                Location/Qualifiers
source                 1..150
                       mol_type = other DNA
                       note = Cos PAC7 pIC403
                       organism = synthetic construct
SEQUENCE: 80
aaaacccgcc aacccccacc gggcacaccc cctgcacacc cgtgcaagac ctcgtacggc  60
ttagtgaaat acctcccttt tgttgtttta tcgttttgtc gactttttgt ttggtggtgt  120
gtgtggtgca gcctgagctt cctgatagtc                                   150

SEQ ID NO: 81          moltype = DNA  length = 150
FEATURE                Location/Qualifiers
source                 1..150
                       mol_type = other DNA
                       note = Cos PAC7 pIC404
                       organism = synthetic construct
SEQUENCE: 81
```

```
aggcaacaga acacaaccaa acatcaaatt ccaacaacaa accacaaaaa cattgattcc  60
atggtgaaaa acccgccaac ccccaccggg cacaccccct gcacacccgt gcaagacctc  120
gtacggctta gtgaaatacc tcccttttgt                                   150

SEQ ID NO: 82          moltype = DNA  length = 25
FEATURE                Location/Qualifiers
source                 1..25
                       mol_type = other DNA
                       note = IC208 primer
                       organism = synthetic construct
SEQUENCE: 82
gcttccttag cttgcgaaat ctcga                                        25

SEQ ID NO: 83          moltype = DNA  length = 26
FEATURE                Location/Qualifiers
source                 1..26
                       mol_type = other DNA
                       note = IC310 primer
                       organism = synthetic construct
SEQUENCE: 83
gttcggctaa acccaaaagt aaaaac                                       26

SEQ ID NO: 84          moltype = DNA  length = 35
FEATURE                Location/Qualifiers
source                 1..35
                       mol_type = other DNA
                       note = AD1541 primer
                       organism = synthetic construct
SEQUENCE: 84
gttccagctc ttccgaggac cacatcacac ccgtc                             35

SEQ ID NO: 85          moltype = DNA  length = 35
FEATURE                Location/Qualifiers
source                 1..35
                       mol_type = other DNA
                       note = AD1542 primer
                       organism = synthetic construct
SEQUENCE: 85
gttccagctc ttcctgccca ctcctcatca gacac                             35

SEQ ID NO: 86          moltype = DNA  length = 38
FEATURE                Location/Qualifiers
source                 1..38
                       mol_type = other DNA
                       note = IC511 primer
                       organism = synthetic construct
SEQUENCE: 86
gttccagctc ttccgagagg caacagaaca caaccaaa                          38

SEQ ID NO: 87          moltype = DNA  length = 37
FEATURE                Location/Qualifiers
source                 1..37
                       mol_type = other DNA
                       note = IC512 primer
                       organism = synthetic construct
SEQUENCE: 87
gttccagctc ttcctgcgac tatcaggaag ctcaggc                           37

SEQ ID NO: 88          moltype = DNA  length = 37
FEATURE                Location/Qualifiers
source                 1..37
                       mol_type = other DNA
                       note = IC513 primer
                       organism = synthetic construct
SEQUENCE: 88
gttccagctc ttccgagaaa acccgccaac ccccacc                           37

SEQ ID NO: 89          moltype = DNA  length = 38
FEATURE                Location/Qualifiers
source                 1..38
                       mol_type = other DNA
                       note = IC514 primer
                       organism = synthetic construct
SEQUENCE: 89
gttccagctc ttcctgcaca aaagggaggt atttcact                          38

SEQ ID NO: 90          moltype = DNA  length = 21
FEATURE                Location/Qualifiers
source                 1..21
```

-continued

```
                        mol_type = other DNA
                        note = AD1261 primer
                        organism = synthetic construct
SEQUENCE: 90
cagcggcgct gctaagaact t                                            21

SEQ ID NO: 91           moltype = DNA  length = 20
FEATURE                 Location/Qualifiers
source                  1..20
                        mol_type = other DNA
                        note = AD1262 primer
                        organism = synthetic construct
SEQUENCE: 91
ccggctggca aatgaggcat                                              20
```

PHAGE-DERIVED PARTICLES FOR IN SITU DELIVERY OF DNA PAYLOAD INTO C. ACNES POPULATION

CROSS REFERENCE TO RELATED APPLICATIONS

This application is a continuation of U.S. application Ser. No. 18/477,069 filed Sep. 28, 2023, which is a continuation of U.S. application Ser. No. 17/518,936 filed on Nov. 4, 2021, now U.S. Pat. No. 11,820,989 issued on Nov. 21, 2023, which claims the benefit of U.S. application 63/109,832 filed Nov. 4, 2020, U.S. application 63/145,967 filed Feb. 4, 2021, U.S. application 63/109,834 filed Nov. 4, 2020, and U.S. application 63/145,969 filed Feb. 4, 2021, all of which are herein incorporated by reference in their entirety.

REFERENCE TO SEQUENCE LISTING SUBMITTED ELECTRONICALLY

The instant application contains a Sequence Listing which has been submitted electronically in XML format and is hereby incorporated by reference in its entirety. Said XML copy, created on Sep. 27, 2023, is named EB2020-04b_US-Cont.xml and is 450,560 bytes in size.

FIELD OF THE INVENTION

The present invention concerns *Cutibacterium acnes* phagemids and production method thereof.

BACKGROUND OF THE INVENTION

The skin is the largest organ of the human body and the biggest interface between our body and our environment. As such it also acts as a barrier protecting us from physical (e.g., UV, wounds), chemical (e.g., acid, base) and microbial (virus, bacteria, fungi) threats. This protection is not only the result of its passive physical isolating nature made from successive layers of dense and interconnected dead cells (stratum corneum) surrounded by a lipidic matrix. It is also thanks to active mechanisms orchestrated by diverse types of skin and immune cells that secrete antimicrobial peptides (AMP), produce cytokine and chemokine to recruit lymphoid immune cells, sense skin injuries and trigger wound healing mechanisms among other processes[1].

Skin is the first organ in contact with microorganisms after our birth, it is populated with a vast amount of immune cells in close contact with a great diversity of microorganisms and thus, the skin immune system need to develop abilities to recognize beneficial microorganisms from pathogenic ones to avoid constant immune response and inflammation. Part of this education is happening early in life when specific bacterial species are colonizing the skin and modulate immune responses in order for them to be tolerated[2]. These specific bacterial species are then able to stably colonize the skin establishing communities and becoming commensal strains.

Skin is not physiologically and spatially homogeneous throughout the body: oily (e.g cheek, back), moist (e.g., inguinal crease, interdigital web space, antecubital crease) and dry skin (e.g, volar forearm, hypothenar palm) exist depending on the body sites[3]. These different body sites are associated with different physiological conditions and carry distinct microbiomes with oily sites being mostly colonized with *Cutibacterium acnes* (formerly known as *Propionibacterium acnes*), whereas *Staphylococcus* and *Corynebacterium* species are more abundant in moist sites[4]. In addition to these physiological characteristics skin is also heterogeneous in space with different appendages: the sweat glands, the hair follicle, the sebaceous gland. The colonization of these appendages is only recently studied but show differences compared to skin surface (stratum corneum)[4-6].

These skin appendages are specific anatomical places because they do not have stratum corneum. As a consequence, micro-organism inside these appendages are in contact with living keratinocytes and have access to a higher diversity of immune cells due to the dermis proximity. The hair follicle has specific immunological properties. It is able to recruit specific immune cells such as monocyte-derived Langerhans Cells precursors[7] and actively maintain resident memory T cells (TRM)[8] making it a potential essential place for antigen presentation. The hair follicle is also deprived of effector T cells and has a strong immunosuppressive environment making it an immune privileged area[9].

Examples in the published literature indicate that skin-resident bacteria actively engage host immunity through an intact skin barrier, and activate specific immune cells in a species- and strain-dependent manner (Chen et al, Nature 2018; 555(7697):543). For instance, some but not all strains of *S. epidermidis* induce activation of *S. epidermidis*-specific IL-$17^{+}$CD$8^{+}$ T cells that protect against cutaneous infection (Naik et al, Nature 2015, 520(7545):104-108).

Due to the absence of stratum corneum, the skin appendages are also more permeable to chemicals as these will only need to cross the tight-junction barrier and not the stratum corneum which normally prevents water exchange and as a result all water-soluble substances are able to diffuse.

The pilosebaceous subunit comprising the fair follicle and the sebaceous gland is mostly colonized by *C. acnes* that thrive in this sebum rich and anaerobic environment. *Cutibacterium acnes* (formerly *Propionibacterium acnes*) is a gram-positive rod-shaped aerotolerant bacteria, first isolated from skin in 1897. It belongs to the order Actinomycetales, it is part of the Propionibacteriaceae family and it belongs to the genus *Cutibacterium*. This genus includes other human skin species such as *Cutibacterium avidum, Cutibacterium granulosum* and *Cutibacterium humerusii*[10]. *C. acnes* is one of the most prevalent and abundant bacteria on human skin where it can be found both on the skin surface (stratum corneum) and in the hair follicle. Inside the hair follicle, it is in direct contact with a large diversity of living cells such as keratinocytes, stem cells, sebaceous cells and immune cells, unlike on the stratum corneum where it is mostly in contact with the dead corneocyte. *C. acnes* is a commensal bacterium but has also been associated with several skin diseases such as acne vulgaris[11] or progressive macular hypomelanosis[12-14].

In particular, new findings on *C. acnes* reveal that specific phylotypes might play a critical role in acne development11. Precisely, the role of *C. acnes* phylotype IA1 in acne is being widely underscored. Fitz-Gibbon and colleagues demonstrated that chromosomal regions, loci 1, 2 and 3, characteristic of ribotypes RT4 and RT5 (classified within the phylogroup IA1), are strongly associated with acne[15]. Since these chromosomal regions are absent in ribotypes that are associated with healthy skin (i.e., RT6), they represent a potential target to eliminate acne-associated *C. acnes* strains.

Being able to edit *Cutibacterium acnes* population by removing specific proinflammatory strains to prevent or cure disease such as acne vulgaris or leverage their privilege location into the pilosebaceous unit to modulate host immune response or improve wound healing are attractive therapeutic approaches. To implement such approaches, one can either genetically modify *C. acnes* strains in situ or provide in vitro genetically modified *C. acnes*. Because of the large intra-individual and inter-individual microbiome diversity both at the species and at the strain level, it appears difficult to provide a single or cocktail of engineered *C. acnes* strains able to colonize the skin of most patients.

Delivery of DNA in situ to the *C. acnes* population offers a way to circumvent such difficulties by allowing to leverage pre-establish strains potentially without disturbing the local microbiome. However, in situ delivery of genetic material to *C. acnes* is a challenging task for several reasons. First, there are so far no genetic elements such as plasmid able to robustly and autonomously replicate inside *C. acnes*. The few described genetic modifications consist in genomic insertion of synthetic DNA through homologous recombination[16-18]. This in vitro process has been shown to be of very low efficiency and rely on the use of an antibiotic selection marker to select such events. Moreover, these genetic modifications have been restricted to a few specific strains (KPA17202, one RT6 *C. acnes*) and might not be generalizable to all *C. acnes* strains. Second, in order to perform in situ genetic modification of *C. acnes* we need to deliver DNA into *C. acnes*. The only described method for introducing DNA into *C. acnes* is the use of electroporation[19,20], a method that can only be performed in vitro.

The present invention solves both the lack of replicative and stable DNA vectors and their delivery into *C. acnes* using phage-derived particles.

BRIEF SUMMARY OF INVENTION

The invention encompasses *Cutibacterium acnes* phagemids, bacterial cells comprising these phagemids, methods for making phage-derived particles comprising these phagemids, phage-derived particles comprising these phagemids, and methods for using these phagemids, particles, and cells, particularly in treatments of *Cutibacterium acnes* related disorders and/or diseases.

The invention encompasses a recombinant DNA phagemid vector, phage-derived particles comprising these vectors, and *Cutibacterium acnes* carrying the vector, wherein the vector comprises:

- a phage packaging signal allowing packaging of the DNA vector in a *Cutibacterium acnes* phage capsid; and
- a gene of interest.

In one embodiment, the DNA vector comprises:

- a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 66; and
- a gene of interest.

In one embodiment, the DNA vector comprises:

- a phage packaging signal allowing packaging of the DNA vector in a *Cutibacterium acnes* phage capsid;
- a gene of interest; and
- a selection marker allowing for selection of the DNA vector in *Cutibacterium acnes*.

In one embodiment, the DNA vector comprises:

- a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 66;
- a gene of interest; and
- a selection marker allowing for selection of the DNA vector in *Cutibacterium acnes*.

In one embodiment, the DNA vector comprises:

- a phage packaging signal allowing packaging of the DNA vector in a *Cutibacterium acnes* phage capsid;
- a gene of interest;
- an origin of replication allowing replication in *Cutibacterium acnes*; and
- optionally a selection marker allowing for selection of the DNA vector in *Cutibacterium acnes*.

In one embodiment, the DNA vector comprises:

- a phage packaging signal allowing packaging of the DNA vector in a *Cutibacterium acnes* phage capsid; wherein the phage packaging signal sequence is at least 80, 83, 85, 87, 90, 93, 95, 97, 98, 99, or 100% identical to the sequence SEQ ID NO: 66;
- a gene of interest;
- an origin of replication allowing replication in *Cutibacterium acnes*; and
- optionally a selection marker allowing for selection of the DNA vector in *Cutibacterium acnes*.

In one embodiment, the phage packaging signal sequence is at least 80, 83, 85, 87, 90, 93, 95, 97, 98, 99, or 100% identical to a phage packaging signal sequence selected from the group consisting of the sequences SEQ ID NO: 76, SEQ ID NO: 77, SEQ ID NO: 78, SEQ ID NO: 79, SEQ ID NO: 80 and SEQ ID NO: 81.

In one embodiment, the DNA vector further comprises a *C. acnes* phage origin of replication.

In one embodiment, the DNA vector further comprises a *C. acnes* phage origin of replication, wherein the phage origin of replication sequence is identical at least 75, 77, 80, 83, 85, 87, 90, 93, 95, 96, 97, 98, 99 or 100% identical to the sequence SEQ ID NO: 67.

In one embodiment, the gene of interest is a DNA encoding an antigen.

The invention encompasses a *Cutibacterium acnes* producer cell carrying a recombinant DNA vector for the production of *Cutibacterium acnes* phage-derived particles that contain the recombinant DNA vector.

The DNA vector is typically packaged into proteins produced from a *Cutibacterium acnes* phage genome or a helper phage. The *C. acnes* phage genome can be introduced into the *C. acnes* producer cell, for instance, by transformation or transduction with a *C. acnes* phage whereas the helper phage can be introduced into the *C. acnes* producer cell, for instance, by transformation or conjugation before or after introduction of the DNA vector into the *C. acnes* producer cell (FIG. 1).

The *Cutibacterium acnes* producer cell carrying a recombinant DNA vector typically comprises a *Cutibacterium acnes* phage genome leading to the production of phage-derived particles carrying the DNA vector.

In one embodiment, the *Cutibacterium acnes* phage genome is a non-engineered/wild-type genome.

In another embodiment, the *Cutibacterium acnes* phage genome is engineered.

In one embodiment, the DNA vector comprises an origin of replication able to replicate only in the *Cutibacterium acnes* producer cell and not in the *Cutibacterium acnes* receiver cell.

In one embodiment, the DNA vector comprises:

- a phage packaging signal allowing packaging of the DNA vector in a *Cutibacterium acnes* phage capsid;
- at least one gene of interest;
- an origin of replication allowing replication only in *Cutibacterium acnes* producer cell; and
- optionally a selection marker allowing for selection of the DNA vector in *Cutibacterium acnes*.

In one embodiment, the selection marker is an auxotrophic marker and the *Cutibacterium acnes* producer cell growth is dependent on this auxotrophic marker.

In one embodiment, the selection marker is an antibiotic resistance marker.

In one embodiment, the DNA vector further comprises a CRISPR-Cas system.

In one embodiment, the CRISPR-Cas system targets a *C. acnes* chromosome locus. Preferably, the targeted locus is not present in the *C. acnes* producer cell. Preferably, the CRISPR array is expressing one or several crRNA targeting the chromosome locus.

In one embodiment, the CRISPR-Cas system targets several *C. acnes* chromosome loci. Preferably, the targeted loci are not present in the *C. acnes* producer cell. Preferably, the CRISPR array from the CRISPR-Cas system is expressing one or several crRNA targeting the chromosome loci.

In one embodiment, the CRISPR-Cas system targets a *C. acnes* plasmid locus. Preferably, the targeted locus is not present in the *C. acnes* producer cell. Preferably, the CRISPR array from the CRISPR-Cas system is expressing one or several crRNA targeting the plasmid locus.

In one embodiment, the CRISPR-Cas system targets several *C. acnes* plasmid loci. Preferably, the targeted loci are not present in the *C. acnes* producer cell. Preferably, the CRISPR array from the CRISPR-Cas system is expressing one or several crRNA targeting the plasmid loci.

In one embodiment, the CRISPR-Cas system is not expressed in *C. acnes* producer cell. Preferably the CRISPR-Cas system is repressed in *C. acnes* producer cell.

In one embodiment, the CRISPR-Cas system targets a proinflammatory sequence related to host disease.

In one embodiment, the CRISPR-Cas system targets a proinflammatory sequence related to acne vulgaris.

In one embodiment, the DNA vector comprises a CRISPR-Cas system targeting the DNA vector itself.

In one embodiment, the DNA vector comprises a template for homologous recombination in *C. acnes* phages.

In one embodiment, the DNA vector comprises a template for homologous recombination in *C. acnes* chromosome.

In one embodiment, the DNA vector comprises a template for homologous recombination in *C. acnes* endogenous plasmids.

In one embodiment, the DNA vector comprises a template for homologous recombination and a CRISPR-Cas system targeting the DNA vector itself outside of the template region.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the DNA vector comprises an integrase gene expression cassette and a site specific recombination site allow for the integration of the DNA vector inside the chromosome.

In one embodiment, the DNA vector comprises a prime editor gene expression cassette and one or multiple pegRNAs.

In one embodiment, the DNA vector comprises a base editor gene expression cassette and one or multiple crRNAs or sgRNAs.

In one embodiment, the selection marker is catA.

In one embodiment, the selection marker is ermE.

In one embodiment, the selection marker is hygB.

The invention encompasses a *C. acnes* phage-derived particle comprising any of the DNA vectors of the invention.

The invention encompasses a *C. acnes*, in particular an engineered *C. acnes*, comprising any of the DNA vectors of the invention.

In a particular embodiment, the engineered *C. acnes* comprises at least one, two, three or more DNA vectors, in particular DNA vectors of the invention.

In a particular embodiment, the engineered *C. acnes* comprises a DNA vector of the invention which comprises a DNA encoding an antigen.

The invention encompasses a *C. acnes* engineered following transduction of any of the vectors of the invention by phage-derived particles.

The invention encompasses an engineered *C. acnes* whose genome is altered following the transduction by a phage-derived particle containing any of the vectors of the invention.

The invention encompasses an engineered *C. acnes* produced by transducing *C. acnes* with any of the vectors of the invention, modifying the *C. acnes* with a gene of interest carried by the vector, selecting for the modification.

The invention encompasses an engineered *C. acnes* produced by transducing *C. acnes* with any of the vectors of the invention, modifying the *C. acnes* with a gene of interest carried by the vector, selecting for the modification, and curing the engineered *C. acnes* of the vector.

In one embodiment, the engineered *C. acnes* has been modified by a CRISPR-Cas system carried by the vector and transduced by a phage-derived particle containing any vectors from the invention.

In one embodiment, the engineered *C. acnes* has been modified by insertion of an exogenous gene into the *C. acnes* chromosome.

In one embodiment, the engineered *C. acnes* has been modified by insertion of an exogenous gene into the *C. acnes* plasmid.

In one embodiment, the engineered *C. acnes* has been modified by deletion or mutation of an endogenous genetic sequence in the *C. acnes* chromosome.

In one embodiment, the engineered *C. acnes* has been modified by deletion, insertion or substitution of one or several nucleotides into the *C. acnes* chromosome.

In one embodiment, the engineered *C. acnes* has been modified by deletion, insertion or substitution of one or several nucleotides into the *C. acnes* plasmid.

The invention encompasses a method for producing *C. acnes* phage-derived particles that contain any vector of the inventions, comprising the introduction of any of the DNA vectors of the invention into a *C. acnes* producer cell and contacting the producer cell with *C. acnes* phage genome.

The invention encompasses a method for engineering *C. acnes* comprising the introduction of any of the DNA vectors of the invention into a *C. acnes*. The method can further comprise selecting a modified *C. acnes*. The method can further comprise selecting a modified *C. acnes* that has an insertion of an exogenous gene into the *C. acnes* chromosome or into an endogenous plasmid. The method can further comprise selecting a modified *C. acnes* that has one or several deletions, insertions or substitutions of one or several nucleotides into *C. acnes* chromosome or endogenous plasmids.

The invention encompasses a phage-derived particle produced by any of the methods of the invention.

The invention encompasses methods for treating a *C. acnes*-related disorder or disease. In one embodiment, the method comprises administering a phage-derived particle of the invention or a bacterium producing such a phage-derived particle to a subject. The invention further concerns a phage-derived particle of the invention or a bacterium producing such a phage derived particle for use in a method for treating a *C. acnes*-related disorder or disease.

The invention encompasses methods for modifying a *C. acnes* to treat a disorder or disease or skin condition or for cosmetic applications. In one embodiment, the method comprises administering a phage-derived particle of the invention or a bacterium producing such a phage-derived particle to a subject. The invention further concerns a phage-derived particle of the invention or a bacterium producing such a phage-derived particle for use in a method for treating a disorder or disease or skin condition.

In one embodiment, the method is performed ex-situ.

In one embodiment, the method is performed in-situ.

In one embodiment, the method is performed ex-situ with a *C. acnes* strain isolated from the subject.

BRIEF DESCRIPTION OF DRAWINGS

In order to better understand the subject matter that is disclosed herein and to exemplify how it may be carried out in practice, embodiments will be described, by way of non-limiting example, with reference to the accompanying drawings. With specific reference to the drawings, it is stressed that the particulars shown are by way of example and for purposes of illustrative discussion of embodiments of the invention.

FIG. 2A-B depicts host range determination of isolated *C. acnes* bacteriophages. 1 indicates strain infection with full spot lysis; 0.5 indicates lower efficiency in strain infection with single plaques observed instead of full spot lysis.

FIG. 4A depicts a vector (pEB_HR01) containing a single homology arm (HA) to *C. acnes* chromosome which is conjugated into *C. acnes*. Because the vector is not replicative in *C. acnes*, only *C. acnes* cells that perform a single recombination event stably maintain the antibiotic marker and are able to grow on antibiotic plate. Cells that do not perform the first recombination event or cells that perform the first and the second recombination events are not able to grow on antibiotic plates (erythromycin). FIG. 4B depicts a vector (pEB_HR02) containing two homology arms to *C. acnes* chromosome which is conjugated into *C. acnes*. Selection of the final recombinant is performed using an antibiotic selection (ErmE) and a counter selection (SacB).

FIG. 6A depicts a vector, containing an antibiotic selection marker flanked by two homology arms and a CRISPR-Cas system targeting the vector outside the homology regions, which is conjugated into *C. acnes*. The CRISPR-Cas system cuts the vector leading to linearization of the template and plasmid loss. Thus, only recombinant cells are able to grow in presence of antibiotic. FIG. 6B depicts a vector, containing a mutant allele flanked by two homology arms and a CRISPR-Cas system targeting the vector outside the homology regions as well as the non mutated allele of *C. acnes* chromosome, which is conjugated into *C. acnes*. The CRISPR-Cas system cuts the vector leading to linearization of the template and plasmid loss as well as the *C. acnes* chromosome. Thus, only recombinant cells are able to grow in the presence of erythromycin.

Figure 1:
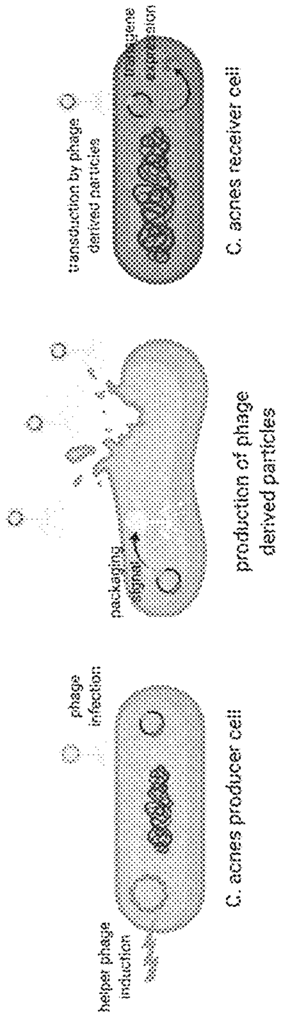
FIG. 1 depicts a *C. acnes* producer cell carrying a DNA vector with a packaging signal and a transgene which is infected by a *C. acnes* phage, phage-derived particles carrying the DNA vector are then produced and upon binding to *C. acnes* receiver cell transduce the DNA vector that replicates and leads to transgene expression. Alternatively, the *C. acnes* producer is not infected by a phage but carries also a helper phage that is induced to trigger phage-derived particle production.

supernatant from strain Ca0s22130, (7) supernatant from strain Ca0s22132, (8) supernatant from strain Ca0s16973, (9) ovalbumin.

DETAILED DESCRIPTION OF INVENTION

The inventors demonstrated, for the first time, the introduction of a recombinant replicative DNA in *C. acnes* by transduction, of a phage-derived particle.

The inventors also demonstrated, for the first time, the production of *C. acnes* phage-derived particles from a *C. acnes* strain, carrying a recombinant self-replicative DNA vector.

The invention relates to a *C. acnes* strain carrying a DNA vector comprising a phage packaging signal and a gene of interest, the production of phage-derived particles containing the DNA vector and the use of this phage-derived particles to transduce *C. acnes* in vitro or in situ and the subsequent expression of the gene of interest in the transduced *C. acnes* cell. The invention also relates to the modified *C. acnes* strains obtained by transduction of a DNA vector by the phage-derived particle, the modified *C. acnes* strains containing or not the DNA vector.

*C. acnes* phages are naturally present in the human skin and have been isolated numerous times since the first isolation in 1964. More recently, sequencing of *C. acnes* phages has revealed an unusual high level of nucleotide conservation with ~85% identity. All *C. acnes* phages described so far are siphoviridae with a genome size constraint around 30 kb and a similar genome architecture. Despite their small genetic diversity, most *C. acnes* phages have the capacity to infect several *C. acnes* phylotypes and thus are considered as broad-host range. Their in-situ infectivity and their broad host range make them a relevant platform to be engineered for transgene delivery into the *C. acnes* population.

The inventors show for the first time that phage-derived particles can be produced from the co-occurrence of a wild-type or engineered *C. acnes* phage genome and a recombinant DNA vector with a packaging signal in a *C. acnes* cell ("producer cell"). The phage-derived particles are able to transduce the DNA vector into a "receiver" *C. acnes* cell and express a transgene such as an antibiotic resistance gene allowing the selection of the transductants. This widely expands the possibility to engineer *C. acnes* population directly on the skin, paving the way for many applications (industrial, therapeutic, cosmetic, environmental). The invention encompasses a *C. acnes* "producer" cell carrying DNA vectors, particularly phagemids, and methods for generating phage-derived particles and their use to modify or kill *C. acnes*.

DNA Vectors

The invention encompasses recombinant DNA vectors for use in *Cutibacterium acnes*. Preferably, the DNA vector is a recombinant DNA vector, which is not integrated into the *C. acnes* chromosome. The vector allows transfer to progeny cells. The vector is preferably a phagemid. The DNA vector preferably comprises an origin of replication allowing replication in *C. acnes* and a phage packaging signal.

In various embodiments, the DNA vector comprises any combination of a phage packaging signal, an origin of replication allowing replication in *C. acnes*, a selection marker allowing for selection of the DNA vector in *C. acnes*, a gene of interest, and an origin of replication allowing replication in *C. acnes* producer cell but no replication in *C. acnes* receiver cell.

In one embodiment, the DNA vector comprises a phage packaging signal, an origin of replication allowing replication in *C. acnes*, a first selection marker allowing for selection of the DNA vector in *C. acnes* and a gene of interest.

In one embodiment, the DNA vector comprises a phage packaging signal, an origin of replication allowing replication in *C. acnes* producer cell but no replication in *C. acnes* receiver cell, a first selection marker allowing for selection of the DNA vector in *C. acnes* and a gene of interest.

Preferably, the gene of interest is exogenous to *C. acnes*, that is, one that is not found naturally in *C. acnes*.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 66; an origin of replication allowing replication in *C. acnes*; a selection marker allowing for selection of the DNA vector in *C. acnes*; and a gene of interest.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 66; an origin of replication allowing replication in *C. acnes*; a selection marker allowing for selection of the DNA vector in *C. acnes*; and a gene of interest.

In one embodiment, the DNA vector comprises a phage packaging signal, wherein the phage packaging signal sequence is at least 80, 83, 85, 87, 90, 93, 95, 97, 98, 99, or 100% identical to the sequence SEQ ID NO: 66; an origin of replication allowing replication in *C. acnes*; a selection marker allowing for selection of the DNA vector in *C. acnes*; a selection marker allowing for selection in a first bacteria wherein the first bacteria is *E. coli*; an origin of replication allowing replication in a first bacteria wherein the first bacteria is *E. coli*; and a gene of interest.

In one embodiment, the DNA vector can be efficiently introduced into and stably replicated in *C. acnes* producer cell using electroporation, using protoplast electroporation, using chemical transformation, using conjugation, using natural competency or using transduction.

In one embodiment, the DNA vector can be efficiently transformed into and stably replicated in *C. acnes* producer cell using physical methods such as electroporation of *C. acnes* cells or electroporation of *C. acnes* protoplast.

In one embodiment, the *C. acnes* protoplasts are generated using Mutanolysin treatment or Lysozyme treatment, Mutanolysin and Lysozyme treatment, or Mutanolysin and Lysozyme and bead-beating treatment followed by resuspension into hypotonique media.

In one embodiment, the DNA vector can be efficiently transformed into and stably replicated in *C. acnes* producer cell using *C. acnes* protoplast mix with DNA vector or DNA vector+glass beads.

In one embodiment, delivery of the DNA vector into *C. acnes* is by transduction. In one embodiment, the DNA vector comprises one packaging signal of a *C. acnes* phage selected from the group consisting of: PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74); and PAC263 (typically of sequence SEQ ID NO: 75), and is packaged into proteins expressed from the genome of a *C. acnes* phage selected from the group consisting of the phages: PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74); and PAC263 (typically of sequence SEQ ID NO: 75) allowing transduction of the DNA vector into *C. acnes*.

In one embodiment, the DNA vector comprises a packaging signal, the sequence of which is at least 80, 83, 85, 87, 90, 93, 95, 97, 98, 99, or 100% identical to the sequence of any of the above packaging signals.

In one embodiment, the phage packaging signal is of sequence at least 80, 83, 85, 87, 90, 93, 95, 97, 98, 99, or 100% identical to a phage packaging signal sequence selected from the group consisting of: SEQ ID NO: 76, SEQ ID NO: 77, SEQ ID NO: 78, SEQ ID NO: 79, SEQ ID NO: 80 and SEQ ID NO: 81.

In one embodiment, delivery of the DNA vector into *C. acnes* is by conjugation.

In one embodiment, the DNA vector comprises an origin of transfer selected from the group consisting of: oriT_pMRC01 (typically of sequence SEQ ID NO: 1); oriT_RSF1010 (typically of sequence SEQ ID NO: 2); oriT_pRS01 (typically of sequence SEQ ID NO: 3); oriT_pMV158 (typically of sequence SEQ ID NO: 4); oriT_pTF1 (typically of sequence SEQ ID NO: 5); oriT_pSC101 (typically of sequence SEQ ID NO: 6); oriT_pBTK445 (typically of sequence SEQ ID NO: 7); oriT_pBBR1 (typically of sequence SEQ ID NO: 8); oriT_R721 (typically of sequence SEQ ID NO: 9); oriT_pRmeGR4a (typically of sequence SEQ ID NO: 10); oriT_ColE1 (typically of sequence SEQ ID NO: 11); oriT_pTiC58 (typically of sequence SEQ ID NO: 12); oriT_pMdT1 (typically of sequence SEQ ID NO: 13); oriT_R1 (typically of sequence SEQ ID NO: 14); oriT_Tn5520 (typically of sequence SEQ ID NO: 15); oriT_QKH54 (typically of sequence SEQ ID NO: 16); oriT_R64 (typically of sequence SEQ ID NO: 17); oriT_R751 (typically of sequence SEQ ID NO: 18); oriT_RP4 (typically of sequence SEQ ID NO: 19); oriT_pKL1 (typically of sequence SEQ ID NO: 20); oriT_RK2 (typically of sequence SEQ ID NO: 21); oriT_R1162 (typically of sequence SEQ ID NO: 22); oriT_Tn4555 (typically of sequence SEQ ID NO: 23); oriT_pHT (typically of sequence SEQ ID NO: 24); oriT_Tn4399 (typically of sequence SEQ ID NO: 25); oriT_Tn916 (typically of sequence SEQ ID NO: 26); oriT_pST12 (typically of sequence SEQ ID NO: 27); oriT_pCU1 (typically of sequence SEQ ID NO: 28); oriT_pSU233 (typically of sequence SEQ ID NO: 29); oriT_F (typically of sequence SEQ ID NO: 30); oriT_pMAB01 (typically of sequence SEQ ID NO: 31); oriT_R388 (typically of sequence SEQ ID NO: 32); oriT_pS7a (typically of sequence SEQ ID NO: 33); oriT_pS7b (typically of sequence SEQ ID NO: 34); oriT_R702 (typically of sequence SEQ ID NO: 35); oriT_pMUR274 (typically of sequence SEQ ID NO: 36); oriT_R100 (typically of sequence SEQ ID NO: 37); oriT_pVCR94deltaX (typically of sequence SEQ ID NO: 38); oriT_R46 (typically of sequence SEQ ID NO: 39); oriT_pGO1 (typically of sequence SEQ ID NO: 40); and oriT_pIP501 (typically of sequence SEQ ID NO: 41).

In one embodiment, the DNA vector comprises the origin of transfer oriT_pMRC01 (typically of sequence SEQ ID NO: 1). In one embodiment, the DNA vector comprises the origin of transfer oriT_RSF1010 (typically of sequence SEQ ID NO: 2). In one embodiment, the DNA vector comprises the origin of transfer oriT_pRS01 (typically of sequence SEQ ID NO: 3). In one embodiment, the DNA vector comprises the origin of transfer oriT_pMV158 (typically of sequence SEQ ID NO: 4). In one embodiment, the DNA vector comprises the origin of transfer oriT_pTF1 (typically of sequence SEQ ID NO: 5). In one embodiment, the DNA vector comprises the origin of transfer oriT_pSC101 (typically of sequence SEQ ID NO: 6). In one embodiment, the DNA vector comprises the origin of transfer oriT_pBTK445 (typically of sequence SEQ ID NO: 7). In one embodiment, the DNA vector comprises the origin of transfer oriT_pBBR1 (typically of sequence SEQ ID NO: 8). In one embodiment, the DNA vector comprises the origin of transfer oriT_R721 (typically of sequence SEQ ID NO: 9). In one embodiment, the DNA vector comprises the origin of transfer oriT_pRmeGR4a (typically of sequence SEQ ID NO: 10). In one embodiment, the DNA vector comprises the origin of transfer oriT_ColE1 (typically of sequence SEQ ID NO: 11). In one embodiment, the DNA vector comprises the origin of transfer oriT_pTiC58 (typically of sequence SEQ ID NO: 12). In one embodiment, the DNA vector comprises the origin of transfer oriT_pMdT1 (typically of sequence SEQ ID NO: 13). In one embodiment, the DNA vector comprises the origin of transfer oriT_R1 (typically of sequence SEQ ID NO: 14). In one embodiment, the DNA vector comprises the origin of transfer oriT_Tn5520 (typically of sequence SEQ ID NO: 15). In one embodiment, the DNA vector comprises the origin of transfer oriT_QKH54 (typically of sequence SEQ ID NO: 16). In one embodiment, the DNA vector comprises the origin of transfer oriT_R64 (typically of sequence SEQ ID NO: 17). In one embodiment, the DNA vector comprises the origin of transfer oriT_R751 (typically of sequence SEQ ID NO: 18). In one embodiment, the DNA vector comprises the origin of transfer oriT_RP4 (typically of sequence SEQ ID NO: 19). In one embodiment, the DNA vector comprises the origin of transfer oriT_pKL1 (typically of sequence SEQ ID NO: 20). In one embodiment, the DNA vector comprises the origin of transfer oriT_RK2 (typically of sequence SEQ ID NO: 21). In one embodiment, the DNA vector comprises the origin of transfer oriT_R1162 (typically of sequence SEQ ID NO: 22). In one embodiment, the DNA vector comprises the origin of transfer oriT_Tn4555 (typically of sequence SEQ ID NO: 23). In one embodiment, the DNA vector comprises the origin of transfer oriT_pHT (typically of sequence SEQ ID NO: 24). In one embodiment, the DNA vector comprises the origin of transfer oriT_Tn4399 (typically of sequence SEQ ID NO: 25). In one embodiment, the DNA vector comprises the origin of transfer oriT_Tn916 (typically of sequence SEQ ID NO: 26). In one embodiment, the DNA vector comprises the origin of transfer oriT_pST12 (typically of sequence SEQ ID NO: 27). In one embodiment, the DNA vector comprises the origin of transfer oriT_pCU1 (typically of sequence SEQ ID NO: 28). In one embodiment, the DNA vector comprises the origin of transfer oriT_pSU233 (typically of sequence SEQ ID NO: 29). In one embodiment, the DNA vector comprises the origin of transfer oriT_F (typically of sequence SEQ ID NO: 30). In one embodiment, the DNA vector comprises the origin of transfer oriT_pMAB01 (typically of sequence SEQ ID NO: 31). In one embodiment, the DNA vector comprises the origin of transfer oriT_R388 (typically of sequence SEQ ID NO: 32). In one embodiment, the DNA vector comprises the origin of transfer oriT_pS7a (typically of sequence SEQ ID NO: 33). In one embodiment, the DNA vector comprises the origin of transfer oriT_pS7b (typically of sequence SEQ ID NO: 34). In one embodiment, the DNA vector comprises the origin of transfer oriT_R702 (typically of sequence SEQ ID NO: 35). In one embodiment, the DNA vector comprises the origin of transfer oriT_pMUR274 (typically of sequence SEQ ID NO: 36). In one embodiment, the DNA vector comprises the origin of transfer oriT_R100 (typically of sequence SEQ ID NO: 37). In one embodiment, the DNA vector comprises the origin of transfer oriT_pVCR94deltaX (typically of sequence SEQ ID NO: 38). In one embodiment, the DNA vector comprises the origin of transfer oriT_R46 (typically of sequence SEQ ID NO: 39). In one embodiment, the DNA vector comprises the origin of transfer oriT_pGO1 (typically of sequence SEQ ID NO: 40). In one embodiment, the DNA vector comprises the origin of transfer oriT_pIP501 (typically of sequence SEQ ID NO: 41).

In one embodiment, the DNA vector comprises an origin of transfer (oriT), the sequence of which is at least 80, 83, 85, 87, 90, 93, 95, 97, 98, 99, or 100% identical to the sequence of any of the above oriT.

In one embodiment, a donor bacterium, such as *E. coli*, carry a conjugative plasmid, a conjugative transposon, or an integrative and conjugative element (ICE) selected from the group consisting of: pMRC01, RSF1010, pRS01, pMV158, pTF1, pSC101, pBTK445, pBBR1, R721, pRmeGR4a, ColE1, pTiC58, pMdT1, R1, Tn5520, QKH54, R64, R751, RP4, pKL1, RK2, R1162, Tn4555, pHT, Tn4399, Tn916, pST12, pCU1, pSU233, F, pMAB01, R388, pS7a, pS7b, R702, pMUR274, R100, pVCR94deltaX, R46, pGO1 and pIP501; and is used to efficiently transfer the DNA vector into *C. acnes* recipient cells. In one embodiment the DNA vector contains an origin of transfer and the associated relaxase of the conjugative plasmid, conjugative transposon and integrative and conjugative element (ICE) selected from the group consisting of pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment the DNA vector comprises an origin of transfer and the relaxase of the following conjugative plasmid, conjugative transposon and integrative and conjugative element (ICE) selected from the group consisting of: pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment the DNA vector comprises an origin of transfer selected from the group consisting of: oriT_pMRC01 (SEQ ID NO: 1); oriT_RSF1010 (SEQ ID NO: 2); oriT_pRS01 (SEQ ID NO: 3); oriT_pMV158 (SEQ ID NO: 4); oriT_pTF1 (SEQ ID NO: 5); oriT_pSC101 (SEQ ID NO: 6); oriT_pBTK445 (SEQ ID NO: 7); oriT_pBBR1 (SEQ ID NO: 8); oriT_R721 (SEQ ID NO: 9); oriT_pRmeGR4a (SEQ ID NO: 10); oriT_ColE1 (SEQ ID NO: 11); oriT_pTiC58 (SEQ ID NO: 12); oriT_pMdT1 (SEQ ID NO: 13); oriT_R1 (SEQ ID NO: 14); oriT_Tn5520 (SEQ ID NO: 15); oriT_QKH54 (SEQ ID NO: 16); oriT_R64 (SEQ ID NO: 17); oriT_R751 (SEQ ID NO: 18); oriT_RP4 (SEQ ID NO: 19); oriT_pKL1 (SEQ ID NO: 20); oriT_RK2 (SEQ ID NO: 21); oriT_R1162 (SEQ ID NO: 22); oriT_Tn4555 (SEQ ID NO: 23); oriT_pHT (SEQ ID NO: 24); oriT_Tn4399 (SEQ ID NO: 25); oriT_Tn916 (SEQ ID NO: 26); oriT_pST12 (SEQ ID NO: 27); oriT_pCU1 (SEQ ID NO: 28); oriT_pSU233 (SEQ ID NO: 29); oriT_F (SEQ ID NO: 30); oriT_pMAB01 (SEQ ID NO: 31); oriT_R388 (SEQ ID NO: 32); oriT_pS7a (SEQ ID NO: 33); oriT_pS7b (SEQ ID NO: 34); oriT_R702 (SEQ ID NO: 35); oriT_pMUR274 (SEQ ID NO: 36); oriT_R100 (SEQ ID NO: 37); oriT_pVCR94deltaX (SEQ ID NO: 38); oriT_R46 (SEQ ID NO: 39); oriT_pGO1 (SEQ ID NO: 40) and oriT_pIP501 (SEQ ID NO: 41).

In one embodiment, the DNA vector comprises an origin of transfer (oriT) that is at least 80, 83, 85, 87, 90, 93, 95, 97, 98, 99, or 100% identical to any of these ICE.

In one embodiment, the invention encompasses a DNA vector comprising an origin of replication allowing replication in *C. acnes*, an oriT allowing conjugation into *C. acnes*, a selection marker allowing for selection in the transconjugant *C. acnes*, and a selection marker allowing for selection in the donor bacteria. In another embodiment, the invention encompasses a DNA vector comprising an origin of replication allowing replication in *C. acnes* and an oriT allowing conjugation into *C. acnes* as defined above.

In one embodiment, origin of replication allowing replication in *C. acnes* is selected from the group consisting of: R6K (typically of sequence SEQ ID NO: 42); RK2 (typically of sequence SEQ ID NO: 43); pBBR1 (typically of sequence SEQ ID NO: 44); pRO1600 (typically of sequence SEQ ID NO: 45); RSF1010 (typically of sequence SEQ ID NO: 46); pAM31 (typically of sequence SEQ ID NO: 47); pLME106 (typically of sequence SEQ ID NO: 48); pTZC1 (typically of sequence SEQ ID NO: 49); pBC1 (typically of sequence SEQ ID NO: 50); pEP2 (typically of sequence SEQ ID NO: 51); pWVO1 (typically of sequence SEQ ID NO: 52); pAP1 (typically of sequence SEQ ID NO: 53); pWKS1 (typically of sequence SEQ ID NO: 54); pLME108 (typically of sequence SEQ ID NO: 55); pLS1 (typically of sequence SEQ ID NO: 56); pUB6060 (typically of sequence SEQ ID NO: 57); p545 (typically of sequence SEQ ID NO: 58); pJD4 (typically of sequence SEQ ID NO: 59); pIJ101 (typically of sequence SEQ ID NO: 60); pSN22 (typically of sequence SEQ ID NO: 61); pGP01 (typically of sequence SEQ ID NO: 62); pIP501 (typically of sequence SEQ ID NO: 63); pCU1 (typically of sequence SEQ ID NO: 64); and pBAV1 K-T5 (typically of sequence SEQ ID NO: 65). In one embodiment, the origin of replication allowing replication in *C. acnes* is R6K (typically of sequence SEQ ID NO: 42). In one embodiment, the origin of replication allowing replication in *C. acnes* is RK2 (typically of sequence SEQ ID NO: 43). In one embodiment, the origin of replication allowing replication in *C. acnes* is pBBR1 (typically of sequence SEQ ID NO: 44). In one embodiment, the origin of replication allowing replication in *C. acnes* is pRO1600 (typically of sequence SEQ ID NO: 45). In one embodiment, the origin of replication allowing replication in *C. acnes* is RSF1010 (typically of sequence SEQ ID NO: 46). In one embodiment, the origin of replication allowing replication in *C. acnes* is pAM31 (typically of sequence SEQ ID NO: 47). In one embodiment, the origin of replication allowing replication in *C. acnes* is pLME106 (typically of sequence SEQ ID NO: 48). In one embodiment, the origin of replication allowing replication in *C. acnes* is pTZC1 (typically of sequence SEQ ID NO: 49). In one embodiment, the origin of replication allowing replication in *C. acnes* is pBC1 (typically of sequence SEQ ID NO: 50). In one embodiment, the origin of replication allowing replication in *C. acnes* is pEP2 (typically of sequence SEQ ID NO: 51). In one embodiment, the origin of replication allowing replication in *C. acnes* is pWVO1 (typically of sequence SEQ ID NO: 52). In one embodiment, the origin of replication allowing replication in *C. acnes* is pAP1 (typically of sequence SEQ ID NO: 53). In one embodiment, the origin of replication allowing replication in *C. acnes* is pWKS1 (typically of sequence SEQ ID NO: 54). In one embodiment, the origin of replication allowing replication in *C. acnes* is pLME108 (typically of sequence SEQ ID NO: 55). In one embodiment, the origin of replication allowing replication in *C. acnes* is pLS1 (typically of sequence SEQ ID NO: 56). In one embodiment, the origin of replication allowing replication in *C. acnes* is pUB6060 (typically of sequence SEQ ID NO: 57). In one embodiment, the origin of replication allowing replication in *C. acnes* is p545 (typically of sequence SEQ ID NO: 58). In one embodiment, the origin of replication allowing replication in *C. acnes* is pJD4 (typically of sequence SEQ ID NO: 59). In one embodiment, the origin of replication allowing replication in *C. acnes* is pIJ101 (typically of sequence SEQ ID NO: 60). In one embodiment, the origin of replication allowing replication in *C. acnes* is pSN22 (typically of sequence SEQ ID NO: 61). In one embodiment, the origin of replication allowing replication in *C. acnes* is pGP01 (typically of sequence SEQ ID NO: 62). In one embodiment, the origin of replication allowing replication in *C. acnes* is pIP501 (typically of sequence SEQ ID NO: 63). In one embodiment, the origin of replication allowing replication in *C. acnes* is pCU1 (typically of sequence SEQ ID NO: 64). In one embodiment, the origin of replication allowing replication in *C. acnes* is pBAV1 K-T5 (typically of sequence SEQ ID NO: 65).

In one embodiment, the DNA vector comprises an origin of replication allowing replication in *C. acnes*. In one embodiment, the DNA vector comprises an origin of replication selected from the group consisting of: R6K (SEQ ID NO: 42); RK2 (SEQ ID NO: 43); pBBR1 (SEQ ID NO: 44); pRO1600 (SEQ ID NO: 45); RSF1010 (SEQ ID NO: 46); pAM31 (SEQ ID NO: 47); pLME106 (SEQ ID NO: 48); pTZC1 (SEQ ID NO: 49); pBC1 (SEQ ID NO: 50); pEP2 (SEQ ID NO: 51); pWVO1 (SEQ ID NO: 52); pAP1 (SEQ ID NO: 53); pWKS1 (SEQ ID NO: 54); pLME108 (SEQ ID NO: 55); pLS1 (SEQ ID NO: 56); pUB6060 (SEQ ID NO: 57); p545 (SEQ ID NO: 58); pJD4 (SEQ ID NO: 59); pIJ101 (SEQ ID NO: 60); pSN22 (SEQ ID NO: 61); pGP01 (SEQ ID NO: 62); pIP501 (SEQ ID NO: 63); pCU1 (SEQ ID NO: 64); and pBAV1 K-T5 (SEQ ID NO: 65).

Preferably, the origin of replication is of sequence at least 80, 83, 85, 87, 90, 93, 95, 97, 98, 99, or 100% identical to the sequence of any of the above origins of replication.

In various embodiments, the selection marker is selected from ermE, catA, hygB, ermX, tetW, erm(50) and other high GC antibiotic resistance genes. In one embodiment, the selection marker is not ermE. In one embodiment, the selection marker is catA. In one embodiment, the selection marker is hygB.

In one embodiment, the DNA vector further comprises a CRISPR-Cas system. Typically, the CRISPR-Cas system comprises a CRISPR array. Typically, the CRISPR-Cas system comprises a RNA guide (crRNA or sgRNA).

In one embodiment, the CRISPR-Cas system targets a *C. acnes* chromosome locus. Preferably, the targeted locus is not present in the *C. acnes* producer cell. Preferably, the CRISPR array from the CRISPR-Cas system is expressing one or several crRNA targeting the chromosome locus.

In one embodiment, the CRISPR-Cas system targets several *C. acnes* chromosome loci. Preferably, the targeted loci are not present in the *C. acnes* producer cell. Preferably, the CRISPR array from the CRISPR-Cas system is expressing one or several crRNA targeting the chromosome loci.

In one embodiment, the CRISPR-Cas system targets a *C. acnes* plasmid locus. Preferably, the targeted locus is not present in the *C. acnes* producer cell. Preferably, the CRISPR array from the CRISPR-Cas system is expressing one or several crRNA targeting the plasmid locus.

In one embodiment, the CRISPR-Cas system targets several *C. acnes* plasmid loci. Preferably, the targeted loci are not present in the *C. acnes* producer cell. Preferably, the CRISPR array from the CRISPR-Cas system is expressing one or several crRNA targeting the plasmid loci.

In one embodiment, the CRISPR-Cas system is not expressed in *C. acnes* producer cell. Preferably the CRISPR-Cas system is repressed in *C. acnes* producer cell.

In one embodiment, the CRISPR-Cas system targets a proinflammatory sequence related to a host disease.

In one embodiment, the CRISPR-Cas system targets a proinflammatory sequence related to acne vulgaris.

In one embodiment, the DNA vector comprises a template for homologous recombination and the CRISPR-Cas system is targeting the DNA vector itself.

In one embodiment, the DNA vector comprises a template for homologous recombination in *C. acnes* phages.

In one embodiment, the DNA vector comprises a template for homologous recombination in *C. acnes* chromosome.

In one embodiment, the DNA vector comprises a template for homologous recombination in *C. acnes* endogenous plasmids.

In one embodiment, the DNA vector comprises a template for homologous recombination and a CRISPR-Cas system targeting the DNA vector itself outside of the template region.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the DNA vector comprises an integrase gene expression cassette and a site specific recombination site allow for the integration of the DNA vector inside the chromosome.

In one embodiment, the DNA vector comprises a base editor gene expression cassette and one or multiple crRNAs or sgRNAs.

In one embodiment, the base editor is used to inactivate the expression of a gene by editing one or several nucleotides involved in transcription or translation of said gene. More specifically the base editor is targeting one or several nucleotides of a promoter, a RBS or a start codon.

In one embodiment, the base editor is used to introduce a premature stop codon.

In one embodiment, the base editor is used to introduce one or several rare codons.

In another embodiment, the base editor is used to modulate the expression of genes by editing one or several nucleotides involved in transcription or translation of said genes. More specifically the base editor is targeting one or several nucleotides of a promoter, a RBS or a start codon, leading to an increase or decrease of gene expression.

In another embodiment, the base editor is used to revert a mutation that leads to the inactivation, decrease or increase in activity of a gene or pathway.

In another embodiment, the base editor is used to revert a mutation that leads to an increase of pathogenicity.

In one embodiment, the base editor is used to modify the regulation of a gene by editing one or several nucleotides involved in its regulation such as nucleotides of operator sequence, transcription factor binding site, riboswitch, RNAse recognition site, protease cleavage site, methylation site or post translational modification site (phosphorylation, glycosylation, acetylation, pupylation . . . ).

In one embodiment, the DNA vector comprises a prime editor gene expression cassette and one or multiple pegRNAs.

In one embodiment, the prime editor is used to introduce one or several premature stop codon.

In one embodiment, the prime editor is used to introduce one or several rare codons.

In one embodiment, the prime editor is used to introduce or delete a nucleotide inducing a frameshift in the reading frame.

In another embodiment, the prime editor is used to modulate the expression of genes by replacing, deleting or inserting one or several nucleotides involved in transcription or translation of said genes. More specifically the prime editor is replacing, deleting or inserting one or several nucleotides in a promoter, a RBS or a start codon. leading to an increase or decrease of gene expression.

In another embodiment, the prime editor is used to revert a mutation that leads to the inactivation or decrease in activity of a gene or pathway.

In another embodiment, the prime editor is used to revert a mutation that leads to an increase of pathogenicity.

In one embodiment, the vector is a plasmid which comprises an *E. coli* replicon and an *E. coli* resistance marker allowing extraction of the plasmid from *C. acnes* and transformation and replication in *E. coli.*

In one embodiment, the vector is a plasmid which comprises an *E. coli* replicon and an *E. coli* resistance marker allowing extraction of the plasmid from *E. coli* and transformation and replication in *C. acnes.*

In one embodiment, the vector comprises 2 origins or replication, one allowing replication in *C. acnes* or *C. acnes* producer cell only, the second origin of replication allowing replication in another bacteria.

In one embodiment, the vector comprising the template DNA for homologous recombination allows expression of genes increasing recombination rate.

In one embodiment, the template for homologous recombination contains homology arms upstream and downstream of recombination points. These homology arms can be at least 50, 100, 500 or at least 1000 bp in size.

In one embodiment, the gene of interest comprised by the DNA vector can be a transgene that is exogenous to the *C. acnes*. Transgenes include but are not limited to:

- a DNA encoding a fluorescent protein (e.g., UnaG) that leads to fluorescent *C. acnes* cells once a specific substrate is added;
- a DNA encoding an enzymatic reporter (e.g., LacZ) that leads to the production of a chromogenic compound by *C. acnes* colonies;
- a DNA encoding a human protein (e.g., an interleukin);
- a DNA encoding an antigen (e.g. a tumor antigen, a viral antigen, a bacterial antigen, a fungal antigen, a self-antigen, an allergen or a graft-specific antigen);
- a CRISPR-Cas system;
- a prime-editing system; or
- a base-editor system.

In a particular embodiment, the gene of interest encoded by the DNA vector is a DNA encoding an antigen, more particularly a DNA encoding an antigen selected from the group consisting of tumor antigens, viral antigens, bacterial antigens, fungal antigens, self-antigens, allergens and graft-specific antigens, as defined below.

*C. acnes* Strains Comprising DNA Vectors and Engineered *C. acnes* Strains

The invention encompasses *C. acnes* comprising any of the DNA vectors of the invention. The invention further encompasses *C. acnes* produced by any of the methods of the invention. Thus, the invention encompasses *C. acnes* that have been modified following transduction of any of the DNA vectors of the invention by a phage-derived particle, whether retaining the DNA vector or subsequently having that DNA vector removed (i.e., cured) from *C. acnes.*

Thus, the invention encompasses *C. acnes* produced by a method comprising producing a phage-derived particle from a *C. acnes* producer cell containing a DNA vector of the invention; contacting these phage-derived particles with *C. acnes* receiver cells leading to transduction of the DNA vector into the *C. acnes* receiver cell and modification of the *C. acnes* receiver cell with a gene of interest carried by the vector (e.g., a CRISPR-Cas system) and/or an exogenous gene inserted into the *C. acnes* chromosome; selecting for the modification; and curing *C. acnes* of the vector.

The invention encompasses an engineered *C. acnes* that has been modified by a CRISPR-Cas system transduced by a phage or phage-derived particle carrying a vector of the invention.

The invention encompasses an engineered *C. acnes* that has been modified by transduction of DNA vector and subsequent insertion of an exogenous gene into the *C. acnes* chromosome.

The invention encompasses an engineered *C. acnes* that has been modified by transduction of DNA vector and subsequent deletion or mutation of an endogenous gene into the *C. acnes* chromosome or *C. acnes* endogenous plasmid.

The invention encompasses *C. acnes* produced by transduction of a DNA vector of the invention.

The invention encompasses an engineered *C. acnes* that has been modified by delivery of a plasmid, in particular by conjugation. In a particular embodiment, said plasmid comprises a CRISPR-Cas system. In another particular embodiment, said plasmid comprises an exogenous gene. In another particular embodiment, said plasmid enables the insertion of an exogenous gene into the *C. acnes* chromosome. In another particular embodiment, said plasmid enables the deletion or mutation of an endogenous gene into the *C. acnes* chromosome or *C. acnes* endogenous plasmid. In a particular embodiment, said plasmid comprises an origin of replication allowing replication in *C. acnes*, as defined above and/or an origin of transfer as defined above.

*Cutibacterium acnes*, previously named *Propionibacterium acnes*, has been historically classified in three major phylotypes based on recA and tly sequencing: IA, IB, II and III. These phylotypes have been further subdivided using different multi-locus sequence typing (MLST) schemes into IA1, IA2, IB, II and III. More recently, Fitz-Gibbon et al (Fitz-Gibbon, S. et al. (2013) J Invest Dermatol 133, 2152-2160) have introduced a new classification based on sequence diversity of 16S rRNA gene (ribotyping) as well as a refined classification of phylotypes: IA-1, IA-2, IB-1, IB-2, IB-3, IC, II, III. The present disclosure refers to this classification but concordance between this classification and others is well-known from the skilled person and can be obtained from the following review (1.Dréno, B. et al. (2018). *Journal of the European Academy of Dermatology and Venereology* 32, 5-14). In a particular embodiment, *C. acnes* may thus be from a phylotype selected from the group consisting of phylotypes IA-1, IA-2, IB-1, IB-2, IB-3, IC, II and III.

By comparing whole genome sequences of strains isolated from acne and healthy volunteers, Fitz-Gibbon and colleagues could identify acne-associated strains (IA-2 and IB-1) and healthy-associated strains (II) in accordance with previous studies. More interestingly, they found specific loci (locus1, locus 2 and locus 3) present in acne associated strains and absent of neutral and healthy strains. Similar loci were found in a subsequent metagenomic analysis confirming the association between the presence of these loci and acne vulgaris (Barnard, E. et al. (2016) *Scientific Reports* 6, srep39491).

The ability of specific strain phylotypes to induce immune response has been recently investigated (Yu et al. (2016) Journal of Investigative Dermatology 136:2221-2228). Yu et al. demonstrated that the different *C. acnes* phylotypes induced different cytokine profiles when incubated with peripheral blood mononuclear cells (PBMC). More particularly, they showed that acne-associated phylotypes IA-2 p+ (i.e. with a large plasmid associated with acne), IB-1, and IC induced high levels of inflammatory IFN-γ and IL-17 but low levels of IL-10, suggesting that these specific phylotypes could induce both Th1 and Th17 responses. They also showed that phylotypes IB-3, II and III induced lower levels of IL-17 (and of IFN-γ for phylotype III) but higher levels of IL-10, suggesting induction of Treg responses. They further showed that phylotypes IA-1, IA-2 p- (i.e. without the large plasmid associated with acne) and IB-2 induced lower levels of IFN-γ and IL-10 and higher levels of IL-17, suggesting induction of mainly Th17 responses.

Therefore, depending on the particular immune response that is desired when using the engineered *C. acnes* of the invention for a particular indication, the use of a given *C. acnes* phylotype or strain may be advantageous. Accordingly, in a particular embodiment, *C. acnes* is from a phylotype selected from the group consisting of phylotypes IA-2 p+, IB-1 and IC. In another embodiment, *C. acnes* is from a phylotype selected from the group consisting of phylotypes IA-1, IA-2 p- and IB-2. In still another embodiment, *C. acnes* is from a phylotype selected from the group consisting of phylotypes IB-3, II and III.

Furthermore, a previous study showed that it was possible, in *S. epidermidis*, to induce different T cell responses with different strains within the same species by engineering said strains (Chen et al. (2019) "Decoding commensal-host communication through genetic engineering of *Staphylococcus epidermidis*" bioRxiv https://doi.org/10.1101/664656).

Therefore, in a particular embodiment, the *C. acnes* is a strain inducing, or engineered to induce, a given T cell response. In a particular embodiment, more particularly when the *C. acnes* cell is intended to be used in the prevention and/or treatment of cancer, said *C. acnes* is a strain inducing, or engineered to induce, increased levels of IFN-γ and/or IL-17a. In a particular embodiment, more particularly when the *C. acnes* cell is intended to be used in the prevention and/or treatment of an infection, said *C. acnes* is a strain inducing, or engineered to induce, increased levels of IFN-γ and/or IL-17. In a particular embodiment, more particularly when the *C. acnes* cell is intended to be used in the prevention and/or treatment of an autoimmune disease, said *C. acnes* is a strain inducing, or engineered to induce, increased levels of IL-10. In a particular embodiment, more particularly when the *C. acnes* cell is intended to be used in the prevention and/or treatment of an allergy, such as asthma, said *C. acnes* is a strain inducing, or engineered to induce, increased levels of IFN-g and/or IL-10. In a particular embodiment, more particularly when the *C. acnes* cell is intended to be used in the prevention and/or treatment of a graft rejection, said *C. acnes* is a strain inducing, or engineered to induce, increased levels of IL-10.

*C. acnes* comprising a recombinant self-replicative DNA vector of the invention (or comprising a plasmid, in particular a conjugative plasmid as defined above) can be generated for the expression of molecules of interest and modulation of *C. acnes*-host interaction. The molecule of interest can be carried on a self-replicative DNA vector in the *C. acnes* (or on a plasmid, in particular a conjugative plasmid) or can be inserted into the chromosome of the *C. acnes* through the action of the self-replicative DNA vector (or of the plasmid, in particular the conjugative plasmid, as defined above).

In one embodiment, the DNA vector is used for *C. acnes* chromosome engineering.

In one embodiment, the DNA vector is used for *C. acnes* plasmid engineering.

In one embodiment, the DNA vector is used for *C. acnes* phage engineering.

In one embodiment, the DNA vector (or the plasmid, in particular the conjugative plasmid, as defined above) is used for the expression of molecules of interest and modulation of *C. acnes*-host interaction. In one embodiment, the DNA vector (or the plasmid, in particular the conjugative plasmid, as defined above) is used for the expression of transgenes in *C. acnes*. A transgene can be cloned into the recombinant autonomously-replicating DNA vector (or in the plasmid, in particular the conjugative plasmid) under the control of a given promoter (constitutive or inducible) and followed by a given terminator. The transfer of this vector into *C. acnes* allows the expression of the transgene. The transgene can be, for example, a CRISPR/Cas system or can encode a human protein, such as an interleukin. In one embodiment the DNA vector (or the plasmid, in particular the conjugative plasmid) encodes several transgenes under the control of a single promoter or under the control of different promoters. The promoters can be endogenous or exogenous, inducible or constitutive.

In one embodiment, the DNA vector (or the plasmid, in particular the conjugative plasmid) is used for the modification of *C. acnes* genome. In one embodiment, the transfer of the vector (or of the plasmid, in particular the conjugative plasmid) into *C. acnes* allows the expression of a CRISPR/Cas system that cleaves the *C. acnes* genome (plasmid or chromosome) at a specific site, leading to modification of the *C. acnes* genome. In one embodiment, the vector (or the plasmid, in particular the conjugative plasmid) further comprises a gene of interest and homology with the site of cleavage to facilitate integration of the gene of interest into the *C. acnes* genome.

Delivery of DNA Vectors into *C. acnes* Strains

In one embodiment, delivery of any DNA vector of the invention into *C. acnes* producer cell is performed by contacting *C. acnes* with any DNA vector of the invention.

In one embodiment, delivery of any DNA vector of the invention into *C. acnes* producer cell is performed by transfection (e.g., electroporation) into *C. acnes* cells, where it stably replicates. In one embodiment the DNA vector transfected is purified from dam(−) *E. coli* cells such as ET12567 and electroporated into *C. acnes* cells made competent at 24° C.

In one embodiment, delivery of any DNA vector of the invention into *C. acnes* producer cell is performed by transfection (e.g., electroporation) into *C. acnes* protoplasts. In one embodiment *C. acnes* protoplasts are generated using Mutanolysin treatment or Lysozyme treatment, Mutanolysin and Lysozyme treatment, or Mutanolysin and Lysozyme and bead-beating treatment followed by resuspension into hypotonique media.

In one embodiment, delivery of any DNA vector of the invention into *C. acnes* producer cell is performed by mixing *C. acnes* protoplasts with the DNA vector. In one embodiment glass beads are added with the DNA vector and bead beating is performed to introduce the DNA into *C. acnes* protoplasts.

In one embodiment, delivery of DNA vectors of the invention into *C. acnes* is by transduction. In one embodiment, the DNA vector comprises one packaging signal of a *C. acnes* phage selected from the group consisting of the phages: PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74) and PAC263 (typically of sequence SEQ ID NO: 75) and is packaged into proteins expressed from the genome of a *C. acnes* phage selected from the group consisting of the phages PAC7 (typically of sequence SEQ ID NO: 68); PAC1 (typically of sequence SEQ ID NO: 69); PAC9 (typically of sequence SEQ ID NO: 70); PAC2 (typically of sequence SEQ ID NO: 71); PAC10 (typically of sequence SEQ ID NO: 72); PAC22 (typically of sequence SEQ ID NO: 73); PAC13 (typically of sequence SEQ ID NO: 74) and PAC263 (typically of sequence SEQ ID NO: 75), allowing transduction of the DNA vector into *C. acnes*.

In one embodiment, delivery of any DNA vector of the invention into *C. acnes* producer cell is by conjugation. In one embodiment, the DNA vector comprises an origin of transfer. In one embodiment, a donor bacterium, such as *E. coli*, is used to efficiently transfer the DNA vector into *C. acnes* recipient cells, where it stably replicates. In one embodiment, the DNA vector comprises an origin of transfer selected from the group consisting of: oriT_pMRC01 (typically of sequence SEQ ID NO: 1); oriT_RSF1010 (typically of sequence SEQ ID NO: 2); oriT_pRS01 (typically of sequence SEQ ID NO: 3); oriT_pMV158 (typically of sequence SEQ ID NO: 4); oriT_pTF1 (typically of sequence SEQ ID NO: 5); oriT_pSC101 (typically of sequence SEQ ID NO: 6); oriT_pBTK445 (typically of sequence SEQ ID NO: 7); oriT_pBBR1 (typically of sequence SEQ ID NO: 8); oriT_R721 (typically of sequence SEQ ID NO: 9); oriT_pRmeGR4a (typically of sequence SEQ ID NO: 10); oriT_ColE1 (typically of sequence SEQ ID NO: 11); oriT_pTiC58 (typically of sequence SEQ ID NO: 12); oriT_pMdT1 (typically of sequence SEQ ID NO: 13); oriT_R1 (typically of sequence SEQ ID NO: 14); oriT_Tn5520 (typically of sequence SEQ ID NO: 15); oriT_QKH54 (typically of sequence SEQ ID NO: 16); oriT_R64 (typically of sequence SEQ ID NO: 17); oriT_R751 (typically of sequence SEQ ID NO: 18); oriT_RP4 (typically of sequence SEQ ID NO: 19); oriT_pKL1 (typically of sequence SEQ ID NO: 20); oriT_RK2 (typically of sequence SEQ ID NO: 21); oriT_R1162 (typically of sequence SEQ ID NO: 22); oriT_Tn4555 (typically of sequence SEQ ID NO: 23); oriT_pHT (typically of sequence SEQ ID NO: 24); oriT_Tn4399 (typically of sequence SEQ ID NO: 25); oriT_Tn916 (typically of sequence SEQ ID NO: 26); oriT_pST12 (typically of sequence SEQ ID NO: 27); oriT_pCU1 (typically of sequence SEQ ID NO: 28); oriT_pSU233 (typically of sequence SEQ ID NO: 29); oriT_F (typically of sequence SEQ ID NO: 30); oriT_pMAB01 (typically of sequence SEQ ID NO: 31); oriT_R388 (typically of sequence SEQ ID NO: 32); oriT_pS7a (typically of sequence SEQ ID NO: 33); oriT_pS7b (typically of sequence SEQ ID NO: 34); oriT_R702 (typically of sequence SEQ ID NO: 35); oriT_pMUR274 (typically of sequence SEQ ID NO: 36); oriT_R100 (typically of sequence SEQ ID NO: 37); oriT_pVCR94deltaX (typically of sequence SEQ ID NO: 38); oriT_R46 (typically of sequence SEQ ID NO: 39); oriT_pGO1 (typically of sequence SEQ ID NO: 40) and oriT_pIP501 (typically of sequence SEQ ID NO: 41). In one embodiment, a donor bacterium, such as *E. coli*, carries a conjugative plasmid, a conjugative transposon or an integrative and conjugative element (ICE) selected from the group consisting of: pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501, and is used to efficiently transfer the DNA vector into *C. acnes* recipient cells. In one embodiment the DNA vector contains an origin of transfer and the associated relaxase of a conjugative plasmid, conjugative transposon or integrative and conjugative element (ICE) selected from the group consisting of: pMRC01; RSF1010; pRS01; pMV158; pTF1; pSC101; pBTK445; pBBR1; R721; pRmeGR4a; ColE1; pTiC58; pMdT1; R1; Tn5520; QKH54; R64; R751; RP4; pKL1; RK2; R1162; Tn4555; pHT; Tn4399; Tn916; pST12; pCU1; pSU233; F; pMAB01; R388; pS7a; pS7b; R702; pMUR274; R100; pVCR94deltaX; R46; pGO1 and pIP501.

In a preferred embodiment the DNA vector comprises the origin of transfer oriT_pMRC01 (typically of sequence SEQ ID NO: 1). In a preferred embodiment, the DNA vector comprises the origin of transfer oriT_RSF1010 (typically of sequence SEQ ID NO: 2). In a preferred embodiment, the DNA vector comprises the origin of transfer oriT_pRS01 (typically of sequence SEQ ID NO: 3). In a preferred embodiment, the DNA vector comprises the origin of transferoriT_pMV158 (typically of sequence SEQ ID NO: 4). In a preferred embodiment, the DNA vector comprises the origin of transfer oriT_pTF1 (typically of sequence SEQ ID NO: 5). In a preferred embodiment, the DNA vector comprises the origin of transfer oriT_pSC101 (typically of sequence SEQ ID NO: 6). In a preferred embodiment, the DNA vector comprises the origin of transfer oriT_pBTK445 (typically of sequence SEQ ID NO: 7). In a preferred embodiment, the DNA vector comprises the origin of transfer oriT_pBBR1 (typically of sequence SEQ ID NO: 8). In a preferred embodiment, the DNA vector comprises the origin of transfer oriT_R721 (typically of sequence SEQ ID NO: 9). In a preferred embodiment, the DNA vector comprises the origin of transfer oriT_pRmeGR4a (typically of sequence SEQ ID NO: 10). In a preferred embodiment, the DNA vector comprises the origin of transfer oriT_ColE1 (typically of sequence SEQ ID NO: 11). In a preferred embodiment, the DNA vector comprises the origin of transfer oriT_pTiC58 (typically of sequence SEQ ID NO: 12). In a preferred embodiment, the DNA vector comprises the origin of transfer oriT_pMdT1 (typically of sequence SEQ ID NO: 13). In a preferred embodiment, the DNA vector comprises the origin of transfer oriT_R1 (typically of sequence SEQ ID NO: 14). In a preferred embodiment, the DNA vector comprises the origin of transfer oriT_Tn5520 (typically of sequence SEQ ID NO: 15). In a preferred embodiment, the DNA vector comprises the origin of transfer oriT_QKH54 (typically of sequence SEQ ID NO: 16). In a preferred embodiment, the DNA vector comprises the origin of transfer oriT_R64 (typically of sequence SEQ ID NO: 17). In a preferred embodiment, the DNA vector comprises the origin of transfer oriT_R751 (typically of sequence SEQ ID NO: 18). In a preferred embodiment, the DNA vector comprises the origin of transfer oriT_RP4 (typically of sequence SEQ ID NO: 19). In a preferred embodiment, the DNA vector comprises the origin of transfer oriT_pKL1 (typically of sequence SEQ ID NO: 20). In a preferred embodiment, the DNA vector comprises the origin of transfer oriT_RK2 (typically of sequence SEQ ID NO: 21). In a preferred embodiment, the DNA vector comprises the origin of transfer oriT_R1162 (typically of sequence SEQ ID NO: 22). In a preferred embodiment, the DNA vector comprises the origin of transfer oriT_Tn4555 (typically of sequence SEQ ID NO: 23). In a preferred embodiment, the DNA vector comprises the origin of transfer oriT_pHT (typically of sequence SEQ ID NO: 24). In a preferred embodiment, the DNA vector comprises the origin of transfer oriT_Tn4399 (typically of sequence SEQ ID NO: 25). In a preferred embodiment, the DNA vector comprises the origin of transfer oriT_Tn916 (typically of sequence SEQ ID NO: 26). In a preferred embodiment, the DNA vector comprises the origin of transfer oriT_pST12 (typically of sequence SEQ ID NO: 27). In a preferred embodiment, the DNA vector comprises the origin of transfer oriT_pCU1 (typically of sequence SEQ ID NO: 28). In a preferred embodiment, the DNA vector comprises the origin of transfer oriT_pSU233 (typically of sequence SEQ ID NO: 29). In a preferred embodiment, the DNA vector comprises the origin of transfer oriT_F (typically of sequence SEQ ID NO: 30). In a preferred embodiment, the DNA vector comprises the origin of transfer oriT_pMAB01 (typically of sequence SEQ ID NO: 31). In a preferred embodiment, the DNA vector comprises the origin of transfer oriT_R388 (typically of sequence SEQ ID NO: 32). In a preferred embodiment, the DNA vector comprises the origin of transfer oriT_pS7a (typically of sequence SEQ ID NO: 33). In a preferred embodiment, the DNA vector comprises the origin of transfer oriT_pS7b (typically of sequence SEQ ID NO: 34). In a preferred embodiment, the DNA vector comprises the origin of transfer oriT_R702 (typically of sequence SEQ ID NO: 35). In a preferred embodiment, the DNA vector comprises the origin of transfer oriT_pMUR274 (typically of sequence SEQ ID NO: 36). In a preferred embodiment, the DNA vector comprises the origin of transfer oriT_R100 (typically of sequence SEQ ID NO: 37). In a preferred embodiment, the DNA vector comprises the origin of transfer oriT_pVCR94deltaX (typically of sequence SEQ ID NO: 38). In a preferred embodiment, the DNA vector comprises the origin of transfer oriT_R46 (typically of sequence SEQ ID NO: 39). In a preferred embodiment, the DNA vector comprises the origin of transfer oriT_pGO1 (typically of sequence SEQ ID NO: 40). In a preferred embodiment, the DNA vector comprises the origin of transfer oriT_pIP501 (typically of sequence SEQ ID NO: 41).

In one embodiment, a donor bacterium is selected from the group consisting of: *Escherichia coli, Pseudomonas aeruginosa, Lactococcus lactis, Lactobacillus casei, Lactobacillus fermentum, Lactobacillus rhamnosus, Propionibacterium freudenreichii, Lactobacillus brevis, Staphylococcus epidermidis, Staphylococcus aureus, Cutibacterium* granulosum, *Cutibacterium humerusii, Enterococcus faecalis* and *Bacillus subtilis*, carrying a conjugative plasmid, a conjugative transposon or an integrative and conjugative element (ICE).

In one embodiment the conjugation is performed growing at high density the donor bacteria, such as *E. coli*, harboring the mobilizable DNA vector and the conjugative machinery (ICE, plasmid, conjugative transposon). Donor cells are pelleted by centrifugation, and washed to remove antibiotics added during growth to maintain mobilizable and conjugative DNA vectors. Donor cells are then mixed in presence of *C. acnes* cells. The mixture donor cells—*C. acnes* is spotted onto *Brucella* agar plates and allowed to mate at 37° C. under anaerobic conditions. After mating, cells are harvested from the mating plate, re-suspended in BHI broth and plated onto *Brucella* agar plates that are supplemented with:

- a compound killing donor cells but not *C. acnes*, or
- an antibiotic selecting the mobilizable DNA vector.

After several days of incubation, *C. acnes* colonies are streaked on *Brucella* agar plates supplemented with the appropriate selection and the presence of the conjugated plasmid is confirmed via specific PCRs. The identity of *C. acnes* as well as the absence of donor cells is also confirmed by PCR analyses.

In one embodiment the conjugation is performed according to the following protocol: 2 mL of overnight cultures of *E. coli* donor cells harboring a mobilizable DNA vector and a conjugative machinery (ICE, plasmid, conjugative transposon) is grown in LB broth and pelleted at 6,000×g for 1 min. Supernatants are discarded and pellets are washed with 500 μL of pre-sterilized LB medium, centrifuged again using the same conditions. Pellet is then re-suspended in 200 μL of exponentially growing (OD600=0.5) *C. acnes* receptor BHI culture concentrated 10×. The mixture *E. coli*-*C. acnes* is spotted (50 μL/spot) onto *Brucella* agar plates and allowed to mate at 37° C. under anaerobic conditions for 24 hours. After that time, cells are harvested from the mating plate, re-suspended in 300 μL of BHI broth and plated onto *Brucella* agar plates that had been supplemented with 50 μg/mL polymyxin B and 5 μg/mL erythromycin or 3.5 μg/mL chloramphenicol depending on the selection marker present in the mobilizable DNA vector. After 7 days, *C. acnes* cells that grow in the presence of selection are streaked on *Brucella* agar plates supplemented with the appropriate selection and the presence of the conjugated plasmid confirmed via specific PCRs. The identity of *C. acnes* as well as the absence of *E. coli* donor strain are also confirmed by PCR analyses.

Methods to Modify Endogenous *C. acnes* Plasmids

Naturally occurring *C. acnes* plasmids have been described[21,22] and some of them are able to be transferred from one *C. acnes* to another by conjugation[20]. Being able to modify such plasmids is of interest to study their effect notably their pro-inflammatory role in acne vulgaris or to use them for further genetic manipulation of *C. acnes*. The inventors have developed methods to modify *C. acnes* plasmids.

In one embodiment, the method comprises, in a first step, introducing into *C. acnes* a replicative vector comprising:

- a selection marker for *C. acnes* as defined above,
- an origin of replication for *C. acnes* as defined above,
- a phage packaging signal as defined above, and
- a template for homologous recombination in the *C. acnes* endogenous plasmid.

In one embodiment, the method comprises, in a first step, introducing in *C. acnes* a replicative vector comprising:

- a selection marker for *C. acnes* as defined above,
- an origin of replication for *C. acnes* as defined above,
- a phage packaging signal as defined above, and
- a CRISPR-Cas system
- a template for homologous recombination with the *C. acnes* endogenous plasmid.

Introduction can be achieved with electroporation, electroporation of protoplast, conjugation, chemical transformation or transduction. *C. acnes* recombinants are then preferably grown in presence of an antibiotic.

Recombinants are then typically infected with *C. acnes* phage to produce phage-derived particles carrying the DNA vectors.

Phage-derived particles are then typically mixed with *C. acnes* receiver cells containing an endogenous plasmid such as pIMPLE-HL096PA1. *C. acnes* transductants are then typically selected on the appropriate antibiotic.

In a second step, *C. acnes* transductants are grown in the presence of an antibiotic A to a high density to increase chances of a homologous recombination event occurring. Homologous recombination typically leads to introduction of a selection marker, giving resistance to an antibiotic B. In the dense culture, *C. acnes* strains carrying wild-type endogenous plasmid and recombinant endogenous plasmid carrying a resistance marker are typically present. The high-density culture is then preferably washed and typically put in the presence of a receiver *C. acnes* strain that is resistant to a third antibiotic C. Selection of transconjugant with antibiotics C and B typically leads to selection of receiver cells with the recombinant plasmid.

Other modifications enabled by the methods of the invention include the insertion of an *E. coli* replicon and an *E. coli* resistant marker on the plasmid allowing extraction of the plasmid from *C. acnes* and transformation and replication in *E. coli*.

Additionally, the plasmid carrying the template DNA for homologous recombination preferably allows the expression of genes that increase recombination rate.

The template for homologous recombination typically contains homology arms upstream and downstream recombination points. These homology arms are preferably 50, 100, 500, 1000 bp long or more.

*C. acnes* Genome Engineering and Engineered *C. acnes* Strains

The invention encompasses methods of *C. acnes* genome engineering and engineered *C. acnes* strains that have been engineered by any of the methods of the invention. An "engineered strain" is a strain that has been obtained by any of the methods of the invention to contain an alteration either found or not found in nature. For example, the engineered *C. acnes* strain can comprise any of the vectors or DNAs of the invention.

The invention encompasses methods for delivering DNA of interest into *C. acnes* strains by conjugation. The invention also encompasses methods for delivering DNA of interest into *C. acnes* strains via phage-derived particles. The invention encompasses methods to engineer the *C. acnes* chromosome with replicative and non-replicative vector methods.

In one embodiment, delivery of the DNA vector into *C. acnes* is by transduction. In one embodiment, the DNA vector comprises a phage packaging signal (cos) originating from *C. acnes* phages. In one embodiment, phage-derived particles containing the DNA vector can be generated and allow the DNA vector to be transduced into *C. acnes* cells.

In one embodiment, the invention encompasses replicative and non-replicative vector methods using a vector comprising at least a recombination template with one or two homology arms.

To engineer the *C. acnes* genome, the inventors have developed methods using replicative and non-replicative vectors.

Non-Replicative Vector Methods

In one embodiment, non replicative vector methods use a vector comprising at least:

- a phage packaging signal, as defined above;
- a selection marker for *C. acnes*, as defined above;
- a recombination template with one or two homology arms;
- an origin of replication allowing replication only in *Cutibacterium acnes* producer cell; and
- optionally a counter selection marker such as SacB.

Non replicative vector methods use vectors that carry a *C. acnes* replicon that replicate only in a *C. acnes* producer cell but not in other *C. acnes* cells. Thus, such vectors are able to replicate in *C. acnes* producer cell, get packaged into phage capsid upon contacting with phage genome leading to a phage-derived particle, and get transduced by the phage-derived particle into *C. acnes* receiver cell where they do not replicate.

Figure 4A:
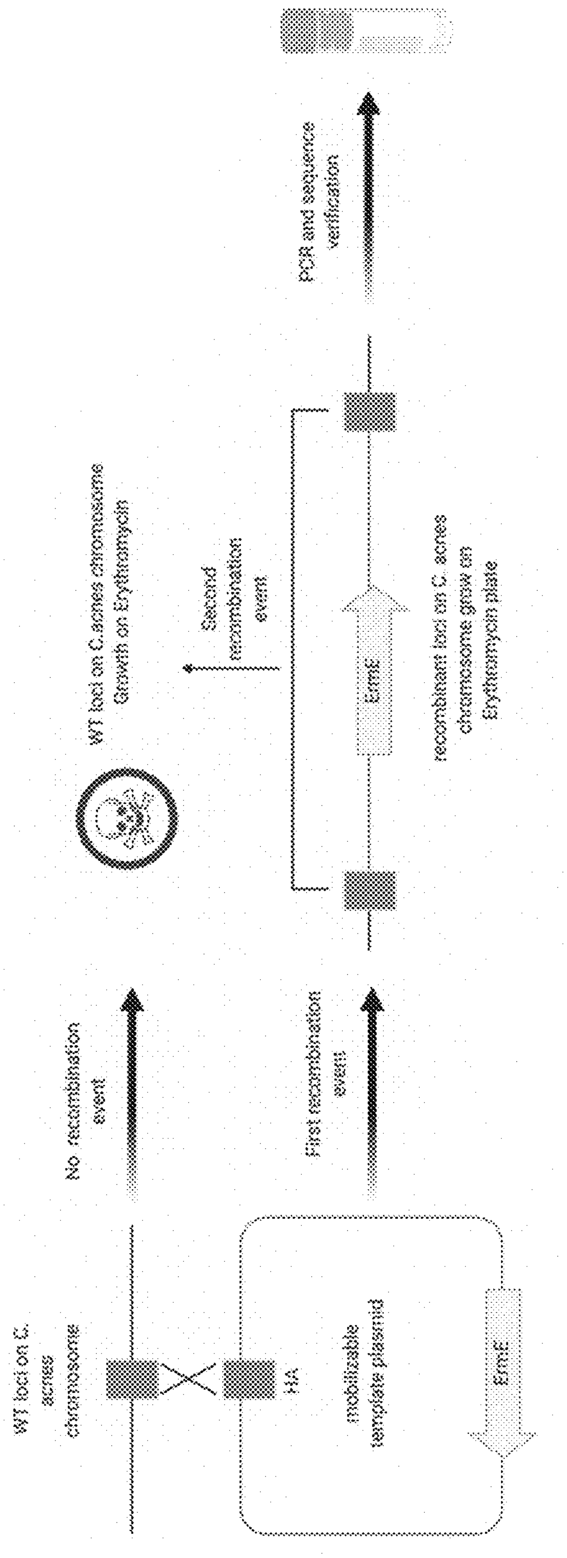
FIGS. 4A and 4B depict a method for *C. acnes* genome engineering using non-replicative vector carrying recombination template.
Figure 4B:
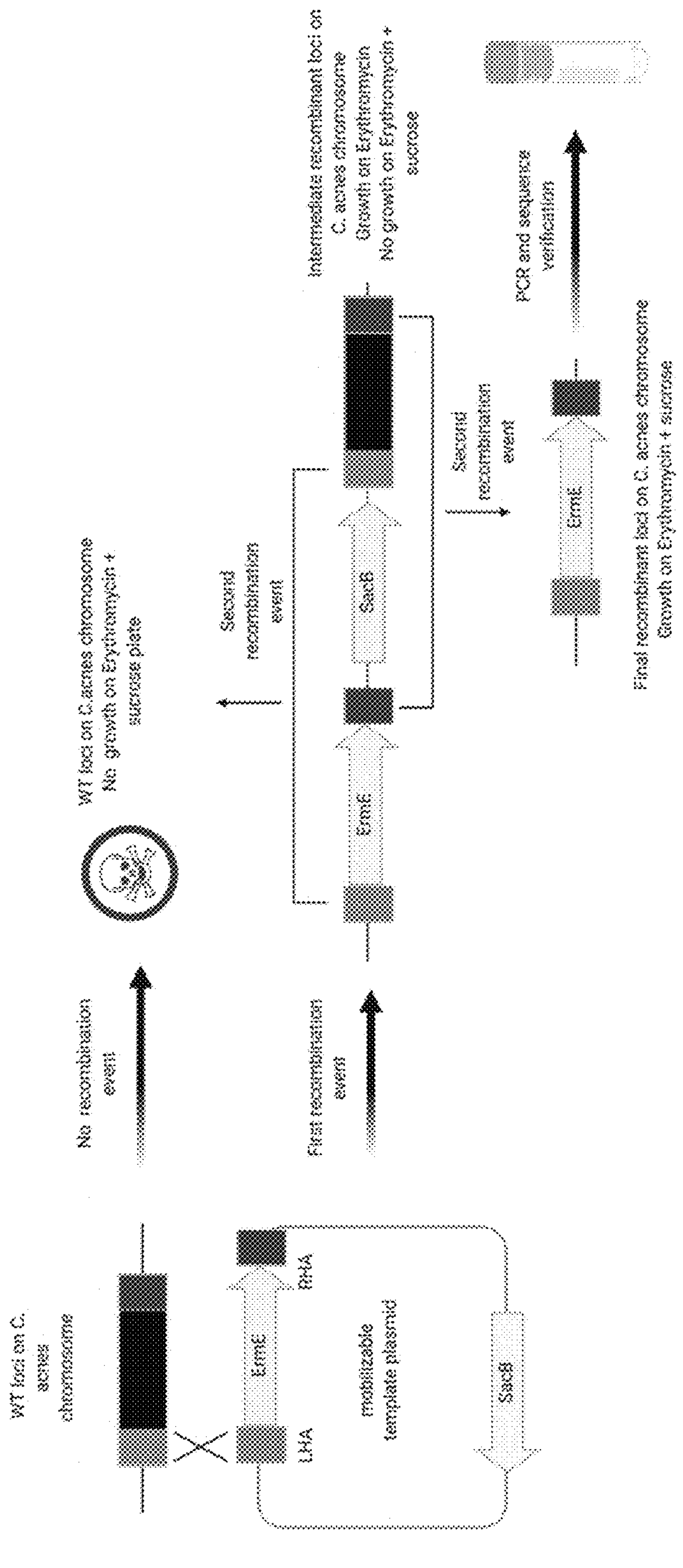

The methods comprise introducing into a *C. acnes* producer cell a plasmid containing a template for homologous DNA recombination inside the genome. The template can contain one (FIG. 4A) or two homologous regions (FIG. 4B) leading to homologous recombination.

In one embodiment, the method comprises a *C. acnes* producer cell, carrying a plasmid containing a template for homologous DNA recombination inside the chromosome where the homologous DNA is not present in the *C. acnes* producer cell, a phage packaging signal (cos) originating from *C. acnes* phages, a selection marker for *C. acnes*, as defined above, and an origin of replication for *C. acnes* producer cell but not replicating in *C. acnes* receiver cell. The template can contain one (FIG. 4A) or two homologous regions (FIG. 4B), leading to homologous recombination. The producer cell is typically infected by a *C. acnes* phage leading to production of phage-derived particles containing the DNA vector with homology arm(s). Phage-derived particles are preferably mixed with *C. acnes* receiver cells (e.g., ATCC 11828). Transductants can be selected on antibiotic plates, streaked on antibiotic plates and plasmid integration screened by PCR. Because the plasmid is not replicative in *C. acnes*, only recombinant cells that stably maintain the antibiotic marker are able to grow on antibiotic plates.

In the case where there are two homology arms present on the template DNA, a first recombination event (also called cross-over) typically leads to the full integration of the plasmid. This is typically followed by a second recombination event that removes the plasmid backbone and leads to either the modification of the chromosome or to the reconstitution of wild-type wt locus.

In one embodiment, the *C. acnes* producer cell carries a vector containing a left homology arm (LHA) and a right homology arm (RHA) flanking a *C. acnes* selection marker, for example, ermE (pEB_HR02). The two homology arms typically do not match the *C. acnes* producer cell chromosome. In one embodiment, the vector also contains a phage packaging signal (cos) originating from *C. acnes* phages, a selection marker for *C. acnes* and an origin of replication for *C. acnes* producer cell but not replicating in *C. acnes* receiver cell. In one embodiment the DNA vector also contains a *C. acnes* counter-selection marker, such as sacB, on the plasmid backbone allowing selection of the second recombination event. The *C. acnes* producer cell carrying pEB_HR02 is typically infected by a phage leading to production of phage-derived particles comprising pEB_HR02. The phage-derived particles are typically put in presence of *C. acnes* receiver cells (e.g., ATCC 11828). Transductants are typically selected on plates supplemented with the antibiotic (e.g., erythromycin), streaked onto plates supplemented with the antibiotic (e.g., erythromycin) and integration of the plasmid confirmed by PCR. Because the plasmid is not replicative in *C. acnes* receiver cell, *C. acnes* clones able to grow in the presence of the antibiotic (e.g., erythromycin), have undergone a single homologous recombination event, which has led to the integration of the full plasmid. To select for final recombinant loci, cells are typically exposed to the counter-selection (e.g., sucrose) and the antibiotic (e.g., erythromycin), which leads to cell death due to sacB activity (the full plasmid remains integrated in the chromosome). Survivors are typically screened by PCR for successful final recombinant loci presence. In one embodiment the DNA vector contains only one homology arm (pEB_HR01). In one embodiment, both pEB_HR01 and pEB_HR02 phage-derived particles are applied on the skin and no antibiotic selection is applied.

In one embodiment, the *C. acnes* producer cell carries a plasmid (vector) containing a left homology arm (LHA) and a right homology arm (RHA) flanking *C. acnes* selection marker ErmE (pEB_HR02). The vector also preferably contains an *E. coli* origin of replication, an *E. coli* selection marker, an oriT and relaxase from a conjugative plasmid and a *C. acnes* counter-selection marker, such as sacB. pEB_HR02 can be transformed into an *E. coli* donor strain (e.g. Ec0s2862). Transformants are typically selected, grown and mixed with *C. acnes* receiver cells (e.g., ATCC 11828). Transconjugants are typically selected on plates supplemented with the antibiotic (e.g., erythromycin), streaked onto plates supplemented with the antibiotic (e.g., erythromycin) and integration of the plasmid confirmed by PCR. Because the plasmid is not replicative in *C. acnes* receiver cell, *C. acnes* clones able to grow in the presence of the antibiotic (e.g., erythromycin), have undergone a single homologous recombination event, which has led to the integration of the full plasmid. To select for final recombinant loci, cells are typically exposed to the counter-selection (e.g., sucrose) and the antibiotic (e.g., erythromycin), which leads to cell death due to sacB activity (the full plasmid remains integrated in the chromosome). Survivors are typically screened by PCR for successful final recombinant loci presence Replicative CRISPR-Cas System Selection Vector Methods The invention encompasses replicative vectors comprising an origin of replication for *C. acnes.*

In one embodiment, a replicative CRISPR-Cas selection vector method uses vector with at least:

- a phage packaging signal (cos) originating from *C. acnes* phages, as defined above;
- a selection marker for *C. acnes*, as defined above;
- an origin of replication for *C. acnes;*
- a recombination template with two homology arms; and
- a CRISPR-Cas system for expression in *C. acnes.*

In one embodiment, a replicative CRISPR-Cas selection vector method uses a vector with at least:

- a selection marker for *E. coli*, as defined above;
- an origin of replication for *E. coli;*
- a selection marker for *C. acnes*, as defined above;
- a recombination template with two homology arms;
- an origin of replication for *C. acnes*; and
- a CRISPR-Cas system that is expressed in *C. acnes.*

Thus, such vectors are able to replicate in *E. coli* and are able to replicate in *C. acnes*. They also carry a CRISPR-Cas system able to induce double stranded breaks at the wild-type loci where recombination is wanted, leading to death of *C. acnes* receiver cell.

Figure 5:
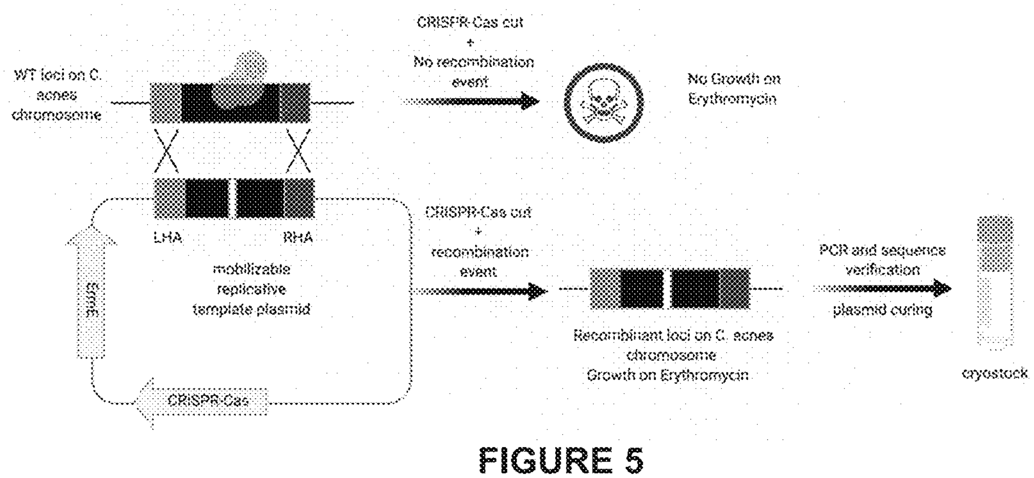
FIG. 5 depicts a method for *C. acnes* genome engineering using replicative CRISPR-Cas system selection vector carrying recombination template. A replicative CRISPR-Cas system selection vector containing a template for homologous DNA recombination with the chromosome is conjugated into *C. acnes*. The template contains two homology arms (LHA and RHA) leading to homologous recombination in *C. acnes* chromosome and removal of the target sequence of the CRISPR-Cas system. Thus only recombinants *C. acnes* are able to grow in the presence of erythromycin when selected for the presence of the vector expressing CRISPR-Cas system.

In one embodiment, the method comprises the use of a *C. acnes* producer cell, for example strain ATCC 6919, carrying a replicative CRISPR-Cas system selection vector containing a template for homologous DNA recombination inside the chromosome and a phage packaging signal (cos) originating from *C. acnes* phages. In one embodiment, the template contains two homologous regions (FIG. 5), leading to homologous recombination. The producer cell preferably does not contain the wild-type loci targeted by the CRISPR-Cas system. The *C. acnes* producer cell is typically infected by a *C. acnes* phage leading to production of phage-derived particles carrying the DNA vector. Phage-derived particles are typically put in contact with *C. acnes* receiver cell. After transduction into *C. acnes* receiver cell, cells that have recombined with the DNA template vector are not targeted by the CRISPR-Cas system because, for example, they do not have the associated PAM sequence anymore. Plating on antibiotic-containing media, e.g., erythromycin plates, typically ensures that the cells that survive have been transduced and still carry the DNA vector (e.g. plasmid) expressing the CRISPR-Cas system. Single colonies are typically streaked on antibiotic-containing media, e.g., erythromycin plates, and recombinant loci are typically confirmed by PCR and sequencing.

In one embodiment, a step of plasmid curing is performed to eliminate the plasmid.

In one embodiment, the *C. acnes* producer cell contains the DNA target of the CRISPR-Cas system but the CRISPR-Cas system is not expressed in the *C. acnes* producer cell but is expressed in *C. acnes* receiver cell. More preferably the CRISPR-Cas system is repressed in the *C. acnes* producer cell but not in *C. acnes* receiver cell.

Such methods can be used for scarless editing such as substitution, deletion or insertion because there is no need to introduce a selection marker to select for recombinants, the selection being done by CRISPR-Cas killing.

Self-Targeted Replicative Vector Methods

In one embodiment, the invention encompasses self-targeted replicative vector methods. In one embodiment, the invention encompasses the use of a CRISPR-Cas system to program cutting of the DNA vector (e.g. plasmid) in one or several target sequences, leading to linearization of the recombination template that have been shown to increase recombination efficiency[9]. To be able to clone a self-targeting vector, an inducible CRISPR-Cas system can be used, for example, using an inducible promoter upstream of the gene encoding the Cas nuclease. By combining this inducible promoter with a riboswitch, even tighter inhibition of CRISPR-Cas system expression can be assured. Another strategy to generate self-targeting CRISPR-Cas system relies on promoters that are repressed in the *C. acnes* producer cell and not in *C. acnes* receiver cell. In this way, the CRISPR-Cas system will only be active once transduced in a *C. acnes* receiver cell.

Figure 6A:
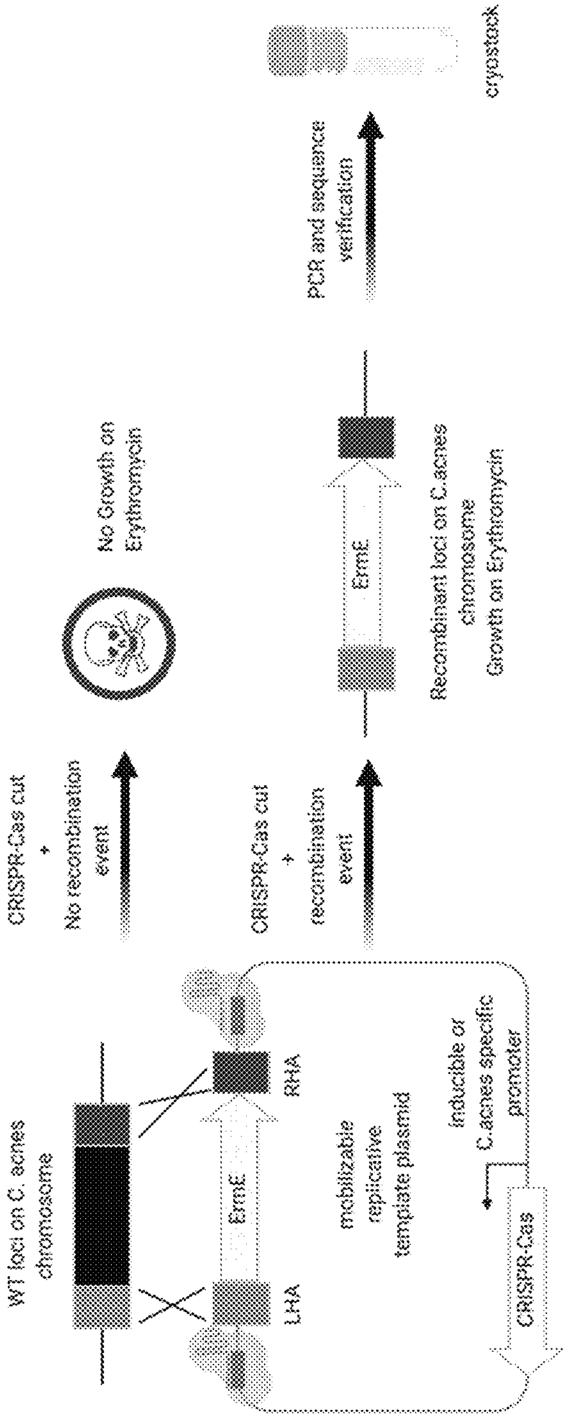
FIGS. 6A and 6B depict a method for *C. acnes* genome engineering using self-targeted replicative vector carrying CRISPR-Cas system and recombination template.
Figure 6B:
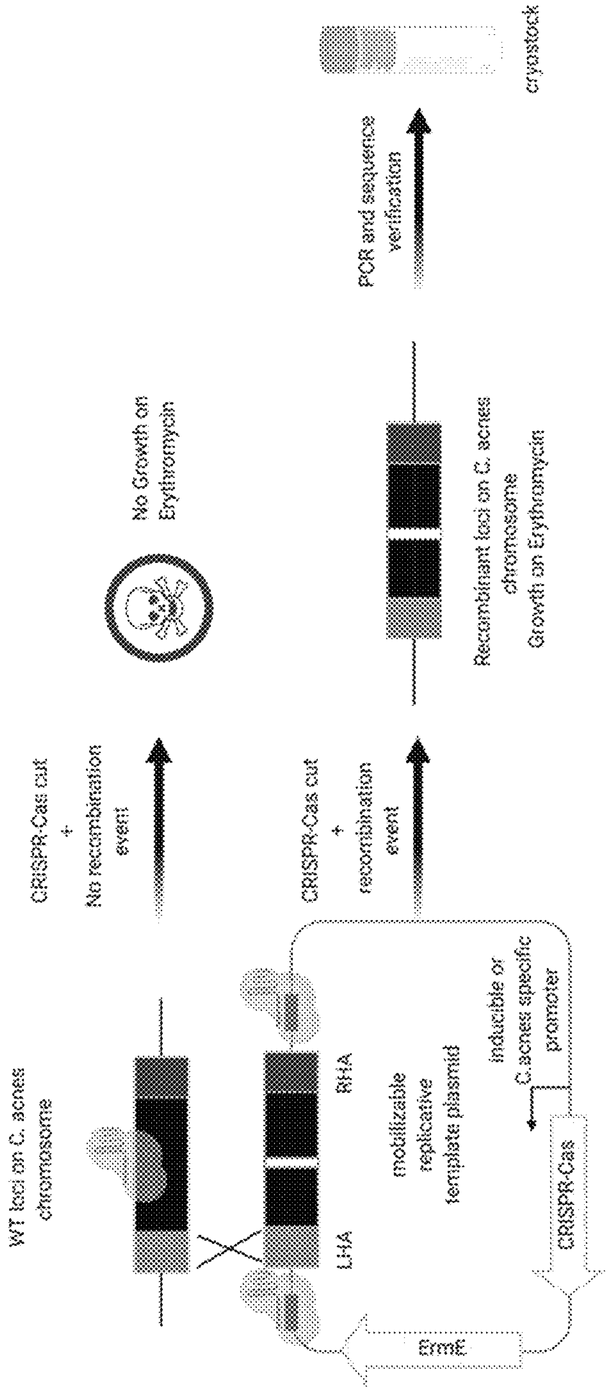
Figure 7:
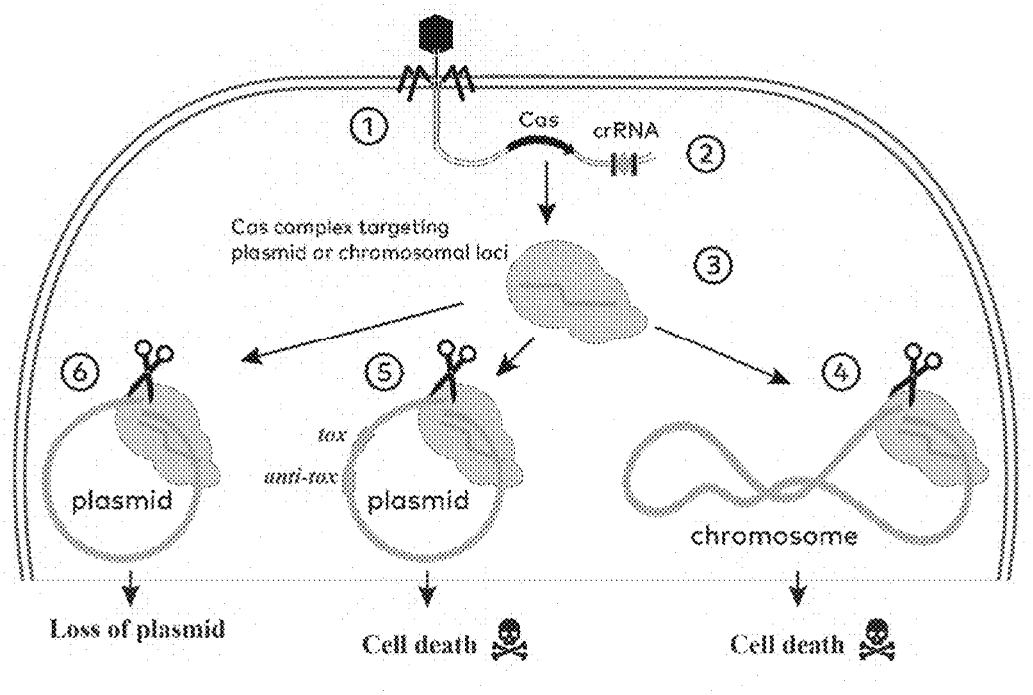
FIG. 7 depicts a method for sequence specific killing or plasmid curing using phage-derived particles. *C. acnes* phage-derived particles bind a *C. acnes* cell (1) allowing injection of a DNA vector encoding a CRISPR-Cas system (2). The CRISPR-Cas system is expressed (3) and cuts the chromosome (4) and/or a plasmid (5 and 6) in a sequence specific manner. Cutting of the chromosome leads to cell death (4) whereas cutting of the plasmid leads to either the plasmid loss (6) or cell death if the plasmid encodes a toxin-antitoxin system (5).

Using such strategy, for example, a gene replacement can be performed using an antibiotic marker flanked by homology arms (FIG. 6A) or by performing scarless recombination using the CRISPR-Cas system ability to kill the bacteria when targeting *C. acnes* chromosome (FIG. 6B).

After introduction and selection of the DNA vector (e.g. plasmid), a homologous event typically takes place leading to removal of a PAM sequence.

Additionally, the DNA vector (e.g. plasmid) carrying the template DNA for homologous recombination typically allows expression of genes increasing recombination rate.

In one embodiment, the DNA vector comprises a template for homologous recombination and a CRISPR-Cas system targeting the DNA vector itself outside of the template region wherein the RNA guide (crRNA or sgRNA) from the CRISPR-Cas system is not perfectly matching the DNA target.

In one embodiment, the invention encompasses replicative vector methods using a vector with at least:

a phage packaging signal (cos) originating from *C. acnes* phages, as defined above;

a selection marker for *C. acnes*, as defined above;

an origin of replication for *C. acnes*, as defined above; and a CRISPR-Cas system for expression in *C. acnes*.

In one embodiment, vectors carry a CRISPR-Cas system able to induce double stranded break leading to death of most *C. acnes* receiver cells except *C. acnes* receiver cells that by spontaneous mutation or recombination do not carry anymore the CRISPR-Cas system target sequence.

Expression of Proteins by Engineered *C. acnes* Strains

The invention encompasses the expression of proteins by engineered *C. acnes* strains. By incorporating an expression cassette into the DNA vector, the protein can be expressed by the transduced *C. acnes*. The promoter within the expression cassette can be inducible or constitutive, allowing inducible or constitutive expression of proteins by engineered *C. acnes* strains. Expression of several proteins can be performed as single transcriptional unit (operon) or as separated transcriptional units. In a particular embodiment, said protein is an antigen, such as a tumor antigen, a viral antigen, a bacterial antigen, a fungal antigen, a self-antigen, an allergen or a graft-specific antigen, as defined below.

*C. acnes* Phage

The invention encompasses the *C. acnes* phage and related engineered phages, methods for producing these phages, and methods for using these phages to transduce *C. acnes*.

Phage-Derived Particles in *C. acnes*

The invention encompasses phage-derived particles comprising any DNA vector of the invention and the methods for the production of these phage-derived particles.

In one embodiment a *C. acnes* strain carrying any DNA vector of the invention is contacted with a *C. acnes* phage leading to introduction of the phage genome into the *C. acnes* strain and the expression of the phage proteins necessary for the assembly of a phage capsid and the packaging of the DNA vector inside the phage capsid.

In one embodiment a *C. acnes* strain carrying any DNA vector comprising: a selection marker for *C. acnes* as defined above, a *C. acnes* phage packaging signal (cos site) as defined above, and an origin of replication for *C. acnes* as defined above, is contacted with a *C. acnes* phage leading to introduction of the phage genome into the *C. acnes* strain and the expression of the phage proteins necessary for the assembly of a phage capsid and the packaging of the DNA vector inside the phage capsid.

In one embodiment, the phage genome is a wild type phage genome.

In one embodiment, the *C. acnes* phage is PAC7 (typically of sequence SEQ ID NO: 68).

In one embodiment, the phage genome is an engineered phage genome.

The phage-derived particles can be purified by methods known in the art. The invention encompasses purified phage-derived particles comprising a DNA vector of the invention. In one embodiment, the purified phage-derived particles are in an isolated composition or pharmaceutical composition. The composition can comprise at least $10^4$, $10^5$, $10^6$, $10^7$, $10^8$, $10^9$, $10^{10}$, $10^{11}$, $10^{12}$, $10^{13}$, $10^{14}$, or more purified phage-derived particles.

Sequence Specific Killing of *C. acnes* by Phage-Derived Particles

In one embodiment, the invention comprises specific killing of *C. acnes* by phage-derived particles carrying CRISPR-Cas system.

Phage-derived particles carrying a vector (e.g. plasmid) encoding CRISPR-Cas system have been recently used to perform in situ sequence specific killing of bacteria[10,11]. The inventors have developed a method for the production of such phage-derived particles to target *C. acnes*, which is encompassed by the invention.

In said method, a *C. acnes* producer strain comprising a DNA vector of the invention is contacted with a *C. acnes* phage, such as PAC7 (typically of sequence SEQ ID NO: 68) to produce a high titer phage suspension.

In one embodiment, the *C. acnes* comprises a DNA vector comprising:

a selection marker for *C. acnes*, as defined above, a *C. acnes* phage packaging signal (cos site), as defined above, an origin of replication for *C. acnes*, as defined above, and a CRISPR-Cas system targeting a specific *C. acnes* receiver cell chromosomal locus (pTarget).

High titer *C. acnes* phage suspensions are typically added to *C. acnes*. The suspensions typically contain a mix of wild-type phages and phage-derived particles carrying the plasmid. Contacting of *C. acnes* cells carrying the locus targeted by the pTarget CRISPR-Cas system is typically performed with phage-derived particles containing pTarget. This can be performed in vivo or in vitro. Sequence specific killing is typically observed for lysate containing phage-derived particles comprising pTarget.

In one embodiment, the phage-derived particles comprising the pTarget vector (e.g. plasmid) are not mixed with phage and allow sequence specific killing of cells carrying the DNA targeted by the CRISPR-Cas system.

*C. acnes* Plasmid Curing

Naturally occurring *C. acnes* plasmids have been described and some of them have been associated with pro-inflammatory phenotypes[15,23] and acne vulgaris[16-18]. Being able to cure such plasmids is of interest to study their effect, notably, their pro-inflammatory role in acne vulgaris. The inventors have developed a method to cure *C. acnes* plasmid.

In a first step, a *C. acnes* producer cell carrying the DNA vector comprising:

a *C. acnes* phage packaging signal as defined above, optionally a selection marker for *C. acnes*, as defined above, an origin of replication that allows replication only in *C. acnes* producer cell, as defined above, and a transgene, such as a CRISPR-Cas system targeting a genetic sequence of an endogenous plasmid to be cured in a target *C. acnes* receiver cell, the sequence being preferably in a conserved region such as the origin of replication or in loci associated with acne vulgaris, is infected by a *C. acnes* phage leading to production of phage-derived particles carrying the DNA vector.

Contacting *C. acnes* phage-derived particles with *C. acnes* receiver cell carrying an endogenous plasmid to be cured, such as pIMPLE-HL096PA1 is performed. This can be performed in vivo or in vitro.

In some embodiments, *C. acnes* transductants can be selected on the appropriate antibiotic. Single colonies are typically streaked on plates with media containing the antibiotic and the presence of the plasmid is typically screened by PCR. Single colonies where no positive PCR for the plasmid pIMPLE-HL096PA1 is obtained, are then cured from the vector (e.g. plasmid) comprising the CRISPR-Cas system, and typically cryostocked.

Treatment Methods

The invention encompasses methods to treat a *C. acnes* related disorder or disease.

The invention encompasses the use of engineered *C. acnes* strains for the treatment and/or prevention of a wide range of skin diseases and disorders.

The invention encompasses methods to treat a decrease in sebum production, follicular hyperkeratinization, colonization of skin bacteria, and inflammation using engineered *C. acnes* strains as defined above.

The invention encompasses the use of engineered *C. acnes* as defined above in cosmetics and other compositions.

In one embodiment, the invention encompasses expression of therapeutic molecules by engineered *C. acnes*.

In one embodiment, the invention encompasses expression of non-therapeutic molecules by engineered *C. acnes*.

*Cutibacterium acnes* is one of the most prevalent and abundant bacteria on human skin, where it can be found both on the skin surface (stratum corneum) and in the hair follicle[12]. Inside the hair follicle, it is in direct contact with a large diversity of living cells such as keratinocytes, stem cells, sebaceous cells and immune cells. This is not the case on the stratum corneum, where it is mostly in contact with the dead corneocyte[13]. Thus, it appears interesting to use *C. acnes* as a bacterial chassis for the production and delivery of therapeutic molecules in situ inside and outside the hair follicle.

Phage-derived particles and/or bacteria producing them can be delivered to the skin by dermal or other appropriate administration method to a subject.

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, or non-mammals such as poultry, that are in need of treatment.

The human subject according to the invention may be a human at the prenatal stage, a new-born, a child, an infant, an adolescent or an adult at any age.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with an engineered *C. acnes* bacteria according to the invention, is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the infection, disorder and/or disease persists.

The form of the pharmaceutical or veterinary compositions, the route of administration and the dose of administration of engineered *C. acnes* bacteria according to the invention, can be adjusted by the man skilled in the art according to the type and severity of the disease, disorder and/or infection (e.g. depending on the bacteria species involved in the disease, disorder and/or infection and its localization in the patient's or subject's body), and to the patient or subject, in particular its age, weight, sex, and general physical condition.

Particularly, the amount of engineered *C. acnes* bacteria according to the invention, to be administered has to be determined by standard procedure well known by those of ordinary skills in the art. Physiological data of the patient or subject (e.g. age, size, and weight) and the routes of administration have to be taken into account to determine the appropriate dosage, so as a therapeutically effective amount will be administered to the patient or subject.

Preferably, total amount of an engineered *C. acnes* bacteria according to the invention, for each administration is comprised between $10^4$ and $10^{15}$ bacteria.

The invention encompasses plasmids for the expression of toxins such as nuclease, more preferably CRISPR-Cas systems to kill transduced *C. acnes* population.

The invention encompasses plasmids for the expression of CRISPR-Cas systems where the CRISPR-Cas systems is targeted towards sequences present only in specific strains and not present in others allowing strain specific killing among the *C. acnes* population.

The invention encompasses modifications of *C. acnes* chromosome or *C. acnes* endogenous plasmid. Modifications such as deletion, substitution and/or insertion leading to alteration in the *C. acnes*-host relation are for example contemplated.

The invention encompasses vectors, e.g. plasmids, for the expression of therapeutic molecules containing one or several genes involved in the production of the therapeutic molecule.

In the case where the therapeutic molecule is not freely diffusing from *C. acnes* cells, such as in the case of a therapeutic protein, a fusion with a signal peptide allowing secretion or export on the cell membrane or wall of *C. acnes* cells is preferably encoded on the vector, e.g. plasmid. Examples of secretion systems or signal peptides include: TAT, SEC and type VII/WXG100 secretion systems. More specifically, the signal peptide can be extracted from proteins selected from the group consisting of the proteins PPA0532 (typically referenced as Q6AAD1 in the UniprotKB database as of Nov. 4, 2020); PPA0533 (typically referenced as Q6AAD0 in the UniprotKB database as of Nov. 4, 2020); PPA0534 (typically referenced as Q6AAC9 in the UniprotKB database as of Nov. 4, 2020); PPA0598 (typically referenced as Q6AA63 in the UniprotKB database as of Nov. 4, 2020); PPA0644 (typically referenced as Q6AA16 in the UniprotKB database as of Nov. 4, 2020); PPA0687 (typically referenced as Q6A9X2 in the UniprotKB database as of Nov. 4, 2020); PPA0721 (typically referenced as Q6A9T8 in the UniprotKB database as of Nov. 4, 2020); PPA0816 (typically referenced as Q6A9J4 in the UniprotKB database as of Nov. 4, 2020); PPA1310 (typically referenced as Q6A856 in the UniprotKB database as of Nov. 4, 2020); PPA1498 (typically referenced as Q6A7MO in the UniprotKB database as of Nov. 4, 2020); PPA1662 (typically referenced as Q6A771 in the UniprotKB database as of Nov. 4, 2020); PPA1715 (typically referenced as Q6A720 in the UniprotKB database as of Nov. 4, 2020); PPA1939 (typically referenced as Q6A6F6 in the UniprotKB database as of Nov. 4, 2020); PPA2097 (typically referenced as Q6A608 in the UniprotKB database as of Nov. 4, 2020); PPA2105 (typically referenced as Q6A601 in the UniprotKB database as of Nov. 4, 2020); PPA2106 (typically referenced as Q6A600 in the UniprotKB database as of Nov. 4, 2020); PPA2142 (typically referenced as Q6A5W4 in the UniprotKB database as of Nov. 4, 2020); PPA2164 (typically referenced as Q6A5U3 in the UniprotKB database as of Nov. 4, 2020); PPA2175 (typically referenced as Q6A5T2 in the UniprotKB database as of Nov. 4, 2020), PPA2152 (typically referenced as Q6A5V4 in the UniprotKB database as of Nov. 4, 2020); PPA1340 (typically referenced as Q6A826 in the UniprotKB database as of Nov. 4, 2020) and PPA2239 (typically referenced as Q6A5MO in the UniprotKB database as of Nov. 4, 2020).

In the case where secretion is not wanted or functional, a lysing module can be added to the vector, e.g. plasmid, in order to lyse the cell and release the therapeutic molecule.

In a particular embodiment, said therapeutic molecule may be displayed on the cell membrane or wall of *C. acnes* cells. To be displayed, a protein of interest typically requires a N-terminal secretion signal peptide such as the ones described above as well as a C-terminal LPXTG motif allowing the class F sortase from *C. acnes* (Girolamo, S. D. et al., *Biochem J* 476, 665-682 (2019)) to covalently link the protein of interest to the cell wall. Additionally a PT rich region might be integrated upstream of the LPXTG motif. Alternatively a more classical cell wall sorting sequence (CWSS) combining a LPxTG motif followed by hydrophobic amino acids and a positively charged C-terminus can be used.

In order to control expression of the therapeutic molecule, one or several of the genes, as an operon or as single isolated genes, can be put under the control of an inducible system, such as an inducible promoter, a riboswitch, a RNA-based induction method or a combination thereof. Several promoters of several transcriptional strengths might be tested and combined with different RBS strengths to optimize for in situ production of the therapeutic molecule. An RBS library approach might be used to select the best RBS variant for in vitro or in situ expression.

Examples of therapeutic molecules include but are not limited to antibodies, antibody-based drugs, Fc fusion proteins, anticoagulants, blood factors, bone morphogenetic proteins, engineered protein scaffolds, enzymes, growth factors, hormones, interferons, interleukins, and thrombolytics. Other examples include those that bind non-covalently to target (e.g., monoclonal antibodies), those that affect covalent bonds (e.g., enzymes), and those that exert activity without specific interactions (e.g., serum albumin).

Also contemplated herein are therapeutic molecules (e.g., recombinant therapeutic proteins) used to treat, for example, cancers, immune disorders, infections and/or other diseases. Engineered proteins, including bispecific mAbs and multispecific fusion proteins, and proteins with optimized pharmacokinetics are also contemplated by the present disclosure.

In some embodiments, the therapeutic proteins is Etanercept, Bevacizumab, Rituximab, Adalimumab, Infliximab, Trastuzumab, Insulin glargine, Epoetin alfa, Pegfilgrastim, Ranibizumab, Darbepoetin alfa, Interferon beta-Ia, Interferon beta-Ia. Insulin aspart, Rhu insulin, Octocog alfa, Insulin lispro, Cetuximab, Peginterferon alfa-2a, Interferon beta-Ib, Eptacog alfa, Insulin aspart, OnabotulinumtoxinA, Epoetin beta, Rec antihemophilic factor, Filgrastin, Insulin detemir, Natalizumab, Insulin (humulin) or Palivizumab.

Examples of antibodies, antibody fragments, and/or Fc fusion proteins that may be expressed in the context of the present disclosure include, without limitation, Abagovomab, Abciximab, Actoxumab, Adalimumab, Adecatumumab, Afelimomab, Afutuzumab, Alacizumab pegol, ALD, Alemtuzumab, Alirocumab, Altumomab pentetate, Amatuximab, Anatumomab mafenatox, Anifrolumab, Anrukinzumab, Apolizumab, Arcitumomab, Aselizumab, Atinumab, Atlizumab (or tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, Cedelizumab, Certolizumab pegol, Cetuximab, Citatuzumab bogatox, Cixutumumab, Clazakizumab, Clenoliximab, Clivatuzumab tetraxetan, Conatumumab, Concizumab, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, Imciromab, lmgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lambrolizumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN, Ticilimumab (or tremelimumab), Tildrakizumab, Tigatuzumab, TNX-, Tocilizumab (or atlizumab), Toralizumab, Tositumomab, Tovetumab, Tralokinumab, Trastuzumab, TRBS, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

Other examples of Fc fusion proteins that may be expressed in the context of the present disclosure include, without limitation, Etanercept, Alefacept, Abatacept, Rilonacept, Romiplostim, Belatacept and Aflibercept.

Examples of anticoagulants and/or blood factors that may be expressed in the context of the present disclosure include, without limitation, Protein C, Protein S, and antithrombin, Factors I-VIII, prothrombinase, prothrombin, thrombin von Willebrand Factor (vWF), fibrinogen, fibrin and fibrinopeptides.

Examples of bone morphogenetic proteins (BMPs) that may be expressed in the context of the present disclosure include, without limitation, BMP1-BMP7, BMP8a, BMP8b, BMP 10, and BMP15.

Examples of enzymes that may be expressed in the context of the present disclosure include, without limitation, any of the enzymes assigned an Enzyme Commission Number (EC) number (e.g., EC1-EC6) by the International Union of Biochemistry and Molecular Biology (IUBMB) (Webb, Edwin C. Enzyme nomenclature 1992: recommendations of the Nomenclature Committee of the International Union of Biochemistry and Molecular Biology on the nomenclature and classification of enzymes. San Diego: Published for the International Union of Biochemistry and Molecular Biology by Academic Press. ISBN 0-12-227164-5 (1992), incorporated by reference herein). Other examples include: styrene monooxygenase (StyAB), toluene dioxygenase (TODC1C2AB), luciferase and lactase. In some embodiments, the enzyme is toluene dioxygenase. In some embodiments, the enzyme is styrene monoxygenase.

Examples of growth factors that may be expressed in the context of the present disclosure include, without limitation, Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-a), Transforming growth factor beta (TGF-P), Tumor necrosis factor-alpha (TNF-), Vascular endothelial growth factor (VEGF), placental growth factor (P1GF), Foetal Bovine Somatotrophin (FBS) and IL-1-IL7.

Examples of peptide hormones that may be expressed in the context of the present disclosure include, without limitation, Amylin (or Islet Amyloid Polypeptide), Antimullerian hormone (or Miillerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Brain natriuretic peptide, Calcitonin, Cholecystokinin, Corticotropin-releasing hormone, Enkephalin, Endothelin, Erythropoietin, Follicle-stimulating hormone, Galanin, Gastrin, Ghrelin, Glucagon, Gonadotropin-releasing hormone, Growth hormone-releasing hormone, Human chorionic gonadotropin, Human placental lactogen, Growth hormone, Inhibin, Insulin, Insulin-like growth factor (or somatomedin), Leptin, Lipotropin, Luteinizing hormone, Melanocyte stimulating hormone, Motilin, Orexin, Oxytocin, Pancreatic polypeptide, Parathyroid hormone, Prolactin, Prolactin releasing hormone, Relaxin, Renin, Secretin, Somatostatin, Thrombopoietin, Thyroid-stimulating hormone (or thyrotropin), and Thyrotropin-releasing hormone.

Examples of interferons (IFNs) that may be expressed in the context of the present disclosure include, without limitation, IFN-α, IFN-β, IFN-ω and IFN-γ.

Examples of interleukins that may be expressed in the context of the present disclosure include, without limitation, interleukin 1-17. In some embodiments, the interleukin is Interleukin-4, Interleukin-6, Interleukin-10, Interleukin-11 or Interleukin-13.

Other examples of therapeutic proteins that may be expressed in the context of the invention present disclosure include, without limitation, Insulin (blood glucose regulator), Pramlintide acetate (glucose control), Growth hormone GH (growth failure), Pegvisoman (growth hormone receptor antagonist), Mecasermin (IGFI, growth failure), Factor VIII (coagulation factor), Factor IX (coagulation factor, Protein C concentrate (anti-coagulation), al-proteinase inhibitor (anti-trypsin inhibitor), Erythropoietin (stimulates erythropoiesis), Filgrastim (granulocyte colony-stimulating factor, G-CSF; stimulates neutrophil proliferation), Sargramostim[36, 37] (granulocytemacrophage colony-stimulating factor, GM-CSF), Oprelvekin (interleukin II, IL11), Human follicle-stimulating hormone (FSH), Human chorionic gonadotropin (HCG), Lutropin-a (human luteinizing hormone), Interleukin 2 (IL2), Interleukin-1 Receptor Agonist, Denileukin diftitox (fusion of IL2 and Diphtheria toxin), Interferon alfacon 1 (consensus interferon), Interferon-2a (IFNa2a), Interferon-2b (IFNa2b), Interferon-n3 (IFNan3), Interferon-pia (rIFN-β), Interferon-β Ib (rIFN-β), Interferon-ylb (IFNy, Salmon calcitonin (32-amino acid linear polypeptide hormone), Teriparatide (part of human parathyroid hormone 1-34 residues), Exenatide (Incretin mimetic with actions similar to glucagon-like peptide 1), Octreotide (octapeptide that mimics natural somatostatin), Dibotermin-a (recombinant human bone morphogenic protein 2), Recombinant human bone morphogenic protein 7, Histrelin acetate (gonadotropin-releasing hormone; GnRH), Palifermin (Keratinocyte growth factor, KGF), Becaplermin (platelet-derived growth factor, PDGF), Nesiritide (recombinant human B-type natriuretic peptide), Lepirudin (recombinant variant of hirudin, another variant is Bivalirudin), Anakinra (interleukin 1 (IL1) receptor antagonist), Enfuviritide (an HIV-1 gp41-derived peptide), p-Glucocerebrosidase (hydrolyzes to glucose and ceramide), Alglucosidase-a (degrades glycogen), Laronidase (digests glycosaminoglycans within lysosomes), Idursulfase (cleaves O-sulfate preventing GAGs accumulation), Galsulfase (cleave terminal sulphate from GAGs), Agalsidase-β (human a-galactosidase A, hydrolyzes glycosphingolipids), Lactase (digest lactose), Pancreatic enzymes (lipase, amylase, protease; digest food), Adenosine deaminase (metabolizes adenosine), Tissue plasminogen activator (tPA, serine protease involved in the breakdown of blood clots), Factor Vila (serine protease, causes blood to clot), Drotrecogin-a (serine protease, human activated protein C), Trypsin (serine protease, hydrolyzes proteins), Botulinum toxin type A (protease, inactivates SNAP-25 which is involved in synaptic vesicle fusion), Botulinum toxin type B (protease that inactivates SNAP-25 which is involved in synaptic vesicle fusion), Collagenase (endopeptidase, digest native collagen), Human deoxyribonuclease I (endonuclease, DNase I, cleaves DNA), Hyaluronidase (hydrolyzes hyaluronan), Papain (cysteine protease, hydrolyzes proteins), L-Asparaginase (catalyzes the conversion of L-asparagine to aspartic acid and ammonia), Rasburicase (urate oxidase, catalyzes the conversion of uric acid to allantoin), Streptokinase (Anistreplase is anisoylated plasminogen streptokinase activator complex (APS AC)), and Antithrombin III (serine protease inhibitor).

Other examples of therapeutic proteins that may be expressed in the context of the present disclosure include antigens, as defined below.

The invention further encompasses engineered *C. acnes* comprising vectors (e.g. plasmids) for the expression of antigens, such as a tumor antigen, a viral antigen, a bacterial antigen, a fungal antigen, a self-antigen, an allergen or a graft-specific antigen.

As used herein, an "antigen" refers to a molecule containing one or more epitopes (e.g., linear, conformational or both) that elicit an immunological response. The antigen may be of any type. In particular, it can be a protein, a polypeptide or a peptide, a carbohydrate, a lipid, a nucleic acid, such as DNA or RNA. In a particular embodiment, it is a protein, a polypeptide or a peptide. As intended herein, "protein" will be understood to encompass protein, polypeptide and peptide. Furthermore, for purposes of the present invention, an "antigen" encompasses a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

In a particular embodiment, said antigen induces the activation or enhancement of an immune response, in particular specific to said antigen. In an alternative embodiment, said antigen results in tolerization or suppression of an immune response, in particular towards said antigen.

In a particular embodiment, said antigen decreases the subject inflammatory response.

In a particular embodiment, said antigen is a tumor antigen.

By "tumor antigen" is meant herein an antigenic substance produced in tumor cells. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen.

Tumor antigens include, but are not limited to, (a) polypeptide-containing tumor antigens, including polypeptides (which can range, for example, from about 8 to about 20 amino acids in length, although lengths outside this range are also common), lipopolypeptides and glycoproteins, and (b) saccharide-containing tumor antigens, including polysaccharides, mucins, gangliosides, glycolipids and glycoproteins. Moreover, tumor antigens can be (a) full length molecules associated with cancer cells, (b) homologs and modified forms of the same, including molecules with deleted, added and/or substituted portions, and (c) fragments of the same. Tumor antigens include, for example, class I-restricted antigens recognized by CD8+ lymphocytes or class II-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CD 4 (associated with, e.g., melanoma), MUM 1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkin's lymphoma), BCR-abl (associated with, e.g., chronic myelogenous leukemia), triosephosphate isomerase, IA 0205, CDC-27, and LDLR-FUT, (c) overexpressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), SA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-I/Melan A, gplOO, MC1R, melanocyte-stimulating hormone receptor, tyrosinase, tyrosinase related protein-1/TRPI and tyrosinase related protein-2/TRP2 (associated with, e.g., melanoma), (e) prostate associated antigens such as PAP, PSA, PSMA, PSH-P1, PSM-P1, PSM-P2 (associated with e.g., prostate cancer), (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Lex (associated with, e.g., breast and colorectal cancer) as well as various mucins; glycoproteins may be coupled to a carrier protein (e.g., MUC-1 may be coupled to LH); (ii) lipopolypeptides (e.g., MUC-1 linked to a lipid moiety); (iii) polysaccharides (e.g., Globo H synthetic hexasaccharide), which may be coupled to a carrier protein (e.g., to KLH), (iv) gangliosides such as GM2, GM12, GD2, GD3 (associated with, e.g., brain, lung cancer, melanoma), which also may be coupled to carrier proteins (e.g., KLH).

Other tumor antigens include pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, pl85erbB2, pl80erbB-3, c-met, mn-23H I, TAG-72-4, CA 19-9, CA 72-4, CAM 17.1, NuMa, K-ras, p 16, TAGE, PSCA, CT7, 43-9F, 5T4, 791 Tgp72, beta-HCG, BCA225, BTAA, CA 125, CA 15-3 (CA 27.29BCAA), CA 195, CA 242, CA-50, CAM43, CD68KP1, CO-029, FGF-5, Ga733 (EpCAM), HTgp-175, M344, MA-50, MG7-Ag, MOV 18, NB/70K, NY-CO-1, RCAS1, SDCCAG16, TA-90 (Mac-2 binding protein\cyclophilin C-associated protein), TAAL6, TAG72, TLP, TPS, and the like.

In another embodiment, said antigen is a viral antigen.

By "viral antigen" is meant herein a protein encoded by a viral genome.

In certain embodiments, viral antigens preferably include epitopes which are exposed on the surface of the virus during at least one stage of its life cycle. Viral antigens are preferably conserved across multiple serotypes or isolates. Viral antigens suitable for use in the context of the invention include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (MI), membrane protein (M2), one or more of the transcriptase components (PB1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In other embodiments, the Paramyxovirus is Nipahvirus or Henipavirus and the antigens are selected from one or more of the following proteins: Fusion (F) protein, Glycoprotein (G) protein, Matrix (M) protein, Nucleocapsid (N) protein, Large (L) protein and Phosphoprotein (P).

Poxviridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M).

Picornavirus: Viral antigens include, but are not limited to, those derived from Picornaviruses, such as Enteroviruses, Rhinoviruses, Heparnavirus, Cardioviruses and Aphthoviruses. In certain embodiments, the antigens are derived from Enteroviruses, while in other embodiments the enterovirus is Poliovirus. In still other embodiments, the antigens are derived from Rhinoviruses.

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VP0, VP1, VP2, VP3 and VP4.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus. Rhinovirus: Viral antigens include, but are not limited to, those derived from rhinovirus. In certain embodiments, the rhinovirus antigens are selected from one or more of the following Capsid proteins: VP0, VP1, VP2, VP2 and VP4.

Heparnavirus: Viral antigens include, but are not limited to, those derived from a Heparnavirus, such as, by way of example only, Hepatitis A virus (HAV).

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3.

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E.

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe).

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the non-structural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity.

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS).

Caliciviridae; Viral antigens include, but are not limited to, those derived from Caliciviridae, such as Norwalk virus, and Norwalk-like Viruses, such as Hawaii Virus and Snow Mountain Virus.

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J, K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: HIVIIIb, HIVSF2, HIVLAV, HIVLAI, HIVMN, HIV-1CM235, HIV-1US4, HIV-1 SF162, HIV-1TV1, HIV-1MJ4. In certain embodiments, the antigens are derived from endogenous human retroviruses, including, but not limited to, HERV-K (“old” HERV-K and “new” HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins λ1, λ2, λ3, μ1, μ2, σ1, σ2, or σ3, or nonstructural proteins σNS, μNS, or σ1s. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Parvovirus, such as Parvovirus B19. In certain embodiments, the Parvovirus antigens are selected from VP-1, VP-2, VP-3, NS-1 and NS-2. In certain embodiments, the Parvovirus antigen is capsid protein VP1 or VP-2.

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus: Viral antigens include, but are not limited to, those derived from a Human Herpesvirus, such as, byway of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins (a), early proteins (β), and late proteins (γ). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, US8, US9, US10, US11, US12, US13, US14, US15, US16, US17, US18, US19, US20, US21, US29, US30 and US34A. CMV antigens may also be fusions of one or more CMV proteins, such as, by way of example only, pp65/IEI (Reap et al., Vaccine (2007) 25:7441-7449).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

In another embodiment, said antigen is a bacterial antigen.

Examples of bacterial antigens suitable for use in the context of the invention include, but are not limited to, proteins, polysaccharides and lipopolysaccharides, which are derived from a bacteria. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

*Neisseria meningitidis: N. meningitidis* antigens include, but are not limited to, proteins, saccharides (including a polysaccharide, or lipooligosaccharide), derived from *N. meningitidis* serogroup such as A, C, W135, Y, X or B. A useful combination of *N. meningitidis* protein antigens includes one, two or three of a NHBA, a fHbp, and/or a NadA immunogen.

*Streptococcus pneumoniae: Streptococcus pneumoniae* antigens include, but are not limited to, a saccharide (including a polysaccharide or an oligosaccharide) and/or protein from *Streptococcus pneumoniae*. In certain embodiments saccharide antigens are selected from one or more of the following pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F. A vaccine or immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. Nos. 6,699,703, 6,800,744, WO97/43303, WO97/37026, WO 02/079241, WO 02/34773, WO 00/06737, WO 00/06738, WO 00/58475, WO 2003/082183, WO 00/37105, WO 02/22167, WO 02/22168, WO 2003/104272, WO 02/08426, WO 01/12219, WO 99/53940, WO 01/81380, WO 2004/092209, WO 00/76540, WO 2007/116322, LeMieux et al., Infect. Imm. (2006) 74:2453-2456, Hoskins et al., J. Bacteriol. (2001) 183:5709-5717, Adamou et al., Infect. Immun. (2001) 69(2):949-958, Briles et al., J. Infect. Dis. (2000) 182:1694-1701, Talkington et al., Microb. Pathog. (1996) 21(1):17-22, Bethe et al., FEMS Microbiol. Lett. (2001) 205(1):99-104, Brown et al., Infect. Immun. (2001) 69:6702-6706, Whalen et al., FEMS Immunol. Med. Microbiol. (2005) 43:73-80, Jomaa et al., Vaccine (2006) 24(24):5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Spl28, SplOI, Spl30, Spl25, Spl33, pneumococcal pilus subunits.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (SfbI), Streptococcal heme-associated protein (Shp), and Streptolysin S (SagA).

*Moraxella catarrhalis: Moraxella* antigens include, but are not limited to, antigens identified in WO 02/18595 and WO 99/58562, outer membrane protein antigens (HMW-OMP), C-antigen, and/or LPS.

*Bordetella pertussis*: Pertussis antigens include, but are not limited to, pertussis toxoid (PT) and filamentous haemagglutinin (FHA) from *B. pertussis*, optionally also combination with pertactin and/or agglutinogens 2 and 3.

*Burkholderia: Burkholderia* antigens include, but are not limited to *Burkholderia mallei, Burkholderia pseudomallei* and *Burkholderia cepacia.*

*Staphylococcus aureus: S. aureus* antigens include, but are not limited to, a polysaccharide and/or protein from *S. aureus. S. aureus* polysaccharides include, but are not limited to, type 5 and type 8 capsular polysaccharides (CP5 and CP8) optionally conjugated to nontoxic recombinant *Pseudomonas aeruginosa* exotoxin A, such as StaphVAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, HlaH35L, CP5, CP8, PNAG, 336PS.

*Staphylococcus epidermis: S. epidermidis* antigens include, but are not limited to, slime-associated antigen (SAA).

*Clostridium tetani* (Tetanus): Tetanus antigens include, but are not limited to, tetanus toxoid (TT).

*Clostridium perfringens*: Antigens include, but are not limited to, Epsilon toxin from *Clostridium perfringens.*

*Clostridium botulinum* (Botulism): Botulism antigens include, but are not limited to, those derived from *C. botulinum.*

*Corynebacterium diphtheriae* (Diphtheria): Diphtheria antigens include, but are not limited to, diphtheria toxin, preferably detoxified, such as CRM 197. In certain embodiments, the diphtheria toxoids are used as carrier proteins.

*Haemophilus influenzae* B (Hib): Hib antigens include, but are not limited to, a Hib saccharide antigen. The Hib antigens may be conjugated.

*Pseudomonas aeruginosa: Pseudomonas* antigens include, but are not limited to, endotoxin A, Wzz protein, *P.*

*aeruginosa* LPS, LPS isolated from PAO1 (O5 serotype), and/or Outer Membrane Proteins, including Outer Membrane Proteins F (OprF).

*Brucella*: Bacterial antigens derived from *Brucella*, including but not limited to, *B. abortus, B. canis, B. melitensis, B. neotomae, B. ovis, B. suis* and *B. pinnipediae.*

*Francisella*: Bacterial antigens derived from *Francisella*, including but not limited to, *F. novicida, F. philomiragia* and *F. tularensis.*

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neiserria gonorrhoeae: Gonorrhoeae* antigens include, but are not limited to, Por (or porin) protein, such as PorB (see Zhu et al., Vaccine (2004) 22:660-669), a transferrin binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis: Chlamydia trachomatis* antigens include, but are not limited to, antigens derived from serotypes A, B, Ba and C (agents of trachoma, a cause of blindness), serotypes L1, L2 & L3 (associated with Lymphogranuloma venereum), and serotypes, D-K. In certain embodiments, *Chlamydia trachomatis* antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): *Ducreyi* antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori: H. pylori* antigens include, but are not limited to, CagA, VacA, NAP, HopX, HopY and/or urease antigen.

*Staphylococcus saprophyticus*: Antigens include, but are not limited to, the 160 kDa hemagglutinin of *S. saprophyticus* antigen.

*Yersinia enterocolitica*: Antigens include, but are not limited to, LPS.

*E. coli: E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405), orf1364, NodT-family outer-membrane-factor-lipoprotein efflux transporter (orf1767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768).

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes.*

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, O1 Inaba O-specific polysaccharides, *V. cholera* O139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein), VIsE Antigenic Variation Protein.

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to tetanus toxoid.

Other bacterial antigens used in the context of the invention include, but are not limited to, capsular antigens, polysaccharide antigens, or protein antigens of any of the above. In certain embodiments, the bacterial antigens used in the context of the invention are derived from gram-negative bacteria, while in other embodiments they are derived from gram-positive bacteria. In certain embodiments, the bacterial antigens used in the context of the invention are derived from aerobic bacteria, while in other embodiments they are derived from anaerobic bacteria.

In another embodiment, said antigen is a fungal antigen.

Examples of fungal antigens used in the context of the invention include, but are not limited to, those derived from one or more of the fungi set forth below.

Fungal antigens may be derived from Dermatophytes, including: *Epidermophyton floccosum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleinii, Trichophyton tonsurans, Trichophyton*

*verrucosum, T. verrucosum* var. *album*, var. *discoides*, var. *ochraceum, Trichophyton violaceum*, and/or *Trichophyton faviforme*.

Fungal antigens may also be derived from *Aspergillus fumigatus, Aspergillus flavus, Aspergillus niger, Aspergillus nidulans, Aspergillus terreus, Aspergillus sydowii, Aspergillus flavarus, Aspergillus glaucus, Blastoschizomyces capitatus, Candida albicans, Candida enolase, Candida tropicalis, Candida glabrata, Candida krusei, Candida parapsilosis, Candida stellatoidea, Candida krusei, Candida parakwsei, Candida lusitaniae, Candida pseudotropicalis, Candida guilliermondii, Cladosporium carrionii, Coccidioides immitis, Blastomyces dermatitidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythium insidiosum, Pityrosporum ovale, Saccharomyces cerevisiae, Saccharomyces boulardii, Saccharomyces pombe, Scedosporium apiospermum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monilinia* spp, *Rhizoctonia* spp, *Paecilomyces* spp, *Pithomyces* spp, and *Cladosporium* spp.

For example, the fungal antigen may elicit an immune response against a *Candida* fungus such as *C. albicans*.

In another embodiment, said antigen is a self-antigen.

In the context of the invention, the term "self-antigen" refers to an immunogenic antigen or epitope which is native to the subject and which may be involved in the pathogenesis of an autoimmune disease.

In some embodiments, the self-antigen is a central nervous system (CNS) antigen. In some embodiments, the self-antigen is a multiple sclerosis-associated antigen, a diabetes mellitus-associated antigen, a rheumatoid arthritis associated antigen, a myocarditis associated self-antigen, or a thyroiditis associated antigen.

Exemplary self-antigens are disclosed, for example, in US Patent Application Publication 2016/0022788, which is incorporated herein by reference in its entirety.

In some embodiments, the self-antigen is a multiple sclerosis-associated antigen. In some embodiments, the self-antigen is an antigenic peptide of or derived from myelin oligodendrocyte glycoprotein (MOG), myelin basic protein (MBP), myelin associated glycoprotein (MAG), alphaB-crystallin, S100beta, or proteolipid protein (PLP).

In some embodiments, the self-antigen is a diabetes mellitus-associated antigen. In some embodiments, the self-antigen is selected from insulin, chromogranin A, glutamic acid decarboxylase (GAD1; GAD67), glutamate decarboxylase 2 (GAD2; GAD65) and islet-specific glucose-6-phosphatase catalytic subunit-related protein and combinations thereof. Antigenic fragments and antigenic derivatives of these antigens are also contemplated. In some embodiments, the antigen can be proinsulin.

In some embodiments, the self-antigen is a rheumatoid arthritis associated antigen. In some embodiments, the rheumatoid arthritis associated self-antigen can be the peptide (Q/R)(K/R)RAA. In some embodiments, the arthritis associated self-antigen can be type II collagen or a fragment thereof.

In some embodiments, the self-antigen is a myocarditis associated self-antigen. In some embodiments, the myocarditis associated self-antigen is myosin or an antigenic fragment or antigenic derivative. In some embodiments, the antigen can be a peptide contained in human myosin. In some embodiments, the antigen can be a peptide contained within a-myosin.

In some embodiments, the self-antigen is a thyroiditis associated antigen. In some embodiments, the self-antigen is selected from thyroid peroxidase (TPO), thyroglobulin, or Pendrin.

In another embodiment, said antigen is an allergen.

An "allergen" is defined as a substance, usually a protein, which elicits the production of IgE antibodies in predisposed individuals. Similar definitions are presented in the following references: Clin. Exp. Allergy, No. 26, pp. 494-516 (1996); Mol. Biol. of Allergy and Immunology, ed. R. Bush, Immunology and Allergy Clinics of North American Series (August 1996). In a particular embodiment, the antigen is a protein allergen, i.e. any amino acid chain likely to trigger an allergic response, including short peptides of about 6 to 20 amino acids, polypeptides, or full proteins.

Non limitative examples of allergens include pollen allergens (such as tree-, herb, weed-, and grass pollen allergens), insect allergens (such as inhalant, saliva and venom allergens, e.g., cockroach and midges allergens, hymenoptera venom allergens), mite allergens, animal hair and dandruff allergens (from e.g. dog, cat, horse, rat, mouse etc.), and food allergens.

For instance, the protein allergen may be selected from the group consisting of a protein allergen of the genus *Dermatophagoides*; a protein allergen of the genus *Felis*; a protein allergen of the genus *Ambrosia*; a protein allergen of the genus *Lolium*; a protein allergen of the genus *Cryptomeria*; a protein allergen of the genus *Alternaria*; a protein allergen of the genus *Alder*; a protein allergen of the genus *Betula*; a protein allergen of the genus of *Blomia*; a protein allergen of the genus *Quercus*; a protein allergen of the genus *Olea*; a protein allergen of the genus *Artemisia*; a protein allergen of the genus *Plantago*; a protein allergen of the genus *Parietaria*; a protein allergen of the genus *Canine*; a protein allergen of the genus *Blattella*; a protein allergen of the genus *Apis*; a protein allergen of the genus *Cupressus*; a protein allergen of the genus *Thuya*; a protein allergen of the genus *Chamaecyparis*; a protein allergen of the genus *Periplaneta*; a protein allergen of the genus *Agropyron*; a protein allergen of the genus *Secale*; a protein allergen of the genus *Triticum*; a protein allergen of the genus *Cynorhodon*; a protein allergen of the genus *Juniperus*; a protein allergen of the genus *Dactylis*; a protein allergen of the genus *Festuca*; a protein allergen of the genus *Poa*; a protein allergen of the genus *Avena*; a protein allergen of the genus *Holcus*; a protein allergen of the genus *Anthoxanthum*; a protein allergen of the genus *Arrhenatherum*; a protein allergen of the genus *Agrostis*; a protein allergen of the genus *Phleum*; a protein allergen of the genus *Phalaris*; a protein allergen of the genus *Paspalum*; and a protein allergen of the genus Sorghum.

Examples of various known protein allergens derived from some of the above-identified genus include: *Betula* (*verrucosa*) Bet v I; Bet v II; *Blomia* Blo t I; Blo t III; Blo t V; Blo t XII; *Cynorhodon* Cyn d I; *Dermatophagoides* (*pteronyssinus* or *farinae*) Der p I; Der p II; Der p III; Der p VII; Der f I; Der f II; Der f III; Der f VII; *Felis* (*domesticus*) Fel d I; *Ambrosia* (*artemiisfolia*) Amb a 1.1; Amb a 1.2; Amb a 1.3; Amb a 1.4; Amb a 11; *Lollium* (*perenne*) Lol p I; Lot p II; Lol p III; Lot p IV; Lol p IX (Lol p V or Lol p Ib); *Cryptomeria* (*japonica*) Cry j I; Cry j II; *Canis* (*familiaris*) Can f I; Can f II; *Juniperus* (*sabinoides* or *virginiana*) Jun s I; Jun v I; *Juniperus* (*ashei*) Jun a I; Jun a II; *Dactylis* (*glomerata*) Dac g I; Dac g V; *Poa* (*pretensis*) *Poa* p I; Phl p I; Phl p V; Phl p VI and *Sorghum* (*halepensis*) Sor h I.

Food allergens may originate from milk and milk products, eggs, legumes (peanuts and soy), tree nuts, cereals (such as wheat), brassicaceae (such as mustard), crustaceans, fish, and mollusks. In particular, food allergens may be ovalbumin or gluten.

The invention also encompasses vaccine and/or immunogenic and/or immunotherapeutic compositions comprising a DNA vector, as defined above, comprising a nucleic acid encoding an antigen, such as a tumor antigen, a viral antigen, a bacterial antigen, a fungal antigen, a self-antigen, an allergen or a graft-specific antigen, as defined above, or an engineered *C. acnes* comprising said DNA vector; and optionally an adjuvant.

Any conventional or exploratory, synthetic or biological adjuvant for vaccination, including heat-labile enterotoxin (LT), cholera-toxin (CT), cholera toxin B subunit (CTB), polymerised liposomes, mutant toxins, probiotic bacteria, oligonucleotides, RNA, siRNA, DNA, lipids can be used.

The invention also encompasses methods to prevent and/or a treat cancer in a subject in need thereof, comprising administering to said subject a therapeutically or prophylactically efficient amount of a DNA vector comprising a nucleic acid encoding a tumor antigen, as defined above, or of an engineered *C. acnes* comprising said DNA vector. The invention also concerns a DNA vector comprising a nucleic acid encoding a tumor antigen, as defined above, or an engineered *C. acnes* comprising said DNA vector for use in a method to prevent and/or treat cancer in a subject.

As used herein, the term "cancer" means a type of hyperproliferative disease that includes a malignancy characterized by deregulated or uncontrolled cell growth. Cancers of virtually every tissue are known. Examples of cancer include, but are not limited to, carcinoma, lymphoma, blastema, sarcoma, and leukemia or lymphoid malignancies. More particular examples of such cancers are noted below and include squamous cell cancer (e.g., epithelial squamous cell cancer), lung cancer (including small-cell lung cancer, non-small cell lung cancer, adenocarcinoma of the lung and squamous carcinoma of the lung), cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer, uterine carcinoma, salivary gland carcinoma, kidney or renal cancer, prostate cancer, thyroid cancer, hepatic carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

The term "cancer," is encompassed within the scope of the broader term "abnormal cellular proliferation", which can also be referred to as "excessive cellular proliferation or "cellular proliferative disease". Examples of diseases associated abnormal cellular proliferation include metastatic tumors, malignant tumors, benign tumors, cancers, precancers, hyperplasias, warts, and polyps, as well as non-cancerous conditions such as benign melanomas, benign chondroma, benign prostatic hyperplasia, moles, dysplastic nevi, dysplasia, hyperplasias, and other cellular growths occurring within the epidermal layers. Classes of precancers include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (high grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma.

The invention also encompasses methods to prevent and/or treat a viral infection in a subject in need thereof, comprising administering to said subject a therapeutically or prophylactically efficient amount of a DNA vector comprising a nucleic acid encoding a viral antigen, as defined above, or of an engineered *C. acnes* comprising said DNA vector. The invention also concerns a DNA vector comprising a nucleic acid encoding a viral antigen, as defined above, or an engineered *C. acnes* comprising said DNA vector for use in a method to prevent and/or treat a viral infection in a subject.

In said embodiment, said antigen preferably induces the activation or enhancement of an immune response, in particular specific to said antigen.

Particular examples of viral infections include, but are not limited to, cytomegalovirus (CMV) pneumonia, enteritis and retinitis; Epstein-Barr virus (EBV) lymphoproliferative disease; chicken pox/shingles (caused by varicella zoster virus, VZV); HSV-1 and -2 mucositis; HSV-6 encephalitis, BK-virus hemorrhagic cystitis; viral influenza; pneumonia from respiratory syncytial virus (RSV); AIDS (caused by HIV); and hepatitis A, B or C. Additional examples of viral infections include infections caused by Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arenaviridae (hemorrhagic fever viruses); Reoviridae (e.g., reoviruses, orbiviruses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class I=internally transmitted; class 2=parenterally transmitted (i.e., Hepatitis C)); Norwalk and related viruses, and astroviruses.

The invention also encompasses methods to prevent and/or treat a bacterial infection in a subject in need thereof, comprising administering to said subject a therapeutically or prophylactically efficient amount of a DNA vector comprising a nucleic acid encoding a bacterial antigen, as defined above, or of an engineered *C. acnes* comprising said DNA vector. The invention also concerns a DNA vector comprising a nucleic acid encoding a bacterial antigen, as defined above, or an engineered *C. acnes* comprising said DNA vector for use in a method to prevent and/or treat a bacterial infection in a subject.

In said embodiment, said antigen preferably induces the activation or enhancement of an immune response, in particular specific to said antigen.

Examples of bacterial infections include, but are not limited to, infections caused by *Helicobacter pyloris, Borrelia burgdorferi, Legionella pneumophila, Mycobacteria* sp. (such as *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira*, and *Actinomyces israelii.*

The invention also encompasses methods to prevent and/or treat a fungal infection in a subject in need thereof, comprising administering to said subject a therapeutically or prophylactically efficient amount of a DNA vector comprising a nucleic acid encoding a fungal antigen, as defined above, or of an engineered *C. acnes* comprising said DNA vector. The invention also concerns a DNA vector comprising a nucleic acid encoding a fungal antigen, as defined above, or an engineered *C. acnes* comprising said DNA vector for use in a method to prevent and/or treat a fungal infection in a subject.

In said embodiment, said antigen preferably induces the activation or enhancement of an immune response, in particular specific to said antigen.

Examples of fungal infections include but are not limited to: aspergillosis; thrush (caused by *Candida albicans*); cryptococcosis (caused by *Cryptococcus*); and histoplasmosis. Thus, examples of fungal infections include, but are not limited to, infections caused by *Cryptococcus neoformans, Histoplasma capsulatum, Coccidioides immitis, Blastomyces dermatitidis, Chlamydia trachomatis*, or *Candida albicans.*

The invention also encompasses methods to prevent and/or treat an auto-immune disease in a subject in need thereof, comprising administering to said subject a therapeutically or prophylactically efficient amount of a DNA vector comprising a nucleic acid encoding a self-antigen, as defined above, or of an engineered *C. acnes* comprising said DNA vector. The invention also concerns a DNA vector comprising a nucleic acid encoding a self-antigen, as defined above, or an engineered *C. acnes* comprising said DNA vector for use in a method to prevent and/or treat an auto-immune disease in a subject.

In said embodiment, said antigen preferably results in tolerization or suppression of an immune response, in particular towards said antigen.

Autoimmune diseases include, but are not limited to, multiple sclerosis, rheumatoid arthritis, myasthenia gravis, psoriasis, systemic lupus erythematosus, autoimmune thyroiditis (Hashimoto's thyroiditis), Graves' disease, inflammatory bowel disease, autoimmune uveoretinitis, myocarditis, polymyositis, and certain types of diabetes, including Type 1 diabetes.

The invention also encompasses methods to prevent and/or treat allergy, such as asthma in a subject in need thereof, comprising administering to said subject a therapeutically or prophylactically efficient amount of a DNA vector comprising a nucleic acid encoding an allergen, as defined above, or of an engineered *C. acnes* comprising said DNA vector. The invention also concerns a DNA vector comprising a nucleic acid encoding an allergen, as defined above, or an engineered *C. acnes* comprising said DNA vector for use in a method to prevent and/or treat allergy, such as asthma in a subject.

In said embodiment, said antigen preferably results in tolerization or suppression of an immune response, in particular towards said antigen.

In the context of the disclosure allergy relates to asthma or to the allergies due to the above-defined allergens.

The invention also encompasses methods to prevent and/or treat graft rejection in a subject in need thereof, comprising administering to said subject a therapeutically or prophylactically efficient amount of a DNA vector comprising a nucleic acid encoding a graft-specific antigen, as defined above, or of an engineered *C. acnes* comprising said DNA vector. The invention also concerns a DNA vector comprising a nucleic acid encoding a graft-specific antigen, as defined above, or an engineered *C. acnes* comprising said DNA vector for use in a method to prevent and/or treat graft rejection in a subject.

In said embodiment, said antigen preferably results in tolerization or suppression of an immune response, in particular towards said antigen.

Unless defined otherwise, all technical and scientific terms used herein have the same meaning as commonly understood by one of ordinary skill in the art to which this invention belongs.

All publications mentioned herein are incorporated herein by reference. It is understood that the present disclosure supersedes any disclosure of an incorporated publication to the extent there is a contradiction.

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

Definitions

«Delivery Vehicle»

As used herein, the term «delivery vehicle» refers to any mean that allows the transfer of a payload into a bacterium.

There are several types of delivery vehicle encompassed by the present invention including, without limitation, bacteriophage scaffold, virus scaffold, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation).

Any combination of delivery vehicles is also encompassed by the present invention.

The delivery vehicle can refer to a bacteriophage derived scaffold and can be obtained from a natural, evolved or engineered capsid.

In some embodiment, the delivery vehicle is the payload as bacteria are naturally competent to take up a payload from the environment on their own.

«Conjugation»

Conjugation is a process by which a donor bacteria actively transfers DNA to a recipient bacteria. DNA transfer involves recognition of an origin of transfer (oriT) by a protein known as the relaxase which nicks and covalently binds to the oriT DNA. The relaxase and single stranded DNA are then typically injected into a recipient cell through a type IV secretion system. During conjugation of a plasmid or ICE (Integrative and Conjugative Elements), transfer of the relaxase is coupled with rolling circle replication of the plasmid or ICE. Once in the recipient, the relaxase will recircularize the transferred strand at the oriT. Smillie et al, Microbiology and Molecular Biology Rev, 2010, P. 434-452.

Examples of conjugative plasmids are F, R388, RP4, RK2, R6K. Plasmids of the following groups are frequently conjugative and carry a type IV secretion system: IncA, IncB/O (Ind O), IncC, IncD, IncE, IncFI, IncF2, IncG, IncHM, IncHI2, Inch, IncI2, IncJ, IncK, IncL/M, IncN, IncP, IncQI, IncQ2, IncR, IncS, IncT, IncU, IncV, IncW, IncXI, IncX2, IncY, IncZ, ColE1, ColE2, ColE3, p15A, pSC101, IncP-2, IncP-5, IncP-7, IncP-8, IncP-9, Ind, Inc4, Inc7, Inc8, Inc9, Incl 1, Inc13, Ind 4 or Ind 8.

List of type IV secretion systems can be found in public databases such as AtlasT4SS.

Conjugation is not limited to plasmids but can also occur from the chromosome of bacteria when an oriT is present. This can happen naturally through the recombination of conjugative plasmids in the chromosome or artificially by introducing an oriT at a position of interest in the chromosome. A particular class of conjugative elements are known as Integrative and Conjugative Elements (ICEs). These are not maintained in a circular plasmidic form but integrate in the host chromosome. Upon transfer, the ICE excises from the chromosome and is then transferred in a manner akin to a conjugative plasmid. Once in a recipient cell, the ICE integrates in the recipient's chromosome. Lists of ICE elements can be found in public databases such as ICEberg.

ICEs or plasmids which carry both an origin of transfer and the type IV secretion system genes are commonly referred to as mobile elements, while ICEs or plasmids that only carry the oriT can be referred to as mobilizable plasmids. Mobilizable elements can only be transferred from the donor cell to a recipient cell if a type IV secretion system is expressed in trans, either by another plasmid or from the chromosome of the host cell.

«Payload»

As used herein, the term «payload» refers to any nucleic acid sequence or amino acid sequence, or a combination of both (such as, without limitation, peptide nucleic acid or peptide-oligonucleotide conjugate) transferred into a bacterium with a delivery vehicle.

The term «payload» may also refer to a plasmid, a vector or a cargo.

The payload can be a phagemid or phasmid obtained from natural, evolved or engineered bacteriophage genome. The payload can also be composed only in part of phagemid or phasmid obtained from natural, evolved or engineered bacteriophage genome.

In some embodiment, the payload is the delivery vehicle as bacteria are naturally competent to take up a payload from the environment on their own.

«Nucleic Acid»

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphophoroamidite linkage and/or deoxyribonucleotides and ribonucleotides nucleic acids. Any combination of the above features of a nucleic acid is also encompassed by the present invention.

«Vector»

As used herein, the term "vector" refers to any construct of sequences that are capable of expression of a polypeptide in a given host cell. If a vector is used then the choice of vector is dependent upon the method that will be used to transform host bacteria as is well known to those skilled in the art. Vectors can include, without limitation, plasmid vectors and recombinant phage vectors, or any other vector known in that art suitable for delivering a polypeptide of the invention to target bacteria. The skilled artisan is well aware of the genetic elements that must be present on the vector in order to successfully transform, select and propagate host cells comprising any of the isolated nucleotides or nucleic acid sequences of the invention.

«Phagemid»

As used herein the term "phagemid" or "phasmid" are equivalent and refer to a recombinant DNA vector comprising at least one sequence of a bacteriophage genome. A phagemid of the disclosure comprises a phage packaging site and optionally an origin of replication (ori), in particular a bacterial and/or phage origin of replication. In one embodiment, the phagemid of the disclosure does not comprise a bacterial origin of replication and thus cannot replicate by itself once injected into a bacterium. Alternatively, the phagemid comprises a plasmid origin of replication, in particular a bacterial and/or phage origin of replication.

«Packaged Phagemid»

As used herein, the term "packaged phagemid" or "phage-derived particle" refers to a phagemid which is encapsidated in a bacteriophage scaffold, bacterial virus particle or capsid. Particularly, it refers to a bacteriophage scaffold, bacterial virus particle or capsid devoid of a bacteriophage genome. The packaged phagemid or phage-derived particle may be produced with a helper phage strategy, well known from the man skilled in the art. The helper phage comprises all the genes coding for the structural and functional proteins that are indispensable for the phagemid according to the invention to be encapsidated. The packaged phagemid or phage-derived particle may be produced with a satellite virus strategy, also known from the man skilled in the art. Satellite virus are subviral agent and are composed of nucleic acid that depends on the co-infection of a host cell with a helper virus for all the morphogenetic functions, whereas for all its episomal functions (integration and immunity, multicopy plasmid replication) the satellite is completely autonomous from the helper. In one embodiment, the satellite genes can encode proteins that promote capsid size reduction of the helper phage, as described for the P4 Sid protein that controls the P2 capsid size to fit its smaller genome.

«Peptide»

As used herein, the term "peptide" refers both to a short chain of at least 2 amino acids linked between each other and to a part of, a subset of, or a fragment of a protein which part, subset or fragment being not expressed independently from the rest of the protein. In some instances, a peptide is a protein. In some other instances, a peptide is not a protein and peptide only refers to a part, a subset or a fragment of a protein. Preferably, the peptide is from 4, 5, 6, 7, 8, 9, 10, 11, 12, 13, 14, 15 amino acids to 4, 5, 6, 7, 8, 9, 10, 11, 12, 13, 14, 15, 20, 25, 30, 40, 50, 100, 200 amino acids in size.

"Engineered"

As used herein, the term "engineered" means that the bacterial cells, phages, phage-derived particles, phagemids or vectors of the invention have been modified by molecular biology techniques. As will be understood by the skilled person, engineering of bacterial cells, phages, phage-derived particles, phagemids or vectors implies a deliberate action to introduce or modify a nucleic acid sequence and does not cover introduction or modification of a nucleic acid sequence through natural evolution of the bacterial cell, phage, phage-derived particle, phagemid or vector.

"Percent of Identity"

As used herein, the percent identity is calculated in relation to polymers (e.g., polynucleotide or polypeptide) whose sequences have been aligned. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4: 11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using a BLOSUM62 matrix, a BLOSUM30 matrix or a PAM250 matrix, and a gap weight of 16, 14, 12, 10, 8, 6, or 4 and a length weight of 1, 2, 3, 4, 5, or 6. In a specific embodiment the BLOSUM30 matrix is used with gap open penalty of 12 and gap extension penalty of 4.

CRISPR-Cas System

A CRISPR-Cas system refers to DNA encoding two distinct elements, i.e. i) an endonuclease, in this case the CRISPR associated nuclease (Cas or "CRISPR associated protein") and ii) a guide RNA. Depending on the type of CRISPR system, the guide RNA may be in the form of a chimeric RNA which consists of the combination of a CRISPR (crRNA) bacterial RNA and a tracrRNA (trans-activating RNA CRISPR) (Jinek et al., Science 2012). The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix.

The CRISPR-Cas system includes two main classes depending on the nuclease mechanism of action:

Class 1 is made of multi-subunit effector complexes and includes type I, III and IV Class 2 is made of single-unit effector modules, like Cas9 nuclease, and includes type II (II-A,II-B,II-C,II-C variant), V (V-A,V-B,V-C,V-D,V-E,V-U1,V-U2,V-U3,V-U4,V-U5) and VI (VI-A,VI-B1,VI-B2,VI-C,VI-D)

The sequence of interest according to the present invention comprises a nucleic acid sequence encoding Cas protein. A variety of CRISPR enzymes are available for use as a sequence of interest on the plasmid according to the present invention. In some embodiments, the CRISPR enzyme is a Type II CRISPR enzyme, a Type II-A or Type II-B CRISPR enzyme. In another embodiment, the CRISPR enzyme is a Type I CRISPR enzyme or a Type III CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a guide RNA or single guide RNA (sgRNA). In certain embodiments, the guide RNA or sgRNA targets a gene selected from the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general and a gene causing a deleterious effect to the host.

The sequence of interest may comprise a nucleic acid sequence encoding a guide RNA or sgRNA to guide the Cas protein endogenous to the targeted bacteria, alone or in combination with a Cas protein and/or a guide RNA encoded by the payload.

Non-limiting examples of Cas proteins as part of a multi-subunit effector or as a single-unit effector include Cas1, Cas1 B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the invention can be obtained from any known Cas9 protein (Fonfara et al., 2014; Koonin et al., 2017). Examples of Cas9 proteins useful in the present invention include, but are not limited to, Cas9 proteins of *Streptococcus pyogenes* (SpCas9), *Streptococcus* thermophiles (St1 Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the invention can be obtained from any known Cpf1 (Cas12a) protein (Koonin et al., 2017). Examples of Cpf1(Cas12a) proteins useful in the present invention include, but are not limited to, Cpf1(Cas12a) proteins of *Acidaminococcus* sp, *Lachnospiraceae bacteriu* and *Francisella novicida.*

The sequence encoding Cas13a (the entire protein or a fragment thereof) as used in the context of the invention can be obtained from any known Cas13a (C2c2) protein (Abudayyeh et al., 2017). Examples of Cas13a (C2c2) proteins useful in the present invention include, but are not limited to, Cas13a (C2c2) proteins of *Leptotrichia wadei*(LwaCas13a).

The sequence encoding Cas13d (the entire protein or a fragment thereof) as used in the context of the invention can be obtained from any known Cas13d protein (Yan et al., 2018). Examples of Cas13d proteins useful in the present invention include, but are not limited to, Cas13d proteins of *Eubacterium* siraeum and Ruminococcus sp.

In a particular embodiment, the nucleic sequence of interest is a CRISPR/Cas9 system for the reduction of gene expression or inactivation a gene selected from the group consisting of an antibiotic resistance gene, virulence factor or protein gene, toxin factor or protein gene, a gene expressing a bacterial receptor, a membrane protein, a structural protein, a secreted protein, a gene expressing resistance to a drug in general and a gene causing a deleterious effect to the host.

In one embodiment, the CRISPR-Cas system is used to target and inactivate a virulence factor. A virulence factor can be any substance produced by a pathogen that alter host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, scavenging factors and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), stx2k, fimA, fimF, fimH, neuC, kpsE, sfa, foc, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be Yersiniapestis virulence factor gene such as, without limitation, yscF (plasmid-borne (pCDI) T3SS external needle subunit). For example, such targeted virulence factor gene can be *Francisella tularensis* virulence factor gene such as, without limitation, fslA. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdI, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft. For example, such targeted virulence factor gene can be *Cutibacterium acnes* porphyrins genes, CAMP-factors (CAMP1, CAMP2, CAMP3, CAMP4), Hyaluronate lyase (HYL-IB/II, HYL-IA), Lipases (GehA, GehB), Haemolysins, Sialidases, Endoglycoceramidases, Endo-β-N-acetylglucosaminidase, Dermatan sulphate adhesin (DsA1, DsA2), Proline-Threonine Repeats (PTRs) or any virulence factors included on the acne associated genomic loci 1, 2, 3(plasmid), 4 such as a tight adhesion locus (tad), Streptolysin S-associated genes (sag), nonribosomal peptide synthetases (NRPS) as described in Tomida et al.

In another embodiment, the CRISPR/Cas9 system is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecI, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FolP, Tetracycline inactivation enzyme TetX, TetA, TetB, TetC, Tet30, Tet31, TetM, TetO, TetQ, Tet32, Tet36, MacAB-TolC, MsbA, MsrA, VgaB, EmrD, EmrAB-TolC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD https://card.mcmaster.ca/).

In another embodiment, the CRISPR/Cas9 system is used to target and inactivate a bacterial toxin gene. Bacterial toxin can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, Staphylococus toxins, Diphteria toxin, Anthrax toxin, Alpha toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

Base Editing

Base editing (BE) refers to the ability to substitute a specific nucleotide base pair on a DNA or RNA molecule by another. Until recently, the only way to perform a specific substitution on DNA in vivo was using recombination of a template DNA, carrying the specific base pair change, with the locus of interest. Base editing technology relies on completely different strategies. There is no exchange of DNA, instead an enzymatic reaction converts a nucleotide to another one leading to a mismatch at the level of dsDNA that is then corrected by the cell machinery.

One of the main challenges for base editing is how to restrict activity of the enzyme performing the nucleotide conversion to the target nucleotide, for example a SNP involved in pathogenicity. This spatial restriction has been achieved recently repurposing the CRISPR-Cas system. Indeed, fusing catalytically impaired or inactive Cas nuclease to base modification enzymes that are active only on single stranded DNA, it's possible to achieve high efficiency base editing. This is possible thanks to the CRISPR-Cas ability to generate locally ssDNA bubble in an 'R loop' when the complex is annealed to its DNA target strand by RNA-DNA base pairing.

So far there are seven types of DNA base editors described:

- Cytosine Base Editor (CBE) that convert C:G into T:A (Komor, A et al. Programmable editing of a target base in genomic DNA without double-stranded DNA cleavage. Nature 533:420-4. (2016).
- Adenine Base Editor (ABE) that convert A:T into G:C (Programmable base editing of A•T to G•C in genomic DNA without DNA cleavage. Nature 551(7681) 464-471 (2017).
- Cytosine Guanine Base Editor (CGBE) that convert C:G into G:C Chen, L et al. Precise and programmable C:G to G:C base editing in genomic DNA. Biorxiv (2020); Kurt, I et al. CRISPR C-to-G base editors for inducing targeted DNA transversions in human cells. Nature Biotechnology (2020).
- Cytosine Adenine Base Editor (CABE) that convert C:G into A:T Zhao, D et al. New base editors change C to A in bacteria and C to G in mammalian cells. Nature Biotechnology (2020).
- Adenine Cytosine Base Editor (ACBE) that convert A:T into C:G (Liu, D et al. A:T to C:G base editors and uses thereof. Patent application WO2020181180 (2020).
- Adenine Thymine Base Editor (ATBE) that convert A:T into T:A (Liu, D et al. A:T to C:G base editors and uses thereof. Patent application WO2020181180 (2020).
- Thymine Adenine Base Editor (TABE) that convert T:A into A:T (Liu, D et al. T:A TO A:T base editing through adenosine methylation. Patent application WO2020181193 (2020); Liu, D et al. T:A TO A:T base editing through thymine alkylation. Patent application WO2020181178 (2020); Liu, D et al. T:A TO A:T base editing through adenine excision. Patent application WO2020181195 (2020).

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY. ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA.TadA* include TadA-8a-e and TadA-7.10.

Except from base modification enzyme there has been also modifications implemented to base editor to increase editing efficacy, precision and modularity:

- the addition of one or two uracil DNA glycosylase inhibitor domain (UGI) to prevent base excision repair mechanism to revert base edition
- the addition of Mu-GAM that decrease insertion-deletion rate by inhibiting Non-homologous end joining mechanism in the cell (NHEJ)
- the use of nickase active Cas9 (nCas9 D10A) that, by creating nicks on the non-edited strand favor its repair and consequently the fixation of the edited base
- the use of divers Cas proteins from for example different organisms, mutants with different PAM motifs or different fidelity or different family (e.g. Cas12a)

Non-limiting examples of DNA based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:

- A cytosine deaminase (rAPOBEC) and base excision repair proteins (e.g. rXRCC1). (Precise and programmable C:G to G:C base editing in genomic DNA. Biorxiv (2020).
- A rat APOBEC1 variant (R33A) protein and an *E. coli*-derived uracil DNA N-glycosylase (eUNG). (Kurt, I et al. CRISPR C-to-G base editors for inducing targeted DNA transversions in human cells. Nature Biotechnology (2020).
- Cytosine Adenine Base Editors (CABE) consist of a Cas9 nickase, a cytidine deaminase (e.g. AID), and a uracil-DNA glycosylase (Ung). Zhao, D et al. New base editors change C to A in bacteria and C to G in mammalian cells. Nature Biotechnology (2020).
- ACBE include a nucleic acid programmable DNA-binding protein and an adenine oxidase. Liu, D et al. A:T to C:G base editors and uses thereof. Patent application WO2020181180 (2020).
- ATBE consist of a Cas9 nickase and one or more adenosine deaminase or an oxidase domain. Liu, D et al. A:T to T:A base editing through adenine deamination and oxidation. Patent application WO2020181202 (2020).
- TABE consist of a Cas9 nickase and an adenosine methyltransferase, a thymine alkyltransferase, or an adenosine deaminase domain. (Liu, D et al. T:A TO A:T base editing through adenosine methylation. Patent application WO2020181193 (2020); Liu, D et al. T:A TO A:T base editing through thymine alkylation. Patent application WO2020181178 (2020); Liu, D et al. T:A TO A:T base editing through adenine excision. Patent application WO2020181195 (2020).

Base editor molecules can also consist of two or more of the above listed editor enzymes fused to a Cas protein (e.g. combination of an ABE and CBE). These biomolecules are named dual base editors and enable the editing of two different bases. (Grunewald, J et al. A dual-deaminase CRISPR base editor enables concurrent adenine and cytosine editing, Nature Biotechnology (2020); Li, C et al. Targeted, random mutagenesis of plant genes with dual cytosine and adenine base editors, Nature Biotechnology (2020).

In one embodiment, the base editor is used to inactivate the expression of a gene by editing one or several nucleotides involved in transcription or translation. More specifically the base editor is targeting one or several nucleotides of a promoter, a RBS, a start codon.

In one embodiment, the base editor is used to introduce a premature stop codon.

In one embodiment, the base editor is used to introduce one or several rare codons.

In another embodiment, the base editor is used to modulate the expression of genes by editing one or several nucleotides involved in transcription or translation. More specifically the base editor is targeting one or several nucleotides of a promoter, a RBS, a start codon. leading to an increase or decrease of gene expression.

In another embodiment, the base editor is used to revert a mutation that leads to the inactivation, decrease or increase in activity of a gene or pathway.

In another embodiment, the base editor is used to revert a mutation that leads to an increase of pathogenicity.

In one embodiment, the base editor is used to modify the regulation of a gene by editing one or several nucleotides involved in its regulation such as nucleotides of operator sequence, transcription factor binding site, riboswitch, RNAse recognition site, protease cleavage site, methylation site, post translational modification site (phosphorylation, glycosylation, acetylation, pupylation . . . ).

RNA Based Editing

RNA base editing is based on the same principle as DNA base editing: an enzyme catalysing the conversion of a RNA base into another has to be brought close to the target base to perform its conversion locally. So far the only enzyme used for RNA editing is an adenosine deaminase from ADAR family that converts Adenosine into Inosine in dsRNA structure. Several seminal studies used this specificity for dsRNA and fused the ADAR deaminase domain (ADARDD) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to an hyperactive mutant of ADAR2 deaminase domain (ADAR2DD-E488Q for REPAIRv1 and ADAR2DD-E488Q-T375G for REPAIRv2) Cox et al improved specificity and efficiency compare to previous RNA editing strategies.

Non-limiting examples of RNA based editor proteins include REPAIRv1, REPAIRv2

In one embodiment, the RNA base editor is used to inactivate the expression of a gene by editing one or several nucleotides involved in translation. More specifically the base editor is targeting one or several nucleotides of a 5'UTR, a RBS, a start codon.

In one embodiment, the RNA base editor is used to introduce a premature stop codon.

In one embodiment, the RNA base editor is used to introduce one or several rare codons.

In another embodiment, the RNA base editor is used to modulate the expression of genes by editing one or several nucleotides involved in translation. More specifically the base editor is targeting one or several nucleotides of a 5'UTR, a RBS, a start codon leading to an increase or decrease of gene expression.

In another embodiment, the RNA base editor is used to revert a mutation that leads to the inactivation or a decrease in activity of a gene or pathway.

In another embodiment, the base editor is used to revert a mutation that leads to an increase of pathogenicity.

Prime Editing

Prime editors (PE), as described in Anzalone et al. (Anzalone, A. V. et al. Search-and-replace genome editing without double-strand breaks or donor DNA. Nature 576, 149-157 (2019) which is hereby incorporated by reference, consist of a nCas9 fused to a reverse transcriptase used in combination with a prime editing RNA (pegRNA; a guide RNA that includes a template region for reverse transcription).

Prime Editing allows introduction of insertions, deletions (indels) and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:

- a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)
- a prime editing guide RNA (pegRNA)

To favor editing the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3inv, PE2, PE3, PE3b, Cas9 Retron precISe Parallel Editing via homologY ('CRISPEY'), a retron RNA fused to the sgRNA and expressed together with Cas9 and the retron proteins including at least the reverse transcriptase (Sharon, E. et al. Functional Genetic Variants Revealed by Massively Parallel Precise Genome Editing. Cell 175, 544-557.e16 (2018).), The SCRIBE strategy: a retron system expressed in combination with a recombinase promoting the recombination of single stranded DNA, also known as single stranded annealing proteins (SSAPs)12. Such recombinases include but are not limited to phage recombinases such as lambda red, recET, Sak, Sak4, and newly described SSAPs described in Wannier et al (Wannier, T. M. et al. Improved bacterial recombineering by parallelized protein discovery. Biorxiv 2020.01.14.906594 (2020) doi:10.1101/2020.01.14.906594.), the targetron system based on group II introns described in Karberg et al. (Karberg, M. et al. Group II introns as controllable gene targeting vectors for genetic manipulation of bacteria. Nat Biotechnol 19, 1162-7 (2001) and which has been adapted to many bacterial species, Other retron based gene targeting approaches, as described in Simon et al (Simon, A. J., Ellington, A. D. & Finkelstein, I. J. Retrons and their applications in genome engineering. Nucleic Acids Res 47, 11007-11019 (2019)).

In one embodiment, the prime editing system is used to inactivate the expression of a gene by replacing, deleting, inserting one or several nucleotides involved in transcription or translation. More specifically the prime editing system is replacing, deleting, inserting one or several nucleotides in a promoter, a RBS, a coding sequence.

In one embodiment, the prime editing system is used to introduce one or several premature stop codon.

In one embodiment, the prime editing system is used to introduce one or several rare codons.

In one embodiment, the prime editing system is used to introduce, delete a nucleotide inducing a frameshift in the reading frame.

In another embodiment, the prime editing system is used to modulate the expression of genes by replacing, deleting, inserting one or several nucleotides involved in transcription or translation. More specifically the prime editing system is replacing, deleting, inserting one or several nucleotides in a promoter, a RBS, a start codon. leading to an increase or decrease of gene expression.

In another embodiment, the prime editing system is used to revert a mutation that leads to the inactivation or a decrease in activity of a gene or pathway.

In another embodiment, the prime editing system is used to revert a mutation that leads to an increase of pathogenicity.

The invention encompasses the following embodiments:

1. A *C. acnes* cell carrying a recombinant DNA vector comprising:
   - a phage packaging signal allowing packaging of the DNA vector in a *Cutibacterium acnes* phage capsid, and
   - a gene of interest.

2. A *C. acnes* producer cell carrying a recombinant DNA vector comprising:
   - a phage packaging signal allowing packaging of the DNA vector in a *Cutibacterium acnes* phage capsid
   - a gene of interest
   - an origin of replication allowing replication in the producer cell, and
   - a selection marker for *C. acnes.*

3. The DNA vector of embodiment 1, further comprising an origin of replication for *C. acnes* and a selection marker for *C. acnes.*

4. The DNA vector of any of embodiments 1-3, wherein the phage packaging signal is at least 90, 93, 95, 97, 98, 99, or 100% identical to SEQ ID NO: 66.

5. The DNA vector of any of embodiments 1-3, wherein the phage packaging signal is at least 90, 93, 95, 97, 98, 99, or 100% identical to phage packaging signal selected from the group consisting of: SEQ ID NO: 76, SEQ ID NO: 77, SEQ ID NO: 78, SEQ ID NO: 79, SEQ ID NO: 80, SEQ ID NO: 81.

6. The DNA vector of any of embodiments 1-5, wherein the DNA vector also comprises a CRISPR-Cas system.

7. The DNA vector of any of embodiments 1-6, comprising a CRISPR-Cas system targeting a *C. acnes* chromosome locus not present in the *C. acnes* producer cell strain.

8. The DNA vector of embodiment 7, wherein the targeted locus is a proinflammatory sequence related to acne vulgaris.

9. The DNA vector of any of embodiments 1-8, wherein the DNA vector comprises a template for homologous recombination in *C. acnes* phages.

10. The DNA vector of any of embodiments 1-9, wherein the DNA vector comprises a template for homologous recombination in *C. acnes* plasmids.

11. The DNA vector of embodiment 6, wherein the DNA vector comprises a template for homologous recombination and wherein the CRISPR-Cas system targets the DNA vector itself.

12. The DNA vector of any of embodiments 1-11, wherein first selection marker and second selection marker are the same.

13. The DNA vector of any of embodiments 1-11, wherein neither the first nor second selection marker is ermE.

14. The DNA vector of any of embodiments 1-11, wherein first selection marker and second selection marker is catA.

15. The DNA vector of any of embodiments 1-11, wherein first selection marker or second selection marker is catA.

16. An engineered *C. acnes* comprising any of the DNA vectors of embodiments 1-15.

17. An engineered *C. acnes* produced by modification with any of the vectors of embodiments 1-15.

18. An engineered *C. acnes* produced by contacting *C. acnes* with any of the vectors of embodiments 1-15, modifying the *C. acnes* with a gene of interest carried by the vector, selecting for the modification, and curing the *C. acnes* of the plasmid.

19. The engineered *C. acnes* of any of embodiments 16-18, wherein the *C. acnes* has been modified by a CRISPR-Cas system carried by the vector.

20. The engineered *C. acnes* of any of embodiments 16-19, wherein the *C. acnes* has been modified by insertion of an exogenous gene into the *C. acnes* chromosome.

21. A method for engineering a *C. acnes* comprising introducing the DNA vector of any of embodiments 1-15 into a *C. acnes.*

22. The method of embodiment 21, further comprising selecting a modified *C. acnes.*

23. The method of embodiment 22, comprising selecting a modified *C. acnes* that has an insertion of an exogenous gene into the *C. acnes* chromosome.

24. A method for the production of phage-derived particles comprising the transformation or the transduction of a *C. acnes* phage genome into the producer cell of embodiment 2.

25. A method for the production of phage-derived particles comprising the introduction of a helper phage into the producer cell of embodiment 2.

26. A phage-derived particle produced by the method of any of embodiments 24-25.

27. A recombinant DNA vector comprising:

an origin of replication allowing replication in *C. acnes;* optionally a first selection marker allowing for selection of the DNA vector in *C. acnes*; and a gene of interest.

28. The DNA vector of embodiment 27 further comprising an oriT allowing conjugation into *C. acnes*; an origin of replication allowing replication in a donor bacteria and a second selection marker allowing for selection in a donor bacteria.

29. The DNA vector of embodiment 27 or 28, wherein the origin of replication allowing replication in *C. acnes* is R6K (typically of sequence SEQ ID NO: 42).

30. The DNA vector of embodiment 27 or 28, wherein the origin of replication allowing replication in *C. acnes* is RK2 (typically of sequence SEQ ID NO: 43).

31. The DNA vector of embodiment 27 or 28, wherein the origin of replication allowing replication in *C. acnes* is pBBR1 (typically of sequence SEQ ID NO: 44).

32. The DNA vector of embodiment 27 or 28, wherein the origin of replication allowing replication in *C. acnes* is pRO1600 (typically of sequence SEQ ID NO: 45).

33. The DNA vector of embodiment 27 or 28, wherein the origin of replication allowing replication in *C. acnes* is RSF1010 (typically of sequence SEQ ID NO: 46).

34. The DNA vector of embodiment 27 or 28, wherein the origin of replication allowing replication in *C. acnes* is pAM31 (typically of sequence SEQ ID NO: 47).

35. The DNA vector of embodiment 27 or 28, wherein the origin of replication allowing replication in *C. acnes* is pLME106 (typically of sequence SEQ ID NO: 48).

36. The DNA vector of embodiment 27 or 28, wherein the origin of replication allowing replication in *C. acnes* is pTZC1 (typically of sequence SEQ ID NO: 49).

37. The DNA vector of embodiment 27 or 28, wherein the origin of replication allowing replication in *C. acnes* is pBC1 (typically of sequence SEQ ID NO: 50).

38. The DNA vector of embodiment 27 or 28, wherein the origin of replication allowing replication in *C. acnes* is pEP2 (typically of sequence SEQ ID NO: 51).

39. The DNA vector of embodiment 27 or 28, wherein the origin of replication allowing replication in *C. acnes* is pWVO1 (typically of sequence SEQ ID NO: 52).

40. The DNA vector of embodiment 27 or 28, wherein the origin of replication allowing replication in *C. acnes* is pAP1 (typically of sequence SEQ ID NO: 53).

41. The DNA vector of embodiment 27 or 28, wherein the origin of replication allowing replication in *C. acnes* is pWKS1 (typically of sequence SEQ ID NO: 54).

42. The DNA vector of embodiment 27 or 28, wherein the origin of replication allowing replication in *C. acnes* is pLME108 (typically of sequence SEQ ID NO: 55).

43. The DNA vector of embodiment 27 or 28, wherein the origin of replication allowing replication in *C. acnes* is pLS1 (typically of sequence SEQ ID NO: 56).

44. The DNA vector of embodiment 27 or 28, wherein the origin of replication allowing replication in *C. acnes* is pUB6060 (typically of sequence SEQ ID NO: 57).

45. The DNA vector of embodiment 27 or 28, wherein the origin of replication allowing replication in *C. acnes* is p545 (typically of sequence SEQ ID NO: 58).

46. The DNA vector of embodiment 27 or 28, wherein the origin of replication allowing replication in *C. acnes* is pJD4 (typically of sequence SEQ ID NO: 59).

47. The DNA vector of embodiment 27 or 28, wherein the origin of replication allowing replication in *C. acnes* is pIJ101 (typically of sequence SEQ ID NO: 60).

48. The DNA vector of embodiment 27 or 28, wherein the origin of replication allowing replication in *C. acnes* is pSN22 (typically of sequence SEQ ID NO: 61).

49. The DNA vector of embodiment 27 or 28, wherein the origin of replication allowing replication in *C. acnes* is pGP01 (typically of sequence SEQ ID NO: 62).

50. The DNA vector of embodiment 27 or 28, wherein the origin of replication allowing replication in *C. acnes* is pIP501 (typically of sequence SEQ ID NO: 63).

51. The DNA vector of embodiment 27 or 28, wherein the origin of replication allowing replication in *C. acnes* is pCU1 (typically of sequence SEQ ID NO: 64).

52. The DNA vector of embodiment 27 or 28, wherein the origin of replication allowing replication in *C. acnes* is pBAV1 K-T5 (typically of sequence SEQ ID NO: 65).

53. The DNA vector of any one of embodiments 28 to 52, wherein the oriT is oriT_pMRC01 (typically of sequence SEQ ID NO: 1).

54. The DNA vector of any one of embodiments 28 to 52, wherein the oriT is oriT_RSF1010 (typically of sequence SEQ ID NO: 2).

55. The DNA vector of any one of embodiments 28 to 52, wherein the oriT is oriT_pRS01 (typically of sequence SEQ ID NO: 3).

56. The DNA vector of any one of embodiments 28 to 52, wherein the oriT is oriT_pMV158 (typically of sequence SEQ ID NO: 4).

57. The DNA vector of any one of embodiments 28 to 52, wherein the oriT is oriT_pTF1 (typically of sequence SEQ ID NO: 5).

58. The DNA vector of any one of embodiments 28 to 52, wherein the oriT is oriT_pSC101 (typically of sequence SEQ ID NO: 6).

59. The DNA vector of any one of embodiments 28 to 52, wherein the oriT is oriT_pBTK445 (typically of sequence SEQ ID NO: 7).

60. The DNA vector of any one of embodiments 28 to 52, wherein the oriT is oriT_pBBR1 (typically of sequence SEQ ID NO: 8).

61. The DNA vector of any one of embodiments 28 to 52, wherein the oriT is oriT_R721 (typically of sequence SEQ ID NO: 9).

62. The DNA vector of any one of embodiments 28 to 52, wherein the oriT is oriT_pRmeGR4a (typically of sequence SEQ ID NO: 10).

63. The DNA vector of any one of embodiments 28 to 52, wherein the oriT is oriT_ColE1 (typically of sequence SEQ ID NO: 11).

64. The DNA vector of any one of embodiments 28 to 52, wherein the oriT is oriT_pTiC58 (typically of sequence SEQ ID NO: 12).

65. The DNA vector of any one of embodiments 28 to 52, wherein the oriT is oriT_pMdT1 (typically of sequence SEQ ID NO: 13).

66. The DNA vector of any one of embodiments 28 to 52, wherein the oriT is oriT_R1 (typically of sequence SEQ ID NO: 14).

67. The DNA vector of any one of embodiments 28 to 52, wherein the oriT is oriT_Tn5520 (typically of sequence SEQ ID NO: 15).

68. The DNA vector of any one of embodiments 28 to 52, wherein the oriT is oriT_QKH54 (typically of sequence SEQ ID NO: 16).

69. The DNA vector of any one of embodiments 28 to 52, wherein the oriT is oriT_R64 (typically of sequence SEQ ID NO: 17).

70. The DNA vector of any one of embodiments 28 to 52, wherein the oriT is oriT_R751 (typically of sequence SEQ ID NO: 18).

71. The DNA vector of any one of embodiments 28 to 52, wherein the oriT is oriT_RP4 (typically of sequence SEQ ID NO: 19).

72. The DNA vector of any one of embodiments 28 to 52, wherein the oriT is oriT_pKL1 (typically of sequence SEQ ID NO: 20).

73. The DNA vector of any one of embodiments 28 to 52, wherein the oriT is oriT_RK2 (typically of sequence SEQ ID NO: 21).

74. The DNA vector of any one of embodiments 28 to 52, wherein the oriT is oriT_R1162 (typically of sequence SEQ ID NO: 22).

75. The DNA vector of any one of embodiments 28 to 52, wherein the oriT is oriT_Tn4555 (typically of sequence SEQ ID NO: 23).

76. The DNA vector of any one of embodiments 28 to 52, wherein the oriT is oriT_pHT (typically of sequence SEQ ID NO: 24).

77. The DNA vector of any one of embodiments 28 to 52, wherein the oriT is oriT_Tn4399 (typically of sequence SEQ ID NO: 25).

78. The DNA vector of any one of embodiments 28 to 52, wherein the oriT is oriT_Tn916 (typically of sequence SEQ ID NO: 26).

79. The DNA vector of any one of embodiments 28 to 52, wherein the oriT is oriT_pST12 (typically of sequence SEQ ID NO: 27).

80. The DNA vector of any one of embodiments 28 to 52, wherein the oriT is oriT_pCU1 (typically of sequence SEQ ID NO: 28).

81. The DNA vector of any one of embodiments 28 to 52, wherein the oriT is oriT_pSU233 (typically of sequence SEQ ID NO: 29).

82. The DNA vector of any one of embodiments 28 to 52, wherein the oriT is oriT_F (typically of sequence SEQ ID NO: 30).

83. The DNA vector of any one of embodiments 28 to 52, wherein the oriT is oriT_pMAB01 (typically of sequence SEQ ID NO: 31).

84. The DNA vector of any one of embodiments 28 to 52, wherein the oriT is oriT_R388 (typically of sequence SEQ ID NO: 32).

85. The DNA vector of any one of embodiments 28 to 52, wherein the oriT is oriT_pS7a (typically of sequence SEQ ID NO: 33).

86. The DNA vector of any one of embodiments 28 to 52, wherein the oriT is oriT_pS7b (typically of sequence SEQ ID NO: 34).

87. The DNA vector of any one of embodiments 28 to 52, wherein the oriT is oriT_R702 (typically of sequence SEQ ID NO: 35).

88. The DNA vector of any one of embodiments 28 to 52, wherein the oriT is oriT_pMUR274 (typically of sequence SEQ ID NO: 36).

89. The DNA vector of any one of embodiments 28 to 52, wherein the oriT is oriT_R100 (typically of sequence SEQ ID NO: 37).

90. The DNA vector of any one of embodiments 28 to 52, wherein the oriT is oriT_pVCR94deltaX (typically of sequence SEQ ID NO: 38).

91. The DNA vector of any one of embodiments 28 to 52, wherein the oriT is oriT_R46 (typically of sequence SEQ ID NO: 39).

92. The DNA vector of any one of embodiments 28 to 52, wherein the oriT is oriT_pGO1 (typically of sequence SEQ ID NO: 40).

93. The DNA vector of any one of embodiments 28 to 52, wherein the oriT is oriT_pIP501 (typically of sequence SEQ ID NO: 41).

94. The DNA vector of any one of embodiments 27 to 93, further comprising:

- a relaxase gene;
- a selection marker allowing for selection in the transconjugant *C. acnes*; and
- a selection marker allowing for selection in the donor bacteria wherein the donor bacteria is an *E. coli* strain carrying a conjugative plasmid, conjugative transposon, or integrative and conjugative element (ICE), expressing a conjugative machinery.

95. The DNA vector of embodiment 94, wherein the donor bacteria is an *E. coli* strain carrying the conjugative plasmid, conjugative transposon or ICE pMRC01.

96. The DNA vector of embodiment 94, wherein the donor bacteria is an *E. coli* strain carrying the conjugative plasmid, conjugative transposon or ICE RSF1010.

97. The DNA vector of embodiment 94, wherein the donor bacteria is an *E. coli* strain carrying the conjugative plasmid, conjugative transposon or ICE pRS01.

98. The DNA vector of embodiment 94, wherein the donor bacteria is an *E. coli* strain carrying the conjugative plasmid, conjugative transposon or ICE pMV158.

99. The DNA vector of embodiment 94, wherein the donor bacteria is an *E. coli* strain carrying the conjugative plasmid, conjugative transposon or ICE pTF1.

100. The DNA vector of embodiment 94, wherein the donor bacteria is an *E. coli* strain carrying the conjugative plasmid, conjugative transposon or ICE pSC101.

101. The DNA vector of embodiment 94, wherein the donor bacteria is an *E. coli* strain carrying the conjugative plasmid, conjugative transposon or ICE pBTK445.

102. The DNA vector of embodiment 94, wherein the donor bacteria is an *E. coli* strain carrying the conjugative plasmid, conjugative transposon or ICE pBBR1.

103. The DNA vector of embodiment 94, wherein the donor bacteria is an *E. coli* strain carrying the conjugative plasmid, conjugative transposon or ICE R721.

104. The DNA vector of embodiment 94, wherein the donor bacteria is an *E. coli* strain carrying the conjugative plasmid, conjugative transposon or ICE pRmeGR4a.

105. The DNA vector of embodiment 94, wherein the donor bacteria is an *E. coli* strain carrying the conjugative plasmid, conjugative transposon or ICE ColE1.

106. The DNA vector of embodiment 94, wherein the donor bacteria is an *E. coli* strain carrying the conjugative plasmid, conjugative transposon or ICE pTiC58.

107. The DNA vector of embodiment 94, wherein the donor bacteria is an *E. coli* strain carrying the conjugative plasmid, conjugative transposon or ICE pMdT1.

108. The DNA vector of embodiment 94, wherein the donor bacteria is an *E. coli* strain carrying the conjugative plasmid, conjugative transposon or ICE R1.

109. The DNA vector of embodiment 94, wherein the donor bacteria is an *E. coli* strain carrying the conjugative plasmid, conjugative transposon or ICE Tn5520.

110. The DNA vector of embodiment 94, wherein the donor bacteria is an *E. coli* strain carrying the conjugative plasmid, conjugative transposon or ICE QKH54.

111. The DNA vector of embodiment 94, wherein the donor bacteria is an *E. coli* strain carrying the conjugative plasmid, conjugative transposon or ICE R64.

112. The DNA vector of embodiment 94, wherein the donor bacteria is an *E. coli* strain carrying the conjugative plasmid, conjugative transposon or ICE R751.

113. The DNA vector of embodiment 94, wherein the donor bacteria is an *E. coli* strain carrying the conjugative plasmid, conjugative transposon or ICE RP4.

114. The DNA vector of embodiment 94, wherein the donor bacteria is an *E. coli* strain carrying the conjugative plasmid, conjugative transposon or ICE pKL1.

115. The DNA vector of embodiment 94, wherein the donor bacteria is an *E. coli* strain carrying the conjugative plasmid, conjugative transposon or ICE RK2.

116. The DNA vector of embodiment 94, wherein the donor bacteria is an *E. coli* strain carrying the conjugative plasmid, conjugative transposon or ICE R1162.

117. The DNA vector of embodiment 94, wherein the donor bacteria is an *E. coli* strain carrying the conjugative plasmid, conjugative transposon or ICE Tn4555.

118. The DNA vector of embodiment 94, wherein the donor bacteria is an *E. coli* strain carrying the conjugative plasmid, conjugative transposon or ICE pHT.

119. The DNA vector of embodiment 94, wherein the donor bacteria is an *E. coli* strain carrying the conjugative plasmid, conjugative transposon or ICE Tn4399.

120. The DNA vector of embodiment 94, wherein the donor bacteria is an *E. coli* strain carrying the conjugative plasmid, conjugative transposon or ICE Tn916.

121. The DNA vector of embodiment 94, wherein the donor bacteria is an *E. coli* strain carrying the conjugative plasmid, conjugative transposon or ICE pST12.

122. The DNA vector of embodiment 94, wherein the donor bacteria is an *E. coli* strain carrying the conjugative plasmid, conjugative transposon or ICE pCU1.

123. The DNA vector of embodiment 94, wherein the donor bacteria is an *E. coli* strain carrying the conjugative plasmid, conjugative transposon or ICE pSU233.

124. The DNA vector of embodiment 94, wherein the donor bacteria is an *E. coli* strain carrying the conjugative plasmid, conjugative transposon or ICE F.

125. The DNA vector of embodiment 94, wherein the donor bacteria is an *E. coli* strain carrying the conjugative plasmid, conjugative transposon or ICE pMAB01.

126. The DNA vector of embodiment 94, wherein the donor bacteria is an *E. coli* strain carrying the conjugative plasmid, conjugative transposon or ICE R388.

127. The DNA vector of embodiment 94, wherein the donor bacteria is an *E. coli* strain carrying the conjugative plasmid, conjugative transposon or ICE pS7a.

128. The DNA vector of embodiment 94, wherein the donor bacteria is an *E. coli* strain carrying the conjugative plasmid, conjugative transposon or ICE pS7b.

129. The DNA vector of embodiment 94, wherein the donor bacteria is an *E. coli* strain carrying the conjugative plasmid, conjugative transposon or ICE R702.

130. The DNA vector of embodiment 94, wherein the donor bacteria is an *E. coli* strain carrying the conjugative plasmid, conjugative transposon or ICE pMUR274.

131. The DNA vector of embodiment 94, wherein the donor bacteria is an *E. coli* strain carrying the conjugative plasmid, conjugative transposon or ICE R100.

132. The DNA vector of embodiment 94, wherein the donor bacteria is an *E. coli* strain carrying the conjugative plasmid, conjugative transposon or ICE pVCR94deltaX.

133. The DNA vector of embodiment 94, wherein the donor bacteria is an *E. coli* strain carrying the conjugative plasmid, conjugative transposon or ICE R46.

134. The DNA vector of embodiment 94, wherein the donor bacteria is an *E. coli* strain carrying the conjugative plasmid, conjugative transposon or ICE pGO1.

135. The DNA vector of embodiment 94, wherein the donor bacteria is an *E. coli* strain carrying the conjugative plasmid, conjugative transposon or ICE pIP501.

136. An engineered *C. acnes* comprising any of the DNA vectors of any one of embodiments 27 to 135.

137. An engineered *C. acnes* produced by contacting *C. acnes* with any of the vectors of any one of embodiments 27 to 135.

138. A method for engineering a *C. acnes* comprising introducing the DNA vector of any one of embodiments 27 to 135 into a *C. acnes*.

139. A recombinant DNA vector comprising:

a phage packaging signal allowing packaging of the DNA vector in a *Cutibacterium acnes* phage capsid, and a gene of interest.

140. A *C. acnes* producer cell carrying a recombinant DNA vector comprising:

a phage packaging signal allowing packaging of the DNA vector in a *Cutibacterium acnes* phage capsid a gene of interest an origin of replication allowing replication in the producer cell, and a selection marker for *C. acnes*.

141. The DNA vector of embodiment 139 further comprising an origin of replication for *C. acnes* and a selection marker for *C. acnes*.

142. The DNA vector of any of embodiments 139-141, wherein the phage packaging signal is at least 90, 93, 95, 97, 98, 99, or 100% identical to (SEQ ID NO: 66).

143. The DNA vector of any of embodiments 139-141, wherein the phage packaging signal is at least 90, 93, 95, 97, 98, 99, or 100% identical to phage packaging signal selected from the group consisting of: SEQ ID NO: 76, SEQ ID NO: 77, SEQ ID NO: 78, SEQ ID NO: 79, SEQ ID NO: 80, SEQ ID NO: 81.

144. The DNA vector of any of embodiments 139-143, wherein the DNA vector also comprises a CRISPR-Cas system.

145. The DNA vector of any of embodiments 139-144, comprising a CRISPR-Cas system targeting a *C. acnes* chromosome locus not present in the *C. acnes* producer cell strain.

146. The DNA vector of embodiment 145, wherein the targeted locus is a proinflammatory sequence related to acne vulgaris.

147. The DNA vector of any of embodiments 139-146, wherein the DNA vector comprises a template for homologous recombination in *C. acnes* phages.

148. The DNA vector of any of embodiments 139-147, wherein the DNA vector comprises a template for homologous recombination in *C. acnes* plasmids.

149. The DNA vector of embodiment 144, wherein the DNA vector comprises a template for homologous recombination and wherein the CRISPR-Cas system targets the DNA vector itself.

150. The DNA vector of any of embodiments 139-149, wherein first selection marker and second selection marker are the same.

151. The DNA vector of any of embodiments 139-149, wherein neither the first nor second selection marker is ermE.

152. The DNA vector of any of embodiments 139-149, wherein first selection marker and second selection marker is catA.

153. The DNA vector of any of embodiments 139-149, wherein first selection marker or second selection marker is catA.

154. The DNA vector of embodiment 139, which comprises a DNA encoding an antigen.

155. An engineered *C. acnes* comprising any of the DNA vectors of embodiments 139-154.

156. The engineered *C. acnes* according to embodiment 155, which comprises a DNA vector as defined in claim 1 which comprises a DNA encoding an antigen.

157. An engineered *C. acnes* produced by modification with any of the vectors of embodiments 139-154.

158. An engineered *C. acnes* produced by contacting *C. acnes* with any of the vectors of embodiments 139-154, modifying the *C. acnes* with a gene of interest carried by the vector, selecting for the modification, and curing the *C. acnes* of the plasmid.

159. The engineered *C. acnes* of any of embodiments 155-158, wherein the *C. acnes* has been modified by a CRISPR-Cas system carried by the vector.

160. The engineered *C. acnes* of any of embodiments 155-158, wherein the *C. acnes* has been modified by insertion of an exogenous gene into the *C. acnes* chromosome.

161. A method for engineering a *C. acnes* comprising introducing the DNA vector of any of embodiments 139-154 into a *C. acnes*.

162. The method of embodiment 161, further comprising selecting a modified *C. acnes*.

163. The method of embodiment 161, comprising selecting a modified *C. acnes* that has an insertion of an exogenous gene into the *C. acnes* chromosome.

164. A method for the production of phage-derived particles comprising the transformation or the transduction of a *C. acnes* phage genome into the producer cell of embodiment 140.

165. A method for the production of phage-derived particles comprising the introduction of a helper phage into the producer cell of embodiment 140.

166. A phage-derived particle produced by the method of any of embodiments 164-165.

167. A vaccine and/or immunogenic compositions comprising engineered *C. acnes* of embodiment 155 comprising a DNA vector comprising a nucleic acid encoding an antigen.

168. A method to prevent and/or treat cancer in a subject in need thereof, comprising administering to said subject a therapeutically or prophylactically efficient amount of an engineered *C. acnes* of embodiment 155 comprising a DNA vector comprising a nucleic acid encoding a tumor antigen.

169. A method to prevent and/or treat a viral infection in a subject in need thereof, comprising administering to said subject a therapeutically or prophylactically efficient amount of an engineered *C. acnes* of embodiment 155 comprising a DNA vector comprising a nucleic acid encoding a viral antigen.

170. A method to prevent and/or treat a bacterial infection in a subject in need thereof, comprising administering to said subject a therapeutically or prophylactically efficient amount of an engineered *C. acnes* of embodiment 155 comprising a DNA vector comprising a nucleic acid encoding a bacterial antigen.

171. A method to prevent and/or treat a fungal infection in a subject in need thereof, comprising administering to said subject a therapeutically or prophylactically efficient amount of an engineered *C. acnes* of embodiment 155 comprising a DNA vector comprising a nucleic acid encoding a fungal antigen.

172. A method to prevent and/or treat an autoimmune disease in a subject in need thereof, comprising administering to said subject a therapeutically or prophylactically efficient amount of an engineered *C. acnes* of embodiment 155 comprising a DNA vector comprising a nucleic acid encoding a self-antigen.

173. A method to prevent and/or treat an allergy in a subject in need thereof, comprising administering to said subject a therapeutically or prophylactically efficient amount of an engineered *C. acnes* of embodiment 155 comprising a DNA vector comprising a nucleic acid encoding an allergen.

174. A method to prevent and/or treat graft rejection in a subject in need thereof, comprising administering to said subject a therapeutically or prophylactically efficient amount of an engineered *C. acnes* of embodiment 155 comprising a DNA vector comprising a nucleic acid encoding a graft-specific antigen.

EXAMPLES

Example 1. Phage-Derived Particles for Delivery of DNA Payload into *C. acnes*

*C. acnes* phage-derived particles containing a synthetic DNA payload and able to inject it inside *C. acnes* were developed. It is demonstrated for the first time the stable and autonomous replication of a recombinant DNA vector that allows for transgene expression. These phage-derived particles are produced upon the co-occurrence of a *C. acnes* phage genome and a DNA payload inside a *C. acnes* producer cell. The DNA payload is introduced into the *C. acnes* producer cell by different methods such as electroporation, electroporation of protoplast, conjugation, chemical transformation, transduction into the *C. acnes* producer cell. Such phage-derived particles open possibilities to deliver DNA encoding a therapeutic molecule into all *C. acnes* strains in situ with high efficiency and specificity, allowing, for example, sequence specific killing due to CRISPR-Cas expression or modulation of the immune system by secretion of immunomodulators.

Being able to edit *Cutibacterium acnes* population by removing specific proinflammatory strains to prevent or cure disease such as acne vulgaris or leverage their privilege location into the pilosebaceous unit to modulate the immune system or improve wound healing are attractive therapeutic approaches. To implement such approaches, one can either genetically modify *C. acnes* strains in situ or provide in vitro genetically modified *C. acnes*. Because of the large intra and inter-individual microbiome diversity both at the species and strain level, it appears difficult to provide a single or cocktail of engineered *C. acnes* strains able to colonize the skin of most patients.

Delivery of DNA in situ to the *C. acnes* population offers a way to circumvent such difficulties by allowing to leverage pre-establish strains potentially without disturbing the local microbiome. However, in situ delivery of genetic material to *C. acnes* is a challenging task for several reasons. First, there are so far no genetic elements such as plasmid able to robustly and autonomously replicate inside *C. acnes*. The few described genetic modifications consist in genomic insertion of synthetic DNA through homologous recombination[26]. This in vitro process has been shown to be very low efficiency and rely on the use of an antibiotic selection marker to select such events. Moreover, these genetic modifications have been restricted to a few specific strains (KPA17202) and might not be generalizable to all *C. acnes* strains. Second, in order to perform in situ genetic modification of *C. acnes* we need to deliver DNA. The only described method for introducing DNA into *C. acnes* is the use of electroporation[26,27], a method that can only be performed in vitro.

The present invention solves both delivery and maintenance of synthetic DNA inside *C. acnes* population in situ. Phage-derived particles composed of a synthetic DNA vector/payload packaged inside the phage capsid at the expense of the phage genome are used. By hijacking the phage-capsid, it was taken advantage of the ability of the phage to transduce DNA into the bacterial host. These phage-derived particles, when put in the presence of the natural bacterial host of the phage, are able to bind to the bacteria and inject the DNA vector/payload inside the bacterial cytoplasm where it can replicate and lead to expression of a protein of interest.

*C. acnes* phage are naturally present on the skin where they infect and replicate using *C. acnes* as a host. *C. acnes* phages have a broad host range, meaning that they can infect most of the *C. acnes* strain diversity isolated so far. This makes the capsid of these phages a really efficient vehicle to deliver DNA in situ into all *C. acnes* strains regardless of their genetic diversity. To develop phage-derived particles from *C. acnes* phages, several phages from the skin of volunteer individuals were first isolated by sampling nose microcomedones using Biore Deep Cleansing Pore Strips (Kao Brands Company), following manufacturer's instructions. After being removed from the nose, microcomedones were collected, homogenized in sterile water and spread onto an RCM agar plate. After incubation under anaerobic conditions at 37° C. for 7 days, plaques could be observed on the lawn of *C. acnes* growth. Plaques were then isolated and the phages amplified on an indicator strain. Phage DNA was extracted using the Promega wizard DNA clean-up System and sent for library preparation by mechanical random fragmentation and sequenced with an Illumina MiSeq platform. Sequencing reads were assembled using Spades. As expected from previous publications, isolated phages were genetically similar to other sequenced phages.

A host-range determination was performed with the different isolated phages against a collection of *C. acnes* strains, covering the known phylogenetic diversity. All phages were able to infect most of the *C. acnes* strains showing, as previously reported, a broad host-range (FIG. 2). PAC7 phage was selected for further experiments.

Genome of phage PAC7 was purified, mechanically sheared to allow for random DNA fragmentation and a PCR-free library preparation was performed prior to paired-end sequencing using illumina Mi-seq. DNA reads were assembled using Spades, a single contig was obtained and annotated. After annotation, cohesive-ends were identified and DNA fragments of different sizes, containing cohesive ends, were cloned in order to identify the packaging sequence (called cos site for phages with cohesive ends) that allow recognition by the small terminase and packaging of the phage genome into the phage capsid. Potential packaging signals from PAC7 were cloned into the pIC086 vector in two different orientations. The pIC086 vector contains:

- an origin of replication allowing replication into *C. acnes*, and
- a selection marker functional in *C. acnes* (here giving resistance to erythromycin).

Cos containing vectors (cosmids) were cloned into the *E. coli* DH10B cloning strain, sequence verified. The DNA vectors (Table 1) were introduced into the *C. acnes* strain ATCC 11828, and recombinants were selected on agar plates with erythromycin.

To produce phage-derived particles, a liquid culture of the different *C. acnes* strains carrying the DNA vector (Table 2) were grown and infected by PAC7. A strain containing a plasmid without cos PAC7 (Ca0s16973) was used as control. After infection, the supernatant was filtered and collected. Because both phage genomes and DNA vectors contain a packaging signal, they compete for packaging into the capsid, giving rise to a phage/phage-derived particle mixture.

Figure 8:
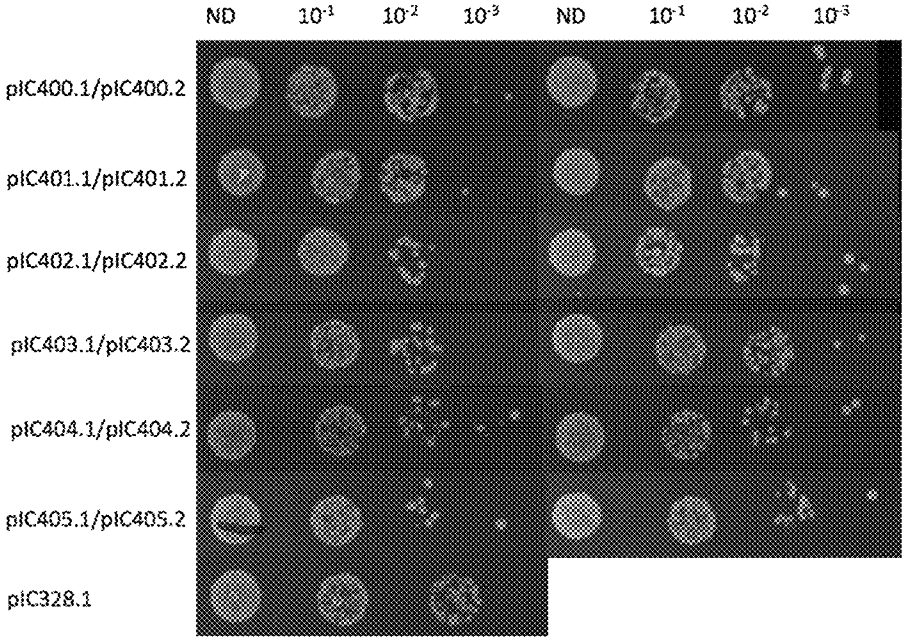
FIG. 8 depicts *C. acnes* transductants of phage-derived particles carrying DNA vector with phage packaging signal (cos) of different sizes. Each suspension of phage-derived particles, also containing phages, was mixed with *C. acnes* ATCC 11828 pseudolysogene, the mixture was incubated for 1 hour at room temperature, diluted and 4 μL of each dilution was plated on *Brucella* plates in presence of erythromycin (5 μg/mL). For each phage-derived particle containing a same DNA vector, two suspensions from independent productions were used (e.g pIC400.1 and pIC400.2).

To quantify the number of phages and phage-derived particles in the suspension, phage and phage-derived particles titration was performed. Titration of phage-derived particles was first performed with *C. acnes* ATCC 6919, showing high efficiency killing due to phage infection but no transductants could be observed. In these conditions, transductants are co-infected with the phage, leading to death of transduced cells and to the underestimation of phage-derived particle titers. To circumvent this, it was decided to perform titration with a *C. acnes* ATCC 11828 pseudolysogene strain. Indeed, *C. acnes* phages are not strictly temperate nor strictly lytic phages in laboratory conditions. They are able to inject their genome into cells and stay dormant in the cell without integrating into the genome. These cells carrying the phage in pseudolysogeny state are immune to phage killing. Using a pseudolysogene culture for phage/phage-derived particles titration, a higher amount of transductants were observed. However due to some residual killing of *C. acnes* by phages, a large variability in phage-derived particle titers can be observed in different productions from infection of the same producer cell (FIG. 8). The concentration of phage was determined by plaque assay and showed a high concentration of phage for all phage/phage-derived particle suspension with a titer of approximatively $10^7$ PFU/μL for each suspension. (Table 3). Several colonies were confirmed to be *C. acnes* harbouring the cosmid by PCR. Phage suspension from infection of Ca0s16973 carrying pIC086 plasmid without cos did not show any transductant, confirming that packaging, and thus, the production of phage-derived particles, was specific to cos carrying plasmids.

Titration of the phage-derived particles carrying the DNA vectors comprising phage packaging signal of different sizes shows (FIG. 8) no significant difference in number of transductants. The phage-derived particles titer was similar between all the different cosmids indicating that they are all functional and allow packaging of the DNA vector inside the phage capsid to produce phage-derived particles.

The results show, for the first time:

- transduction by a phage-derived particle of a synthetic DNA vector in *C. acnes*
- replication of the DNA vector in *C. acnes*
- expression of a transgene (erythromycin resistance gene) carried by the replicative DNA vector.

This is a key milestone for the development of in situ DNA delivery, genetic modification and transgene expression in *C. acnes*.

Materials and Methods:

Cosmids construction: Cos fragments were extracted by PCR on diluted phage PAC7 suspension, gel purified and cloned using SapI golden gate reaction and the pIC086 vector.

Introduction of cosmids in *C. acnes* can be performed by methods such as electroporation, protoplast electroporation, chemical transformation, using conjugation, natural competency, transduction.

*C. acnes* conjugation: 2 mL of overnight cultures of *E. coli* donor harboring the different mobilizable shuttle plasmids, grown in LB broth (Fisher Scientific), were pelleted in a benchtop centrifuged at 6,000×g for 1 min. Supernatants were discarded and pellets were washed with 500 μL of pre-sterilized LB medium and centrifuged again using the same conditions. Each pellet was then re-suspended in 200 μL of exponentially growing ($OD_{600}$=0.5) *C. acnes* receptor BHI culture concentrated 10× (BHI broth, Oxoid). The mixture *E. coli*-*C. acnes* was spotted (50 μL/spot) onto *Brucella* agar plates (Sigma-Aldrich) and allowed to mate at 37° C. under anaerobic conditions for 24 hours. After that time, cells were harvested from the mating plate, re-suspended in 300 μL of BHI broth and plated onto *Brucella* agar plates that had been supplemented with 50 μg/mL polymyxin B (Sigma-Aldrich) and 5 μg/mL erythromycin (Sigma-Aldrich) or 5 μg/mL chloramphenicol (Sigma-Aldrich). After 7 days, *C. acnes* cells that grew in the presence of selection were streaked on *Brucella* agar plates supplemented with the appropriate selection and the presence of the conjugated plasmid was confirmed via specific PCRs. The identity of *C. acnes* as well as the absence of *E. coli* donor strain were also confirmed by PCR analyses.

Phage/phage-derived particles production: Overnight cultures of *C. acnes* ATCC 11828 harbouring the different vectors (two clones per construct) were set in 10 mL BHI cultures supplemented with 5 μg/mL erythromycin. Production from phagemid pIC328 was used as a positive control. After overnight culture, once the OD600 had reached 0.8-1, 15 mL of each culture were taken and spin down at 3,000×g for 5 min. The supernatant was discarded and the pellet was re-suspended in 200 μL of PAC7 phage suspension and left on the bench at room temperature for 30 min so phages infect the cells. After one hour, 15 mL of BHI medium were added to each culture and allowed to grow/infect overnight under anaerobic conditions at 37° C. After overnight incubation, cultures were very clear, indicating that infection had taken place. Cultures were spun down at 3, 000×g for 5 min, and the supernatant was filtered through a 0.45 μm filter.

Phage titration: Serial dilutions of the phage/packaged phagemid mixture were made in $MgSO_4$ 5 mM and 4 μL of each dilution were spotted onto *Brucella* plates containing a top layer of agarose 4.5 g/L and the strain ATCC 11828. After overnight incubation under anaerobic conditions at 37° C., lysis plaques were counted.

Phage-derived particles titration: 90 μL of an overnight culture ($OD_{600}$ approx 0.8-1, concentrated ×10) of *C. acnes* ATCC 11828 pseudolysogene cells were mixed with 10 μL of Phage/Phage-derived particles from non-diluted to dilution $10^{-4}$ (dilution in $MgSO_4$ 5 mM). A control of cells with no phage was included in the assay. The cultures were incubated at room temperature for 1 hour. After this first incubation period, the cultures (bacteria+phages/phage-derived particles at different dilutions) were serially diluted up to $10^{-7}$ in BHI and incubated for 3-4 hours under anaerobic conditions at 37° C. After incubation, 4 μL of each dilution were spotted onto *Brucella* plates in the presence and absence of erythromycin (5 μg/mL). After 5 days of incubation at 37° C. under anaerobic conditions, colonies on BHI plates and BHI+erythromycin 5 μg/mL plates were scanned (FIG. 8).

Pseudolysogene production: strains were freshly made prior to the transduction test. PAC7 phage was added to a suspension of *C. acnes* ATCC 11828 cells and plated onto BHI agar plates. After 3 to 4 incubation days, cells growing on plates were recovered and either plated again to have more cells or used for titration. If successive growth on plates is needed, *C. acnes* phages are added to the culture in order to maintain strains in the pseudolysogene state.

Figure 3:
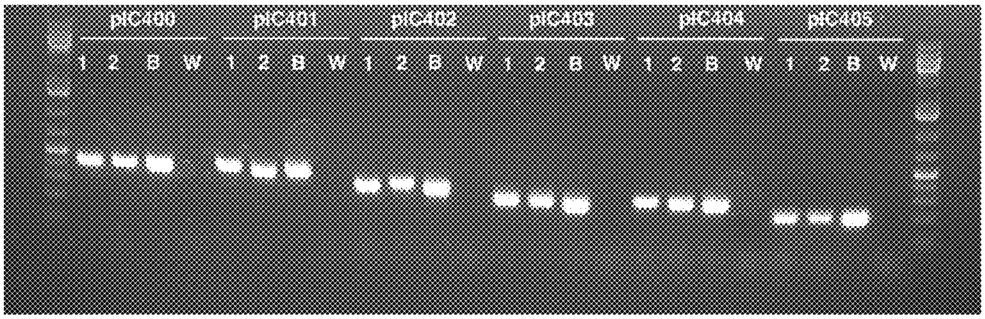
FIG. 3 depicts a gel. Individual colonies from phage-derived particles titration were streaked and a PCR on an individual colony was performed with primers IC208 (SEQ ID NO: 82)/IC310 (SEQ ID NO: 83) to confirm the presence of the phagemid. 1 and 2 refer to transductants coming from the independent production and titration of phage-derived particles carrying the same phagemid. B and W are respectively PCR on the phagemid extraction (positive control) and the ATCC 11828 strain (negative control). Presence of the plasmid after restreak confirms that transductants carry the replicative phagemid.

Confirmation of the phagemid transduction into *C. acnes* cells: colonies observed on BHI plates supplemented with erythromycin were re-isolated on BHI+erythromycin plates. Individual erythromycin resistant colonies obtained after streaking were then tested by PCR to confirm the presence of the phagemid (FIG. 3).

PCR verification of the transductant: colony PCR to check the presence of the phagemid was performed with primers IC208/IC310. A PCR performed with primers AD1261/AD1262 was also included to confirm *C. acnes* identity.

TABLE 1

Mobilizable DNA vectors including packaging signal of PAC7 phage

| DNA vector Name | Cos region | Primers for cloning | Mobilisable vector |
|---|---|---|---|
| pIC328 | PAC7 Cos region 1 in orientation 1 (383 bp) | AD1542/AD1541 | pIC086 |
| pIC400 | PAC7 Cos region 1 in orientation 1 (317 bp) | IC511/AD1542 | pIC086 |
| pIC401 | PAC7 Cos region 1 in orientation 2 (317 bp) | AD1541/IC512 | pIC086 |
| pIC402 | PAC7 Cos region 2 in orientation 1 (217 bp) | IC511/IC512 | pIC086 |
| pIC403 | PAC7 Cos region 2 in orientation 2 (167 bp) | IC513/IC512 | pIC086 |
| pIC404 | PAC7 Cos region 3 in orientation 1 (167 bp) | IC511/IC514 | pIC086 |
| pIC405 | PAC7 Cos region 3 in orientation 2 (83 bp) | IC513/IC514 | pIC086 |

TABLE 2

List of *C. acnes* strains generated

| name | Strain description | plasmid |
|---|---|---|
| Ca0s16973 | *Cutibacterium acnes* ATCC 11828 | pIC086 |
| Ca0s18253 | *Cutibacterium acnes* ATCC 11828 | pIC328 |
| Ca0s19443 | *Cutibacterium acnes* ATCC 11828 | pIC400 |
| Ca0s19444 | *Cutibacterium acnes* ATCC 11828 | pIC401 |
| Ca0s19445 | *Cutibacterium acnes* ATCC 11828 | pIC402 |
| Ca0s19446 | *Cutibacterium acnes* ATCC 11828 | pIC403 |
| Ca0s19447 | *Cutibacterium acnes* ATCC 11828 | pIC404 |
| Ca0s19448 | *Cutibacterium acnes* ATCC 11828 | pIC405 |

TABLE 3

Results of phage titration

| strain infected | DNA payload | Phage used for infection | Phage titer (PFU/μL) on *C. acnes* ATCC 11828 indicator strain |
|---|---|---|---|
| Ca0s16973 | pIC086 | PAC7 | ~1E+8 |
| Ca0s18253 | pIC328 | PAC7 | ~1E+7 |
| Ca0s19443 | pIC400 | PAC7 | ~1E+7 |
| Ca0s19444 | pIC401 | PAC7 | ~1E+7 |
| Ca0s19445 | pIC402 | PAC7 | ~1E+7 |
| Ca0s19446 | pIC403 | PAC7 | ~1E+7 |
| Ca0s19447 | pIC404 | PAC7 | ~1E+7 |
| Ca0s19448 | pIC405 | PAC7 | ~1E+7 |

TABLE 4

Primers sequences

| Primers name | Primers sequence |
|---|---|
| AD1541 | GTTCCAGCTCTTCCGAGGACCACATCACACCCGTC (SEQ ID NO: 84) |
| AD1542 | GTTCCAGCTCTTCCTGCCCACTCCTCATCAGACAC (SEQ ID NO: 85) |
| IC511 | GTTCCAGCTCTTCCGAGAGGCAACAGAACACAACCAAA (SEQ ID NO: 86) |
| IC512 | GTTCCAGCTCTTCCTGCGACTATCAGGAAGCTCAGGC (SEQ ID NO: 87) |
| IC513 | GTTCCAGCTCTTCCGAGAAAACCCGCCAACCCCCACC (SEQ ID NO: 88) |
| IC514 | GTTCCAGCTCTTCCTGCACAAAAGGGAGGTATTTCACT (SEQ ID NO: 89) |
| AD1261 | CAGCGGCGCTGCTAAGAACTT (SEQ ID NO: 90) |
| AD1262 | CCGGCTGGCAAATGAGGCAT (SEQ ID NO: 91) |
| IC208 | GCTTCCTTAGCTTGCGAAATCTCGA (SEQ ID NO: 82) |
| IC310 | GTTCGGCTAAACCCAAAAGTAAAAAC (SEQ ID NO: 83) |

Example 2

Effects of genetically modified *C. acnes* strains are tested in vitro for their effects on immune cells, in particular for their ability to induce specific cytokines or immune profiles, according to previously described protocols.

In particular, the protocol disclosed in Yu et al. (2016) Journal of Investigative Dermatology 136:2221-2228, with optional modifications and/or adaptations if needed, is implemented on said strains.

Example 3: Secretion of Antigens by Engineered *C. acnes* Strains

The pilosebaceous unit (PSU) is a complex skin appendage containing a diverse set of cells such as immune cells, sebaceous cells and stem cells. It is also a highly vascularized area making it an entry point for systemic delivery of molecules. The PSU microbiota is dominated by *C. acnes*, therefore the ability to engineer *C. acnes* to secrete recombinant proteins in situ is of great interest to both modulate the activity of the cells present as well as for the delivery of molecules in the blood. The present example demonstrates the use of DNA vectors that once introduced into *C. acnes* lead to the secretion of recombinant proteins, here the chicken ovalbumin antigen protein. This invention opens possibilities to use engineered *C. acnes* strains secreting specific proteins of interest such as antigens as skin probiotics. Alternatively engineered phages or phage-derived particles can be used to deliver DNA vectors, encoding for the secretion of protein of interest, in the *C. acnes* population already present in the PSU.

*C. acnes* is one of the, if not the, most abundant and prevalent bacterial commensal of the human skin. It resides mostly in the PSU even if it can also be isolated from the skin surface. Specific strains belonging to specific phylotypes have been associated with acne vulgaris disease and are considered to be "pro-inflammatory". In order to characterize the difference between the different *C. acnes* phylotypes, a few studies have been characterizing the secretome in order to identify potential proteins specific to the pro-inflammatory phenotypes. Using a subset of the identified secreted proteins, the present inventors were able to identify putative secretion signal peptides (Table 5) using signalP (Armenteros, J. et al. SignalP 5.0 improves signal peptide predictions using deep neural networks. *Nat Biotechnol* 37, 420-423 (2019)).

To test the ability of these secretion signal peptides to drive secretion of a recombinant protein in *C. acnes*, the present inventors built several replicative plasmids comprising:

- a promoter driving the expression of the recombinant protein,
- a signal peptide addressing the proteins to secretion systems fused to the N-terminal of a chicken ovalbumin CDS codon optimized for *C. acnes,*
- an erythromycin selection marker for *C. acnes*, and
- an origin of replication functional in *C. acnes.*

Figure 9A:
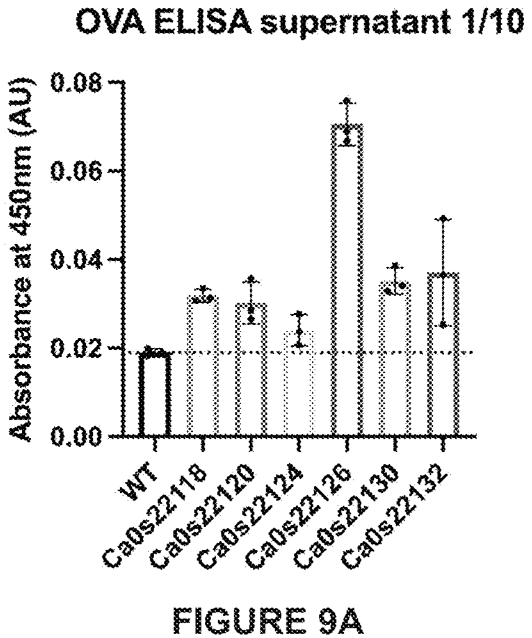
FIGS. 9A and 9B depicts absorbance values from ELISAs for the presence of chicken ovalbumin (OVA) protein in different *C. acnes* culture supernatant diluted 1/10. 9A and 9B represent two independent replicas. Bar graphs represent the mean of three technical replicates of the same supernatant culture. *C. acnes* strains ATCC 11828 (WT) was used as negative control.
Figure 9B:
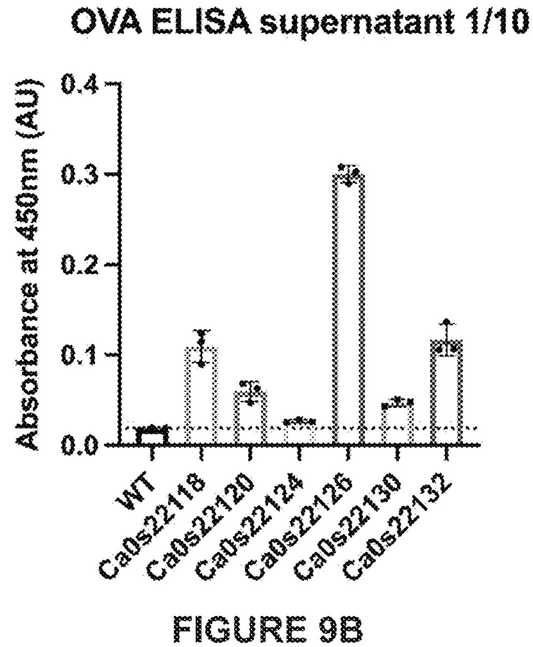
Figure 10:
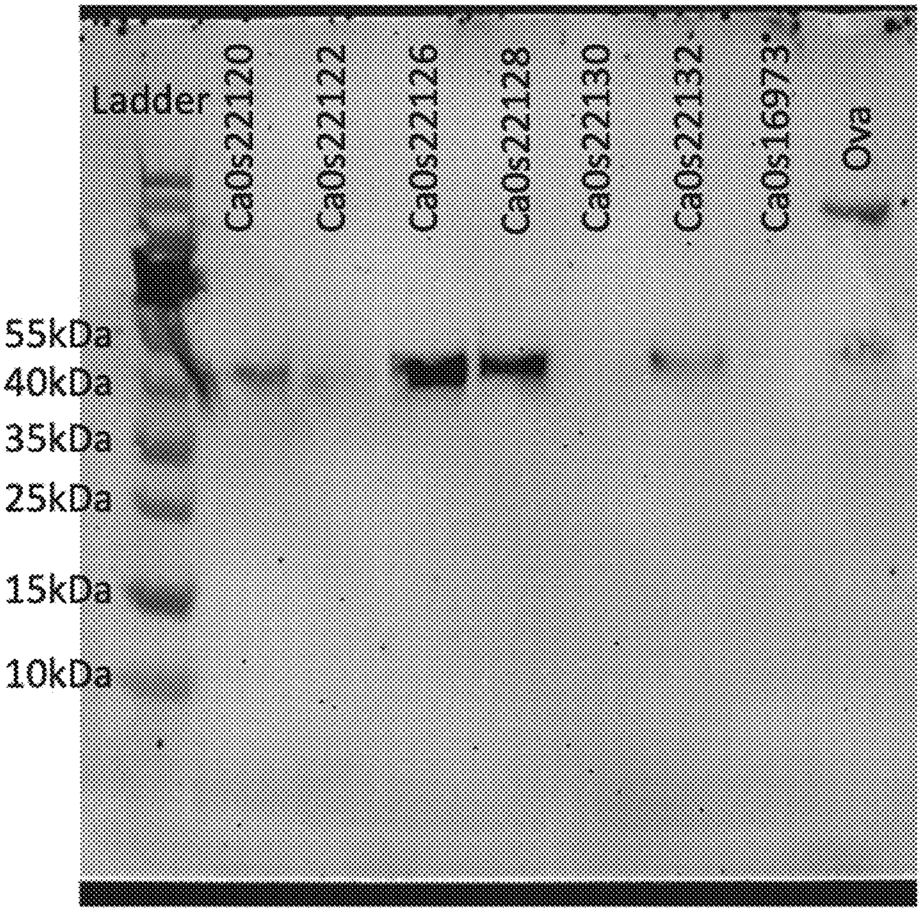
FIG. 10 depicts an ovalbumin specific western blot on culture supernatant from different *C. acnes* strains engineered to secrete ovalbumin. From left to right: (1) Pageruler ladder, (2) supernatant from strain Ca0s22120, (3) supernatant from strain Ca0s22122, (4) supernatant from strain Ca0s22126, (5) supernatant from strain Ca0s22128, (6)

The different DNA vectors (Table 6) were introduced into *C. acnes* ATCC 11828 (Table 7). Introduction into *C. acnes* cells can be performed by different methods such as electroporation, electroporation of protoplast, conjugation, chemical transformation, transduction into the *C. acnes*. Presence of the DNA vectors into *C. acnes* was confirmed, after streaking on selective plates, by colony PCR. Secretion of chicken ovalbumin protein in the different *C. acnes* culture supernatants was monitored using ELISA (FIG. 9) and Western Blot (FIG. 10). As shown in FIG. 9, both replicas of ELISA experiment show a significantly higher absorbance for most engineered *C. acnes* strains, except Ca0s22124, compared to wild-type *C. acnes* (*C. acnes* ATCC 11828). Strain Ca0s22126 was repeatedly giving the highest signal indicating higher level of secreted ovalbumin in culture supernatant. Secretion was further confirmed by Western blot (FIG. 10). A single band just above 40 kDa was observed for culture supernatant from strains Ca0s22120, Ca0s22122, Ca0s22126, Ca0s22128 and Ca0s22132. This band corresponds to ovalbumin size (43 kDa) and to the faint band from the ovalbumin control well. No band was observed for control strain Ca0s16973 that carries the empty plasmid used for cloning the different secretion plasmids. More intense band was found for Ca0s22126 confirming the results of the ELISA.

In conclusion, the present inventors describe for the first time the use of endogenous *C. acnes* secretion peptide for the secretion of recombinant protein by *C. acnes* using replicative DNA plasmids.

Materials and Methods:

Plasmids construction: Synthetic DNA fragments were ordered and assembled using SapI golden gate cloning in the p1047 plasmid (pIC086).

Conjugation: As described in Materials and methods of Example 1.

ELISA: The different *C. acnes* strains were streaked from cryostock into BHI+erythromycin plate, except for the control strain without plasmid that was streaked on BHI without antibiotic, and plates were incubated at 37° C. in anaerobic conditions for 4-7 days. When fully grown, 10 mL cultures of BHI+5 μg/mL erythromycin were inoculated with an inoculum from the corresponding streak and incubated one overnight at 37° C. in anaerobic conditions. After incubation, $OD_{600\ nm}$ was measured to control for difference in growth. 1 mL of culture was dispensed into a 1.5 mL tube and centrifuged 6 min at 6000 g. 10 μL of the supernatant was transferred to a high-binding 96 well-plate (Greiner 655061) prefiled with 90 μL of 1×PBS. Incubation of the covered plate during 2 hours at 37° C. was performed. After incubation, samples were discarded from the plate, 100 μL of PBS+5% bovine serum albumin (BSA) was added and the covered plate was incubated for 1 hour at 37° C. Three consecutive washing steps with 100 μL of PBS+0.05% Tween 20 were performed prior to the addition of 100 μL of primary antibody solution (Anti-OVA innovagen PA-0323-100 diluted 1/1000 in PBS 1×+1% BSA+0.05% Tween 20). The covered plate was incubated at RT for 1 hour. Following incubation, three consecutive washing steps with 100 μL of PBS+0.05% Tween 20 were performed prior to the addition of 100 μL of secondary antibody solution (Anti-rabbit Invitrogen A16035 antibody diluted 1/5000 in PBS 1×+1% BSA+0.05% Tween 20) and incubation at RT for 1 hour. After incubation, samples were discarded from the plate and final three consecutive washing steps with 100 μL of PBS+0.05% Tween 20 were performed. 100 μL of TMB-ELISA substrate (Thermo Scientific 34028) was added to each well and incubation was performed under light protection for 10 to 12 min at RT. 100 μL of 1 M sulfuric acid was added to each well to stop the reaction. Absorbance measurement at 450 nm was performed using an infinite reader (Tecan).

Western blot: The different *C. acnes* strains were streaked from cryostock into BHI+erythromycin plate, except for the control strain without plasmid that was streaked on BHI without antibiotic, and plates were incubated at 37° C. in anaerobic conditions for 4-7 days. When fully grown, 10 mL cultures of BHI+5 μg/mL erythromycin were inoculated with an inoculum from the corresponding streak and incubated one overnight at 37° C. in anaerobic conditions. After incubation, $OD_{600}$ was measured to control for difference in growth. 1 mL of culture was dispensed into a 1.5 mL tube and centrifuged 6 min at 6000 g. Filtration of the supernatant using 0.2 μm filter. 30 μL of the filtered supernatant was supplemented with 7.5 μL of LDS sample buffer (B0008 Invitrogen™) and 3 μL of Bolt™ antioxidant (BT0005 Invitrogen™) before boiling at 100° C. for 10 min. 30 μL of the mixture was loaded into a Bolt™ 4 to 12% Bis-Tris gel (NW04120 Invitrogen™). After migration, transfer on nitrocellulose membrane was performed. After the transfer, the membrane was: soaked first in 5% skim milk solution in PBS+0.05% Tween 20 for 1 h, then soaked in 20 mL 5% skim milk solution in PBS+0.05% Tween 20 containing the primary antibody (Anti-OVA innovagen PA-0323-100) diluted 1:1000 overnight at 4° C., washed three times with PBS+Tween 0.05%, soaked 1 h in 20 mL 5% skim milk solution in PBS+0.05% Tween 20 containing the secondary antibody (Anti-rabbit Invitrogen A16035 antibody) diluted 1:5000, washed three times with PBS+Tween 0.05%. Final step of revelation was performed using chemiluminescent substrate (34580 Thermofisher). Imaging was done using iBright CL1000 (Invitrogen™)

TABLE 5

Secreted proteins used to extract secretion signals

| Protein id | SignalP 5.0 prediction |
|---|---|
| YP_056615.1 | Prediction: Signal peptide (Sec/SPI) Cleavage site between pos. 23 and 24: GAA-TP. Probability: 0.4339 |
| YP_056817.1 | Prediction: Lipoprotein signal peptide (Sec/SPII) Cleavage site between pos. 20 and 21: LSA-CG. Probability: 0.9859 |
| YP_055402.1 | Prediction: Signal peptide (Sec/SPI) Cleavage site between pos. 28 and 29: AHA-VE. Probability: 0.9710 |
| YP_056047 | Prediction: Signal peptide (Sec/SPI) Cleavage site between pos. 28 and 29: AHA-AP. Probability: 0.8551 |

TABLE 6

DNA vectors encoding secretion of ovalbumin

| DNA vector Name | Promoter | signal peptide from | protein |
|---|---|---|---|
| p2152 | P138 | YP_056047 | chicken ovalbumin |
| p2154 | P138 | YP_055402.1 | chicken ovalbumin |
| p2156 | P138 | YP_056817.1 | chicken ovalbumin |
| p2158 | P138 | YP_056615.1 | chicken ovalbumin |
| p2160 | ProxP | YP_056047 | chicken ovalbumin |
| p2162 | ProxP | YP_055402.1 | chicken ovalbumin |
| p2164 | ProxP | YP_056817.1 | chicken ovalbumin |
| p2166 | ProxP | YP_056615.1 | chicken ovalbumin |

TABLE 7

List of *C. acnes* strains generated

| name | Strain description | plasmid |
|---|---|---|
| Ca0s22118 | *Cutibacterium acnes* ATCC 11828 | p2152 |
| Ca0s22120 | *Cutibacterium acnes* ATCC 11828 | p2154 |
| Ca0s22122 | *Cutibacterium acnes* ATCC 11828 | p2156 |
| Ca0s22124 | *Cutibacterium acnes* ATCC 11828 | p2158 |
| Ca0s22126 | *Cutibacterium acnes* ATCC 11828 | p2160 |
| Ca0s22128 | *Cutibacterium acnes* ATCC 11828 | p2162 |
| Ca0s22130 | *Cutibacterium acnes* ATCC 11828 | p2164 |
| Ca0s22132 | *Cutibacterium acnes* ATCC 11828 | p2166 |
| Ca0s16973 | *Cutibacterium acnes* ATCC 11828 | p1047 (pIC86) |

REFERENCES

1. Pasparakis, M., Haase, I. & Nestle, F. O. Mechanisms regulating skin immunity and inflammation. *Nature Reviews Immunology* 14, 289-301 (2014).
2. Scharschmidt, T. C. et al. A Wave of Regulatory T Cells into Neonatal Skin Mediates Tolerance to Commensal Microbes. *Immunity* 43, 1011-1021 (2015).
3. Oh, J. et al. Biogeography and individuality shape function in the human skin metagenome. *Nature* 514, 59-64 (2014).
4. Oh, J. et al. Biogeography and individuality shape function in the human skin metagenome. *Nature* 514, 59-64 (2014).
5. Nakatsuji, T. et al. The microbiome extends to subepidermal compartments of normal skin. *Nat Commun* 4, 1431 (2013).
6. Bay, L. et al. Universal Dermal Microbiome in Human Skin. *Mbio* 11, (2020).

7. Nagao, K. et al. Stress-induced production of chemokines by hair follicles regulates the trafficking of dendritic cells in skin. *Nat Immunol* 13, 744-752 (2012).
8. Adachi, T. et al. Hair follicle-derived IL-7 and IL-15 mediate skin-resident memory T cell homeostasis and lymphoma. *Nat Med* 21, 1272-1279 (2015).
9. Paus, R., Ito, N., Takigawa, M. & Ito, T. The Hair Follicle and Immune Privilege. *J Invest Derm Symp P* 8, 188-194 (2003).
10. Scholz, C. F. & Kilian, M. The natural history of cutaneous propionibacteria, and reclassification of selected species within the genus *Propionibacterium* to the proposed novel genera Acidipropionibacterium gen. nov., *Cutibacterium* gen. nov. and Pseudopropionibacterium gen. nov. *International Journal of Systematic and Evolutionary Microbiology* 66, 4422-4432 (2016).
11. McLaughlin, J. et al. *Propionibacterium acnes* and Acne Vulgaris: New Insights from the Integration of Population Genetic, Multi-Omic, Biochemical and Host-Microbe Studies. *Microorganisms* 7, 128 (2019).
12. Barnard, E. et al. Strains of the *Propionibacterium acnes* type III lineage are associated with the skin condition progressive macular hypomelanosis. *Scientific reports* 6, 31968 (2016).
13. Petersen, R. L. W., Scholz, C. F. P., Jensen, A., Brüggemann, H. & Lomholt, H. B. *Propionibacterium acnes* phylogenetic type III is associated with progressive macular hypomelanosis. *European J Microbiol Immunol* 7, 37-45 (2017).
14. McDowell, A., McLaughlin, J. & Layton, A. M. Is *Cutibacterium* (previously *Propionibacterium*) *acnes* a potential pathogenic factor in the aetiology of the skin disease progressive macular hypomelanosis? *J European Acad Dermatology Venereol Jeadv* (2020) doi:10.1111/jdv.16789.
15. Fitz-Gibbon, S. et al. *Propionibacterium acnes* Strain Populations in the Human Skin Microbiome Associated with Acne. *J Invest Dermatol* 133, 2152-2160 (2013).
16. Sorensen, M. et al. Mutagenesis of *Propionibacterium acnes* and analysis of two CAMP factor knock-out mutants. *Journal of Microbiological Methods* 83, 211-216 (2010).
17. Allhorn, M., Arve, S., Brüggemann, H. & Lood, R. A novel enzyme with antioxidant capacity produced by the ubiquitous skin colonizer *Propionibacterium acnes. Sci Rep-uk* 6, 36412 (2016).
18. Nazipi, S., Stodkilde, K., Scavenius, C. & Brüggemann, H. The Skin Bacterium *Propionibacterium acnes* Employs Two Variants of Hyaluronate Lyase with Distinct Properties. Microorg 5, 57 (2017).
19. Kasimatis, G., Fitz-Gibbon, S., Tomida, S., Wong, M. & Li, H. Analysis of Complete Genomes of *Propionibacterium acnes* Reveals a Novel Plasmid and Increased Pseudogenes in an Acne Associated Strain. *BioMed Research International* 2013, 1-11 (2013).
20. Davidsson, S. et al. Prevalence of Flp Pili-Encoding Plasmids in *Cutibacterium acnes* Isolates Obtained from Prostatic Tissue. *Frontiers in microbiology* 8, 2241 (2017).
21. Aoki, S., Nakase, K., Hayashi, N. & Noguchi, N. Transconjugation of erm(X) conferring high-level resistance of clindamycin for *Cutibacterium acnes. Journal of Medical Microbiology* (2018) doi:10.1099/jmm.0.000875.
22. Aoki, S. et al. Transferable Multidrug-Resistance Plasmid Carrying a Novel Macrolide-Clindamycin Resistance Gene, erm (50), in *Cutibacterium acnes. Antimicrob Agents Ch* 64, (2019).
23. Barnard, E., Shi, B., Kang, D., Craft, N. & Li, H. The balance of metagenomic elements shapes the skin microbiome in acne and health. *Scientific Reports* 6, srep39491 (2016).
24. Rouet, P., Smih, F. & Jasin, M. Expression of a site-specific endonuclease stimulates homologous recombination in mammalian cells. *Proc National Acad Sci* 91, 6064-6068 (1994).
25. Arazoe, T. et al. Site-specific DNA double-strand break generated by I-Scel endonuclease enhances ectopic homologous recombination in *Pyricularia oryzae. Fems Microbiol Lett* 352, 221-229 (2014).
26. Liu, J. et al. The diversity and host interactions of *Propionibacterium acnes* bacteriophages on human skin. *The ISME Journal* 9, 2078 (2015).
27. Lood, R. & Collin, M. Characterization and genome sequencing of two *Propionibacterium acnes* phages displaying pseudolysogeny. *BMC Genomics* 12, 198 (2011).

We claim:

1. A *C. acnes* phage-derived particle comprising a phagemid lacking genes encoding phage structural proteins, said phagemid comprising:

a phage packaging signal allowing packaging of the phagemid in a *Cutibacterium acnes* phage capsid, wherein the phage packaging signal is at least 87% identical to SEQ ID NO: 76, a gene of interest, and a CRISPR-Cas system.

2. The *C. acnes* phage-derived particle according to claim 1, wherein the CRISPR-Cas system targets a *C. acnes* chromosome locus.

3. The *C. acnes* phage-derived particle according to claim 1, wherein the CRISPR-Cas system targets a *C. acnes* plasmid locus.

4. The *C. acnes* phage-derived particle according to claim 1, wherein the gene of interest is a transgene that is exogenous to *C. acnes.*

5. The *C. acnes* phage-derived particle according to claim 4, wherein the transgene encodes a human protein.

6. The *C. acnes* phage-derived particle according to claim 4, wherein the transgene encodes an antigen.

7. The *C. acnes* phage-derived particle according to claim 4, wherein the transgene encodes an interleukin.

8. The *C. acnes* phage-derived particle according to claim 1, wherein the phagemid further comprises an origin of replication for *C. acnes* and a selection marker for *C. acnes.*

9. The *C. acnes* phage-derived particle according to claim 8, wherein the selection marker is not ermE.

10. A phagemid lacking genes encoding phage structural proteins comprising:

a phage packaging signal allowing packaging of the phagemid in a *Cutibacterium acnes* phage capsid, wherein the phage packaging signal is at least 87% identical to SEQ ID NO: 76, a gene of interest, and a CRISPR-Cas system.

11. The phagemid according to claim 10, wherein the CRISPR-Cas system targets a *C. acnes* chromosome locus.

12. The phagemid according to claim 10, wherein the CRISPR-Cas system targets a *C. acnes* plasmid locus.

13. The phagemid according to claim 10, wherein the gene of interest encodes a human protein.

14. The phagemid according to claim 10, wherein the gene of interest encodes an antigen.

15. The phagemid according to claim 10, wherein the gene of interest encodes an interleukin.

16. The phagemid according to claim 10, wherein the phagemid further comprises an origin of replication for *C. acnes* and a selection marker for *C. acnes.*

17. The phagemid according to claim 16, wherein the selection marker is not ermE.

* * * * *